United States Patent
Mondal et al.

(10) Patent No.: US 12,378,312 B2
(45) Date of Patent: *Aug. 5, 2025

(54) POLYNUCLEOTIDES ENCODING HUMAN BETA KLOTHO ANTIBODIES OR BINDING FRAGMENTS THEREOF AND METHODS OF USE THEREOF

(71) Applicant: NGM Biopharmaceuticals, Inc., South San Francisco, CA (US)

(72) Inventors: Kalyani Mondal, San Mateo, CA (US); Betty Chan Li, Millbrae, CA (US); Yu Chen, Foster City, CA (US); Taruna Arora, Palo Alto, CA (US); Hugo Matern, San Mateo, CA (US); Wenyan Shen, Redwood City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/153,643

(22) Filed: Jan. 12, 2023

(65) Prior Publication Data

US 2023/0256070 A1 Aug. 17, 2023

Related U.S. Application Data

(63) Continuation of application No. 16/928,862, filed on Jul. 14, 2020, now Pat. No. 11,596,676, which is a continuation of application No. 16/103,613, filed on Aug. 14, 2018, now Pat. No. 10,744,191, which is a continuation of application No. 15/659,177, filed on Jul. 25, 2017, now Pat. No. 10,093,735, which is a continuation of application No. 14/604,592, filed on Jan. 23, 2015, now Pat. No. 9,738,716.

(60) Provisional application No. 61/931,531, filed on Jan. 24, 2014.

(51) Int. Cl.
*C12N 15/13* (2006.01)
*A61K 39/00* (2006.01)
*C07K 16/28* (2006.01)
*G01N 33/66* (2006.01)

(52) U.S. Cl.
CPC ...... *C07K 16/28* (2013.01); *A61K 39/001154* (2018.08); *A61K 2039/505* (2013.01); *C07K 2317/24* (2013.01); *C07K 2317/34* (2013.01); *C07K 2317/75* (2013.01); *G01N 33/66* (2013.01)

(58) Field of Classification Search
None
See application file for complete search history.

(56) References Cited

U.S. PATENT DOCUMENTS

| | | |
|---|---|---|
| 6,579,850 B1 | 6/2003 | Nabeshima |
| 6,635,468 B2 | 10/2003 | Ashkenazi |
| 6,716,626 B1 | 4/2004 | Itoh |
| 6,806,352 B2 | 10/2004 | Desnoyers |
| 6,812,339 B1 | 11/2004 | Venter |
| 6,987,121 B2 | 1/2006 | Kliewer |
| 7,115,415 B2 | 10/2006 | Goddard |
| 7,129,072 B1 | 10/2006 | Schlessinger |
| 7,208,312 B1 | 4/2007 | Desnoyers |
| 7,259,248 B2 | 8/2007 | Itoh |
| 7,288,406 B2 | 10/2007 | Bogin |
| 7,390,879 B2 | 6/2008 | Ashkenazi |
| 7,459,540 B1 | 12/2008 | Thomason |
| 7,491,697 B2 | 2/2009 | Beals |
| 7,537,902 B2 | 5/2009 | Kuro-O |
| 7,576,190 B2 | 8/2009 | Glaesner |
| 7,582,607 B2 | 9/2009 | Frye |
| 7,622,445 B2 | 11/2009 | Frye |
| 7,655,627 B2 | 2/2010 | Frye |
| 7,667,005 B2 | 2/2010 | Nabeshima |
| 7,667,008 B2 | 2/2010 | Thomason |
| 7,705,195 B2 | 4/2010 | French |
| 7,723,297 B2 | 5/2010 | Itoh |
| 7,947,866 B2 | 5/2011 | Sparks |
| 8,012,931 B2 | 9/2011 | Cujec |
| 8,034,770 B2 | 10/2011 | Belouski |
| 8,188,040 B2 | 5/2012 | Belouski |
| 8,324,160 B2 | 12/2012 | Li |
| 8,361,963 B2 | 1/2013 | Belouski |
| 8,372,952 B2 | 2/2013 | Smith |
| 8,383,365 B2 | 2/2013 | Cujec |
| 8,410,051 B2 | 4/2013 | Belouski |
| 8,420,088 B2 | 4/2013 | Glass |
| 8,481,031 B2 | 7/2013 | Glass |

(Continued)

FOREIGN PATENT DOCUMENTS

| | | |
|---|---|---|
| CN | 102858802 A | 1/2013 |
| DE | 10100588 | 7/2002 |

(Continued)

OTHER PUBLICATIONS

Adams et al., "FGF21 requires βklotho to act in vivo," PloS One, 2012, 7(11):e49977.

(Continued)

*Primary Examiner* — Christine J Saoud
(74) *Attorney, Agent, or Firm* — Fish & Richardson P.C.

(57) ABSTRACT

The present disclosure provides binding proteins, such as antibodies or binding fragments thereof, that bind beta klotho, including human beta klotho, and methods of their use such as in producing an antibody or binding fragment thereof. The present disclosure also provides vectors and cells comprising polynucleotides encoding antibodies or binding fragments thereof that bind beta klotho, including human beta klotho.

23 Claims, 23 Drawing Sheets

Specification includes a Sequence Listing.

(56) References Cited

U.S. PATENT DOCUMENTS

| | | |
|---|---|---|
| 8,535,912 B2 | 9/2013 | Sonoda |
| 8,541,369 B2 | 9/2013 | Dickinson |
| 8,580,936 B2 | 11/2013 | Williams |
| 8,618,053 B2 | 12/2013 | Belouski |
| 8,642,546 B2 | 2/2014 | Belouski |
| 8,673,860 B2 | 3/2014 | Schellenberger |
| 8,741,841 B2 | 6/2014 | Darling |
| 8,795,985 B2 | 8/2014 | Belouski |
| 8,802,697 B2 | 8/2014 | Bifulco |
| 8,809,499 B2 | 8/2014 | Fan |
| 8,835,385 B2 | 9/2014 | Belouski |
| 8,883,726 B2 | 11/2014 | Dickinson |
| 8,889,426 B2 | 11/2014 | Mohammadi |
| 8,889,621 B2 | 11/2014 | Mohammadi |
| 8,927,492 B2 | 1/2015 | Darling |
| 8,932,589 B2 | 1/2015 | Glass |
| 8,951,966 B2 | 2/2015 | Ling |
| 8,962,557 B2 | 2/2015 | Blaber |
| 8,975,223 B2 | 3/2015 | Vignati |
| 8,993,727 B2 | 3/2015 | Walker |
| 8,999,929 B2 | 4/2015 | Mohammadi |
| 9,006,400 B2 | 4/2015 | Boettcher |
| 9,089,525 B1 | 7/2015 | Ling |
| 9,273,107 B2 | 3/2016 | Ling |
| 9,290,557 B2 | 3/2016 | Ling |
| 9,580,483 B2 | 2/2017 | Ling |
| 9,670,260 B2 | 6/2017 | Ling |
| 9,738,716 B2 | 8/2017 | Mondal |
| 9,751,924 B2 | 9/2017 | Ling |
| 9,878,008 B2 | 1/2018 | Ling |
| 9,878,009 B2 | 1/2018 | Ling |
| 9,889,177 B2 | 2/2018 | Ling |
| 9,889,178 B2 | 2/2018 | Ling |
| 9,895,416 B2 | 2/2018 | Ling |
| 9,925,242 B2 | 3/2018 | Ling |
| 10,093,735 B2 | 10/2018 | Mondal et al. |
| 10,744,191 B2 | 8/2020 | Mondal et al. |
| 10,800,843 B2 | 8/2020 | Mondal et al. |
| 11,596,676 B2 | 3/2023 | Mondal et al. |
| 11,667,708 B2 | 6/2023 | Mondal et al. |
| 2002/0012961 A1 | 1/2002 | Botstein |
| 2002/0042367 A1 | 4/2002 | Stewart |
| 2002/0082205 A1 | 6/2002 | Itoh |
| 2002/0151496 A1 | 10/2002 | Bringmann |
| 2002/0155543 A1 | 10/2002 | Adams |
| 2003/0045489 A1 | 3/2003 | Murphy |
| 2003/0065140 A1 | 4/2003 | Vernet |
| 2003/0105302 A1 | 6/2003 | Itoh |
| 2003/0113718 A1 | 6/2003 | Ashkenazi |
| 2003/0119112 A1 | 6/2003 | Baker |
| 2003/0125521 A1 | 7/2003 | Baker |
| 2003/0166051 A1 | 9/2003 | Desnoyers |
| 2003/0170822 A1 | 9/2003 | Itoh |
| 2003/0180890 A1 | 9/2003 | Conklin |
| 2003/0185846 A1 | 10/2003 | Ashkenazi |
| 2003/0220246 A1 | 11/2003 | Conklin |
| 2004/0014658 A1 | 1/2004 | Bogin |
| 2004/0126852 A1 | 7/2004 | Stewart |
| 2004/0146908 A1 | 7/2004 | Adams |
| 2004/0185494 A1 | 9/2004 | Itoh |
| 2005/0026243 A1 | 2/2005 | Stewart |
| 2005/0026832 A1 | 2/2005 | Adams |
| 2005/0107475 A1 | 5/2005 | Jones |
| 2005/0153305 A1 | 7/2005 | Vernet |
| 2005/0181375 A1 | 8/2005 | Aziz |
| 2005/0196842 A1 | 9/2005 | Botstein |
| 2006/0160181 A1 | 7/2006 | Luethy |
| 2006/0172386 A1 | 8/2006 | Itoh |
| 2006/0246540 A1 | 11/2006 | Ashkenazi |
| 2006/0275794 A1 | 12/2006 | Carrino |
| 2006/0281679 A1 | 12/2006 | Itoh |
| 2007/0037165 A1 | 2/2007 | Venter |
| 2007/0042395 A1 | 2/2007 | Botstein |
| 2007/0077626 A1 | 4/2007 | Botstein |
| 2007/0238657 A1 | 10/2007 | Itoh |
| 2007/0253966 A1 | 11/2007 | Glaesner |
| 2008/0057076 A1 | 3/2008 | Bringmann |
| 2008/0124759 A1 | 5/2008 | Conklin |
| 2008/0261236 A1 | 10/2008 | Kuro-o |
| 2009/0081658 A1 | 3/2009 | Belouchi |
| 2009/0098603 A1 | 4/2009 | Botstein |
| 2009/0196876 A1 | 8/2009 | Sparks |
| 2009/0226459 A1 | 9/2009 | Powers |
| 2009/0312265 A1 | 12/2009 | Schmidtchen |
| 2010/0158914 A1 | 6/2010 | Desnoyers |
| 2010/0184665 A1 | 7/2010 | Suzuki |
| 2010/0215657 A1 | 8/2010 | Glass |
| 2010/0239554 A1 | 9/2010 | Schellenberger |
| 2010/0240587 A1 | 9/2010 | Schlein |
| 2010/0323954 A1 | 12/2010 | Li |
| 2010/0330062 A1 | 12/2010 | Koeffler |
| 2011/0015345 A1 | 1/2011 | Pinkstaff |
| 2011/0053787 A1 | 3/2011 | Brulliard |
| 2011/0104152 A1 | 5/2011 | Sonoda |
| 2011/0107439 A1 | 5/2011 | De Wit |
| 2011/0135657 A1 | 6/2011 | Hu |
| 2011/0150903 A1 | 6/2011 | Baurin |
| 2011/0190207 A1 | 8/2011 | Mohammadi |
| 2011/0195077 A1 | 8/2011 | Glass |
| 2011/0195895 A1 | 8/2011 | Walker |
| 2011/0207912 A1 | 8/2011 | Botstein |
| 2011/0306129 A1 | 12/2011 | Nistor |
| 2011/0312881 A1 | 12/2011 | Silverman |
| 2012/0003216 A1 | 1/2012 | Belouski |
| 2012/0064544 A1 | 3/2012 | Econs |
| 2012/0172314 A1 | 7/2012 | Koeffler |
| 2012/0178699 A1 | 7/2012 | Wolf |
| 2012/0288886 A1 | 11/2012 | Mohammadi |
| 2012/0294861 A1 | 11/2012 | Sonoda |
| 2012/0308580 A1 | 12/2012 | Bertoletti |
| 2012/0328616 A1 | 12/2012 | Li |
| 2013/0004492 A1 | 1/2013 | Marshall |
| 2013/0023474 A1 | 1/2013 | Ling |
| 2013/0116171 A1 | 5/2013 | Jonker |
| 2013/0122004 A1 | 5/2013 | Glass |
| 2013/0122020 A1 | 5/2013 | Liu |
| 2013/0129725 A1 | 5/2013 | Fachini |
| 2013/0143796 A1 | 6/2013 | Li |
| 2013/0172275 A1 | 7/2013 | Mohammadi |
| 2013/0183294 A1 | 7/2013 | Pai |
| 2013/0183319 A1 | 7/2013 | Bange |
| 2013/0184211 A1 | 7/2013 | Mohammadi |
| 2013/0231277 A1 | 9/2013 | Mohammadi |
| 2013/0324458 A1 | 12/2013 | Glass |
| 2013/0324701 A1 | 12/2013 | Williams |
| 2013/0331317 A1 | 12/2013 | Mohammadi |
| 2013/0331325 A1 | 12/2013 | Mohammadi |
| 2014/0094406 A1 | 4/2014 | Mohammadi |
| 2014/0148388 A1 | 5/2014 | Sonoda |
| 2014/0155316 A1 | 6/2014 | Mohammadi |
| 2014/0189893 A1 | 7/2014 | Li |
| 2014/0194352 A1 | 7/2014 | Ling |
| 2014/0243260 A1 | 8/2014 | Mohammadi |
| 2014/0243266 A1 | 8/2014 | Ling |
| 2014/0363435 A1 | 12/2014 | Desnoyers |
| 2015/0079065 A1 | 3/2015 | Wolf |
| 2015/0111821 A1 | 4/2015 | Suh |
| 2015/0210764 A1 | 7/2015 | Mondal |
| 2015/0284442 A1 | 10/2015 | Ling |
| 2015/0291677 A1 | 10/2015 | Ling |
| 2016/0045565 A1 | 2/2016 | Ling |
| 2016/0166642 A1 | 6/2016 | Ling |
| 2016/0168215 A1 | 6/2016 | Ling |
| 2016/0168216 A1 | 6/2016 | Ling |
| 2016/0168217 A1 | 6/2016 | Ling |
| 2016/0168218 A1 | 6/2016 | Ling |
| 2016/0168219 A1 | 6/2016 | Ling |
| 2016/0168220 A1 | 6/2016 | Ling |
| 2016/0168221 A1 | 6/2016 | Ling |
| 2016/0168222 A1 | 6/2016 | Ling |
| 2016/0200788 A1 | 7/2016 | Ling |
| 2016/0252497 A1 | 9/2016 | Ling |
| 2017/0182122 A1 | 6/2017 | Ling |
| 2017/0182123 A1 | 6/2017 | Ling |

(56) References Cited

U.S. PATENT DOCUMENTS

| | | | |
|---|---|---|---|
| 2017/0232067 A1 | 8/2017 | Lindhout | |
| 2017/0327551 A1 | 11/2017 | Ling | |
| 2018/0100014 A1 | 4/2018 | Mondal et al. | |
| 2019/0106490 A1 | 4/2019 | Mondal et al. | |
| 2019/0338046 A1 | 11/2019 | Mondal et al. | |
| 2021/0030857 A1 | 2/2021 | Mondal et al. | |
| 2021/0115133 A1 | 4/2021 | Mondal et al. | |

FOREIGN PATENT DOCUMENTS

| | | |
|---|---|---|
| DE | 10100587 | 11/2002 |
| EP | 2163626 A1 | 3/2010 |
| EP | 2510009 B1 | 4/2017 |
| JP | 2001072607 A | 3/2001 |
| JP | 2002112772 A | 4/2002 |
| JP | 2003334088 A | 11/2003 |
| JP | 2006158339 A | 6/2006 |
| JP | 2006240990 A | 9/2006 |
| JP | 2009039117 A | 2/2009 |
| JP | 2013194049 A | 9/2013 |
| NZ | 602702 | 3/2014 |
| WO | WO 1998/029544 | 7/1998 |
| WO | WO 2000/060085 | 10/2000 |
| WO | WO 2001/018209 A1 | 3/2001 |
| WO | WO 2001/038529 A1 | 5/2001 |
| WO | WO 2001/049740 A1 | 7/2001 |
| WO | WO 2001/049849 A1 | 7/2001 |
| WO | WO 2001/061007 A2 | 8/2001 |
| WO | WO 2002/036732 A2 | 5/2002 |
| WO | WO 2002/041911 A2 | 5/2002 |
| WO | WO 2002/055693 A2 | 7/2002 |
| WO | WO 2003/080803 A2 | 10/2003 |
| WO | WO 2004/026228 A2 | 4/2004 |
| WO | WO 2004/063355 A2 | 7/2004 |
| WO | WO 2006/004076 A1 | 1/2006 |
| WO | WO 2006/048291 A2 | 5/2006 |
| WO | WO 2006/049854 A2 | 5/2006 |
| WO | WO 2008/021196 A2 | 2/2008 |
| WO | WO 2008/030273 A2 | 3/2008 |
| WO | WO 2008/123625 A1 | 10/2008 |
| WO | WO 2008/135993 A1 | 11/2008 |
| WO | WO 2009/009173 A2 | 1/2009 |
| WO | WO 2009/076478 A2 | 6/2009 |
| WO | WO 2009/090553 A2 | 7/2009 |
| WO | WO 2009/095372 A1 | 8/2009 |
| WO | WO 2009/116861 A2 | 9/2009 |
| WO | WO 2010/004204 A2 | 1/2010 |
| WO | WO 2010/006214 A1 | 1/2010 |
| WO | WO 2010/042747 A2 | 4/2010 |
| WO | WO 2010/065439 A1 | 6/2010 |
| WO | WO 2010/080976 A1 | 7/2010 |
| WO | WO 2010/083051 A2 | 7/2010 |
| WO | WO 2010/129600 A2 | 11/2010 |
| WO | WO 2010/139741 A1 | 12/2010 |
| WO | WO 2010/142665 A1 | 12/2010 |
| WO | WO 2010/148142 A1 | 12/2010 |
| WO | WO 2011/047267 A1 | 4/2011 |
| WO | WO 2011/068893 A1 | 6/2011 |
| WO | WO 2011/071783 A1 | 6/2011 |
| WO | WO 2011/084808 A2 | 7/2011 |
| WO | WO 2011/089203 A1 | 7/2011 |
| WO | WO 2011/092234 A1 | 8/2011 |
| WO | WO 2011/130417 A2 | 10/2011 |
| WO | WO 2011/130729 A2 | 10/2011 |
| WO | WO 2011/154349 A2 | 12/2011 |
| WO | WO 2012/010553 A1 | 1/2012 |
| WO | WO 2012/031603 A2 | 3/2012 |
| WO | WO 2012/062078 A1 | 5/2012 |
| WO | WO 2012/066075 A1 | 5/2012 |
| WO | WO 2012/086809 A1 | 6/2012 |
| WO | WO 2012/138919 A2 | 10/2012 |
| WO | WO 2012/140650 A2 | 10/2012 |
| WO | WO 2012/154263 A1 | 11/2012 |
| WO | WO 2012/158704 A1 | 11/2012 |
| WO | WO 2012/170438 A2 | 12/2012 |
| WO | WO 2012/170704 A2 | 12/2012 |
| WO | WO 2012/177481 A2 | 12/2012 |
| WO | WO 2013/006486 A2 | 1/2013 |
| WO | WO 2013/010780 A1 | 1/2013 |
| WO | WO 2013/027191 A1 | 2/2013 |
| WO | WO 2013/033452 A2 | 3/2013 |
| WO | WO 2013/049234 A2 | 4/2013 |
| WO | WO 2013/109856 A2 | 7/2013 |
| WO | WO 2013/131091 A1 | 9/2013 |
| WO | WO 2013/151671 A1 | 10/2013 |
| WO | WO 2013/173158 A1 | 11/2013 |
| WO | WO 2013/184958 A1 | 12/2013 |
| WO | WO 2013/184960 A2 | 12/2013 |
| WO | WO 2013/184962 A1 | 12/2013 |
| WO | WO 2013/188182 A1 | 12/2013 |
| WO | WO 2014/031420 A1 | 2/2014 |
| WO | WO 2014/037373 A1 | 3/2014 |
| WO | WO 2014/085365 A2 | 6/2014 |
| WO | WO 2014/105939 A1 | 7/2014 |
| WO | WO 2014/130659 A1 | 8/2014 |
| WO | WO 2014/149699 A1 | 9/2014 |
| WO | WO 2014/152090 A1 | 9/2014 |
| WO | WO 2015/065897 A1 | 5/2015 |
| WO | WO 2015/100366 A1 | 7/2015 |
| WO | WO 2015/112886 A2 | 7/2015 |
| WO | WO 2015/183890 A2 | 12/2015 |
| WO | WO 2015/195509 A2 | 12/2015 |
| WO | WO 2016/065106 A1 | 4/2016 |
| WO | WO 2016/073855 A1 | 5/2016 |
| WO | WO 2017/083276 A1 | 5/2017 |
| WO | WO 2018/039557 A1 | 3/2018 |
| WO | WO 2018/044778 A1 | 3/2018 |

OTHER PUBLICATIONS

Aranha et al., "Bile acid levels are increased in the liver of patients with steatohepatitis," Eur. J. Gastroenterol. Hepatol., 2008, 20(6):519-525.

Beenken et al., "The FGF family: biology, pathophysiology and therapy," Nat. Rev. Drug Discov., 2009, 8:235-253.

Beuers et al., "Medical treatment of primary sclerosing cholangitis: a role for novel bile acids and other (post-) transcriptional modulators?," Clin. Rev. Allergy Immunol., 2009, 36(1):52-61.

Bromberg et al., "Stat3 as an oncogene," Cell, 1999, 98:295-303.

Calvisi et al., "Ubiquitous activation of Ras and Jak/Stat pathways in human HCC," Gastroenterol., 2006, 130:1117-1128.

Camilleri et al., "Measurement of Serum 7α-hydroxy-4-cholesten-3-one (or 7αC4), a Surrogate Test for Bile Acid Malabsorption in Health, Ileal Disease and Irritable Bowel Syndrome using Liquid Chromatography-Tandom Mass Spectrometry," Neurogastroenterol, 2009, Motil., 21(7):734-43.

Casset et al., "A peptide mimetic of an anti-CD4 monoclonal antibody by rational design," Biochem. Biophys. Res. Commun., 2003, 307:198-205.

Chazouilleres, "Primary sclerosing cholangitis and bile acids," Clinics and Research in Hepatology and Gastroenterology, 2012, 36:S21-S25.

Chen et al., "Selection and Analysis of an Optimized Anti-VEGF Antibody: Crystal Structure of an Affinity-matured Fab in Complex with Antigen," J. Mol. Biol., 1999, 293:865-881.

Chen et al., "Soluble FGFR4 extracellular domain inhibits FGF19-induced activation of FGFR4 signaling and prevents nonalcoholic fatty liver disease," Biochem. Biophys. Res. Comm., 2011, 409:651-656.

Chen et al., "Sorafenib overcomes TRAIL resistance of hepatocellular carcinoma cells through the inhibition of STAT3," Clin. Cancer Res., 2010, 16:5189-5199.

Claudel et al., "Role of Nuclear Receptors for Bile Acid Metabolism, Bile Secretion, Cholestasis, and Gallstone Disease," Biochim. Biophys. Acta, 2011, 1812:867-878.

Davidson et al., "A high-throughput shotgun mutagenesis approach to mapping B-cell antibody epitopes," Immunology, Sep. 2014, 143(1):13-20.

De Pascalis et al., "Grafting of 'Abbreviated' Complementarity-Determining Regions Containing Specificity-Determining Residues

(56) References Cited

OTHER PUBLICATIONS

Essential for Ligand Contact to Engineer a Less Immunogenic Humanized Monoclonal Antibody," J. Immunol., 2002, 169:3076-3084.
Desnoyers et al., "Targeting FGF19 inhibits tumor growth in colon cancer xenograft and FGF19 transgenic hepatocellular carcinoma models," Oncogene, 2008, 27:85-97.
Ďurovcová et al., "Plasma Concentration of Fibroblast Growth Factors 21 and 19 in Patients with Cushing's Syndrome," Physiol. Res., 2010, 59:415-422.
Foltz et al., "Supplementary Materials For: Treating Diabetes and Obesity with an FGF21-Mimetic Antibody Activating the βKlotho/FGFR 1c Receptor Complex," Sci. Transl. Med., 2012, 4:162ra153, 1-13.
Foltz et al., "Treating Diabetes and Obesity with an FGF21-Mimetic Antibody Activating the βKlotho/FGFR1c Receptor Complex," Sci. Transl. Med., 2012, 4(162):1-10.
French et al., "Targeting FGFR4 Inhibits Hepatocellular Carcinoma in Preclinical Mouse Models," PLoS One, 2012, 7(5):e36713, 1-12.
Fukumoto et al., "FGF23 is a hormone-regulating phosphate metabolism—unique biological characteristics of FGF23," Bone, 2007, 40(5):1190-1195.
Ge et al., "Characterization of a FGF19 Variant with Altered Receptor Specificity Revealed a Central Role for FGFR1c in the Regulation of Glucose Metabolism," PLoS One, 2012, 7(3):e33603, 1-9.
GenBank EHH53620.1: Beta-klotho (Macaca fascicularis)[online] Nov. 4, 2011 [retrieved Mar. 28, 2015]. Available on the internet: < URL: //www.ncbi.nlm.nih.gov/protein/355749221?sat-=37&satkey=109028311>, 2 pages.
Goetz et al., "Molecular insights into the klotho-dependent, endocrine mode of action of fibroblast growth factor 19 subfamily members," Mol. Cell. Biol., 2007, 27(9):3417-3428.
Harmer et al., "The Crystal Structure of Fibroblast Growth Factor (FGF) 19 Reveals Novel Features of the FGF Family and Offers a Structural Basis for Its Unusual Receptor Affinity," Biochemistry, 2004, 43:629-640.
Hasegawa, "The expansion of PROMININ-1-positive epithelial-mesenchymal cells within periportal fibrosis of rotavirus induced biliary atresia," Hepatol., 2013, 58:802A.
He et al., "Hepatocyte IKKbeta/NF-kappaB inhibits tumor promotion and progression by preventing oxidative stress-driven STAT3 activation," Cancer Cell, 2010, 17:286-297.
He et al., "Identification of liver cancer progenitors whose malignant progression depends on autocrine IL-6 signaling," Cell, 2013, 155:384-396.
He et al., "NF-κB and STAT3—key players in liver inflammation and cancer," Cell Res., 2011, 21:159-168.
Hofmann et al., "Chronic diarrhea due to excessive bile acid synthesis and not defective ileal transport: A new syndrome of defective FGF19 release," Clin. Gastroenterol. Hepatol., 2009, 7(11):1151-1154.
Holm et al., "Functional mapping and single chain construction of the anti-cytokeratin 8 monoclonal antibody TS1," Mol. Immunol., 2007, 44:1075-1084.
Holt et al., "Definition of a novel growth factor-dependent signal cascade for the suppression of bile acid biosynthesis," Genes Dev., 2003, 17:1581-1591.
Ikeda et al., "Leptin receptor somatic mutations are frequent in HCV-infected cirrhotic liver and associated with hepatocellular carcinoma," Gastroenterol., 2014, 146:222-232.
Inagaki et al., "Fibroblast Growth Factor 15 Functions as an Enterohepatic Signal to Regulate Bile Acid Homeostasis," Cell Metabolism, 2005, 2:217-225.
Ito et al., "Molecular cloning and expression analyses of mouse beta klotho, which encodes a novel Klotho family protein," Mech. Dev., 2000, 98(1-2):115-119.

Kakumu et al., "Interleukin 6 production by peripheral blood mononuclear cells in patients with chronic hepatitis B virus infection and primary biliary cirrhosis," Gastroenterologia Japonica, 1993, 28:18-24.
Karras et al., "STAT3 regulates the growth and immunoglobulin production of BCL(1) B cell lymphoma through control of cell cycle progression," Cellular Immunol., 2000, 202:124-135.
Kenakin et al., "Signalling bias in new drug discovery: detection, quantification and therapeutic impact," Nat. Rev. Drug Discov., 2013, 12:205-216.
Kir et al., "Roles of FGF19 in Liver Metabolism," Cold Spring Harb. Symp. Quant. Biol., 2011, 76:139-144.
Kumar et al., "Molecular cloning and expression of the Fabs of human autoantibodies in *Escherichia coli*. Determination of the heavy or light chain contribution to the anti-DNA/-cardiolipin activity of the Fab," J. Biol. Chem., 2000, 275:35129-35136.
KURO-O; *Endocrine FGFs and Klothos*, Springer-Verlag, New York, chapter 2, 2012, pp. 25-40.
Kurosu et al., "Regulation of fibroblast growth factor-23 signaling by klotho," J. Biol. Chem., 2006, 281(10):6120-6123.
Kurosu et al., "Supplemental Data For: Tissue-specific Expression of βKlotho and Fibroblast Growth Factor (FGF) Receptor Isoforms Determines Metabolic Activity of FGF19 and FGF21," J. Biol. Chem., (2007) (available at: http://www.jbc.org/content/suppl/2007/07/11/M704165200.DC1/Kurosu_Suppl_Data.pdf (last visited Jul. 23, 2014), 2 pages.
Kurosu et al., "Tissue-specific Expression of βKlotho and Fibroblast Growth Factor (FGF) Receptor Isoforms Determines Metabolic Activity of FGF19 and FGF21," J. Biol. Chem., 2007, 282(37):26687-26695.
Lee et al., "Structures of β-klotho reveal a 'zip code'-like mechanism for endocrine FGF signaling," Nature, 2018, 553:501-505, Extended Data.
Lin et al., "Liver-specific Activities of FGF19 Require Klotho beta," J. Biol. Chem., 2007, 282(37):27277-27284.
Lin et al., "The STAT3 inhibitor NSC 74859 is effective in hepatocellular cancers with disrupted TGF-beta signaling," Oncogene, 2009, 28:961-972.
Lindor, "Ursodeoxycholic acid for the treatment of primary biliary cirrhosis," New Engl. J Med., 2007, 357:1524-1529.
Ling et al., "Identification of Gut Factors that Mimic the Metabolic Benefits Seen After Gastric Bypass Surgery," American Diabetes Association, 72nd Scientific Sessions, Jun. 8-12, 2012, Philadelphia, PA, http://www.abstactsonline.com.
Ling et al., NGM Biopharmaceuticals, Identification of Gut Factors that Mimic the Metabolic Benefits of Gastric Bypass Surgery, p. 1, Jun. 8-12, 2012, Abstract.
Luo et al., "A nontumorigenic variant of FGF19 treats cholestatic liver diseases," Sci. Transl. Med., 2014, 6:247ra100, 1-11.
Maccallum et al., "Antibody-antigen Interactions: Contact Analysis and Binding Site Topography," J. Mol.Biol., 1996, 262:732-745.
Mellor, "Targeted inhibition of the FGF19-FGFR4 pathway in hepatocellular carcinoma; translational safety considerations," Liver Int., 2014, e1-e9.
Micanovic et al., "Different roles of N- and C-termini in the functional activity of FGF21," J. Cell. Physiol., 2009, 219:227-234.
Miyata et al., "Involvement of Multiple Elements in FXR-mediated Transcriptional Activation of FGF19," J. Steroid Biochm. Mol. Biol., 2012, 132:41-47.
Moyers et al., "Molecular determinants of FGF-21 activity-synergy and cross-talk with PPARgamma signaling," J. Cell. Physiol., 2007, 210(1):1-6.
NCBI Reference Sequence: NP_783864.1: beta-klotho (*Homo sapiens*) [online] Nov. 2, 2013 [retrieved Mar. 28, 2015]. Available on the internet: <URL:http://www.uniprot.org/uniprot/Q86Z14.txt?version=93>, 3 pages.
Nicholes et al., "A Mouse Model of Hepatocellular Carcinoma: Ectopic Expression of Fibroblast Growth Factor in Skeletal Muscle of Transgenic Mice," Amer. J. Pathol., 2002, 160:2295-2307.
Ogawa et al., "Beta Klotho is Required for Metabolic Activity of Fibroblast Growth Factor 21," Proc. Natl. Acad. Sci. USA, 2007, 104:7432-7437.

(56) References Cited

OTHER PUBLICATIONS

Pai et al., "Antibody-Mediated Inhibition of Fibroblast Growth Factor 19 Results in Increased Bile Acids Synthesis and Ileal Malabsorption of Bile Acids in Cynomolgus Monkeys," Toxicological Sciences, 2012, 126(2):446-456.
Pattni et al., "Fibroblast Growth Factor 19 and 7α-Hydroxy-4-Cholesten-3-one in the Diagnosis of Patients With Possible Bile Acid Diarrhea," Clinical and Translational Gastroenterology, 2012, 3:e18, 7 pages.
Potthoff et al., "Endocrine Fibroblast Growth Factors 15/19 and 21: From Feast to Famine," Genes Dev., 2012, 26:312-324.
Pusl et al., "Intrahepatic cholestasis of pregnancy," Orphanet. J Rare Diseases, 2007, 2:26.
R&D Systems, "Monoclonal Anti-human/mouse Klotho β Antibody," catalog No. MAB3738, Feb. 6, 2007, 1 page.
Rose et al., "Molecular Control of Systemic Bile Acid Homeostasis by the Liver Glucocorticoid Receptor," Cell Metabolism, 2011, 14:123-130.
Rossi et al., "Ngm282, a Novel Specific Inhibitor of Cyp7a1-Mediated Bile Acid Synthesis, is Safe and Well Tolerated with Predictable Pharmacokinetics in Healthy Human Subjects," Journal of Hepatology, 2014, 60(1): S533.
Ryan et al., "FXR is a Molecular Target for the Effects of Vertical Sleeve Gastroectomy," Nature, 509(7499):183-188, 2014, epub ahead of print Mar. 26, 2014.
Sawey et al., "Identification of a Therapeutic Strategy Targeting Amplified FGF19 in Liver Cancer by Oncogenomic Screening," Cancer Cell, 2011, 19(3):347-358.
Schaap et al., "High expression of the bile salt-homeostatic hormone fibroblast growth factor 19 in the liver of patients with extrahepatic cholestasis," Hepatol., 2009, 49:1228-1235.
Schaap, "Role of Fibroblast Growth Factor 19 in the Control of Glucose Homeostasis," Curr. Opin. Clin. Nutr. Metab. Care, 2012, 15(4):386-391.
Smith et al., "FGF21 Can Be Mimicked In Vitro and In Vivo by a Novel Anti-FGFR 1c/b-Klotho Bispecific Protein," PLoS One, 2013, 8(4):1-11.
Smith-Gill et al., "Contributions of Immunoglobulin Heavy and Light Chains to Antibody Specificity for Lysozyme and Two Haptens," J. Immunol., 1987, 139:4135-4144.
Song et al., "Light Chain of Natural Antibody Plays a Dominant Role in Protein Antigen Binding," Biochem. Biophys. Res. Comm., 2000, 268:390-394.
Tartaglia et al., "Identification and expression cloning of a leptin receptor, Ob-R," Cell, 1995, 83:1263-1271.
Tomlinson et al., "Transgenic Mice Expressing Human Fibroblast Growth Factor-19 Display Increased Metabolic Rate and Decreased Adiposity," Endocrinology, 2002, 143(5):1741-1747.
Urakawa et al., "Klotho converts canonical FGF receptor into a specific receptor for FGF23," Nature, 2006, 444(7210):770-774.
Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.
Walters et al., "Managing bile acid diarrhoea," Ther. Adv. Gastroenterol., 2010, 3(6):349-357.
Walters, "A variant of FGF19 for treatment of disorders of cholestasis and bile acid metabolism," Ann. Transl. Med., 2015, 3(S1):S7.
Wang et al., "Leptin in hepatocellular carcinoma," World J. Gastroenterol., 2010, 16:5801-5809.
Wu et al., "FGF19 Regulates Cell Proliferation, Glucose and Bile Acid Metabolism via FGFR4-Dependent and Independent Pathways," PLoS One, 2011, 6(3):e17868, 1-11.
Wu et al., "C-terminal Tail of FGF19 Determines Its Specificity toward Klotho C-receptors," J. Biol. Chem., 2008, 283(48):33304-33309.
Wu et al., "FGF19-induced Hepatocyte Proliferation is Mediated Through FGFR4 Activation," J. Biol. Chem., 2010, 285(8):5165-5170.
Wu et al., "Humanization of a Murine Monoclonal Antibody by Simultaneous Optimization of Framework and CDR Residues," J. Mol. Biol., 1999, 294:151-162.
Wu et al., "Role of FGF19 Induced FGFR4 Activation in the Regulation of Glucose Homeostasis," Aging, 2009, 1(12):1023-1027.
Wu et al., "Selective Activation of FGFR4 by an FGF19 Variant Does Not Improve Glucose Metabolism in ob/ob Mice," Proc. Natl. Acad. Sci. USA, 2009, 106(34):14379-14384.
Wu et al., "Separating Mitogenic and Metabolic Activities of Fibroblast Growth Factor 19 (FGF19)," Proc. Natl. Acad. Sci. USA, 2010, 107(32):14158-14163.
Wu et al., "Therapeutic Utilities of Fibroblast Growth Factor 19," Expert Opin. Ther. Targets, 2011, 15(11):1307-1316.
Xie et al., "FGF-19, A Novel Fibroblast Growth Factor with Unique Specificity for FGFR4," Cytokine, 1999, 11(10):729-735.
Zhang et al., "Adenovirus-adeno-associated virus hybrid for large-scale recombinant adeno-associated virus production," Hum. Gene Ther., 2009, 20:922-929.
Zhang et al., "Fibroblast growth factor 21 analogs for treating metabolic disorders," Front. Endocrinol., 2015, 6(168):1-9.
Zhou et al., "Engineered fibroblast growth factor 19 reduces liver injury and resolves sclerosing cholangitis in Mdr2-deficient mice," Hepatology, 2016, 63(3):914-929.
Zhou et al., "Separating Tumorigenicity from Bile Acid Regulatory Activity for Endocrine Hormone FGF19," Cancer Research, 2014, 74(12):3306-3316.

```
                              31----35           50--abc-----60---65
Kabat     1           10        22                                       65
AbM       1           10        22      26----35    50--abc-----58      65
Chothia   1           10        22      26----32       abc--55          65
Contact   1           10        22      30----35    47--abc----58       65
IMGT      1           10        23      27----38  40    56-------65     74
AHon      1                      23         27    41                 76
                                            42

5H23   QVQLQQSGPELVKPGALVKISCKAS GYTFTS-YDIN WVKQRPGQGLEWIG WIYP--GDGSTKYNEKFKG
1C17   QVQLQESGPGLVKPSQSLSLTCSVT GYSITSGYYWN WIRQFPGNKLEWMG YIN---YDGNSNYTPSLKN
1D19   QVQPQESGPELVKPGALVKISCKAS GYTFTR-YDIN WMKQRPGQGLEWIG WIYP--GDSSTKFNENFKD
2L12   QVQLQQSGPELVKPGALVKISCKAS GYTFTR-YDIN WVKKRPGQGLEWIG WIYP--GDDSTKYNEKFKG
3L3    QVQLQESGPELVKPGTLVKISCKAS GYTFTS-YDIN WVKQRPGQGLEWIG WIYP--GDGSPKYDEKFKG
3N20   QVQLQESGAELARPGASVKLSCKVS GYIFTN-YGIS WVKQRTGQGLEWIG EIYP--RSGNTYYNEKFKG
4P5    QVQLQQSGPELVKPGALVKISCKAS GYTFTR-YDIN WVKKRPGQGLEWIG WIYP--GDDSTKYNEKFKG
5C23   QVQPQESGPELVKPGALVKISCKAS GYTFTR-YDIN WVKKRPGQGLEWIG WIYP--GDGSTKYNEKFEG
5F7    QVQPQESGPELVKPGALVKISCKAS GYTFTR-YDIN WVKQRPGQGLEWIG WIYP--GDISTKYNEKFKG
1G19   QVQLQESGPGLVKPSQSLSLTCSVT GYSITSGYYWN WIRQFPGNKLEWMG YIN---YGGSNNYNPSLKN

95--100----102
Kabat     70        80   abc        90                          110
AbM       70        80   abc        90        95--100----102    110
Chothia   70        80   abc        90        96-100----101     110
Contact   70        80   abc        90        93---100---101    110
IMGT      75             89              105---------117
AHon                                     106 109      138

5H23   KATLTADKSSRTAYMQLSSLTSENSAVYFCAR SDYYGSRSF--AY   WGQGTLVTVSA (SEQ ID NO:25)
1C17   RISITRDTSKNQFFLKLNSVTPEDTATYYCAR KGAYYSNYDSFDV   WGTGTTVTVSS (SEQ ID NO:51)
1D19   KATLTADKSSSTAYMQLSSLTSENSTVYFCAR SDYYGSRSF--TY   WGQGTLVTVSA (SEQ ID NO:77)
2L12   KATLTADKSSSTAYMQLSSLTSENSAVYFCAR SDYYGSRSF--VY   WGQGTLVTVSA (SEQ ID NO:103)
3L3    KATLTADKSSSTAYMQLSSLTSENSAVYFCAR SDYYGSRSF--VY   WGQGTSLTVSS (SEQ ID NO:129)
3N20   KATLTADMSSSTAYMDLRSLTSEDSAVYFCAR HWDGVLDYF--DY   WGQGTLVTVSS (SEQ ID NO:155)
4P5    KATLTADKSSSTAYMQLSSLTSENSAVYFCAR SDYYGSRSF--VY   WGQGTLVTVSA (SEQ ID NO:181)
5C23   KATLTADKSSSTAYMQLSSLTSENSAVYFCAR SDYYGSRSF--VY   WGQGTLVTVSA (SEQ ID NO:207)
5F7    KATLTADKSSSTAYMQLNSLTSENSAVYFCAR SDYYGSRSF--VY   WGQGTLVTVSA (SEQ ID NO:233)
1G19   RISITRDTSKNQFFLKLTSVTTEDTATYYCAR RGAYYSNYDSFDV   WGTGTTVTVSS (SEQ ID NO:259)
```

FIGURE 1A

```
Kabat      1            10           20                24-27abcd----34           40            50----56
AbM        1            10           20                24----30abcd----34        40            50----56
Chothia    1            10           20                26--30abcd--32            40            50----56
Contact    1            10           20                         30abcd------36   40            50--
IMGT       1            10           20        23      27--------38   41         46-----------56-65 69
                                                                                                1
AHon                    1            23                         42                58            72
5H23       DIVLTQSPASLAVSLGQRATISC RASKSVST--SGYVYMH WNQQKPGQPPKLLIY LASYLES
1C17       DIKMTQSPSSMYASLGERVTITC KASQDINS------YLS WVQQKPGKSPKTLIY RANRLVD
1D19       DIVLTQSPASLAVSLGQRATISC RASKSVST--SGYSYMH WYQQKPGQPPKLLIY LASNLES
2L12       DIVLTQSPASLPVSLGQRATISC RASKSVST--SGYSYLH WYQQKPGQPPKLLIY LASNLES
3L3        DIVMTQSPSSLSVSAGEKVTMSC KSSQSLLNSGNQKNYLA WYQQKPGQPPKLLIY GASTRES
3N20       DILLTQSPASLAVSLGQRATISC RASKSVST--SGYSYMH WYQQKPGQPPKLLIY LASNLES
4P5        DIVLTQSPDSLTVSLGQRATISC RASKSVST--SGYSYMH WYQQKPGQPPKLLIY LASNLES
5C23       DIVLTQSPASLAVSLGQRATISC RASKSVST--SGYSYMH WYQQKPGQPPKLLIY LASNLES
5F7        DIKMTQSPSSMYASLGERVTITC KASQDINS------YLS WFQQKPGKSPKTLIY RANRLVD
1G19       DIKMTQSPSSMYASLGERVTITC KASQDINS------YLS WFQQKPGKSPKTLIY RANRLVD Kabat       60           70           80           89              97
AbM         60           70           80           89              97
Chothia     60           70           80                   91----96
Contact     60           70           80           89              96
IMGT        70                   89                105----117
AHon        73                   91                107       138
5H23       GVPARFSGSGSGSGTDFTLNIHPVEREDAAIYYC QHSRDLTFP FGGGTKLEIK (SEQ ID NO:26)
1C17       GVPSRFSGSGSGSGQDYSLTISSLEYEDMGIYYC LQYDEFPFT FGSGTKLEIK (SEQ ID NO:52)
1D19       GVPARFSGSGSGSGTDFTLNIHPVEEEDAATYYC QHSRELPYT FGGGTKLEIK (SEQ ID NO:78)
2L12       GVPARFSGSGSGSGTDFTLNIHPVEEEDAATYYC QHSGELPYT FGGGTKLEIK (SEQ ID NO:104)
3L3        GVPDRFTGSGSGTDFTLTISSVQAEDLAVYYC LNDHSYPFT FGAGTKLELK (SEQ ID NO:130)
3N20       GVPARFSGRSGSGSGTDFTLNIHPVEEEDAATYYC HHSGELPYT FGGGTKLEIK (SEQ ID NO:156)
4P5        GVPSRFSGSGSGSGTDFTLNIHPVEEEDAATYYC QHSRELPYT FGGGTKLEIK (SEQ ID NO:182)
5C23       GVPARFSGSGSGSGTDFTLNIHPVEEEDAATYYC QHSRELPYT FGGGTKLEIK (SEQ ID NO:208)
5F7        GVPSRFSGSGSGSGQDYSLTISSLEYEEMGIYYC LQYDEFPYT FGGGTKVEIK (SEQ ID NO:234)
1G19       GVPSRFSGSGSGSGQDYSLTISSLEYEEMGIYYC LQYDEFPYT FGGGTKLEIK (SEQ ID NO:260)
```

FIGURE 1B

```
VH Domain

Kabat     1           22              31----35          40                50--abc------60----65
AbM       1    10     22          26--------35          40                50--abc------58      65
Chothia   1    10     22          26--------32          40                    abc--55          65
Contact   1    10     22              30----35          40                50--abc------58      65
IMGT      1    10     23          27--------38    41                      56----------65       74
AHon      1           23                      42                          57                   76

5H23   QVQLQQSGPELVKPGALVKISCKAS GYTFTS-YDIN WVKQRPGQGLEWIG WIYP---GDGSTKYNEKFKG
1D19   QVQPQESGPELVKPGALVKISCKAS GYTFTR-YDIN WMKQRPGQGLEWIG WIYP---GDSSTKFNENFKD
2L12   QVQLQQSGPELVKPGALVKISCKAS GYTFTR-YDIN WVKKRPGQGLEWIG WIYP---GDDSTKYNEKFKG
3L3    QVQPQESGPELVKPGTLVKISCKAS GYTFTS-YDIN WVKKRPGQGLEWIG WIYP---GDGSPKYDEKFKG
4P5    QVQLQQSGPELVKPGALVKISCKAS GYTFTR-YDIN WVKKRPGQGLEWIG WIYP---GDDSTKYNEKFKG
5C23   QVQPQESGPELVKPGALVKISCKAS GYTFTR-YDIN WVKQRPGQGLEWIG WIYP---GDGSTKYNEKFEG
5F7    QVQPQESGPELVKPGALVKISCKAS GYTFTR-YDIN WVKQRPGQGLEWIG WIYP---GDISTKYNEKFKG consensus                        GYTFTR-YDIN              WIYP--GDX$_1$STKYNEKFKG
                                 (SEQ ID NO:1)            where X$_1$ = G,D,S,I
                                                          (SEQ ID NO:262)

or
consensus                        GYTFT X$_1$-YDIN         WIYP--GDX$_1$STKYNEKFKG
                                 where X$_1$ = R,S        where X$_1$ = G,D,S,I
                                 (SEQ ID NO:261)          (SEQ ID NO:262)

1C17   QVQLQESGPGLVKPSQSLSLTCSVT GYSITSGYYWN WIRQFPGNKLEWMG YIN----YDGNSNYTPSLKN
1G19   QVQLQESGPGLVKPSQSLSLTCSVT GYSITSGYYWN WIRQFPGNKLEWMG YIN----YGGSNNYNPSLKN consensus                        GYSITSGYYWN                YIN----YX$_1$GX$_2$X$_3$NYX$_4$PSLKN
                                 (SEQ ID NO:27)             where X$_1$ = D,G
                                                            where X$_2$ = N,S
                                                            where X$_3$ = S,N
                                                            where X$_4$ = T,N
                                                            (SEQ ID NO:264)

3N20   QVQLQESGAELARPGASVKLSCKVS GYIFTN-YGIS WVKQRTGQGLEWIG EIYP---RSGNTYYNEKFKG
```

FIGURE 2A-1

```
VH Domain (continued)

Kabat      70          80  abc                    90          95--100----102              110
AbM        70          80  abc                    90          95--100----102              110
Chothia    70          80  abc                    90          96-100---101                110
Contact    70          80  abc                    90          ---100---101                110
IMGT     75             89                       93----------105-------------117
AHon                                                           106 109              138

5H23    KATLTADKSSRTAYMQLSSLTSENSAVYFCAR SDYYGSRSF--AY WGQGTLVTVSA  (SEQ ID NO:25)
1D19    KATLTADKSSSTAYMQLSSLTSENSTVYFCAR SDYYGSRSF--TY WGQGTLVTVSA  (SEQ ID NO:77)
2L12    KATLTADKSSSTAYMQLSSLTSENSAVYFCAR SDYYGSRSF--VY WGTGTLVTVSA  (SEQ ID NO:103)
3L3     KATLTADKSSSTAYMQLSSLTSENSAVYFCAR SDYYGSRSF--VY WGQGTLVTVSA  (SEQ ID NO:129)
4P5     KATLTADKSSSTAYMQLSSLTSENSAVYFCAR SDYYGSRSF--VY WGQGTLVTVSA  (SEQ ID NO:181)
5C23    KATLTADKSSSTAYMQLSSLTSENSAVYFCAR SDYYGSRSF--VY WGQGTLVTVSA  (SEQ ID NO:207)
5F7     KATLTADKSSSTAYMQLNSLTSENSAVYFCAR SDYYGSRSF--VY WGQGTLVTVSA  (SEQ ID NO:233)
consensus                                SDYYGSRSF--VY
or                                       (SEQ ID NO:81)

consensus                                SDYYGSRSF--X₁Y  where X₁ = V,T,A
                                         (SEQ ID NO:263)

1C17    RISITRDTSKNQFFLKLNSVTPEDTATYYCAR KGAYYSNYDSFDV WGTGTTVTVSS  (SEQ ID NO:51)
1G19    RISITRDTSKNQFFLKLTSVTTEDTATYYCAR RGAYYSNYDSFDV WGTGTTVTVSS  (SEQ ID NO:259)
consensus                                X₁GAYYSNYDSFDV  where X₁ = K,R
                                         (SEQ ID NO:265)

3N20    KATLTADMSSSTAYMDLRSLTSEDSAVYFCAR HWDGVLDYF--DY WGQGTSLTVSS  (SEQ ID NO:155)
```

FIGURE 2A-2

```
VL Domain

Kabat     1           10                     20                        24--27abcd-------34           40                                  50-----56
AbM       1           10                     20                        24----30abcd-----34           40                                  50-----56
Chothia   1           10                     20                        26--30abcd-------32           40                                  50---
Contact   1           10                     20                              30abcd-----36           40                             46---------55
IMGT      1                                                                  27---------38  41                                         56-65  69
                                                        23                                                                          |      |
AHon      1                          23                                                42                                           58     72
5H23          DIVLTQSPASLAVSLGQRATISC         RASKSVST--SGYVYMH         WNQQKPGQPPKLLIY LASYLES
5D19          DIVLTQSPASLAVSLGQRATISC         RASKSVST--SGYSYMH         WYQQKPGQPPKLLIY LASNLES
2L12          DIVLTQSPASLPVSLGQRATISC         RASKSVST--SGYSYLH         WYQQKPGQPPKLLIY LASNLES
3L3           DIVLTQSPASLAVSLGQRATISC         RASKSVST--SGYSYVH         WYQQKPGQPPKLLIY LASNLES
4P5           DILLTQSPASLAVSLGQRATISC         RASKSVST--SGYSYMH         WYQQKPGQPPKLLIY LASNLES
5C23          DIVLTQSPDSLTVSLGQRATISC         RASKSVST--SGYSYMH         WYQQKPGQPPKLLIY LASNLES
5F7           DIVLTQSPASLAVSLGQRATISC         RASKSVST--SGYSYMH         WYQQKPGQPPKLLIY LASNLES
consensus                                     RASKSVST--SGYSYMH                         LASNLES
                                              (SEQ ID NO:56)                            (SEQ ID NO: 57)
or
consensus                                     RASKSVST--SGYSYX₁H                        LASNLES
                                              where X₁ = M,L,V
                                              (SEQ ID NO:266)                           (SEQ ID NO: 57)

1C17          DIKMTQSPSSMYASLGERVTITC         KASQDINS-------YLS        WVQQKPGKSPKTLIY RANRLVD
1G19          DIKMTQSPSSMYASLGERVTITC         KASQDINS-------YLS        WFQQKPGKSPKTLIY RANRLVD
consensus                                     KASQDINS-------YLS                        RANRLVD
                                              (SEQ ID NO:30)                            (SEQ ID NO: 31)
or
3N20          DIVMTQSPSSLSVSAGEKVTMSC         KSSQSLLNSGNQKNYLA         WYQQKPGQPPKLLIY GASTRES
```

FIGURE 2B-1

```
VL Domain (continued)

Kabat         60              70              80          89------97
AbM           60              70              80          89------97
Chothia       60              70              80          91---96
Contact       60              70              80          89---96
IMGT    70              89                              105-----117
AHon    73              91                              107     138
5H23    GVPARFSGSGSGTDFTLNIHPVEEEDAAIYYC QHSRDLTFP FGGGTKLEIK (SEQ ID NO:26)
1D19    GVPARFSGSGSGTDFTLNIHPVEEEDAATYYC QHSRELPYT FGGGTKLEIK (SEQ ID NO:78)
2L12    GVPARFSGSGSGTDFTLNIHPVEEEDAATYYC QHSGELPYT FGGGTKLEIK (SEQ ID NO:104)
3L3     GVPARFSGRGSGTDFTLNIHPVEEEDAATYYC QHSGELPYT FGGGTKLEIK (SEQ ID NO:130)
4P5     GVPARFSGRGSGTDFTLNIHPVEEEDAATYYC HHSGELPYT FGGGTKLEIK (SEQ ID NO:182)
5C23    GVPARFSGSGSGTDFTLNIHPVEEEDAATYYC QHSRELPYT FGGGTKLEIK (SEQ ID NO:208)
5F7     GVPARFSGSGSGTDFTLNIHPVEEEDAATYYC QHSRELPYT FGGGTKVEIK (SEQ ID NO:234)
consensus                                         $X_1HSX_2ELPYT$ where $X_1$ = Q,H; where $X_2$ = R,G
                                                  (SEQ ID NO:267)

1C17    GVPSRFSGSGSGQDYSLTISSLEYEDMGIYYC LQYDEFFT  FGSGTKLEIK (SEQ ID NO:52)
1G19    GVPSRFSGSGSGQDYSLTISSLEYEEMGIYYC LQYDEFPYT FGGGTKLEIK (SEQ ID NO:260)
consensus                                         $LQYDEFPX_1T$ where $X_1$ = F,Y
                                                  (SEQ ID NO:268)

3N20    GVPDRFTGSGSGTDFTLTISSVQAEDLAVYYC LNDHSYPFT FGAGTKLELK (SEQ ID NO:156)
```

FIGURE 2B-2

| VH Domain | | | | | | | | |
|---|---|---|---|---|---|---|---|---|
| Kabat | 1 | 10 | 22 | 31---35 | 40 | 50---a----60---65 | | |
| AbM | 1 | 10 | 22 | 26------35 | 40 | 50---a-----58 | 65 | |
| Chothia | 1 | 10 | 22 | 26----32 | 40 | a-55 | 65 | |
| Contact | 1 | 10 | 22 | 30----38 | 40 | a-----58 | 65 | |
| IMGT | 1 | | 23 | 27----38 41 | | 56-----65 | 74 | |
| AHon | 1 | | 23 | 27 42 | | 57 | 76 | |
| 5H23      | QVQLQQSGPELVKPGALVKISCKAS | GYTFTSYDIN | WVKQRPGQGLEWIG | WIYPGDGSTKYNEKFKG |
| 5H23v1-3  | QVQLVQSGAEVKKPGASVKVSCKAS | GYTFTSYDIN | WVRQAPGQRLEWMG | WIYPGDGSTKYNEKFKG |
| vH1       | QVQLVQSGAEVKKPGASVKVSCKAS | GYTFTSYDIN | WVRQAPGQGLEWMG | WIYPGDGSTKYNEKFKG |
| vH2       | QVQLVQSGPEVKKPGASVKVSCKAS | GYTFTSYDIN | WVRQRPGQGLEWMG | WIYPGDGSTKYNEKFKG |
| vH3       | QVQLQQSGAEVKKPGASVKVSCKAS | GYTFTSYDIN | WVRQAPGQGLEWIG | WIYPGDGSTKYNEKFKG |
| vH4       | QVQLVQSGPEVKKPGASVKVSCKAS | GYTFTSYDIN | WVRQRPGQGLEWIG | WIYPGDGSTKYNEKFKG |
| vH5       | QVQLVQSGAEVKKPGASVKVSCKAS | GYTFTSYDIN | WVRQAPGQGLEWIG | WIYPGDGSTKYNEKFKG |
| vH6       | QVQLVQSGAEVKKPGASVKVSCKAS | GYTFTSYDIN | WVKQAPGQGLEWIG | WIYPGDGSTKYNEKFKG |
| 5H23v1-69 | QVQLVQSGAEVKKPGSSVKVSCKAS | GYTFTSYDIN | WVRQAPGQGLEWMG | WIYPGDGSTKYNEKFKG |
| vH7       | QVQLVQSGAEVKKPGSSVKVSCKAS | GYTFTSYDIN | WVRQAPGQGLEWIG | WIYPGDGSTKYNEKFKG |
| vH8       | QVQLVQSGAEVKKPGSSVKVSCKAS | GYTFTSYDIN | WVRQAPGQGLEWIG | WIYPGDGSTKYNEKFKG |
| vH9       | QVQLVQSGAEVKKPGSSVKVSCKAS | GYTFTSYDIN | WVRQAPGQGLEWIG | WIYPGDGSTKYNEKFKG |

FIGURE 3A-1

```
VH Domain (continued)

Kabat        70              80    abc           90        95--100--102           110
AbM          70              80    abc           90        95--100--102           110
Chothia      70              80    abc           90        96-100-101             110
Contact      70              80    abc           90        ---100-101             110
IMGT                 75                    89            105-----------117
AHon                                                 106 109         138

5H23        KATLTADKSSRTAYMQLSSLTSENSAVYFCAR SDYYGSRSFAY WGQGTLVTVSS (SEQ ID NO:25)
5H23v1-3    RVTITRDTSASTAYMELSSLRSEDTAVYYCAR SDYYGSRSFAY WGQGTLVTVSS (SEQ ID NO:323)
vH1         RVTITRDTSASTAYMELSSLTSEDTAVYYCAR SDYYGSRSFAY WGQGTLVTVSS (SEQ ID NO:269)
vH2         RVTITADKSARTAYMELSSLTSEDTAVYYCAR SDYYGSRSFAY WGQGTLVTVSS (SEQ ID NO:270)
vH3         KATITRDTSASTAYMELSSLRSEDTAVYFCAR SDYYGSRSFAY WGQGTLVTVSS (SEQ ID NO:271)
vH4         RVTITADKSARTAYMELSSLTSEDTAVYYCAR SDYYGSRSFAY WGQGTLVTVSS (SEQ ID NO:272)
vH5         KATLTADTSASTAYMELSSLRSENTAVYYCAR SDYYGSRSFAY WGQGTLVTVSS (SEQ ID NO:273)
vH6         KATLTADKSARTAYMELSSLRSENTAVYFCAR SDYYGSRSFAY WGQGTLVTVSS (SEQ ID NO:274)

5H23v1-69   RVTITADESTSTAYMELSSLRSEDTAVYYCAR SDYYGSRSFAY WGQGTLVTVSS (SEQ ID NO:414)
vH7         RATLTADKSTSTAYMELSSLRSEDTAVYYCAR SDYYGSRSFAY WGQGTLVTVSS (SEQ ID NO:320)
vH8         RATLTADKSTRTAYMELSSLRSEDTAVYYCAR SDYYGSRSFAY WGQGTLVTVSS (SEQ ID NO:321)
vH9         RATITADKSTSTAYMELSSLRSEDTAVYYCAR SDYYGSRSFAY WGQGTLVTVSS (SEQ ID NO:322)
```

FIGURE 3A-2

VL Domain

```
Kabat       1          10          20          24-27abcd----34                    40          50-------56
AbM         1          10          20          24----30ab----34                   40          50-------56
Chothia     1          10          20          26---30ab--32                      40          50---
Contact     1          10          20                30ab------36                 40                 55
IMGT        1                                   27---------38   41    42                      56-65  69

AHon        1                     23                                                          58        72
5H23                DIVLTQSPASLAVSLGQRATISC RASKSVSTSGYVYMH                 WNQQKPGQPPKLLIY LASYLES
5H23v4-1            DIVMTQSPDSLAVSLGERATINC RASKSVSTSGYVYMH                 WYQQKPGQPPKLLIY LASYLES
vL1                 DIVLTQSPDSLAVSLGERATINC RASKSVSTSGYVYMH                 WNQQKPGQPPKLLIY LASYLES
vL2                 DIVMTQSPDSLAVSLGERATINC RASKSVSTSGYVYMH                 WYQQKPGQPPKLLIY LASYLES
vL3                 DIVMTQSPDSLAVSLGERATINC RASKSVSTSGYVYMH                 WNQQKPGQPPKLLIY LASYLES
vL4                 DIVLTQSPDSLAVSLGERATINC RASKSVSTSGYVYMH                 WNQQKPGQPPKLLIY LASYLES
vL5                 DIVMTQSPDSLAVSLGERATINC RASKSVSTSGYVYMH                 WNQQKPGQPPKLLIY LASYLES

Kabat       60          70          80          89-------97
AbM         60          70          80          89-------97
Chothia     60          70          80               91----96
Contact     60          70          80          89-------96
IMGT        70                89                105------117
AHon        73                91                107       138
5H23                GVPARFSGSGSGTDFTLNIHPVEEEDAAIYYC QHSRDLTFP FGGGTKLEIK (SEQ ID NO:26)
5H23v4-1            GVPDRFSGSGSGTDFTLTISSLQAEDVAVYYC QHSRDLTFP FGGGTKLEIK (SEQ ID NO:355)
vL1                 GVPDRFSGSGSGTDFTLTISSVQAEDAAIYYC QHSRDLTFP FGGGTKLEIK (SEQ ID NO:275)
vL2                 GVPDRFSGSGSGTDFTLTISSVQAEDVAVYYC QHSRDLTFP FGGGTKLEIK (SEQ ID NO:276)
vL3                 GVPDRFSGSGSGTDFTLTISSVQAEDVAIYYC QHSRDLTFP FGGGTKLEIK (SEQ ID NO:277)
vL4                 GVPDRFSGSGSGTDFTLTISSLQAEDVAVYYC QHSRDLTFP FGGGTKVEIK (SEQ ID NO:325)
vL5                 GVPDRFSGSGSGTDFTLTISSLQAEDVAVYYC QHSRDLTFP FGGGTKVEIK (SEQ ID NO:326)
```

FIGURE 3B

| VL Domain | | | | | | | |
|---|---|---|---|---|---|---|---|
| Kabat | 1 | 10 | 20 | 24-27abcd----34 | 40 | 50-----56 | |
| AbM | 1 | 10 | 20 | 24-----30ab----34 | 40 | 50-----56 | |
| Chothia | 1 | 10 | 20 | 26--30ab----32 | 40 | 50--- | |
| Contact | 1 | 10 | 20 | 30ab-----36 | 40 | 46-----55 | |
| IMGT | 1 | | 23 | 27-------38 41 | | 56-65 69 | |
| | | | | | | | |
| AHon | 1 | | 23 | 42 | | 58 72 | |
| 5H23 | DIVLTQSPASLAVSLGQRATISC | | | RASKSVSTSGYVYMH | WNQQKPGQPPKLLIY | | LASYLES |
| 5H23v1-39 | DIQMTQSPSSLSASVGDRVTITC | | | RASKSVSTSGYVYMH | WYQQKPGKAPKLLIY | | LASYLES |
| v1-39a | DIQMTQSPSSLSASVGDRVTITC | | | RASKSVSTSGYVYMH | WYQQKPGKAPKLLIY | | LASYLES |
| v1-39b | DIQMTQSPSSLSASVGDRVTITC | | | RASKSVSTSGYVYMH | WNQQKPGKAPKLLIY | | LASYLES |
| v1-39c | DIQMTQSPSSLSASVGDRVTITC | | | RASKSVSTSGYVYMH | WYQQKPGKAPKLLIY | | LASYLES |
| v1-39d | DIQLTQSPSSLSASVGDRVTITC | | | RASKSVSTSGYVYMH | WYQQKPGKAPKLLIY | | LASYLES |
| v1-39e | DIQLTQSPSSLSASVGDRVTITC | | | RASKSVSTSGYVYMH | WYQQKPGKPPKLLIY | | LASYLES |
| v1-39f | DIQLTQSPSSLSASVGDRVTITC | | | RASKSVSTSGYVYMH | WYQQKPGKPPKLLIY | | LASYLES |
| v1-39g | DIQMTQSPSSLSASVGDRVTITC | | | RASKSVSTSGYVYMH | WYQQKPGKPPKLLIY | | LASYLES |
| v1-39h | DIQMTQSPSSLSASVGDRVTITC | | | RASKSVSTSGYVYMH | WNQQKPGKPPKLLIY | | LASYLES |
| v1-39i | DIQMTQSPSSLSASVGDRVTITC | | | RASKSVSTSGYVYMH | WYQQKPGKAPKLLIY | | LASYLES |
| v1-39j | DIQMTQSPSSLSASVGDRVTITC | | | RASKSVSTSGYVYMH | WYQQKPGKPPKLLIY | | LASYLES |
| v1-39k | DIQMTQSPSSLSASVGDRVTITC | | | RASKSVSTSGYVYMH | WNQQKPGKPPKLLIY | | LASYLES |
| v1-39l | DIQLTQSPSSLSASVGDRVTITC | | | RASKSVSTSGYVYMH | WNQQKPGKPPKLLIY | | LASYLES |
| v1-39m | DIQMTQSPSSLSASVGDRVTITC | | | RASKSVSTSGYVYMH | WYQQKPGKPPKLLIY | | LASYLES |
| v1-39n | DIQMTQSPSSLSASVGDRVTITC | | | RASKSVSTSGYVYMH | WYQQKPGKPPKLLIY | | LASYLES |
| v1-39o | DIQMTQSPSSLSASVGDRVTITC | | | RASKSVSTSGYVYMH | WYQQKPGKPPKLLIY | | LASYLES |
| v1-39p | DIQMTQSPSSLSASVGDRVTITC | | | RASKSVSTSGYVYMH | WYQQKPGKPPKLLIY | | LASYLES |

FIGURE 3C-1

VL Domain (continued)

| | | | | | | |
|---|---|---|---|---|---|---|
| Kabat | 60 | 70 | 80 | | 89------97 | |
| AbM | 60 | 70 | 80 | | 89------97 | |
| Chothia | 60 | 70 | 80 | | 91---96 | |
| Contact | 60 | 70 | 80 | | 89------96 | |
| IMGT | 70 | 89 | | | 105------117 | |
| AHon | 73 | 91 | | | 107    138 | |
| 5H23 | GVPARFSGSGSGTDFTLNIHPVEEEDAAIYYC | | | QHSRDLTFP | FGGGTKLEIK | (SEQ ID NO:26) |
| 5H23v1-39 | GVPSRFSGSGSGTDFTLTISSLQPEDFATYYC | | | QHSRDLTFP | FGGGTKLEIK | (SEQ ID NO:353) |
| v1-39a | GVPSRFSGSGSGTDFTLTISSLQPEDFATYYC | | | QHSRDLTFP | FGQGTKLEIK | (SEQ ID NO:327) |
| v1-39b | GVPSRFSGSGSGTDFTLTISSVQPEDFATYYC | | | QHSRDLTFP | FGGGTKLEIK | (SEQ ID NO:328) |
| v1-39c | GVPSRFSGSGSGTDFTLTISSLQPEDFATYYC | | | QHSRDLTFP | FGGGTKLEIK | (SEQ ID NO:329) |
| v1-39d | GVPSRFSGSGSGTDFTLTISSLQPEDFATYYC | | | QHSRDLTFP | FGGGTKLEIK | (SEQ ID NO:330) |
| v1-39e | GVPSRFSGSGSGTDFTLTISSVQPEDFATYYC | | | QHSRDLTFP | FGGGTKLEIK | (SEQ ID NO:331) |
| v1-39f | GVPSRFSGSGSGTDFTLTISSVQPEDFATYYC | | | QHSRDLTFP | FGGGTKLEIK | (SEQ ID NO:332) |
| v1-39g | GVPSRFSGSGSGTDFTLTISSVQPEDFATYYC | | | QHSRDLTFP | FGGGTKLEIK | (SEQ ID NO:333) |
| v1-39h | GVPSRFSGSGSGTDFTLTISSVQPEDFATYYC | | | QHSRDLTFP | FGGGTKLEIK | (SEQ ID NO:334) |
| v1-39i | GVPSRFSGSGSGTDFTLTISSLQEEDFATYYC | | | QHSRDLTFP | FGGGTKLEIK | (SEQ ID NO:335) |
| v1-39j | GVPSRFSGSGSGTDFTLTISSVQEEDFATYYC | | | QHSRDLTFP | FGGGTKLEIK | (SEQ ID NO:336) |
| v1-39k | GVPSRFSGSGSGTDFTLTISSVQEEDFATYYC | | | QHSRDLTFP | FGGGTKLEIK | (SEQ ID NO:337) |
| v1-39l | GVPSRFSGSGSGTDFTLTISSVQEEDAATYYC | | | QHSRDLTFP | FGGGTKLEIK | (SEQ ID NO:338) |
| v1-39m | GVPSRFSGSGSGTDFTLTISSVQEEDAATYYC | | | QHSRDLTFP | FGGGTKLEIK | (SEQ ID NO:339) |
| v1-39n | GVPSRFSGSGSGTDFTLTISSVQEEDFATYYC | | | QHSRDLTFP | FGGGTKLEIK | (SEQ ID NO:340) |
| v1-39o | GVPSRFSGSGSGTDFTLTISSVQPEDFATYYC | | | QHSRDLTFP | FGQGTKLEIK | (SEQ ID NO:341) |
| v1-39p | GVPSRFSGSGSGTDFTLTISSVQEEDFATYYC | | | QHSRDLTFP | FGQGTKLEIK | (SEQ ID NO:342) |

FIGURE 3C-2

VL Domain

```
Kabat      1              10              20              23  24-27abcd----34              40          50-----56
AbM        1              10              20              23  24----30ab----34             40          50-----56
Chothia    1              10              20              23  26---30ab---32               40          50---
Contact    1              10              20              23                 30ab------36   40          
IMGT       1                                                  27-------38       41    46-----55  56-65  69

AHon       1                                                                                     58     72
5H23           DIVLTQSPASLAVSLGQRATISC RASKSVSTSGYVYMH       42    WNQQKPGQPPKLLIY LASYLES
5H23v3-20      EIVLTQSPATLSLSPGERATLSC RASKSVSTSGYVYMH             WYQQKPGQAPRLLIY LASYLES
v3-20a         EIVLTQSPATLSLSPGERATLSC RASKSVSTSGYVYMH             WYQQKPGQAPRLLIY LASYLES
v3-20b         EIVLTQSPATLSLSPGERATLSC RASKSVSTSGYVYMH             WYQQKPGQAPRLLIY LASYLES
v3-20c         EIVLTQSPATLSLSPGERATLSC RASKSVSTSGYVYMH             WYQQKPGQAPRLLIY LASYLES
v3-20d         EIVLTQSPATLSLSPGERATLSC RASKSVSTSGYVYMH             WNQQKPGQAPRLLIY LASYLES
v3-20e         EIVLTQSPATLSLSPGERATLSC RASKSVSTSGYVYMH             WYQQKPGQPPRLLIY LASYLES
v3-20f         EIVLTQSPATLSLSPGERATLSC RASKSVSTSGYVYMH             WYQQKPGQAPRLLIY LASYLES
v3-20g         EIVLTQSPATLSLSPGERATLSC RASKSVSTSGYVYMH             WNQQKPGQAPRLLIY LASYLES
v3-20h         EIVLTQSPATLSLSPGERATLSC RASKSVSTSGYVYMH             WYQQKPGQAPRLLIY LASYLES
v3-20i         EIVLTQSPATLSLSPGERATLSC RASKSVSTSGYVYMH             WNQQKPGQPPRLLIY LASYLES
v3-20j         EIVLTQSPATLSLSPGERATLSC RASKSVSTSGYVYMH             WNQQKPGQPPRLLIY LASYLES
```

FIGURE 3D-1

VL Domain (continued)

| | | | | | | |
|---|---|---|---|---|---|---|
| Kabat | 60 | 70 | 80 | 89-------97 | | |
| AbM | 60 | 70 | 80 | 89-------97 | | |
| Chothia | 60 | 70 | 80 | 91-----96 | | |
| Contact | 60 | 70 | 80 | 89-----96 | | |
| IMGT | 70 | 89 | | 105------117 | | |
| AHon | 73 | 91 | | 107    138 | | |
| 5H23 | GVPARFSGSGSGTDFTLNIHPVEEEDAAIYYC | QHSRDLTFP | FGGGTKLEIK | (SEQ ID NO:26) |
| 5H23v3-20 | GIPARFSGSGSGTDFTLTISRLEPEDFAVYYC | QHSRDLTFP | FGQGTKLEIK | (SEQ ID NO:354) |
| v3-20a | GIPARFSGSGSGTDFTLTISRLEPEDFAVYYC | QHSRDLTFP | FGGGTKLEIK | (SEQ ID NO:343) |
| v3-20b | GIPARFSGSGSGTDFTLTISRVEPEDFAVYYC | QHSRDLTFP | FGGGTKLEIK | (SEQ ID NO:344) |
| v3-20c | GIPARFSGSGSGTDFTLTISRLEPEDFAVYYC | QHSRDLTFP | FGGGTKLEIK | (SEQ ID NO:345) |
| v3-20d | GIPARFSGSGSGTDFTLTISRLEPEDFAVYYC | QHSRDLTFP | FGGGTKLEIK | (SEQ ID NO:346) |
| v3-20e | GIPARFSGSGSGTDFTLTISRLEPEDAAVYYC | QHSRDLTFP | FGGGTKLEIK | (SEQ ID NO:347) |
| v3-20f | GIPARFSGSGSGTDFTLTISRVEPEDFAVYYC | QHSRDLTFP | FGGGTKLEIK | (SEQ ID NO:348) |
| v3-20g | GIPARFSGSGSGTDFTLTISRLEEEDFAVYYC | QHSRDLTFP | FGGGTKLEIK | (SEQ ID NO:349) |
| v3-20h | GIPARFSGSGSGTDFTLTISRVEEEDFAVYYC | QHSRDLTFP | FGGGTKLEIK | (SEQ ID NO:350) |
| v3-20i | GIPARFSGSGSGTDFTLTISRVEEEDFAVYYC | QHSRDLTFP | FGGGTKLEIK | (SEQ ID NO:351) |
| v3-20j | GIPARFSGSGSGTDFTLTISRVEEEDAAVYYC | QHSRDLTFP | FGGGTKLEIK | (SEQ ID NO:352) |

```
                                                                      40                                                      80
human     MKPGCAAGSPGNEWIFFSTDEITTRYRNTMSNGGLQRSVILSALILLRAVTGFSGDGRAIWSKNPNFTPVNESQLFLYDT
chMoHu    MKTGCAAGSPGNEWIFFSSDERNTRSRKTMSNGGLQRSVILSALILLRAVTGFSGDGKAIWDKKQYVSPVNPSQLFLYDT
chHuMo    MKPGCAAGSPGNEWIFFSTDEITTRYRNTMSNGGLQRSVILSALILLRAVTGFSGDGRAIWSKNPNFTPVNESQLFLYDT
mouse     MKTGCAAGSPGNEWIFFSSDERNTRSRKTMSNRALQRSAVLSAFVLLRAVTGFSGDGKAIWDKKQYVSPVNPSQLFLYDT 120                                                     160
human     FPKNFFWGIGTGALQVEGSWKKDGKGPSIWDHFIHTHLKNVSSTNGSSDSYIFLEKDLSALDFIGVSFYQFSISWPRLFP
chMoHu    FPKNFSWGVGTGAFQVEGSWKTDGRGPSIWDRYVYSHLRGVNGTDRSTDSYIFLEKDLLALDFLGVSFYQFSISWPRLFP
chHuMo    FPKNFFWGIGTGALQVEGSWKKDGKGPSIWDHFIHTHLKNVSSTNGSSDSYIFLEKDLSALDFIGVSFYQFSISWPRLFP
mouse     FPKNFSWGVGTGAFQVEGSWKTDGRGPSIWDRYVYSHLRGVNGTDRSTDSYIFLEKDLLALDFLGVSFYQFSISWPRLFP 200                                                     240
human     DGIVTVANAKGLQYYSTLLDALVLRNIEPIVTLYHWDLPLALQEKYGGWKNDTIIDIFNDYATYCFQMFGDRVKYWITIH
chMoHu    NGTVAAVNAQGLRYYRALLDSLVLRNIEPIVTLYHWDLPLTLQEEYGGWKNATMIDLFNDYATYCFQTFGDRVKYWITIH
chHuMo    DGIVTVANAKGLQYYSTLLDALVLRNIEPIVTLYHWDLPLALQEKYGGWKNDTIIDIFNDYATYCFQMFGDRVKYWITIH
mouse     NGTVAAVNAQGLRYYRALLDSLVLRNIEPIVTLYHWDLPLTLQEEYGGWKNATMIDLFNDYATYCFQTFGDRVKYWITIH 280                                                     320
human     NPYLVAWHGYGTGMHAPGEKGNLAAVYTVGHNLIKAHSKVWHNYNTHFRPHQKGWLSITLGSHWIEPNRSENTMDIFKCQ
chMoHu    NPYLVAWHGFGTGMHAPGEKGNLTAVYTVGHNLIKAHSKVWHNYDKNFRPHQKGWLSITLGSHWIEPNRTDNMEDVINCQ
chHuMo    NPYLVAWHGYGTGMHAPGEKGNLAAVYTVGHNLIKAHSKVWHNYNTHFRPHQKGWLSITLGSHWIEPNRSENTMDIFKCQ
mouse     NPYLVAWHGFGTGMHAPGEKGNLTAVYTVGHNLIKAHSKVWHNYDKNFRPHQKGWLSITLGSHWIEPNRTDNMEDVINCQ 360                                                     400
human     QSMVSVLGWFANPIHGDGDYPEGMRKKLFSVLPIFSEAEKHEMRGTADFFAFSFGPNNFKPLNTMAKMGQNVSLNLREAL
chMoHu    HSMSSVLGWFANPIHGDGDYPEGMRKKLFSVLPIFSEAEKHEMRGTADFFAFSFGPNNFKPLNTMAKMGQNVSLNLREAL
chHuMo    QSMVSVLGWFANPIHGDGDYPEGMRKKLFSVLPIFSEAEKHEMRGTADFFAFSFGPNNFKPLNTMAKMGQNVSLNLREAL
mouse     HSMSSVLGWFANPIHGDGDYPEGMRKKLFSVLPIFSEAEKHEMRGTADFFAFSFGPNNFKPLNTMAKMGQNVSLNLREAL 440                                                     480
human     NWIKLEYNNPRILIAENGWFTDSRVKTEDTTAIYMMKNFLSQVLQAIRLDEIRVFGYTAWSLLDGFEWQDAYTIRRGLFY
chMoHu    NWIKLEYDDPQILISENGWFTDSYIKTEDTTAIYMMKNFLNQVLQAIKFDEIRVFGYTAWTLLDGFEWQDAYTTRRGLFY
chHuMo    NWIKLEYNNPRILIAENGWFTDSRVKTEDTTAIYMMKNFLSQVLQAIRLDEIRVFGYTAWSLLDGFEWQDAYTIRRGLFY
mouse     NWIKLEYDDPQILISENGWFTDSYIKTEDTTAIYMMKNFLNQVLQAIKFDEIRVFGYTAWTLLDGFEWQDAYTTRRGLFY
```

FIGURE 4B

```
                                                                                          560
human   VDFNSKQKERKPKSSAHYYKQIIRENGFSLKESTPDVQGQFPCDFSWGVTESVLKPESVASSPQFSDPHLYVWNATGNRL
chMoHu  VDFNSEQKERKPKSSAHYYKQIIQDNGFSLKESTPDVQGQFPCDFSWGVTESVLKPESVASSPQFSDPHLYVWNATGNRL
chHuMo  VDFNSKQKERKPKSSAHYYKQIIRENGFPLKESTPDMKGRFPCDFSWGVTESVLKPEFTVSSPQFTDPHLYVWNVTGNRL
mouse   VDFNSEQKERKPKSSAHYYKQIIQDNGFPLKESTPDMKGRFPCDFSWGVTESVLKPEFTVSSPQFTDPHLYVWNVTGNRL
                                                                                          640
human   LHRVEGVRLKTRPAQCTDFVNIKKQLEMLARMKVTHYRFALDWASVLPTGNLSAVNRQALRYRCVVSEGLKLGISAMVT
chMoHu  LHRVEGVRLKTRPAQCTDFVNIKKQLEMLARMKVTHYRFALDWASVLPTGNLSAVNRQALRYRCVVSEGLKLGISAMVT
chHuMo  LYRVEGVRLKTRPSQCTDYVSIKKRVEMLAKMKVTHYQFALDWTSILPTGNLSKVNRQVLRYYRCVVSEGLKLGVFPMVT
mouse   LYRVEGVRLKTRPSQCTDYVSIKKRVEMLAKMKVTHYQFALDWTSILPTGNLSKVNRQVLRYYRCVVSEGLKLGVFPMVT
                                                                                          720
human   LYYPTHAHLGLPEPLLHADGWLNPSTAEAFQAYAGLCFQELGDLVKLWITINEPNRLSDIYNRSGNDTYGAAHNLLVAHA
chMoHu  LYYPTHAHLGLPEPLLHADGWLNPSTAEAFQAYAGLCFQELGDLVKLWITINEPNRLSDIYNRSGNDTYGAAHNLLVAHA
chHuMo  LYHPTHSHLGLPLPLLSSGGWLNMNTAKAFQDYAELCFRELGDLVKLWITINEPNRLSDMYNRTSNDTYRAAHNLMIAHA
mouse   LYHPTHSHLGLPLPLLSSGGWLNMNTAKAFQDYAELCFRELGDLVKLWITINEPNRLSDMYNRTSNDTYRAAHNLMIAHA
                                                                                          800
human   LAWRLYDRQFRPSQRGAVSLSLHADWAEPANPYADSHWRAAERFLQFEIAWFAEPLFKTGDYPAAMREYIASKHRRGLSS
chMoHu  LAWRLYDRQFRPSQRGAVSLSLHADWAEPANPYADSHWRAAERFLQFEIAWFAEPLFKTGDYPAAMREYIASKHRRGLSS
chHuMo  QVWHLYDRQYRPVQHGAVSLSLHCDWAEPANPFVDSHWKAAERFLQFEIAWFADPLFKTGDYPSVMKEYIASKNQRGLSS
mouse   QVWHLYDRQYRPVQHGAVSLSLHCDWAEPANPFVDSHWKAAERFLQFEIAWFADPLFKTGDYPSVMKEYIASKNQRGLSS
                                                                                          880
human   SALPRLTEAERRLLKGTVDFCALNHFTTRFVMHEQLAGSRYDSDRDIQFLQDITRLSSPTRLAVIPWGVRKLLRWVRRNY
chMoHu  SALPRLTEAERRLLKGTVDFCALNHFTTRFVMHEQLAGSRYDSDRDIQFLQDITRLSSPTRLAVIPWGVRKLLRWVRRNY
chHuMo  SVLPRFTAKESRLVKGTVDFYALNHFTTRFVIHKQLNTNRSVADRDVQFLQDITRLSSPSRLAVTPWGVRKLLAWIRRNY
mouse   SVLPRFTAKESRLVKGTVDFYALNHFTTRFVIHKQLNTNRSVADRDVQFLQDITRLSSPSRLAVTPWGVRKLLAWIRRNY
                                                                                          960
human   GDMDIYITASGIDDQALEDDRLRKYYLGKYLQEVLKAYLIDKVRIKGYYAFKLAEEKSKPRFGFFTSDFKAKSSIQFYNK
chMoHu  GDMDIYITASGIDDQALEDDRLRKYYLGKYLQEVLKAYLIDKVRIKGYYAFKLAEEKSKPRFGFFTSDFKAKSSIQFYNK
chHuMo  RDRDIYITTANGIDDLALEDDQIRKYYLEKYVQEALKAYLIDKVKIKGYYAFKLTEEKSKPRFGFFTSDFRAKSSVQFYSK
mouse   RDRDIYITTANGIDDLALEDDQIRKYYLEKYVQEALKAYLIDKVKIKGYYAFKLTEEKSKPRFGFFTSDFRAKSSVQFYSK
```

FIGURE 4C

```
                                                                                1040
                    1000
human   VISSRGFPFENSSSRCSQTQENTECTVCLFLVQKKPLIFLGCCFFSTLVLLLSIAIFQRQKRKFWKAKNLQHIPLKKGK
chMoHu  VISSRGFPFENSSSRCSQTQENTECTVCLFLVQKKPLIFLGCCFFSTLVLLLSIAIFQRQKRKFWKAKNLQHIPLKKGK
chHuMo  LISSSGLPAENRSPACGQPAEDTDCTICSFLVEKKPLIFFGCCFISTLAVLLSITVFHHQKRRKFQKARNLQNIPLKKGH
mouse   LISSSGLPAENRSPACGQPAEDTDCTICSFLVEKKPLIFFGCCFISTLAVLLSITVFHHQKRRKFQKARNLQNIPLKKGH human   -RVVS  (SEQUENCE ID 297)
chMoHu  -RVVS  (SEQUENCE ID 376)
chHuMo  SRVFS  (SEQUENCE ID 374)
mouse   SRVFS  (SEQUENCE ID 301)
```

FIGURE 5A

```
                                                                    60
human    MKPGCAAGSPGNEWIFFSTDEITTRYRNTMSNGGLQRSVILSALILLRAVTGFSGDGRAI
cyno     MKPGCAAGSPGNEWIFFSTDEITIRYRNTMSNGGLQRSVILSALTLLRAVTGFSGDGRAV
mouse    MKTGCAAGSPGNEWIFFSSDERNTRSRKTMSNRALQRSAVLSAFVLLRAVTGFSGDGKAI
rabbit   MKPGCAAGSPGNEWSFCTDERNRRCRETMSSGRLRRSVMLSAFILLRAVTGFPGDGRAV
hamster  MKAGCAAGSPGNEWIFLSSYERNTRSKKTMSNRALQRSVVLSAFVLLRAVTGLSGDGKAI
rat      MKTGCAAGSPGNEWVFFSSDERSTRSRKTMSNGALQRSAVLSALVLLRAVTGFSGDGKAI
dog      MKPGCAAGSPGNEWIFLSTDESNTHYRKTMCNHGLQRSVILSAFILLGAVPGFSGDGRAI
         ** ********** *  ** *  *  * **     *** ** * * ***     ** *

120
human    WSKNPNFTPVNESQLFLYDTFPKNFFWGIGTGALQVEGSWKKDGKGPSIWDHFIHTHLKN
cyno     WSKNPNFTPVNESQLFLYDTFPKNFFWGVGTGALQVEGSWKKDGKGPSIWDHFVHTHLKN
mouse    WDKKQYVSPVNPSQLFLYDTFPKNFSWGVGTGAFQVEGSWKTDGRGPSIWDRYVYSHLRG
rabbit   WSQNPNLSPVNESQLFLYDTFPKNFFWGVGTGAFQVEGSWKKDGKGLSVWDHFIATHLN-
hamster  WDKKQYVSPVNASQLFLYDTFPKNFFWGVGTGAFQVEGNWQADGRGPSIWDRFIYTHLRD
rat      WDKKQYVSPVNPGQLFLYDTFPKNFFWGVGTGAFQVEGSWKADGRGPSIWDRYVDSHLRG
dog      WSKNPHFSPVNESQLFLYDTFPKNFFWGVGTGAFQVEGNWKTDGKGPSIWDHFIHTHLKN
         *        **  ************  **  ****  *** *  ** *  **    *

180
human    VSSTNGSSDSYIFLEKDLSALDFIGVSFYQFSISWPRLFPDGIVTTVANAKGLQYYSTLLD
cyno     VSSTNGSSDSYIFLEKDLSALDFIGVSFYQFSISWPRLFPDGIVTTVANAKGLQYNTLLD
mouse    VNGTDRSTDSYIFLEKDLLALDFLGVSFYQFSISWPRLFPNGTVAAVNAQGLRYRALLD
rabbit   VSSRDGSSDSYIFLEKDLSALDFLGVSFYQFSISWPRLFPDGTVAVANAKGLQYNRLLD
hamster  VSITEKSADSYIFLEKDLLALDFLGVSFYQFSISWPRLFPNGTVASVNAKGLQYYNKLLD
rat      VNSTDRSTDSYVFLEKDLLALDFLGVSFYQFSISWPRLFPNGTVAAVNAKGLQYYRALLD
dog      VNSMNSSSDSYIFLEKDLSALDFIGVSFYQFSISWPRLFPDGIAAVANAKGLQYYNSLLD
         *     ***  *****  **** *****************  *  * *** **   ***
```

FIGURE 5B

```
                                                                           240
                         210
human    ALVLRNIEPIVTLYHWDLPLALQEKYGGWKNDTIIDIFNDYATYCFQMFGDRVKYWITIH
cyno     SLVLRNIEPIVTLYHWDLPLALQEKYGGWKNDTIIDIFNDYATYCFQTFGDRVKYWITIH
mouse    SLVLRNIEPIVTLYHWDLPLTLQEEYGGWKNATMIDLFNDYATYCFQTFGDRVKYWITIH
rabbit   SLLLRNIEPVVTLYHWDLPWALQEKYGGWKNETLIDLFNDYATYCFQTFGDRVKYWITIH
hamster  SLILRNIEPVVTLYHWDLPLALQEDYGGWKNATMIDLFNDYATYCFQTFGDRVKYWITIH
rat      SLVLRNIEPIVTLYHWDLPLTLQEEYGGWKNATMIDLFNDYATYCFQTFGDRVKYWITIH
dog      ALVLRNIEPIVTLYHWDLPLALQEKYGGWKNETTTDIFNDYATYCFQTFGDRVKYWITIH
          * ***** ********** ** *** ***** * * *****************

300
                         270
human     NPYLVAWHGYGTGMHAPGEKGNLAAVYTVGHNLIKAHSKVWHNYNTHFRPHQKGWLSITL
cyno      NPYLVAWHGYGTGMHAPGEKGNLAAVYTVGHNLIKAHSKVWHNYNTHFRPHQKGWLSITL
mouse     NPYLVAWHGFGTGMHAPGEKGNLTAVYTVGHNLIKAHSKVWHNYDKNFRPHQKGWLSITL
rabbit    NPYLVAWHGYGTGLHAPGEKGNVAAVYTVGHNLLKAHSKVWHNYNRNFRPHQKGWLSITL
hamster   NPYLVAWHGFATGMHAPGETGNLTAVYIVGHNLTAVYTVGHNLIKAHSKVWHNYDKNFRPHQKGLLSITL
rat       NPYLVAWHGFGTGMHAPGEKGNLTAVYTVGHNLIKAHSKVWHNYNTNFRPHQKGWLSITL
dog       NPYLVAWHGYGTGMHAPGEKGNLAAVYTVGHNLIKAHSKVWHNYNTNFRPYQKGLLSITL
          ******** ** * ***** ** *** * ***** ********* ***   ** ****

360
                         330
human     GSHWIEPNRSENTMDIFKCQQSMVSVLGWFANPIHGDGDYPEGMRKKLFSVLPIFSEAEK
cyno      GSHWIEPNRSENTMDILKCQQSMVSVLGWFANPIHGDGDYPEGMKKKLLSILPLFSEAEK
mouse     GSHWIEPNRTDNMEDVINCQHSMSSVLGWFANPIHGDGDYPEFMKT--GAMIPEFSEAEK
rabbit    GSHWIEPNRAESIVDILKCQQSMVSVLGWFANPIHGDGDYPEVMTKKLLSVLPAFSEAEK
hamster   GSHWIEPNKTENMADTISCQHSMAFVLGWFANPIHADGDYPEFMKT--LSTMPVFSEAEK
rat       GSHWIEPNRTENMEDVINCQHSMSSVLGWFANPIHGDGDYPEFMKT--SSVIPEFSEAEK
dog       GSHWIEPNRSENMMDILKCQQSMVSVLGWFANPIHGNGDYPEVMKKKLLSTLPLFSEAEK
          ******  *  ** *  ** ** * ********* * **** *    *   * *****
```

FIGURE 5C

```
                                                                       420
         390
human    HEMRGTADFFAFSFGPNNFKPLNTMAKMGQNVSLNLREALNWIKLEYNNPRILIAENGWF
cyno     NEVRGTADFFAFSFGPNNFKPLNTMAKMGQNVSLNLREALNWIKLEYNNPRILIAENGWF
mouse    EEVRGTADFFAFSFGPNNFRPSNTVVKMGQNVSLNLRQVLNWIKLEYDDPQILISENGWF
rabbit   NEVRGTADFFAFSFGPNNFKPLNTMAKMGQNVSLNLRQVLNWIKLEYGNPRILIAENGWF
hamster  EEVRGTADFFAFSFGPNNFRPSNTVVKMGQNVSLNLRQVLNWIKLEYDNPRILISENGWF
rat      EEVRGTADFFAFSFGPNNFRPSNTVVKMGQNVSLNLRQVLNWIKLEYDNPRILISENGWF
dog      NEVRGTADFFAFSFGPNNFKPQNTMAKMGQNVSLNLREVLNWIKLEYGNPRILIAENGWF
         * *************** *** * ********* ***** ******** *** ******

480
         450
human    TDSRVKTEDTTAIYMMKNFLSQVLQAIRLDEIRVFGYTAWSLLDGFEWQDAYTIRRGLFY
cyno     TDSHVKTEDTTAIYMMKNFLSQVLQAIRLDEIRVFGYTAWSLLDGFEWQDAYTIRRGLFY
mouse    TDSYIKTEDTTAIYMMKNFLNQVLQAIKFDEIRVFGYTAWTLLDGFEWQDAYTTRRGLFY
rabbit   TDSYVQTEDTTAIYMMKNFLNQVLQAIRLDGVRVFGYTAWSLLDGFEWQDAYNTRRGLFY
hamster  TDSDIKTEDTTAIYMMKHFLNQVLQAIQFDEIRVFGYTAWSLLDGFEWQYAYTSRRGLFY
rat      TDSYIKTEDTTAIYMMKNFLNQVLQAIKFDEIQVFGYTAWTLLDGFEWQDAYTTRRGLFY
dog      TDSHVKTEDTTAIYMMKNFLNQVLQAIRFDEIQVFGYTAWSLLDGFEWQDAYSTRRGLFY
         ***  ************ ** ****  *   ********* ******** **  *****

540
         510
human    VDFNSKQKERKPKSSAHYYKQIIRENGFSLKESTPDVQGQFPCDFSWGVTESVLKPESVA
cyno     VDFNSKQKERKPKSSAHYYKQIIRENGFSLKEATPDVQGQFPCDFSWGVTESVLKPESVA
mouse    VDFNSEQKERKPKSSAHYYKQIIQDNGFPLKESTPDMKGREFPCDFSWGVTESVLKPEFTV
rabbit   VDFNSEQRERRPKSSAHYYKQVIGENGFTLREATPDLQGQFPCDFSWGVTESVLKPESVA
hamster  VDFNSEQKERKPKTSAHYYKQIIQENGFPLKESTPDMQGQFPCDFSWGVTESVLKPEFMV
rat      VDFNSEQKERKPKSSAHYYKQIIQDNGFPLQESTPDMKGQFPCDFSWGVTESVLKPEFTV
dog      VDFNSKQKERKPKSSAYYYKQIIQENGFTFKESTPDVQGQFPCDFSWGVTESVLPKVVA
         ***** * ** ** ** ****  * ***    ****  *  *************   *
```

FIGURE 5D

```
                                570                                            600
human    SSPQFSDPHLYVWNATGNRLLHRVEGVRLKTRPAQCTDFVNIKKQLEMLARMKVTHYRFA
cyno     SSPQFSDPYLYVWNATGNRLLHRVEGVRLKTRPAQCTDFVNIKKQLEMLARMKVTHYRFA
mouse    SSPQFTDPHLYVWNVTGNRLLYRVEGVRLKTRPSQCTDYVSIKKRVEMLAKMKVTHYQFA
rabbit   SSPQFSDPHLYVWNATGNRLLHRVEGVRLKTRPAQCTDFITIKKQLEMLARMKVTHFRFA
hamster  SSPQFTDPHLYVWNATGNRLLQRVEGVRLKTKPSHCTDYVSIKKRVEMLAKMKVTHYQFA
rat      SSPQFTDPHLYVWNVTGNRLLYRVEGVRLKTRPSQCTDYVSIKKRVEMLAKMKVTHYQFA
dog      SSPQFSDPHLYVWNVTGNRLLHRVEGVRLKTRPAQCTDFVSIKRQLEMLARMNVTHYRFA
         *****:***:****.******:************:***:.**::*:****:****:**

630                                            660
human    LDWASVLPTGNLSAVNRQALRYYRCVVSEGLKLGISAMVTLYYPTHAHLGLPEPLLHADG
cyno     LDWASVLPTGNLSAVNRQALRYYRCVVSEGLKLGISAMVTLYYPTHAHLGLPEPLLHAGG
mouse    LDWTSILPTGNLSKVNRQVLRYYRCVVSEGLKLGVFPMVTLYHPTHSHLGLPLPLLSSGG
rabbit   LDWASVLPTGNLSEVNRQALRYYRCVVTEGLKLNISPMVTLYPTHAHLGLPAPLLHSGG
hamster  LDWATILPTGNLSKVNRQVLRYYRCVVSEGLKLGVSPMVTLYHPTHSHLGLPEPLLNSGG
rat      LDWTSILPTGNLSKINRQVLRYYRCVVSEGLKLGISPMVTLYHPTHSHLGLPMPLLSSGG
dog      LDWPSILPTGNLSTVNRQALRYYRCVVSESLKLSISPMVTLYPTHAHLGLPSPLLHSGG
         ***.::******.::***.**:*****:*:***.: .****:***:***** **: *

690                                            720
human    WLNPSTAEAFQAYAGLCFQELGDLVKLWITINEPNRLSDIYNRSGNDTYGAAHNLLVAHA
cyno     WLNPSTVEAFQAYAGLCFQELGDLVKLWITINEPNRLSDIYNRSGNDTYGAAHNLLVAHA
mouse    WLNMNTAKAFQDYAELCFRELGDLVKLWITINEPNRLSDMYNRTSNDTYRAAHNLMIAHA
rabbit   WLDPSTAKAFRDYAGLCFRELGDLVKLWITINEPNRLSDVYNRTSNDTYRAAHNLMIAHA
hamster  WLNTYTAKAFQDYAGLCFQELGDLVKLWITINEPNRLSDMYNRTSNDTYQAAHNLLIAHA
rat      WLNTNTAKAFQDYAGLCFKELGDLVKLWITINEPNRLSDMYNRTSNDTYRAAHNLMIAHA
dog      WLNASTARAFQDYAGLCFQELGDLVKLWITINEPNRLSDVYSHTSSDTYRAAHNLLIAHA
         **: *.:**: **.***:*********************:*.::.:*** ******:.***
```

FIGURE 5E

```
                                                       750                                                         780
human    LAWRLYDRQFRPSQRGAVSLSLHADWAEPANPYADSHWRAAERFLQFEIAWFAEPLFKTG
cyno     LAWRLYDRQFRPSQRGAVSLSLHADWAEPANPYADSHWRAAERFLQFEIAWFAEPLFKTG
mouse    QVWHLYDRQYRPVQHGAVSLSLHCDWAEPANPFVDSHWKAAERFLQFEIAWFADPLFKTG
rabbit   LVWHLYDRQYRPSQRGALSLSLHSDWAEPANPYVASHWQAAERFLQFEIAWFAEPLFKTG
hamster  QVWHLYDRQYRPVQHGAVSLSLHSDWVEPANPYVDSHWKAAERFLLFEIAWFADPLFKTG
rat      QVWHLYDRQYRPVQHGAVSLSLHSDWAEPANPYVESHWKAAERFLQFEIAWFAEPLFKTG
dog      LVWHLYDRRYRPAQRGAVSLSLHSDWAEPANPYADSHWKAAERFLQFEIAWFAEPLFKTG
         * ****  * *   * *****  ** ****** *** **  **** **** *******

810                                                         840
human    DYPAAMREYIASKHRRGLSSSALPRLTEAERRLLKGTVDFCALNHFTTRFVMHEQLAGSR
cyno     DYPAAMREYIASKHRRGLSSSALPRLTEAERRLLKGTVDFCALNHFTTRFVMHEQLAGSR
mouse    DYPSVMKEYIASKNQRGLSSSVLPRFTAKESRLVKGTVDFYALNHFTTRFVIHKQLNTNR
rabbit   DYPVAMREYIASKTRRGLSSSVLPRFSDAERRLVKGAADFYALNHFTTRFVMHEQQNGSR
hamster  DYPLAMKEYIASKNQQGLSRSVLPRFTPEESRLVKGTIDFYALNHFTTRFVIHKQLNSSR
rat      DYPLAMKEYIASKKQRGLSSSVLPRFTLKESRLVKGTIDFYALNHFTTRFVIHKQLNTNC
dog      DYPPAMREYIASKNRQGLSRSTLPRFTDEERRLVKGAADFYALNHFTTRFVMHARQNGSR
         ***  * ***** ::** * :* *:*:  :** **   * *:**:***::** * :

870                                                         900
human    YDSDRDIQFLQDITRLSSPTRLAVIPWGVRKLLRWVRRNYGDMDIYITASGIDDQALEDD
cyno     YDSDRDIQFLQDITRLSSPTRLAVIPWGVRKLLRWVRRNYGDMDIYITASGIDDQALEDD
mouse    SVADRDVQFLQDITRLSSPTRLAVTPWGVRKLLAWIRRNYRDRDIYITANGIDDLALEDD
rabbit   YDSDRDVQFLQDITRLSSPSRLASPSRLRWMRNNYGDLDVYITANGIDDQALQND
hamster  SMADRDVQFLQDITRLSSPSRLAVMPWGARKLLGWIQRNYGDMDIYITANGIDDLALEND
rat      SVADRDVQFLQDITRLSSPSRLAVTPWGMRKLLGWIRRNYRDMDIYVTANGIDDLALEDD
dog      YDADRDVQFLQDITCLSSPSRLAVLPWGERKVLRWIQKNYGDVDVYITASGIDDQSLEND
          : *** :****** ****:***   *     *  :.** :  * ***.****  * :
```

FIGURE 5F

```
human    RLRKYYLGKYLQEVLKAYLIDKVRIKGYYAFKLAEEKSKPREGFFTSDFKAKSSIQFYNK
cyno     RLRKYYLEKYLQEVLKAYLIDKVRIKGYYAFKLAEEKSKPREGFFTSDFKAKSSIQFYNK
mouse    QIRKYLEKYVQEALKAYLIDKVKIKIKGYYAFKLTEEKSKPREGFFTSDFRAKSSVQFYSK
rabbit   QLRQYYLEKYVQEALKAYLIDKVKIKIKGYYAFKLTEEKSKPREGFFTSDFKAKSSIQFYNK
hamster  GIRKYYLEKYIQEALKAYLIDKVKIKIKGYYAFKLTEEKSKPREGFFTSDFKAKSSVEFYSK
rat      QIRKYYLEKYVQEALKAYLIDKVKIKIKGYYAFKLTEEKSKPREGFFTSDFKAKSSVQFYSK
dog      ELRKYYLEKYIQEALKAHLIDKVKVKGYYAFKLTEEKSKPREGFFTSEFKAKSSVQLYNK
            * *   * *   ****** *******  **  * human    VISSRGFPFENSSSRCSQTQENTECTVCLEFLVQKKPLIFLGCCFFSTLVLLLSIAIFQRQ
cyno     MISSSGFPSENSSSRCSQTQKNTECTVCLFLVQKKPLIFLGCCFFSTLVLLLSITIFHRQ
mouse    LISSSGLPAENRSPACGQPAEDTDCTICSFLVEKKPLIFFGCCFISTLAVLLSITVFHHQ
rabbit   LITSNGFPSENGGPRCNQTQGNPECTVCLLLLQKKPLIFFSCCFFCTLVLLSSITIFHRR
hamster  LISRSGFPSETSNPACGQPPEDTDCTICSFFTQKKSLIFFGCCFISTLAVLLSITIFHHR
rat      LISSSGFSSENRSPACGQPPEDTECAICSFLTQKKPLIFFGCCFISTLAALLSITIFHHR
dog      LISNSGFPSENRSPRCSETQRNTECMVCLFLVQKKPLIFFSCCFFSTLVLLSSITILHKR
          *     *   *  * *     * ** * *  *      *   *     ** * human    KRRKFWKAKNLQHIPLKKGKRVVS-    (SEQ ID NO:297)
cyno     KRRKFWKAKNLQHIPLKKGKRVLS-    (SEQ ID NO:299)
mouse    KRRKFQKARNLQNIPLKKGHSRVFS    (SEQ ID NO:301)
rabbit   KRRKFWKAKDLQHIPLKKGHKRVLS    (SEQ ID NO:410)
hamster  KRR-FHKSKNLENIPLKEGHSRVLS    (SEQ ID NO:408)
rat      KRRKFQKARNLQNIPLKKGHSRVFS    (SEQ ID NO:356)
dog      KRRKIWKAKNLQHIPLKKSKNSLQS    (SEQ ID NO:412)
          ***   *  * *  ***        ****
```

POLYNUCLEOTIDES ENCODING HUMAN BETA KLOTHO ANTIBODIES OR BINDING FRAGMENTS THEREOF AND METHODS OF USE THEREOF

CROSS-REFERENCE TO RELATED APPLICATIONS

This application is a continuation of U.S. patent application Ser. No. 16/928,862, filed Jul. 14, 2020, now U.S. Pat. No. 11,596,676, which is a continuation of U.S. patent application Ser. No. 16/103,613, filed Aug. 14, 2018, now U.S. Pat. No. 10,744,191, which is a continuation of U.S. patent application Ser. No. 15/659,177, filed Jul. 25, 2017, now U.S. Pat. No. 10,093,735, which is a continuation of U.S. patent application Ser. No. 14/604,592, filed Jan. 23, 2015, now U.S. Pat. No. 9,738,716, which claims the benefit of priority of U.S. Provisional Application Ser. No. 61/931,531, filed Jan. 24, 2014, the entire contents of each of which are incorporated herein by reference.

SEQUENCE LISTING

This application contains a Sequence Listing that has been submitted electronically as an XML file named 47702-0002005SEQ.xml. The XML file, created on Feb. 13, 2023, is 611,285 bytes in size. The material in the XML file is hereby incorporated by reference in its entirety.

FIELD

The present disclosure relates generally to binding proteins, such as antibodies, that bind to beta klotho, including human beta klotho, and methods of their use.

BACKGROUND

Beta klotho, which belongs to the Klotho family, is a single-pass type 1 membrane protein. Beta klotho has an extracellular domain consisting of two internal repeats which share homology with members of the family 1 glycosidases but lack glucosidase catalytic activity. Beta klotho expression is primarily detected in the liver, pancreas and adipose tissue. Ito and colleagues have reported that beta klotho-deficient (KLB-/-) mice have elevated mRNA levels of CYP7A1 and CY8B1 and exhibit increased synthesis and excretion of bile acid (Ito et al., 2005, J Clin Invest 115: 2202-2208). Beta klotho forms a complex with fibroblast growth factor (FGF) receptors and functions as a co-receptor for FGFs, including FGF19 and FGF21.

Twenty-two members of the human FGF family have been identified and four tyrosine kinase receptors that bind to FGF (FGFR1-FGFR4) have been identified. The interaction between FGF and its receptor results in FGFR dimerization, which enables the cytoplasmic domains of the receptor to transphosphorylate and become activated, which in turn leads to the phosphorylation and activation of downstream signaling molecules.

The high affinity receptor for FGF19 is FGFR4 and the binding of FGF19 to FGFR4 is facilitated by beta klotho. It has been reported that FGF19 transgenic mice have decreased adiposity, increased metabolic rate, reduced liver triglycerides, increased fatty acid oxidation, reduced glucose levels and increased insulin sensitivity (Tomlinson et al., 2002, Endocrinology 143: 1741-1747). In addition, these transgenic mice were reported not to become obese or diabetic on a high-fat diet (Tomlinson et al., 2002, Endocrinology 143: 1741-1747). It has also been reported that FGF19 treatment prevented or reversed diabetes in mice made obese by genetic ablation of brown adipose tissue or the genetic absence of leptin (Fu et al., 2004, Endocrinology 145: 2594-2603).

FGF21 acts through the interaction of FGFRs and beta klotho. FGFR1 is an abundant receptor in white adipose tissue and is most likely the main functional receptor for FGF21 in white adipose tissue. FGF21 expression is detected in the liver, thymus, adipose tissue, and islet beta-cells in the pancreas. It has been reported that the interaction of FGF21 with the beta klotho-FGFR complex stimulates glucose uptake, decreases glucagon secretion, improves insulin sensitivity and glucose clearance, promotes white adipose tissue in response to fasting, increases ketogenesis in liver in response to fasting, reduces plasma triglyceride levels, and increases energy expenditure (Iglesias et al., 2012, European Journal of Endocrinology 167: 301-309).

Since FGF19 and FGF21 require both FGFRs and beta klotho for cell signaling, agents which mimic FGF19 and/or FGF21 may be desirable for their effects or glucose metabolism or lipid metabolism. However, it is not clear what features are required for an agent to confer FGF19-like or FGF21-like cell signaling activity.

SUMMARY

The present disclosure provides proteins that bind to beta klotho, including binding proteins such as antibodies that bind to beta klotho. Such binding proteins including antibodies, may bind to a beta klotho polypeptide, a beta klotho fragment and/or a beta klotho epitope. Such binding proteins, including antibodies, may be agonists (e.g., induce FGF19-like or FGF21-like signaling of a FGF receptor or activate a beta klotho/FGF receptor complex).

The present disclosure also provides binding proteins, including antibodies or fragments thereof, that (i) bind to human beta klotho, (ii) induce FGF19-like signaling and/or FGF21-like signaling, and (iii) do not compete with FGF19 and/or FGF21 for the interaction with beta klotho.

In some embodiments, the anti-beta klotho antibodies are humanized antibodies that bind to a beta klotho polypeptide, a beta klotho fragment, or a beta klotho epitope. In certain embodiments, an anti-beta klotho antibody comprises a VH CDR1, VH CDR2, VH CDR3, VL CDR1, VL CDR2, and/or VL CDR3 of a monoclonal antibody designated 5H23, 1C17, 1D19, 2L12, 3L3, 3N20, 4P5, 5C23, 5F7 or 1G19 as described herein, or a humanized variant thereof. In certain embodiments, an anti-beta klotho antibody can further comprise a VH FR1, VH FR2, VH FR3, VH FR4, VL FR1, VL FR2, VL FR3, and/or VL FR4 of a human immunoglobulin amino acid sequence or a variant thereof.

In some embodiments, a binding protein (e.g., an anti-beta klotho antibody) comprises six CDRs or less than six CDRs. In some embodiments, a binding protein (e.g., an anti-beta klotho antibody) comprises one, two, three, four, five, or six CDRs selected from VH CDR1, VH CDR2, VH CDR3, VL CDR1, VL CDR2, and/or VL CDR3. In some embodiments, a binding protein (e.g., an anti-beta klotho antibody) comprises one, two, three, four, five, or six CDRs selected from VH CDR1, VH CDR2, VH CDR3, VL CDR1, VL CDR2, and/or VL CDR3 of a monoclonal antibody designated as 5H23, 1C17, 1D19, 2L12, 3L3, 3N20, 4P5, 5C23, 5F7 or 1G19 as described herein, or a humanized variant thereof. In some embodiments, a binding protein (e.g., an anti-beta klotho antibody) further comprises a scaffold region or frame work region, including a VH FR1, VH FR2, VH FR3, VH FR4, VL FR1, VL FR2, VL FR3, and/or VL FR4 of a human immunoglobulin amino acid sequence or a variant thereof.

In some embodiments, the antibody is a humanized antibody, a monoclonal antibody, a recombinant antibody, an antigen binding fragment or any combination thereof. In some embodiments, the antibody is a humanized monoclonal antibody, or antigen binding fragment thereof, that binds to a beta klotho polypeptide (e.g., a cell surface-expressed or soluble beta klotho), a beta klotho fragment, or a beta klotho epitope.

The present disclosure also provides binding proteins such as anti-beta klotho antibodies (i) that competitively block (e.g., in a dose-dependent manner) an anti-beta klotho antibody provided herein from binding to a beta klotho polypeptide (e.g., a cell surface-expressed or soluble beta klotho), a beta klotho fragment, or a beta klotho epitope and/or (ii) that bind to a beta klotho epitope that is bound by an anti-beta klotho antibody provided herein. In other embodiments, the binding proteins such as anti-beta klotho antibody competitively blocks (e.g., in a dose-dependent manner) monoclonal antibody 5H23 or 1G19 described herein or a humanized variant thereof from binding to a beta klotho polypeptide (e.g., a cell surface-expressed or soluble beta klotho), a beta klotho fragment, or a beta klotho epitope. In other embodiments, the binding proteins such as anti-beta klotho antibody binds to a beta klotho epitope that is bound (e.g., recognized) by monoclonal antibody 5H23, or 1G19 described herein or a humanized variant thereof.

The present disclosure also provides binding proteins, including antibodies or fragments thereof, that (i) bind to an epitope of human beta klotho and cynomologous monkey beta klotho recognized by an antibody comprising a heavy chain variable region having the amino acid sequence of SEQ ID NO:25 and a light chain variable region having the amino acid sequence of SEQ ID NO:26; or (ii) compete for the binding to human beta klotho with an antibody comprising a heavy chain variable region having the amino acid sequence of SEQ ID NO:25 and a light chain variable region having the amino acid sequence of SEQ ID NO:26. In some embodiments, binding proteins, including antibodies or fragments thereof, are provided herein that bind to a region, including an epitope, of human beta klotho or cyno beta klotho. In some embodiments, binding proteins, including antibodies or fragments thereof, bind to a region of human beta klotho or cycno beta klotho including, for example, those that bind to: (i) a KLB2 domain of human beta klotho comprising amino acid residues 509 to 1044 of SEQ ID NO:297; (ii) a glycosyl hydrolase 1 region of a KLB2 domain of human beta klotho comprising amino acid residues 517 to 967 of SEQ ID NO:297; (iii) a region of human beta klotho comprising amino acid residues 657 to 703 of SEQ ID NO:297; or (iv) a region of cyno beta klotho comprising amino acid residues 657 to 703 of SEQ ID NO:299.

In some embodiments, binding proteins, including antibodies or fragments thereof, are provided herein that bind to a specific epitope of human beta klotho, including, for example, those that bind to: (i) an epitope of human beta klotho comprising at least one of amino acid residues 657, 701 and/or 703 of human beta klotho (SEQ ID NO: 297); (ii) an epitope of human beta klotho comprising at least amino acid residue 657 of SEQ ID NO: 297; (iii) an epitope of human beta klotho comprising at least amino acid residue 701 of SEQ ID NO: 297; (iv) an epitope of human beta klotho comprising at least amino acid residue 703 of SEQ ID NO: 297; (v) an epitope of human beta klotho comprising at least amino acid residues 657 and 701 of SEQ ID NO: 297; (vi) an epitope of human beta klotho comprising at least amino acid residues 657 and 703 of SEQ ID NO: 297; (vii) an epitope of human beta klotho comprising at least amino acid residues 701 and 703 of SEQ ID NO: 297; or (viii) an epitope of human beta klotho comprising at least amino acid residues 657, 701 and 703 of SEQ ID NO: 297. Such antibodies provided above can, in some embodiments, induce FGF19-like signaling and/or FGF21-like signaling or activate a beta klotho/FGF receptor complex in a cell that expresses human beta klotho and an FGF receptor. Additionally, in some embodiments, the antibody is a monoclonal antibody, for example, a humanized, human or chimeric antibody.

In some embodiments, the binding proteins such as antibeta klotho antibodies provided herein are conjugated or recombinantly linked to a diagnostic agent, detectable agent or therapeutic agent. In some aspects, the therapeutic agent is a drug, including one or more drugs such as biguanides and sulphonylureas (e.g., metformin tolbutamide, chlorpropamide, acetohexamide, tolazamide, glibenclamide, glyburide, and glipizide), thiazolidinediones (e.g., rosiglitazone, pioglitazone), GLP-1 analogues, PPAR gamma agonists (e.g., pioglitazone and rosiglitazone), dipeptidyl peptidase-4 (DPP-4) inhibitors, (e.g., JANUVIN®, ONGLYZA®) bromocriptine formulations and bile acid sequestrants (e.g., colesevelam), and insulin (e.g., bolus and basal analogs), alpha glucosidase inhibitors (e.g., acarbose, roglibose), metformin (e.g., metformin hydrochloride) with or without a thiazolidinedione (TZD), SGLT-2 inhibitors, appetite suppression or weight loss drugs (e.g., Meridia®/sibutramine, Xenical®/ortistat). In some aspects, the detectable agent is a radioisotope, an enzyme, a fluorescent compound, a bioluminescent compound or a chemiluminescent compound.

In certain embodiments, compositions are provided comprising a binding protein such as an anti-beta klotho antibody described herein. Also provided herein are pharmaceutical compositions comprising a binding protein such as an beta klotho antibody as described herein.

The present disclosure also provides isolated nucleic acid molecules encoding an immunoglobulin heavy chain, an immunoglobulin light chain, VH region, VL region, VH CDR1, VH CDR2, VH CDR3, VL CDR1, VL CDR2, and/or VL CDR3 of binding proteins (e.g., anti-beta klotho antibodies) that bind to a beta klotho polypeptide, a beta klotho polypeptide fragment, or a beta klotho epitope. In some embodiments, the nucleic acid molecule encodes a VH region, VL region, VH CDR1, VH CDR2, VH CDR3, VL CDR1, VL CDR2, and/or VL CDR3 of a monoclonal antibody designated as 5H23, 1C17, 1D19, 2L12, 3L3, 3N20, 4P5, 5C23, 5F7 or 1G19 as described herein, or a humanized variant thereof. In some embodiments, the nucleic acid molecule further encodes a scaffold region or a framework region, including VH FR1, VH FR2, VH FR3, VH FR4, VL FR1, VL FR2, VL FR3, and/or VL FR4 of a human immunoglobulin amino acid sequence or a variant thereof. Also provided herein are vectors and host cells comprising the nucleic acid molecules encoding an a binding protein such as anti-beta klotho antibody, as well as methods of producing a binding protein such as an anti-beta klotho antibody by culturing the host cells provided herein under conditions that promote the production of a binding protein such as an anti-beta klotho antibody.

The present disclosure also provides methods of treating, preventing or alleviating a disease, disorder or condition (e.g., one or more symptoms) comprising administering a therapeutically effective amount of a binding protein such as an anti-beta klotho antibody provided herein to a subject, including a subject in need thereof, thereby treating, preventing or alleviating the disease, disorder or condition. In some embodiments, the disease, disorder or condition is caused by or otherwise associated with beta klotho, such as those related to FGF19-like and/or FGF21-like signaling in a subject. In certain embodiments, the disease is treatable by lowering blood glucose, insulin or serum lipid levels (e.g., Type 2 diabetes, obesity, dyslipidemia, NASH, cardiovascular disease, metabolic syndrome).

In some embodiments, the disease, disorder or condition is related to glucose metabolism or lipid metabolism. In some embodiments, the disease, disorder or condition is selected from the group of a hyperglycemic condition. (e.g., diabetes, such as Type 1 diabetes, Type 2 diabetes, gestational diabetes, insulin resistance, hyperinsulinemia, glucose intolerance, metabolic syndrome, or obesity).

In some embodiments, the methods of treating, preventing or ameliorating include methods of improving glucose metabolism and/or methods of improving lipid metabolism. In some embodiments, the methods of treating, preventing or ameliorating result in reduced glucose levels (e.g., reduced blood glucose), increased insulin sensitivity, reduced insulin resistance, reduced glycogen, improved glucose tolerance, improved glucose tolerance, improved glucose metabolism, improved homeostasis, improved pancreatic function, reduced triglycerides, reduced cholesterol, reduced IDL, reduced LDL, reduced VLDL, decreased blood pressure, decreased internal thickening of a blood vessel and/or decreased body mass or weight gain.

The present disclosure provides methods of treating a disease, disorder or condition associated with human FGF19 and/or human FGF21, which includes any disease, disorder or condition whose onset in a subject (e.g., a patient) is caused by, at least in part, the induction of FGF19-like and/or FGF21-like signaling, which is initiated in vivo by the formation of a complex comprising FGFR1c, FGFR2c, FGFR3c or FGFR4 and beta klotho and FGF19 or FGF21. The severity of the disease or condition can also be decreased by the induction of FGF19-like and/or FGF21-like signaling. Examples of diseases and conditions that can be treated with the binding proteins such as anti-beta klotho antibodies include type 2 diabetes, obesity, dyslipidemia, NASH, cardiovascular disease, and metabolic syndrome.

As such, the binding proteins such as anti-beta klotho antibodies described herein can be used to treat type 2 diabetes, obesity, dyslipidemia (e.g., hypertriglyceridemia), NASH, cardiovascular disease, and/or metabolic syndrome, as well as any disease, disorder, or condition in which it is desirable to mimic or augment the in vivo effects of FGF19 and/or FGF21, or can be employed as a prophylactic treatment administered, for example, daily, weekly, biweekly, monthly, bimonthly, biannually, etc. to prevent or reduce the frequency and/or severity of symptoms (e.g., elevated plasma glucose levels, elevated triglycerides and cholesterol levels), including, for example, to thereby provide an improved glycemic and/or cardiovascular risk factor profile. The present disclosure provides methods of improving metabolic parameters by administering to a subject a binding protein, including an antibody or fragment thereof as described herein or an pharmaceutical composition described herein, including, for example, wherein the improvement includes a decrease in body weight, body mass index, abdominal circumference, skinfold thickness, glucose, insulin and/or triglycerides.

The present disclosure also provides methods of inducing FGF19-like or FGF21-like signaling of cells having cell surface expression of beta klotho and one or more FGF receptors, such as FGFR1, FGFR2, FGFR3, or FGFR4 comprising contacting the cells with an effective amount of a binding protein (e.g., an antibody) that binds to beta klotho as described herein. In some embodiments, the cell is an adipocyte or hepatocyte. In other embodiments, the cell is a cell transfected with a gene encoding beta klotho and optionally a gene encoding an FGF receptor. Additional methods provided include using an anti-beta klotho antibody as described herein, with activity to mediate FGF19-like and/or FGF21 like signaling effects.

The present disclosure also provides methods of modulating an FGF19-like or FGF21-like signaling in a subject comprising administering an effective amount of a binding protein such as an anti-beta klotho antibody as described herein to a subject, including a subject in need thereof. In some embodiments, the modulating comprises FGF19-like activation. In some embodiments, the modulating comprises FGF21-like activation. In some embodiments, the modulating comprises increasing glucose metabolism (e.g., reducing glucose levels such as blood glucose levels).

The present disclosure also provides methods for detecting beta klotho in a sample comprising contacting the sample with a binding protein such as an anti-beta klotho antibody as described herein, that comprises a detectible agent. In certain embodiments, the sample comprises a cell expressing beta klotho on its surface.

The present disclosure also provides kits comprising a binding protein such as an anti-beta klotho antibody that binds to a beta klotho polypeptide, a beta klotho fragment or a beta klotho epitope as described herein.

BRIEF DESCRIPTION OF THE FIGURES

FIG. 1A-1B shows a sequence alignment of the heavy chain variable regions and light chain variable regions of the anti-beta klotho antibodies designated 5H23, 1C17, 1D19, 2L12, 3L3, 3N20, 4P5, 5C23, 5F7 and 1G19. Boundaries of CDRs are indicated by Kabat, AbM, Chothia, Contact and IMGT numbering.

FIGS. 2A-1 and 2A-2 shows sequence alignments of the heavy chain variable regions of the anti-beta klotho antibodies providing consensus CDR sequences. Top grouping consists of antibodies designated 5H23, 1 D19, 2L12, 3L3, 4P5, 5C23 and 5F7. Lower grouping consists of antibodies designated 1C17 and 1G19. Bottom grouping consists only of the antibody designated 3N20 Variable residues are presented by "X." Boundaries of CDRs are indicated by Kabat, AbM, Chothia, Contact and IMGT numbering.

FIGS. 2B-1 and 2B-2 shows sequence alignments of the light chain variable regions of the anti-beta klotho antibodies providing consensus CDR sequences. Top grouping consists of antibodies designated 5H23, 1 D19, 2L12, 3L3, 4P5, 5C23 and 5F7. Lower grouping consists of antibodies designated 1C17 and 1G19. Bottom grouping consists only of the antibody designated 3N20. Variable residues are presented by "X." Boundaries of CDRs are indicated by Kabat, AbM, Chothia, Contact and IMGT numbering.

FIGS. 3A-1 and 3A-2 shows a sequence alignment of the heavy chain variable region of anti-beta klotho antibody designated 5H23 with the humanized sequences (vH1-vH9). Residues that are bolded indicate exemplary residues that have been modified from the original antibody. Residues that are bolded and underlined indicate residues altered back to a mouse residue.

FIG. 3B shows a sequence alignment of the light chain variable region of anti-beta klotho antibody designated 5H23 with the humanized sequences (vL1-vL5). Residues that are bolded indicate exemplary residues that have been modified. Residues that are bolded and underlined indicate residues altered back to a mouse residue.

FIGS. 3C-1 and 3C-2 shows a sequence alignment of the light chain variable region of anti-beta klotho antibody designated 5H23 with the humanized sequences (v1-39a-v1-39p). Residues that are bolded indicate exemplary residues that have been modified.

FIGS. 3D-1 and 3D-2 shows a sequence alignment of a light chain variable region of anti-beta klotho antibody designated 5H23 with various humanized sequences (v3-20a-v3-20j). Residues that are bolded indicate exemplary residues that have been modified.

FIG. 4A-4C shows a sequence alignment between human, mouse and chimeric beta klotho polypeptides. Chimeric polypeptide chMoHu indicates mouse KLB(M1-F506)-human KLB(S509-S1044). Chimeric polypeptide chHuMo indicates human KLB (M1-F508)-mouse KLB (P507-S1043). Residues corresponding to mouse residues are bolded and italicized.

FIG. 5A-5F shows a sequence alignment between beta klotho polypeptides from various species described herein.

DETAILED DESCRIPTION

Figure 6:
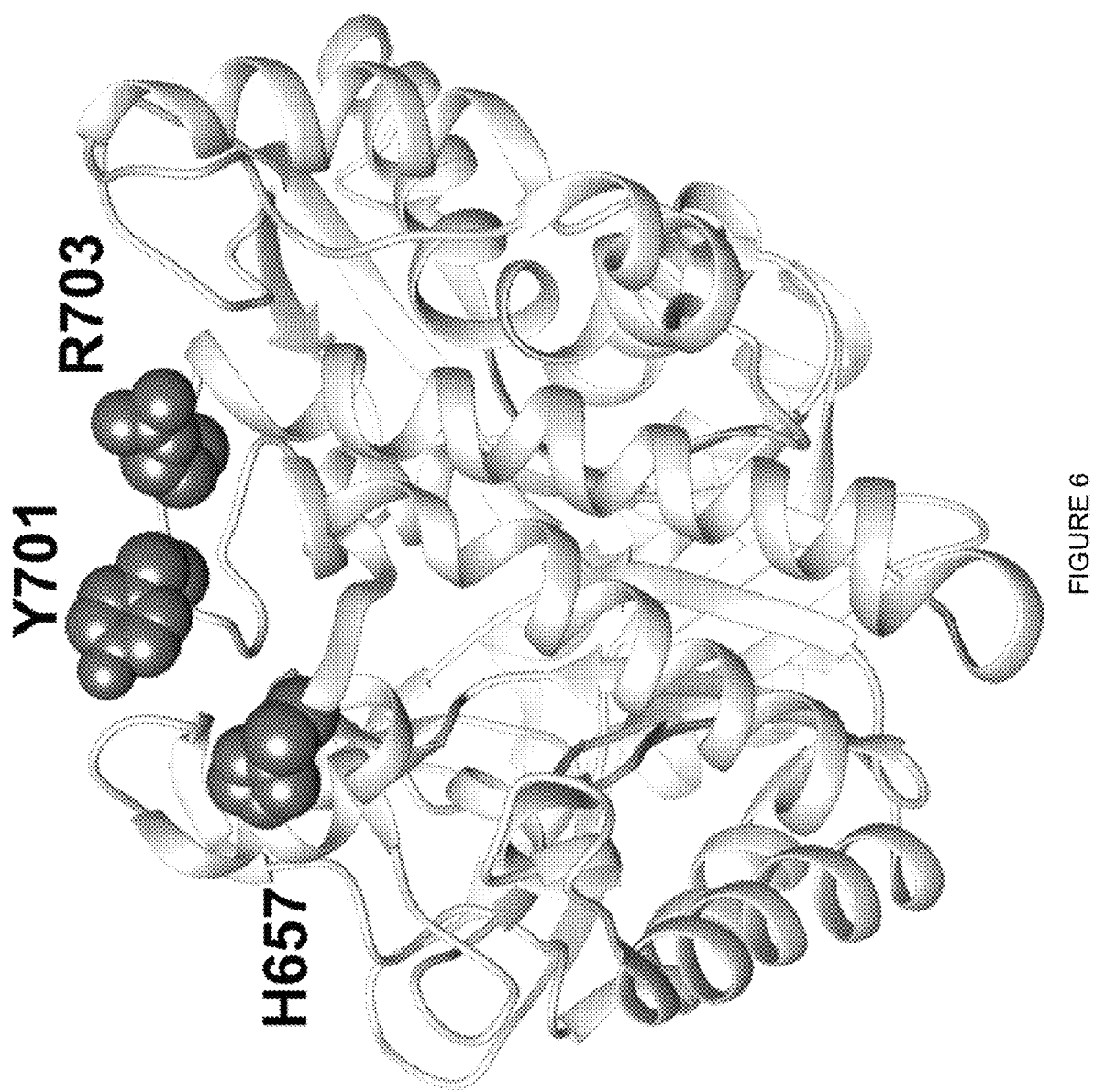
FIG. 6 shows a three-dimensional model of the three identified binding residues (dark spheres) at the equivalent positions on human cytosolic beta-glucosidase. The structure shows the equivalent of Klotho-beta residues 521-963.

Binding proteins, such as antibodies that bind beta klotho, including human and/or cyno beta klotho, are provided herein. A unique property of such binding proteins, including antibodies disclosed herein, is their agonistic nature, including the ability to mimic the in vivo effect of FGF19 and/or FGF21 and to induce FGF19-like signaling and/or FGF21-like signaling. More remarkably and specifically, some of the binding proteins such as antibodies to beta klotho disclosed herein (i) bind to human and cyno beta klotho, (ii) do not compete for binding with FGF19 and/or FGF21, and (iii) induce FGF19-like signaling and/or FGF21-like signaling, including, for example, in several in vitro cell-based assays. Such assays may include (1) an ELK-luciferase reporter assay (see, e.g., Example 4); (2) a recombinant FGF19 receptor mediated cell assay for ERK-phosphorylation (see, e.g., Example 4); and (3) a human adipocyte assay for ERK-phosphorylation (see, e.g., Example 5). Binding proteins such as anti-beta klotho antibodies, as described herein, therefore are expected to exhibit activities in vivo that are consistent with the natural biological function of FGF19 and/or FGF21. This property makes the disclosed binding proteins, including anti-beta klotho antibodies, viable therapeutics for the treatment of metabolic diseases (e.g., Type 2 diabetes, obesity, dyslipidemia, NASH, cardiovascular disease, metabolic syndrome) and broadly any disease, disorder, or condition in which it is desirable to mimic or augment the in vivo effects of FGF19 and/or FGF21.

The binding proteins, such as antibodies that bind beta klotho, that are provided herein share the common feature of competing with each other for the binding of beta klotho (see, e.g., Example 3 describing antibodies in the 5H23 epitope bin). This competitive inhibition indicates that each antibody binds to the same region of beta klotho (e.g., the same epitope), thereby asserting similar effects. The anti-beta klotho antibodies provided herein include humanized anti-beta klotho antibodies, including humanized anti-beta klotho antibodies derived from or based on 5H23, 1C17, 1D19, 2L12, 3L3, 3N20, 4P5, 5C23, 5F7 and/or 1G19 having CDR sequence as described in Tables 1-10 or FIGS. 1-3, such as anti-beta klotho antibodies, including humanized anti-beta klotho antibodies, bind to a specific domain of human beta klotho (e.g., KL2 (residues S509-S1044); see Example 9). Moreover, such binding can be largely attributed to particular amino acid residues within the KL2 region (e.g., H657, Y701 and R703), which comprise the epitope recognized by the anti-beta klotho antibodies described herein. Taken together, the results described herein demonstrate that the effects observed for an anti-beta klotho antibody that is derived from or based on 5H23 or an antibody in the 5H23 eptitope bin, including an antibody having one or more CDRs described in Tables 1-10 or FIGS. 1-3, can be extrapolated to other anti-beta klotho antibodies described herein having the same or similar eptitope specificity (e.g., the same or similar CDRs). For example, the in vitro activities of antibodies as shown in Examples 4-7 and 9, as well as the in vivo effects demonstrated in Example 8 for an exemplary humanized anti-beta klotho antibody, are representative of the activates and effects of the the anti-beta klotho antibodies described herein.

In some embodiments of the present disclosure, the binding proteins such as anti-beta klotho antibodies may comprise immunoglobulin variable regions which comprise one or more complementary determining regions (CDRs) as described in Tables 1-10. In such binding proteins (e.g., anti-beta klotho antibodies), the CDRs may be joined with one or more scaffold regions or framework regions, which orient(s) the CDR(s) such that the proper antigen binding properties of the CDR(s) is achieved. Such binding proteins, including anti-beta klotho antibodies as described herein, can facilitate or enhance the interaction between FGFR1c and beta klotho, and can induce FGF19-like and/or FGF21-like signaling.

General Techniques

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (F. M. Ausubel, et al. eds., (2003)); Therapeutic Monoclonal Antibodies: From Bench to Clinic, Z. An, ed, Wiley, Hoboken N.J. (2009); Monoclonal Antibodies: Methods and Protocols, M. Albitar, ed., Humana Press, Totawa, N.J. (2010); and Antibody Engineering, 2nd Ed., Vols 1 and 2, Kontermann and Dubel, eds., Springer-Verlag, Heidelberg, 2010.

Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications and other publications are incorporated by reference in their entirety. In the event that any description of terms set forth conflicts with any document incorporated herein by reference, the description of term set forth below shall control.

The term "beta klotho" or "beta klotho polypeptide" and similar terms refers to a polypeptide ("polypeptide," and "protein" are used interchangeably herein) or any native beta klotho from any vertebrate source, including mammals such as primates (e.g., humans, cynomolgus monkey (cyno)), dogs, and rodents (e.g., mice and rats), unless otherwise indicated, and, in certain embodiments, included related beta klotho polypeptides, including SNP variants thereof. Beta klotho comprises two domains, beta klotho 1 (KLB1) and beta klotho 2 (KLB2). Each beta klotho domain comprises a glycosyl hydrolase 1 region. For example, the KLB1 domain of human beta klotho comprises amino acid residues 1-508 with the glycosyl hydrolase 1 region comprising amino acid residues 77-508, and the KLB2 domain of human beta klotho comprises amino acid residues 509-1044 with the glycosyl hydrolase 1 region comprising amino acid residues 517-967. The amino acid sequence of human beta klotho is provided below:

```
                                                    (SEQ ID NO: 297)
   1 MKPGCAAGSP GNEWIFFSTD EITTRYRNTM SNGGLQRSVI LSALILLRAV

51 TGFSGDGRAI WSKNPNFTPV NESQLFLYDT FPKNFFWGIG TGALQVEGSW

101 KKDGKGPSIW DHFIHTHLKN VSSTNGSSDS YIFLEKDLSA LDFIGVSFYQ

151 FSISWPRLFP DGIVTVANAK GLQYYSTLLD ALVLRNIEPI VTLYHWDLPL

201 ALQEKYGGWK NDTIIDIFND YATYCFQMFG DRVKYWITIH NPYLVAWHGY

251 GTGMHAPGEK GNLAAVYTVG HNLIKAHSKV WHNYNTHFRP HQKGWLSITL

301 GSHWIEPNRS ENTMDIFKCQ QSMVSVLGWF ANPIHGDGDY PEGMRKKLFS

351 VLPIFSEAEK HEMRGTADFF AFSFGPNNFK PLNTMAKMGQ NVSLNLREAL

401 NWIKLEYNNP RILIAENGWF TDSRVKTEDT TAIYMMKNFL SQVLQAIRLD

451 EIRVFGYTAW SLLDGFEWQD AYTIRRGLFY VDFNSKQKER KPKSSAHYYK

501 QIIRENGFSL KESTPDVQGQ FPCDFSWGVT ESVLKPESVA SSPQFSDPHL

551 YVWNATGNRL LHRVEGVRLK TRPAQCTDFV NIKKQLEMLA RMKVTHYRFA

601 LDWASVLPTG NLSAVNRQAL RYYRCVVSEG LKLGISAMVT LYYPTHAHLG

651 LPEPLLHADG WLNPSTAEAF QAYAGLCFQE LGDLVKLWIT INEPNRLSDI

701 YNRSGNDTYG AAHNLLVAHA LAWRLYDRQF RPSQRGAVSL SLHADWAEPA

751 NPYADSHWRA AERFLQFEIA WFAEPLFKTG DYPAAMREYI ASKHRRGLSS

801 SALPRLTEAE RRLLKGTVDF CALNHFTTRF VMHEQLAGSR YDSDRDIQFL

851 QDITRLSSPT RLAVIPWGVR KLLRWVRRNY GDMDIYITAS GIDDQALEDD

901 RLRKYYLGKY LQEVLKAYLI DKVRIKGYYA FKLAEEKSKP RFGFFTSDFK

951 AKSSIQFYNK VISSRGFPFE NSSSRCSQTQ ENTECTVCLF LVQKKPLIFL

1001 GCCFFSTLVL LLSIAIFQRQ KRRKFWKAKN LQHIPLKKGK RVVS
```

An encoding nucleic acid sequence of human beta klotho is provided below:

```
                                              (SEQ ID NO: 298)
atgaagccaggctgtgcggcaggatctccagggaatgaatggattttctt cagcactgatgaaataaccacacgctataggaatacaatgtccaacgggg gattgcaaagatctgtcatcctgtcagcacttattctgctacgagctgtt actggattctctggagatggaagagctatatggtctaaaaatcctaatttt tactccggtaaatgaaagtcagctgttttctctatgacactttccctaaaa acttttctggggtattgggactggagcattgcaagtggaagggagttgg aagaaggatggaaaaggaccttctatatgggatcatttcatccacacaca ccttaaaaatgtcagcagcacgaatggttccagtgacagttatattttc tggaaaaagacttatcagccctggattttataggagtttcttttatcaa ttttcaatttcctggccaaggcttttccccgatggaatagtaacagttgc caacgcaaaaggtctgcagtactacagtactcttctggacgctctagtgc ttagaaacattgaacctatagttactttataccactgggatttgcctttg gcactacaagaaaatatggggggtggaaaaatgataccataatagatat cttcaatgactatgccacatactgtttccagatgtttggggaccgtgtca aatattggattacaattcacaacccatatctagtggcttggcatgggtat gggacaggtatgcatgccctggagagaaggggaaatttagcagctgtcta cactgtgggacacaacttgatcaaggctcactcgaaagtttggcataact acaacacacatttccgcccacatcagaagggttggttatcgatcacgttg ggatctcattggatcgagccaaaccggtcggaaaacacgatggatatatt caaatgtcaacaatccatggtttctgtgcttggatggtttgccaaccccta tccatggggatggcgactatccagaggggatgagaaagaagttgttctcc
```

-continued
```
gttctacccatttttctctgaagcagagaagcatgagatgagaggcacagc
tgatttctttgccttttcttttggacccaacaacttcaagcccctaaaca
ccatggctaaaatgggacaaaatgtttcacttaatttaagagaagcgctg
aactggattaaactggaatacaacaaccctcgaatcttgattgctgagaa
tggctggttcacagacagtcgtgtgaaaacagaagacaccacggccatct
acatgatgaagaatttcctcagccaggtgcttcaagcaataaggttagat
gaaatacgagtgtttggttatactgcctggtctctcctggatggctttga
atggcaggatgcttacaccatccgccgaggattattttatgtggatttta
acagtaaacagaaagagcggaaacctaagtcttcagcacactactacaaa
cagatcatacgagaaatggtttttctttaaaagagtccacgccagatgt
gcagggccagtttcctgtgacttctcctggggtgtcactgaatctgttc
ttaagcccgagtctgtggcttcgtcccacagttcagcgatcctcatctg
tacgtgtggaacgccactggcaacagactgttgcaccgagtggaaggggt
gaggctgaaaacacgacccgctcaatgcacagattttgtaaacatcaaaa
aacaacttgagatgttggcaagaatgaaagtcacccactaccggtttgct
ctggattgggcctcggtccttcccactggcaacctgtccgcggtgaaccg
acaggccctgaggtactacaggtgcgtggtcagtgaggggctgaagcttg
gcatctccgcgatggtcaccctgtattatccgacccacgcccacctaggc
ctccccgagcctctgttgcatgccgacgggtggctgaacccatcgacggc
cgaggccttccaggcctacgctgggctgtgcttccaggagctggggacc
tggtgaagctctggatcaccatcaacgagcctaaccggctaagtgacatc
tacaaccgctctggcaacgacacctacggggcggcgcacaacctgctggt
```

-continued
```
ggcccacgccctggcctggcgcctctacgaccggcagttcaggccctcac
agcgcggggccgtgtcgctgtcgctgcacgcggactgggcggaacccgcc
aaccctatgctgactcgcactggagggcggccgagcgcttcctgcagtt
cgagatcgcctggttcgccgagccgtcttcaagaccggggactacccg
cggccatgagggaatacattgcctccaagcaccgacgggggctttccagc
tcggccctgccgcgcctcaccgaggccgaaaggaggctgctcaagggcac
ggtcgacttctgcgcgctcaaccacttcaccactaggttcgtgatgcacg
agcagctggccggcagccgctacgactcggacagggacatccagtttctg
caggacatcacccgcctgagctcccccacgcgcctggctgtgattccctg
gggggtgcgcaagctgctgcggtgggtccggaggaactacggcgacatgg
acatttacatcaccgccagtggcatcgacgaccaggctctggaggatgac
cggctccggaagtactacctagggaagtaccttcaggaggtgctgaaagc
atacctgattgataaagtcagaatcaaaggctattatgcattcaaactgg
ctgaagagaaatctaaacccagatttggattcttcacatctgattttaaa
gctaaatcctcaatacaattttacaacaaagtgatcagcagcaggggctt
cccttttgagaacagtagttctagatgcagtcagacccaagaaaatacag
agtgcactgtctgcttattccttgtgcagaagaaaccactgatattcctg
ggttgttgcttcttctccaccctggttctactcttatcaattgccatttt
tcaaaggcagaagagaagaaagttttggaaagcaaaaaacttacaacaca
taccattaaagaaaggcaagagagttgttagc
```

The amino acid sequence of beta klotho from cynomolgus monkey (cyno), scientific name *Macaca fascicularis*, is provided below:

(SEQ ID NO: 299)
```
  1 MKPGCAAGSP GNEWIFFSTD EITIRYRNTM SNGGLQRSVI LSALTLLRAV
 51 TGFSGDGRAV WSKNPNFTPV NESQLFLYDT FPKNFFWGVG TGALQVEGSW
101 KKDGKGPSIW DHFVHTHLKN VSSTNGSSDS YIFLEKDLSA LDFIGVSFYQ
151 FSISWPRLFP DGIVTVANAK GLQYYNTLLD SLVLRNIEPI VTLYHWDLPL
201 ALQEKYGGWK NDTIIDIFND YATYCFQTFG DRVKYWITIH NPYLVAWHGY
251 GTGMHAPGEK GNLAAVYTVG HNLIKAHSKV WHNYNTHFRP HQKGWLSITL
301 GSHWIEPNRS ENTMDILKCQ QSMVSVLGWF ANPIHGDGDY PEGMKKKLLS
351 ILPLFSEAEK NEVRGTADFF AFSFGPNNFK PLNTMAKMGQ NVSLNLREAL
401 NWIKLEYNNP RILIAENGWF TDSHVKTEDT TAIYMMKNFL SQVLQAIRLD
451 EIRVFGYTAW SLLDGFEWQD AYTIRRGLFY VDFNSKQKER KPKSSAHYYK
501 QIIRENGFSL KEATPDVQGQ FPCDFSWGVT ESVLKPESVA SSPQFSDPYL
551 YVWNATGNRL LHRVEGVRLK TRPAQCTDFV NIKKQLEMLA RMKVTHYRFA
601 LDWASVLPTG NLSAVNRQAL RYYRCVVSEG LKLGISAMVT LYYPTHAHLG
651 LPEPLLHAGG WLNPSTVEAF QAYAGLCFQE LGDLVKLWIT INEPNRLSDI
701 YNRSGNDTYG AAHNLLVAHA LAWRLYDRQF RPSQRGAVSL SLHADWAEPA
751 NPYADSHWRA AERFLQFEIA WFAEPLFKTG DYPAAMREYI ASKHRRGLSS
801 SALPRLTEAE RRLLKGTVDF CALNHFTTRF VMHEQLAGSR YDSDRDIQFL
```

```
851 QDITRLSSPT RLAVIPWGVR KLLRWVRRNY GDMDIYITAS GIDDQALEDD

901 RLRKYYLEKY LQEVLKAYLI DKVRIKGYYA FKLAEEKSKP RFGFFTSDFK

951 AKSSIQFYNK MISSSGFPSE NSSSRCSQTQ KNTECTVCLF LVQKKPLIFL

1001 GCCFFSTLVL LLSITIFHRQ KRRKFWKAKN LQHIPLKKGK RVLS
```

An encoding nucleic acid sequence of cyno beta klotho is provided below:

(SEQ ID NO: 300)

```
atgaagcctggatgtgccgccggaagccccggcaacgagtggatcttctt
cagcaccgacgagatcaccatccggtacagaaacaccatgagcaacggcg
gcctgcagcggagcgtgatcctgtctgctctgaccctgctgagagccgtg
accggcttcagcggagatggcagagccgtgtggtccaagaaccccaactt
cacccccgtgaacgagagccagctgttcctgtacgataccttccccaaga
acttcttctggggcgtgggcacaggcgccctgcaggtggaaggatcctgg
aagaaggacggcaagggccccagcatctgggaccactttgtgcacaccca
cctgaagaacgtgtccagcaccacggcagcagcgacagctacatctttct
ggaaaaggacctgagcgccctggacttcatcggcgtgtccttctaccagt
tcagcatcagctggcccagactgttccccgacggcatcgtgacagtggcc
aatgccaagggcctgcagtactacaacaccctgctggacagcctggtgct
gcggaacatcgagcccatcgtgaccctgtaccactgggacctgccactgg
ctctgcaggagaaatacggcggctggaagaacgacaccatcatcgacatc
ttcaacgactacgccacctactgcttccagaccttcggcgacagagtgaa
gtactggatcacaatccacaaccctacctggtggcctggcacggctatg
gcaccggaatgcatgcccctggcgagaagggaaatctggccgccgtgtac
accgtgggccacaacctgatcaaggcccacgcaaagtgtggcacaacta
caatacccacttccggccccaccagaagggctggctgtctatcacactgg
gcagccactggatcgagcctaaccgcagcgagaacaccatggacatcctg
aagtgccagcagagcatggtgtccgtgctgggatggttcgccaaccccat
tcacggcgacggcgattaccccgagggcatgaagaagaagctgctgagca
tcctgcccctgttcagcgaggccgagaagaacgaagtgcggggcaccgcc
gatttcttcgcctttagcttcggccccaacaacttcaagcccctgaatac
catggccaagatgggccagaatgtgtccctgaacctgagagaggccctga
actggatcaagctggagtacaacaaccccgatcctgatcgccgagaac
ggctggttcaccgacagccacgtgaaaaccgaggacaccaccgccatcta
tatgatgaagaacttcctgagccaggtgctgcaggctatccggctggatg
agatccgggtgttcggctacaccgcctggtcactgctggacggcttcgaa
tggcaggacgcctacaccatcagacggggcctgttctacgtggacttcaa
cagcaagcagaaagagcggaagcccaagagcagcgcccactactacaagc
agatcatcagagagaatggcttcagcctgaaagaggccaccccgacgtg
cagggccagttcccttgtgatttctcttggggcgtgaccgagagcgtgct
gaagcctgaaagcgtggccagcagcccccagttcagcgaccccttacctgt
acgtgtggaacgccaccggcaaccggctgctgcatagagtggaaggcgtg
cggctgaaaaccagacccgcccagtgcaccgacttcgtgaacatcaagaa
acagctggaaatgctggcccggatgaaagtgacccactacagattcgccc
tggactgggccagcgtgctgcctaccggaaatctgagcgccgtgaacaga
caggccctgcggtactacagatgcgtggtgtccgagggcctgaagctggg
catcagcgccatggtcaccctgtactaccctaccacgcccacctgggac
tgcctgaacctctgctgcatgctggcggctggctgaaccctagcaccgtg
gaagcctttcaggcctacgccgggctgtgcttccaggaactgggcgacct
cgtgaagctgtggatcaccatcaacgagcccaacagactgagcgacatct
acaacagaagcggcaacgacacctacggcgctgcccacaatctgctggtg
gctcatgccctggcttggcggctgtacgacagacagttccggccttctca
gcggggagccgtgtctctgtctctgcatgccgattgggccgagcccgcca
accctttacgccgactctcattggagagccgccgagcggttcctgcagttc
gagatcgcttggtttgccgagcccctgttcaagaccggcgattaccctgc
cgccatgagagagtatatcgccagcaagcacagacggggcctgagcagct
ctgccctgcctagactgaccgaggccgagcggagactgctgaagggaacc
gtggatttctgcgccctgaaccacttcaccaccagattcgtgatgcacga
gcagctggccggcagcagatacgacagcgaccgggacatccagtttctgc
aggacatcacccggctgagcagccctacaagactggccgtgatcccttgg
ggagtgcggaagctgctgagatgggtgcgcagaaactacggcgacatgga
tatctacatcaccgccagcggcatcgacgaccaggccctggaagatgacc
ggctgcggaagtactacctggaaaagtacctgcaggaagtgctgaaggcc
tacctgatcgacaaagtgcggatcaagggctactacgccttcaagctggc
cgaggaaaagagcaagcccagattcggcttcttcaccagcgacttcaagg
ccaagagcagcatccagttctacaacaagatgatcagcagcagcggcttc
cccagcgagaacagcagctccagatgcagccagacccagaaaaacaccga
gtgtaccgtgtgcctgttcctggtgcagaagaagcccctgatcttcctgg
gctgctgcttctttagcaccctggtgctgctgctgtccatcaccatcttc
caccggcagaagcggaaaagttctggaaggccaaaaacctgcagcacat
cccccctgaagaaaggcaagcgggtgctgagctga
```

The amino acid sequence of beta klotho homolog from mouse, scientific name *Mus musculus*, is provided below:

(SEQ ID NO: 301)

```
   1 MKTGCAAGSP GNEWIFFSSD ERNTRSRKTM SNRALQRSAV LSAFVLLRAV
  51 TGFSGDGKAI WDKKQYVSPV NPSQLFLYDT FPKNFSWGVG TGAFQVEGSW
 101 KTDGRGPSIW DRYVYSHLRG VNGTDRSTDS YIFLEKDLLA LDFLGVSFYQ
 151 FSISWPRLFP NGTVAAVNAQ GLRYYRALLD SLVLRNIEPI VTLYHWDLPL
 201 TLQEEYGGWK NATMIDLFND YATYCFQTFG DRVKYWITIH NPYLVAWHGF
 251 GTGMHAPGEK GNLTAVYTVG HNLIKAHSKV WHNYDKNFRP HQKGWLSITL
 301 GSHWIEPNRT DNMEDVINCQ HSMSSVLGWF ANPIHGDGDY PEFMKTGAMI
 351 PEFSEAEKEE VRGTADFFAF SFGPNNFRPS NTVVKMGQNV SLNLRQVLNW
 401 IKLEYDDPQI LISENGWFTD SYIKTEDTTA IYMMKNFLNQ VLQAIKFDEI
 451 RVFGYTAWTL LDGFEWQDAY TTRRGLFYVD FNSEQKERKP KSSAHYYKQI
 501 IQDNGFPLKE STPDMKGRFP CDFSWGVTES VLKPEFTVSS PQFTDPHLYV
 551 WNVTGNRLLY RVEGVRLKTR PSQCTDYVSI KKRVEMLAKM KVTHYQFALD
 601 WTSILPTGNL SKVNRQVLRY YRCVVSEGLK LGVFPMVTLY HPTHSHLGLP
 651 LPLLSSGGWL NMNTAKAFQD YAELCFRELG DLVKLWITIN EPNRLSDMYN
 701 RTSNDTYRAA HNLMIAHAQV WHLYDRQYRP VQHGAVSLSL HCDWAEPANP
 751 FVDSHWKAAE RFLQFEIAWF ADPLFKTGDY PSVMKEYIAS KNQRGLSSSV
 801 LPRFTAKESR LVKGTVDFYA LNHFTTRFVI HKQLNTNRSV ADRDVQFLQD
 851 ITRLSSPSRL AVTPWGVRKL LAWIRRNYRD RDIYITANGI DDLALEDDQI
 901 RKYYLEKYVQ EALKAYLIDK VKIGYYAFK LTEEKSKPRF GFFTSDFRAK
 951 SSVQFYSKLI SSSGLPAENR SPACGQPAED TDCTICSFLV EKKPLIFFGC
1001 CFISTLAVLL SITVFHHQKR RKFQKARNLQ NIPLKKGHSR VFS
```

An encoding nucleic acid sequence of mouse beta klotho is provided below:

(SEQ ID NO: 302)

```
atgaagacaggctgtgcagcagggtctccggggaatgaatggatttttc
ttcagctctgatgaaagaaacacacgctctaggaaaacaatgtccaac
agggcactgcaaagatctgccgtgctgtctgcgtttgttctgctgcga
gctgttaccggcttctccggagacgggaaagcaatatggggataaaaaa
cagtacgtgagtccggtaaacccaagtcagctgttcctctatgacact
ttccctaaaaacttttcctggggcgttgggaccggagcatttcaagtg
gaagggagttggaagacagatggaagaggaccctcgatctgggatcgg
tacgtctactcacacctgagaggtgtcaacggcacagacagatccact
gacagttacatctttctggaaaaagacttgttggctctggattttta
ggagtttctttttatcagttctcaatctcctggccacggttgtttccc
aatggaacagtagcagcagtgaatgcgcaaggtctccggtactaccgt
gcacttctggactcgctggtacttaggaatatcgagcccattgttacc
ttgtaccattgggatttgcctctgacgctccaggaagaatatgggggc
tggaaaaatgcaactatgatagatctcttcaacgactatgccacatac
tgcttccagacccttggagaccgtgtcaaatattggattacaattcac
aacccttaccttgttgcttggcatgggtttggcacaggtatgcatgca
ccaggagagaagggaaatttaacagctgtctacactgtgggacacaac
ctgatcaaggcacattcgaaagtgtggcataactacgacaaaaacttc
cgccctcatcagaagggttggctctccatcaccttggggtcccattgg
atagagccaaacagaacagacaacatggaggacgtgatcaactgccag
cactccatgtcctctgtgcttggatggttcgccaaccccatccacggg
gacggcgactaccctgagttcatgaagacgggcgccatgatccccgag
ttctctgaggcagagaaggaggaggtgaggggcacggctgatttcttt
gccttttccttcgggcccaacaacttcaggccctcaaacaccgtggtg
aaaatgggacaaaatgtatcactcaacttaaggcaggtgctgaactgg
attaaactggaatacgatgaccctcaaatcttgatttcggagaacggc
tggttcacagatagctatataaagacagaggacaccacggccatctac
atgatgaagaatttcctaaaccaggttcttcaagcaataaaatttgat
gaaatccgcgtgtttggttatacggcctggactctcctggatggcttt
gagtggcaggatgcctatacgacccgacgagggctgttttatgtggac
tttaacagtgagcagaaagagaggaaacccaagtcctcggctcattac
tacaagcagatcatacaagacaacggcttcccttttgaaagagtccacg
ccagacatgaagggtcggttcccctgtgatttctcttggggagtcact
```

```
gagtctgttcttaagcccgagtttacggtctcctccccgcagtttacc
gatcctcacctgtatgtgtggaatgtcactggcaacagattgctctac
cgagtggaaggggtaaggctgaaaacaagaccatcccagtgcacagat
tatgtgagcatcaaaaaacgagttgaaatgttggcaaaaatgaaagtc
acccactaccagtttgctctggactggacctctatccttcccactggc
aatctgtccaaagttaacagacaagtgttaaggtactataggtgtgtg
gtgagcgaaggactgaagctgggcgtcttccccatggtgacgttgtac
cacccaacccactcccatctcggcctcccctgccacttctgagcagt
ggggggtggctaaacatgaacacagccaaggccttccaggactacgct
gagctgtgcttccgggagttgggggacttggtgaagctctggatcacc
atcaatgagcctaacaggctgagtgacatgtacaaccgcacgagtaat
gacacctaccgtgcagcccacaacctgatgatcgccatgcccaggtc
tggcacctctatgataggcagtataggccggtccagcatggggctgtg
tcgctgtccttacattgcgactgggcagaacctgccaaccccttgtg
gattcacactggaaggcagccgagcgcttcctccagtttgagatcgcc
tggtttgcagatccgctcttcaagactggcgactatccatcggttatg
aaggaatacatcgcctccaagaaccagcgagggctgtctagctcagtc
ctgccgcgcttcaccgcgaaggagagcaggctggtgaagggtaccgtc
gacttctacgcactgaaccacttcactacgaggttcgtgatacacaag
cagctgaacaccaaccgctcagttgcagacagggacgtccagttcctg
caggacatcacccgcctaagctcgcccagccgcctggctgtaacaccc
tggggagtgcgcaagctccttgcgtggatccggaggaactacagagac
agggatatctacatcacagccaatggcatcgatgacctggctctagag
gatgatcagatccgaaagtactacttggagaagtatgtccaggaggct
ctgaaagcatatctcattgacaaggtcaaaatcaaaggctactatgca
ttcaaactgactgaagagaaatctaagcctagatttggattttttcacc
tctgacttcagagctaagtcctctgtccagttttacagcaagctgatc
agcagcagtggcctccccgctgagaacagaagtcctgcgtgtggtcag
cctgcggaagacacagactgcaccattttgctcatttctcgtggagaag
aaaccactcatcttcttcggttgctgcttcatctccactctggctgta
ctgctatccatcaccgttttcatcatcaaaagagaagaaattccag
aaagcaaggaacttacaaaatataccattgaagaaaggccacagcaga
gttttcagc
```

The amino acid sequence of beta klotho from rat, scientific name *Rattus norvegicus*, is provided below:

```
                                        (SEQ ID NO: 356)
MKTGCAAGSPGNEVVVFFSSDERSTRSRKTMSNGALQRSAVLSALVLLR

AVTGFSGDGKAIWDKKQYVSPVNPGQLFLYDTFPKNFSWGVGTGAFQVE

GSWKADGRGPSIWDRYVDSHLRGVNSTDRSTDSYVFLEKDLLALDFLGV

SFYQFSISWPRLFPNGTVAAVNAKGLQYYRALLDSLVLRNIEPIVTLYH

WDLPLTLQEEYGGWKNATMIDLFNDYATYCFQTFGDRVKYWITIHNPYL

VAWHGFGTGMHAPGEKGNLTAVYTVGHNLIKAHSKVWHNYDKNFRPHQK

GWLSITLGSHWIEPNRTENMEDVINCQHSMSSVLGWFANPIHGDGDYPE

FMKTSSVIPEFSEAEKEEVRGTADFFAFSFGPNNFRPSNTVVKMGQNVS

LNLRQVLNWIKLEYDNPRILISENGWFTDSYIKTEDTTAIYMMKNFLNQ

VLQAIKFDEIQVFGYTAVVTLLDGFEWQDAYTTRRGLFYVDFNSEQKER

KPKSSAHYYKQIIQDNGFPLQESTPDMKGQFPCDFSWGVTESVLKPEFT

VSSPQFTDPHLYVWNVTGNRLLYRVEGVRLKTRPSQCTDYVSIKKRVEM

LAKMKVTHYQFALDVVTSILPTGNLSKINRQVLRYYRCVVSEGLKLGIS

PMVTLYHPTHSHLGLPMPLLSSGGWLNTNTAKAFQDYAGLCFKELGDLV

KLWITINEPNRLSDMYNRTSNDTYRAAHNLMIAHAQVWHLYDRQYRPVQ

HGAVSLSLHSDWAEPANPYVESHWKAAERFLQFEIAWFADPLFKTGDYP

LAMKEYIASKKQRGLSSSVLPRFTLKESRLVKGTIDFYALNHFTTRFVI

HKQLNTNCSVADRDVQFLQDITRLSSPSRLAVTPWGMRKLLGWIRRNYR

DMDIYVTANGIDDLALEDDQIRKYYLEKYVQEALKAYLIDKVKIKGYYA

FKLTEEKSKPRFGFFTSDFKAKSSVQFYSKLISSSGFSSENRSPACGQP

PEDTECAICSFLTQKKPLIFFGCCFISTLAALLSITIFHHRKRRKFQKA

RNLQNIPLKKGHSRVFS
```

An encoding nucleic acid sequence of rat beta klotho is provided below:

```
                                        (SEQ ID NO: 357)
ATGAAGACAGGCTGTGCAGCAGGGTCTCCAGGGAATGAATGGGTTTTCTT

CAGCTCTGATGAAAGAAGCACACGCTCTAGGAAAACAATGTCCAACGGAG

CACTGCAAAGATCTGCCGTGCTGTCTGCATTGGTTCTGCTGCGAGCTGTT

ACCGGCTTCTCTGGAGACGGAAAAGCAATATGGGATAAAAAACAATACGT

GAGTCCGGTAAACCCAGGTCAGCTGTTCCTCTATGACACTTTCCCTAAAA

ACTTTTCCTGGGGCGTTGGGACCGGAGCATTTCAAGTGGAAGGGAGTTGG

AAGGCAGATGGAAGAGGACCCTCGATCTGGGACCGTTATGTCGACTCACA

CCTGAGAGGTGTCAACAGCACAGACAGATCCACTGACAGTTATGTCTTTC

TGGAAAAGGACTTGCTGGCTCTGGATTTTTTAGGAGTTTCTTTTTATCAG

TTCTCAATCTCCTGGCCGCGGTTGTTCCCCAACGGAACAGTAGCAGCTGT

GAATGCAAAAGGTCTCCAGTACTACAGAGCACTTCTGGACTCGCTGGTAC

TTAGGAATATCGAACCCATTGTTACCTTATACCATTGGGATTTGCCTTTG

ACGCTACAGGAAGAATATGGGGGCTGGAAAAATGCAACTATGATAGATCT

CTTCAATGACTATGCCACATACTGCTTCCAGACCTTTGGAGACCGTGTCA

AATATTGGATTACAATTCACAACCCTTACCTCGTTGCTTGGCATGGGTTT

GGCACAGGTATGCATGCGCCAGGAGAGAAGGGAAATTTAACAGCTGTCTA

CACTGTGGGACACAACCTGATCAAGGCGCATTCGAAAGTGTGGCATAACT

ACGACAAAAACTTCCGCCCTCATCAGAAGGGTTGGCTCTCCATCACCTTG

GGGTCCCATTGGATAGAACCAAACAGAACAGAAAACATGGAGGACGTGAT

CAACTGCCAGCACTCCATGTCTTCTGTGCTCGGATGGTTTGCCAACCCCA
```

-continued
```
TCCACGGAGACGGCGACTACCCCGAGTTCATGAAGACGAGCTCCGTAATC
CCTGAGTTCTCTGAGGCAGAGAAGGAGGAGGTGCGGGGCACTGCTGACTT
CTTTGCCTTTTCCTTCGGGCCCAACAATTTCAGGCCCTCGAACACCGTGG
TAAAAATGGACAAAATGTATCACTCAACTTAAGACAGGTGCTGAACTGG
ATTAAACTAGAATATGACAACCCTCGAATCTTGATTTCGGAGAACGGCTG
GTTCACAGATAGTTATATAAAGACGGAAGATACCACGGCCATCTACATGA
TGAAGAATTTCCTCAACCAGGTTCTTCAAGCAATAAAGTTTGATGAAATA
CAAGTGTTTGGTTATACGGCTTGGACTCTCCTGGATGGCTTTGAGTGGCA
GGATGCCTACACGACCCGACGAGGGCTGTTTTATGTGGACTTTAATAGTG
AGCAGAAAGAGAGGAAACCCAAGTCCTCCGCTCATTACTACAAACAGATT
ATACAAGACAACGGTTTCCCTTTGCAAGAATCCACACCAGACATGAAGGG
TCAGTTTCCCTGTGACTTCTCCTGGGGAGTCACTGAGTCTGTTCTTAAGC
CGGAGTTTACGGTGTCCTCCCCACAGTTTACTGATCCTCACCTGTATGTG
TGGAATGTCACTGGCAACAGATTGCTATACCGAGTGGAAGGAGTCAGGCT
AAAAACAAGACCGTCCCAATGCACAGATTATGTGAGCATCAAAAAACGAG
TTGAAATGTTGGCCAAAATGAAAGTCACCCACTACCAGTTTGCTCTGGAC
TGGACCTCTATCCTCCCTACCGGAAATCTGTCTAAAATTAATAGACAAGT
GTTGAGGTACTATAGGTGTGTGGTGAGCGAAGGACTGAAGCTGGGCATCT
CCCCTATGGTGACGTTGTACCACCCGACCCACTCCCATCTAGGCCTCCCC
ATGCCACTTCTGAGCAGTGGGGATGGCTAAACACCAACACAGCCAAGGC
CTTCCAGGACTACGCAGGCCTGTGCTTCAAGGAGCTGGGGGACTTGGTAA
AGCTCTGGATCACCATCAATGAACCCAATAGGCTGAGTGACATGTACAAC
CGCACGAGTAACGACACCTACCGTGCGGCCCACAACCTGATGATCGCCCA
TGCCCAGGTCTGGCACCTCTATGATAGGCAGTATAGGCCGGTCCAGCACG
GGGCTGTGTCGCTGTCCTTACATTCCGACTGGGCAGAACCTGCCAACCCC
TATGTGGAGTCTCACTGGAAGGCAGCCGAGCGCTTCCTCCAGTTTGAGAT
CGCCTGGTTTGCGGATCCACTCTTCAAGACTGGTGACTACCCGCTGGCCA
TGAAGGAATACATCGCCTCCAAGAAGCAGCGAGGGCTGTCTAGCTCAGTC
CTGCCGCGCTTTACCTTGAAGGAGAGCAGGCTGGTGAAGGGGACCATCGA
CTTTTACGCACTGAACCACTTCACTACTAGATTCGTGATACACAAGCAGT
TGAATACCAACTGCTCAGTGGCAGACAGGGACGTCCAGTTCCTGCAGGAC
ATCACCCGCCTGAGCTCGCCCAGTCGCCTAGCCGTAACGCCCTGGGGAAT
GCGCAAGCTCCTTGGGTGGATCCGGAGGAACTACAGAGACATGGATATCT
ACGTCACAGCCAATGGCATTGATGATCTTGCTCTAGAGGACGATCAGATT
AGAAAGTACTACTTGGAGAAGTACGTCCAGGAGGCTCTGAAAGCATATCT
GATTGACAAGGTCAAAATCAAAGGCTACTATGCATTCAAACTGACTGAAG
AGAAATCTAAGCCTAGATTTGGATTTTTCACATCTGACTTCAAAGCTAAA
TCTTCTGTACAGTTTTATAGCAAGCTGATCAGCAGCAGCGGCTTCTCCTC
TGAGAACAGAAGTCCTGCCTGTGGTCAGCCTCCAGAAGACACAGAATGCG
CCATTTGCTCCTTCCTTACACAGAAGAAACCACTCATCTTCTTTGGTTGT
TGCTTCATCTCCACTCTGGCTGCACTGCTATCAATCACTATTTTTCATCA
TCGGAAGAGAAGAAAATTCCAGAAAGCAAGGAACTTACAAAATATACCAT
TGAAGAAAGGGCACAGCAGAGTTTTTAGCTAA
```

The amino acid sequence of beta klotho from Hamster, scientific name *Cricetulus griseus*, is provided below:

(SEQ ID NO: 408)
```
MKAGCAAGSPGNEWIFLSSYERNTRSKKTMSNRALQRSVVLSAFVLLRAV
TGLSGDGKAIWDKKQYVSPVNASQLFLYDTFPKNFFWGVGTGAFQVEGNW
QADGRGPSIWDRFIYTHLRDVSITEKSADSYIFLEKDLLALDFLGVSFYQ
FSISWPRLFPNGTVASVNAKGLQYYNKLLDSLILRNIEPVVTLYHWDLPL
ALQEDYGGWKNATMIDLFNDYATYCFQTFGDRVKYWITIHNPYLVAWHGF
ATGMHAPGETGNLTAVYIVGHNLIKAHSKVWHNYDKNFRPHQKGLLSITL
GSHWIEPNKTENMADTISCQHSMAFVLGWFANPIHADGDYPEFMKTLSTM
PVFSEAEKEEVRGTADFFAFSFGPNNFRPSNTVVKMGQNVSLNLRQVLNW
IKLEYDNPRILISENGWFTDSDIKTEDTTAIYMMKHFLNQVLQAIQFDEI
RVFGYTAWSLLDGFEWQYAYTSRRGLFYVDFNSEQKERKPKTSAHYYKQI
IQENGFPLKESTPDMQGQFPCDFSWGVTESVLKPEFMVSSPQFTDPHLYV
WNATGNRLLQRVEGVRLKTKPSHCTDYVSIKKRVEMLAKMKVTHYQFALD
WATILPTGNLSEVNRQVLRYYRCVVSEGLKLGVSPMVTLYHPTHSHLGLP
EPLLNSGGWLNTYTAKAFQDYAGLCFQELGDLVKLWITINEPNRLSDMYN
RTSNDTYRAAHNLMIAHAQVWRLYDRQYRPVQHGAVSLSLHSDWVEPANP
YVDSHWKAAERFLLFEIAWFADPLFKTGDYPLAMKEYIASKNQQGLSRSV
LPRFTPEESRLVKGTIDFYALNHFTTRFVIHKQLNSSRSMADRDVQFLQD
ITRLSSPSRLAVMPWGARKLLGWIQRNYGDMDIYITANGIDDLALENDGI
RKYYLEKYIQEALKAYLIDKVKIKGYYAFKLTEEKSKPRFGFFTSDFKAK
SSVEFYSKLISRSGFPSETSNPACGQPPEDTDCTICSFFTQKKSLIFFGC
CFISTLAVLLSITIFHHRKRRFHKSKNLENIPLKEGHSRVLS
```

An encoding nucleic acid sequence of Hamster beta klotho is provided below:

(SEQ ID NO: 409)
```
atgtccaacagggcactgcaaagatctgtcgtgctgtcagcgtttgttct
gctgcgagctgttaccggattgtctggagacgggaaagcgatatgggata
aaaaacagtacgtgagtccggtgaatgcaagtcagctgtttctctatgac
actttccctaaaaacttttctgggtgttggaactggagcatttcaagt
ggaagggaattggcaggcagacggaagaggaccctcgatttgggatcgtt
tcatctacacacacctgagagatgtcagcatcacagagaaatccgccgac
agttacattttctggaaaagatttgttggctctggatttttaggagt
ttcttttttatcagttctcaatctcctggccacggttgttccccaatggaa
cagtagcatccgtgaatgcaaaaggtctccaatactacaacaaacttctg
gactcgctgatacttaggaatattgagcccgttgttaccttataccattg
ggatttgcctttggcgctacaggaagactatgggggttggaaaaatgcaa
```

```
ctatgatagatctcttcaatgactatgccacatactgcttccagaccttt
ggagaccgtgtcaagtattggattacaattcacaaccccttacctggttgc
ttggcatgggtttgccacaggtatgcatgcgccaggagagacgggaaatt
taacagctgtctacattgtgggacacaacctgatcaaggctcattcgaaa
gtgtggcataactacgacaaaaacttccgcccccatcagaagggtttgct
gtccattaccttggggtcccactggatagaaccaaacaaaacagaaaaca
tggccgatacaatcagctgccagcactctatggcttttgtgcttgggtgg
tttgccaacccatccatgcagacggcgactaccctgagttcatgaaaac
attgtccaccatgccagtgttctctgaggcagagaaggagggaggtgaggg
gcacagctgacttctttgccttttcctttgggcccaacaatttcaggccc
tcgaacactgtagtgaaaatgggacaaaatgtatcactcaacttaagaca
ggtgctgaactggattaaattagaatatgacaaccctcgaatcttgattt
cggagaatggctggttcacagatagtgacataaagacagaggacaccaca
gccatctacatgatgaagcatttcctcaaccaggttcttcaagcaataca
gtttgatgaaatacgagtgtttggttacacggcctggtctctcctggatg
gctttgaatggcagtatgcctacacgtctcgccgaggactgttttatgtg
gactttaatagtgaacagaaagaaaggaaacccaagacctcggcacatta
ctacaaacagatcatacaagaaatggtttccctttgaaagagtccacgc
cagacatgcagggtcagtttccctgtgacttctcctggggggtcaccgag
tctgttcttaagccggagtttatggtttcctccccacagtttaccgaccc
tcacctgtatgtgtggaatgccactggcaacagattgctacagcgagtag
aaggagtaaggctaaaaacaaaaccatcccactgcacagactatgttagc
atcaaaaaacgagttgagatgttggccaaaatgaaagtcacccactacca
gtttgctctggactgggccaccatccttcccactggcaatctgtctgaag
ttaatagacaagtactaaggtactataggtgtgtggtgagcgaaggactg
aagctgggcgtctctcccatggtgacgttgtaccaccccacccactccca
tctaggcctccctgagccgcttcttaacagtggggatggctaaacactt
acaccgccaaggccttccaggactacgcaggactgtgcttccaggaacta
ggggacttggtgaagctctggatcaccatcaatgagcctaataggctgag
tgacatgtacaaccgcacgagtaatgacacctaccgtgcagcccataacc
tgatgattgccatgcccaggtctggcgtctctacgacaggcagtataagg
ccagtccagcatggagctgtgtcgctgtccctacattctgactgggtgga
acctgccaacccctatgtggactcacactggaaggcagcggagcgcttcc
tcctgtttgagatcgcctggttcgctgatccgctcttcaagactggcgac
tatccactggccatgaaggagtacatcgcctccaagaaccagcaagggct
gtcccgctcagtcctgccgcgcttcaccccagaggagagcaggctggtga
agggcaccatcgacttctacgcactgaaccacttcactactaggttcgtg
atacacaaacagctcaacagcagccgctctatggcagacagggacgtcca
gttcctgcaggacatcacccgcctgagctcgcccagccgcctggctgtta
tgccctggggagcacgcaagctgcttgggtggatccagaggaactatggg
gacatggacatctacatcacagccaatggcatcgatgatctggctctgga
``` gaatgatgggatccgaaagtactacttggagaagtacatccaggaggctc tgaaagcatacctcattgacaaagtcaaaatcaaaggctattatgcattc aaactgactgaagagaaatctaagcctagatttggattttttcacatctga cttcaaagctaagtcatctgtagagttttatagcaagttgatcagcagaa gtggcttcccctctgagactagcaatcccgcatgtggtcagcctccagaa gacacagactgcaccatctgctcattttccactcagaagaaatctctgat cttctttggttgttgcttcatctccactctggctgtactgctgtcaatca ccatttttcatcatcgaaagagaagatttcataaatcaaagaacttagaa aatataccattgaaggaaggccacagtagagttcttagctaa The amino acid sequence of beta klotho from rabbit, scientific name Oryctolagus *cuniculus*, is provided below:

(SEQ ID NO: 410)
MKPGCAAGSPGNEWVSFCTDERNRRCRETMSSGRLRRSVMLSAFILLRAV
TGFPGDGRAVWSQNPNLSPVNESQLFLYDTFPKNFFWGVGTGAFQVEGSW
KKDGKGLSVWDHFIATHLNVSSRDGSSDSYIFLEKDLSALDFLGVSFYQF
SISWPRLFPDGTVAVANAKGLQYYNRLLDSLLLRNIEPVVTLYHWDLPWA
LQEKYGGWKNETLIDLFNDYATYCFQTFGDRVKYWITIHNPYLVAWHGYG
TGLHAPGEKGNVAAVYTVGHNLLKAHSKVWHNYNRNFRPHQKGWLSITLG
SHWIEPNRAESIVDILKCQQSMVSVLGWFANPIHGDGDYPEVMTKKLLSV
LPAFSEAEKNEVRGTADFFAFSFGPNNFKPLNTMAKMGQNVSLNLRQVLN
WIKLEYGNPRILIAENGWFTDSYVQTEDTTAIYMMKNFLNQVLQAIRLDG
VRVFGYTAWSLLDGFEWQDAYNTRRGLFYVDFNSEQRERRPKSSAHYYKQ
VIGENGFTLREATPDLQGQFPCDFSWGVTESVLKPESVASSPQFSDPHLY
VWNATGNRMLHRVEGVRLKTRPAQCTDFITIKKQLEMLARMKVTHFRFAL
DWASVLPTGNLSEVNRQALRYYRCVVTEGLKLNISPMVTLYYPTHAHLGL
PAPLLHSGGWLDPSTAKAFRDYAGLCFRELGDLVKLWITINEPNRLSDVY
NRTSNDTYQAAHNLLIAHALVWHLYDRQYRPSQRGALSLSLHSDWAEPAN
PYVASHWQAAERFLQFEIAWFAEPLFKTGDYPVAMREYIASKTRRGLSSS
VLPRFSDAERRLVKGAADFYALNHFTTRFVMHEQQNGSRYDSDRDVQFLQ
DITRLASPSRLAVMPWGEGKLLRWMRNNYGDLDVYITANGIDDQALQNDQ
LRQYYLEKYVQEALKAYLIDKIKIKGYYAFKLTEEKSKPRFGFFTSDFKA
KSSIQFYNKLITSNGFPSENGGPRCNQTQGNPECTVCLLLLQKKPLIFFS
CCFFCTLVLLSSITIFHRRKRRKFWKAKDLQHIPLKKGHKRVLS

An encoding nucleic acid sequence of rabbit beta klotho is provided below:

(SEQ ID NO: 411)
tgaagccgtgataagacggtcccgcagttcgtggcaaatgaagccaggct gtgcggcaggatctccagggaatgaatgggtttccttctgcaccgatgaa agaaacagacgctgtagggaaacgatgtccagcggacgcctgcggagatc tgtcatgctgtcagccttcatcctgctgcgagccgtgactgggttccccg

```
gagacggaagagctgtatggtcgcaaaatcctaatttgagtccggtaaac
gaaagtcagctgtttctctatgacactttcccaaaaaacttttttctgggg
tgtggggactggagccttccaagtggaagggagttggaagaaggatggga
aaggactctctgtatgggatcatttcatcgctacacacctgaacgtcagc
agccgcgatggctccagtgacagctacattttttggagaaagacttatc
ggcgctggatttttaggagtctctttttatcagttttcaatttcctggc
caagactgttcccggatggcacagtagcagtcgccaatgcaaaaggtctc
cagtactataatcggctcctggactctctgctacttagaaacattgaacc
tgtagtcactttataccattgggatctgccttgggcgctacaagaaaaat
acgggggtggaaaaacgagacgttgattgatttattcaatgactatgcc
acctactgtttccagacgtttggggaccgtgtcaaatactggatcaccat
tcacaatccctatctggtggcttggcatggctacgggacaggtctgcatg
ctccgggagagaagggaatgtggcagctgtctacactgtgggacacaac
ctgcttaaggctcattcaaaagtctggcacaactacaacaggaatttccg
cccgcatcagaaaggctggctgtcgatcacgctgggatcccactggattg
agccaaacagagcggaaagcatcgtggacatactcaagtgccagcagtcc
atggtctcggtgctgggctggtttgccaacccgatccacggggacgggga
ctacccagaggtgatgacaaagaagctgctctccgtcctgcccgctttct
cagaagcagagaagaacgaggtacgaggcaccgcagacttctttgccttt
tcgtttggaccaacaacttcaagcccttaaacaccatggctaaaatggg
gcagaatgtgtcactcaatctaagacaggtgctgaactggattaaactgg
aatatggcaaccctcgaatcctgatcgctgagaacggctggttcacagac
agttacgtgcaaacagaagacaccacagccatctacatgatgaagaattt
cctcaaccaggttcttcaagcaataaggttggatggagtccgagtgtttg
gctacactgctggtctctcctggatggcttcgaatggcaggacgcttac
aacacccgccgtggactgttttatgtggacttcaacagcgaacagagaga
agaaggcccaagtcctcggcgcattactataaacaggtcataggagaaa
acggcttcacgctcagagaggccaccccggatctgcaggggcagtttccc
tgtgacttctcctggggcgtcaccgagtctgttcttaagcccgagtcggt
ggcttcctcgccacagttcagcgaccctcacctctacgtgtggaacgcca
ctggcaaccgaatgcttcaccgggtggaaggggtgaggctgaaaacacgg
cccgctcagtgcacagatttcatcaccatcaagaaacaactcgagatgtt
ggcaagaatgaaagtcacccacttccggtttgctctggactgggcctcgg
tccttcccacgggcaacctgtccgaggtgaaccgacaagccctgaggtac
tacaggtgtgtggtcaccgaggggctgaagctcaacatctcgcccatggt
caccttgtactacccgacccatgcccacctgggcctgcccgccgctgc
tgcacagcgggggtggctggacccatccacggccaaggccttccgcgac
tacgcagggctgtgcttccgggagctgggggacctggtgaagctctggat
caccatcaacgagcccaacggctgagcgacgtctacaaccgcaccagca
acgacacctaccaggccgcccacaacctgctgatcgcgcacgcgctcgtg
tggcacctgtacgaccgccagtaccggccgtcgcagcgcggggcgctgtc gctgtccctgcactcggactgggccgagcccgccaaccctacgtggcct
cgcactggcaggcggccgagcgcttcctgcagttcgagattgcgtggttc
gccgagcccctgttcaagaccggggactaccggtggccatgagggagta
catcgcctccaagacccggcgcgggctctccagctccgtgctgccccgct
tcagcgacgccgagcggcggctggtcaagggcgccgccgacttctacgcc
ctcaaccacttccaccaccaggttcgtgatgcacgagcagcagaacggcag
ccgctacgactcggacagggacgtgcagttcctgcaggacatcaccccgcc
tggcctcacccagccgcctggccgtgatgccctggggcgagggcaagctg
ctgcggtggatgcggaacaactacggagacctggacgtctacatcacggc
caatggcatcgacgaccaggccctgcagaacgaccagcttcgccagtact
acctggagaagtacgtccaggaggctctgaaagcatatctgatagataaa
ataaaaatcaaaggctattatgcattcaaactgactgaagaaaaatctaa
acccaggtttggattcttcacctctgatttcaaagccaagtcttcaatac
agttttacaacaaactaattaccagcaacggcttcccgtctgagaacggc
ggtcctagatgcaatcagactcaaggaaatcccgagtgcaccgtctgctt
actcctcctgcagaagaagccgctgatattctttagctgctgcttcttct
gcaccctggttctactctcatcaattaccatctttcacagacggaagaga
agaaaattttggaaagcaaaggacttacaacacataccattaaagaaagg
ccacaagagagtccttagctaaagtgaacttatttctctctgaagagtttt
agaaattcactccagttccatatgctggtaacacaaaagacatacccgta
ttgtacacagagtatttgagatactgtgctaaccaaggcgatgacaatca
aaacctctgccatgtggttgaatgcattttcccttaagcggtgacaatca
gcgaactcagttcttggttctaaaggaggcttcgcactgccactaggcta
tgagtattacctgacgcattgctttgtcaagtttgatgagctgtttcgca
tcattctctagcttcttagataccaatagctactatggtaaaagttgt
ttttaaaagtcaaactctgtaaggcttcacagcagatttaaaactattct
ttacactggatctgtgattttgtcactcgtagcaaggtgctttcccctttt
tggtcctagtggctctcaaatagaaagcaaacacatcttagggtaatcta
cttatctatagccaatcacagcactgacccacaactacacaaatccgtta
gctcttctccataaaacacctaattttgtgatcttttaagtaatctgaaa
tgtaaaagtatgacttccgtaacccatctcatgaaagatcgactaagga
gagccatacccagctgtgaggacaatttagtcactaatctcaccgtactg
caacttcctccttttagagcaggcattccttaccatttttgtaagatgaca
tgatttagcatctagaaacccctatctgcagtttctttctatggcttacct
acatttcaagaatattgaacggaaaatttcagaaagatttccaagttta
aattgtgtactagcattagtgcatgatgaaatctcatttcttgctcca
tcctgcacaggatgtgaaacatccctctgtccagcaagtccaagctacct
atattactcacttgatagtcaccatggttatccagctgttattacttgct
catacccaggtaacccttttttatttaatatagctccaaagtataagac
tagtgatgaaaaggaggtaagtcatcaaatatggaaggacagattaactc
```

-continued

```
tggcactaagtgggaatgctgcaggttttacaggaaaacaaaattcagtc
agtggtttaaagcatcctctgaggtacctggggcacaatctccacagata
aggggaaagagcactgacaaagactaaacatcctaaaaagacgcaatgtt
ctacttactggccatcagaataatggccaaaggaccctatacttgcttgc
tctctagccaagtttcgctgcacataggtgtagaatgcagcgactgaccc
tggatgcgattcagaatgctgatctgagtgaactagttttttatacagca
cttttttaaagcctagaattcttccatctgaacttgggagttttgactttt
ttgaaattaattgtgcttaagatttattcagtgattctaaacactggagg
tagaaaactgtatacccattatgcctattaatttttcttgattagccaac
atttaaataaccacaaagtggccagtcgttgtctttcccttcaggaatt
taagtcaaaggatgctgctgcctgcgatgctggcacttcataggggtgac
agtttgtgtccctgcggttccacttcctatccagctccctgctaatggct
tgggagagccctgcacccacatgggagacccaaaagcagatcctgctgct
ttcagcctgctgcggccacttggagtatgaaccagtggatggaagatcaa
tgtctctcccaacaattctttgaataaattttttcaaagtcaaaataaa
attctccagctcaaaaagctttagtagaaaacgatcctacattaaggcgg
ttgtgattgtatcccaagtgcatctacgttacaaaccaaattgagtatgc
aattcagtatgctactagactataaggagaaaacagccaattcaaacaaa
ataccaaagtcacgtgcagttaatttgctttctggttggccaaatgtttt
ttttctcttcttgccaccactgttttacatgtactttagaagaaattttg
acttttgcttcctttgagaaatcactattatcaaaggcaattcataatt
acaagtggtccattgtcttaagagctcaagattatagcccttcaaacttg
ccaaactcctcaaatagtgaagctcctaacgaagggtttacaacatcctg
ttccttaggggttatattttaagtgactgtaatttacctaacaaattta
atctggctatctattggtaatacatgtaatattcaggtttatcataaacc
cacttaaaaactaaaggttaagtggaagttgctgcttttcaaagtaacag
gcttctcaggggaaaatatcaccttagcgtccacctggtactacatctcg
tgtattcactgtaacccatcttccgaacatgtctgatatatgaaac
aacactagtgcttagcctctggaaatgaggccaggattttgtgattaaat
gtctaatttattccaaataaactgatttacgccaata
```

The amino acid sequence of beta klotho from dog, scientific name Canis lupus familiaris, is provided below:

```
                                   (SEQ ID NO: 412)
MKPGCAAGSPGNEWIFLSTDESNTHYRKTMCNHGLQRSVILSAFILLGAV

PGFSGDGRAIWSKNPHFSPVNESQLFLYDTFPKNFFWGVGTGAFQVEGNW

KTDGKGPSIWDHFIHTHLKNVNSMNSSSDSYIFLEKDLSALDFIGVSFYQ

FSISWPRLFPDGIAAVANAKGLQYYNSLLDALVLRNIEPIVTLYHWDLPL

ALQEKYGGWKNETITDIFNDYATYCFQTFGDRVKYWITIHNPYLVAWHGY

GTGMHAPGEKGNLAAVYTVGHNLIKAHSKVWHNYNTNFRPYQKGLLSITL

GSHWIEPNRSENMMDILKCQQSMVSVLGWFANPIHGNGDYPEVMKKKLLS

TLPLFSEAEKNEVRGTADFFAFSFGPNNFKPQNTMAKMGQNVSLNLREVL

NWIKLEYGNPRILIAENGWFTDSHVKTEDTTAIYMMKNFLNQVLQAIRFD

EIQVFGYTAWSLLDGFEWQDAYSTRRGLFYVDFNSKQKERKPKSSAYYYK

QIIQENGFTFKESTPDVQGQFPCDFSWGVTESVLKPKWASSPQFSDPHLY

VWNVTGNRLLHRVEGVRLKTRPAQCTDFVSIKRQLEMLARMNVTHYRFAL

DWPSILPTGNLSTVNRQALRYYRCVVSESLKLSISPMVTLYYPTHAHLGL

PSPLLHSGGWLNASTARAFQDYAGLCFQELGDLVKLWITINEPNRLSDVY

SHTSSDTYRAAHNLLIAHALVWHLYDRRYRPAQRGAVSLSLHSDWAEPAN

PYADSHWKAAERFLQFEIAWFAEPLFKTGDYPPAMREYIASKNRQGLSRS

TLPRFTDEERRLVKGAADFYALNHFTTRFVMHARQNGSRYDADRDVQFLQ

DITCLSSPSRLAVLPWGERKVLRWIQKNYGDVDVYITASGIDDQSLENDE

LRKYYLEKYIQEALKAHLIDKVKVKGYYAFKLTEEKSKPRFGFFTSEFKA

KSSVQLYNKLISNSGFPSENRSPRCSETQRNTECMVCLFLVQKKPLIFFS

CCFFSTLVLLSSITILHKRKRRKIWKAKNLQHIPLKKSKNSLQS
```

An encoding nucleic acid sequence of dog beta klotho is provided below:

```
                                   (SEQ ID NO: 413)
acaatcacaagcttttactgaagcgttgataagacaggcgagcagttagt ggcaaatgaagccaggctgtgcggctggatctccagggaatgaatggatt ttcctcagcaccgatgaaagcaacacacactataggaaaacaatgtgcaa ccacgggctacagagatctgtcatcctgtcagcatttattctcctaggag ctgttcctggattctctggagacggaagagctatatggtctaaaaatcct cattttagtccggtaaatgaaagtcagctgtttctctatgacactttttcc taaaaacttttttggggcgttgggactggagcatttcaagtggaaggga attggaagacagatggaaaaggaccctctatatgggatcatttcatccac acacaccttaaaaatgtcaacagcatgaatagttccagtgacagttacat ttttctggaaaaagacctatcagccctggattttatcggagtttcttttt atcaatttcaatttcctggccaaggcttttccccgatggaatagcagca gttgccaacgcaaaaggtctccagtactacaattctcttctcgatgctct agtacttaggaacattgaacctatagttactttataccattgggatttgc ctttggcactacaagaaaaatatgggggtggaaaaatgaaaccataacg gatatcttcaatgactatgccacctactgttccagacgttcggggatcg tgtcaaatactggattacaattcacaatccatatctagttgcttggcatg ggtatgggacaggtatgcacgcgcctggagagaagggaaacttagcagct gtctacactgtgggacacaacctaatcaaggctcattcgaaagtttggca taactacaacacaaatttccgcccatatcagaagggtttgttatcaatca cgttgggatcccattggattgaaccaaacagatcagaaaacatgatggat atactcaaatgtcaacaatccatggtttcagtgctcgggtggtttgccaa ccccatccatgggaatggagactatccagaagtgatgaaaaagaagttgc tctccactctaccccttttctctgaagcagagaagaatgaagtgagggc acagctgacttcttttgccttttcctttggacccaacaatttcaagcccca
```

-continued

```
gaacaccatggctaaaatgggacaaaatgtgtcactcaatttaagagaag
tgctgaattggattaaactggaatatggcaaccccgaatcttgattgct
gagaatggctggttcacagacagtcatgtgaaaacagaagataccacagc
catttacatgatgaagaatttcctcaaccaggttcttcaagcaataaggt
ttgacgaaatacaagtgtttggctacactgcttggtctctcctggatggc
tttgaatggcaggatgcttactccactcgccgaggattattttatgtgga
ttttaatagtaaacaaaagaaagaaagcccaagtcttcggcatattact
ataaacagatcatacaagaaaatggttttactttcaaagagtccaccca
gatgtgcagggtcagtttcctgtgacttctcatggggtgtcaccgaatc
tgtccttaagcccaaagtcgtggcttcctccccacagttcagcgaccctc
acctgtacgtgtggaatgtgacaggcaacagactgttgcaccgagtggaa
gggggtgaggctgaagacacggccggctcaatgcacagattttgtcagcat
caaaagacaacttgagatgttggcgaggatgaacgtcactcactacaggt
ttgctctggactggccctccatccttcccaccggcaacctgtccacggtt
aaccgacaagccctgaggtactacaggtgtgtggtcagcgagtcgctgaa
gctcagcatctccccgatggtcacgctgtactacccgacccacgccacc
tgggcctcccctcgccgctgctgcacagcgggggctggctgaacgcgtcc
accgcccgcgccttccaggactatgccgggctgtgcttccaggagctggg
ggacctggtgaagctctggatcaccatcaatgagcccaaccggctgagtg
acgtctacagccacaccagcagcgacacctaccgggcagcgcacaacctg
ctgatcgcccacgccctggtgtggcacctgtacgaccggcggtaccggcc
ggcgcagcgcggggccgtgtcgctgtccctgcactcggactgggcggagc
ccgccaacccctacgccgactcgcactggaaggcggccgagcgcttcctg
cagttcgaaatcgcctggttcgccgagccgctcttcaagaccggggacta
cccgccggccatgagggagtacatcgcctccaagaacaggcaggggctct
cgcgctccaccctgcccgcttcaccgacgaggagaggaggctggtcaag
ggcgccgccgacttctacgcgctgaaccacttcaccaccaggttcgtgat
gcacgcgcgccagaacggcagccgctacgacgcggaccgcgacgtccagt
tcctgcaggacatcacctgcctgagctcccccagccgcctggccgtcctg
ccctgggggagcgcaaggtgctcaggtggatccagaagaactacggaga
cgtggacgtgtacatcacggccagtggcatcgatgaccagtctctggaaa
atgatgagctcagaaaatactacttggagaaatacatccaggaggctctg
aaagcacacctaattgataaagtcaaagtcaaaggctattatgcattcaa
actgactgaagaaaaatctaaacccagatttggattcttcacgtctgaat
tcaaagctaaatcctcagttcagctttacaacaaactgatcagcaacagt
ggcttcccttctgagaacaggagtcctagatgcagtgagactcaaagaaa
cacagagtgcatggtctgcttatttcttgtgcaaaagaaaccactgatat
tctttagttgttgcttcttctctaccctggttctactttcatcgattacc
attcttcataagcgaaagagaagaaaaatttggaaagcaaagaacttaca
acatataccattaaagtgaggccacagaaagttcttagtgaaactgatcc
tatttctgtctgcatgatagaaagtctaaaaattcactccagtcccaaat
actggtaacatagaagacaatttgaaacactagtagtaaccaaggtgatg
acaatcaaggtctctgctgtgtggtccaaatgaattttccattaggtgtt
gacatcactgaatacagttttttagatctgaagactaagatctagagagta
agctaggattatctgatacaatgcttcattaagtttaataagctgttatc
catcattcttctctggcttccttctagaaataccaatagctaattatagc
aacttagaaaaaagtgcaacttttgctagactccatagcagaaatctaaa
actcttaacactggatattcagtgattattctatcacttctaacaaggtg
cttttcccttagaagatatacaatagggtaaatagtgctcctttatca
tccattccagcactttttttttccagcatagactcttaaacacattgatc
ctagttttctcaatagaaataaaaaatcatttagaaaacatggaatttt
gtgaggtctctccttgcattagatctgagttttttttaaaaaaaagactt
aacttccataacccatctcatgggaagatcacaggactaagattaaggag
agttagacccatcaactgcctgaggagacagcactcaacctcacagtaca
gcaaattccttgggacaaactgacagcaatcttccgcacttggattgttg
aggcagcacacaagatcttaacatacttaggaaagttaaatattctaaaa
agatgtaaagttttatttttattatcaagtcttcaaaggaccatattatt
ccataagacttgctctctcctgagttccactcttctgacactatgtgtat
atggggacactcaaactgcaccttgacattgcaactttggatacaattca
gaatgtaaatgtttgaaggacttaaaacttttctccactgcacctttttgaa
gctgggattaagtaaatacgaactgggagtttgacttttttgaactctgt
gcttgatttattcactgtattctaaattttaaggaaaacctgaatgtaaa
cccattcataccctttctttgggttagtaaacatttaaccacccatttc
a.
```

The amino acid sequence of human/mouse beta klotho chimeric protein (human KLB (M1-F508)-mouse KLB (P507-S1043)) is provided below:

(SEQ ID NO: 374)
MKPGCAAGSPGNEWIFFSTDEITTRYRNTMSNGGLQRSVILSALILLRAV
TGFSGDGRAIWSKNPNFTPVNESQLFLYDTFPKNFFWGIGTGALQVEGSW
KKDGKGPSIWDHFIHTHLKNVSSTNGSSDSYIFLEKDLSALDFIGVSFYQ
FSISWPRLFPDGIVTVANAKGLQYYSTLLDALVLRNIEPIVTLYHWDLPL
ALQEKYGGWKNDTIIDIFNDYATYCFQMFGDRVKYWITIHNPYLVAWHGY
GTGMHAPGEKGNLAAVYTVGHNLIKAHSKVWHNYNTHFRPHQKGWLSITL
GSHWIEPNRSENTMDIFKCQQSMVSVLGWFANPIHGDGDYPEGMRKKLFS
VLPIFSEAEKHEMRGTADFFAFSFGPNNFKPLNTMAKMGQNVSLNLREAL
NWIKLEYNNPRILIAENGWFTDSRVKTEDTTAIYMMKNFLSQVLQAIRLD
EIRVFGYTAWSLLDGFEWQDAYTIRRGLFYVDFNSKQKERKPKSSAHYYK
QIIRENGFPLKESTPDMKGRFPCDFSWGVTESVLKPEFTVSSPQFTDPHL
YVWNVTGNRLLYRVEGVRLKTRPSQCTDYVSIKKRVEMLAKMKVTHYQFA
LDWTSILPTGNLSKVNRQVLRYYRCVVSEGLKLGVFPMVTLYHPTHSHLG
LPLPLLSSGGWLNMNTAKAFQDYAELCFRELGDLVKLWITINEPNRLSDM

-continued

YNRTSNDTYRAAHNLMIAHAQVWHLYDRQYRPVQHGAVSLSLHCDWAEPA

NPFVDSHWKAAERFLQFEIAWFADPLFKTGDYPSVMKEYIASKNQRGLSS

SVLPRFTAKESRLVKGTVDFYALNHFTTRFVIHKQLNTNRSVADRDVQFL

QDITRLSSPSRLAVTPWGVRKLLAWIRRNYRDRDIYITANGIDDLALEDD

QIRKYYLEKYVQEALKAYLIDKVKIKGYYAFKLTEEKSKPRFGFFTSDFR

AKSSVQFYSKLISSSGLPAENRSPACGQPAEDTDCTICSFLVEKKPLIFF

GCCFISTLAVLLSITVFHHQKRRKFQKARNLQNIPLKKGHSRVFS.

An encoding nucleic acid sequence of human/mouse beta klotho chimeric protein is provided below:

(SEQ ID NO: 375)
ATGAAGCCAGGCTGTGCGGCAGGATCTCCAGGGAATGAATGGATTTTCTT

CAGCACTGATGAAATAACCACACGCTATAGGAATACAATGTCCAACGGGG

GATTGCAAAGATCTGTCATCCTGTCAGCACTTATTCTGCTACGAGCTGTT

ACTGGATTCTCTGGAGATGGAAGAGCTATATGGTCTAAAAATCCTAATTT

TACTCCGGTAAATGAAAGTCAGCTGTTTCTCTATGACACTTTCCCTAAAA

ACTTTTTCTGGGGTATTGGGACTGGAGCATTGCAAGTGGAAGGGAGTTGG

AAGAAGGATGGAAAAGGACCTTCTATATGGGATCATTTCATCCACACACA

CCTTAAAAATGTCAGCAGCACGAATGGTTCCAGTGACAGTTATATTTTTC

TGGAAAAAGACTTATCAGCCCTGGATTTTATAGGAGTTTCTTTTTATCAA

TTTTCAATTTCCTGGCCAAGGCTTTTCCCCGATGAATAGTAACAGTTGC

CAACGCAAAAGGTCTGCAGTACTACAGTACTCTTCTGGACGCTCTAGTGC

TTAGAAACATTGAACCTATAGTTACTTTATACCACTGGGATTTGCCTTTG

GCACTACAAGAAAAATATGGGGGGTGGAAAAATGATACCATAATAGATAT

CTTCAATGACTATGCCACATACTGTTTCCAGATGTTTGGGGACCGTGTCA

AATATTGGATTACAATTCACAACCCATATCTAGTGGCTTGGCATGGGTAT

GGGACAGGTATGCATGCCCCTGGAGAGAAGGGAAATTTAGCAGCTGTCTA

CACTGTGGGACACAACTTGATCAAGGCTCACTCGAAAGTTTGGCATAACT

ACAACACACATTTCCGCCCACATCAGAAGGGTTGGTTATCGATCACGTTG

GGATCTCATTGGATCGAGCCAAACCGGTCGGAAAACACGATGGATATATT

CAAATGTCAACAATCCATGGTTTCTGTGCTTGGATGGTTTGCCAACCCTA

TCCATGGGGATGGCGACTATCCAGAGGGGATGAGAAAGAAGTTGTTCTCC

GTTCTACCCATTTTCTCTGAAGCAGAGAAGCATGAGATGAGAGGCACAGC

TGATTTCTTTGCCTTTTCTTTTGGACCCAACAACTTCAAGCCCCTAAACA

CCATGGCTAAAATGGGACAAAATGTTTCACTTAATTTAAGAGAAGCGCTG

AACTGGATTAAACTGGAATACAACAACCCTCGAATCTTGATTGCTGAGAA

TGGCTGGTTCACAGACAGTCGTGTGAAAACAGAAGACACCACGGCCATCT

ACATGATGAAGAATTTCCTCAGCCAGGTGCTTCAAGCAATAAGGTTAGAT

GAAATACGAGTGTTTGGTTATACTGCCTGGTCTCTCCTGGATGGCTTTGA

ATGGCAGGATGCTTACACCATCCGCCGAGGATTATTTTATGTGGATTTA

ACAGTAAACAGAAAGAGCGGAAACCTAAGTCTTCAGCACACTACTACAAA

CAGATCATACGAGAAATGGTTTTCCTTTGAAAGAGTCCACGCCAGACAT

GAAGGGTCGGTTCCCCTGTGATTTCTCTTGGGGAGTCACTGAGTCTGTTC

TTAAGCCCGAGTTTACGGTCTCCTCCCCGCAGTTTACCGATCCTCACCTG

TATGTGTGGAATGTCACTGGCAACAGATTGCTCTACCGAGTGGAAGGGGT

AAGGCTGAAAACAAGACCATCCCAGTGCACAGATTATGTGAGCATCAAA

AACGAGTTGAAATGTTGGCAAAAATGAAAGTCACCCACTACCAGTTTGCT

CTGGACTGGACCTCTATCCTTCCCACTGGCAATCTGTCCAAAGTTAACAG

ACAAGTGTTAAGGTACTATAGGTGTGTGGTGAGCGAAGGACTGAAGCTGG

GCGTCTTCCCCATGGTGACGTTGTACCACCCAACCCACTCCCATCTCGGC

CTCCCCCTGCCACTTCTGAGCAGTGGGGGGTGGCTAAACATGAACACAGC

CAAGGCCTTCCAGGACTACGCTGAGCTGTGCTTCCGGGAGTTGGGGGACT

TGGTGAAGCTCTGGATCACCATCAATGAGCCTAACAGGCTGAGTGACATG

TACAACCGCACGAGTAATGACACCTACCGTGCAGCCCACAACCTGATGAT

CGCCCATGCCCAGGTCTGGCACCTCTATGATAGGCAGTATAGGCCGGTCC

AGCATGGGGCTGTGTCGCTGTCCTTACATTGCGACTGGGCAGAACCTGCC

AACCCCTTTGTGGATTCACACTGGAAGGCAGCCGAGCGCTTCCTCCAGTT

TGAGATCGCCTGGTTTGCAGATCCGCTCTTCAAGACTGGCGACTATCCAT

CGGTTATGAAGGAATACATCGCCTCCAAGAACCAGCGAGGGCTGTCTAGC

TCAGTCCTGCCCGCGCTTCACCGCGAAGGAGAGCAGGCTGGTGAAGGGTAC

CGTCGACTTCTACGCACTGAACCACTTCACTACGAGGTTCGTGATACACA

AGCAGCTGAACACCAACCGCTCAGTTGCAGACAGGGACGTCCAGTTCCTG

CAGGACATCACCCGCCTAAGCTCGCCCAGCCGCCTGGCTGTAACACCCTG

GGGAGTGCGCAAGCTCCTTGCGTGGATCCGGAGGAACTACAGAGACAGGG

ATATCTACATCACAGCCAATGGCATCGATGACCTGGCTCTAGAGGATGAT

CAGATCCGAAAGTACTACTTGGAGAAGTATGTCCAGGAGGCTCTGAAAGC

ATATCTCATTGACAAGGTCAAAATCAAAGGCTACTATGCATTCAAACTGA

CTGAAGAGAAATCTAAGCCTAGATTTGGATTTTTCACCTCTGACTTCAGA

GCTAAGTCCTCTGTCCAGTTTTACAGCAAGCTGATCAGCAGCAGTGGCCT

CCCCGCTGAGAACAGAAGTCCTGCGTGTGGTCAGCCTGCGGAAGACACAG

ACTGCACCATTTGCTCATTTCTCGTGGAGAAGAAACCACTCATCTTCTTC

GGTTGCTGCTTCATCTCCACTCTGGCTGTACTGCTATCCATCACCGTTTT

TCATCATCAAAAGAGAAGAAAATTCCAGAAAGCAAGGAACTTACAAAATA

TACCATTGAAGAAAGGCCACAGCAGAGTTTTCAGCTGA

The amino acid sequence of mouse/human beta klotho chimeric protein (mouse KLB (M1-F506)-human KLB (S509-S1044)) is provided below:

(SEQ ID NO: 376)
MKTGCAAGSPGNEWIFFSSDERNTRSRKTMSNRALQRSAVLSAFVLLRAV

TGFSGDGKAIWDKKQYVSPVNPSQLFLYDTFPKNFSWGVGTGAFQVEGSW

KTDGRGPSIWDRYVYSHLRGVNGTDRSTDSYIFLEKDLLALDFLGVSFYQ

FSISWPRLFPNGTVAAVNAQGLRYYRALLDSLVLRNIEPIVTLYHWDLPL

TLQEEYGGWKNATMIDLFNDYATYCFQTFGDRVKYWITIHNPYLVAWHGF

GTGMHAPGEKGNLTAVYTVGHNLIKAHSKVWHNYDKNFRPHQKGWLSITL

GSHWIEPNRTDNMEDVINCQHSMSSVLGWFANPIHGDGDYPEFMKTGAMI

PEFSEAEKEEVRGTADFFAFSFGPNNFRPSNTVVKMGQNVSLNLRQVLNW

IKLEYDDPQILISENGWFTDSYIKTEDTTAIYMMKNFLNQVLQAIKFDEI

RVFGYTAWTLLDGFEWQDAYTTRRGLFYVDFNSEQKERKPKSSAHYYKQI

IQDNGFSLKESTPDVQGQFPCDFSWGVTESVLKPESVASSPQFSDPHLYV

WNATGNRLLHRVEGVRLKTRPAQCTDFVNIKKQLEMLARMKVTHYRFALD

WASVLPTGNLSAVNRQALRYYRCVVSEGLKLGISAMVTLYYPTHAHLGLP

EPLLHADGWLNPSTAEAFQAYAGLCFQELGDLVKLWITINEPNRLSDIYN

RSGNDTYGAAHNLLVAHALAWRLYDRQFRPSQRGAVSLSLHADWAEPANP

YADSHWRAAERFLQFEIAWFAEPLFKTGDYPAAMREYIASKHRRGLSSSA

LPRLTEAERRLLKGTVDFCALNHFTTRFVMHEQLAGSRYDSDRDIQFLQD

ITRLSSPTRLAVIPWGVRKLLRWVRRNYGDMDIYITASGIDDQALEDDRL

RKYYLGKYLQEVLKAYLIDKVRIKGYYAFKLAEEKSKPRFGFFTSDFKAK

SSIQFYNKVISSRGFPPFENSSSRCSQTQENTECTVCLFLVQKKPLIFLGC

CFFFSTLVLLLSIAIFQRQKRRKFWKAKNLQHIPLKKGKRVVS

An encoding nucleic acid sequence of mouse/human beta klotho chimeric protein is provided below:

(SEQ ID NO: 377)
ATGAAGACAGGCTGTGCAGCAGGGTCTCCGGGGAATGAATGGATTTTCTT

CAGCTCTGATGAAAGAAACACACGCTCTAGGAAAACAATGTCCAACAGGG

CACTGCAAAGATCTGCCGTGCTGTCTGCGTTTGTTCTGCTGCGAGCTGTT

ACCGGCTTCTCCGGAGACGGGAAAGCAATATGGGATAAAAAACAGTACGT

GAGTCCGGTAAACCCAAGTCAGCTGTTCCTCTATGACACTTTCCCTAAAA

ACTTTTCCTGGGGCGTTGGGACCGGAGCATTTCAAGTGGAAGGGAGTTGG

AAGACAGATGGAAGAGGACCCTCGATCTGGGATCGGTACGTCTACTCACA

CCTGAGAGGTGTCAACGGCACAGACAGATCCACTGACAGTTACATCTTTC

TGGAAAAAGACTTGTTGGCTCTGGATTTTTTAGGAGTTTCTTTTTATCAG

TTCTCAATCTCCTGGCCACGGTTGTTTCCCAATGGAACAGTAGCAGCAGT

GAATGCGCAAGGTCTCCGGTACTACCGTGCACTTCTGGACTCGCTGGTAC

TTAGGAATATCGAGCCCATTGTTACCTTGTACCATTGGGATTTGCCTCTG

ACGCTCCAGGAAGAATATGGGGGCTGGAAAAATGCAACTATGATAGATCT

CTTCAACGACTATGCCACATACTGCTTCCAGACCTTTGGAGACCGTGTCA

AATATTGGATTACAATTCACAACCCTTACCTTGTTGCTTGGCATGGGTTT

GGCACAGGTATGCATGCACCAGGAGAGAAGGGAAATTTAACAGCTGTCTA

CACTGTGGGACACAACCTGATCAAGGCACATTCGAAAGTGTGGCATAACT

ACGACAAAAACTTCCGCCCTCATCAGAAGGGTTGGCTCTCCATCACCTTG

GGGTCCCATTGGATAGAGCCAAACAGAACAGACAACATGGAGGACGTGAT

CAACTGCCAGCACTCCATGTCCTCTGTGCTTGGATGGTTCGCCAACCCCA

TCCACGGGGACGGCGACTACCCTGAGTTCATGAAGACGGGCGCCATGATC

CCCGAGTTCTCTGAGGCAGAGAAGGAGGAGGTGAGGGGCACGGCTGATTT

CTTTGCCTTTTCCTTCGGGCCCAACAACTTCAGGCCCTCAAACACCGTGG

TGAAAATGGGACAAAATGTATCACTCAACTTAAGGCAGGTGCTGAACTGG

ATTAAACTGGAATACGATGACCCTCAAATCTTGATTTCGGAGAACGGCTG

GTTCACAGATAGCTATATAAAGACAGAGGACACCACGGCCATCTACATGA

TGAAGAATTTCCTAAACCAGGTTCTTCAAGCAATAAAATTTGATGAAATC

CGCGTGTTTGGTTATACGGCCTGGACTCTCCTGGATGGCTTTGAGTGGCA

GGATGCCTATACGACCCGACGAGGGCTGTTTTATGTGGACTTTAACAGTG

AGCAGAAGAGAGGAAACCCAAGTCCTCGGCTCATTACTACAAGCAGATC

ATACAAGCAACGCTTCTCTTTAAAAGAGTCCACGCCAGATGTGCAGGG

CCAGTTTCCCTGTGACTTCTCCTGGGGTGTCACTGAATCTGTTCTTAAGC

CCGAGTCTGTGGCTTCGTCCCCACAGTTCAGCGATCCTCATCTGTACGTG

TGGAACGCCACTGGCAACAGACTGTTGCACCGAGTGGAAGGGGTGAGGCT

GAAAACACGACCCGCTCAATGCACAGATTTTGTAAACATCAAAAAACAAC

TTGAGATGTTGGCAAGAATGAAAGTCACCCACTACCGGTTTGCTCTGGAT

TGGGCCTCGGTCCTTCCCACTGGCAACCTGTCCGCGGTGAACCGACAGGC

CCTGAGGTACTACAGGTGCGTGGTCAGTGAGGGGCTGAAGCTTGGCATCT

CCGCGATGGTCACCCTGTATTATCCGACCCACGCCCACCTAGGCCTCCCC

GAGCCTCTGTTGCATGCCGACGGGTGGCTGAACCCATCGACGGCCGAGGC

CTTCCAGGCCTACGCTGGGCTGTGCTTCCAGGAGCTGGGGGACCTGGTGA

AGCTCTGGATCACCATCAACGAGCCTAACCGGCTAAGTGACATCTACAAC

CGCTCTGGCAACGACACCTACGGGGCGGCGCACAACCTGCTGGTGGCCCA

CGCCCTGGCCTGGCGCCTCTACGACCGGCAGTTCAGGCCCTCACAGCGCG

GGGCCGTGTCGCTGTCGCTGCACGCGGACTGGGCGGAACCCGCCAACCCC

TATGCTGACTCGCACTGGAGGGCGGCCGAGCGCTTCCTGCAGTTCGAGAT

CGCCTGGTTCGCCGAGCCGCTCTTCAAGACCGGGGACTACCCCGCGGCCA

TGAGGGAATACATTGCCTCCAAGCACCGACGGGGCTTTCCAGCTCGGCC

CTGCCGCGCCTCACCGAGGCCGAAAGGAGGCTGCTCAAGGGCACGGTCGA

CTTCTGCGCGCTCAACCACTTCACCACTAGGTTCGTGATGCACGAGCAGC

TGGCCGGCAGCCGCTACGACTCGGACAGGGACATCCAGTTTCTGCAGGAC

ATCACCCGCCTGAGCTCCCCACGCGCCTGGCTGTGATTCCTGGGGGGT

GCGCAAGCTGCTGCGGTGGGTCCGGAGGAACTACGGCGACATGGACATTT

ACATCACCGCCAGTGGCATCGACGACCAGGCTCTGGAGGATGACCGGCTC

CGGAAGTACTACCTAGGGAAGTACCTTCAGGAGGTGCTGAAAGCATACCT

GATTGATAAAGTCAGAATCAAAGGCTATTATGCATTCAAACTGGCTGAAG

AGAAATCTAAACCCAGATTTGGATTCTTCACATCTGATTTTAAAGCTAAA

TCCTCAATACAATTTTACAACAAAGTGATCAGCAGCAGGGGCTTCCCTTT

TGAGAACAGTAGTTCTAGATGCAGTCAGACCCAAGAAAATACAGAGTGCA

CTGTCTGCTTATTCCTTGTGCAGAAGAAACCACTGATATTCTGGGTTGT

TGCTTCTTCTCCACCCTGGTTCTACTCTTATCAATTGCCATTTTTCAAAG

```
-continued
GCAGAAGAGAAGAAAGTTTTGGAAAGCAAAAAACTTACAACACATACCAT

TAAAGAAAGGCAAGAGAGTTGTTAGCTAG
```

Related beta klotho polypeptides include allelic variants (e.g., SNP variants); splice variants; fragments; derivatives; substitution, deletion, and insertion variants; fusion polypeptides; and interspecies homologs, preferably, which retain beta klotho activity and/or are sufficient to generate an anti-beta klotho immune response. As those skilled in the art will appreciate, an anti-beta klotho antibody provided herein can bind to a beta klotho polypeptide, a beta klotho polypeptide fragment, a beta klotho antigen, and/or a beta klotho epitope. An epitope may be part of a larger beta klotho antigen, which may be part of a larger beta klotho polypeptide fragment, which, in turn, may be part of a larger beta klotho polypeptide. Beta klotho may exist in a native or denatured form. Beta klotho polypeptides described herein may be isolated from a variety of sources, such as from human tissue types or from another source, or prepared by recombinant or synthetic methods. A beta klotho polypeptide may comprise a polypeptide having the same amino acid sequence as a corresponding beta klotho polypeptide derived from nature. Beta klotho polypeptides encompass truncated or secreted forms of a beta klotho polypeptide (e.g., an extracellular domain sequence), variant forms (e.g., alternatively spliced forms) and allelic variants of the polypeptide. Orthologs to the beta klotho polypeptide are also well known in the art.

The term "beta klotho" encompasses "full-length," unprocessed beta klotho as well as any form of beta klotho that results from processing in the cell. The term also encompasses naturally occurring variants or mutations of beta klotho (e.g., splice variants, allelic variants, SNP variants and isoforms). The beta klotho polypeptides described herein may be isolated from a variety of sources, such as from human tissue types or from another source, or prepared by recombinant or synthetic methods.

The terms "FGF19-like signaling" and "induces FGF19-like signaling," when applied to a binding protein such an antibody that binds to beta klotho of the present disclosure, means that the binding protein (e.g., antibody) mimics, or modulates, an in vivo biological effect induced by the binding of (i) beta klotho; (ii) FGFR1c, FGFR2c, FGFR3c, and FGFR4; or (iii) a complex comprising beta klotho and one of FGFR1c, FGFR2c, FGFR3c, and FGFR4 and induces a biological response that otherwise would result from FGF19 binding to (i) beta klotho; (ii) FGFR1c, FGFR2c, FGFR3c or FGFR4; or (iii) a complex comprising beta klotho and one of FGFR1c, FGFR2c, FGFR3c, and FGFR4 in vivo. In assessing the binding and specificity of anti-beta klotho antibody, for example, an antibody or fragment thereof, that binds to beta klotho (e.g., human beta klotho), an antibody or fragment thereof is deemed to induce a biological response when the response is equal to or greater than 5%, and preferably equal to or greater than 10%, 15%, 20%, 25%, 30%, 35%, 40%, 45%, 50%, 55%, 60%, 65%, 70%, 75%, 80%, 85%, 90% or 95%, of the activity of a wild type FGF19 standard comprising the mature form of SEQ ID NO:304 (e.g., the mature form of human FGF19) and has the following properties: exhibiting an efficacy level of equal to or more than 5% of an FGF19 standard, with an EC50 of equal to or less than 100 nM, e.g., 90 nM, 80 nM, 70 nM, 60 nM, 50 nM, 40 nM, 30 nM, 20 nM or 10 nM in (1) a recombinant FGF19 receptor mediated luciferase-reporter cell assay (see, e.g., Example 4); (2) ERK-phosphorylation in a recombinant FGF19 receptor mediated cell assay (see, e.g., Example 4); or (3) ERK-phosphorylation in human adipocytes (see, e.g., Example 5).

The term "FGF19R" may refer to a multimeric receptor complex that FGF19 is known or suspected to form in vivo. In various embodiments, FGF19R comprises (i) an FGFR, e.g., FGFR1c, FGFR2c, FGFR3c or FGFR4, and (ii) beta klotho.

The terms "FGF21-like signaling" and "induces FGF21-like signaling," when applied to a binding protein such an antibody that binds to beta klotho of the present disclosure, means that the binding protein (e.g., antibody) mimics, or modulates, an in vivo biological effect induced by the binding of (i) beta klotho; (ii) FGFR1c, FGFR2c, FGFR3c, and FGFR4; or (iii) a complex comprising beta klotho and one of FGFR1c, FGFR2c, FGFR3c, and FGFR4 and induces a biological response that otherwise would result from FGF21 binding to (i) beta klotho; (ii) FGFR1c, FGFR2c, FGFR3c or FGFR4; or (iii) a complex comprising beta klotho and one of FGFR1c, FGFR2c, FGFR3c, and FGFR4 in vivo. In assessing the binding and specificity of anti-beta klotho antibody, for example, an antibody or fragment thereof that binds to beta klotho (e.g., human beta klotho), an antibody or fragment thereof is deemed to induce a biological response when the response is equal to or greater than 5%, and preferably equal to or greater than 10%, 15%, 20%, 25%, 30%, 35%, 40%, 45%, 50%, 55%, 60%, 65%, 70%, 75%, 80%, 85%, 90% or 95%, of the activity of a wild type FGF21 standard comprising the mature form of SEQ ID NO:306 or 429 (e.g., the mature form of the human FGF21 sequence) and has the following properties: exhibiting an efficacy level of equal to or more than 5% of an FGF21 standard, with an EC50 of equal to or less than 100 nM, e.g., 90 nM, 80 nM, 70 nM, 60 nM, 50 nM, 40 nM, 30 nM, 20 nM or 10 nM in (1) a recombinant FGF21 receptor mediated luciferase-reporter cell assay (see, e.g., Example 4); (2) ERK-phosphorylation in the recombinant FGF21 receptor mediated cell assay (see, e.g., Example 4); or (3) ERK-phosphorylation in human adipocytes (see, e.g., Example 5).

The term "FGF21 R" may refer to a multimeric receptor complex that FGF21 is known or suspected to form in vivo. In various embodiments, FGF21R comprises (i) an FGFR, e.g., FGFR1c, FGFR2c, FGFR3c or FGFR4, and (ii) beta klotho.

The term "binding protein" refers to a protein comprising a portion (e.g., one or more binding regions such as CDRs) that binds to beta klotho, including human and/or cyno beta klotho and, optionally, a scaffold or framework portion (e.g., one or more scaffold or framework regions) that allows the binding portion to adopt a conformation that promotes binding of the binding protein to a beta klotho polypeptide, fragment or epitope. Examples of such binding proteins include antibodies, such as a human antibody, a humanized antibody; a chimeric antibody; a recombinant antibody; a single chain antibody; a diabody; a triabody; a tetrabody; a Fab fragment; a F(ab') 2 fragment; an IgD antibody; an IgE antibody; an IgM antibody; an IgG1 antibody; an IgG2 antibody; an IgG3 antibody; or an IgG4 antibody, and fragments thereof. The binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, Proteins: Structure, Function, and Bioinformatics, 53(1):

121-129 (2003); Roque et al., Biotechnol. Prog. 20:639-654 (2004). In addition, peptide antibody mimetics ("PAMs") can be used, as well as scaffolds based on antibody mimetics utilizing fibronectin components as a scaffold. In the context of the present disclosure, a binding protein is said to specifically bind or selectively bind to beta klotho, for example, when the dissociation constant ($K_D$) is $\leq 10^{-8}$ M. The binding protein (e.g., antibody) may specifically bind beta klotho with high affinity when the $K_D$ is $\leq 10^{-9}$ M or $K_D$ is $\leq 10^{-10}$ M. In some embodiments, the binding proteins (e.g., antibodies) may bind to beta klotho or a complex comprising FGFR1c and beta klotho, including with a $K_D$ of between about $10^{-7}$ M and about $10^{-12}$ M and in other embodiments, the binding proteins (e.g., antibodies) may bind with a $K_D$ of $1-2 \times 10^{-9}$ M.

The term "antibody" and "immunoglobulin" or "Ig" are used interchangeably herein, and is used in the broadest sense and specifically covers, for example, individual anti-beta klotho monoclonal antibodies (including agonist, antagonist, neutralizing antibodies, full length or intact monoclonal antibodies), anti-beta klotho antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-beta klotho antibodies, and fragments of anti-beta klotho antibodies, as described below. An antibody can be human, humanized, chimeric and/or affinity matured as well as an antibody from other species, for example mouse, rabbit etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See, Borrebaeck (ed.) (1995) Antibody Engineering, Second Ed., Oxford University Press.; Kuby (1997) Immunology, Third Ed., W. H. Freeman and Company, New York). In specific embodiments, the specific molecular antigen can be bound by an antibody provided herein includes a beta klotho polypeptide, beta klotho fragment or beta klotho epitope. Antibodies also include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments (e.g., antigens-binding fragments such as beta klotho binding fragments) of any of the above, which refers a portion of an antibody heavy or light chain polypeptide that retains some or all of the binding activity of the antibody from which the fragment was derived. Non-limiting examples of functional fragments (e.g., antigens-binding fragments such as beta klotho binding fragments) include single-chain Fvs (scFv) (e.g., including monospecific, bispecific, etc.), Fab fragments, F(ab') fragments, F(ab)2 fragments, F(ab')2 fragments, disulfide-linked Fvs (sdFv), Fd fragments, Fv fragments, diabody, triabody, tetrabody and minibody. In particular, antibodies provided herein include immunoglobulin molecules and immunologically active portions of immunoglobulin molecules, for example, antigen binding domains or molecules that contain an antigen-binding site that binds to a beta klotho antigen (e.g., one or more complementarity determining regions (CDRs) of an anti-beta klotho antibody). Such antibody fragments can be found described in, for example, Harlow and Lane, Antibodies: A Laboratory Manual, Cold Spring Harbor Laboratory, New York (1989); Myers (ed.), Molec. Biology and Biotechnology: A Comprehensive Desk Reference, New York: VCH Publisher, Inc.; Huston et al., Cell Biophysics, 22:189-224 (1993); Pluckthun and Skerra, Meth. Enzymol., 178:497-515 (1989) and in Day, E. D., Advanced Immunochemistry, Second Ed., Wiley-Liss, Inc., New York, NY (1990). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. Anti-beta klotho antibodies may be agonistic antibodies or antagonistic antibodies. Provided herein are agonistic antibodies to beta klotho, including antibodies that induce FGF19-like signaling and/or FGF21-like signaling. Preferred agonistic antibodies to beta klotho do not compete for the binding of FGF19 and/or FGF21 to an FGF receptor including, for example, FGFR1c, FGFR2c, FGFR3c, or FGFR4c.

The term "fibroblast growth factors" refers to a family of growth factors, including twenty-two members of the human FGF family. The FGF19 subfamily of fibroblast growth factors consists of human FGF21, FGF23 and FGF19 and mouse FGF15. The effects of FGF family members are the result of their heparin-dependent binding to one or more members of the FGF receptor tyrosine kinase (FGFR) family, which includes four members each having a tyrosine kinase domain, FGFR1, FGFR2, FGFR3 and FGFR4, as well as two splice variants each of FGFR1, FGFR2 and FGFR3. These splice variants, which occur in exon 3 of FGFR1, FGFR2 and FGFR3, are designated as "b" and "c" variants (e.g., FGFR1 b, FGFR2b, FGFR3c, FGFR1c, FGFR2c and FGFR3c, which are also known as FGFR1(III) b, FGFR2(III)b, FGFR3(III)c, FGFR1(III)c, FGFR2(III)c and FGFR3(III)c, respectively). For example, FGF19 targets and has effects on both adipocytes and hepatocytes. Mice treated with recombinant human FGF19 (rhFGF19), despite being on a high-fat diet, show increased metabolic rates, increased lipid oxidation, a lower respiratory quotient and weight loss. Moreover, such mice showed lower serum levels of leptin, insulin, cholesterol and triglycerides, and normal levels of blood glucose despite the high-fat diet and without appetite diminishment. In addition, obese mice that lacked leptin but included a FGF19 transgene showed weight loss, lowered cholesterol and triglycerides, and did not develop diabetes. In addition, obese, diabetic mice that lack leptin, when injected with rhFGF19, showed reversal of their metabolic characteristics in the form of weight loss and lowered blood glucose. For example, FGF21 is expressed primarily by the liver and has metabolic effects similar to that of FGF19, such as increased metabolism via its effects on adipose tissue, weight loss, lowered blood glucose levels, and resistance to obesity and diabetes. FGF21-transgenic mice were also resistant to diet-induced obesity, and, in diabetic rodent models, FGF21 administration lowered blood glucose and triglyceride levels. FGF19 and FGF21 metabolic effects occur via their binding FGF receptors, including the FGFR1c, FGFR2c and FGFR3c receptors, and required beta klotho for the binding. for the binding. The binding of FGF19 and FGF21 to FGFR1c and FGFR2c are significant. FGF19 has also been shown to have metabolic effects distinct from FGF21, including regulating bile production by the liver via its liver-specific effects, negatively regulating bile production in response to postprandial bile-production, and liver mitogenic effects that are not observed with respect to FGF21. For example, FGF19 transgenic mice develop hepatic adenocarcinoma due to increased proliferation and dysplasia of hepatocytes, and rhFGF19-treated mice exhibit hepatocyte proliferation of hepatocytes. These additional activities of FGF19 appear to be mediated via its binding to FGFR4. FGF19 can bind FGFR4 in both a beta klotho-dependent and beta klotho-independent manner. Although FGF21 has also been shown to bind FGFR4 in a beta klotho-dependent manner, efficient signaling has not previously been observed from the binding of FGF21 to FGFR4.

Binding proteins, such as anti-beta klotho antibodies, as disclosed herein can induce FGF19-like signaling, as described herein. In vivo, the mature form of FGF19 is the active form of the molecule. A nucleic acid sequence encoding full length FGF19 is provided below; the nucleotides encoding the signal sequence are underlined.

(SEQ ID NO: 303)
<u>atgcggagcgggtgtgtggtggtccacgtatggatcctggccggcctctg</u>

<u>gctggccgtggccgggcgcccctcgccttctcggacgcggggccccacg</u> tgcactacggctggggcgaccccatccgctgcggcacctgtacacctcc ggccccacgggctctccagct*gct*tcctgcgcatccgtgccgacggcgt cgtggactgcgcgcggggccagagcgcgcacagtttgctggagatcaagg cagtcgctctgcggaccgtggccatcaagggcgtgcacagcgtgcggtac ctctgcatggg*cgc*cgacggcaagatgcaggggctgcttcagtactcgga ggaagactgtgctttcgaggaggagatccgcccagatggctacaatgtgt accgatccgagaagca*ccg*cctcccggtctccctgagcagtgccaaacag cggcagctgtacaagaacagaggctttcttccactctctcatttcctgcc catgctgcccatggtcccagaggagcctgaggacctcaggggccacttgg aatctgacatgttctcttcgcccctggagaccgacagcatggacccatttt gggcttgtcaccggact*ggaggc*cgtgaggagtcccagctttgaagta a The amino acid sequence of full length FGF19 is provided; the amino acids that make up the signal sequence are underlined:

(SEQ ID NO: 304)
<u>mrsgcvvvhvwilaglwlavag</u>RPLAFSDAGPH*VHYGW*GDPIRLRHLYTS

GPHGLSSCFLRIRADGVVDCARGQSAHSLLEIKAVA*LRTV*AIKGVH*SVRY*

LCMGADGKMQGLLQYSEEDCAFEEEIRPDGYNVYRSEKHRLPVSLSSAKQ

RQLYKNRGFLPLSHFLPMLPMVPEEPEDLRGHLESDMFSSPLETDSMDPF

GLVTGLEAVRSPSFEK

Binding proteins, such as anti-beta klotho antibodies, as described herein can induce FGF21-like signaling, as described herein. In vivo, the mature form of FGF21 is the active form of the molecule. A nucleic acid sequence encoding a full length FGF21 is provided; the nucleotides encoding the signal sequence are underlined:

(SEQ ID NO: 305)
atg gac tcg gac gag acc ggg ttc gag cac tca gga ctg tgg gtt tct gtg ctg gct ggt ctt ctg ctg gga <u>gcc tgc cag gca</u> cac ccc atc cct gac tcc agt cct ctc *ctg* caa ttc ggg ggc caa gtc cgg cag cgg tac ctc tac aca gat gat gcc cag cag aca gaa gcc cac ctg gag atc agg gag gat *ggg* acg gtg ggg ggc gct gct gac cag agc ccc gaa agt ctc ctg cag ctg aaa gcc ttg aag ccg gga gtt att caa atc ttg gga gtc aag aca tcc agg ttc ctg tgc cag cgg cca gat ggg gcc ctg tat gga tcg ctc cac ttt gac cct gag gcc tgc agc ttc cgg gag ctg ctt ctt gag gac gga tac aat gtt tac cag tcc gaa gcc cac ggc ctc ccg ctg cac ctg cca ggg aac aag tcc cca cac cgg gac cct gca ccc cga gga cca gct cgc ttc ctg cca cta cca ggc ctg ccc ccc gca ccc ccg gag cca ccc gga atc ctg gcc ccc cag ccc ccc gat gtg ggc tcc tcg gac cct ctg agc atg gtg gga cct tcc cag ggc cga agc ccc agc tac gct tcc tga.

An amino acid sequence of a full length FGF21 is provided below; the amino acids that make up the signal sequence are underlined:

(SEQ ID NO: 306)
<u>m d s d e t g f e h s g l w v s y l a g l l l g a c g a</u> H P I P D S S P L L Q F G G Q V R Q R Y

L Y T D D A Q Q T E A H L E I R E D G T V G G A

A D Q S P E S L L Q L K A L K P G V I Q I L G V

K T S R F L C Q R P D G A L Y G S L H F D P E A

C S F R E L L L E D G Y N V Y Q S E A H G L P L

H L P G N K S P H R D P A P R G P A R F L P L P

G L P P A P P E P P G I L A P Q P P D V G S S D

P L S M V G P S Q G R S P S Y A S.

A nucleic acid sequence also encoding a full length FGF21 is provided; the nucleotides encoding the signal sequence are underlined:

(SEQ ID NO: 428)
<u>atggactcggacgagaccgggttcgagcactcaggactgtgggtttctgt gctggctggtcttctgctgggagcctgccaggca</u>CACCCCATCCCTGACT

CCAGTCCTCTCCTGCAATTCGGGGGCCAAGTCCGGCAGCGGTACCTCTAC

ACAGATGATGCCCAGCAGACAGAAGCCCACCTGGAGATCAGGGAGGATGG

GACGGTGGGGGGCGCTGCTGACCAGAGCCCCGAAAGTCTCCTGCAGCTGA

AAGCCTTGAAGCCGGGAGTTATTCAAATCTTGGGAGTCAAGACATCCAGG

TTCCTGTGCCAGCGGCCAGATGGGGCCCTGTATGGATCGCTCCACTTTGA

CCCTGAGGCCTGCAGCTTCCGGGAGCTGCTTCTTGAGGACGGATACAATG

TTTACCAGTCCGAAGCCCACGGCCTCCCGCTGCACCTGCCAGGGAACAAG

TCCCCACACCGGGACCCTGCACCCCGAGGACCAGCTCGCTTCCTGCCACT

ACCAGGCCTGCCCCCGCACTCCCGGAGCCACCCGGAATCCTGGCCCCCC

AGCCCCCGATGTGGGCTCCTCGGACCCTCTGAGCATGGTGGGACCTTCC

CAGGGCCGAAGCCCCAGCTACGCTTCCTGA.

An amino acid sequence also encoding a full length FGF21 is provided; the amino acids encoding the signal sequence are underlined:

(SEQ ID NO: 429)
mdsdetgfehsglwvsvlaglllgacgaHPIPDSSPLLQFGGQVRQRYLY

TDDAQQTEAHLEIREDGTVGGAADQSPESLLQLKALKPGVIQILGVKTSR

FLCQRPDGALYGSLHFDPEACSFRELLLEDGYNVYQSEAHGLPLHLPGNK

SPHRDPAPRGPARFLPLPGLPPALPEPPGILAPQPPDVGSSDPLSMVGPS

QGRSPSYAS

Binding proteins, such as anti-beta klotho antibodies, as described herein bind to beta klotho alone or in complex with an FGF receptor, such as FGFR1c. An encoding nucleic acid sequence of human FGFR1c (GenBank Accession Number NM 023110; also designated FGFRαIIIc) is provided below:

(SEQ ID NO: 307)
atgtggagctggaagtgcctcctcttctgggctgtgctggtcacagcc acactctgcaccgctaggccgtccccgaccttgcctgaacaagcccag ccctggggagcccctgtggaagtggagtccttcctggtccacccggt gacctgctgcagcttcgctgtcggctgcgggacgatgtgcagagcatc aactggctgcgggacggggtgcagctggcggaaagcaaccgcacccg cat cacaggggaggaggtggaggtgcaggactccgtgcccgcagact ccggcctctatgcttgcgtaaccagcagccctcgggcagtgacacca cctacttctccgtcaatgtttcagatgctctcccctcctcggaggatga tgatgatgatgatgactcctcttcagaggagaaagaaacagataaca ccaaaccaaaccgtatgcccgtagctccatattggacatcaccagaaa agatggaaaagaaattgcatgcagtgccggctgccaagacagtgaag ttcaaatgccttccagtgggacaccaaacccaacactgcgctggttg aaaaatggcaaagaattcaaacctgaccacagaattggaggctacaa ggtccgttatgccacctggagcatcataatggactctgtggtgccctc tgacaagggcaactacacctgcattgtggagaatgagtacgcagca tcaaccacacataccagctggatgtcgtggagcggtcccctcaccggc ccatcctgcaagcagggttgcccgccaacaaaacagtggccctgggt agcaacgtggagttcatgtgtaaggtgtacagtgacccgcagccgcac atccagtggctaaagcacatcgaggtgaatgggagcaagattggccc agacaacctgccttatgtccagatcttgaagactgctggagttaatac caccgacaaagagatggaggtgcttcacttaagaaatgtctcctttga ggacgcaggggagtatacgtgcttggcgggtaactctatcggactctc ccatcactctgcatggttgaccgttctggaagccctggaagagaggcc ggcagtgatgacctcgcccctgtacctggagatcatcatctattgcac aggggccttcctcatctcctgcatggtggggtcggtcatcgtctacaa gatgaagagtggtaccaagaagagtgacttccacagccagatggctg tgcacaagctggccaagagcatccctctgcgcagacaggtaacagtg tctgctgactccagtgcatccatgaactctggggttcttctggttcggc catcacggctctcctccagtgggactcccatgctagcaggggtctctg agtatgagcttcccgaagaccctcgctgggagctgcctcgggacagac tggtcttaggcaaaccctgggagagggctgctttgggcaggtggtgt tggcagaggctatcgggctggacaaggacaaacccaaccgtgtgacc aaagtggctgtgaagatgttgaagtcggacgcaacagagaaagactt gtcagacctgatctcagaaatggagatgatgaagatgatcgggaagc ataagaatatcatcaacctgctgggggcctgcacgcaggatggtccct tgtatgtcatcgtggagtatgcctccaagggcaacctgcgggagtacc tgcaggcccggaggccccccagggctggaatactgctacaacccagc cacaacccagaggagcagctctcctccaaggacctggtgtcctgcgcc taccaggtggcccgaggcatggagtatctggcctccaagaagtgcata caccgagacctggcagccaggaatgtcctggtgacagaggacaatgt gatgaagatagcagactttggcctcgcacgggacattcaccacatcga ctactataaaaagacaaccaacggccgactgcctgtgaagtggatgg cacccgaggcattatttgaccggatctacacccaccagagtgatgtgt ggtctttcggggtgctcctgtgggagatcttcactctgggcggctcccc atacccggtgtgcctgtggaggaacttttcaagctgctgaaggaggg tcaccgcatggacaagcccagtaactgcaccaacgagctgtacatgat gatgcgggactgctggcatgcagtgccctcacagagaccacccttcaa gcagctggtggaagacctggaccgcatcgtggccttgacctccaacca ggagtacctggacctgtccatgcccctggaccagtactccccagctt tcccgacacccggagctctacgtgctcctcaggggaggattccgtctt ctctcatgagccgctgcccgaggagccctgcctgccccgacacccagc ccagcttgccaatggcggactcaaacgccgctga.

The amino acid sequence of human FGFR1c (GenBank Accession Number NP 075598) (also designated FGFRαIIIC) is provided below:

(SEQ ID NO: 308)
MWSWKCLLFWAVLVTATLCTARPSPTLPEQAQPWGAPVEVESFLVHPG

DLLQLRCRLRDDVQSINWLRDGVQLAESNRTRITGEEVEVQDSVPADS

GLYACVTSSPSGSDTTYFSVNVSDALPSSEDDDDDDSSSEEKETDNT

KPNRMPVAPYWTSPEKMEKKLHAVPAAKTVKFKCPSSGTPNPTLRWLK

NGKEFKPDHRIGGYKVRYATWSIIMDSVVPSDKGNYTCIVENEYGSIN

```
HTYQLDVVERSPHRPILQAGLPANKTVALGSNVEFMCKVYSDPQPHIQ

WLKHIEVNGSKIGPDNLPYVQILKTAGVNTTDKEMEVLHLRNVSFEDA

GEYTCLAGNSIGLSHHSAWLTVLEALEERPAVMTSPLYLEIIIYCTGA

FLISCMVGSVIVYKMKSGTKKSDFHSQMAVHKLAKSIPLRRQVTVSAD

SSASMNSGVLLVRPSRLSSSGTPMLAGVSEYELPEDPRWELPRDRLVL

GKPLGEGCFGQVVLAEAIGLDKDKPNRVTKVAVKMLKSDATEKDLSDL

ISEMEMMKMIGKHKNIINLLGACTQDGPLYVIVEYASKGNLREYLQAR

RPPGLEYCYNPSHNPEEQLSSKDLVSCAYQVARGMEYLASKKCIHRDL

AARNVLVTEDNVMKIADFGLARDIHHIDYYKKTTNGRLPVKWMAPEAL

FDRIYTHQSDVWSFGVLLWEIFTLGGSPYPGVPVEELFKLLKEGHRMD

KPSNCTNELYMMMRDCWHAVPSQRPTFKQLVEDLDRIVALTSNQEYLD

LSMPLDQYSPSFPDTRSSTCSSGEDSVFSHEPLPEEPCLPRHPAQLAN

GGLKRR.
```

Binding proteins, such as anti-beta klotho antibodies, described herein may bind to beta klotho in complex with the extracellular portion of an FGF receptor such as FGFR1c. An example of an extracellular region of FGFR1c is:

```
                                        (SEQ ID NO: 309)
MWSWKCLLFWAVLVTATLCTARPSPTLPEQAQPWGAPVEVESFLVHPGD

LLQLRCRLRDDVQSINWLRDGVQLAESNRTRITGEEVEVQDSVPADSGL

YACVISSPSGSDITYFSVNVSDALPSSEDDDDDDDSSSEEKETDNTKPN

RMPVAPYWTSPEKMEKKLHAVPAAKTVKFKCPSSGTPNPTLRWLKNGKE

FKPDHRIGGYKVRYATWSIIMDSVVPSDKGNYTCIVENEYGSINHTYQL

DVVERSPHRPILQAGLPANKTVALGSNVEFMCKVYSDPQPHIQWLKHIE

VNGSKIGPDNLPYVQILKTAGVNTTDKEMEVLHLRNVSFEDAGEYTCLA

GNSIGLSHHSAWLTVLEALEERPAVMTSPLY.
```

An example of an extracellular region of FGFR1c (αIIIc) is:

```
                                        (SEQ ID NO: 427)
RPSPTLPEQAQPWGAPVEVESFLVHPGDLLQLRCRLRDDVQSINWLRDGV

QLAESNRTRITGEEVEVQDSVPADSGLYACVTSSPSGSDTTYFSVNVSDA

LPSSEDDDDDDDSSSEEKETDNTKPNRMPVAPYWTSPEKMEKKLHAVPAA

KTVKFKCPSSGTPNPTLRWLKNGKEFKPDHRIGGYKVRYATWSIIMDSVV

PSDKGNYTCIVENEYGSINHTYQLDVVERSPHRPILQAGLPANKTVALGS

NVEFMCKVYSDPQPHIQWLKHIEVNGSKIGPDNLPYVQILKTAGVNTTDK

EMEVLHLRNVSFEDAGEYTCLAGNSIGLSHHSAWLTVLEALEERPAVMTS

PLYE.
```

An example of an extracellular region of FGFR1c (βIIIc) is:

```
                                        (SEQ ID NO: 426)
RPSPTLPEQDALPSSEDDDDDDDSSSEEKETDNTKPNPVAPYWTSPEKME

KKLHAVPAAKTVKFKCPSSGTPNPTLRWLKNGKEFKPDHRIGGYKVRYAT

WSIIMDSVVPSDKGNYTCIVENEYGSINHTYQLDVVERSPHRPILQAGLP

ANKTVALGSNVEFMCKVYSDPQPHIQWLKHIEVNGSKIGPDNLPYVQILK

TAGVNTTDKEMEVLHLRNVSFEDAGEYTCLAGNSIGLSHHSAWLTVLEAL

EERPAVMTSPLYLE.
```

As described herein, FGFR1c proteins can also include fragments. As used herein, the terms are used interchangeably to mean a receptor, in particular and unless otherwise specified, a human receptor, that upon association with beta klotho and FGF21 induces FGF21-like signaling activity.

The term FGFR1c also includes post-translational modifications of the FGFR1c amino acid sequence, for example, possible N-linked glycosylation sites. Thus, the antigen binding proteins can bind to or be generated from proteins glycosylated at one or more of the positions.

Binding proteins, such as anti-beta klotho antibodies, as described herein bind to beta klotho alone or in complex with an FGF receptor, such as FGFR2c. An encoding nucleic acid sequence of human FGFR2c is provided below:

```
                                        (SEQ ID NO: 310)
atggtcagctggggtcgtttcatctgcctggtcgtggtcaccatggcaacc ttgtccctggcccggccctccttcagtttagttgaggataccacattagag ccagaagagccaccaaccaaataccaaatctctcaaccagaagtgtacgtg gctgcgccaggggagtcgctagaggtgcgctgcctgttgaaagatgccgcc gtgatcagttggactaaggatggggtgcacttggggcccaacaataggaca gtgcttattggggagtacttgcagataaagggcgccacgcctagagactcc ggcctctatgcttgtactgccagtaggactgtagacagtgaaacttggtac ttcatggtgaatgtcacagatgccatctcatccggagatgatgaggatgac accgatggtgcggaagattttgtcagtgagaacagtaacaacaagagagca ccatactggaccaacacagaaaagatggaaaagcggctccatgctgtgcct gcggccaacactgtcaagtttcgctgcccagccgggggaacccaatgcca accatgcggtggctgaaaaacgggaaggagtttaagcaggagcatcgcatt ggaggctacaaggtacgaaaccagcactggagcctcattatggaaagtgtg gtcccatctgacaagggaaattatacctgtgtagtggagaatgaatacggg tccatcaatcacacgtaccacctggatgttgtggagcgatgcctcaccgg cccatcctccaagccggactgccggcaaatgcctccacagtggtcggagga gacgtagagtttgtctgcaaggtttacagtgatgcccagccccacatccag tggatcaagcacgtggaaaagaacggcagtaaatacgggcccgacgggctg ccctacctcaaggttctcaaggccgccggtgttaacaccacggacaaagag attgaggttctctatattcggaagtaacttttgaggacgctggggaatata cgtgcttggcgggtaattctattgggatatcctttcactctgcatggttga cagtctgccagcgcctggaagagaaaggagattacagcttccccagact
```

```
acctggagatagccatttactgcatagggtgtcttcttaatcgcctgtatgg tggtaacagtcatcctgtgccgaatgaagaacacgaccaagaagccagact tcagcagccagccggctgtgcacaagctgaccaaacgtatcccctgcgga gacaggtaacagtttcggctgagtccagctcctccatgaactccaacaccc cgctggtgaggataacaacacgcctctcttcaacggcagacaccccatgc tggcaggggtctccgagtatgaacttccagaggacccaaaatggggagtttc caagagataagctgacactgggcaagcccctgggagaaggttgctttgggc aagtggtcatggcggaagcagtgggaattgacaaagacaagcccaaggagg cggtcaccgtggccgtgaagatgttgaaagatgatgccacagagaaagacc tttctgatctggtgtcagagatggagatgatgaagatgattgggaaacaca agaatatcataaatcttcttggagcctgcacacaggatgggcctctctatg tcatagttgagtatgcctcaaaggcaacctccgagaatacctccgagccc ggaggccacccgggatggagtactcctatgacattaacgtgttcctgagg agcagatgaccttcaaggacttggtgtcatgcacctaccagctggccagag gcatggagtacttggcttcccaaaaatgtattcatcgagatttagcagcca gaaatgttttggtaacagaaaacaatgtgatgaaaatagcagactttggac tcgccagagatatcaacaatatagactattacaaaaagaccaccaatgggc ggcttccagtcaagtggatggctccagaagccctgtttgatagagtataca ctcatcagagtgatgtctggtccttcggggtgttaatgtgggagatcttca ctttaggggctcgccctacccagggattcccgtggaggaacttttttaagc tgctgaaggaaggacacagaatggataagccagccaactgcaccaacgaac tgtacatgatgatgagggactgttggcatgcagtgccctcccagagaccaa cgttcaagcagttggtagaagacttggatcgaattctcactctcacaacca atgaggaatacttggacctcagccaacctctcgaacagtattcacctagtt accctgacacaagaagttcttgttcttcaggagatgattctgttttttctc cagaccccatgccttacgaaccatgccttcctcagtatccacacataaacg gcagtgttaaaacatga
```

The amino acid sequence of human FGFR2c is provided below; the amino acids that make up the signal sequence are underlined:

```
                                      (SEQ ID NO: 311)
mvswgrficlvvytmatlslaRPSFSLVEDTTLEPEEPPIKYQISQPEVYV

AAPGESLEVRCLLKDAAVISWTKDGVHLGPNNRTVLIGEYLQIKGATPRDS

GLYACTASRTVDSETWYFMVNVTDAISSGDDEDDIDGAEDFVSENSNNKRA

PYWINTEKMEKRLHAVPAANTVKFRCPAGGNPMPIMRWLKNGKEFKQEHRI

GGYKVRNQHWSLIMESVVPSDKGNYTCVVENEYGSINHTYHLDVVERSPHR

PILQAGLPANASTVVGGDVEFVCKVYSDAQPHIQWIKHVEKNGSKYGPDGL

PYLKVLKAAGVNTTDKEIEVLYIRNVTFEDAGEYTCLAGNSIGISFHSAWL

TVLPAPGREKEITASPDYLEIAIYCIGVFLIACMVVTVILCRMKNTTKKPD

FSSQPAVHKLTKRIPLRRQVTVSAESSSSMNSNTPLVRITTRLSSTADTPM

LAGVSEYELPEDPKWEFPRDKLTLGKPLGEGCFGQVVMAEAVGIDKDKPKE
```

```
AVTVAVKMLKDDATEKDLSDLVSEMEMMKMIGKHKNIINLLGACTQDGPLY

VIVEYASKGNLREYLRARRPPGMEYSYDINRVPEEQMTFKDLVSCTYQLAR

GMEYLASQKCIHRDLAARNVLVTENNVMKIADFGLARDINNIDYYKKTING

RLPVKWMAPEALFDRVYTHQSDVWSFGVLMWEIFTLGGSPYPGIPVEELFK

LLKEGHRMDKPANCTNELYMMMRDCWHAVPSQRPTFKQLVEDLDRILTLTT

NEEYLDLSQPLEQYSPSYPDTRSSCSSGDDSVFSPDPMPYEPCLPQYPHIN

GSVKT
```

Binding proteins, such as anti-beta klotho antibodies, as described herein bind to beta klotho alone or in complex with an FGF receptor, such as FGFR3c. An encoding nucleic acid sequence of human FGFR3c (GenBank Accession Number NP 000133) is provided below:

```
                                     (SEQ ID NO: 312)
atgggcgcccctgcctgcgccctcgcgctctgcgtggccgtggccatcgtg gccggcgcctcctcggagtccttggggacggagcagcgcgtcgtggggcga gcggcagaagtcccgggcccagagcccggccagcaggagcagttggtcttc ggcagcggggatgctgtggagctgagctgtccccgcccggggtggtccc atgggcccactgtctgggtcaaggatggcacagggctggtgccctcggag cgtgtcctggtggggcccagcggctgcaggtgctgaatgcctcccacgag gactccggggcctacagctgccggcagcggctcacgcagcgcgtactgtgc cacttcagtgtgcgggtgacagacgctccatcctcgggagatgacgaagac ggggaggacgaggctgaggacacaggtgtggacacaggggcccttactgg acacggcccgagcggatggacaagaagctgctggccgtgccggccgccaac accgtccgcttccgctgcccagccgctggcaaccccactccctccatctcc tggctgaagaacggcagggagttccgcggcgagcaccgcattggaggcatc aagctgcggcatcagcagtggagcctggtcatggaaagcgtggtgccctcg gaccgcggcaactacacctgcgtcgtggagaacaagtttggcagcatccgg cagacgtacacgctggacgtgctggagcgccccgcaccggcccatcctgc aggcggggctgccggccaaccagacggcggtgctgggcagcgacgtggagt tccactgcaaggtgtacagtgacgcacagccccacatccagtggctcaagc acgtggaggtgaatggcagcaaggtgggcccggacggcacaccctacgtta ccgtgctcaagacggcgggcgctaacaccaccgacaaggagctagaggttc tctccttgcacaacgtcacctttgaggacgccggggagtacacctgcctgg cgggcaattctattgggttttctcatcactctgcgtggctggtggtgctgc cagccgaggaggagctggtggaggctgacgaggcgggcagtgtgtatgcag gcatcctcagctacggggtggcttcttcctgttcatcctggtggtggcgg ctgtgacgctctgccgcctgcgcagccccccaagaaaggcctgggctccc ccaccgtgcacaagatctcccgcttcccgctcaagcgacaggtgtccctgg agtccaacgcgtccatgagctccaacacaccactggtgcgcatcgcaaggc tgtcctcaggggagggccccacgctggccaatgtctccgagctcgagctgc ctgccgaccccaaatgggagctgtctcggggcccggctgaccctgggcaagc
```

```
-continued
cccttggggagggctgcttcggccaggtggtcatggcggaggccatcggca ttgacaaggaccgggccgccaagcctgtcaccgtagccgtgaagatgctga aagacgatgccactgacaaggacctgtcggacctggtgtctgagatggaga tgatgaagatgatcgggaaacacaaaaacatcatcaacctgctgggcgcct gcacgcagggcgggcccctgtacgtgctggtggagtacgcggccaagggta acctgcgggagtttctgcgggcgcggcggcccccgggcctggactactcct tcgacacctgcaagccgcccgaggagcagctcaccttcaaggacctggtgt cctgtgcctaccaggtggcccggggcatggagtacttggcctcccagaagt gcatccacagggacctggctgcccgcaatgtgctggtgaccgaggacaacg tgatgaagatcgcagacttcgggctggcccgggacgtgcacaacctcgact actacaagaagacaaccaacggccggctgcccgtgaagtggatggcgcctg aggccttgtttgaccgagtctacactcaccagagtgacgtctggtcctttg gggtcctgctctgggagatcttcacgctgggggctccccgtaccccggca tccctgtggaggagctcttcaagctgctgaaggagggccaccgcatggaca agcccgccaactgcacacacgacctgtacatgatcatgcgggagtgctggc atgccgcgccctcccagaggcccaccttcaagcagctggtggaggacctgg accgtgtccttaccgtgacgtccaccgacgagtacctggacctgtcggcgc ctttcgagcagtactccccgggtggccaggacacccccagctccagctcct caggggacgactccgtgtttgcccacgacctgctgccccggccccaccca gcagtggggctcgcggacgtga
```

The amino acid sequences of human FGFR3c is provided below; the amino acids that make-up the signal sequence are underlined:

(SEQ ID NO: 313)
<u>mgapacalalcvavaivagass</u>ESLGTEQRVVGRAAEVPGPEPGQQEQLVF

GSGDAVELSCPPPGGGPMGPTVWVKDGTGLVPSERVLVGPQRLQVLNASHE

DSGAYSCRQRLTQRVLCHFSVRVTDAPSSGDDEDGEDEAEDTGVDTGAPYW

TRPERMDKKLLAVPAANTVRFRCPAAGNPTPSISWLKNGREFRGEHRIGGI

KLRHQQWSLVMESVVPSDRGNYTCVVENKFGSIRQTYTLDVLERSPHRPIL

QAGLPANQTAVLGSDVEFHCKVYSDAQPHIQWLKHVEVNGSKVGPDGTPYV

TVLKTAGANTTDKELEVLSLHNVTFEDAGEYTCLAGNSIGFSHHSAWLVVL

PAEEELVEADEAGSVYAGILSYGVGFFLFILVVAAVTLCRLRSPPKKGLGS

PTVHKISRFPLKRQVSLESNASMSSNTPLVRIARLSSGEGPTLANVSELEL

PADPKWELSRARLTLGKPLGEGCFGQVVMAEAIGIDKDRAAKPVTVAVKML

KDDATDKDLSDLVSEMEMMKMIGKHKNIINLLGACTQGGPLYVLVEYAAKG

NLREFLRARRPPGLDYSFDTCKPPEEQLTFKDLVSCAYQVARGMEYLASQK

CIHRDLAARNVLVTEDNVMKIADFGLARDVHNLDYYKKTTNGRLPVKWMAP

EALFDRVYTHQSDVWSFGVLLWEIFTLGGSPYPGIPVEELFKLLKEGHRMD

KPANCTHDLYMIMRECWHAAPSQRPTFKQLVEDLDRVLTVTSTDEYLDLSA

PFEQYSPGGQDTPSSSSSGDDSVFAHDLLPPAPPSSGGSRT

Binding proteins, such as anti-beta klotho antibodies, as described herein bind to beta klotho alone or in complex with an FGF receptor, such as FGFR4. An encoding nuclic acid sequence of human FGFR4 is provided below:

(SEQ ID NO: 314)
```
atgcggctgctgctggccctgttgggggtcctgctgagtgtgcctgggcct ccagtcttgtccctggaggcctctgaggaagtggagcttgagccctgcctg gctcccagcctggagcagaagagcaggagctgacagtagcccttgggcag cctgtgcgtctgtgctgtgggcgggctgagcgtggtggccactggtacaag gagggcagtcgcctggcacctgctggccgtgtacggggctggagggggccgc ctagagattgccagcttcctacctgaggatgctggccgctacctctgcctg gcacgaggctccatgatcgtcctgcagaatctcaccttgattacaggtgac tccttgacctccagcaacgatgatgaggaccccaagtcccatagggacccc tcgaataggcacagttaccccagcaagcacctactggacacaccccag cgcatggagaagaaactgcatgcagtacctgcggggaacaccgtcaagttc cgctgtccagctgcaggcaaccccacgcccaccatccgctggcttaaggat ggacaggcctttcatggggagaaccgcattggaggcattcggctgcgccat cagcactggagtctcgtgatggagagcgtggtgccctcggaccgcggcaca tacacctgcctggtagagaacgctgtgggcagcatccgctataactacctg ctagatgtgctggagcggtccccgcaccggccatcctgcaggccgggctc ccggccaacaccacagccgtggtgggcagcgacgtggagctgctgtgcaag gtgtacagcgatgcccagccccacatccagtggctgaagcacatcgtcatc aacggcagcagcttcggagccgacggtttccctatgtgcaagtcctaaag actgcagacatcaatagctcagaggtggaggtcctgtacctgcggaacgtg tcagccgaggacgcaggcgagtacacctgcctcgcaggcaattccatcggc ctctcctaccagtctgcctggctcacggtgctgccagaggaggacccaca tggaccgcagcagcgcccgaggccaggtatacggacatcatcctgtacgcg tcgggctccctggccttggctgtgctcctgctgctggccgggctgtatcga gggcaggcgctccacggccggcaccccgcccgcccgccactgtgcagaag ctctcccgcttccctctggcccgacagttctccctggagtcaggctcttcc ggcaagtcaagctcatccctggtacgaggcgtgcgtctctcctccagcggc cccgccttgctcgccggcctcgtgagtctagatctacctctcgacccacta tgggagttccccgggacaggctggtgcttgggaagcccctaggcgagggc tgctttggccaggtagtacgtgcagaggcctttggcatggaccctgcccgg cctgaccaagccagcactgtggccgtcaagatgctcaaagacaacgcctct gacaaggacctggccgacctggtctcggagatggaggtgatgaagctgatc ggccgacacaagaacatcatcaacctgcttggtgtctgcacccaggaaggg cccctgtacgtgatcgtggagtgcgccgccaaggggaaacctgcgggagttc ctgcgggcccggcgccccccaggccccgacctcagccccgacggtcctcgg agcagtgagggccgctctccttcccagtcctggtctcctgcgcctaccag gtggcccgaggcatgcagtatctggagtcccggaagtgtatccaccgggac ctggctgccgcaatgtgctggtgactgaggacaatgtgatgaagattgct gactttgggctggcccgcggcgtccaccacattgactactataagaaaacc
```

-continued

```
agcaacggccgcctgcctgtgaagtggatggcgcccgaggccttgtttgac cgggtgtacacacaccagagtgacgtgtggtcttttgggatcctgctatgg gagatcttcaccctcgggggctccccgtatcctggcatcccggtggaggag ctgttctcgctgctgcgggagggacatcggatggaccgaccccccacactgc ccccagagctgtacgggctgatgcgtgagtgctggcacgcagcgccctcc cagaggcctaccttcaagcagctggtggaggcgctggacaaggtcctgctg gccgtctctgaggagtacctcgacctccgcctgaccttcggaccctattcc ccctctggtggggacgccagcagcacctgctcctccagcgattctgtcttc agccacgacccctgccattgggatccagctccttccccttcgggtctggg gtgcagacatga
```

The amino acid sequence of human FGFR4 (GenBank Accession Number NP. 002002.3) is provided below, the amino acids that make-up the signal sequence are underlined:

(SEQ ID NO: 315)
mrlllallgyllsvpgppvlsLEASEEVELEPCLAPSLEQQEQELTVALGQ

PVRLCCGRAERGGHWYKEGSRLAPAGRVRGWRGRLEIASFLPEDAGRYLCL

ARGSMIVLQNLTLITGDSLTSSNDDEDPKSHRDPSNRHSYPQQAPYWTHPQ

RMEKKLHAVPAGNTVKFRCPAAGNPTPTIRWLKDGQAFHGENRIGGIRLRH

QHWSLVMESVVPSDRGTYTCLVENAVGSIRYNYLLDVLERSPHRPILQAGL

PANTTAVVGSDVELLCKVYSDAQPHIQWLKHIVINGSSFGADGFPYVQVLK

TADINSSEVEVLYLRNVSAEDAGEYTCLAGNSIGLSYQSAWLTVLPEEDPT

WTAAAPEARYTDIILYASGSLALAVLLLLAGLYRGQALHGRHPRPPATVQK

LSRFPLARQFSLESGSSGKSSSSLVRGVRLSSSGPALLAGLVSLDLPLDPL

WEFPRDRLVLGKPLGEGCFGQVVRAEAFGMDPARPDQASTVAVKMLKDNAS

DKDLADLVSEMEVMKLIGRHKNIINLLGVCTQEGPLYVIVECAAKGNLREF

LRARRPPGPDLSPDGPRSSEGPLSFPVLVSCAYQVARGMQYLESRKCIHRD

LAARNVLVTEDNVMKIADFGLARGVHHIDYYKKTSNGRLPVKWMAPEALFD

RVYTHQSDVWSFGILLWEIFTLGGSPYPGIPVEELFSLLREGHRMDRPPHC

PPELYGLMRECWHAAPSQRPTFKQLVEALDKVLLAVSEEYLDLRLTFGPYS

PSGGDASSTCSSSDSVFSHDPLPLGSSSFPFGSGVQT

An "antigen" is a predetermined antigen to which an antibody can selectively bind. A target antigen may be a polypeptide, carbohydrate, nucleic acid, lipid, hapten or other naturally occurring or synthetic compound. Preferably, the target antigen is a polypeptide.

The term "antigen binding fragment," "antigen binding domain," "antigen binding region," and similar terms refer to that portion of an antibody which comprises the amino acid residues that interact with an antigen and confer on the binding agent its specificity and affinity for the antigen (e.g., the complementarity determining regions (CDRs)).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. The strength of the total non-covalent interactions between a single antigen-binding site on an antibody and a single epitope of a target molecule, such as beta klotho, is the affinity of the antibody or functional fragment for that epitope. The ratio of association (k1) to dissociation (k-1) of an antibody to a monovalent antigen (k1/k-1) is the association constant K, which is a measure of affinity. The value of K varies for different complexes of antibody and antigen and depends on both k1 and k-1. The association constant K for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent beta klotho, come in contact with antibodies containing multiple binding sites, the interaction of antibody with antigen at one site will increase the probability of a reaction at a second site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The terms "antibodies that specifically bind to beta klotho," "antibodies that specifically bind to a beta klotho epitope," and analogous terms are also used interchangeably herein and refer to antibodies that specifically bind to a beta klotho polypeptide, such as a beta klotho antigen, or fragment, or epitope (e.g., human beta klotho such as a human beta klotho polypeptide, antigen or epitope). An antibody that specifically binds to beta klotho, (e.g., human beta klotho) may bind to the extracellular domain or peptide derived from the extracellular domain of beta klotho beta klotho. An antibody that specifically binds to a beta klotho antigen (e.g., human beta klotho) may be cross-reactive with related antigens (e.g., cyno beta klotho). In certain embodiments, an antibody that specifically binds to a beta klotho antigen does not cross-react with other antigens. An antibody that specifically binds to a beta klotho antigen can be identified, for example, by immunoassays, Biacore, or other techniques known to those of skill in the art. An antibody binds specifically to a beta klotho antigen when it binds to a beta klotho antigen with higher affinity than to any cross reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., Paul, ed., 1989, *Fundamental Immunology Second Edition*, Raven Press, New York at pages 332 336 for a discussion regarding antibody specificity. An antibody "which binds" an antigen of interest (e.g., a target antigen such as beta klotho) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein, for example, as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope. In certain embodiments, an antibody that binds to beta klotho has a dissociation constant (Kd) of less than or equal to 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. The lower the $K_D$, the higher the affinity of the anti-beta klotho antibody. In certain embodiments, anti-beta klotho antibody binds to an epitope of beta klotho that is conserved among beta klotho from different species (e.g., between human and cyno beta klotho).

The term "compete" when used in the context of anti-beta klotho antibodies (e.g., agonistic antibodies and binding proteins that bind to (i) beta klotho; or (ii) a complex comprising beta klotho and one of FGFR1c, FGFR2c, FGFR3c, and FGFR4) that compete for the same epitope or binding site on a target means competition between as determined by an assay in which the antibody (or binding fragment) thereof under study prevents or inhibits the specific binding of a reference molecule (e.g., a reference ligand, or reference antigen binding protein, such as a reference antibody) to a common antigen (e.g., beta klotho or a fragment thereof). Numerous types of competitive binding assays can be used to determine if a test antibody competes with a reference antibody for binding to beta klotho (e.g., human beta klotho). Examples of assays that can be employed include solid phase direct or indirect radioimmunoassay (RIA), solid phase direct or indirect enzyme immunoassay (EIA), sandwich competition assay (see, e.g., Stahli et al., (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane, (1988) Antibodies, A Laboratory Manual, Cold Spring Harbor Press); solid phase direct label RIA using 1-125 label (see, e.g., Morel et al., (1988) Molec. Immunol. 25:7-15); solid phase direct biotin-avidin EIA (see, e.g., Cheung, et al., (1990) Virology 176:546-552); and direct labeled RIA (Moldenhauer et al., (1990) Scand. J. Immunol. 32:77-82). Typically, such an assay involves the use of a purified antigen (e.g., beta klotho such as human beta klotho) bound to a solid surface or cells bearing either of an unlabelled test antigen binding protein (e.g., test anti-beta klotho antibody) or a labeled reference antigen binding protein (e.g., reference anti-beta klotho antibody). Competitive inhibition may be measured by determining the amount of label bound to the solid surface or cells in the presence of the test antigen binding protein. Usually the test antigen binding protein is present in excess. Antibodies identified by competition assay (competing antibodies) include antibodies binding to the same epitope as the reference antibody and/or antibodies binding to an adjacent epitope sufficiently proximal to the epitope bound by the reference for antibodies steric hindrance to occur. Additional details regarding methods for determining competitive binding are described herein. Usually, when a competing antibodies protein is present in excess, it will inhibit specific binding of a reference antibodies to a common antigen by at least 23%, for example 40%, 45%, 50%, 55%, 60%, 65%, 70% or 75%]]. In some instance, binding is inhibited by at least 80%, 85%, 90%, 95%, 96% or 97%, 98%, 99% or more.

The term "anti-beta klotho antibody" or "an antibody that binds to beta klotho" includes an antibody that is capable of binding beta klotho with sufficient affinity such that the antibody is useful as a diagnostic and/or therapeutic agent in targeting beta klotho. Preferably, the extent of binding of an anti-beta klotho antibody to an unrelated, non-beta klotho protein is less than about 10% of the binding of the antibody to beta klotho as measured, for example, by fluorescence activated cell sorting (FACS) analysis or an immunoassay such as a radioimmunoassay (RIA). An antibody that "specifically binds to" or is "specific for" beta klotho is Illustrated above. In certain embodiments, an antibody that binds to beta klotho, as described herein has a dissociation constant (Kd) of less than or equal to 10 nM, 9 nM, 8 nM, 7 nM, 6 nM, 5 nM, 4 nM, 0.9 nM, 0.8 nM, 0.7 nM, 0.6 nM, 0.5 nM, 0.4 nM, 0.3 nM, 0.2 nM, or 0.1 nM, and/or is greater than or equal to 0.1 nM. In certain embodiments, anti-beta klotho antibody binds to an epitope of beta klotho that is conserved among beta klotho from different species (e.g., between human and cyno beta klotho).

An "isolated" antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 25%, 20%, 15%, 10%, 5%, or 1% (by dry weight) of heterologous protein (also referred to herein as a "contaminating protein"). In certain embodiments, when the antibody is recombinantly produced, it is substantially free of culture medium, e.g., culture medium represents less than about 20%, 15%, 10%, 5%, or 1% of the volume of the protein preparation. In certain embodiments, when the antibody is produced by chemical synthesis, it is substantially free of chemical precursors or other chemicals, for example, it is separated from chemical precursors or other chemicals which are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 1951), such as 96%, 97%, 98%, or 99%, by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In specific embodiments, antibodies provided herein are isolated.

A 4-chain antibody unit is a heterotetrameric glycoprotein composed of two identical light (L) chains and two identical heavy (H) chains. In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, CT, 1994, page 71 and Chapter 6.

The term "variable region" or "variable domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases forming part of, the β sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, MD, 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. The variability in sequence is concentrated in the CDRs while the less variable portions in the variable region are referred to as framework regions (FR). The CDRs of the light and heavy chains are primarily responsible for the interaction of the antibody with antigen. In specific embodiments, the variable region is a human variable region.

The term "variable region residue numbering as in Kabat" or "amino acid position numbering as in Kabat", and variations thereof, refers to the numbering system used for heavy chain variable regions or light chain variable regions of the compilation of antibodies in Kabat et al., Sequences of Proteins of Immunological Interest, 5th Ed. Public Health Service, National Institutes of Health, Bethesda, MD. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc, according to Kabat) after heavy chain FR residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, including, for example, by AbM, Chothia, Contact, IMGT and AHon. Various numbers systems are illustrated in FIGS. 1-3.

An "intact" antibody is one comprising an antigen-binding site as well as a CL and at least heavy chain constant regions, CH1, CH2 and CH3. The constant regions may include human constant regions or amino acid sequence variants thereof. Preferably, an intact antibody has one or more effector functions.

"Antibody fragments" comprise a portion of an intact antibody, preferably the antigen binding or variable region of the intact antibody. Examples of antibody fragments include, without limitation, Fab, Fab', F(ab')2, and Fv fragments; diabodies and di-diabodies (see, e.g., Holliger, P. et al., (1993) Proc. Natl. Acad. Sci. 90:6444-8; Lu, D. et al., (2005) J. Biol. Chem. 280:19665-72; Hudson et al., Nat. Med. 9:129-134 (2003); WO 93/11161; and U.S. Pat. Nos. 5,837,242 and 6,492,123); single-chain antibody molecules (see, e.g., U.S. Pat. Nos. 4,946,778; 5,260,203; 5,482,858 and 5,476,786); dual variable domain antibodies (see, e.g., U.S. Pat. No. 7,612,181); single variable domain antibodies (SdAbs) (see, e.g., Woolven et al., Immunogenetics 50: 98-101, 1999; Streltsov et al., Proc Natl Acad Sci USA.

101:12444-12449, 2004); and multispecific antibodies formed from antibody fragments.

A "functional fragment" or "binding fragment" or "antigen binding fragment" of a therapeutic antibody will exhibit at least one if not some or all of the biological functions attributed to the intact antibody, the function comprising at least binding to the target antigen, (e.g., a beta klotho binding fragment or fragment that binds to beta klotho).

The term "fusion protein" as used herein refers to a polypeptide that comprises an amino acid sequence of an antibody and an amino acid sequence of a heterologous polypeptide or protein (e.g., a polypeptide or protein not normally a part of the antibody (e.g., a non-anti-beta klotho antigen binding antibody)). The term "fusion" when used in relation to beta klotho or to an anti-beta klotho antibody refers to the joining of a peptide or polypeptide, or fragment, variant and/or derivative thereof, with a heterologous peptide or polypeptide. In certain embodiments, the fusion protein retains the biological activity of the beta klotho or anti-beta klotho antibody. In certain embodiments, the fusion protein comprises a beta klotho antibody VH region, VL region, VH CDR (one, two or three VH CDRs), and/or VL CDR (one, two or three VL CDRs), wherein the fusion protein binds to a beta klotho epitope, a beta klotho fragment and/or a beta klotho polypeptide.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, (e.g., isotypes) referred to as alpha ($\alpha$), delta ($\delta$), epsilon ($\epsilon$), gamma ($\gamma$) and mu ($\mu$), based on the amino acid sequence of the heavy chain constant region. The distinct heavy chains differ in size: $\alpha$, $\delta$ and $\gamma$ contain approximately 450 amino acids, while $\mu$ and $\epsilon$ contain approximately 550 amino acids. When combined with a light chain, these distinct types of heavy chains give rise to five well known classes (e.g., isotypes) of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa ($\kappa$) of lambda ($\lambda$) based on the amino acid sequence of the constant domains. Light chain amino acid sequences are well known in the art. A light chain can be a human light chain.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "monoclonal antibody" as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell, wherein the antibody binds to only a beta klotho epitope as determined, for example, by ELISA or other antigen-binding or competitive binding assay known in the art. The term "monoclonal" is not limited to any particular method for making the antibody. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). Exemplary methods of producing monoclonal antibodies are provided in the Examples herein.

The term "native" when used in connection with biological materials such as nucleic acid molecules, polypeptides, host cells, and the like, refers to those which are found in nature and not manipulated, modified, and/or changed (e.g., isolated, purified, selected) by a human being.

The antibodies provided herein can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)).

"Humanized" forms of nonhuman (e.g., murine) antibodies are chimeric antibodies that include human immunoglobulins (e.g., recipient antibody) in which the native CDR residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., Nature, 321:522-525 (1986); Riechmann et al., Nature, 332:323-329 (1988); and Presta, Curr. Op. Struct. Biol., 2:593-596 (1992); Carter et al., Proc. Natl. Acd. Sci. USA 89:4285-4289 (1992); and U.S. Pat. No. 6,800,738 (issued Oct. 5, 2004), U.S. Pat. No. 6,719,971 (issued Sep. 27, 2005), U.S. Pat. No. 6,639,055 (issued Oct. 28, 2003), U.S. Pat. No. 6,407,213 (issued Jun. 18, 2002), and U.S. Pat. No. 6,054,297 (issued Apr. 25, 2000).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (Hoogenboom and Winter, J. Mol. Biol., 227:381 (1991); Marks et al., J. Mol. Biol., 222:581 (1991) and yeast display libraries (Chao et al., Nature Protocols 1: 755-768 (2006)). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., mice (see, e.g., Jakobovits, A., Curr. Opin. Biotechnol. 1995, 6(5):561-6; Bruggemann and Taussing, Curr. Opin. Biotechnol. 1997, 8(4):455-8; and U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL R-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., J. Biol. Chem. 252:6609-6616 (1977); Kabat, Adv. Prot. Chem. 32:1-75 (1978)). CDR region sequences also have been defined structurally by Chothia as those residues that are not part of the conserved R-sheet framework, and thus are able to adapt different conformations (Chothia and Lesk, J. Mol. Biol. 196:901-917 (1987)). Both terminologies are well recognized in the art. CDR region sequences have also been defined by AbM, Contact and IMGT. CDR region sequences are illustrated in FIGS. 1-3. The positions of CDRs within a canonical antibody variable region have been determined by comparison of numerous structures (Al-Lazikani et al., J. Mol. Biol. 273:927-948 (1997); Morea et al., Methods 20:267-279 (2000)). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra (1997)). Such nomenclature is similarly well known to those skilled in the art.

The term "hypervariable region", "HVR", or "HV", when used herein refers to the regions of an antibody variable region that are hypervariable in sequence and/or form structurally defined loops. Generally, antibodies comprise six hypervariable regions; three in the VH (H1, H2, H3), and three in the VL (L1, L2, L3).

A number of hypervariable region delineations are in use and are encompassed herein. The Kabat Complementarity Determining Regions (CDRs) are based on sequence variability and are the most commonly used (see, e.g., Kabat et al., Sequences of Proteins of Immunological Interest, 5th Ed. Public Health Service, National Institutes of Health, Bethesda, MD. (1991)). Chothia refers instead to the location of the structural loops (see, e.g., Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). The "contact" hypervariable regions are based on an analysis of the available complex crystal structures. The residues from each of these hypervariable regions or CDRs are noted below.

Recently, a universal numbering system has been developed and widely adopted, ImMunoGeneTics (IMGT) Information System® (Lafranc et al., Dev. Comp. Immunol. 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Pluckthun, J. Mol. Biol. 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra) and is also illustrated in FIGS. 1-3. An Exemplary system, shown herein combines Kabat and Chothia.

|  | Exemplary | IMGT | Kabat | AbM | Chothia | Contact |
| --- | --- | --- | --- | --- | --- | --- |
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (L1), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. As used herein, the terms "HVR" and "CDR" are used interchangeably.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CH1, CH2 and CH3 regions of the heavy chain and the CL region of the light chain.

The term "framework" or "FR" residues are those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

An "affinity matured" antibody is one with one or more alterations (e.g., amino acid sequence variations, including changes, additions and/or deletions) in one or more HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. For review, see Hudson and Souriau, Nature Medicine 9:129-134 (2003); Hoogenboom, Nature Biotechnol. 23: 1105-1116 (2005); Quiroz and Sinclair, Revista Ingeneria Biomedia 4: 39-51 (2010).

A "blocking" antibody or an "antagonist" antibody is one which inhibits or reduces biological activity of the antigen it binds. For example, blocking antibodies or antagonist antibodies may substantially or completely inhibit the biological activity of the antigen.

An "agonist antibody" is an antibody that triggers a response, e.g., one that mimics at least one of the functional activities of a polypeptide of interest (e.g., FGF19 or FGF21). An agonist antibody includes an antibody that is a ligand mimetic, for example, wherein a ligand binds to a cell surface receptor and the binding induces cell signaling or activities via an intercellular cell signaling pathway and wherein the antibody induces a similar cell signaling or activation.

An "agonist" of beta klotho refers to a molecule that is capable of activating or otherwise increasing one or more of the biological activities of beta klotho, such as in a cell expressing beta klotho and a FGF receptor. In some embodiments, an agonist of beta klotho (e.g., an agonistic antibody as described herein) may, for example, act by activating or otherwise increasing the activation and/or cell signaling pathways of a cell expressing a beta klotho protein and a FGF receptor, thereby increasing a beta klotho-mediated biological activity of the cell relative to the beta klotho-mediated biological activity in the absence of agonist. In some embodiments the antibodies provided herein are agonistic anti-beta klotho antibodies, including antibodies that induce FGF19-like signaling and/or FGF21-like signaling.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a radiolabeled antigen binding assay (RIA), for example, performed with the Fab version of an antibody of interest and its antigen (Chen, et al., (1999) J. Mol Biol 293:865-881). The $K_D$ or $K_D$ value may also be measured by using surface plasmon resonance assays by Biacore, using, for example, a BIAcore™-2000 or a BIAcore™-3000 BIAcore, Inc., Piscataway, NJ), or by biolayer interferometry using, for example, the OctetQK384 sytem (ForteBio, Menlo Park, CA). An "on-rate" or "rate of association" or "association rate" or "kon" may can also be determined with the same surface plasmon resonance or biolayer interferometry techniques described above using, for example, a BIAcore™-2000 or a BIAcore™-3000 (BIAcore, Inc., Piscataway, NJ), or the OctetQK384 sytem (ForteBio, Menlo Park, CA).

The phrase "substantially similar" or "substantially the same" denotes a sufficiently high degree of similarity between two numeric values (e.g., one associated with an antibody of the present disclosure and the other associated with a reference antibody) such that one of skill in the art would consider the difference between the two values to be of little or no biological and/or statistical significance within the context of the biological characteristic measured by the values (e.g., $K_D$ values). For example, the difference between the two values may be less than about 50%, less than about 40%, less than about 30%, less than about 20%, less than about 10%, less than about 5%, as a function of the value for the reference antibody.

The phrase "substantially reduced," or "substantially different", as used herein, denotes a sufficiently high degree of difference between two numeric values (e.g., one associated with an antibody of the present disclosure and the other associated with a reference antibody) such that one of skill in the art would consider the difference between the two values to be of statistical significance within the context of the biological characteristic measured by the values. For example, the difference between said two values may be preferably greater than about 10%, greater than about 20%, greater than about 30%, greater than about 40%, greater than about 50% as a function of the value for the reference antibody.

Antibody "effector functions" refer to those biological activities attributable to the Fc region (e.g., a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding region or binding domain (e.g., an antibody variable region or domain) and can be assessed using various assays as disclosed.

A "native sequence Fc region" comprises an amino acid sequence identical to the amino acid sequence of an Fc region found in nature, and not manipulated, modified, and/or changed (e.g., isolated, purified, selected, including or combining with other sequences such as variable region sequences) by a human. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, (e.g., substituting, addition, or deletion) preferably one or more amino acid substitution(s). Preferably, the variant Fc region has at least one amino acid substitution compared to a native sequence Fc region or to the Fc region of a parent polypeptide, for example, from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and more preferably at least about 90% homology therewith, for example, at least about 95% homology therewith. For example, a variant with two amino acid changes to alanine at two positions in the human IgG1 Fc sequence are shown bolded in the amino acid sequence provided below:

(SEQ ID NO: 316)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPALAGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPGK

Such a variant sequence may be used in humanized heavy chain constructs such as shown below for a humanized 5H23-vH3 (see, e.g., Example 7) designated 5H23(vH3)-hIgG1(E233A)(L235A) as provided below, the amino acids that make up the signal sequence are underlined and the variable region sequence is bolded:

(SEQ ID NO: 317)
<u>mdmrvpaqllglllllwlrgarc</u>QVQLQQSGAEVKKPGASVKVSCKASGYT

FTSYDINWVRQAPGQGLEWIGWIYPGDGSTKYNEKFKGKATITRDTSAST

AYMELSSLRSEDTAVYFCARSDYYGSRSFAYWGQGTLVTVSSASTKGPSV

FPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHT

CPPCPAPALAGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSC

SVMHEALHNHYTQKSLSLSPGK

A "light chain constant region" includes kappa and lambda constant regions. An exemplary kappa constant region is provided below:

(SEQ ID NO: 318)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

Such a kappa constant region sequence may be used in humanized light chain constructs such as shown below for a humanized 5H23-vL2 (see, e.g., Example 7) as provided below, the amino acids that make up the signal sequence are underlined and the variable region sequence is bolded:

(SEQ ID NO: 319)
<u>mdmrvpaqllglllllwlrgarc</u>DIVMTQSPDSLAVSLGERATINCRASKS

VSTSGYVYMHWYQQKPGQPPKLLIYLASYLESGVPDRFSGSGSGTDFTLT

ISSVQAEDVAVYYCQHSRDLTFPFGGGTKLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC

The term "variant" when used in relation to beta klotho or to an anti-beta klotho antibody may refer to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified beta klotho sequence. For example, a beta klotho variant may result from one or more (such as, for example, about 1 to about 25, about 1 to about 20, about 1 to about 15, about 1 to about 10, or about 1 to about 5) changes to an amino acid sequence of a native beta klotho. Also by way of example, a variant of an anti-beta klotho antibody may result from one or more (such as, for example, about 1 to about 25, about 1 to about 20, about 1 to about 15, about 1 to about 10, or about 1 to about 5) changes to an amino acid sequence of a native or previously unmodified anti-beta klotho antibody. Variants may be naturally occurring, such as allelic or splice variants, or may be artificially constructed. Polypeptide variants may be prepared from the corresponding nucleic acid molecules encoding the variants. In specific embodiments, the beta klotho variant or anti-beta klotho antibody variant at least retains beta klotho or anti-beta klotho antibody functional activity, respectively. In specific embodiments, an anti-beta klotho antibody variant binds beta klotho and/or is antagonistic to beta klotho activity. In specific embodiments, an anti-beta klotho antibody variant binds beta klotho and/or is agonistic to beta klotho activity. In certain embodiments, the variant is encoded by a single nucleotide polymorphism (SNP) variant of a nucleic acid molecule that encodes beta klotho or anti-beta klotho antibody VH or VL regions or subregions, such as one or more CDRs.

The term "vector" refers to a substance that is used to carry or include a nucleic acid sequences, including for example, in order to introduce a nucleic acid sequence into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain or an antibody VH and VL) both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g. an anti-beta klotho antibody as described herein), and it is further understood that expression levels can be optimized to obtain sufficient expression using methods well known in the art. [00134] "Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is known (see, e.g., Table 3, page 464, Ravetch and Kinet, Annu. Rev. Immunol. 9:457-92 (1991)). To assess ADCC activity of a molecule of interest, an in vitro ADCC assay, (see, e.g., U.S. Pat. No. 5,500,362 or 5,821,337) may be performed. Useful effector cells for such assays include peripheral blood mononuclear cells (PBMC) and Natural Killer (NK) cells. Alternatively, or additionally, ADCC activity of the molecule of interest may be assessed in vivo, for example, in an animal model (see, e.g., Clynes et al. (USA) 95:652-656 (1998)). Antibodies with little or no ADCC activity may be selected for use.

"Fc receptor" or "FcR" describes a receptor that binds to the Fc region of an antibody. The preferred FcR is a native sequence human FcR. Moreover, a preferred FcR is one that binds an IgG antibody (e.g., a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof (see, e.g., review Daeron, Annu. Rev. Immunol. 15:203-234 (1997)). FcRs are known (see, e.g., Ravetch and Kinet, Annu. Rev. Immunol. 9:457-492 (1991); Capel et al., Immunomethods 4:25-34 (1994); and de Haas et al., J. Lab. Clin. Med. 126:330-41 (1995)). Other FcRs, including those to be identified in the future, are encompassed by the term "FcR" herein. The term also includes the neonatal receptor, FcRn, which is responsible for the transfer of maternal IgGs to the fetus (see, e.g., Guyer et al., J. Immunol. 117:587 (1976) and Kim et al., J. Immunol. 24:249 (1994)). Antibody variants with improved or diminished binding to FcRs have been described (see, e.g., in WO 2000/42072; U.S. Pat. Nos. 7,183,387, 7,332, 581 and 7,335,742; Shields et al. J. Biol. Chem. 9(2):6591-6604 (2001)).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, (see, e.g., Gazzano-Santoro et al., J. Immunol. Methods 202:163 (1996)), may be performed. Polypeptide variants with altered Fc region amino acid sequences (polypeptides with a variant Fc region) and increased or decreased C1q binding capability have been described, (see, e.g., U.S. Pat. No. 6,194,551, WO 1999/51642, Idusogie et al. J. Immunol. 164: 4178-4184 (2000)). Antibodies with little or no CDC activity may be selected for use.

A beta klotho polypeptide "extracellular domain" or "ECD" refers to a form of the beta klotho polypeptide that is essentially free of the transmembrane and cytoplasmic domains. For example, a beta klotho polypeptide ECD may have less than 1% of such transmembrane and/or cytoplasmic domains and preferably, may have less than 0.5% of such domains. The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (e.g., an "algorithm"). Methods that can be used to calculate the identity of the aligned nucleic acids or polypeptides include those described in Computational Molecular Biology, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) SIAM J. Applied Math. 48:1073.

In calculating percent identity, the sequences being compared may be aligned in a way that gives the largest match between the sequences. Computer program may be used to determine percent identity is the GCG program package, which includes GAP (Devereux et al., (1984) Nucl. Acid Res. 12:387; Genetics Computer Group, University of Wisconsin, Madison, Wis.). The computer algorithm GAP used to align the two polypeptides or polynucleotides for which the percent sequence identity is to be determined. The sequences may be aligned for optimal matching of their respective amino acid or nucleotide (the "matched span", as determined by the algorithm). A gap opening penalty (which is calculated as 3. times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992) Proc. Natl. Acad. Sci. U.S.A. 89:10915-10919 for the BLOSUM 62 comparison matrix) is also used by the algorithm.

Exemplary parameters for determining percent identity for polypeptides or nucleotide sequences using the GAP program are the following: (i) Algorithm: Needleman et al., 1970, J. Mol. Biol. 48:443-453; (ii) Comparison matrix: BLOSUM 62 from Henikoff et al., 1992, supra; (iii) Gap Penalty: 12 (but with no penalty for end gaps) (iv) Gap Length Penalty: 4; and (v) Threshold of Similarity: 0.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (e.g., the GAP program) can be adjusted if so desired to result in an alignment that spans a number of amino acids, for example, at least 50 contiguous amino acids of the target polypeptide.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

A "modification" of an amino acid residue/position refers to a change of a primary amino acid sequence as compared to a starting amino acid sequence, wherein the change results from a sequence alteration involving said amino acid residue/positions. For example, typical modifications include substitution of the residue with another amino acid (e.g., a conservative or non-conservative substitution), insertion of one or more (e.g., generally fewer than 5, 4 or 3) amino acids adjacent to said residue/position, and/or deletion of said residue/position.

An "epitope" is the site on the surface of an antigen molecule to which a single antibody molecule binds, such as a localized region on the surface of an antigen, such as a beta klotho polypeptide, a beta klotho polypeptide fragment or a beta klotho epitope, that is capable of being bound to one or more antigen binding regions of an antibody, and that has antigenic or immunogenic activity in an animal, such as a mammal (e.g., a human), that is capable of eliciting an immune response.

An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. The term, "epitope" specifically includes linear epitopes and conformational epitopes. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a beta klotho epitope is a three-dimensional surface feature of a beta klotho polypeptide. In other embodiments, a beta klotho epitope is linear feature of a beta klotho polypeptide. Generally an antigen has several or many different epitopes and may react with many different antibodies.

An antibody binds "an epitope" or "essentially the same epitope" or "the same epitope" as a reference antibody, when the two antibodies recognize identical, overlapping or adjacent epitopes in a three-dimensional space. The most widely used and rapid methods for determining whether two antibodies bind to identical, overlapping or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies is measured using radioactive, fluorescent or enzyme labels.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three dimensional structure of the protein is in an altered confirmation, such as following activation or binding of another protein or ligand (e.g., the binding of beta klotho to an FCF receptor such as FGRFR1c, FGFR2c, FGFR3c, or FGFR4c.

"Epitope binning" is the process of grouping antibodies based on the epitopes they recognize. More particularly, epitope binning comprises methods and systems for discriminating the epitope recognition properties of different antibodies, using competition assays combined with computational processes for clustering antibodies based on their epitope recognition properties and identifying antibodies having distinct binding specificities.

A "beta klotho-mediated disease" and "beta klotho-mediated disorder" and "beta klotho-mediated condition" are used interchangeably and refer to any disease, disorder or condition that is completely or partially caused by or is the result of beta klotho or the interaction of a beta klotho with an FGF receptor such as FGFR1c, FGFR2c, FGFR3c, or FGFR4 and/or alternatively any disease, disorder, or condition in which it is desirable to mimic or augment the in vivo effects of FGF19 and/or FGF21.

The term "therapeutically effective amount" as used herein refers to the amount of an agent (e.g., an antibody described herein or any other agent described herein) that is sufficient to reduce and/or ameliorate the severity and/or duration of a given disease, disorder or condition, and/or a symptom related thereto. A therapeutically effective amount of a agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody provided herein). A "therapeutically effective amount" of a substance/molecule/agent of the present disclosure (e.g., an anti-beta klotho antibody) may vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of an antibody or other agent (e.g., or drug) effective to "treat" a disease, disorder, or condition, in a subject or mammal.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition, including, for example, diabetes, obesity, dyslipidemia, cardiovascular disease, metabolic syndrome or broadly any disease, disorder, or condition in which it is desirable to mimic or augment the in vivo effects of FGF19 and/or FGF21. In some embodiments, the effective amount is a therapeutically effective amount or a prophylactically effective amount. A "therapeutically effective amount" is an amount sufficient to remedy a disease, disorder, or condition (e.g., Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21) or symptoms, particularly a disease, disorder, or condition, or symptoms associated with such a disease, disorder, or condition, or otherwise prevent, hinder, retard or reverse the progression of the disease, disorder, or condition, or any other undesirable symptom associated with such a disease, disorder, or condition, in any way whatsoever. A "prophylactically effective amount" is an amount of a pharmaceutical composition that, when administered to a subject, will have the intended prophylactic effect, e.g., preventing or delaying the onset (or reoccurrence) of diabetes, obesity or dyslipidemia, or reducing the likelihood of the onset (or reoccurrence) of a disease, disorder, or condition or associated symptom(s), including, for example, diabetes, obesity, dyslipidemia, cardiovascular disease, metabolic syndrome or broadly any disease, disorder, or condition in which it is desirable to mimic or augment the in vivo effects of FGF19 and/or FGF21) or associated symptoms. The full therapeutic or prophylactic effect does not necessarily occur by administration of one dose, and may occur only after administration of a series of doses. Thus, a therapeutically or prophylactically effective amount may be administered in one or more administrations.

A "prophylactically effective amount" refers to an amount effective, at dosages and for periods of time necessary, to achieve the desired prophylactic result. Typically, but not necessarily, since a prophylactic dose is used in subjects prior to or at an earlier stage of a disease, disorder, or condition, a prophylactically effective amount may be less than a therapeutically effective amount.

"Chronic" administration refers to administration of the agent(s) in a continuous mode (e.g., for a period of time such as days, weeks, months or years) as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (e.g., concurrent) and consecutive administration in any order. The term "in combination" in the context of the administration of other therapies (e.g., other agents) includes the use of more than one therapy (e.g., one agent). The use of the term "in combination" does not restrict the order in which therapies are administered to a subject. A first therapy (e.g., agent) can be administered before (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 8 weeks, 8 weeks, 9 weeks, 10 weeks, 11 weeks, or 12 weeks), concurrently, or after (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 7 weeks, 8 weeks, 9 weeks, 10 weeks, 11 weeks, or 12 weeks) the administration of a second therapy (e.g., agent) to a subject which had, has, or is susceptible to a beta klotho-mediated disease.

Any additional therapy (e.g., agent) can be administered in any order with the other additional therapies (e.g., agents). In certain embodiments, the antibodies can be administered in combination with one or more therapies such as agents (e.g., therapies, including agents, that are not the antibodies that are currently administered) to prevent, treat, manage, and/or ameliorate a beta klotho-mediated disease. Non-limiting examples of therapies (e.g., agents) that can be administered in combination with an antibody include, for example, analgesic agents, anesthetic agents, antibiotics, or immunomodulatory agents or any other agent listed in the *U.S. Pharmacopoeia* and/or *Physician's Desk Reference*. Examples of agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors. Other agents for combination include steroids such as prednisolone, prednisone, methylprednisolone, betamethasone, dexamethasone, or hydrocortisone. Such a combination may be especially advantageous, since one or more side-effects of the steroid can be reduced or even eliminated by tapering the steroid dose required when treating patients in combination with the present antibodies. Additional examples of agents for combinations include cytokine suppressive anti-inflammatory drug(s) (CSAIDs); antibodies to or antagonists of other human cytokines or growth factors, for example, TNF, LT, IL-1β, IL-2, IL-6, IL-7, IL-8, IL-15, IL-16, IL-18, EMAP-II, GM-CSF, FGF, or PDGF. Combinations of agents may include TNF antagonists like chimeric, humanized or human TNF antibodies, REMICADE, anti-TNF antibody fragments (e.g., CDP870), and soluble p55 or p75 TNF receptors, derivatives thereof, p75TNFRIgG (ENBREL®) or p55TNFR1gG (LENERCEPT®), soluble IL-13 receptor (sIL-13), and also TNFα converting enzyme (TACE) inhibitors; similarly IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination therapy include interferon-β1a (AVONEX); interferon-β1b (BETASERON®); copaxone; hyperbaric oxygen; intravenous immunoglobulin; clabribine; and antibodies to or antagonists of other human cytokines or growth factors (e.g., antibodies to CD40 ligand and CD80).

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™. The term "carrier" can also refer to a diluent, adjuvant (e.g., Freund's adjuvant (complete or incomplete)), excipient, or vehicle with which the therapeutic is administered. Such carriers, including pharmaceutical carriers, can be sterile liquids, such as water and oils, including those of petroleum, animal, vegetable or synthetic origin, such as peanut oil, soybean oil, mineral oil, sesame oil and the like. Water is a exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Compositions can take the form of solutions, suspensions, emulsion, tablets, pills, capsules, powders, sustained-release formulations and the like. Oral compositions, including formulations, can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990) Mack Publishing Co., Easton, PA. Compositions, including pharmaceutical compounds, may contain a prophylactically or therapeutically effective amount of an anti-beta klotho antibody, for example, in isolated or purified form, together with a suitable amount of carrier so as to provide the form for proper administration to the subject (e.g., patient). The formulation should suit the mode of administration.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

The term "pharmaceutical formulation" refers to a preparation which is in such form as to permit the biological activity of the active ingredient (e.g., an anti-beta klotho antibody) to be effective, and which contains no additional components which are unacceptably toxic to a subject to which the formulation would be administered. Such formulation may be sterile.

A "sterile" formulation is aseptic or free from all living microorganisms and their spores.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., Chapter 11 in: *Short Protocols in Molecular Biology*, (2002) 5th Ed., Ausubel et al., eds., John Wiley and Sons, New York).

An "isolated nucleic acid" is a nucleic acid, for example, an RNA, DNA, or a mixed polymer, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides. A cell that produces an anti-beta klotho antibody of the present disclosure may include a parent hybridoma cell, as well as bacterial and eukaryotic host cells into which nucleic acid encoding the antibodies have been introduced. Suitable host cells are disclosed below.

Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "package insert" is used to refer to instructions customarily included in commercial packages of therapeutic products, that contain information about the indications, usage, dosage, administration, contraindications and/or warnings concerning the use of such therapeutic products.

The terms "prevent," "preventing," and "prevention" refer to the total or partial inhibition of the development, recurrence, onset or spread of a beta klotho-mediated disease and/or symptom related thereto, resulting from the administration of a therapy or combination of therapies provided herein (e.g., a combination of prophylactic or therapeutic agents, such as an antibody provided herein).

The term "prophylactic agent" refers to any agent that can totally or partially inhibit the development, recurrence, onset or spread of a beta klotho-mediated disease and/or symptom related thereto in a subject. In certain embodiments, the term "prophylactic agent" refers to an anti-beta klotho antibody as described herein. In certain other embodiments, the term "prophylactic agent" refers to an agent other than an anti-beta klotho antibody as described herein. In certain embodiments, a prophylactic agent is an agent which is known to be useful to or has been or is currently being used to prevent a beta klotho-mediated disease, disorder, or condition, and/or a symptom related thereto or impede the onset, development, progression and/or severity of a beta klotho-mediated disease, disorder, or condition, and/or a symptom related thereto. In specific embodiments, the prophylactic agent is a humanized anti-beta klotho antibody, such as a humanized anti-beta klotho monoclonal antibody.

In certain embodiments, a "prophylactically effective serum titer" is the serum titer in a subject, preferably a human, that totally or partially inhibits the development, recurrence, onset or spread of a beta klotho-mediated disease, disorder, or condition, and/or symptom related thereto in the subject.

In certain embodiments, a "therapeutically effective serum titer" is the serum titer in a subject, preferably a human, that reduces the severity, the duration and/or the symptoms associated with a beta klotho-mediated disease, disorder, or condition, in the subject.

The term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created or isolated by any other means that involves splicing of immunoglobulin gene sequences to other DNA sequences. Such recombinant antibodies can have variable and constant regions, including those derived from human germline immunoglobulin sequences (See Kabat, E. A. et al. (1991) Sequences of Proteins of Immunological Interest, Fifth Edition, U.S. Department of Health and Human Services, NIH Publication No. 91-3242). In certain embodiments, however, such recombinant antibodies may be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "serum titer" refers to an average serum titer in a subject from multiple samples (e.g., at one time present or multiple time points) or in a population of least 10, such as at least 20, or at least 40 subjects, up to about 100, 1000 or more.

The term "side effects" encompasses unwanted and/or adverse effects of a therapy (e.g., a prophylactic or therapeutic agent). Unwanted effects are not necessarily adverse. An adverse effect from a therapy (e.g., a prophylactic or therapeutic agent) might be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (68th ed., 2014).

The terms "subject" and "patient" may be used interchangeably. As used herein, in certain embodiments, a subject is a mammal, such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a beta klotho-mediated disease, disorder or condition. In another embodiment, the subject is a mammal (e.g., a human) at risk of developing a beta klotho-mediated disease, disorder, or condition.

"Substantially all" refers to refers to at least about 60%, at least about 65%, at least about 70%, at least about 75%, at least about 80%, at least about 85%, at least about 90%, at least about 95%, at least about 98%, at least about 99%, or about 100%.

The term "therapeutic agent" refers to any agent that can be used in treating, preventing or alleviating a disease, disorder or condition, including in the treatment, prevention or alleviation of one or more symptoms of a beta klotho-mediated disease, disorder, or condition and/or a symptom related thereto. In certain embodiments, a therapeutic agent refers to an anti-beta klotho antibody as described herein. In certain other embodiments, a therapeutic agent refers to an agent other than an antibody provided herein. In certain embodiments, a therapeutic agent is an agent which is known to be useful for, or has been or is currently being used for the treatment, prevention or alleviation of one or more symptoms of a beta klotho-mediated disease, disorder, or condition, or a symptom related thereto.

The combination of therapies (e.g., use of agents, including therapeutic agents) can be more effective than the additive effects of any two or more single therapy (e.g., synergistic). A synergetic effect is unexpected and can not be predicted. For example, a synergistic effect of a combination of therapeutic agents permits the use of lower dosages of one or more of the agents and/or less frequent administration of the agents to a subject with a beta klotho-mediated disease. The ability to utilize lower dosages of therapeutic therapies and/or to administer the therapies less frequently reduces the toxicity associated with the administration of the therapies to a subject without reducing the efficacy of the therapies in the prevention, treatment or alleviation of one or more symptom of a beta klotho-mediated disease. In addition, a synergistic effect can result in improved efficacy of therapies in the prevention, treatment or alleviation of one or more symptom of a beta klotho-mediated disease. Finally, synergistic effect of a combination of therapies (e.g., therapeutic agents) may avoid or reduce adverse or unwanted side effects associated with the use of any single therapy.

The term "therapy" refers to any protocol, method and/or agent that can be used in the prevention, management, treatment and/or amelioration of a beta klotho-mediated disease, disorder, or conditions. In certain embodiments, the terms "therapies" and "therapy" refer to a biological therapy, supportive therapy, and/or other therapies useful in the prevention, management, treatment and/or amelioration of a beta klotho-mediated disease, disorder or condition, known to one of skill in the art such as medical personnel.

The term "detectable probe" refers to a composition that provides a detectable signal. The term includes, without limitation, any fluorophore, chromophore, radiolabel, enzyme, antibody or antibody fragment, and the like, that provide a detectable signal via its activity.

The term "diagnostic agent" refers to a substance administered to a subject that aids in the diagnosis of a disease, disorder, or conditions. Such substances can be used to reveal, pinpoint, and/or define the localization of a disease causing process. In certain embodiments, a diagnostic agent includes a substance that is conjugated to an anti-beta klotho antibody as described herein, that when administered to a subject or contacted to a sample from a subject aids in the diagnosis a beta klotho-mediated disease.

The term "detectable agent" refers to a substance that can be used to ascertain the existence or presence of a desired molecule, such as an anti-beta klotho antibody as described herein, in a sample or subject. A detectable agent can be a substance that is capable of being visualized or a substance that is otherwise able to be determined and/or measured (e.g., by quantitation).

The term "encode" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The term "excipient" refers to an inert substance which is commonly used as a diluent, vehicle, preservative, binder, or stabilizing agent, and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, *Remington's Pharmaceutical Sciences* (1990) Mack Publishing Co., Easton, PA, which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, beta klotho fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250, at least 300, at least 350, at least 400, at least 450, at least 500, at least 550, at least 600, at least 650, at least 700, at least 750, at least 800, at least 850, at least 900, or at least 950, contiguous amino acid residues of the amino acid sequence of a beta klotho polypeptide or an antibody that binds to a beta klotho polypeptide. In a specific embodiment, a fragment of a beta klotho polypeptide or an antibody that binds to a beta klotho antigen retains at least 1, at least 2, or at least 3 or more functions of the polypeptide or antibody.

The terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents, such as an antibody provided herein) to "manage" a beta klotho-mediated disease, one or more symptoms thereof, so as to prevent the progression or worsening of the disease.

The terms "about" or "approximately" mean within 20%, within 15%, within 10%, within 9%, within 8%, within 7%, within 6%, within 5%, within 4%, within 3%, within 2%, within or 1% or less of a given value or range.

"Administer" or "administration" refers to the act of injecting or otherwise physically delivering a substance as it exists outside the body (e.g., an anti-beta klotho antibody as described herein) into a patient, such as by mucosal, intradermal, intravenous, intramuscular delivery and/or any other method of physical delivery described herein or known in the art. When a disease, disorder, or condition, or a symptom thereof, is being treated, administration of the substance typically occurs after the onset of the disease, disorder, or condition, or symptoms thereof. When a disease, disorder, or condition or symptoms thereof, are being prevented, administration of the substance typically occurs before the onset of the disease, disorder, or condition, or symptoms thereof.

In the context of a polypeptide, the term "analog" as used herein refers to a polypeptide that possesses a similar or identical function as a beta klotho polypeptide, a fragment of a beta klotho polypeptide, or an anti-beta klotho antibody but does not necessarily comprise a similar or identical amino acid sequence of a beta klotho polypeptide, a fragment of a beta klotho polypeptide, or an anti-beta klotho antibody, or possess a similar or identical structure of a beta klotho polypeptide, a fragment of a beta klotho polypeptide, or an anti-beta klotho antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a beta klotho polypeptide (e.g., SEQ ID NO:297, a fragment of a beta klotho polypeptide, or an anti-beta klotho antibody described herein; (b) a polypeptide encoded by a nucleotide sequence that hybridizes under stringent conditions to a nucleotide sequence encoding a beta klotho polypeptide, a fragment of a beta klotho polypeptide, or an anti-beta klotho antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) *Molecular Cloning: A Laboratory Manual*, Cold Spring Harbor Laboratory Press, Cold Spring Harbor, NY; Maniatis et al. (1982) *Molecular Cloning: A Laboratory Manual*, Cold Spring Harbor Press, Cold Spring Harbor, NY); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a beta klotho polypeptide, a fragment of a beta klotho polypeptide, or an anti-beta klotho antibody (or VH or VL region thereof) described herein. A polypeptide with similar structure to a beta klotho polypeptide, a fragment of a beta klotho polypeptide, or an anti-beta klotho antibody described herein refers to a polypeptide that has a similar secondary, tertiary or quaternary structure of a beta klotho polypeptide, a fragment of a beta klotho, or a beta klotho antibody described herein. The structure of a polypeptide can determined by methods known to those skilled in the art, including but not limited to, X-ray crystallography, nuclear magnetic resonance, and crystallographic electron microscopy.

The term "composition" is intended to encompass a product containing the specified ingredients (e.g., an antibody provided herein) in, optionally, the specified amounts, as well as any product which results, directly or indirectly, from combination of the specified ingredients in, optionally, the specified amounts.

In the context of a polypeptide, the term "derivative" as used herein refers to a polypeptide that comprises an amino acid sequence of a beta klotho polypeptide, a fragment of a beta klotho polypeptide, or an antibody that binds to a beta klotho polypeptide which has been altered by the introduction of amino acid residue substitutions, deletions or additions. The term "derivative" as used herein also refers to a beta klotho polypeptide, a fragment of a beta klotho polypeptide, or an antibody that binds to a beta klotho polypeptide which has been chemically modified, e.g., by the covalent attachment of any type of molecule to the polypeptide. For example, but not by way of limitation, a beta klotho polypeptide, a fragment of a beta klotho polypeptide, or a beta klotho antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a beta klotho polypeptide, a fragment of a beta klotho polypeptide, or a beta klotho antibody may be chemically modified by chemical modifications using techniques known to those of skill in the art, including, but not limited to specific chemical cleavage, acetylation, formulation, metabolic synthesis of tunicamycin, etc. Further, a derivative of a beta klotho polypeptide, a fragment of a beta klotho polypeptide, or a beta klotho antibody may contain one or more non-classical amino acids. A polypeptide derivative possesses a similar or identical function as a beta klotho polypeptide, a fragment of a beta klotho polypeptide, or a beta klotho antibody described herein.

Compositions and Methods of Making the Same

Binding proteins such as antibodies that bind to beta klotho (e.g., human and/or cyno beta klotho) are provided. Antibodies of the present disclosure are useful, for example, for the diagnosis or treatment of diseases, disorders, or conditions associated with expression, of beta klotho. In certain embodiments, antibodies of the present disclosure are useful for the diagnosis or treatment of a diseases, disorder, or condition, such as Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21.

Provided herein are antibodies that bind to a beta klotho polypeptide, a beta klotho polypeptide fragment, beta klotho peptide, or a beta klotho epitope. In some embodiments, the anti-beta klotho antibodies bind to the extracellular domain (ECD) of beta klotho. Also provided are antibodies that competitively block an anti-beta klotho antibody provided herein from binding to a beta klotho polypeptide. The anti-beta klotho antibodies provided herein can also be conjugated or recombinantly fused to a diagnostic agent, detectable agent or therapeutic agent. Further provided are compositions comprising an beta klotho antibody.

Also provided herein are isolated nucleic acid molecules encoding an immunoglobulin heavy chain, light chain, VH region, VL region, VH CDR1, VH CDR2, VH CDR3, VL CDR1, VL CDR2, and/or VL CDR3 of anti-beta klotho antibodies that bind to a beta klotho polypeptide, a beta klotho polypeptide fragment, a beta klotho peptide or a beta klotho epitope. Further provided are vectors and host cells comprising nucleic acid molecules encoding anti-beta klotho antibodies that bind to a beta klotho polypeptide, a beta klotho polypeptide fragment, a beta klotho peptide or a beta klotho epitope. Also provided are methods of making antibodies that bind to a beta klotho polypeptide, a beta klotho polypeptide fragment, a beta klotho peptide or a beta klotho epitope.

Methods of using the anti-beta klotho antibodies are provided. The methods include treating, preventing or alleviating a disease, disorder or condition, including treating, preventing or alleviating one or more symptoms of a disease, disorder or condition in a subject. Non limiting examples of diseases, disorders, or conditions include glucose utilization disorders and the sequelae associated therewith, including diabetes mellitus (Type 1 and Type-2), gestational diabetes, hyperglycemia, insulin resistance, abnormal glucose metabolism, "pre-diabetes" (Impaired Fasting Glucose (IFG) or Impaired Glucose Tolerance (IGT)), or other physiological disorders associated with, or that result from, the hyperglycemic condition, including, for example, histopathological changes such as pancreatic β-cell destruction. For example subjects with a diseases, disorders, or condition, in need of treatment may have a fasting plasma glucose (FPG) level greater than about 100 mg/dl. Other hyperglycemic-related disorders, include kidney damage (e.g., tubule damage or nephropathy), liver degeneration, eye damage (e.g., diabetic retinopathy or cataracts), and diabetic foot disorders. Other of diseases, disorders, or conditions include dyslipidemias and their sequelae such as, for example, atherosclerosis, coronary artery disease, cerebrovascular disorders and the like or other of diseases, disorders, or conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), or thromboses, hypercoagulable and prothrombotic states (arterial and venous), hypertension, cardiovascular disease, stroke and heart failure. These diseases, disorders, or conditions include atherosclerosis, chronic inflammatory bowel diseases (e.g., Crohn's disease and ulcerative colitis), asthma, lupus erythematosus, arthritis, or other inflammatory rheumatic disorders. Other diseases, disorders, or conditions include adipose cell tumors, lipomatous carcinomas including, for example, liposarcomas, solid tumors, and neoplasms. Other diseases, disorders, or conditions include neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome. Other diseases, disorders, or conditions include skin and dermatological disorders and/or disorders of wound healing processes, including erythemato-squamous dermatoses. Other diseases, disorders, or conditions include syndrome X, osteoarthritis, and acute respiratory distress syndrome. As used herein, the term "hyperglycemic" or "hyperglycemia," when used in reference to a disease, disorder, or condition of a subject refers to a transient or chronic abnormally high level of glucose present in the blood of a subject. The disease, disorder, or condition may be caused by a delay in glucose metabolism or absorption such that the subject exhibits glucose intolerance or a state of elevated glucose not typically found in normal subjects (e.g., in glucose-intolerant pre-diabetic subjects at risk of developing diabetes, or in diabetic subjects). For example, fasting plasma glucose (FPG) levels for normoglycemia may be less than about 100 mg/dl, for impaired glucose metabolism, between about 100 and 126 mg/dl, and for diabetics greater than about 126 mg/dl. Methods of preventing (e.g., in subjects predisposed to having a particular disorder(s)), relate to delaying, slowing or inhibiting progression of, the onset of, or treating (e.g., ameliorating) obesity or an undesirable body mass (e.g., a greater than normal body mass index, or "BMI" relative to an appropriate matched subject of comparable age, gender, race, etc.). Methods of treating obesity or an undesirable body mass (including the co-morbid conditions of obesity, for example, obstructive sleep apnea, arthritis, cancer (e.g., breast, endometrial, and colon), gallstones or hyperglycemia, include contacting or administering a binding protein such as an anti-beta klotho antibody as described herein in an amount effective to treat obesity or an undesirable body mass. For example, a subject may have a body mass index greater than 25, for example, 25-30, 30-35, 35-40, or greater than 40. Methods of preventing (e.g., in subjects predisposed to having a particular disorder(s)), relate to delaying, slowing or inhibiting the progression of, the onset of, or treating undesirable levels or abnormally elevated serum/plasma LDL, VLDL, triglycerides or cholesterol, all of which, alone or in combination, can lead to, for example, plaque formation, narrowing or blockage of blood vessels, and increased risk of hypertension, stroke and coronary artery disease. Such diseases, disorders, or conditions may be due to, for example, genetic predisposition or diet.

Anti-Beta Klotho Antibodies

In one embodiment, the present disclosure provides anti-beta klotho antibodies that may find use herein as therapeutic agents. Exemplary antibodies include polyclonal, monoclonal, humanized, human, bispecific, and heteroconjugate antibodies, as well as variants thereof having improved affinity or other properties.

In some embodiments, provided herein are antibodies that bind to beta klotho, including a beta klotho polypeptide, a beta klotho polypeptide fragment, a beta klotho peptide or a beta klotho epitope. In some embodiments the anti-beta klotho antibodies are humanized antibodies (e.g., comprising human constant regions) that bind beta klotho, including beta klotho polypeptide, a beta klotho polypeptide fragment, a beta klotho peptide or a beta klotho epitope.

In certain embodiments, the anti-beta klotho antibody comprises a VH region, VL region, VH CDR1, VH CDR2, VH CDR3, VL CDR1, VL CDR2, and/or VL CDR3 of any one of the murine monoclonal antibodies described herein, such as an amino acid sequence depicted in Tables 1-10. Accordingly, in some embodiments, the isolated antibody or functional fragment thereof provided herein comprises one, two, and/or three heavy chain CDRs and/or one, two, and/or three light chain CDRs from: (a) the antibody designated 5H23; (b) the antibody designated 1C17; (c) the antibody designated 1D19; (d) the antibody designated 2L12; (e) the antibody designated 3L3; (f) the antibody designated 3N20; (g) the antibody designated 4P5; (h) the antibody designated 5C23; (i) the antibody designated 5F7; (j) the antibody designated 1G19, as shown in Tables 1-10.

The antibody designated 5H23 comprises a VH sequence that is SEQ ID NO:25 and a VL sequence that is SEQ ID NO:26.

The antibody designated 1C17 comprises a VH sequence that is SEQ ID NO:51 and a VL sequence that is SEQ ID NO:52.

The antibody designated 1D19 comprises a VH sequence that is SEQ ID NO:77 and a VL sequence that is SEQ ID NO:78.

The antibody designated 2L12 comprises a VH sequence that is SEQ ID NO:103 and a VL sequence that is SEQ ID NO:104.

The antibody designated 3L3 comprises a VH sequence that is SEQ ID NO:129 and a VL sequence that is SEQ ID NO:130.

The antibody designated 3N20 comprises a VH sequence that is SEQ ID NO:155 and a VL sequence that is SEQ ID NO:156.

The antibody designated 4P5 comprises a VH sequence that is SEQ ID NO:181 and a VL sequence that is SEQ ID NO:182.

The antibody designated 5C23 comprises a VH sequence that is SEQ ID NO:207 and a VL sequence that is SEQ ID NO:208.

The antibody designated 5F7 comprises a VH sequence that is SEQ ID NO:233 and a VL sequence that is SEQ ID NO:234.

The antibody designated IG19 comprises a VH sequence that is SEQ ID NO:259 and a VL sequence that is SEQ ID NO:260.

TABLE 1

Antibody 5H23 CDR Sequences

| | | Exemplary | IMGT | Kabat |
|---|---|---|---|---|
| VH CDR Seq. | VH CDR1 | GYTFTSYDIN (SEQ ID NO: 1) | GYTFTSYD (SEQ ID NO: 7) | SYDIN (SEQ ID NO: 12) |
| | VH CDR2 | WIYPGDGSTKYNEKFKG (SEQ ID NO: 2) | IYPGDGST (SEQ ID NO: 8) | WIYPGDGSTKYNEKFKG (SEQ ID NO: 2) |
| | VH CDR3 | SDYYGSRSFAY (SEQ ID NO: 3) | ARSDYYGSRSFAY (SEQ ID NO: 9) | SDYYGSRSFAY (SEQ ID NO: 3) |
| VL CDR Seq. | VL CDR1 | RASKSVSTSGYVYMH (SEQ ID NO: 4) | KSVSTSGYVY (SEQ ID NO: 10) | RASKSVSTSGYVYMH (SEQ ID NO: 4) |
| | VL CDR2 | LASYLES (SEQ ID NO: 5) | LAS (SEQ ID NO: 11) | LASYLES (SEQ ID NO: 5) |
| | VL CDR3 | QHSRDLTFP (SEQ ID NO: 6) | QHSRDLTFP (SEQ ID NO: 6) | QHSRDLTFP (SEQ ID NO: 6) |
| | | Chothia | Contact | AbM |
| VH CDR Seq. | VH CDR1 | GYTFTSY (SEQ ID NO: 13) | TSYDIN (SEQ ID NO: 18) | GYTFTSYDIN (SEQ ID NO: 1) |
| | VH CDR2 | PGDG (SEQ ID NO: 14) | WIGWIYPGDGSTK (SEQ ID NO: 19) | WIYPGDGSTK (SEQ ID NO: 24) |
| | VH CDR3 | DYYGSRSFA (SEQ ID NO: 15) | ARSDYYGSRSFA (SEQ ID NO: 20) | SDYYGSRSFAY (SEQ ID NO: 3) |
| VL CDR Seq. | VL CDR1 | SKSVSTSGYVY (SEQ ID NO: 16) | STSGYVYMHWN (SEQ ID NO: 21) | RASKSVSTSGYVYMH (SEQ ID NO: 4) |
| | VL CDR2 | LAS (SEQ ID NO: 11) | LLIYLASYLE (SEQ ID NO: 22) | LASYLES (SEQ ID NO: 5) |
| | VL CDR3 | SRDLTF (SEQ ID NO: 17) | QHSRDLTF (SEQ ID NO: 23) | QHSRDLTFP (SEQ ID NO: 6) |

VH Sequence:
QVQLQQSGPELVKPGALVKISCKASGYTFTSYDINWVKQRPGQGLEWIGWIYPGDGSTKYNEKFKGKATLTADK
SSRTAYMQLSSLTSENSAVYFCARSDYYGSRSFAYWGQGTLVTVSA (SEQ ID NO: 25)

VL Sequence:
DIVLTQSPASLAVSLGQRATISCRASKSVSTSGYVYMHWNQQKPGQPPKLLIYLASYLESGVPARFSGSGSGTD
FTLNIHPVEEEDAAIYYCQHSRDLTFPFGGGTKLEIK (SEQ ID NO: 26)

TABLE 2

Antibody 1C17 CDR Sequences

| | | Exemplary | IMGT | Kabat |
|---|---|---|---|---|
| VH CDR Seq. | VH CDR1 | GYSITSGYYWN (SEQ ID NO: 27) | GYSITSGYY (SEQ ID NO: 33) | SGYYWN (SEQ ID NO: 38) |
| | VH CDR2 | YINYDGNSNYTPSLKN (SEQ ID NO: 28) | INYDGNS (SEQ ID NO: 34) | YINYDGNSNYTPSLKN (SEQ ID NO: 28) |
| | VH CDR3 | KGAYYSNYDSFDV (SEQ ID NO: 29) | ARKGAYYSNYDSFDV (SEQ ID NO: 35) | KGAYYSNYDSFDV (SEQ ID NO: 29) |

TABLE 2-continued

Antibody 1C17 CDR Sequences

| | | | | |
|---|---|---|---|---|
| VL CDR Seq. | VL CDR1 | KASQDINSYLS (SEQ ID NO: 30) | QDINSY (SEQ ID NO: 36) | KASQDINSYLS (SEQ ID NO: 30) |
| | VL CDR2 | RANRLVD (SEQ ID NO: 31) | RAN (SEQ ID NO: 37) | RANRLVD (SEQ ID NO: 31) |
| | VL CDR3 | LQYDEFPFT (SEQ ID NO: 32) | LQYDEFPFT (SEQ ID NO: 32) | LQYDEFPFT (SEQ ID NO: 32) |

| | | Chothia | Contact | AbM |
|---|---|---|---|---|
| VH CDR Seq. | VH CDR1 | GYSITSGY (SEQ ID NO: 39) | TSGYYWN (SEQ ID NO: 44) | GYSITSGYYWN (SEQ ID NO: 27) |
| | VH CDR2 | YDG (SEQ ID NO: 40) | WMGYINYDGNSN (SEQ ID NO: 45) | YINYDGNSN (SEQ ID NO: 50) |
| | VH CDR3 | GAYYSNYDSFD (SEQ ID NO: 41) | ARKGAYYSNYDSFD (SEQ ID NO: 46) | KGAYYSNYDSFDV (SEQ ID NO: 29) |
| VL CDR Seq. | VL CDR1 | SQDINSY (SEQ ID NO: 42) | NSYLSWV (SEQ ID NO: 47) | KASQDINSYLS (SEQ ID NO: 30) |
| | VL CDR2 | RAN (SEQ ID NO: 37) | TLIYRANRLV (SEQ ID NO: 48) | RANRLVD (SEQ ID NO: 31) |
| | VL CDR3 | YDEFPF (SEQ ID NO: 43) | LQYDEFPF (SEQ ID NO: 49) | LQYDEFPFT (SEQ ID NO: 32) |

VH Sequence:
QVQLQESGPGLVKPSQSLSLTCSVTGYSITSGYYWNWIRQFPGNKLEWMGYINYDGNSNYTPSLKNRISITRDTSKN
QFFLKLNSVTPEDTATYYCARKGAYYSNYDSFDVWGTGTTVTVSS (SEQ ID NO: 51)

VL Sequence:
DIKMTQSPSSMYASLGERVTITCKASQDINSYLSWQQKPGKSPKTLIYRANRLVDGVPSRFSGSGSGQDYSLTISS
LEYEDMGIYYCLQYDEFPFTFGSGTKLEIK (SEQ ID NO: 52)

TABLE 3

Antibody 1D19 CDR Sequences

| | | Exemplary | IMGT | Kabat |
|---|---|---|---|---|
| VH CDR Seq. | VH CDR1 | GYTFTRYDIN (SEQ ID NO: 53) | GYTFTRYD (SEQ ID NO: 59) | RYDIN (SEQ ID NO: 64) |
| | VH CDR2 | WIYPGDSSTKFNENFKD (SEQ ID NO: 54) | IYPGDSST (SEQ ID NO: 60) | WIYPGDSSTKFNENFKD (SEQ ID NO: 54) |
| | VH CDR3 | SDYYGSRSFTY (SEQ ID NO: 55) | ARSDYYGSRSFTY (SEQ ID NO: 61) | SDYYGSRSFTY (SEQ ID NO: 55) |
| VL CDR Seq. | VL CDR1 | RASKSVSTSGYSYMH (SEQ ID NO: 56) | KSVSTSGYSY (SEQ ID NO: 62) | RASKSVSTSGYSYMH (SEQ ID NO: 56) |
| | VL CDR2 | LASNLES (SEQ ID NO: 57) | LAS (SEQ ID NO: 63) | LASNLES (SEQ ID NO: 57) |
| | VL CDR3 | QHSRELPYT (SEQ ID NO: 58) | QHSRELPYT (SEQ ID NO: 58) | QHSRELPYT (SEQ ID NO: 58) |

| | | Chothia | Contact | AbM |
|---|---|---|---|---|
| VH CDR Seq. | VH CDR1 | GYTFTRY (SEQ ID NO: 65) | TRYDIN (SEQ ID NO: 70) | GYTFTRYDIN (SEQ ID NO: 53) |
| | VH CDR2 | PGDS (SEQ ID NO: 66) | WIGWIYPGDSSTK (SEQ ID NO: 71) | WIYPGDSSTK (SEQ ID NO: 76) |
| | VH CDR3 | DYYGSRSFT (SEQ ID NO: 67) | ARSDYYGSRSFT (SEQ ID NO: 72) | SDYYGSRSFTY (SEQ ID NO: 55) |
| VL CDR Seq. | VL CDR1 | SKSVSTSGYSY (SEQ ID NO: 68) | STSGYSYMHWY (SEQ ID NO: 73) | RASKSVSTSGYSYMH (SEQ ID NO: 56) |
| | VL CDR2 | LAS (SEQ ID NO: 63) | LLIYLASNLE (SEQ ID NO: 74) | LASNLES (SEQ ID NO: 57) |
| | VL CDR3 | SRELPY (SEQ ID NO: 69) | QHSRELPY (SEQ ID NO: 75) | QHSRELPYT (SEQ ID NO: 58) |

VH Sequence:
QVQPQESGPELVKPGALVKISCKASGYTFTRYDINWMKQRPGQGLEWIGWIYPGDSSTKFNENFKDKATLTADKS
SSTAYMQLSSLTSENSTVYFCARSDYYGSRSFTYWGQGTLVTVSA (SEQ ID NO: 77)

VL Sequence:
DIVLTQSPASLAVSLGQRATISCRASKSVSTSGYSYMHWYQQKPGQPPKLLIYLASNLESGVPARFSGSGSGTDF
TLNIHPVEEEDAATYYCQHSRELPYTFGGGTKLEIK (SEQ ID NO: 78)

TABLE 4

Antibody 2L12 CDR Sequences

|  |  | Exemplary | IMGT | Kabat |
|---|---|---|---|---|
| VH CDR Seq. | VH CDR1 | GYTFTRYDIN (SEQ ID NO: 79) | GYTFTRYD (SEQ ID NO: 85) | RYDIN (SEQ ID NO: 90) |
|  | VH CDR2 | WIYPGDDSTKYNEKFKG (SEQ ID NO: 80) | IYPGDDST (SEQ ID NO: 86) | WIYPGDDSTKYNEKFKG (SEQ ID NO: 80) |
|  | VH CDR3 | SDYYGSRSFVY (SEQ ID NO: 81) | ARSDYYGSRSFVY (SEQ ID NO: 87) | SDYYGSRSFVY (SEQ ID NO: 81) |
| VL CDR Seq. | VL CDR1 | RASKSVSTSGYSYLH (SEQ ID NO: 82) | KSVSTSGYSY (SEQ ID NO: 88) | RASKSVSTSGYSYLH (SEQ ID NO: 82) |
|  | VL CDR2 | LASNLES (SEQ ID NO: 83) | LAS (SEQ ID NO: 89) | LASNLES (SEQ ID NO: 83) |
|  | VL CDR3 | QHSGELPYT (SEQ ID NO: 84) | QHSGELPYT (SEQ ID NO: 84) | QHSGELPYT (SEQ ID NO: 84) |
|  |  | Chothia | Contact | AbM |
| VH CDR Seq. | VH CDR1 | GYTFTRY (SEQ ID NO: 91) | TRYDIN (SEQ ID NO: 96) | GYTFTRYDIN (SEQ ID NO: 79) |
|  | VH CDR2 | PGDD (SEQ ID NO: 92) | WIGWIYPGDDSTK (SEQ ID NO: 97) | WIYPGDDSTK (SEQ ID NO: 102) |
|  | VH CDR3 | DYYGSRSFV (SEQ ID NO: 93) | ARSDYYGSRSFV (SEQ ID NO: 98) | SDYYGSRSFVY (SEQ ID NO: 81) |
| VL CDR Seq. | VL CDR1 | SKSVSTSGYSY (SEQ ID NO: 94) | STSGYSYLHWY (SEQ ID NO: 99) | RASKSVSTSGYSYLH (SEQ ID NO: 82) |
|  | VL CDR2 | LAS (SEQ ID NO: 89) | LLIYLASNLE (SEQ ID NO: 100) | LASNLES (SEQ ID NO: 83) |
|  | VL CDR3 | SGELPY (SEQ ID NO: 95) | QHSGELPY (SEQ ID NO: 101) | QHSGELPYT (SEQ ID NO: 84) |

VH Sequence:
QVQLQQSGPELVKPGALVKISCKASGYTFTRYDINWVKKRPGQGLEWIGWIYPGDDSTKYNEKFKGKATLTADKS
SSTAYMQLSSLTSENSAVYFCARSDYYGSRSFVYWGQGTLVTVSA (SEQ ID NO: 103)

VL Sequence:
DIVLTQSPASLPVSLGQRATISCRASKSVSTSGYSYLHWYQQKPGQPPKLLIYLASNLESGVPARFSGSGSGTDF
TLNIHPVEEEDAATYYCQHSGELPYTFGGGTKLEIK (SEQ ID NO: 104)

TABLE 5

Antibody 3L3 CDR Sequences

|  |  | Exemplary | IMGT | Kabat |
|---|---|---|---|---|
| VH CDR Seq. | VH CDR1 | GYTFTSYDIN (SEQ ID NO: 105) | GYTFTSYD (SEQ ID NO: 111) | SYDIN (SEQ ID NO: 116) |
|  | VH CDR2 | WIYPGDGSPKYDEKFKG (SEQ ID NO: 106) | IYPGDGSP (SEQ ID NO: 112) | WIYPGDGSPKYDEKFKG (SEQ ID NO: 106) |
|  | VH CDR3 | SDYYGSRSFVY (SEQ ID NO: 107) | ARSDYYGSRSFVY (SEQ ID NO: 113) | SDYYGSRSFVY (SEQ ID NO: 107) |
| VL CDR Seq. | VL CDR1 | RASKSVSTSGYSYVH (SEQ ID NO: 108) | KSVSTSGYSY (SEQ ID NO: 114) | RASKSVSTSGYSYVH (SEQ ID NO: 108) |
|  | VL CDR2 | LASNLES (SEQ ID NO: 109) | LAS (SEQ ID NO: 115) | LASNLES (SEQ ID NO: 109) |
|  | VL CDR3 | QHSGELPYT (SEQ ID NO: 110) | QHSGELPYT (SEQ ID NO: 110) | QHSGELPYT (SEQ ID NO: 110) |
|  |  | Chothia | Contact | AbM |
| VH CDR Seq. | VH CDR1 | GYTFTSY (SEQ ID NO: 117) | TSYDIN (SEQ ID NO: 122) | GYTFTSYDIN (SEQ ID NO: 105) |
|  | VH CDR2 | PGDG (SEQ ID NO: 118) | WIGWIYPGDGSPK (SEQ ID NO: 123) | WIYPGDGSPK (SEQ ID NO: 128) |
|  | VH CDR3 | DYYGSRSFV (SEQ ID NO: 119) | ARSDYYGSRSFV (SEQ ID NO: 124) | SDYYGSRSFVY (SEQ ID NO: 107) |

TABLE 5-continued

Antibody 3L3 CDR Sequences

| VL CDR Seq. | VL CDR1 | SKSVSTSGYSY (SEQ ID NO: 120) | STSGYSYVHWY (SEQ ID NO: 125) | RASKSVSTSGYSYVH (SEQ ID NO: 108) |
|---|---|---|---|---|
| | VL CDR2 | LAS (SEQ ID NO: 115) | LLIYLASNLE (SEQ ID NO: 126) | LASNLES (SEQ ID NO: 109) |
| | VL CDR3 | SGELPY (SEQ ID NO: 121) | QHSGELPY (SEQ ID NO: 127) | QHSGELPYT (SEQ ID NO: 110) |

VH Sequence:
QVQPQESGPELVKPGTLVKISCKASGYTFTSYDINWVKQRPGQGLEWIGWIYPGDSPKYDEKFKGKATLTADKS
SSTAYMQLSSLTSENSAVYFCARSDYYGSRSFVYWGQGTLVTVSA (SEQ ID NO: 129)

VL Sequence:
DIVLTQSPASLAVSLGQRATISCRASKSVSTSGYSYVHWYQQKPGQPPKLLIYLASNLESGVPARFSGRGSTDF
TLNIHPVEEEDAATYYCQHSGELPYTFGGGTKLEIK (SEQ ID NO: 130)

TABLE 6

Antibody 3N20 CDR Sequences

| | | Exemplary | IMGT | Kabat |
|---|---|---|---|---|
| VH CDR Seq. | VH CDR1 | GYIFTNYGIS (SEQ ID NO: 131) | GYIFTNYG (SEQ ID NO: 137) | NYGIS (SEQ ID NO: 142) |
| | VH CDR2 | EIYPRSGNTYYNEKFKG (SEQ ID NO: 132) | IYPRSGNT (SEQ ID NO: 138) | EIYPRSGNTYYNEKFKG (SEQ ID NO: 132) |
| | VH CDR3 | HWDGVLDYFDY (SEQ ID NO: 133) | ARHWDGVLDYFDY (SEQ ID NO: 139) | HWDGVLDYFDY (SEQ ID NO: 133) |
| VL CDR Sequences | VL CDR1 | KSSQSLLNSGNQKNYLA (SEQ ID NO: 134) | QSLLNSGNQKNY (SEQ ID NO: 140) | KSSQSLLNSGNQKNYLA (SEQ ID NO: 134) |
| | VL CDR2 | GASTRES (SEQ ID NO: 135) | GAS (SEQ ID NO: 141) | GASTRES (SEQ ID NO: 135) |
| | VL CDR3 | LNDHSYPFT (SEQ ID NO: 136) | LNDHSYPFT (SEQ ID NO: 136) | LNDHSYPFT (SEQ ID NO: 136) |

| | | Chothia | Contact | AbM |
|---|---|---|---|---|
| VH CDR Seq. | VH CDR1 | GYIFTNY (SEQ ID NO: 143) | TNYGIS (SEQ ID NO: 148) | GYIFTNYGIS (SEQ ID NO: 131) |
| | VH CDR2 | PRSG (SEQ ID NO: 144) | WIGEIYPRSGNTY (SEQ ID NO: 149) | EIYPRSGNTY (SEQ ID NO: 154) |
| | VH CDR3 | WDGVLDYFD (SEQ ID NO: 145) | ARHWDGVLDYFD (SEQ ID NO: 150) | HWDGVLDYFDY (SEQ ID NO: 133) |
| VL CDR Sequences | VL CDR1 | SQSLLNSGNQKNY (SEQ ID NO: 146) | LNSGNQKNYLAWY (SEQ ID NO: 151) | KSSQSLLNSGNQKNYLA (SEQ ID NO: 134) |
| | VL CDR2 | GAS (SEQ ID NO: 141) | LLIYGASTRE (SEQ ID NO: 152) | GASTRES (SEQ ID NO: 135) |
| | VL CDR3 | DHSYPF (SEQ ID NO: 147) | LNDHSYPF (SEQ ID NO: 153) | LNDHSYPFT (SEQ ID NO: 136) |

VH Sequence:
QVQLQESGAELARPGASVKLSCKVSGYIFTNYGISWVKQRTGQGLEWIGEIYPRSGNTYYNEKFKGKATLTADMS
SSTAYMDLRSLTSEDSAVYFCARHWDGVLDYFDYWGQGTSLTVSS (SEQ ID NO: 155)

VL Sequence:
DIVMTQSPSSLSVSAGEKVTMSCKSSQSLLNSGNQKNYLAWYQQKPGQPPKLLIYGASTRESGVPDRFTGSGSGT
DFTLTISSVQAEDLAVYYCLNDHSYPFTFGAGTKLELK (SEQ ID NO: 156)

TABLE 7

Antibody 4P5 CDR Sequences

| | | Exemplary | IMGT | Kabat |
|---|---|---|---|---|
| VH CDR Seq. | VH CDR1 | GYTFTRYDIN (SEQ ID NO: 157) | GYTFTRYD (SEQ ID NO: 163) | RYDIN (SEQ ID NO: 168) |
| | VH CDR2 | WIYPGDDSTKYNEKFKG (SEQ ID NO: 158) | IYPGDDST (SEQ ID NO: 164) | WIYPGDDSTKYNEKFKG (SEQ ID NO: 158) |

TABLE 7-continued

Antibody 4P5 CDR Sequences

|  |  |  |  |  |
|---|---|---|---|---|
|  | VH CDR3 | SDYYGSRSFVY (SEQ ID NO: 159) | ARSDYYGSRSFVY (SEQ ID NO: 165) | SDYYGSRSFVY (SEQ ID NO: 159) |
| VL CDR Seq. | VL CDR1 | RASKSVSTSGYSYMH (SEQ ID NO: 160) | KSVSTSGYSY (SEQ ID NO: 166) | RASKSVSTSGYSYMH (SEQ ID NO: 160) |
|  | VL CDR2 | LASNLES (SEQ ID NO: 161) | LAS (SEQ ID NO: 167) | LASNLES (SEQ ID NO: 161) |
|  | VL CDR3 | HHSGELPYT (SEQ ID NO: 162) | HHSGELPYT (SEQ ID NO: 162) | HHSGELPYT (SEQ ID NO: 162) |

|  |  | Chothia | Contact | AbM |
|---|---|---|---|---|
| VH CDR Seq. | VH CDR1 | GYTFTRY (SEQ ID NO: 169) | TRYDIN (SEQ ID NO: 174) | GYTFTRYDIN (SEQ ID NO: 157) |
|  | VH CDR2 | PGDD (SEQ ID NO: 170) | WIGWIYPGDDSTK (SEQ ID NO: 175) | WIYPGDDSTK (SEQ ID NO: 180) |
|  | VH CDR3 | DYYGSRSFV (SEQ ID NO: 171) | ARSDYYGSRSFV (SEQ ID NO: 176) | SDYYGSRSFVY (SEQ ID NO: 159) |
| VL CDR Seq. | VL CDR1 | SKSVSTSGYSY (SEQ ID NO: 172) | STSGYSYMHWY (SEQ ID NO: 177) | RASKSVSTSGYSYMH (SEQ ID NO: 160) |
|  | VL CDR2 | LAS (SEQ ID NO: 167) | LLIYLASNLE (SEQ ID NO: 178) | LASNLES (SEQ ID NO: 161) |
|  | VL CDR3 | SGELPY (SEQ ID NO: 173) | HHSGELPY (SEQ ID NO: 179) | HHSGELPYT (SEQ ID NO: 162) |

VH Sequence:
QVQLQQSGPELVKPGALVKISCKASGYTFTRYDINWVKKRPGQGLEWIGWIYPGDDSTKYNEKFKGKATLTADKS
SSTAYMQLSSLTSENSAVYFCARSDYYGSRSFVYWGQGTLVTVSA (SEQ ID NO: 181)

VL Sequence:
DILLTQSPASLAVSLGQRATISCRASKSVSTSGYSYMHWYQQKPGQPPKLLIYLASNLESGVPARFSGRSGSTDF
TLNIHPVEEEDAATYYCHHSGELPYTFGGGTKLEIK (SEQ ID NO: 182)

TABLE 8

Antibody 5C23 CDR Sequences

|  |  | Exemplary | IMGT | Kabat |
|---|---|---|---|---|
| VH CDR Seq. | VH CDR1 | GYTFTRYDIN (SEQ ID NO: 183) | GYTFTRYD (SEQ ID NO: 189) | RYDIN (SEQ ID NO: 194) |
|  | VH CDR2 | WIYPGDGSTKYNEKFEG (SEQ ID NO: 184) | IYPGDGST (SEQ ID NO: 190) | WIYPGDGSTKYNEKFEG (SEQ ID NO: 184) |
|  | VH CDR3 | SDYYGSRSFVY (SEQ ID NO: 185) | ARSDYYGSRSFVY (SEQ ID NO: 191) | SDYYGSRSFVY (SEQ ID NO: 185) |
| VL CDR Seq. | VL CDR1 | RASKSVSTSGYSYMH (SEQ ID NO: 186) | KSVSTSGYSY (SEQ ID NO: 192) | RASKSVSTSGYSYMH (SEQ ID NO: 186) |
|  | VL CDR2 | LASNLES (SEQ ID NO: 187) | LAS (SEQ ID NO: 193) | LASNLES (SEQ ID NO: 187) |
|  | VL CDR3 | QHSRELPYT (SEQ ID NO: 188) | QHSRELPYT (SEQ ID NO: 188) | QHSRELPYT (SEQ ID NO: 188) |

|  |  | Chothia | Contact | AbM |
|---|---|---|---|---|
| VH CDR Seq. | VH CDR1 | GYTFTRY (SEQ ID NO: 195) | TRYDIN (SEQ ID NO: 200) | GYTFTRYDIN (SEQ ID NO: 183) |
|  | VH CDR2 | PGDG (SEQ ID NO: 196) | WIGWIYPGDGSTK (SEQ ID NO: 201) | WIYPGDGSTK (SEQ ID NO: 206) |
|  | VH CDR3 | DYYGSRSFV (SEQ ID NO: 197) | ARSDYYGSRSFV (SEQ ID NO: 202) | SDYYGSRSFVY (SEQ ID NO: 185) |

TABLE 8-continued

Antibody 5C23 CDR Sequences

| VL CDR Seq. | VL CDR1 | SKSVSTSGYSY (SEQ ID NO: 198) | STSGYSYMHWY (SEQ ID NO: 203) | RASKSVSTSGYSYMH (SEQ ID NO: 186) |
|---|---|---|---|---|
| | VL CDR2 | LAS (SEQ ID NO: 193) | LLIYLASNLE (SEQ ID NO: 204) | LASNLES (SEQ ID NO: 187) |
| | VL CDR3 | SRELPY (SEQ ID NO: 199) | QHSRELPY (SEQ ID NO: 205) | QHSRELPYT (SEQ ID NO: 188) |

VH Sequence:
QVQPQESGPELVKPGALVKISCKASGYTFTRYDINWVKKRPGQGLEWIGWIYPGDGSTKYNEKFEGKATLTADKS
SSTAYMQLSSLTSENSAVYFCARSDYYGSRSFVYWGQGTLVTVSA (SEQ ID NO: 207)

VL Sequence:
DIVLTQSPDSLTVSLGQRATISCRASKSVSTSGYSYMHWYQQKPGQPPKLLIYLASNLESGVPARFSGSGSGTDF
TLNIHPVEEEDAATYYCQHSRELPYTFGGGTKLEIK (SEQ ID NO: 208)

TABLE 9

Antibody 5F7 CDR Sequences

| | | Exemplary | IMGT | Kabat |
|---|---|---|---|---|
| VH CDR Seq. | VH CDR1 | GYTFTRYDIN (SEQ ID NO: 209) | GYTFTRYD (SEQ ID NO: 215) | RYDIN (SEQ ID NO: 220) |
| | VH CDR2 | WIYPGDISTKYNEKFKG (SEQ ID NO: 210) | IYPGDIST (SEQ ID NO: 216) | WIYPGDISTKYNEKFKG (SEQ ID NO: 210) |
| | VH CDR3 | SDYYGSRSFVY (SEQ ID NO: 211) | ARSDYYGSRSFVY (SEQ ID NO: 217) | SDYYGSRSFVY (SEQ ID NO: 211) |
| VL CDR Seq. | VL CDR1 | RASKSVSTSGYSYMH (SEQ ID NO: 212) | KSVSTSGYSY (SEQ ID NO: 218) | RASKSVSTSGYSYMH (SEQ ID NO: 212) |
| | VL CDR2 | LASNLES (SEQ ID NO: 213) | LAS (SEQ ID NO: 219) | LASNLES (SEQ ID NO: 213) |
| | VL CDR3 | QHSRELPYT (SEQ ID NO: 214) | QHSRELPYT (SEQ ID NO: 214) | QHSRELPYT (SEQ ID NO: 214) |
| | | Chothia | Contact | AbM |
| VH CDR Seq. | VH CDR1 | GYTFTRY (SEQ ID NO: 221) | TRYDIN (SEQ ID NO: 226) | GYTFTRYDIN (SEQ ID NO: 209) |
| | VH CDR2 | PGDI (SEQ ID NO: 222) | WIGWIYPGDISTK (SEQ ID NO: 227) | WIYPGDISTK (SEQ ID NO: 232) |
| | VH CDR3 | DYYGSRSFV (SEQ ID NO: 223) | ARSDYYGSRSFV (SEQ ID NO: 228) | SDYYGSRSFVY (SEQ ID NO: 211) |
| VL CDR Seq. | VL CDR1 | SKSVSTSGYSY (SEQ ID NO: 224) | STSGYSYMHWY (SEQ ID NO: 229) | RASKSVSTSGYSYMH (SEQ ID NO: 212) |
| | VL CDR2 | LAS (SEQ ID NO: 219) | LLIYLASNLE (SEQ ID NO: 230) | LASNLES (SEQ ID NO: 213) |
| | VL CDR3 | SRELPY (SEQ ID NO: 225) | QHSRELPY (SEQ ID NO: 231) | QHSRELPYT (SEQ ID NO: 214) |

VH Sequence:
QVQPQESGPELVKPGALVKISCKASGYTFTRYDINWVKQRPGQGLEWIGWIYPGDISTKYNEKFKGKATLTADKS
SSTAYMQLNSLTSENSAVYFCARSDYYGSRSFVYWGQGTLVTVSA (SEQ ID NO: 233)

VL Sequence:
DIVLTQSPASLAVSLGQRATISCRASKSVSTSGYSYMHWYQQKPGQPPKLLIYLASNLESGVPARFSGSGSGTDF
TLNIHPVEEEDAATYYCQHSRELPYTFGGGTKVEIK (SEQ ID NO: 234)

TABLE 10

Antibody 1G19 CDR Sequences

| | | Exemplary | IMGT | Kabat |
|---|---|---|---|---|
| VH CDR Seq. | VH CDR1 | GYSITSGYYWN (SEQ ID NO: 235) | GYSITSGYY (SEQ ID NO: 241) | SGYYWN (SEQ ID NO: 246) |
| | VH CDR2 | YINYGGSNNYNPSLKN (SEQ ID NO: 236) | INYGGSN (SEQ ID NO: 242) | YINYGGSNNYNPSLKN (SEQ ID NO: 236) |

TABLE 10-continued

Antibody 1G19 CDR Sequences

|  |  |  |  |  |
|---|---|---|---|---|
|  | VH CDR3 | RGAYYSNYDSFDV (SEQ ID NO: 237) | ARRGAYYSNYDSFDV (SEQ ID NO: 243) | RGAYYSNYDSFDV (SEQ ID NO: 237) |
| VL CDR Seq. | VL CDR1 | KASQDINSYLS (SEQ ID NO: 238) | QDINSY (SEQ ID NO: 244) | KASQDINSYLS (SEQ ID NO: 238) |
|  | VL CDR2 | RANRLVD (SEQ ID NO: 239) | RAN (SEQ ID NO: 245) | RANRLVD (SEQ ID NO: 239) |
|  | VL CDR3 | LQYDEFPYT (SEQ ID NO: 240) | LQYDEFPYT (SEQ ID NO: 240) | LQYDEFPYT (SEQ ID NO: 240) |
|  |  | Chothia | Contact | AbM |
| VH CDR Seq. | VH CDR1 | GYSITSGY (SEQ ID NO: 247) | TSGYYWN (SEQ ID NO: 252) | GYSITSGYYWN (SEQ ID NO: 235) |
|  | VH CDR2 | YGG (SEQ ID NO: 248) | WMGYINYGGSNN (SEQ ID NO: 253) | YINYGGSNN (SEQ ID NO: 258) |
|  | VH CDR3 | GAYYSNYDSFD (SEQ ID NO: 249) | ARRGAYYSNYDSFD (SEQ ID NO: 254) | RGAYYSNYDSFDV (SEQ ID NO: 237) |
| VL CDR Seq. | VL CDR1 | SQDINSY (SEQ ID NO: 250) | NSYLSWF (SEQ ID NO: 255) | KASQDINSYLS (SEQ ID NO: 238) |
|  | VL CDR2 | RAN (SEQ ID NO: 245) | TLIYRANRLV (SEQ ID NO: 256) | RANRLVD (SEQ ID NO: 239) |
|  | VL CDR3 | YDEFPY (SEQ ID NO: 251) | LQYDEFPY (SEQ ID NO: 257) | LQYDEFPYT (SEQ ID NO: 240) |

VH Sequence:
QVQLQESGPGLVKPSQSLSLTCSVTGYSITSGYYWNWIRQFPGNKLEWMGYINYGGSNNYNPSLKNRISITRDTSKNQF
FLKLTSVTTEDTATYYCARRGAYYSNYDSFDVWGTGTTVTVSS (SEQ ID NO: 259)

VL Sequence:
DIKMTQSPSSMYASLGERVTITCKASQDINSYLSWFQQKPGKSPKTLIYRANRLVDGVPSRFSGSGSGQDYSLTISSLE
YEEMGIYYCLQYDEFPYTFGGGTKLEIK (SEQ ID NO: 260)

In some embodiments, the antibodies provided herein comprise a VH region or VH domain In other embodiments, the antibodies provided herein comprise a VL region or VL chain. In some embodiments, the antibodies provided herein have a combination of (i) a VH domain or VH region; and/or (ii) a VL domain or VL region.

In some embodiments, an antibody provided herein comprises or consists of six CDRs, for example, VH CDR1, VH CDR2, VH CDR3, VL CDR1, VL CDR2, and/or VL CDR3 identified in Tables 1-10. In some embodiments, an antibody provided herein can comprise less than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3 identified in tables 1-10. In some embodiments, the antibody comprises or consists of one, two, three, four, or five CDRs selected from the group consisting of VH CDR1, VH CDR2, VH CDR3, VL CDR1, VL CDR2, and/or VL CDR3 of the murine monoclonal antibody selected from the group consisting of: (a) the antibody designated 5H23; (b) the antibody designated 1C17; (c) the antibody designated 1D19; (d) the antibody designated 2L12; (e) the antibody designated 3L3; (f) the antibody designated 3N20; (g) the antibody designated 4P5; (h) the antibody designated 5C23; (i) the antibody designated 5F7; (j) the antibody designated 1G19; described herein. Accordingly, in some embodiments, the antibody comprises or consists of one, two, three four or five CDRs of anyone of the VH CDR1, VH CDR2, VH CDR3, VL CDR1, VL CDR2, and/or VL CDR3 identified in Tables 1-10.

In some embodiments, the antibodies provided herein comprise one or more (e.g., one, two or three) VH CDRs listed in Tables 1-10. In other embodiments, the antibodies provided herein comprise one or more (e.g., one, two or three) VL CDRs listed in Tables 1-10. In yet other embodiments, the antibodies provided herein comprise one or more (e.g., one, two or three) VH CDRs listed in Tables 1-10 and one or more VL CDRs listed in Tables 1-10. Accordingly, in some embodiments, the antibodies comprise a VH CDR1 having the amino acid sequence of any one of SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252. In some embodiments, the antibodies comprise a VH CDR2 having the amino acid sequence of any one of SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258. In some embodiments, the antibodies comprise a VH CDR3 having the amino acid sequence of any one of SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254. In some embodiments, the antibodies comprise a VH CDR1 and/or a VH CDR2 and/or a VH CDR3 independently selected from a VH CDR1, VH CDR2, VH CDR3 as depicted in any one of the amino acid sequences depicted in Table 1-10. In some embodiments, the antibodies comprise a VL CDR1 having the amino acid sequence of any one of SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255. In another embodiment, the antibodies comprise a VL CDR2 having the amino acid sequence of any one of SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256. In some embodiments, the antibodies comprise a VL CDR3 having the amino acid sequence of any one of SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257. In some embodiments, the antibodies comprise a VL CDR1 and/or a VL CDR2 and/or a VL CDR3 independently selected from a VL CDR1, VL CDR2, VL CDR3 as depicted in any one of the amino acid sequences depicted in Tables 1-10.

In some embodiments, the antibodies provided herein comprise a heavy chain variable (VH) region comprising: (1) a VH CDR1 having an amino acid sequence of selected from the group consisting of: (i) SEQ ID NO:1, 27, 53, 79, 105, 131, 157, 183, 209, and or 235, (ii) SEQ ID NO:7, 33, 59, 85, 111, 137, 163, 189, 215 or 241, (iii) SEQ ID NO:12, 38, 64, 90, 116, 142, 168, 194, 220 or 246, (iv) SEQ ID NO:13, 39, 65, 91, 117, 143, 169, 195, 221 or 247, and (v) SEQ ID NO:18, 44, 70, 96, 122, 148, 174, 200, 226 or 252; (2) a VH CDR2 having an amino acid sequence of selected from the group consisting of: (i) SEQ ID NO:2, 28, 54, 80, 106, 132, 158, 184, 210, and or 236, (ii) SEQ ID NO:8, 34, 60, 86, 112, 138, 164, 190, 216 or 242, (iii) SEQ ID NO:14, 40, 66, 92, 118, 144, 170, 196, 222 or 248, (iv) SEQ ID NO:19, 45, 71, 97, 123, 149, 175, 201, 227 or 253, and (v) SEQ ID NO:24, 50, 76, 102, 128, 154, 180, 206, 232 or 258; and (3) a VH CDR3 having an amino acid sequence of selected from the group consisting of: (i) SEQ ID NO: 3, 29, 55, 81, 107, 133, 159, 185, 211, and or 237, (ii) SEQ ID NO:9, 35, 61, 87, 113, 139, 165, 191, 217 or 243, (iii) SEQ ID NO:15, 41, 67, 93, 119, 145, 171, 197, 223 or 249, and (iv) SEQ ID NO:20, 46, 72, 98, 124, 150, 176, 202, 228 or 254; and/or a light chain variable (VL) region comprising: (1) a VL CDR1 having an amino acid sequence of selected from the group consisting of: (i) SEQ ID NO:4, 30, 56, 82, 108, 134, 160, 186, 212, and or 238, (ii) SEQ ID NO:10, 36, 52, 88, 114, 140, 166, 192, 218 or 244, (iii) SEQ ID NO:16, 42, 68, 94, 120, 146, 172, 198, 224 or 250, and (iv) SEQ ID NO:21, 47, 73, 99, 125, 151, 177, 203, 229 or 255; (2) a VL CDR2 having an amino acid sequence of selected from the group consisting of: (i) SEQ ID NO:5, 31, 57, 83, 109, 135, 161, 187, 213, and or 239, (ii) SEQ ID NO:11, 37, 63, 89, 115, 141, 167, 193, 219 or 245, and (iii) SEQ ID NO:22, 48, 74, 100, 126, 152, 178, 204, 230 or 256; and (3) a VL CDR3 having an amino acid sequence of selected from the group consisting of: (i) SEQ ID NO:6, 32, 58, 84, 110, 136, 162, 188, 214, and or 240, (ii) SEQ ID NO:17, 43, 69, 95, 121, 147, 173, 199, 225 or 251, and (iii) SEQ ID NO:23, 49, 75, 101, 127, 153, 179, 205, 231 or 257.

In some embodiments, the antibodies provided herein comprise a heavy chain variable (VH) region comprising: (1) a VH CDR1 having an amino acid sequence of selected from the group consisting of: (i) SEQ ID NO:1, 27, 53, 79, 105, 131, 157, 183, 209, and or 235, (ii) SEQ ID NO:7, 33, 59, 85, 111, 137, 163, 189, 215 or 241, (iii) SEQ ID NO:12, 38, 64, 90, 116, 142, 168, 194, 220 or 246, (iv) SEQ ID NO:13, 39, 65, 91, 117, 143, 169, 195, 221 or 247, and (v) SEQ ID NO:18, 44, 70, 96, 122, 148, 174, 200, 226 or 252; (2) a VH CDR2 having an amino acid sequence of selected from the group consisting of: (i) SEQ ID NO:2, 28, 54, 80, 106, 132, 158, 184, 210, and or 236, (ii) SEQ ID NO:8, 34, 60, 86, 112, 138, 164, 190, 216 or 242, (iii) SEQ ID NO:14, 40, 66, 92, 118, 144, 170, 196, 222 or 248, (iv) SEQ ID NO:19, 45, 71, 97, 123, 149, 175, 201, 227 or 253, and (v) SEQ ID NO:24, 50, 76, 102, 128, 154, 180, 206, 232 or 258; and (3) a VH CDR3 having an amino acid sequence of selected from the group consisting of: (i) SEQ ID NO: 3, 29, 55, 81, 107, 133, 159, 185, 211, and or 237, (ii) SEQ ID NO:9, 35, 61, 87, 113, 139, 165, 191, 217 or 243, (iii) SEQ ID NO:15, 41, 67, 93, 119, 145, 171, 197, 223 or 249, and (iv) SEQ ID NO:20, 46, 72, 98, 124, 150, 176, 202, 228 or 254.

In some embodiments, the antibodies provided herein comprise a light chain variable (VL) region comprising: (1) a VL CDR1 having an amino acid sequence of selected from the group consisting of: (i) SEQ ID NO:4, 30, 56, 82, 108, 134, 160, 186, 212, and or 238, (ii) SEQ ID NO:10, 36, 52, 88, 114, 140, 166, 192, 218 or 244, (iii) SEQ ID NO:16, 42, 68, 94, 120, 146, 172, 198, 224 or 250, and (iv) SEQ ID NO:21, 47, 73, 99, 125, 151, 177, 203, 229 or 255; (2) a VL CDR2 having an amino acid sequence of selected from the group consisting of: (i) SEQ ID NO:5, 31, 57, 83, 109, 135, 161, 187, 213, and or 239, (ii) SEQ ID NO:11, 37, 63, 89, 115, 141, 167, 193, 219 or 245, and (iii) SEQ ID NO:22, 48, 74, 100, 126, 152, 178, 204, 230 or 256; and (3) a VL CDR3 having an amino acid sequence of selected from the group consisting of: (i) SEQ ID NO:6, 32, 58, 84, 110, 136, 162, 188, 214, and or 240, (ii) SEQ ID NO:17, 43, 69, 95, 121, 147, 173, 199, 225 or 251, and (iii) SEQ ID NO:23, 49, 75, 101, 127, 153, 179, 205, 231 or 257.

Also provided herein are antibodies comprising one or more VH CDRs and one or more (e.g., one, two or three) VL CDRs listed in Tables 1-10. In particular, provided herein is an antibody comprising a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252.) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252); a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VH CDR1 (SEQ ID NOS 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252) VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257) and a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258); a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258); and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and aVL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and aVL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); aVH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257);a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and aVL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); aVH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252.), aVL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); aVH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS: 1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR1 (SEQ ID NOS: 4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), aVH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS: 3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254) and a VL CDR2 (SEQ ID NOS: 5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS: 2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS: 6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256); a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256), and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR1 (SEQ ID NOS:1, 7, 12, 13, 18, 27, 33, 38, 39, 44, 53, 59, 64, 65, 70, 79, 85, 90, 91, 96, 105, 111, 116, 117, 122, 131, 137, 142, 143, 148, 157, 163, 168, 169, 174, 183, 189, 194, 195, 200, 209, 215, 220, 221, 226, 235, 241, 246, 247, and 252), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256), and a VL CDR3 (SEQ ID NOS:6, 17, 23, 32, 43, 49, 58, 69, 75, 84, 95, 101, 110, 121, 127, 136, 147, 153, 162, 173, 179, 188, 199, 205, 214, 225, 231, 240, 251, and 257); a VH CDR2 (SEQ ID NOS:2, 8, 14, 19, 24, 28, 34, 40, 45, 50, 54, 60, 66, 71, 76, 80, 86, 92, 97, 102, 106, 112, 118, 123, 128, 132, 138, 144, 149, 154, 158, 164, 170, 175, 180, 184, 190, 196, 201, 206, 210, 216, 222, 227, 232, 236, 242, 248, 253, and 258), a VH CDR3 (SEQ ID NOS:3, 9, 15, 20, 29, 35, 41, 46, 55, 61, 67, 72, 81, 87, 93, 98, 107, 113, 119, 124, 133, 139, 145, 150, 159, 165, 171, 176, 185, 191, 197, 202, 211, 217, 223, 228, 237, 243, 249, and 254), a VL CDR1 (SEQ ID NOS:4, 10, 16, 21, 30, 36, 42, 47, 56, 62, 68, 73, 82, 88, 94, 99, 108, 114, 120, 125, 134, 140, 146, 151, 160, 166, 172, 177, 186, 192, 198, 203, 212, 218, 224, 229, 238, 244, 250, and 255), a VL CDR2 (SEQ ID NOS:5, 11, 22, 31, 37, 48, 57, 63, 74, 83, 89, 100, 109, 115, 126, 135, 141, 152, 161, 167, 178, 187, 193, 204, 213, 219, 230, 239, 245, and 256) or any combination thereof of the VH CDRs and VL CDRs listed in Tables 1-10.

In yet another aspect, the CDRs disclosed herein include consensus sequences derived from groups of related antibodies (see, e.g., Tables 1-10). As described herein, a "consensus sequence" refers to amino acid sequences having conserved amino acids common among a number of sequences and variable amino acids that vary within a given amino acid sequences. The CDR consensus sequences provided include CDRs corresponding to CDRH1, CDRH2, CDRH3, CDRL1, CDRL2 and/or CDRL3. Consensus sequences of CDRs of anti-beta klotho antibodies are shown in FIG. 2.

In certain embodiments, an antibody of fragment thereof described herein comprises a VH region that comprises: (1) a VH FR1 having an amino acid sequence selected from the group consisting of SEQ ID NOS: 278, 279, 280 and 378; (2) a VH FR2 having an amino acid sequence selected from the group consisting of SEQ ID NOS: 281, 282, and 283; (3) a VH FR3 having an amino acid sequence selected from the group consisting of SEQ ID NOS: 284, 285, 286, 287 and 379-381; and/or (4) a VH FR4 having an amino acid of SEQ ID NO: 288. Accordingly, in some aspects, the humanized antibody comprises a VH region that includes a VH FR1 having an amino acid sequence selected from the group consisting of SEQ ID NOS: 278, 279, 280 and 378. In some aspects, the humanized antibody comprises a VH region that includes a VH FR2 having an amino acid sequence selected from the group consisting of SEQ ID NOS: 281, 282, and 283. In some aspects, the humanized antibody comprises a VH region that includes a VH FR3 having an amino acid sequence selected from the group consisting of SEQ ID NOS: 284, 285, 286, 287 and 379-381. In some aspects, the humanized antibody comprises a VH region that includes a VH FR4 having an amino acid of SEQ ID NO: 288.

In certain embodiments, an antibody of fragment thereof described herein comprises a VL region that comprises: (1) a VL FR1 having an amino acid sequence selected from the group consisting of SEQ ID NOS: 289, 290 and 382-384; (2) a VL FR2 having an amino acid sequence selected from the group consisting of SEQ ID NOS: 291, 292 and 385-392; (3) a VL FR3 having an amino acid sequence selected from the group consisting of SEQ ID NOS: 293, 294, 295 and 393-404; and/or (4) a VL FR4 having an amino acid of SEQ ID NO: 296 and 405-407. Accordingly, in some aspects, the humanized antibody comprises a VL region that includes a VL FR1 having an amino acid sequence selected from the group consisting of SEQ ID NOS: 289, 290 and 382-384. In some aspects, the humanized antibody comprises a VL region that includes a VL FR2 having an amino acid sequence selected from the group consisting of SEQ ID NOS: 291, 292 and 385-392. In some aspects, the humanized antibody comprises a VL region that includes a VL FR3 having an amino acid sequence selected from the group consisting of SEQ ID NOS: 293, 294, 295 and 393-404. In some aspects, the humanized antibody comprises a VL region that includes a VL FR4 having an amino acid of SEQ ID NO: 296 and 405-407.

In certain embodiments, an antibody of fragment thereof described herein comprises a VH region and a VL region, wherein the VH region further comprises: (1) a VH FR1 having an amino acid sequence selected from the group consisting of SEQ ID NOS: 278, 279, 280 and 378; (2) a VH FR2 having an amino acid sequence selected from the group consisting of SEQ ID NOS: 281, 282, and 283; (3) a VH FR3 having an amino acid sequence selected from the group consisting of SEQ ID NOS: 284, 285, 286, 287 and 379-381; and/or (4) a VH FR4 having an amino acid sequence of SEQ ID NO: 288; and wherein the VL region further comprises: (1) a VL FR1 having an amino acid sequence selected from the group consisting of SEQ ID NOS: 289, 290 and 382-384; (2) a VL FR2 having an amino acid sequence selected from the group consisting of SEQ ID NOS: 291, 292 and 385-392; (3) a VL FR3 having an amino acid sequence selected from the group consisting of SEQ ID NOS: 293, 294, 295 and 393-404; and/or (4) a VL FR4 having an amino acid of SEQ ID NO: 296 and 405-407.

Also provided herein are antibodies comprising one or more (e.g., one, two, three or four) VH FRs and one or more VL FRs listed in Table 19. In particular, provided herein is an antibody comprising a VH FR1 (SEQ ID NOS:278, 279, 280 and 378) and a VL FR1 (SEQ ID NOS:289, 290 and 382-384); a VH FR1 (SEQ ID NOS:278, 279, 280 and 378)

and a VL FR2 (SEQ ID NOS:291, 292 and 385-392); a VH FR1 (SEQ ID NOS:278, 279, 280 and 378) and a VL FR3 (SEQ ID NOS:293, 294, 295 and 393-404); a VH FR1 (SEQ ID NOS:278, 279, 280 and 378) and a VL FR4 (SEQ ID NO:296 and 405-407); a VH FR2 (SEQ ID NOS:281, 282, and 283) and a VL FR1 (SEQ ID NOS:289, 290 and 382-384); a VH FR2 (SEQ ID NOS:281, 282, and 283) and a VL FR2 (SEQ ID NOS:291, 292 and 385-392); a VH FR2 (SEQ ID NOS:281, 282, and 283) and a VL FR3 (SEQ ID NOS:293, 294, 295 and 393-404); a VH FR2 (SEQ ID NOS:281, 282, and 283) and a VL FR4 (SEQ ID NO:296 and 405-407); a VH FR3 (SEQ ID NOS:284, 285, 286, 287 and 379-381) and a VH FR1 (SEQ ID NOS:278, 279, 280 and 378); a VH FR3 (SEQ ID NOS:284, 285, 286, 287 and 379-381) and a VL FR2 (SEQ ID NOS:291, 292 and 385-392); a VH FR3 (SEQ ID NOS:284, 285, 286, 287 and 379-381) and a VL FR3 (SEQ ID NOS:293, 294, 295 and 393-404); a VH FR3 (SEQ ID NOS:284, 285, 286, 287 and 379-381) and a VL FR4 (SEQ ID NO:296 and 405-407); a VH FR1 (SEQ ID NOS:278, 279, 280 and 378), a VH FR2 (SEQ ID NOS:281, 282, and 283) and a VL FR1 (SEQ ID NOS:289, 290 and 382-384); a VH FR1 (SEQ ID NOS:278, 279, 280 and 378), a VH FR2 (SEQ ID NOS:281, 282, and 283) and a VL FR2 (SEQ ID NOS:291, 292 and 385-392); a VH FR1 (SEQ ID NOS:278, 279, 280 and 378), a VH FR2 (SEQ ID NOS:281, 282, and 283) and a VL FR3 (SEQ ID NOS:293, 294, 295 and 393-404);a VH FR1 (SEQ ID NOS:278, 279, 280 and 378), a VH FR2 (SEQ ID NOS:281, 282, and 283) and a VL FR4 (SEQ ID NO:296 and 405-407);a VH FR2 (SEQ ID NOS:281, 282, and 283), a VH FR3 (SEQ ID NOS:284, 285, 286, 287 and 379-381) and a VL FR1 (SEQ ID NOS:289, 290 and 382-384), a VH FR2 (SEQ ID NOS:281, 282, and 283), a VH FR3 (SEQ ID NOS:284, 285, 286, 287 and 379-381) and a VL FR2 (SEQ ID NOS:291, 292 and 385-392); a VH FR2 (SEQ ID NOS:281, 282, and 283), a VH FR3 (SEQ ID NOS:284, 285, 286, 287 and 379-381) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381) and a VL FR4 (SEQ ID NO:296 and 405-407); a VH FR1 (SEQ ID NOS:278, 279, 280 and 378), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VL FR1 (SEQ ID NOS:289, 290 and 382-384) and a VL FR4 (SEQ ID NO:296 and 405-407); a VH FR1 (SEQ ID NOS:278, 279, 280 and 378), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VL FR2 (SEQ ID NOS:291, 292 and 385-392) and a VL FR4 (SEQ ID NO:296 and 405-407); a VH FR2 (SEQ ID NOS:281, 282, and 283), a VL FR1 (SEQ ID NOS:289, 290 and 382-384) and a VL FR2 (SEQ ID NOS:291, 292 and 385-392); a VH FR2 (SEQ ID NOS:281, 282, and 283), a VL FR1 (SEQ ID NOS:289, 290 and 382-384) and a VL FR3 (SEQ ID NOS:293, 294, 295 and 393-404); a VH FR2 (SEQ ID NOS:281, 282, and 283), a VL FR1 (SEQ ID NOS:289, 290 and 382-384) and a VL FR4 (SEQ ID NO:296 and 405-407); a VH FR2 (SEQ ID NOS:281, 282, and 283) and a VL FR3 (SEQ ID NOS:293, 294, 295 and 393-404); a VH FR2 (SEQ ID NOS:281, 282, and 283), a VL FR2 (SEQ ID NOS:291, 292 and 385-392) and a VL FR4 (SEQ ID NO:296 and 405-407); a VH FR3 (SEQ ID NOS:284, 285, 286, 287 and 379-381), a VL FR1 (SEQ ID NOS:289, 290 and 382-384) and a VL FR2 (SEQ ID NOS:291, 292 and 385-392); a VH FR3 (SEQ ID NOS:284, 285, 286, 287 and 379-381), a VL FR1 (SEQ ID NOS:289, 290 and 382-384) and a VL FR3 (SEQ ID NOS:293, 294, 295 and 393-404); a VH FR3 (SEQ ID NOS:284, 285, 286, 287 and 379-381), a VL FR1 (SEQ ID NOS:289, 290 and 382-384) and a VL FR4 (SEQ ID NO:296 and 405-407); a VH FR3 (SEQ ID NOS:284, 285, 286, 287 and 379-381), a VL FR2 (SEQ ID NOS:291, 292 and 385-392) and a VL FR3 (SEQ ID NOS:293, 294, 295 and 393-404); a VH FR3 (SEQ ID NOS:284, 285, 286, 287 and 379-381), a VL FR2 (SEQ ID NOS:291, 292 and 385-392) and a VL FR4 (SEQ ID NO:296 and 405-407); a VH FR4 (SEQ ID NO:288), a VL FR1 (SEQ ID NOS:289, 290 and 382-384) and a VL FR2 (SEQ ID NOS:291, 292 and 385-392); a VH FR4 (SEQ ID NO:288), a VL FR1 (SEQ ID NOS:289, 290 and 382-384) and a VL FR3 (SEQ ID NOS:293, 294, 295 and 393-404); a VH FR4 (SEQ ID NO:288), a VL FR1 (SEQ ID NOS:289, 290 and 382-384) and a VL FR4 (SEQ ID NO:296 and 405-407); a VH FR4 (SEQ ID NO:288), a VL FR2 (SEQ ID NOS:291, 292 and 385-392) and a VL FR3 (SEQ ID NOS:293, 294, 295 and 393-404); a VH FR4 (SEQ ID NO:288), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381) and a VL FR1 (SEQ ID NOS:289, 290 and 382-384); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288) and a VL FR1 (SEQ ID NOS:289, 290 and 382-384); a VH FR1 (SEQ ID NOS:278, 279, 280 and 378), a VH FR2 (SEQ ID NOS:281, 282, and 283), a VH FR4 (SEQ ID NO:288) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR4 (SEQ ID NO:288) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR4 (SEQ ID NO:288) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VH FR4 (SEQ ID NO:288) and a VL FR1 (SEQ ID NOS:289, 290 and 382-384); a VH FR1 (SEQ ID NOS:278, 279, 280 and 378), a VH FR3 (SEQ ID NOS:284, 285, 286, 287 and 379-381), a VH FR4 (SEQ ID NO:288) and a VL FR2 (SEQ ID NOS:291, 292 and 385-392); a VH FR1 (SEQ ID NOS:278, 279, 280 and 378), a VH FR3 (SEQ ID NOS:284, 285, 286, 287 and 379-381), a VH FR4 (SEQ ID NO:288) and a VL FR3 (SEQ ID NOS:293, 294, 295 and 393-404); a VH FR1 (SEQ ID NOS:278, 279, 280 and 378), a VH FR3 (SEQ ID NOS:284, 285, 286, 287 and 379-381), a VH FR4 (SEQ ID NO:288) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288) and a VL FR1 (SEQ ID NOS:289, 290 and 382-384); a VH FR2 (SEQ ID NOS:281, 282, and 283), a VH FR3 (SEQ ID NOS:284, 285, 286, 287 and 379-381), a VH FR4 (SEQ ID NO:288) and a VL FR2 (SEQ ID NOS:291, 292 and 385-392); a VH FR2 (SEQ ID NOS:281, 282, and 283), a VH FR3 (SEQ ID NOS:284, 285, 286, 287 and 379-381), a VH FR4 (SEQ ID NO:288) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VH FR4 (SEQ ID NO:288) and a VL FR4 (SEQ ID NO:296 and 405-407); a VH FR1 (SEQ ID NOS:278, 279, 280 and 378), a VH FR2 (SEQ ID NOS:281, 282, and 283), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR4 (SEQ ID NO:288), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR4 (SEQ ID NO:288), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR4 (SEQ ID NO:288), a VL FR1 (SEQ ID NOS:289, 290 and 382-384) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR2 (SEQ ID NOS:291, 292 and 385-392); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR4 (SEQ ID NO:296 and 405-407); a VH FR2 (SEQ ID NOS:281, 282, and 283), a VH FR4 (SEQ ID NO:288), a VL FR1 (SEQ ID NOS:289, 290 and 382-384) and a VL FR2 (SEQ ID NOS:291, 292 and 385-392); a VH FR2 (SEQ ID NOS:281, 282, and 283), a VH FR4 (SEQ ID NO:288), a VL FR1 (SEQ ID NOS:289, 290 and 382-384) and a VL FR3 (SEQ ID NOS:293, 294, 295 and 393-404); a VH FR2 (SEQ ID NOS:281, 282, and 283), a VH FR4 (SEQ ID NO:288), a VL FR1 (SEQ ID NOS:289, 290 and 382-384) and a VL FR4 (SEQ ID NO:296 and 405-407); a VH FR3 (SEQ ID NOS:284, 285, 286, 287 and 379-381), a VH FR4 (SEQ ID NO:288), a VL FR1 (SEQ ID NOS:289, 290 and 382-384) and a VL FR2 (SEQ ID NOS:291, 292 and 385-392); a VH FR3 (SEQ ID NOS:284, 285, 286, 287 and 379-381), a VH FR4 (SEQ ID NO:288), a VL FR1 (SEQ ID NOS:289, 290 and 382-384) and a VL FR3 (SEQ ID NOS:293, 294, 295 and 393-404); a VH FR3 (SEQ ID NOS:284, 285, 286, 287 and 379-381), a VH FR4 (SEQ ID NO:288), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR2 (SEQ ID NOS:281, 282, and 283), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR3 (SEQ ID NOS:284, 285, 286, 287 and 379-381), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR4 (SEQ ID NO:288), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR4 (SEQ ID NO:288), a VL FR2 (SEQ ID NOS:291, 292 and 385-392) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392) and a VL FR4 (SEQ ID NO:296 and 405-407); a VH FR2 (SEQ ID NOS:281, 282, and 283), a VH FR4 (SEQ ID NO:288), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VH FR4 (SEQ ID NO:288), a VL FR2 (SEQ ID NOS:291, 292 and 385-392) and a VL FR4 (SEQ ID NO:296 and 405-407); a VH FR3 (SEQ ID NOS:284, 285, 286, 287 and 379-381), a VH FR4 (SEQ ID NO:288), a VL FR2 (SEQ ID NOS:291, 292 and 385-392) and a VL FR3 (SEQ ID NOS:293, 294, 295 and 393-404); a VH FR3 (SEQ ID NOS:284, 285, 286, 287 and 379-381), a VH FR4 (SEQ ID NO:288), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR4 (SEQ ID NO:288), a VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR3 (SEQ ID NOS:293, 294, 295 and 393-404) and a VL FR4 (SEQ ID NO:296 and 405-407); a VH FR2 (SEQ ID NOS:281, 282, and 283), a VH FR4 (SEQ ID NO:288), a VL FR3 (SEQ ID NOS:293, 294, 295 and 393-404) and a VL FR4 (SEQ ID NO:296 and 405-407); a VH FR3 (SEQ ID NOS:284, 285, 286, 287 and 379-381), a VH FR4 (SEQ ID NO:288), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VL FR1 (SEQ ID NOS:289, 290 and 382-384), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VL FR1 (SEQ ID NOS:289, 290 and 382-384), a VL FR2 (SEQ ID NOS:291, 292 and 385-392) and a VL FR4 (SEQ ID NO:296 and 405-407); a VH FR1 (SEQ ID NOS:278, 279, 280 and 378), a VL FR1 (SEQ ID NOS:289, 290 and 382-384), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VL FR2 (SEQ ID NOS:291, 292 and 385-392), a VL FR3 (SEQ ID NOS:293, 294, 295 and 393-404) and a VL FR4 (SEQ ID NO:296 and 405-407); a VH FR2 (SEQ ID NOS:281, 282, and 283), a VL FR1 (SEQ ID NOS:289, 290 and 382-384), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VL FR1 (SEQ ID NOS:289, 290 and 382-384), a VL FR2 (SEQ ID NOS:291, 292 and 385-392) and a VL FR4 (SEQ ID NO:296 and 405-407); a VH FR2 (SEQ ID NOS:281, 282, and 283), a VL FR1 (SEQ ID NOS:289, 290 and 382-384), a VL FR3 (SEQ ID NOS:293, 294, 295 and 393-404) and a VL FR4 (SEQ ID NO:296 and 405-407); a VH FR2 (SEQ ID NOS:281, 282, and 283), a VL FR2 (SEQ ID NOS:291, 292 and 385-392), a VL FR3 (SEQ ID NOS:293, 294, 295 and 393-404) and a VL FR4 (SEQ ID NO:296 and 405-407); a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392) and a VL FR3 (SEQ ID NOS:293, 294, 295 and 393-404); a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392) and a VL FR4 (SEQ ID NO:296 and 405-407); a VH FR3 (SEQ ID NOS:284, 285, 286, 287 and 379-381), a VL FR1 (SEQ ID NOS:289, 290 and 382-384), a VL FR3 (SEQ ID NOS:293, 294, 295 and 393-404) and a VL FR4 (SEQ ID NO:296 and 405-407); a VH FR3 (SEQ ID NOS:284, 285, 286, 287 and 379-381), a VL FR2 (SEQ ID NOS:291, 292 and 385-392), a VL FR3 (SEQ ID NOS:293, 294, 295 and 393-404) and a VL FR4 (SEQ ID NO:296 and 405-407); a VH FR4 (SEQ ID NO:288), a VL FR1 (SEQ ID NOS:289, 290 and 382-384), a VL FR2 (SEQ ID NOS:291, 292 and 385-392) and a VL FR3 (SEQ ID NOS:293, 294, 295 and 393-404); a VH FR4 (SEQ ID NO:288), a VL FR1 (SEQ ID NOS:289, 290 and 382-384), a VL FR2 (SEQ ID NOS:291, 292 and 385-392) and a VL FR4 (SEQ ID NO:296 and 405-407); a VH FR4 (SEQ ID NO:288), a VL FR1 (SEQ ID NOS:289, 290 and 382-384), a VL FR3 (SEQ ID NOS:293, 294, 295 and 393-404) and a VL FR4 (SEQ ID NO:296 and 405-407); a VH FR4 (SEQ ID NO:288), a VL FR2 (SEQ ID NOS:291, 292 and 385-392), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288) and a VL FR1 (SEQ ID NOS:289, 290 and 382-384); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR4 (SEQ ID NO:288), a VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384) and a VL FR2 (SEQ ID NOS:291, 292 and 385-392); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VH FR4 (SEQ ID NO:288), a VL FR2 (SEQ ID NOS:291, 292 and 385-392) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR2 (SEQ ID NOS:281, 282, and 283), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR1 (SEQ ID NOS:278, 279, 280 and 378), a VH FR2 (SEQ ID NOS:281, 282, and 283), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR2 (SEQ ID NOS:281, 282, and 283), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR4 (SEQ ID NO:288), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR1 (SEQ ID NOS:278, 279, 280 and 378), a VH FR4 (SEQ ID NO:288), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR1 (SEQ ID NOS:278, 279, 280 and 378), a VH FR4 (SEQ ID NO:288), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR4 (SEQ ID NO:288), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR2 (SEQ ID NOS:281, 282, and 283), a VH FR4 (SEQ ID NO:288), a VL FR1 (SEQ ID NOS:289, 290 and 382-384), a VL FR2 (SEQ ID NOS:291, 292 and 385-392), and a VL FR3 (SEQ ID NOS:293, 294, 295 and 393-404); a VH FR2 (SEQ ID NOS:281, 282, and 283), a VH FR4 (SEQ ID NO:288), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR2 (SEQ ID NOS:281, 282, and 283), a VH FR4 (SEQ ID NO:288), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR2 (SEQ ID NOS:281, 282, and 283), a VH FR4 (SEQ ID NO:288), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR3 (SEQ ID NOS:284, 285, 286, 287 and 379-381), a VH FR4 (SEQ ID NO:288), a VL FR1 (SEQ ID NOS:289, 290 and 382-384), a VL FR2 (SEQ ID NOS:291, 292 and 385-392), and a VL FR4 (SEQ ID NO:296 and 405-407); a VH FR3 (SEQ ID NOS:284, 285, 286, 287 and 379-381), a VH FR4 (SEQ ID NO:288), a VL FR1 (SEQ ID NOS:289, 290 and 382-384), a VL FR3 (SEQ ID NOS:293, 294, 295 and 393-404), and a VL FR4 (SEQ ID NO:296 and 405-407); a VH FR3 (SEQ ID NOS:284, 285, 286, 287 and 379-381), a VH FR4 (SEQ ID NO:288), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VL FR1 (SEQ ID NOS:289, 290 and 382-384), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR2 (SEQ ID NOS:281, 282, and 283), a VL FR1 (SEQ ID NOS:289, 290 and 382-384), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR4 (SEQ ID NO:288), a VL FR1 (SEQ ID NOS:289, 290 and 382-384), a VL FR2 (SEQ ID NOS:291, 292 and 385-392), a VL FR3 (SEQ ID NOS:293, 294, 295 and 393-404), and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384) and a VL FR2 (SEQ ID NOS:291, 292 and 385-392); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR2 (SEQ ID NOS:291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VH FR4 (SEQ ID NO:288), a VL FR1 (SEQ ID NOS:289, 290 and 382-384), VL FR2 (SEQ ID NOS:291, 292 and 385-392) and a VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VH FR4 (SEQ ID NO:288), a VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VH FR4 (SEQ ID NO:288), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384), VL FR2 (SEQ ID NOS:291, 292 and 385-392) and a VL FR3 (SEQ ID NOS:293, 294, 295 and 393-404); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384), VL FR2 (SEQ ID NOS:291, 292 and 385-392) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384), VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR4 (SEQ ID NO:288), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR2 (SEQ ID NOS:281, 282, and 283), a VH FR4 (SEQ ID NO:288), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR3 (SEQ ID NOS:284, 285, 286, 287 and 379-381), a VH FR4 (SEQ ID NO:288), a VL FR1 (SEQ ID NOS:289, 290 and 382-384), a VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384), VL FR2 (SEQ ID NOS: 291, 292 and 385-392) and a VL FR3 (SEQ ID NOS:293, 294, 295 and 393-404); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR1 (SEQ ID NOS:289, 290 and 382-384), VL FR2 (SEQ ID NOS:291, 292 and 385-392) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VH FR4 (SEQ ID NO:288), VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR3 (SEQ ID NOS:284, 285, 286, 287 and 379-381), a VL FR1 (SEQ ID NOS:289, 290 and 382-384), VL FR2 (SEQ ID NOS:291, 292 and 385-392), VL FR3 (SEQ ID NOS:293, 294, 295 and 393-404) and a VL FR4 (SEQ ID NO:296 and 405-407); a VH FR1 (SEQ ID NOS:278, 279, 280 and 378), a VH FR2 (SEQ ID NOS:281, 282, and 283), a VH FR4 (SEQ ID NO:288), a VL FR1 (SEQ ID NOS:289, 290 and 382-384), VL FR2 (SEQ ID NOS:291, 292 and 385-392), VL FR3 (SEQ ID NOS: 293, 294, 295 and 393-404) and a VL FR4 (SEQ ID NO:296 and 405-407); a VH FR2 (SEQ ID NOS:281, 282, and 283), a VH FR3 (SEQ ID NOS:284, 285, 286, 287 and 379-381), a VH FR4 (SEQ ID NO:288), a VL FR1 (SEQ ID NOS:289, 290 and 382-384), VL FR2 (SEQ ID NOS:291, 292 and 385-392), VL FR3 (SEQ ID NOS:293, 294, 295 and 393-404) and a VL FR4 (SEQ ID NO:296 and 405-407); or any combination thereof of the VH FRs (SEQ ID NOS: 278, 279, 280, 378, 281, 282, 283, 284, 285, 286, 287, 379-381 and 288) and VL FRs (SEQ ID NOS: 289, 290, 382-384, 291, 292, 385-392, 293, 294, 295, 393-404, 296, 405-407) listed in Table 19.

In yet another aspect, antibodies are provided that compete with one of the exemplified antibodies or functional fragments for binding to (i) beta klotho or (ii) a complex comprising beta klotho and one of FGFR1c, FGFR2c, FGFR3c, and FGFR4. Such antibodies may also bind to the same epitope as one of the herein exemplified antibodies, or an overlapping epitope. Antibodies and fragments that compete with or bind to the same epitope as the exemplified antibodies are expected to show similar functional properties. The exemplified antigen binding proteins and fragments include those with the VH and VL regions, and CDRs provided herein, including those in Tables 1-10. Thus, as a specific example, the antibodies that are provided include those that compete with an antibody comprising: (a) 1, 2, 3, 4, 5 or all 6 of the CDRs listed for an antibody listed in Tables 1-10; (b) a VH and a VL selected from the VH and a VL regions listed for an antibody listed in Tables 1-10, such as for antibody 5H23 (Table 1) or (c) two light chains and two heavy chains comprising a VH and a VL as specified for an antibody listed in Tables 1-10.

In still yet another aspect, antibodies are provided herein that bind to a region, including an epitope, of human beta klotho or cyno beta klotho. For example, in some embodiments, an antibody provided herein binds to a KLB2 domain of human beta klotho comprising amino acid residues 509 to 1044 of SEQ ID NO:297. As another example, in some embodiments, an antibody provided herein binds to a glycosyl hydrolase 1 region of a KLB2 domain of human beta klotho comprising amino acid residues 517 to 967 of SEQ ID NO:297. As yet another example, in some embodiments, an antibody provided herein binds to a region of human beta klotho comprising amino acid residues 657 to 703 of SEQ ID NO:297. As still another example, in some embodiments, an antibody provided herein binds to a region of cyno beta klotho comprising amino acid residues 657 to 703 of SEQ ID NO:299.

In another aspect, antibodies are provided herein that bind to a specific epitope of human beta klotho. For example, in some embodiments, an antibody provided herein binds an epitope of human beta klotho comprising at least one of amino acid residues 657, 701 and/or 703 of human beta klotho (SEQ ID NO: 297). Accordingly, in some embodiments, an antibody provided herein binds to an epitope of human beta klotho, wherein the epitope of human beta klotho comprise at least amino acid residue 657 of SEQ ID NO: 297. In some embodiments, an antibody provided herein binds to an epitope of human beta klotho, wherein the epitope of human beta klotho comprise at least amino acid residue 701 of SEQ ID NO: 297. In some embodiments, an antibody provided herein binds to an epitope of human beta klotho, wherein the epitope of human beta klotho comprise at least amino acid residue 703 of SEQ ID NO: 297. In some embodiments, an antibody provided herein binds to an epitope of human beta klotho, wherein the epitope of human beta klotho comprise at least amino acid residues 657 and 701 of SEQ ID NO: 297. In some embodiments, an antibody provided herein binds to an epitope of human beta klotho, wherein the epitope of human beta klotho comprise at least amino acid residues 657 and 703 of SEQ ID NO: 297. In some embodiments, an antibody provided herein binds to an epitope of human beta klotho, wherein the epitope of human beta klotho comprise at least amino acid residues 701 and 703 of SEQ ID NO: 297. In some embodiments, an antibody provided herein binds to an epitope of human beta klotho, wherein the epitope of human beta klotho comprise at least amino acid residues 657, 701 and 703 of SEQ ID NO: 297. Such antibodies provided above can, in some embodiments, induce FGF19-like signaling and/or FGF21-like signaling in a cell that expresses human beta klotho and an FGF receptor. Additionally, in some embodiments, the antibody is a humanized, human or chimeric antibody.

1. Polyclonal Antibodies

The antibodies of the present disclosure may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a beta klotho polypeptide or a fusion protein thereof. It may be useful to conjugate the immunizing agent to a protein known to be immunogenic in the mammal being immunized or to immunize the mammal with the protein and one or more adjuvants. Examples of such immunogenic proteins include but are not limited to keyhole limpet hemocyanin, serum albumin, bovine thyroglobulin, and soybean trypsin inhibitor. Examples of adjuvants which may be employed include Ribi, CpG, Poly 1C, Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for beta klotho antibody titer. If desired, the mammal can be boosted until the antibody titer increases or plateaus. Additionally or alternatively, lymphocytes may be obtained from the immunized animal for fusion and the preparation of monoclonal antibodies from hybridoma as described below.

2. Monoclonal Antibodies

The antibodies of the present disclosure may alternatively be monoclonal antibodies. Monoclonal antibodies may be made using the hybridoma method first described by Kohler et al., Nature, 256:495 (1975), or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as SP-2 and derivatives, for example, X63-Ag8-653 cells available from the American Type Culture Collection, Manassas, Virginia, USA and those derived from MOPC-21 and MPC-11 mouse tumors available from the Salk Institute Cell Distribution Center, San Diego, California USA. Human myeloma and mouse-human heteromyeloma cell lines also have been described for the production of human monoclonal antibodies (Kozbor, J., *Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA.

Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In some embodiments, an antibody that binds a beta klotho epitope comprises an amino acid sequence of a VH domain and/or an amino acid sequence of a VL domain encoded by a nucleotide sequence that hybridizes to (1) the complement of a nucleotide sequence encoding any one of the VH and/or VL domain described herein under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In some embodiments, an antibody that binds a beta klotho epitope comprises an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Tables 1-10 under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3)

In a further embodiment, monoclonal antibodies or antibody fragments can be isolated from antibody phage libraries generated using the techniques described in, for example, *Antibody Phage Display: Methods and Protocols*, P. M. O'Brien and R. Aitken, eds, Humana Press, Totawa N.J., 2002. In principle, synthetic antibody clones are selected by screening phage libraries containing phage that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., *Ann. Rev. Immunol.,* 12: 433-455 (1994).

Repertoires of VH and VL genes can be separately cloned by polymerase chain reaction (PCR) and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J,* 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, *J. Mol. Biol.,* 227: 381-388 (1992).

Screening of the libraries can be accomplished by various techniques known in the art. For example, beta klotho, (e.g., a beta klotho polypeptide, fragment or epitope) can be used to coat the wells of adsorption plates, expressed on host cells affixed to adsorption plates or used in cell sorting, or conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., *Proteins,* 8: 309-314 (1990) and in WO 92/09690, and a low coating density of antigen as described in Marks et al., *Biotechnol.,* 10: 779-783 (1992).

Anti-beta klotho antibodies can be obtained by designing a suitable antigen screening procedure to select for the phage clone of interest followed by construction of a full length anti-beta klotho antibody clone using VH and/or VL sequences (e.g., the Fv sequences), or various CDR sequences from VH and VL sequences, from the phage clone of interest and suitable constant region (e.g., Fc) sequences described in Kabat et al., *Sequences of Proteins of Immunological Interest,* Fifth Edition, NIH Publication 91-3242, Bethesda MD (1991), vols. 1-3.

3. Antibody Fragments

The present disclosure provides antibodies and antibody fragments that bind to beta klotho. In certain circumstances there are advantages of using antibody fragments, rather than whole antibodies. The smaller size of the fragments allows for rapid clearance, and may lead to improved access to cells, tissues or organs. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli* or yeast cells, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894; and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. (See, e.g., Antibody Engineering, ed. Borrebaeck, supra). The antibody fragment may also be a "linear antibody", for example, as described, for example, in the references cited above. Such linear antibodies may be monospecific or multi-specific, such as bispecific.

Smaller antibody-derived binding structures are the separate variable domains (V domains) also termed single variable domain antibodies (SdAbs). Certain types of organisms, the camelids and cartilaginous fish, possess high affinity single V-like domains mounted on an Fc equivalent domain structure as part of their immune system. (Woolven et al., *Immunogenetics* 50: 98-101, 1999; Streltsov et al., *Proc Natl Acad Sci USA.* 101:12444-12449, 2004). The V-like domains (called VhH in camelids and V-NAR in sharks) typically display long surface loops, which allow penetration of cavities of target antigens. They also stabilize isolated VH domains by masking hydrophobic surface patches.

These VhH and V-NAR domains have been used to engineer sdAbs. Human V domain variants have been designed using selection from phage libraries and other approaches that have resulted in stable, high binding VL- and VH-derived domains.

Antibodies that bind to beta klotho as provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments, (e.g., beta klotho binding fragments) of any of the above. Non-limiting examples of functional fragments (e.g., fragments that bind to beta klotho) include single-chain Fvs (scFv) (e.g., including monospecific, bispecific, etc.), Fab fragments, F(ab') fragments, F(ab)2 fragments, F(ab')2 fragments, disulfide-linked Fvs (sdFv), Fd fragments, Fv fragments, diabody, triabody, tetrabody and minibody.

Antibodies provided herein include, but are not limited to, immunoglobulin molecules and immunologically active portions of immunoglobulin molecules, for example, molecules that contain an antigen binding site that bind to a beta klotho epitope. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

Variants and derivatives of antibodies include antibody functional fragments that retain the ability to bind to a beta klotho epitope. Exemplary functional fragments include Fab fragments (e.g., an antibody fragment that contains the antigen-binding domain and comprises a light chain and part of a heavy chain bridged by a disulfide bond); Fab' (e.g., an antibody fragment containing a single anti-binding domain comprising an Fab and an additional portion of the heavy chain through the hinge region); F(ab')2 (e.g., two Fab' molecules joined by interchain disulfide bonds in the hinge regions of the heavy chains; the Fab' molecules may be directed toward the same or different epitopes); a bispecific Fab (e.g., a Fab molecule having two antigen binding domains, each of which may be directed to a different epitope); a single chain Fab chain comprising a variable region, also known as, a sFv (e.g., the variable, antigen-binding determinative region of a single light and heavy chain of an antibody linked together by a chain of 10-25 amino acids); a disulfide-linked Fv, or dsFv (e.g., the variable, antigen-binding determinative region of a single light and heavy chain of an antibody linked together by a disulfide bond); a camelized VH (e.g., the variable, antigen-binding determinative region of a single heavy chain of an antibody in which some amino acids at the VH interface are those found in the heavy chain of naturally occurring camel antibodies); a bispecific sFv (e.g., a sFv or a dsFv molecule having two antigen-binding domains, each of which may be directed to a different epitope); a diabody (e.g., a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (e.g., a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody comprises a single-chain Fv ("scFv"). scFvs are antibody fragments comprising the VH and VL domains of an antibody, wherein these domains are present in a single polypeptide chain. The scFv polypeptide may further comprise a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

4. Humanized Antibodies

The present disclosure provides humanized antibodies that bind beta klotho, including human and/or cyno beta klotho. Humanized antibodies of the present disclosure may comprise one or more CDRs as shown in Tables 1-10. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody.

In some cases, the humanized antibodies are constructed by CDR grafting, in which the amino acid sequences of the six complementarity determining regions (CDRs) of the parent non-human antibody (e.g., rodent) are grafted onto a human antibody framework. For example, Padlan et al. (FASEB J. 9:133-139, 1995) determined that only about one third of the residues in the CDRs actually contact the antigen, and termed these the "specificity determining residues," or SDRs. In the technique of SDR grafting, only the SDR residues are grafted onto the human antibody framework (see, e.g., Kashmiri et al., Methods 36: 25-34, 2005).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence which is closest to that of the rodent may be selected as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623. In some cases, the framework is derived from the consensus sequences of the most abundant human subclasses, $V_L6$ subgroup I ($V_L6I$) and $V_H$ subgroup III ($V_HIII$). In another method, human germline genes are used at the source of the framework regions.

In an alternative paradigm based on comparison of CDRs, called Superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., J. Immunol. 169: 1119-1125, 2002).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, Protein Eng. 13: 819-824, 2000), Modeller (Sali and Blundell, J. Mol. Biol. 234: 779-815, 1993), and Swiss PDB Viewer (Guex and Peitsch, Electrophoresis 18: 2714-2713, 1997). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes and the differences are scored as HSC. The target sequence is then humanized by maximizing its HSC rather than using a global identity measure to generate multiple diverse humanized variants. (Lazar et al., *Mol. Immunol.* 44: 1986-1998, 2007).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome and yeast display libraries as well as by bacterial colony screening (see, e.g., Hoogenboom, *Nat. Biotechnol.* 23: 1105-1116, 2005; Dufner et al., Trends *Biotechnol.* 24: 523-529, 2006; Feldhaus et al., *Nat. Biotechnol.* 21: 163-70, 2003; Schlapschy et al., *Protein Eng. Des. Sel.* 17: 847-60, 2004).

In the FR library approach, a collection of residue variants are introduced at specific positions in the FR followed by selection of the library to select the FR that best supports the grafted CDR. The residues to be substituted may include some or all of the "Vernier" residues identified as potentially contributing to CDR structure (see, e.g., Foote and Winter, *J. Mol. Biol.* 224: 487-499, 1992), or from the more limited set of target residues identified by Baca et al. (J. Biol. Chem. 272: 10678-10684, 1997).

In FR shuffling, whole FRs are combined with the non-human CDRs instead of creating combinatorial libraries of selected residue variants (see, e.g., Dall'Acqua et al., *Methods* 36: 43-60, 2005). The libraries may be screened for binding in a two-step selection process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity and thermal stability (see, e.g., Damschroder et al., *Mol. Immunol.* 44: 3049-60, 2007).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple sub-classes with distinct human V-segment CDRs. Humaneering allows for isolation of antibodies that are 91-96% homologous to human germline gene antibodies. (see, e.g., Alfenito, Cambridge Healthtech Institute's Third Annual PEGS, The Protein Engineering Summit, 2007).

The "human engineering" method involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or are substituted with human residues. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering, 7: 805-814 (1994), U.S. Pat. Nos. 5,766,886, 5,770,196, 5,821,123, and 5,869,619, and PCT Application Publication WO 93/11794.

5. Human Antibodies

Human anti-beta klotho antibodies can be constructed by combining Fv clone variable domain sequence(s) selected from human-derived phage display libraries with known human constant domain sequences(s). Alternatively, human monoclonal anti-beta klotho antibodies of the present disclosure can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is also possible to produce transgenic animals (e.g., mice) that are capable, upon immunization, of producing a full repertoire of human antibodies in the absence of endogenous immunoglobulin production. Transgenic mice that express human antibody repertoires have been used to generate high-affinity human sequence monoclonal antibodies against a wide variety of potential drug targets (see, e.g., Jakobovits, A., *Curr. Opin. Biotechnol.* 1995, 6(5):561-6; Brüggemann and Taussing, *Curr. Opin. Biotechnol.* 1997, 8(4):455-8; U.S. Pat. Nos. 6,075,181 and 6,150,584; and Lonberg et al., *Nature Biotechnol.* 23: 1117-1125, 2005).

Alternatively, the human antibody may be prepared via immortalization of human B lymphocytes producing an antibody directed against a target antigen (e.g., such B lymphocytes may be recovered from an individual or may have been immunized in vitro) (see, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373).

Gene shuffling can also be used to derive human antibodies from non-human, for example, rodent, antibodies, where the human antibody has similar affinities and specificities to the starting non-human antibody. According to this method, which is also called "epitope imprinting" or "guided selection", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, (e.g., the epitope guides (imprints) the choice of the human chain partner). When the process is repeated in order to replace the remaining non-human chain, a human antibody is obtained (see, e.g., PCT WO 93/06213; and Osbourn et al., Methods., 36, 61-68, 2005). Unlike traditional humanization of non-human antibodies by CDR grafting, this technique provides completely human antibodies, which have no FR or CDR residues of non-human origin. Examples of guided selection to humanize mouse antibodies towards cell surface antigens include the folate-binding protein present on ovarian cancer cells (see, e.g., Figini et al., *Cancer Res.*, 58, 991-996, 1998) and CD147, which is highly expressed on hepatocellular carcinoma (see, e.g., Bao et al., *Cancer Biol. Ther.*, 4, 1374-1380, 2005).

A potential disadvantage of the guided selection approach is that shuffling of one antibody chain while keeping the other constant could result in epitope drift. In order to maintain the epitope recognized by the non-human antibody, CDR retention can be applied (see, e.g., Klimka et al., *Br. J. Cancer.*, 83, 252-260, 2000; VH CDR2 Beiboer et al., *J. Mol. Biol.*, 296, 833-49, 2000) In this method, the non-human VH CDR3 is commonly retained, as this CDR may be at the center of the antigen-binding site and may be to be the most important region of the antibody for antigen recognition. In some instances, however, VH CDR3 and VL CDR3, as well as VH CDR3, VL CDR3 and VL CFR1, of the non-human antibody may be retained.

6. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for beta klotho and the other is for any other antigen. In some embodiments, one of the binding specificities is for beta klotho, and the other is for another surface antigen expressed on cells expressing beta klotho and a FGF receptor (e.g., FGFR1c, FGFR2c, FGFR3c, FGFR4). In certain embodiments, bispecific antibodies may bind to two different epitopes of beta klotho. Bispecific antibodies can be prepared as full length antibodies or antibody fragments (e.g., F(ab')$_2$ bispecific antibodies).

Methods for making bispecific antibodies are known in the art, such as, for example, by co-expression of two immunoglobulin heavy chain-light chain pairs, where the two heavy chains have different specificities (see, e.g., Milstein and Cuello, Nature, 305: 537 (1983)). For further details of generating bispecific antibodies see, for example, *Bispecific Antibodies*, Kontermann, ed., Springer-Verlag, Hiedelberg (2011).

7. Multivalent Antibodies

A multivalent antibody may be internalized (and/or catabolized) faster than a bivalent antibody by a cell expressing an antigen to which the antibodies bind. The antibodies of the present disclosure can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Fc Engineering

It may be desirable to modify an antibody to beta klotho via Fc engineering, including, with respect to effector function, for example, so as to decrease or remove antigen-dependent cell-mediated cyotoxicity (ADCC) and/or complement dependent cytotoxicity (CDC) of the antibody. This may be achieved by introducing one or more amino acid substitutions in an Fc region of the antibody. For example, substitutions into human IgG1 using IgG2 residues as positions 233-236 and IgG4 residues at positions 327, 330 and 331 were shown to greatly reduce ADCC and CDC (see, e.g., Armour et al., *Eur. J. Immunol.* 29:(8):2613-24 (1999); Shields et al., *J. Biol. Chem.* 276(9): 6591-604 (2001).

To increase the serum half life of the antibody, one may incorporate a salvage receptor binding epitope into the antibody (especially an antibody fragment), for example, as described in U.S. Pat. No. 5,739,277. Term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

9. Alternative Binding Agents

The present disclosure encompasses non-immunoglobulin binding agents that specifically bind to the same epitope as an anti-beta klotho antibody disclosed herein. In some embodiments, a non-immunoglobulin binding agent is identified an agent that displaces or is displaced by an anti-beta klotho antibody of the present disclosure in a completive binding assay. These alternative binding agents may include, for example, any of the engineered protein scaffolds known in the art. Such scaffolds may comprise one or more CDRs as shown in Tables 1-10. Such scaffolds include, for example, anticalins, which are based upon the lipocalin scaffold, a protein structure characterized by a rigid beta-barrel that supports four hypervariable loops which form the ligand binding site. Novel binding specificities may be engineered by targeted random mutagenesis in the loop regions, in combination with functional display and guided selection (see, e.g., Skerra (2008) *FEBS J.* 275: 2677-2683). Other suitable scaffolds may include, for example, adnectins, or monobodies, based on the tenth extracellular domain of human fibronectin III (see, e.g., Koide and Koide (2007) Methods Mol. Biol. 352: 95-109); affibodies, based on the Z domain of staphylococcal protein A (see, e.g., Nygren et al. (2008) *FEBS J.* 275: 2668-2676)); DARPins, based on ankyrin repeat proteins (see, e.g., Stumpp et al. (2008) *Drug. Discov. Today* 13: 695-701); fynomers, based on the SH3 domain of the human Fyn protein kinase Grabulovski et al. (2007) *J. Biol. Chem.* 282: 3196-3204); affitins, based on Sac7d from *Sulfolobus acidolarius* (see, e.g., Krehenbrink et al. (2008) *J. Mol. Biol.* 383: 1058-1068); affilins, based on human γ-B-crystallin (see, e.g., Ebersbach et al. (2007) *J. Mol. Biol.* 372: 172-185); avimers, based on the A domains of membrane receptor proteins (see, e.g., Silverman et al. (2005) *Biotechnol.* 23: 1556-1561); cysteine-rich knottin peptides (see, e.g., Kolmar (2008) *FEBS J.* 275: 2684-2690); and engineered Kunitz-type inhibitors (see, e.g., Nixon and Wood (2006) *Curr. Opin. Drug. Discov. Dev.* 9: 261-268) For a review, see, for example, Gebauer and Skerra (2009) *Curr. Opin. Chem. Biol.* 13: 245-255.

Antibody Variants

In some embodiments, amino acid sequence modification (s) of the antibodies that bind to beta klotho or described herein are contemplated. For example, it may be desirable to improve the binding affinity and/or other biological properties of the antibody, including but not limited to specificity, thermostability, expression level, effector functions, glycosylation, reduced immunogenicity or solubility. This, in addition to the anti-beta klotho antibodies described herein, it is contemplated that anti-beta klotho antibody variants can be prepared. For example, anti-beta klotho antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-beta klotho antibody, such as changing the number or position of glycosylation sites or altering the membrane anchoring characteristics.

In some embodiments, antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited, to specific chemical cleavage, acetylation, formulation, metabolic synthesis of tunicamycin, etc. Additionally, the antibody may contain one or more non-classical amino acids.

Variations may be a substitution, deletion or insertion of one or more codons encoding the antibody or polypeptide that results in a change in the amino acid sequence as compared with the native sequence antibody or polypeptide. Amino acid substitutions can be the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In certain embodiments, the substitution, deletion or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the substitution is a conservative amino acid substitution made at one or more predicted non-essential amino acid residues. The variation allowed may be determined by systematically making insertions, deletions or substitutions of amino acids in the sequence and testing the resulting variants for activity exhibited by the full-length or mature native sequence.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for antibody-directed enzyme prodrug therapy) or a polypeptide which increases the serum half-life of the antibody.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Alternatively, conservative (e.g., within an amino acid group with similar properties and/or sidechains) substitutions may be made, so as to maintain or not significantly change the properties. Amino acids may be grouped according to similarities in the properties of their side chains (see, e.g., A. L. Lehninger, in *Biochemistry*, 2nd Ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His(H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions entail exchanging a member of one of these classes for another class. Such substituted residues also may be introduced into the conservative substitution sites or, into the remaining (non-conserved) sites. Accordingly, in one embodiment, an antibody or fragment thereof that binds to a beta klotho epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a murine monoclonal antibody described herein. In one embodiment, an antibody or fragment thereof that binds to a beta klotho epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in Tables 1-10. In yet another embodiment, an antibody or fragment thereof that binds to a beta klotho epitope comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence depicted in Tables 1-10 and/or a VL CDR amino acid sequence depicted in Tables 1-10. The variations can be made using methods known in the art such as oligonucleotide-mediated (site-directed) mutagenesis, alanine scanning, and PCR mutagenesis. Site-directed mutagenesis (see, e.g., Carter et al., *Nucl. Acids Res.*, 13:4331 (1986); Zoller et al., *Nucl. Acids Res.*, 10:6487 (1987)), cassette mutagenesis (see, e.g., Wells et al., *Gene*, 34:315 (1985)), restriction selection mutagenesis (see, e.g., Wells et al., *Philos. Trans. R. Soc. London SerA*, 317:415 (1986)) or other known techniques can be performed on the cloned DNA to produce the anti-beta klotho antibody variant DNA.

Any cysteine residue not involved in maintaining the proper conformation of the anti-beta klotho antibody also may be substituted, for example, with with another amino acid such as alanine or serine, to improve the oxidative stability of the molecule and prevent aberrant crosslinking. Conversely, cysteine bond(s) may be added to the anti-beta klotho antibody to improve its stability (e.g., where the antibody is an antibody fragment such as an Fv fragment).

In some embodiments, an anti-beta klotho antibody molecule of the present disclosure is a "de-immunized" antibody. A "de-immunized" anti-beta klotho antibody is an antibody derived from a humanized or chimeric anti-beta klotho antibody, that has one or more alterations in its amino acid sequence resulting in a reduction of immunogenicity of the antibody, compared to the respective original non-de-immunized antibody. One of the procedures for generating such antibody mutants involves the identification and removal of T-cell epitopes of the antibody molecule. In a first step, the immunogenicity of the antibody molecule can be determined by several methods, for example, by in vitro determination of T-cell epitopes or in silico prediction of such epitopes, as known in the art. Once the critical residues for T-cell epitope function have been identified, mutations can be made to remove immunogenicity and retain antibody activity. For review, see, for example, Jones et al., *Methods in Molecular Biology* 525: 405-423, 2009.

1. In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed as Fab, scFv or V domain fragments either on the surface of an organism (e.g., phage, bacteria, yeast or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Preferred affinity matured antibodies will have nanomolar or even picomolar affinities for the target antigen.

Phage display is a widepread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and infected in bacteria to produce phage for further rounds of selection. For review, see, for example, Hoogenboom, *Methods. Mol. Biol.* 178: 1-37, 2002; Bradbury and Marks, *J. Immuno. Methods* 290: 29-49, 2004).

In a yeast display system (see, e.g., Boder et al., *Nat. Biotech.* 15: 553-57, 1997; Chao et al., *Nat. Protocols* 1:755-768, 2006), the antibody may be displayed as single-chain variable fusions (scFv) in which the heavy and light chains are connected by a flexible linker. The scFv is fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the scFv. Expression has been shown to correlate with the stability of the displayed protein, and thus antibodies can be selected for improved stability as well as affinity (see, e.g., Shusta et al., *J. Mol. Biol.* 292: 949-956, 1999). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently 'titrated' while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., US Patent Publication 2003/0186, 374; Blaise et al., *Gene* 342: 211-218, 2004).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reversed transcribed back into cDNA, which can then undergo mutagenesis and be used in the next round of selection (see, e.g., Fukuda et al., *Nucleic Acids Res.* 34, e127, 2006). In mRNA display, a covalent bond between antibody and mRNA is established using puromycin as an adaptor molecule (Wilson et al., *Proc. Natl. Acad. Sci. USA* 98, 3750-3755, 2001).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

Diversity may be introduced into the CDRs or the whole V genes of the antibody libraries in a targeted manner or via random introduction. The former approach includes sequentially targeting all the CDRs of an antibody via a high or low level of mutagenesis or targeting isolated hot spots of somatic hypermutations (see, e.g., Ho, et al., *J. Biol. Chem.* 280: 607-617, 2005) or residues suspected of affecting affinity on experimental basis or structural reasons. Random mutations can be introduced throughout the whole V gene using *E. coli* mutator strains, error-prone replication with DNA polymerases (see, e.g., Hawkins et al., *J. Mol. Biol.* 226: 889-896, 1992) or RNA replicases. Diversity may also be introduced by replacement of regions that are naturally diverse via DNA shuffling or similar techniques (see, e.g., Lu et al., *J. Biol. Chem.* 278: 43496-43507, 2003; U.S. Pat.

Nos. 5,565,332; 6,989,250). Alternative techniques target hypervariable loops extending into framework-region residues (see, e.g., Bond et al., *J. Mol. Biol.* 348: 699-709, 2005) employ loop deletions and insertions in CDRs or use hybridization-based diversification (see, e.g., US Patent Publication No. 2004/0005709). Additional methods of generating diversity in CDRs are disclosed, for example, in U.S. Pat. No. 7,985,840.

Screening of the libraries can be accomplished by various techniques known in the art. For example, beta klotho can be immobilized onto solid supports, columns, pins or cellulose/poly(vinylidene fluoride) membranes/other filters, expressed on host cells affixed to adsorption plates or used in cell sorting, or conjugated to biotin for capture with streptavidin-coated beads, or used in any other method for panning display libraries.

For review of in vitro affinity maturation methods, see, e.g., Hoogenboom, *Nature Biotechnology* 23: 1105-1116, 2005 and Quiroz and Sinclair, Revista Ingeneria Biomedia 4: 39-51, 2010 and references therein.

2. Modifications of Anti-Beta Klotho Antibodies

Covalent modifications of anti-beta klotho antibodies are included within the scope of the present disclosure. Covalent modifications include reacting targeted amino acid residues of an anti-beta klotho antibody with an organic derivatizing agent that is capable of reacting with selected side chains or the N- or C-terminal residues of the anti-beta klotho antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., T. E. Creighton, *Proteins: Structure and Molecular Properties*, W. H. Freeman & Co., San Francisco, pp. 79-86 (1983)), acetylation of the N-terminal amine, and amidation of any C-terminal carboxyl group.

Other types of covalent modification of the anti-beta klotho antibody included within the scope of this present disclosure include altering the native glycosylation pattern of the antibody or polypeptide (see, e.g., Beck et al., *Curr. Pharm. Biotechnol.* 9: 482-501, 2008; Walsh, *Drug Discov. Today* 15: 773-780, 2010), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192 or 4,179,337.

An anti-beta klotho antibody of the present disclosure may also be modified to form chimeric molecules comprising an anti-beta klotho antibody fused to another, heterologous polypeptide or amino acid sequence, for example, an epitope tag (see, e.g., Terpe, *Appl. Microbiol. Biotechnol.* 60: 523-533, 2003) or the Fc region of an IgG molecule (see, e.g., Aruffo, "Immunoglobulin fusion proteins" in Antibody Fusion Proteins, S. M. Chamow and A. Ashkenazi, eds., Wiley-Liss, New York, 1999, pp. 221-242).

Also provided herein are fusion proteins comprising an antibody provided herein that binds to a beta klotho antigen and a heterologous polypeptide. In some embodiments, the heterologous polypeptide to which the antibody is fused is useful for targeting the antibody to cells having cell surface-expressed beta klotho.

Also provided herein are panels of antibodies that bind to a beta klotho antigen. In specific embodiments, panels of antibodies have different association rate constants different dissociation rate constants, different affinities for beta klotho antigen, and/or different specificities for a beta klotho antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96 well or 384 well plates, such as for assays such as ELISAs.

Preparation of Anti-Beta Klotho Antibodies

Anti-beta klotho antibodies may be produced by culturing cells transformed or transfected with a vector containing anti-beta klotho antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression and purification are further described, in Plückthun et al., (1996) in *Antibody Engineering: Producing antibodies in Escherichia coli*: From PCR to fermentation (McCafferty, J., Hoogenboom, H. R., and Chiswell, D. J., eds), 1 Ed., pp. 203-252, IRL Press, Oxford; Kwong, K. & Rader, C., *E. coli* expression and purification of Fab antibody fragments, Current protocols in protein science editorial board John E Coligan et al., Chapter 6, Unit 6.10 (2009); Tachibana and Takekoshi, "Production of Antibody Fab Fragments in Escherischia *coli*," in *Antibody Expression and Production*, M. Al-Rubeai, Ed., Springer, New York, 2011; *Therapeutic Monoclonal Antibodies: From Bench to Clinic* (ed Z. An), John Wiley & Sons, Inc., Hoboken, NJ, USA.

It is, of course, contemplated that alternative methods, which are well known in the art, may be employed to prepare anti-beta klotho antibodies. For instance, the appropriate amino acid sequence, or portions thereof, may be produced by direct peptide synthesis using solid-phase techniques (see, e.g., Stewart et al., *Solid-Phase Peptide Synthesis*, W. H. Freeman Co., San Francisco, CA (1969); Merrifield, *J. Am. Chem. Soc.*, 85:2149-2154 (1963)). In vitro protein synthesis may be performed using manual techniques or by automation. Various portions of the anti-beta klotho antibody may be chemically synthesized separately and combined using chemical or enzymatic methods to produce the desired anti-beta klotho antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

Immunoconjugates

The present disclosure also provides conjugates comprising any one of the anti-beta klotho antibodies of the present disclosure covalently bound by a synthetic linker to one or more non-antibody agents.

A variety of radioactive isotopes are available for the production of radioconjugated antibodies. Examples include $At^{211}$, I4, I4, Y4, Re4, Re4, Sm4, Bi4, P4, Pb4 and radioactive isotopes of Lu. When the conjugate is used for detection, it may comprise a radioactive atom for scintigraphic studies, for example tc4 or 14, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron. The radioisotopes may be incorporated in the conjugate in known ways as described, e.g., in Reilly, "The radiochemistry of monoclonal antibodies and peptides," in Monoclonal Antibody and Peptide-Targeted Radiotherapy of Cancer, R. M. Reilly, ed., Wiley, Hoboken N.J., 2010.

In some embodiments, antibodies provided herein are conjugated or recombinantly fused to a diagnostic, detectable or therapeutic agent or any other molecule. The conjugated or recombinantly fused antibodies can be useful, for example, for monitoring or prognosing the onset, development, progression and/or severity of a beta klotho-mediated disease as part of a clinical testing procedure, such as determining the efficacy of a particular therapy.

Such diagnosis and detection can accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; chemiluminescent material, such as but not limited to, an acridinium based compound or a HALOTAG; radioactive materials, such as, but not limited to, iodine ($^{131}$I, $^{125}$I, $^{123}$I, and $^{121}$I,), carbon ($^{14}$C), sulfur ($^{35}$S), tritium ($^3$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Also provided herein are antibodies that are conjugated or recombinantly fused to a therapeutic moiety (or one or more therapeutic moieties), as well as uses thereof. The antibody may be conjugated or recombinantly fused to a therapeutic moiety, including a cytotoxin such as a cytostatic or cytocidal agent, a therapeutic agent or a radioactive metal ion such as alpha-emitters. A cytotoxin or cytotoxic agent includes any agent that is detrimental to cells.

Further, an antibody provided herein may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, e.g., International Publication No. WO 97/33899), AIM II (see, e.g., International Publication No. WO 97/34911), Fas Ligand (see, e.g., Takahashi et al., 1994, *J. Immunol.*, 6:1567-1574), and VEGF (see, e.g., International Publication No. WO 99/23105), an antiangiogenic agent, including, for example angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90 or about 100 amino acids) to generate fusion proteins, as well as uses thereof. In particular, provided herein are fusion proteins comprising an antigen-binding fragment of an antibody provided herein (e.g., a Fab fragment, Fd fragment, Fv fragment, F(ab)$_2$ fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses beta klotho or an beta klotho receptor. For example, an antibody that binds to a cell surface receptor expressed by a particular cell type (e.g., an immune cell) may be fused or conjugated to a modified antibody provided herein.

In addition, an antibody provided herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described, for example, in Denardo et al., 1998, *Clin Cancer Res.* 4(10):2483-90; Peterson et al., 1999, *Bioconjug. Chem.* 10(4):553-7; and Zimmerman et al., 1999, *Nucl. Med. Biol.* 26(8):943-50.

Moreover, antibodies provided herein can be fused to marker or "tag" sequences, such as a peptide to facilitate purification. In specific embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-824, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, *Cell* 37:767), and the "FLAG" tag.

Methods for fusing or conjugating therapeutic moieties (including polypeptides) to antibodies are well known, (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of anti-beta klotho antibodies as provided herein, including, for example, antibodies with higher affinities and lower dissociation rates (see, e.g., U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313). Antibodies, or the encoded antibodies, may be altered by being subjected to random mutagenesis by error-prone PCR, random nucleotide insertion or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described, for example, in U.S. Pat. No. 4,676,980.

The therapeutic moiety or drug conjugated or recombinantly fused to an antibody provided herein that binds to beta klotho (e.g., a beta klotho polypeptide, fragment, epitope) should be chosen to achieve the desired prophylactic or therapeutic effect(s). In certain embodiments, the antibody is a modified antibody. A clinician or other medical personnel may consider, for example, the following when deciding on which therapeutic moiety or drug to conjugate or recombinantly fuse to an antibody provided herein: the nature of the disease, the severity of the disease, and the condition of the subject.

Antibodies that bind to beta klotho as provided herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The linker may be a "cleavable linker" facilitating release of the conjugated agent in the cell, but non-cleavable linkers are also contemplated herein. Linkers for use in the conjugates of the present disclosure include without limitation acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (see, e.g., Chari et al., *Cancer Research* 52:127-131 (1992); U.S. Pat. No. 5,208,020), thioether linkers, or hydrophilic linkers designed to evade multidrug transporter-mediated resistance (see, e.g. Kovtun et al., *Cancer Res.* 70: 2528-2537, 2010).

Conjugates of the antibody and agent may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate). The present disclosure further contemplates that conjugates of antibodies and agents may be prepared using any suitable methods as disclosed in the art, (see, e.g., in Bioconjugate Techniques, 2nd Ed., G. T. Hermanson, ed., Elsevier, San Francisco, 2008).

Conventional conjugation strategies for antibodies and agents have been based on random conjugation chemistries involving the ε-amino group of Lys residues or the thiol group of Cys residues, which results in heterogenous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (see, e.g., Junutula et al., *J. Immunol. Meth.* 332: 41-52 (2008); Junutula et al., *Nat. Biotechnol.* 26: 925-932, 2008). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., *Proc. Natl. Acad. Sci. USA* 105: 12451-12456 (2008); Hofer et al., *Biochemistry* 48(50): 12047-12057, 2009).

Pharmaceutical Formulations

Anti-beta klotho antibodies of the present disclosure may be administered by any route appropriate to the condition to be treated. The antibody will typically be administered parenterally, for example, infusion, subcutaneous, intramuscular, intravenous, intradermal, intrathecal and epidural. The antibody dose will vary, including depending on the nature and/or severity of the disease as well as the condition of the subject, may include doses between 1 mg and 100 mg. Doses may also include those between 1 mg/kg and 15 mg/kg. In some embodiments, the dose is between about 5 mg/kg and about 7.5 mg/kg. In some embodiments, the dose is about 5 mg/kg. In some embodiments, the dose is about 7.5 mg/kg. Flat doses selected from the group consisting of: (a) 375-400 mg every two weeks and (b) 550-600 mg every three weeks. In some embodiments, the flat dose is 375-400 mg every two weeks. In some embodiments, the flat dose is 550-600 mg every three weeks. In some embodiments the flat dose is 400 mg every two weeks. In some embodiments the flat dose is 600 mg every three weeks. In some embodiments of sequential dosing, a first dose and a second dose are each between 1 mg/kg and 15 mg/kg with the second dose following the first does by between 1 and 4 weeks. In some embodiments, the first dose and the second dose are each between 5 mg/kg and 7.5 mg/kg and the second dose follows the first dose by between 2 and 3 weeks. In some embodiments, the first dose and the second dose are each 5 mg/kg and the second dose follows the first dose by 2 weeks. In some embodiments, the first dose and the second dose are each 7.5 mg/kg and the second dose follows the first dose by 3 weeks.

For treating diseases, disorders and conditions, the antibody in some embodiments is administered via intravenous infusion. The dosage administered via infusion is in the range of about 1 µg/m² to about 10,000 µg/m² per dose, generally one dose per week for a total of one, two, three or four doses. Alternatively, the dosage range is of about 1 µg/m² to about 1000 µg/m², about 1 µg/m² to about 800 µg/m², about 1 µg/m² to about 600 µg/m², about 1 µg/m² to about 400 µg/m²; alternatively, about 10 µg/m² to about 500 µg/m², about 10 µg/m² to about 300 µg/m², about 10 µg/m² to about 200 µg/m², and about 1 µg/m² to about 200 µg/m². The dose may be administered once per day, once per week, multiple times per week, but less than once per day, multiple times per month but less than once per day, multiple times per month but less than once per week, once per month or intermittently to relieve or alleviate symptoms of the disease, disorder, or condition. Administration may continue at any of the disclosed intervals until amelioration of the disease, disorder or condition, or amelioration of symptoms of the disease, disorder or condition being treated. Administration may continue after remission or relief of symptoms is achieved where such remission or relief is prolonged by such continued administration.

In one aspect, the present disclosure further provides pharmaceutical formulations comprising at least one anti-beta klotho antibody of the present disclosure. In some embodiments, a pharmaceutical formulation comprises 1) an anti-beta klotho antibody, and 2) a pharmaceutically acceptable carrier. In some embodiments, a pharmaceutical formulation comprises 1) an anti-beta klotho antibody and/or an immunoconjugate thereof, and optionally, 2) at least one additional therapeutic agent.

Pharmaceutical formulations comprising an antibody is prepared for storage by mixing the antibody having the desired degree of purity with optional physiologically acceptable carriers, excipients or stabilizers (see, e.g., Remington's Pharmaceutical Sciences 16th edition, Osol, A. Ed. (1980)) in the form of aqueous solutions or lyophilized or other dried formulations. The formulations herein may also contain more than one active compound as necessary for the particular indication being treated, preferably those with complementary activities that do not adversely affect each other. For example, in addition to an anti-beta klotho antibody, it may be desirable to include in the one formulation, an additional antibody, e.g., a second anti-beta klotho antibody which binds a different epitope on the beta klotho polypeptide, or an antibody to some other target. Alternatively, or additionally, the composition may further comprise another agent, including, for example, a chemotherapeutic agent, cytotoxic agent, cytokine, growth inhibitory agent, anti-hormonal agent, and/or cardioprotectant. In some embodiments the formulation includes an alkylating agent (e.g., chlorambucil, bendamustine hydrochloride or cyclophosphamide) a nucleoside analog (e.g., fludarabine, pentostatin, cladribine or cytarabine) a corticosteroid (e.g., prednisone, prednisolone or methylprednisolone), an immunomodulatory agent (e.g., lenalidomide), an antibiotic (e.g., doxorubicin, daunorubicin idarubicin or mitoxentrone), a synthetic flavon (e.g., flavopiridol), a Bcl2 antagonist, (e.g., oblimersen or ABT-263), a hypomethylating agent (e.g., azacytidine or decitabine), an FLT3 inhibitor (e.g., midostaurin, sorafenib and AC220). Such molecules are suitably present in combination in amounts that are effective for the purpose intended.

The antibodies of the present disclosure may be formulated in any suitable form for delivery to a target cell/tissue, e.g., as microcapsules or macroemulsions (Remington's Pharmaceutical Sciences, 16th edition, Osol, A. Ed. (1980); Park et al., Molecules 10: 146-161 (2005); Malik et al., Curr. Drug. Deliv. 4: 141-151 (2007)); as sustained release formulations (Putney and Burke, Nature Biotechnol. 16: 153-157, (1998)) or in liposomes (Maclean et al., Int. J. Oncol. 11: 235-332 (1997); Kontermann, Curr. Opin. Mol. Ther. 8: 39-45 (2006)).

An antibody provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed, for example, in Remington's Pharmaceutical Sciences (1990) Mack Publishing Co., Easton, PA.

Various delivery systems are known and can be used to administer a prophylactic or therapeutic agent (e.g., an antibody that binds to beta klotho as described herein), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. In another embodiment, a prophylactic or therapeutic agent, or a composition provided herein can be delivered in a controlled release or sustained release system. In one embodiment, a pump may be used to achieve controlled or sustained release (see, e.g., Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibody that binds to beta klotho as described herein) or a composition of the invention (see, e.g., Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of the therapeutic target, for example, the nasal passages or lungs, thus requiring only a fraction of the systemic dose (see, e.g., Goodson, in Medical Applications of Controlled Release, supra, vol. 2, pp. 115-138 (1984)). Controlled release systems are discussed, for example, by Langer (1990, Science 249:1527-1533). Any technique known to one of skill in the art can be used to produce sustained release formulations comprising one or more antibodies that bind to beta klotho as described herein. (See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760).

Therapeutic Methods

An antibody of the present disclosure may be used in, for example, in vitro, ex vivo, and in vivo therapeutic methods. In one aspect, the present disclosure provides methods for treating or preventing a disease, disorder, or condition, either in vivo or in vitro, the method comprising exposing a cell to an anti-beta klotho antibody.

In one aspect, an antibody of the present disclosure is used to treat or prevent a disease, disorder, or condition, including, for example, Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21.

In one aspect, methods are provided for treating a disease, disorder or condition comprising administering to an individual an effective amount of an anti-beta klotho antibody or fragment thereof. In certain embodiments, a method for treating a disease, disorder, or condition comprises administering to an individual an effective amount of a pharmaceutical formulation comprising an anti-beta klotho antibody and, optionally, at least one additional therapeutic agent, such as those described herein.

An anti-beta klotho antibody or fragment thereof can be administered to a human for therapeutic purposes. Moreover, an anti-beta klotho antibody or fragment thereof can be administered to a non-human mammal expressing beta klotho with which the antibody cross-reacts (e.g., a primate, pig, rat, or mouse) for veterinary purposes or as an animal model of human disease. Regarding the latter, such animal models may be useful for evaluating the therapeutic efficacy of antibodies of the present disclosure (e.g., testing of dosages and time courses of administration).

Antibodies of the present disclosure can be used either alone or in combination with other compositions in a therapy. For example, an anti-beta klotho antibody of the present disclosure may be co-administered with at least one additional therapeutic agent and/or adjuvant. In some embodiments, the additional compound is a therapeutic antibody other than an anti-beta klotho antibody.

Such combination therapies noted above encompass combined administration (where two or more therapeutic agents are included in the same or separate formulations), and separate administration, in which case, administration of an anti-beta klotho antibody or fragment thereof of the present disclosure can occur prior to, simultaneously, and/or following, administration of the additional therapeutic agent and/or adjuvant. Antibodies of the present disclosure can also be used in combination with additional therapeutic regimens including, without limitation, those described herein.

An antibody of the present disclosure (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody or conjugate is suitably administered by pulse infusion, particularly with declining doses of the antibody or fragment thereof. Dosing can be by any suitable route, for example, by injections, such as intravenous or subcutaneous injections, depending in part on whether the administration is brief or chronic.

Antibodies of the present disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The anti-beta klotho antibody need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a disease, disorder, or condition, the appropriate dosage of an anti-beta klotho antibody of the present disclosure (when used alone or in combination with one or more other additional therapeutic agents, such as agents described herein) will depend on the type of disease, disorder, or condition, to be treated, the type of antibody, the severity and course of the disease, disorder, or condition, whether the antibody is administered for preventive or therapeutic purposes, previous therapy, the patient's clinical history and response to the antibody, and the discretion of the attending physician. The anti-beta klotho antibody is suitably administered to the patient at one time or over a series of treatments. Depending on the type and severity of the disease, about 1 µg/kg to 100 mg/kg (e.g., 0.1 mg/kg-20 mg/kg, 1 mg/kg-15 mg/kg, etc.) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Exemplary dosages of the antibody may be in the range from about 0.05 mg/kg to about 10.0 mg/kg. Thus, one or more doses of about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, or 10.0 mg/kg (or any combination thereof) of antibody may be administered to the patient. Such doses may be administered intermittently, e.g., every week or every three weeks (e.g., such that the patient receives from about two to about twenty, or e.g., about six doses of the antibody). An initial higher loading dose, followed by one or more lower doses may be administered. An exemplary dosing regimen comprises administering an initial loading dose, followed by a maintenance dose (e.g., weekly) of the antibody. The initial loading dose may be greater than the maintenance dose. However, other dosage regimens may be useful. The progress of this therapy is easily monitored by conventional techniques and assays.

Diagnostic Methods and Methods of Detection

In one aspect, anti-beta klotho antibodies and fragments thereof of the present disclosure are useful for detecting the presence of beta klotho in a biological sample. Such anti-beta klotho antibodies may include those that bind to human and/or cyno beta klotho, but do not induce FGF19-like signaling and/or FGF21-like signaling activity. The term "detecting" as used herein encompasses quantitative or qualitative detection. In certain embodiments, a biological sample comprises a cell or tissue.

In one aspect, the present disclosure provides a method of detecting the presence of beta klotho in a biological sample. In certain embodiments, the method comprises contacting the biological sample with an anti-beta klotho antibody under conditions permissive for binding of the anti-beta klotho antibody to beta klotho, and detecting whether a complex is formed between the anti-beta klotho antibody and beta klotho.

In one aspect, the present disclosure provides a method of diagnosing a disorder associated with expression of beta klotho. In certain embodiments, the method comprises contacting a test cell with an anti-beta klotho antibody; determining the level of expression (either quantitatively or qualitatively) of beta klotho by the test cell by detecting binding of the anti-beta klotho antibody to beta klotho; and comparing the level of expression of beta klotho by the test cell with the level of expression of beta klotho by a control cell (e.g., a normal cell of the same tissue origin as the test cell or a cell that expresses beta klotho at levels comparable to such a normal cell), wherein a higher level of expression of beta klotho by the test cell as compared to the control cell indicates the presence of a disorder associated with increased expression of beta klotho. In certain embodiments, the test cell is obtained from an individual suspected of having a disease, disorder or condition associated with expression of beta klotho and/or a disease, disorder or condition in which it is desirable to mimic or augment the in vivo effects of FGF19 and/or FGF21. In certain embodiments, the disease, disorder or condition is, for example, Type 2 diabetes, obesity, dyslipidemia, NASH, cardiovascular disease or metabolic syndrome. Such exemplary diseases, disorders or conditions may be diagnosed using an anti-beta klotho antibody of the present disclosure.

In certain embodiments, a method of diagnosis or detection, such as those described above, comprises detecting binding of an anti-beta klotho antibody to beta klotho expressed on the surface of a cell or in a membrane preparation obtained from a cell expressing beta klotho on its surface. In certain embodiments, the method comprises contacting a cell with an anti-beta klotho antibody under conditions permissive for binding of the anti-beta klotho antibody to beta klotho, and detecting whether a complex is formed between the anti-beta klotho antibody and beta klotho on the cell surface. An exemplary assay for detecting binding of an anti-beta klotho antibody to beta klotho expressed beta klotho on the surface of a cell is a "FACS" assay.

Certain other methods can be used to detect binding of anti-beta klotho antibodies to beta klotho. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-beta klotho antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, for example, through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, for example, firefly luciferase and bacterial luciferase (see, e.g., U.S. Pat. No. 4,737,456), luciferin, 2,3-dihydrophthalazin-ediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, anti-beta klotho antibodies are immobilized on an insoluble matrix. Immobilization entails separating the anti-beta klotho antibody from any beta klotho that remains free in solution. This conventionally is accomplished by either insolubilizing the anti-beta klotho antibody before the assay procedure, as by adsorption to a water-insoluble matrix or surface (see, e.g., Bennich et al., U.S. Pat. No. 3,720,760), or by covalent coupling (for example, using glutaraldehyde cross-linking), or by insolubilizing the anti-beta klotho antibody after formation of a complex between the anti-beta klotho antibody and beta klotho, for example, by immunoprecipitation.

Any of the above embodiments of diagnosis or detection may be carried out using an immunoconjugate of the present disclosure in place of or in addition to an anti-beta klotho antibody.

Assays

Anti-beta klotho antibodies of the present disclosure may be characterized for their physical/chemical properties and/or biological activities by various assays known in the art.

1. Activity Assays

In one aspect, assays are provided for identifying anti-beta klotho antibodies thereof having biological activity. Biological activity may include, for example, assays which measure effects on glucose and/or lipid metabolism. For example, a blood glucose assay may be used. Blood glucose (e.g., in mouse tail snip or in a human blood sample) may be measured using ACCU-CHEK Active test strips read by ACCU-CHEK Active meter (Roche Diagnostics, Indianapolis, IN) following manufacturer's instruction. In addition, for example, a lipid profile assay may be used. Whole blood (e.g., from mouse tail snips or from a human blood sample) may be collected into plain capillary tubes (BD Clay Adams SurePrep, Becton Dickenson and Co. Sparks, MD). Serum and blood cells can be separated by spinning the tubes in an Autocrit Ultra 3 (Becton Dickinson and Co. Sparks, MD). Serum samples can be assayed for lipid profile (triglyceride, total cholesterol, HDL, and non-HDL) using Integra 400 Clinical Analyzer (Roche Diagnostics, Indianapolis, IN) following the manufacturer's instructions.

2. Binding Assays and Other Assays

In one aspect, an anti-beta klotho antibody is tested for its antigen binding activity. For example, in certain embodiments, an anti-beta klotho antibody is tested for its ability to bind to exogenous or endogenous beta klotho expressed on the surface of a cell. A FACS assay may be used for such testing.

A panel of monoclonal antibodies raised against beta klotho may be grouped based upon the epitopes they recognize, a process known as epitope binning. Epitope binning is typically carried out using competition assays, which evaluate an antibody's ability to bind to an antigen in the presence of another antibody. In an exemplary competition assay, immobilized beta klotho is incubated in a solution comprising a first labeled antibody that binds to beta klotho and a second unlabeled antibody that is being tested for its ability to compete with the first antibody for binding to beta klotho. The second antibody may be present in a hybridoma supernatant. As a control, immobilized beta klotho is incubated in a solution comprising the first labeled antibody but not the second unlabeled antibody. After incubation under conditions permissive for binding of the first antibody to beta klotho, excess unbound antibody is removed, and the amount of label associated with immobilized beta klotho is measured. If the amount of label associated with immobilized beta klotho is substantially reduced in the test sample relative to the control sample, then that indicates that the second antibody is competing with the first antibody for binding to beta klotho. In certain embodiments, immobilized beta klotho is present on the surface of a cell or in a membrane preparation obtained from a cell expressing beta klotho on its surface.

High-throughput methods of epitope binning are also known in the art (see, e.g., Jia et al., *J. Immunol. Methods* 2004, 288(1-2):91-98, describing a method of multiplexed competitive antibody binning for the characterization of monoclonal antibodies; and Miller et al., *J. Immunol. Methods* 2011, 365(1-2):118-25, describing epitope binning of murine monoclonal antibodies by a multiplexed pairing assay).

3. Epitope Mapping

Epitope mapping is the process of identifying the binding sites, or epitopes, of an antibody on its target protein antigen. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

A variety of methods are known in the art for mapping antibody epitopes on target protein antigens. These include mutagenesis methods, peptide scanning methods, display methods, methods involving and mass spectroscopy, and structural determination.

The site directed mutagenesis method involves targeted site-directed mutagenesis where critical amino acids are identified by systematically introducing substitutions along the protein sequence and then determining the effects of each substitution on antibody binding. This may be done by "alanine scanning mutagenesis," as described, for example, by Cunningham and Wells (1989) *Science* 244: 1081-1085, or some other form of point mutagenesis of amino acid residues in human beta klotho. Mutagenesis studies, however, may also reveal amino acid residues that are crucial to the overall three-dimensional structure of beta klotho but that are not directly involved in antibody-antigen contacts, and thus other methods may be necessary to confirm a functional epitope determined using this method.

Shotgun mutagenesis mapping utilizes a comprehensive plasmid-mutation library for the target gene, with each clone in the library bearing a unique amino acid mutation and the entire library covering every amino acid in the target protein. The clones that constitute the mutation library are individually arranged in microplates, expressed within living mammalian cells, and tested for immunoreactivity with antibodies of interest. Amino acids critical for antibody epitopes are identified by a loss of reactivity and are then mapped onto a protein structure to visualize epitopes. By automating the analysis, new epitope maps can be derived within days to weeks. Because it uses the native structure of proteins within mammalian cells, the technique allows both linear and conformational epitope structures to be mapped on complex proteins. (See, e.g., Paes et al., *J. Am. Chem. Soc.* 131(20): 6952-6954 (2009); Banik and Doranz, *Genetic Engineering and Biotechnology News* 3(2): 25-28 (2010)).

The epitope bound by an anti-beta klotho antibody may also be determined using peptide scanning methods. In peptide scanning, libraries of short peptide sequences from overlapping segments of the target protein, beta klotho, are tested for their ability to bind antibodies of interest. The peptides are synthesized and screened for binding, e.g., using ELISA or BIACORE, or on a chip, by any of the multiple methods for solid-phase screening (see, e.g., Reineke et al., *Curr. Opin. Biotechnol.* 12: 59-64, 2001) as in the "pepscan" methodology (see, e.g., WO 84/03564; WO 93/09872). Such peptide screening methods may not be capable of detecting some discontinuous functional epitopes, i.e. functional epitopes that involve amino acid residues that are not contiguous along the primary sequence of the beta klotho polypeptide chain.

A recently developed technology termed CLIPS (chemical linkage of peptides onto scaffolds) may be used to map conformational epitopes. The loose ends of the peptides are affixed onto synthetic scaffolds, so that the scaffolded peptide may be able to adopt the same spatial structure as the corresponding sequence in the intact protein. CLIPS technology is used to fix linear peptides into cyclic structures ('single-loop' format), and to bring together different parts of a protein binding site ('double-loop', 'triple-loop', etc. format), so as to create conformational epitopes that may be assayed for antibody binding (see, e.g., U.S. Pat. No. 7,972, 993).

The epitopes bound by antibodies of the present disclosure may also be mapped using display techniques, including, for example, phage display, microbial display, and ribosome/mRNA display as described above. In these methods, libraries of peptide fragments are displayed on the surface of the phage or cell. Epitopes are then mapped by screening mAbs against these fragments using selective binding assays. A number of computational tools have been developed which allow the prediction of conformational epitopes based upon linear affinity-selected peptides obtained using phage display (see, e.g., Mayrose et al., *Bioinformatics* 23: 3244-3246, 2007). Methods are also available for the detection of conformational epitopes by phage display. Microbial display systems may also be used to express properly folded antigenic fragments on the cell surface for identification of conformational epitopes (see, e.g., Cochran et al., *J. Immunol. Meth.* 287: 147-158, 2004; Rockberg et al., *Nature Methods* 5: 1039-1045, 2008).

Methods involving proteolysis and mass spectroscopy may also be used to determine antibody epitopes (see, e.g., Baerga-Ortiz et al., *Protein Sci.* 2002 June; 11(6): 1300-1308). In limited proteolysis, the antigen is cleaved by different proteases, in the presence and in the absence of the antibody, and the fragments are identified by mass spectrometry. The epitope is the region of the antigen that becomes protected from proteolysis upon binding of the antibody (see, e.g., Suckau et al., *Proc. Natl. Acad. Sci. USA* 87:9848-9852, 1990). Additional proteolysis based methods include, for example, selective chemical modification (see, e.g., Fiedler et al., *Bioconjugate Chemistry* 1998, 9(2): 236-234, 1998), epitope excision (see, e.g., Van de Water et al., *Clin. Immunol. Immunopathol.* 1997, 85(3): 229-235, 1997), and the recently developed method of hydrogen-deuterium (H/D) exchange (see, e.g., Flanagan, N., *Genetic Engineering and Biotechnology News* 3(2): 25-28, 2010).

The epitope bound by antibodies of the present disclosure may also be determined by structural methods, such as X-ray crystal structure determination (see, e.g., WO 2005/044853), molecular modeling and nuclear magnetic resonance (NMR) spectroscopy, including NMR determination of the H-D exchange rates of labile amide hydrogens when free and when bound in a complex with an antibody of interest (see, e.g., Zinn-Justin et al. (1992) *Biochemistry* 31:11335-11347; Zinn-Justin et al. (1993) *Biochemistry* 32:6884-6891).

Additional antibodies binding to the same epitope as an antibody of the present disclosure may be obtained, for example, by screening of antibodies raised against beta klotho for binding to the epitope, by immunization of an animal with a peptide comprising a fragment of human beta klotho comprising the epitope sequence, or by selection of antibodies using phage display for binding to the epitope sequence. Antibodies that bind to the same functional epitope might be expected to exhibit similar biological activities, such as blocking a biological activity of beta klotho, and such activities can be confirmed by functional assays of the antibodies.

Additional Activity Assays

In one embodiment, an anti-beta klotho antibody of the present disclosure is an antagonist antibody that inhibits a biological activity of beta klotho. The anti-beta klotho antibodies of the present disclosure may be assayed to determine if they inhibit a biological activity of beta klotho.

In one aspect, purified anti-beta klotho antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In one embodiment, the present disclosure contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. An in vitro assay to assess ADCC activity of a molecule of interest is described, for example, in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, for example, in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, for example, as described in Gazzano-Santoro et al., *J. Immunol. Methods* 202:163 (1996), may be performed. FcRn binding and in vivo clearance/half life determinations can also be performed using methods known in the art.

Although the foregoing present disclosure has been described in some detail by way of illustration and example for purposes of clarity of understanding, the descriptions and examples should not be construed as limiting the scope of the present disclosure. The disclosures of all patent and scientific literatures cited herein are expressly incorporated in their entirety by reference.

EXAMPLES

The following are examples of methods and compositions of the present disclosure.

Example 1: Generation of Antibodies to Beta Klotho

Antibodies to beta klotho were generated, for example, by immunizations of mice (i) with cells expressing human beta klotho (HuKLB) and FGF receptor 1c (FGFR1c or R1c) and (ii) with HuKLB and cynomologous beta klotho (cyno KLB) protein.

For example, beta klotho expressing cells were prepared as follows. 293EXPI (Invitrogen) cells were transiently co-transfected with nucleic acid sequences encoding a variant of FGFR1c with a mutation at amino acid position 623 (see, e.g., SEQ ID NO:308 but with a mutation D623N) and HuKLB (SEQ ID NO:297). Cells were analyzed for expression of R1c and HuKLB by the respective specific antibodies by FACS. Cells were washed 2 times in PBS, pelleted by centrifugation and frozen in individual vials at $6 \times 10^7$ cells for immunization. 129/B6 animals were immunized with $1 \times 10^7$ cells with adjuvants (Ribi, CpG, and PolyIC). Animals were boosted every 2 weeks for the duration necessary to induce a suitable titer. Animals were boosted with HuKLB and CyKLB protein after 4 boosts with R1c and HuKLB overexpressing-293EXPI cells. Titers were determined by ELISA and FACS. Single cell suspensions of lymphocytes were obtained from spleen and draining lymph nodes of animals with suitable titers. Cells were fused with SP2/0 myeloma cells at a ratio of 1:2 by electrofusion. Fused cells were plated at $2.5 \times 10^6$ cells per plate in 70 μL into twenty-four×384-well plates in the presence of HAT selection. After 7 days, 50 μL of supernatant were removed and replaced with fresh HAT containing media. After 10-14 days of culture, supernatants were collected and subjected to screening by FACS using R1c and HuKLB overexpressing-293EXPI cells or by Biacore using HuKLB protein to confirm binding. Positive clones were further selected and subjected to subcloning.

In a first campaign of immunizations and fusions, at least 25-30 384 well plates were screened for binding to HuKLB (e.g., HuKLB protein and/or cells expressing HuKLB). In a second campaign for immunizations and fusions, a similar number of plates were screened as described for the first campaign. Thousands of clones were screened and hundreds of clones were selected for additional study, including in assays for binding, affinity and epitope specificity as described in Examples 2 and 3. Hundreds of hybridoma supernatants were also tested in functional assays as described, in Examples 4 and 5, including for agonist activity similar to FGF receptor ligands FGF19 and/or FGF21 (e.g., FGF19-like and/or FGF21-like signaling activity).

Example 2: Screening and Selection of Antibodies to Beta Klotho

Antibodies to beta klotho were generated from hybridomas, for example, such as described in Example 1. Hybridoma supernatants were screened for binding to beta klotho (e.g., human and/or cyno beta klotho) in FACS-based and/or Biacore-based assays.

For example, after 2 weeks of culture, hybridoma supernatants were screened for monoclonal antibodies binding to human beta klotho by a FACS based binding screen. Briefly, hybridoma supernatants were co-incubated with human beta klotho over-expressing cells for 30 minutes at 4° C. After washing with PBS/1% BSA/0.1% azide, human beta klotho over-expressing cells were co-incubated with labeled anti-mouse Fc (Jackson Immunoresearch) for 30 minutes at 4° C. After washing with PBS/1% BSA/0.1% azide, cells were acquired on flow cytometer (FACS Calibur) and analyzed by cytometric analytical software (FlowJo). A binding antibody is one that shows a shift from cells incubated with labeled anti-mouse Fc only.

For example, after 2 weeks of culture, hybridoma supernatants were screened for monoclonal antibodies binding to human beta klotho by a Biacore based binding screen. Briefly, anti-mouse Fc antibody (Sigma-Aldrich, St. Louis, MO) was immobilized on all four flow cells of a CM5 chip using amine coupling reagents (GE Healthcare LifeSciences, Piscataway, NJ). Hybridoma supernatants were diluted three fold with PBS-P buffer (PBS containing 0.005% P20) and injected for 30 seconds on flow cells 2,3 and 4 to capture the antibody (flow cell 1 was used as a reference). This was followed by a short injection of human beta klotho (25 nM, R&D Systems, Minneapolis, MN) for 60 seconds at a flow rate of 30 µL/min to test for binding to captured antibody on each flow cell.

From two immunization and fusion campaigns as described in Example 1, fifty-sixty 384 well plates of hybridoma supernatants were assayed for binding by FACS and/or Biacore. From these assays, approximately of 250 antibodies were identified as binders to human beta klotho. These antibodies were purified and subsequently tested for their binding affinity to human beta klotho and cyno beta klotho by Biacore and for their functional activity by reporter assays as described in Example 3.

In additional Biacore-based binding/screening assays, the binding affinity of antibodies to human and cyno beta klotho were measured. For example, antibodies were rank ordered based on their binding affinity to human beta klotho and cyno beta klotho by low resolution $K_D$ measurement by Biacore. Briefly, anti-mouse Fc antibody (Sigma-Aldrich, St. Louis, MO) was immobilized on all four flow cells of a CM5 chip using amine coupling reagents (GE Healthcare LifeSciences, Piscataway, NJ). Purified antibodies were captured (~100 RUs) on flow cells 2, 3 and 4 using flow cell 1 as a reference. This was followed by injection of human or cyno beta klotho (25 nM in PBS-P buffer) at a flow rate of 70 µL/min and monitoring the binding kinetics at 25° C.

Binding affinity measurements were also made in additional Biacore based assays. For example, equilibrium dissociation constant ($K_D$) measurements were carried out with purified antibodies to evaluate their binding to human beta klotho and cyno beta klotho. As mentioned above, anti-mouse Fc antibody (Sigma-Aldrich, St. Louis, MO) was immobilized on all four flow cells of a CM5 chip using amine coupling reagents (GE Healthcare LifeSciences, Piscataway, NJ). Purified antibodies were captured (~100 RUs) on flow cells 2, 3 and 4 using flow cell 1 as a reference. This was followed by injection of different concentrations of human or cyno beta klotho (1.56 nM to 25 nM, two-fold dilutions in PBS-P buffer) at a flow rate of 70 µL/min and the binding kinetics were evaluated at 25° C.

Representative results are reported as $K_D$ (nM) values as shown in Table 11 below.

TABLE 11

| | Affinity KD (nM) | |
|---|---|---|
| | HuKLB | Cyno KLB |
| 5H23 | ~pM | 0.72 |
| 1C17 | 0.89 | 3.1 |
| 1D19 | 1.25 | 2.9 |
| 2L12 | 0.22 | 1.42 |
| 3L3 | 1.14 | 2.2 |
| 3N20 | 3.3 | 3.52 |
| 4P5 | 0.26 | 0.44 |
| 5F7 | 1.7 | 2.5 |
| 1G19 | N/A | N/A |
| 5C23 | 1.2 | 2.4 |

Example 3: Screening and Selection of Antibodies to Beta Klotho

Antibodies that were selected for binding to beta klotho, for example, such as described in Example 2, were evaluated in competition binding assays and epitope binning experiments.

For example, for competition binding assays by FACS analysis, antibody standards were prepared that were conjugated to a fluorochrome using either A488 or A647 antibody labeling kit (Invitrogen) following manufacturer's instructions. A dose titration of the conjugated antibody standard was evaluated using HuKLB overexpressing cells. The plateau of the maximal signal of antibody binding is EC=100 and the background signal is EC=0. Competition by FACS against the fluorochrome labeled antibody was performed by pre-incubating HuKLB overexpressing cells with hybridoma supernatants for 15 minutes at room temperature. Without washing, an EC=10 concentration of A488 or A647 labelled antibody standard was added. EC=10 for an individual antibody was determined by 10% of signal using the maximum signal as (100%) and background signal as (0%). After 30 minutes at 4° C., cells are washed and analyzed by FACS. In these assays, a competing antibody is one that shows signal comparable to the competition by 5H23. A non-competing antibody is one that shows signal equal to labelled antibody alone. A partial competing antibody is one sample that show signal between labelled antibody alone and background. Antibodies that show complete competition against the same standard antibody are considered to be in the same bin.

In exemplary competition binding experiments by FACS, antibody 5H23 or 3I13 was used as an antibody standard for a positive control (competing antibody) or a negative control (non-competing antibody), respectively. Representative results are shown in Table 12 below reported as mean fluorescence intensity (MFI). For these experiments, signal comparable to labeled antibody alone is a non-competing antibody, while signal comparable to the competition by 5H23 is a competing antibody.

TABLE 12

| Antibody | Mean Florescence Intensity (MFI) | |
|---|---|---|
| | 5H23 - Alexa647 | 3I13- Alexa488 |
| 5H23 | 2.3 | 29.8 |
| 1C17 | 2.4 | 26.7 |
| 1D19 | 2.5 | 30.6 |
| 2L12 | 3.1 | 30.9 |
| 3L3 | 4.2 | 28.7 |
| 3N20 | 2.4 | 30.5 |
| 4P5 | 2.4 | 30.1 |
| 5C23 | 2.4 | 29.3 |
| 5F7 | 2.3 | 28.5 |
| 1G19 | 2.2 | 29.0 |
| 3I13 | 9.4 | 7.4 |
| Labeled antibody alone | 10.8 | 32.4 |

To further evaluate the binding sites of the antibodies on human beta klotho, competition experiments were also set up on the Biacore. For example, two antibodies were immobilized on two flow cells of a CM5 chip. Human beta klotho-antibody complexes were prepared with different antibodies (antibody concentration was titrated from 0.1-50 nM while keeping beta klotho concentration constant at 5 nM) in a 96-well micro plate and injected on the antibody surfaces. The measured signal (Response Unit, RU) was plotted against the solution antibody concentration [nM]. If the antibody in solution recognized the same epitope as the antibody immobilized on the chip surface, then a decrease in RU was observed with increase in concentration of antibody in solution (demonstrating competition for the binding site on beta klotho). However, if the antibody in solution recognized a distinct epitope relative to the immobilized antibody, an increase in RU was observed. In the latter scenario, the antibody-klotho complex could bind to the immobilized antibody surface leading to the observed increase in signal.

In exemplary competition binding experiments by Biacore, antibody 5H23 competed with itself for binding to HuKLB and additional antibodies 1C17, 1 D19, 2L12, 3L3, 3N20, 4P5, 5C23, 5F7 and 1G19 competed with 5H23. These antibodies were designated as members of the 5H23 epitope bin. The sequences for these epitope-related antibodies are aligned and shown in FIGS. 1 and 2. FIG. 2 also shows conserved amino acid sequences for the CDRs of these related antibodies.

Example 4: Functional Assays

Antibodies to beta klotho generated, for example, such as described in Example 1, were tested for their functional activity in cell-based reporter assays.

For example, ELK1-luciferase reporter assays, which measure FGFR1c/beta klotho signaling, were performed using transiently transfected HEK293, HEK293T, or L6 cells (ATCC). The transfecting plasmids consisted of two reporter plasmids Gal4-Elk1 and 5×UAS-Luc (Agilent Technologies PathDetect Elk1 trans-reporting system Cat #219005), and plasmids encoding human beta klotho (GeneCopoeia Cat #EX-E1104-MO2) or cynomolgus monkey beta klotho (cyno beta klotho) and human FGFR1c (GeneCopoeia Cat #EX-A0260-MO2). In these assays, activation of recombinantly expressed FGFR1c/beta klotho receptor complex in the cells induces intracellular signaling transduction, which leads to ERK and then Elk1 phosphorylation. Once Gal4-Elk1 is phosphorylated, Gal4-Elk1 binds to the 5×UAS promoter region and turns on luciferase reporter gene transcription. The activity of luciferase is then measured in luciferase enzymatic assays.

For these experiments, the above mentioned four plasmids (e.g., 2 reporter plasmids, beta klotho, R1c) were transfected into newly harvested cells in suspension using FuGene6 or Fugene HD transfection reagent (Promega). Cell density and transfection reagent amount were optimized for each cell type and each Fugene batch. Beta klotho and FGFR1c DNA ratio in transfection was optimized for each cell line and varied between 6:1 to 27:1. Transfected cells were seeded into 96-well (30,000 cells/100 μL/well), or 384-well plate (7500 cells/25 μL/well) in normal growth medium. After overnight incubation at 37° C., a variety of antibodies to beta klotho were added. After 6 hrs of 37° C. incubation with the antibodies, an equal volume of Bright-Glo reagent (Promega) was added and luminescence signal was read using Enspire reader (Perkin Elmer).

Representative results using human beta klotho and cyno beta klotho, transfected into HEK 293 cells, are reported as EC50 values as shown in Table 13 and Table 14, respectively, below.

TABLE 13

| mAb | Experiment - A HEK293 huKLB/R1c reporter assay EC50 (pM) | Experiment - B HEK293 huKLB/R1c reporter assay EC50 (pM) |
|---|---|---|
| control* | 45.3 | 27.9 |
| 5H23 | 102 | 34.2 |
| 1D19 | 620 | |
| 2L12 | 373 | |
| 3L3 | 773 | |
| 3N20 | 527 | |
| 4P5 | 600 | 78.3 |
| 1G19 | 231 | 127 |

*Control mAB comprises SEQ ID NO: 358 and SEQ ID NO: 360

TABLE 14

| mAb | Experiment - A HEK293 cynoKLB/R1c reporter assay EC50 (pM) | Experiment - B HEK293 cynoKLB/R1c reporter assay EC50 (pM) |
|---|---|---|
| control* | 108 | 227 |
| | 178 | |
| 5H23 | 165 | 218 |
| 1D19 | | 954 |
| 2L12 | 260 | 410 |
| 3L3 | 3576 | 1672 |
| 3N20 | 2464 | >10000 |

TABLE 14-continued

| mAb | Experiment - A<br>HEK293<br>cynoKLB/R1c reporter<br>assay EC50<br>(pM) | Experiment - B<br>HEK293<br>cynoKLB/R1c reporter<br>assay EC50<br>(pM) |
|---|---|---|
| 4P5 | 347 | 465 |
| 1G19 | 2354 | 2447 |

*Control mAB comprises SEQ ID NO: 358 and SEQ ID NO: 360

Representative results using human beta klotho, transfected into L6 cells, are reported as EC50 values as shown in Table 15 below.

TABLE 15

| mAb | L6<br>huKLB/R1c<br>reporter assay<br>EC50<br>(nM) | L6<br>huKLB/R2c<br>reporter assay<br>EC50<br>(nM) | L6<br>huKLB/R3c<br>reporter assay<br>EC50<br>(nM) | L6<br>huKLB/R4<br>reporter assay<br>EC50<br>(nM) |
|---|---|---|---|---|
| control | FGF19: 2.66 | FGF19: 0.16 | FGF19: 2.1 | FGF19: 0.05 |
| 5H23 | 0.28 | >67 | >67 | >67 |
| 2L12 | 4.65 | >67 | >67 | >67 |
| 4P5 | 0.39 | >67 | >67 | >67 |

L6 cells lack endogenous receptors and are often used to investigate antibody specificity to various transfected FGF receptor subtypes. Activation of the receptor via FGFR1c/beta klotho signaling in the absence of ligand (e.g., FGF19 (e.g., SEQ ID NO: 304) or FGF21(e.g., SEQ ID NO: 429)) by the exemplary anti-beta klotho antibodies of the present disclosure was observed with L6 cells transfected with FGFR1c (R1c), but not with L6 cells transfected with FGFR2c (R2c), FGFR3c (R3c), or FGFR4 (R4), whereas activation by the FGF19 control was observed with L6 cells transfected with R1c, R2c, R3c and R4.

Example 5: Additional Functional Assays

Antibodies to beta klotho generated, for example, as described in Example 1, were tested for their functional activity in a cell-based assay, such as an adipocyte assay, which measures endogenous FGFR1c/beta klotho signaling. FGF19 or FGF21 stimulate ERK phosphorylation, increase glucose uptake and lipolyses in cultured adipocytes. Adipocytes are considered physiologically relevant for demonstrating the functional activity of receptor ligands or agonist antibodies which mimic the function of ligands (e.g., signaling of the receptor by the ligands).

For example, frozen human preadipocytes (Lonza Cat #PT-5005) were thawed on day 1, differentiated on day 3 and maintained in differentiation medium for about two weeks before the experiment (e.g., then starved on day 17, and assayed on day 18). The seeding medium was 1:1 DMEM/F12K+10% FBS. Seeding cell density was 25,000 cells/100 µL/well in 96-well plate. On day 3, medium was replaced with human adipocytes differentiation medium (Cell Applications Inc). From then on, fresh differentiation medium was added onto cells every 2-3 days. On day 17 (the day before the assay), the cells were rinsed two times and left with DMEM/0.1% BSA (Sigma cat #A3803 essential fatty acids free BSA) overnight. The next day, fresh DMEM/0.1% BSA medium was added for 1 hour before the cells were treated with test anti-beta klotho antibodies for 15 minutes at 37° C. Cis-bio Cellul'erk assay kit (Cat #64ERKPEH) was used to assay for ERK phosphorylation level following the manufacturer's protocol.

Representative results using human adipocytes are reported as EC50 values as shown in Table 16 below:

TABLE 16

| mAb | Experiment - A<br>hAdip pERK assay | Experiment - B<br>hAdip pERK assay<br>EC50 (nM) |
|---|---|---|
| Control | +++ | FGF19<br>5.49 |
| 5H23 | +++ | 1.66 |
| 1C17 | ++ | >>67 |
| 1D19 | +++ | >67 |
| 2L12 | +++ | 1.23 |
| 3L3 | +++ | ~30~ |
| 3N20 | +++ | >67 |
| 4P5 | +++ | 0.89 |
| 5F7 | ++ | >67 |
| 5C23 | ++ | >>67 |
| 1G19 | +++ | 1.3 |

Example 6: Ligand Competition

Ligand (FGF19 or FGF21) competition assays were conducted to evaluate whether antibody-human beta klotho interaction influences the binding of beta klotho to its natural ligand, FGF19 or FGF21.

For example, Biacore-based competition assays were set up in which FGF19 (e.g., SEQ ID NO: 304) or FGF21(e.g., SEQ ID NO: 429) was immobilized on a flow cell (Fc2) of a CM5 chip (using Fc1 as a reference surface). Human beta klotho-antibody complexes were prepared with exemplary antibodies of the present disclosure, such as 5H23 (e.g., VH SEQ ID NO: 25 and VL SEQ ID NO: 26) or a humanized 5H23 (e.g., VH SEQ ID NO: 271 and VL SEQ ID NO: 276)). For example, concentrations of 5H23 and a control antibody were titrated from 0.1-67 nM while keeping beta klotho concentration constant at 5 nM in a 96-well micro plate and injected on the FGF19 surface. For another example, concentrations of a humanized 5H23 (e.g., VH SEQ ID NO: 271 and VL SEQ ID NO: 276) were titrated from 0.001-67 nM while keeping beta klotho concentration constant at 2.5 nM in a 96-well micro plate and injected on the FGF 21 surface. The measured signal (Response Unit, RU) was plotted against the solution antibody concentration [nM]. If the antibody in solution recognized the same epitope as FGF19 ligand or FGF21 ligand immobilized on the chip surface, then a decrease in RU was observed with increase in concentration of antibody in solution, demonstrating competition with FGF19 ligand or FGF21 ligand for the binding site on beta klotho. However, if the antibody in solution recognized a distinct epitope relative to the immobilized FGF19 ligand or FGF21 ligand, an increase in RU was observed. In the latter scenario, the antibody-klotho complex could bind to the immobilized FGF19 ligand surface or immobilized FGF21 ligand surface leading to the observed increase in signal. In the exemplary data shown below in Table 17A, a control antibody partially competed with the FGF19 ligand resulting in a significant reduction of RU signal, where 5H23 did not compete with the FGF19 ligand for binding to beta klotho. In the exemplary data shown below in Table 17B, a control antibody competed with the FGF21 ligand resulting in a significant reduction in RU signal, where a humanized 51H23 did not compete with the FGF21 ligand for binding to beta klotho.

TABLE 17A

| Experiment 1 | RU | % Change | Remark |
|---|---|---|---|
| RU signal for 5 nM β-Klotho (no complex) | 127 | 100% | Control antibody* |
| RU signal for klotho-Control antibody complex | 60 | 47% reduction | Partial competition between Control antibody* and FGF19 for binding to β-klotho |
| RU signal for 5 nM β-Klotho (no complex) | 109 | 100% | Control antibody* |
| RU signal for klotho-5H23 complex | 125 | 114% increase | 5H23-klotho complex binds to FGF19, hence no competition |

*Control antibody comprises SEQ ID NO: 358 and SEQ ID NO: 360

TABLE 17B

| Experiment 1 | Normalized RU | % Change | Remark |
|---|---|---|---|
| RU signal for 2.5 nM β-Klotho (no complex) | 1 | 100% | Control antibody* |
| RU signal for klotho-FGF21 complex | 0.03 | 97% reduction | FGF21 competes with itself for binding to β-klotho |
| RU signal for 2.5 nM β-Klotho (no complex) | 1 | 100% | Control antibody* |
| RU signal for klotho-humanized 5H23 complex | 1.1 | 110% increase | Humanized 5H23-klotho complex binds to FGF21, hence no competition |

*Control antibody comprises SEQ ID NO: 358 and SEQ ID NO: 360

Because 51H23 and a humanized 51H23 antibody bind to a different epitope of beta klotho as compared to endogenous ligands, such as FGF19 and FGF21, experiments were conducted to test if there were synergistic effects between FGF21 and 5H-23 or a humanized 5H-23 antibody. In a HEK293 reporter assay (see, e.g., Example 4), combinations of FGF21 and a humanized 5H-23 antibody (e.g., VH SEQ ID NO: 271 and VL SEQ ID NO: 276) were tested in a 1:1 molar ratio or fixing one and titrating the concentration of the other. No evidence of synergistic effects was observed; the maximum effect of FGF21 was not enhanced by the humanized 5H23 antibody, and vice versa.

Example 7: Humanization

Humanized anti-beta klotho antibodies were generated, including from antibodies selected as described in Examples 1-6.

A number of anti-beta klotho antibodies were selected for sequencing and their VH and VL regions, including their CDRs, are shown in Tables 1-10 and in FIGS. 1 and 2. An exemplary anti-beta klotho antibody, 5H23, was selected for humanization. Several methods of humanization were utilized. For some of the humanized antibodies, the method for humanization was empirical and based in part on structural information related to immunoglobulin variable regions including molecular models and requirements of antibody structural stability (see, e.g., Ewert et al., 2004, Methods 34:184-199; Honegger, 2008, Handb. Exp. Pharmacol. 181: 47-68; Kugler et al., 2009, Protein Eng. Des. Sel. 22: 135-147). The method was also based in part on considerations of antigen contact residues and/or framework stability residues. For example, consideration of typical antigen contact residues depends on the size of the antigen particularly residues outside CDRs which can contact the antigen, upper core, central core and lower core divisions, VH:VL interface residues, conserved Pro/Gly (positive phi angles) and VH subtype correlated residues match (see, e.g., Ewert et al., supra; Honegger, supra; Kügler et al., *supra*).

For example, human VH sequences homologous to the 5H23 VH framework sequences were searched for and the VH sequence encoded by the human germline IGHV1-3*01 (see, e.g., Ehrenmann et al., 2011, Cold Spring Harbor Protoc. G:737-749) was chosen as an acceptor for humanization. For some of the humanized antibodies, the CDR sequences of 5H23 VH were first transferred to the corresponding positions of IGHV1-3*01. Next, a number of amino acid residues of 5H23 VH were substituted for the corresponding human residues individually or in combinations.

Also, for example, human VL sequences homologous to the 5H23 VL framework sequences, were searched for and the human VK region encoded by the IGKV4-1*01 (see, e.g., Ehrennmann et al., supra) was chosen as an acceptor for humanization. For some of the humanized antibodies, the CDR sequences of 5H23 VL were first transferred to the corresponding positions of IGKV4-1*01. Next, a number of amino acid residues of 5H23 VL were substituted for the corresponding human residues individually or in combinations.

For some of the humanized antibodies, the method of humanization used an algorithm to construct a three-dimensional map of the mouse variable regions. This method also identified framework amino acids and residues important for the formation of CDR structure or necessary for binding to beta klotho. In addition, human VH and VL amino acid sequences with high homology to the mouse sequences were selected for possible framework sequences for humanization. As described above, the CDR sequences of 5H23 antibody may be transferred to such additional human framework sequences. A variety of human framework sequences, including germline sequences (e.g., IGHV1-3, IGHV1-46, IGHV1-69, IGKV4-1, IGKV1-39 or IGKV3-20) and mature individual sequences, may be suitable for the method of humanization. Next, a number of amino acid residues of 5H23 VH and/or 5H23 VL may be substituted for the corresponding human residues individually or in combination.

For some of the humanized light chains, IG BLAST searches were used to identify human germline sequences that were close matches in sequence with 5H23 VL and/or that were commonly used sequences, including, for example, IGKV1-39 and IGKV3-20. For some of the humanized light chains, the CDR sequences of 5H23 VL were first transferred to the corresponding positions of IGKV1-39 or IGKV3-20 and then certain amino acids were selected empirically for substation.

The amino acid sequences of the resulting humanized VH (vH1-vH9) and VL (vL1 to vL5, v1-39a to v1-39p and v3-20a to v3-20j) sequences are shown with 5H23 VH and VL sequences in FIG. 3A-3D. For example, using the various humanization methods described in this Example, a number of amino acid residues of 5H23 VH and VL were substituted for the corresponding human residue to obtain humanized sequences as shown in FIG. 3A-3D.

Humanized beta klotho antibodies may be prepared using any of the CDR sequences in Table 18 in combination with any of the framework sequences in Table 19.

TABLE 18

CDR Sequences for Humanized Anti-Beta Klotho Antibodies

VH CDR1

SEQ ID NO: 1 GYTFTSYDIN

SEQ ID NO: 27 GYSITSGYYWN

SEQ ID NO: 53 GYTFTRYDIN

SEQ ID NO: 79 GYTFTRYDIN

SEQ ID NO: 105 GYTFTSYDIN

SEQ ID NO: 131 GYIFTNYGIS

SEQ ID NO: 157 GYTFTRYDIN

SEQ ID NO: 183 GYTFTRYDIN

SEQ ID NO: 209 GYTFTRYDIN

SEQ ID NO: 235 GYSITSGYYWN

VH CDR2

SEQ ID NO: 2 WIYPGDGSTKYNEKFKG

SEQ ID NO: 28 YINYDGNSNYTPSLKN

SEQ ID NO: 54 WIYPGDSSTKFNENFKD

SEQ ID NO: 80 WIYPGDDSTKYNEKFKG

SEQ ID NO: 106 WIYPGDGSPKYDEKFKG

SEQ ID NO: 132 EIYPRSGNTYYNEKFKG

SEQ ID NO: 158 WIYPGDDSTKYNEKFKG

SEQ ID NO: 184 WIYPGDGSTKYNEKFEG

SEQ ID NO: 210 WIYPGDISTKYNEKFKG

SEQ ID NO: 236 YINYGGSNNYNPSLKN

VH CDR3

SEQ ID NO: 3 SDYYGSRSFAY

SEQ ID NO: 29 KGAYYSNYDSFDV

SEQ ID NO: 55 SDYYGSRSFTY

SEQ ID NO: 81 SDYYGSRSFVY

SEQ ID NO: 107 SDYYGSRSFVY

SEQ ID NO: 133 HWDGVLDYFDY

SEQ ID NO: 159 SDYYGSRSFVY

SEQ ID NO: 185 SDYYGSRSFVY

SEQ ID NO: 211 SDYYGSRSFVY

SEQ ID NO: 237 RGAYYSNYDSFDV

VL CDR1

SEQ ID NO: 4 RASKSVSTGYVYMH

SEQ ID NO: 30 KASQDINSYLS

SEQ ID NO: 56 RASKSVSTGYSYMH

SEQ ID NO: 82 RASKSVSTGYSYLH

SEQ ID NO: 108 RASKSVSTGYSYVH

TABLE 18-continued

CDR Sequences for Humanized Anti-Beta Klotho Antibodies

SEQ ID NO: 134 KSSQSLLNSGNQKNYLA

SEQ ID NO: 160 RASKSVSTGYSYMH

SEQ ID NO: 186 RASKSVSTGYSYMH

SEQ ID NO: 212 RASKSVSTGYSYMH

SEQ ID NO: 238 KASQDINSYLS

VL CDR2

SEQ ID NO: 5 LASYLES

SEQ ID NO: 31 RANRLVD

SEQ ID NO: 57 LASNLES

SEQ ID NO: 83 LASNLES

SEQ ID NO: 109 LASNLES

SEQ ID NO: 135 GASTRES

SEQ ID NO: 161 LASNLES

SEQ ID NO: 187 LASNLES

SEQ ID NO: 213 LASNLES

SEQ ID NO: 239 RANRLVD

VL CDR3

SEQ ID NO: 6 QHSRDLTFP

SEQ ID NO: 32 LQYDEFPFT

SEQ ID NO: 58 QHSRELPYT

SEQ ID NO: 84 QHSGELPYT

SEQ ID NO: 110 QHSGELPYT

SEQ ID NO: 136 LNDHSYPFT

SEQ ID NO: 162 HHSGELPYT

SEQ ID NO: 188 QHSRELPYT

SEQ ID NO: 214 QHSRELPYT

SEQ ID NO: 240 LQYDEFPYT

TABLE 19

Framework Sequences for Humanized Anti-Beta Klotho Antibodies

VH Framework 1 (FR1)

SEQ ID NO: 278 QVQLVQSGAEVKKPGASVKVSCKAS

SEQ ID NO: 279 QVQLQQSGAEVKKPGASVKVSCKAS

SEQ ID NO: 280 QVQLVQSGPEVKKPGASVKVSCKAS

SEQ ID NO: 378 QVQLVQSGAEVKKPGSSVKVSCKAS

TABLE 19-continued

Framework Sequences for Humanized Anti-Beta Klotho Antibodies

Framework 2 (FR2)

SEQ ID NO: 281 WVRQAPGQGLEWMG

SEQ ID NO: 282 WVRQAPGQGLEWIG

SEQ ID NO: 283 WVKQAPGQGLEWIG

Framework 3 (FR3)

SEQ ID NO: 284 RVTITRDTSASTAYMELSSLRSEDTAVYYCAR

SEQ ID NO: 285 KATITRDTSASTAYMELSSLRSEDTAVYFCAR

SEQ ID NO: 286 KATLTADTSASTAYMELSSLRSENTAVYFCAR

SEQ ID NO: 287 KATLTADKSARTAYMELSSLRSENTAVYFCAR

SEQ ID NO: 379 RATLTADKSTSTAYMELSSLRSEDTAVYYCAR

SEQ ID NO: 380 RATLTADKSTRTAYMELSSLRSEDTAVYYCAR

SEQ ID NO: 381 RATITADKSTSTAYMELSSLRSEDTAVYYCAR

Framework 4 (FR4)

SEQ ID NO: 288 WGQGTLVTVSS

VL
Framework 1 (FR1)

SEQ ID NO: 289 DIVLTQSPDSLAVSLGERATINC

SEQ ID NO: 290 DIVMTQSPDSLAVSLGERATINC

SEQ ID NO: 382 DIQMTQSPSSLSASVGDRVTITC

SEQ ID NO: 383 DIQLTQSPSSLSASVGDRVTITC

SEQ ID NO: 384 EIVLTQSPATLSLSPGERATLSC

Framework 2 (FR2)

SEQ ID NO: 291 WNQQKPGQPPKLLIY

SEQ ID NO: 292 WYQQKPGQPPKLLIY

SEQ ID NO: 385 WYQQKPGKAPKLLIY

SEQ ID NO: 386 WNQQKPGKAPKLLIY

SEQ ID NO: 387 WYQQKPGKPPKLLIY

SEQ ID NO: 388 WNQQKPGKPPKLLIY

SEQ ID NO: 389 WYQQKPGQAPRLLIY

SEQ ID NO: 390 WNQQKPGQAPRLLIY

SEQ ID NO: 391 WYQQKPGQPPRLLIY

SEQ ID NO: 392 WNQQKPGQPPRLLIY

Framework 3 (FR3)

SEQ ID NO: 293 GVPDRFSGSGSGTDFTLTISSVQAEDAAIYYC

SEQ ID NO: 294 GVPDRFSGSGSGTDFTLTISSVQAEDVAVYYC

SEQ ID NO: 295 GVPDRFSGSGSGTDFTLTISSVQAEDVAIYYC

SEQ ID NO: 393 GVPDRFSGSGSGTDFTLTISSLQAEDVAVYYC

SEQ ID NO: 394 GVPSRFSGSGSGTDFTLTISSLQPEDFATYYC

SEQ ID NO: 395 GVPSRFSGSGSGTDFTLTISSVQPEDFATYYC

SEQ ID NO: 396 GVPSRFSGSGSGTDFTLTISSLQEEDFATYYC

SEQ ID NO: 397 GVPSRFSGSGSGTDFTLTISSVQEEDFATYYC

SEQ ID NO: 398 GVPSRFSGSGSGTDFTLTISSVQEEDAATYYC

SEQ ID NO: 399 GIPARFSGSGSGTDFTLTISRLEPEDFAVYYC

SEQ ID NO: 400 GIPARFSGSGSGTDFTLTISRVEPEDFAVYYC

SEQ ID NO: 401 GIPARFSGSGSGTDFTLTISRLEPEDAAVYYC

SEQ ID NO: 402 GIPARFSGSGSGTDFTLTISRLEEEDFAVYYC

SEQ ID NO: 403 GIPARFSGSGSGTDFTLTISRVEEEDFAVYYC

SEQ ID NO: 404 GIPARFSGSGSGTDFTLTISRVEEEDAAVYYC

Framework 4 (FR4)

SEQ ID NO: 296 FGGGTKLEIK

SEQ ID NO: 405 FGGGTKVEIK

SEQ ID NO: 406 FGQGTKLEIK

SEQ ID NO: 407 FGGQTKLEIK

For example, a humanized anti-beta klotho antibody may comprise a heavy chain variable region (VH) comprising: FR1 (e.g., SEQ ID NO:278, 279, 280, or 378); CDR1 (e.g., SEQ ID NO:1, 27, 53, 79, 105, 131, 157, 183, 209, 235); FR2 (e.g., SEQ ID NO:281, 282, or 283); CDR2 (e.g., SEQ ID NO:2, 28, 54, 80, 106, 132, 158, 184, 210, or 236); FR3 (e.g., SEQ ID NO:284, 285, 286, 287, 379, 380, or 381); CDR3 (e.g., SEQ ID NO:3, 29, 55, 81, 107, 133, 159, 185, 211, or 237); and/or FR4 (e.g., SEQ ID NO:288); and/or a light chain variable region (VL) comprising: FR1 (e.g., SEQ ID NO:289, 290, 382, 383, or 384); CDR1 (e.g., SEQ ID NO:4, 30, 56, 82, 108, 134, 160, 186, 212, or 238); FR2 (e.g., SEQ ID NO:291, 292, or 385-392); CDR2 (e.g., SEQ ID NO:5, 31, 57, 83, 109, 135, 161, 187, 213, or 239); FR3 (e.g., SEQ ID NO:293, 294, 295, or 393-404); CDR3 (e.g., SEQ ID NO:6, 32, 58, 84, 110, 136, 162, 188, 214, 240); and/or FR4 (e.g., SEQ ID NO:296, 405, 406, or 407).

As described in this Example, humanized anti-beta klotho antibodies were empirically designed and expressed as beta klotho binding proteins, including nine humanized variants of the VH region of antibody 5H23 and thirty-one humanized variants of the VL region of antibody 5H23 that were created. The sequences of these exemplary humanized 5H23 VH and VL regions are shown in FIG. 3A-3D.

Humanized antibodies were prepared with humanized VH and humanized VL regions with sequences as shown in FIG. 3A-3D. For example, eighteen (6×3) combinations of vH 1-6 and vL1-3 were constructed using an IgG1 (ala-ala) constant region (SEQ ID NO:316) and a kappa constant region (SEQ ID NO:318): vH1-VL1, vH1-vL2, vH1-vL3, vH2-vL1, vH2-vL2, vH2-vL3, vH3-vL1, vH3-vL2, vH3-vL3, vH4-vL1, vH4-vL2, vH4-vL3, vH5-vL1, vH5-vL2, vH5-vL3, vH6-vL1, vH6-vL2, vH6-vL3, with sequences as shown in FIG. 3A-3D. Additionally, humanized antibodies were constructed with an exemplary humanized VH region (e.g., vH3) and twenty-six humanized VL regions (vi-39a to v1-39p and v3-20a to v3-20j) with sequences as shown in FIG. 3A-3D.

The humanized antibodies were tested from their activity in a variety of assays, including, for example, as described in Examples 2-6. Expression of the humanized antibodies with light chains comprising vL3 or v1-39c was low and those antibodies were not further tested. Exemplary results with a variety of humanized anti-beta klotho antibodies are shown in Table 20A and 20B below.

TABLE 20A

| Antibody | Expression (mg/L) | KD-huKLB (nM) | KD-cyKLB (nM) | EC50 reporter assay (nM) | EC50-adipocyte (nM) |
|---|---|---|---|---|---|
| Control mAb | | 0.08 | 0.7 | 0.2, 0.54 | 3.4 |
| 5H23 | | 0.05 | 0.7 | 0.27, 0.51 | 3.4 |
| vL1 | | | | | |
| vH1 | 80 | 1.5 | ≥50 | 2.7 | ND |
| vH2 | 80 | 1.7 | ≥50 | 3.2 | ND |
| vH3 | 50 | 0.43 | ≥50 | 1.1 | ND |
| vH4 | 80 | 2.26 | ≥50 | 3.0 | ND |
| vH5 | 20 | 0.81 | ≥50 | 8.2 | ND |
| vH6 | | | | | NA |
| vL2 | | | | | |
| vH1 | 200 | 0.21 | 0.95 | NA | 8.4 |
| vH2 | 66 | 0.41 | 0.75 | 1.3 | 13.3 |
| vH3 | 50-60 | 0.23 | 0.59 | 0.68 | 5.5 |
| vH4 | 66 | 0.33 | 0.61 | 3.5 | 16.4 |
| vH5 | 30 | 0.19 | 0.61 | 1.1 | 8.1 |
| vH6 | 20 | 0.4 | 0.83 | 1.7 | 15.3 |

TABLE 20B

| Antibody | Estimated Titer (mg/L) | KD-huKLB (nM) | EC50 reporter assay (nM) | EC50 adipocyte (nM) |
|---|---|---|---|---|
| h5H23 (Prep 1) | — | 0.64 | — | — |
| h5H23 (Prep 2) | — | 0.58 | 0.6 | 11.2 |
| vH3 | | | | |
| VL v1-39a | 50 | 0.90 | — | — |
| VL v1-39b | 50 | 0.53 | 1.03 | — |
| VL v1-39c | 10 | — | — | — |
| VL v1-39d | 50 | 0.73 | 1.49 | — |
| VL v1-39e | >100 | 1.00 | — | — |
| VL v1-39f | >100 | 0.28 | 0.80 | 21.4 |
| VL v1-39g | >100 | 1.10 | — | — |
| VL v1-39h | 10 | 2.10 | — | — |
| VL v1-39i | 50 | 0.63 | 1.12 | — |
| VL v1-39j | 100 | 0.70 | — | — |
| VL v1-39k | 100 | 1.50 | — | — |
| VL v1-39l | 100 | — | — | — |
| VL v1-39m | 50 | <0.1 | — | — |
| VL v1-39n | >100 | <0.1 | — | — |
| VL v1-39o | 25 | 0.36 | — | — |
| VL v1-39p | 10 | 0.36 | — | — |
| VL v3-20a | 25 | 0.64 | — | — |
| VL v3-20b | 50 | 1.90 | — | — |
| VL v3-20c | 0 | 1.60 | — | — |
| VL v3-20d | 50 | — | — | — |
| VL v3-20e | 50 | 1.60 | — | — |
| VL v3-20f | 10 | 1.80 | — | — |
| VL v3-20g | — | — | — | — |
| VL v3-20h | 25 | 1.50 | — | — |
| VL v3-20i | 10 | — | — | — |
| VL v3-20j | 10 | — | — | — |

Prep 1 = humanized 5H23 antibody (e.g., VH SEQ ID NO: 271 and VL SEQ ID NO: 276) preparation expressed at the same time as LC variants;
Prep 2 = humanized 5H23 antibody (e.g., VH SEQ ID NO: 271 and VL SEQ ID NO: 276) purified preparation.
Control antibody = VH SEQ ID NO: 358 and VL SEQ ID NO: 360.

In additional assays, for example, reporter assays with HEK293T cells as described in Example 4, wherein the cells were transfected with plasmids encoding mouse beta klotho (e.g., SEQ ID NO: 301), rat beta klotho (e.g., SEQ ID NO: 356), hamster beta klotho (e.g., SEQ ID NO: 408), rabbit beta klotho (e.g., SEQ ID NO: 410), or dog beta klotho (e.g., SEQ ID NO: 412) and were also transfected with plasmids encoding chimeric mouse FGFR1-βIIIc receptor (e.g., SEQ ID NO: 416), chimeric rat FGFR1-βIIIc receptor (e.g., SEQ ID NO: 419), chimeric hamster FGFR1-βIIIc receptor (e.g., SEQ ID NO: 417), chimeric rabbit FGFR1-βIIIc receptor (e.g., SEQ ID NO: 420), or dog FGFR1-βIIIc receptor (e.g., SEQ ID NO: 418), respectively, when treated with an anti-beta klotho antibody such as a humanized 5H23 antibody (e.g., VH SEQ ID NO: 271 and VL SEQ ID NO: 276), did not activate the chimeric mouse, rat, hamster, rabbit or dog beta klotho-FGFR1c receptor complex, respectively. The anti-beta klotho antibodies as described herein, including 5H23 and humanized 5H23 antibodies, as well as antibodies that compete with 5H23 (e.g., 1C17, 1 D19, 2L12, 3L3, 3N20, 4P5, 5C23, 5F7 and 1G19 as described in Example 3) with CDR sequences as shown in Tables 1-10, activate a human and cyno beta klotho/FGF receptor complex, but not mouse, rat, hamster, rabbit, or dog beta klotho/FGF receptor complexes as demonstrated by reporter assays described above. When a monovalent Fab of anti-beta klotho antibody prepared from a papain digestion of an anti-beta klotho antibody, such as a humanized 5H23 antibody (e.g., VH SEQ ID NO: 271 and VL SEQ ID NO: 276), was tested in a HEK293 reporter assay for its ability to activate human FGFR1c/KLB receptor complex, the Fab showed no antibody activity up to 67 nM, whereas the humanized 5H23 antibody showed activity with low nanomolar concentrations similar to that shown in Table 20B.

Example 8: Animal Studies

Effects of anti-beta klotho antibodies are evaluated in animal studies, including with cynomolgus monkeys.

In obese cynomolgus monkey studies, an exemplary anti-beta klotho antibody that binds to human beta klotho and cyno beta klotho (e.g., antibody 5H23 or humanized variant thereof), as well as an antibody comprising one or more of the CDRs of 5H23 as shown in Table 1 or alternatively, an antibody comprising one or more of the CDRs of an antibody or humanized variant thereof shown in Tables 2-10 that compete for the binding of 5H23 to human beta klotho as described in Example 3, is administered. Effects on a variety of metabolic parameters may be measured. Exemplary parameters include food intake, body weight, body mass index (BMI), abdominal circumference (AC), skin fold thickness (SFT), oral glucose tolerance test (OGTT), fasting and/or fed (e.g., postprandial) blood (e.g., serum) glucose levels, insulin levels, and/or triglyceride levels.

In an actual study, twenty spontaneous obese cynomolgus monkeys with body mass index equal to or above 40 are selected and randomized into vehicle (n=10) and antibody treatment (n=10) groups. Animals receive subcutaneous injection of either vehicle or anti-beta klotho antibody on days 1 and 14. Food intake for each meal is recorded and body weight is measured once a week. Blood samples are taken once a week for 7 weeks for the measurements of plasma (alternatively, serum) glucose, insulin, lipids and parameters of interest. On days 14, 28 and 49, an oral glucose tolerance test is conducted.

Exemplary treatment effects may include reduced food intake, decreased body weight, decreased BMI, AC and/or SFT, improved glucose tolerance, decreased insulin levels, decreased fasting and/or fed (e.g., postprandial) plasma (alternatively, serum) glucose levels, insulin levels, and/or reduced triglyceride levels. These effects indicate improved metabolic parameters with treatment with anti-beta klotho antibodies.

For example, twenty male cynomolgus monkeys were selected for treatment with a humanized 5H23 antibody (e.g., VH SEQ ID NO: 271 and VL SEQ ID NO: 276) or a vehicle control based on their BMI (>40) and were trained for chair restraint, subcutaneous injection, blood draw, and oral gavage. A routine feeding schedule was established.

Baseline values of various parameters of interest were measured prior to the treatments. For example, on day −7, baseline body weight, BMI, abdominal circumference, and skin fold thickness were measured, and a dual energy X-ray absorptiometry ("DEXA") scan was conducted to the cynomolgus monkeys under ketamine anesthesia to measure bone mineral density. Blood samples were taken on day −3, following an overnight fast. Baseline levels of serum glucose, insulin, total cholesterol, LDL, HDL, triglyceride, and a panel of hematology and clinical chemistry parameters were measured and analyzed. Immediately after the baseline samples, animals were subjected to oral glucose tolerance test (OGTT) by receiving a gavage of 4 g/kg glucose and were sampled at 5, 15, 30, 60, 120 and 180 minutes after the glucose challenge, and serum glucose and insulin were measured. Based on the baseline data, the animals were assigned into two groups with 10 animals in each group (e.g., one group for antibody treatment and the other group as a vehicle control group) to achieve similar baseline levels of the various parameters, e.g., body weight, BMI, and levels of serum glucose, insulin, and triglyceride.

Starting from day 0, one group of animals (n=10) received a dose of subcutaneous injection of 10 mg/kg of an anti-beta klotho antibody, such as a humanized 5H23 antibody (e.g., VH SEQ ID NO: 271 and VL SEQ ID NO: 276) biweekly (e.g., on days 0, 14, 28, and 42) for 4 doses. The vehicle control group received matched vehicles on the same days. The treatments were carried out in the morning 30 minutes before the morning meal, and the dosing volume was 0.1 to 0.2 mL/kg.

Parameters of interest, e.g., food intake, body weight, clinical chemistry, and OGTT, were monitored throughout the study. For example, food intake was measured daily. Body weight, BMI, abdominal circumference, and skin fold thickness were measured weekly, e.g., on days 7, 14, 21, 28, 35, 42, 49, 56, 63, 70, 77, 84, 91, and 98. Blood samples were collected weekly, e.g., on days 7, 14, 21, 28, 35, 42, 49, 56, 63, and 70, following an overnight fast, to measure glucose, insulin, and lipids, such as triglyceride. An additional blood sample was taken on day 98, following an overnight fast. OGTTs were conducted after the initiation of the study, e.g., on days 14, 28, and 56, in which animals received a gavage of 4 g/kg glucose and were sampled at 5, 15, 30, 60, 120 and 180 minutes after the glucose challenge, and serum glucose and insulin were measured. A DEXA scan was conducted on days 30 and 72. In addition, a hematology and clinical chemistry panel was analyzed on days 28 and 70. Two animals from vehicle group and two animals from the anti-beta klotho antibody group were euthanized and necropsy was performed on day 50 for safety assessment. During the study, all animals were closely monitored for their health.

Exemplary results from this study are shown in Tables 21 to 25 below. As shown in Table 21, the body weight of animals treated with vehicle remained constant (with slight increase over the course); while the body weight of animals treated with the anti-beta klotho antibody progressively decreased, and the body weight did not return to baseline level during weeks 8-14 (e.g., recovery phase). Similarly, as shown in Table 22, animals treated with vehicle showed relatively stable BMI throughout the study, while animals treated with the anti-beta klotho antibody showed decreased level of BMI over the course of the study. BMI level also did not come back to baseline values (e.g., during the recovery phase). These results suggest that the anti-beta klotho antibody treatment resulted in reduction of fat mass.

As shown in Table 23, the serum insulin levels in animals treated with vehicle increased over the course of the study; while the serum insulin levels in animals treated with the anti-beta klotho antibody significantly decreased. The serum glucose levels were also reduced in animals treated the anti-beta klotho antibody, as shown in Table 24. Similarly, as shown in Table 25, the triglyceride levels in animals treated with vehicle increased over the course of the study; while the triglyceride levels in animals treated with the anti-beta klotho antibody were significantly reduced.

Results of OGTTs demonstrated that before treatments, baseline levels of insulin were not significantly different between the vehicle and the anti-beta klotho antibody groups. In contrast, after treatment, there was a trend towards glucose reduction and insulin levels were reduced in animals treated with the anti-beta klotho antibody compared with animals treated with vehicle.

TABLE 21A

Body Weight (kg)

| | Week | −1 | 0 | 1 | 2 | 3 | 4 | 5 | 6 |
|---|---|---|---|---|---|---|---|---|---|
| Vehicle | Mean | 10.84 | 10.75 | 10.66 | 10.63 | 10.61 | 10.75 | 10.67 | 10.66 |
| | sem | 0.49 | 0.50 | 0.50 | 0.48 | 0.48 | 0.47 | 0.48 | 0.46 |
| h5H23 | Mean | 10.87 | 10.84 | 10.60 | 10.45 | 10.27 | 10.21 | 10.00 | 9.86 |
| | sem | 0.33 | 0.36 | 0.36 | 0.38 | 0.37 | 0.40 | 0.41 | 0.41 |

| | Week | 7 | 8 | 9 | 10 | 11 | 12 | 13 | 14 |
|---|---|---|---|---|---|---|---|---|---|
| Vehicle | Mean | 10.75 | 10.98 | 10.96 | 11.08 | 11.09 | 11.12 | 11.23 | 11.18 |
| | sem | 0.47 | 0.59 | 0.59 | 0.61 | 0.60 | 0.59 | 0.58 | 0.59 |
| h5H23 | Mean | 9.76 | 9.58 | 9.52 | 9.46 | 9.43 | 9.43 | 9.39 | 9.27 |
| | sem | 0.42 | 0.50 | 0.51 | 0.51 | 0.53 | 0.56 | 0.53 | 0.56 |

TABLE 21B

Body Weight Change (kg)

| | Week | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Vehicle | Mean | 0.00 | −0.09 | −0.12 | −0.14 | 0.00 | −0.08 | −0.09 | 0.00 | 0.14 | 0.13 | 0.24 | 0.26 | 0.28 | 0.39 | 0.34 |
| | sem | 0.00 | 0.05 | 0.07 | 0.09 | 0.09 | 0.09 | 0.10 | 0.10 | 0.12 | 0.13 | 0.13 | 0.14 | 0.17 | 0.18 | 0.17 |
| h5H23 | Mean | 0.00 | −0.24 | −0.39 | −0.57 | −0.63 | −0.84 | −0.98 | −1.08 | −1.07 | −1.13 | −1.19 | −1.22 | −1.22 | −1.25 | −1.38 |
| | sem | 0.00 | 0.05 | 0.08 | 0.10 | 0.13 | 0.15 | 0.17 | 0.19 | 0.26 | 0.27 | 0.28 | 0.31 | 0.34 | 0.31 | 0.34 |

TABLE 22

BMI

| | Week | −1 | 0 | 1 | 2 | 3 | 4 | 5 | 6 |
|---|---|---|---|---|---|---|---|---|---|
| Vehicle | Mean | 57.59 | 57.06 | 56.59 | 56.44 | 56.33 | 57.08 | 56.63 | 56.59 |
| | sem | 2.41 | 2.45 | 2.45 | 2.33 | 2.31 | 2.28 | 2.30 | 2.23 |
| h5H23 | Mean | 57.52 | 57.32 | 56.03 | 55.24 | 54.28 | 53.95 | 52.82 | 52.07 |
| | sem | 2.53 | 2.61 | 2.50 | 2.51 | 2.44 | 2.50 | 2.52 | 2.54 |

| | Week | 7 | 8 | 9 | 10 | 11 | 12 | 13 | 14 |
|---|---|---|---|---|---|---|---|---|---|
| Vehicle | Mean | 57.06 | 58.27 | 58.17 | 58.76 | 58.86 | 59.00 | 59.60 | 59.33 |
| | sem | 2.25 | 2.55 | 2.52 | 2.60 | 2.60 | 2.53 | 2.46 | 2.51 |
| h5H23 | Mean | 51.54 | 48.85 | 48.56 | 48.24 | 48.09 | 48.07 | 47.94 | 47.28 |
| | sem | 2.48 | 2.29 | 2.30 | 2.32 | 2.44 | 2.54 | 2.46 | 2.60 |

TABLE 23

Insulin (uU/mL)

| | Week | −1 to 0 | 1 | 2 | 3 | 4 | 5 | 6 | 7 | 8 | 9 | 10 |
|---|---|---|---|---|---|---|---|---|---|---|---|---|
| Vehicle | Mean | 114.85 | 100.09 | 91.06 | 124.79 | 187.36 | 159.20 | 226.53 | 145.78 | 186.75 | 204.96 | 181.32 |
| | sem | 32.75 | 19.94 | 26.33 | 37.48 | 62.09 | 51.60 | 130.94 | 34.74 | 39.85 | 52.63 | 52.28 |
| h5H23 | Mean | 89.18 | 34.73 | 36.19 | 38.11 | 46.75 | 48.28 | 35.42 | 37.95 | 57.29 | 63.23 | 55.30 |
| | sem | 9.51 | 4.91 | 4.14 | 7.24 | 6.54 | 6.80 | 4.98 | 5.03 | 12.99 | 12.43 | 13.62 |

TABLE 24

Glucose (mg/dL)

| | Week | −1 to 0 | 1 | 2 | 3 | 4 | 5 | 6 | 7 | 8 | 9 | 10 |
|---|---|---|---|---|---|---|---|---|---|---|---|---|
| Vehicle | Mean | 90.81 | 93.69 | 95.41 | 90.21 | 94.51 | 98.31 | 97.70 | 95.78 | 94.73 | 93.53 | 90.06 |
| | sem | 10.00 | 9.07 | 9.73 | 7.93 | 9.17 | 10.46 | 13.12 | 10.21 | 11.62 | 12.09 | 12.49 |
| h5H23 | Mean | 90.85 | 87.37 | 83.19 | 84.92 | 85.62 | 80.52 | 80.97 | 79.60 | 81.90 | 78.20 | 76.60 |
| | sem | 11.67 | 6.61 | 6.92 | 8.02 | 6.75 | 5.67 | 6.32 | 4.30 | 4.97 | 7.07 | 5.49 |

TABLE 25

Triglyceride (mmol/L)

| | Week | −1 to 0 | 1 | 2 | 3 | 4 | 5 | 6 | 7 | 8 | 9 | 10 |
|---|---|---|---|---|---|---|---|---|---|---|---|---|
| Vehicle | Mean | 0.93 | 0.76 | 0.92 | 0.70 | 1.36 | 0.90 | 1.15 | 1.20 | 1.54 | 1.35 | 1.26 |
| | sem | 0.25 | 0.08 | 0.16 | 0.10 | 0.27 | 0.14 | 0.38 | 0.22 | 0.35 | 0.38 | 0.37 |
| h5H23 | Mean | 1.05 | 0.65 | 0.65 | 0.59 | 0.70 | 0.59 | 0.56 | 0.70 | 0.90 | 0.73 | 0.71 |
| | sem | 0.17 | 0.09 | 0.12 | 0.08 | 0.10 | 0.05 | 0.07 | 0.12 | 0.13 | 0.08 | 0.10 |

In another exemplary study, forty spontaneous obese male cynomolgus were selected, trained and fed as described above.

Baseline values of various parameters were measured prior to the treatments as discussed above. For example, baseline body weight, BMI, abdominal circumference and skin fold thickness were measured on day −4, and baseline blood samples were taken for measurements of serum glucose, insulin, total cholesterol, LDL, HDL and triglyceride on day −3, following an overnight fast. Based on these baseline data, animals were assigned into 5 groups (8 animals in each group) with 4 groups to receive various doses of an anti-beta klotho antibody such as a humanized 5H23 antibody (e.g., VH SEQ ID NO: 271 and VL SEQ ID NO: 276) and one group to receive a vehicle control.

On day 0, the first group of animals (n=8) received a single dose of subcutaneous injection of 0.1 mg/kg of the anti-beta klotho antibody; the second group of animals (n=8) received a single dose of subcutaneous injection of 1 mg/kg the anti-beta klotho antibody, and the third group of animals (n=8) received a single dose of subcutaneous injection of 10 mg/kg the anti-beta klotho antibody. Starting from day 0, the fourth group of animals (n=8) received a dose of subcutaneous injection of 0.1 mg/kg of the anti-beta klotho antibody once every 4 weeks for a duration of 12 weeks. As a control, the fifth group of animals (n=8) received a dose of vehicle once every 4 weeks for 12 weeks. The treatments were carried out in the morning 30 minutes before the morning meal, and the dosing volume was 0.2 mL/kg.

Parameters of interest were monitored throughout the study. For example, food intake was measured for each meal. Body weight, BMI, abdominal circumference, and skin fold thickness were measured weekly. Blood examples were taken at, e.g., 3, 6, 12 and 24 hours and 3, 4, 7, 10, 14, 21, 28, 35, 42, 49, 56, 63, 70, 77, 84, and 112 days after the dose(s), and parameters of interest, e.g., serum glucose, insulin, total cholesterol, LDL, HDL and triglyceride, were measured. During the study, all animals were closely monitored for their health as described above.

Exemplary results of this dose-response study are shown in Tables 26-29. Table 26 shows the relative body weight changes in animals treated with the anti-beta klotho antibody compared with the body weight changes in animals treated with vehicle. As shown, a single dose of subcutaneous injection of 0.1 mg/kg, 1 mg/kg, or 10 mg/kg the anti-beta klotho antibody, or four doses of subcutaneous injection of 1 mg/kg the anti-beta klotho antibody significantly reduced body weight. In addition, the reduced body weight was maintained on day 112 for animals receiving a single dose of 10 mg/kg the anti-beta klotho antibody, or for animals receiving four doses of 1 mg/kg the anti-beta klotho antibody compared with vehicle.

As shown in Table 27, a single dose of subcutaneous injection of 0.1 mg/kg, 1 mg/kg, or 10 mg/kg the anti-beta klotho antibody, or four doses of subcutaneous injection of 1 mg/kg the anti-beta klotho antibody reduced serum insulin level compared with the vehicle control group. In addition, four doses of subcutaneous injection of 1 mg/kg the anti-beta klotho antibody significantly reduced serum glucose level, as shown in Table 28. Furthermore, serum triglyceride levels in animals treated with a single dose of subcutaneous injection of 1 mg/kg, or 10 mg/kg the anti-beta klotho antibody, or four doses of subcutaneous injection of 1 mg/kg the anti-beta klotho antibody, were reduced compared the animals treated with vehicle, as shown in Table 29.

TABLE 26A

| | | | | | | | Body Weight | | | | | | | | | |
|---|---|---|---|---|---|---|---|---|---|---|---|---|---|---|---|---|
| Days | | −4 | 4 | 10 | 14 | 21 | 28 | 35 | 42 | 49 | 56 | 63 | 70 | 77 | 84 | 112 |
| Vehicle | Mean | 10.17 | 10.07 | 9.89 | 9.87 | 9.91 | 9.83 | 9.82 | 9.73 | 9.71 | 9.63 | 9.61 | 9.57 | 9.53 | 9.45 | 9.24 |
| | sem | 0.78 | 0.80 | 0.77 | 0.79 | 0.81 | 0.81 | 0.82 | 0.82 | 0.83 | 0.83 | 0.83 | 0.83 | 0.83 | 0.83 | 0.81 |
| 5H23 (0.1 mg/ kg SD) | Mean | 10.00 | 9.92 | 9.70 | 9.62 | 9.52 | 9.47 | 9.37 | 9.28 | 9.27 | 9.36 | 9.34 | 9.27 | 9.34 | 9.34 | 9.21 |
| | sem | 0.67 | 0.71 | 0.69 | 0.71 | 0.73 | 0.76 | 0.76 | 0.79 | 0.79 | 0.81 | 0.83 | 0.85 | 0.86 | 0.87 | 0.85 |
| 5H23 (1 mg/ kg SD) | Mean | 9.84 | 9.69 | 9.49 | 9.36 | 9.28 | 9.19 | 9.05 | 8.92 | 8.90 | 8.85 | 8.85 | 8.83 | 8.89 | 8.93 | 9.24 |
| | sem | 0.54 | 0.55 | 0.54 | 0.53 | 0.54 | 0.55 | 0.55 | 0.55 | 0.55 | 0.54 | 0.55 | 0.55 | 0.55 | 0.55 | 0.56 |
| 5H23 (10 mg/ kg SD) | Mean | 10.07 | 9.95 | 9.73 | 9.61 | 9.49 | 9.33 | 9.20 | 9.07 | 8.98 | 8.88 | 8.80 | 8.73 | 8.74 | 8.67 | 8.51 |
| | sem | 0.58 | 0.56 | 0.57 | 0.57 | 0.59 | 0.59 | 0.58 | 0.58 | 0.56 | 0.56 | 0.58 | 0.55 | 0.55 | 0.54 | 0.50 |
| 5H23 (1 mg/ kg q4w) | Mean | 10.05 | 9.86 | 9.66 | 9.51 | 9.40 | 9.31 | 9.14 | 8.92 | 8.84 | 8.74 | 8.63 | 8.53 | 8.45 | 8.41 | 8.29 |
| | sem | 0.42 | 0.45 | 0.43 | 0.42 | 0.44 | 0.44 | 0.43 | 0.43 | 0.42 | 0.41 | 0.42 | 0.40 | 0.40 | 0.39 | 0.38 |

TABLE 26B

| | | | Body Weight Change (kg) | | | | | | |
|---|---|---|---|---|---|---|---|---|---|
| Days | | −4 | 4 | 10 | 14 | 21 | 28 | 35 | 42 |
| Vehicle | Mean | 0.00 | −0.09 | −0.28 | −0.30 | −0.26 | −0.34 | −0.35 | −0.44 |
| | sem | 0.00 | 0.05 | 0.05 | 0.04 | 0.06 | 0.08 | 0.10 | 0.13 |
| 5H23 (0.1 mg/ kg SD) | Mean | 0.00 | −0.08 | −0.30 | −0.38 | −0.49 | −0.54 | −0.64 | −0.72 |
| | sem | 0.00 | 0.08 | 0.06 | 0.09 | 0.11 | 0.15 | 0.17 | 0.20 |
| 5H23 (1 mg/ kg SD) | Mean | 0.00 | −0.16 | −0.35 | −0.48 | −0.56 | −0.65 | −0.79 | −0.93 |
| | sem | 0.00 | 0.03 | 0.04 | 0.04 | 0.05 | 0.07 | 0.08 | 0.09 |
| 5H23 (10 mg/ kg SD) | Mean | 0.00 | −0.12 | −0.34 | −0.47 | −0.59 | −0.74 | −0.88 | −1.00 |
| | sem | 0.00 | 0.05 | 0.07 | 0.08 | 0.10 | 0.12 | 0.12 | 0.11 |
| 5H23 (1 mg/ kg q4w) | Mean | 0.00 | −0.18 | −0.38 | −0.54 | −0.65 | −0.74 | −0.90 | −1.13 |
| | sem | 0.00 | 0.08 | 0.06 | 0.05 | 0.05 | 0.06 | 0.08 | 0.10 |

TABLE 26B-continued

| | | Body Weight Change (kg) | | | | | | |
|---|---|---|---|---|---|---|---|---|
| Days | | 49 | 56 | 63 | 70 | 77 | 84 | 112 |
| Vehicle | Mean | −0.45 | −0.53 | −0.56 | −0.60 | −0.64 | −0.71 | −0.93 |
| | sem | 0.14 | 0.16 | 0.18 | 0.19 | 0.22 | 0.23 | 0.27 |
| 5H23 (0.1 mg/kg SD) | Mean | −0.74 | −0.65 | −0.66 | −0.74 | −0.66 | −0.66 | −0.80 |
| | sem | 0.22 | 0.24 | 0.26 | 0.28 | 0.30 | 0.31 | 0.28 |
| 5H23 (1 mg/kg SD) | Mean | −0.95 | −0.99 | −1.00 | −1.01 | −0.95 | −0.91 | −0.60 |
| | sem | 0.11 | 0.13 | 0.15 | 0.19 | 0.21 | 0.22 | 0.20 |
| 5H23 (10 mg/kg SD) | Mean | −1.10 | −1.20 | −1.27 | −1.35 | −1.34 | −1.40 | −1.56 |
| | sem | 0.15 | 0.15 | 0.16 | 0.17 | 0.15 | 0.16 | 0.23 |
| 5H23 (1 mg/kg q4w) | Mean | −1.20 | −1.30 | −1.41 | −1.52 | −1.60 | −1.64 | −1.75 |
| | sem | 0.11 | 0.13 | 0.15 | 0.15 | 0.16 | 0.17 | 0.26 |

TABLE 27

| | | Insulin | | | | | | | | | | | |
|---|---|---|---|---|---|---|---|---|---|---|---|---|---|
| Days | | −3 d | 7 d | 14 d | 21 d | 28 d | 35 d | 42 d | 49 d | 56 d | 70 d | 84 d | 112 d |
| Vehicle | Mean | 78.96 | 75.44 | 85.96 | 98.23 | 90.35 | 80.65 | 71.70 | 76.54 | 80.11 | 80.61 | 70.61 | 51.41 |
| | sem | 17.16 | 16.65 | 15.18 | 23.76 | 21.01 | 15.17 | 13.01 | 12.82 | 16.32 | 20.81 | 17.91 | 11.05 |
| 5H23 (0.1 mg/kg SD) | Mean | 118.28 | 64.70 | 65.09 | 65.83 | 61.15 | 62.26 | 84.34 | 68.17 | 85.20 | 82.99 | 95.31 | 57.32 |
| | sem | 62.16 | 20.06 | 22.84 | 20.26 | 22.41 | 19.93 | 37.61 | 24.82 | 41.19 | 45.77 | 46.91 | 20.74 |
| 5H23 (1 mg/kg SD) | Mean | 74.75 | 54.52 | 51.50 | 54.88 | 42.31 | 46.42 | 46.28 | 38.83 | 56.57 | 40.89 | 51.84 | 64.91 |
| | sem | 14.42 | 15.27 | 10.80 | 15.55 | 13.92 | 11.97 | 10.53 | 7.93 | 16.04 | 7.15 | 14.73 | 21.66 |
| 5H23 (10 mg/kg SD) | Mean | 84.03 | 51.57 | 46.50 | 54.45 | 53.42 | 38.67 | 37.25 | 34.70 | 32.83 | 25.49 | 33.33 | 22.38 |
| | sem | 18.06 | 10.75 | 7.19 | 14.43 | 15.43 | 7.95 | 5.16 | 5.04 | 6.61 | 3.18 | 7.10 | 2.46 |
| 5H23 (1 mg/kg q4w) | Mean | 133.82 | 52.88 | 61.67 | 109.20 | 49.94 | 38.83 | 37.60 | 47.85 | 40.18 | 32.42 | 30.58 | 22.14 |
| | sem | 57.35 | 18.45 | 14.30 | 40.07 | 13.96 | 9.93 | 12.32 | 13.85 | 11.96 | 8.21 | 10.73 | 4.17 |

TABLE 28

| | | Glucose | | | | | | | | | | | |
|---|---|---|---|---|---|---|---|---|---|---|---|---|---|
| Days | | −3 d | 7 d | 14 d | 21 d | 28 d | 35 d | 42 d | 49 d | 56 d | 70 d | 84 d | 112 d |
| Vehicle | Mean | 90.95 | 76.41 | 69.57 | 68.60 | 63.90 | 59.94 | 68.27 | 70.79 | 58.12 | 70.16 | 73.60 | 71.46 |
| | sem | 8.29 | 9.37 | 5.55 | 7.89 | 6.31 | 3.46 | 6.14 | 7.93 | 4.42 | 7.37 | 7.52 | 11.33 |
| 5H23 (0.1 mg/kg SD) | Mean | 92.54 | 72.59 | 67.10 | 63.23 | 54.14 | 58.19 | 62.37 | 62.53 | 62.46 | 64.24 | 79.27 | 73.80 |
| | sem | 15.41 | 5.49 | 4.54 | 4.52 | 4.82 | 3.37 | 3.69 | 3.39 | 5.17 | 3.60 | 10.90 | 6.91 |
| 5H23 (1 mg/kg SD) | Mean | 97.67 | 73.82 | 64.51 | 57.74 | 54.72 | 67.07 | 62.39 | 62.96 | 65.25 | 65.88 | 68.56 | 70.02 |
| | sem | 11.08 | 4.64 | 2.69 | 3.29 | 4.38 | 4.98 | 3.91 | 2.36 | 2.59 | 8.34 | 5.21 | 6.84 |
| 5H23 (10 mg/kg SD) | Mean | 89.71 | 73.24 | 68.74 | 61.13 | 58.93 | 60.55 | 66.49 | 61.11 | 63.14 | 59.11 | 69.59 | 66.49 |
| | sem | 11.76 | 5.56 | 3.10 | 5.11 | 1.92 | 2.68 | 2.14 | 3.56 | 2.21 | 2.52 | 3.98 | 3.11 |
| 5H23 (1 mg/kg q4w) | Mean | 130.01 | 87.28 | 81.11 | 77.56 | 71.89 | 67.82 | 67.79 | 66.98 | 65.34 | 63.23 | 72.56 | 69.50 |
| | sem | 21.21 | 15.15 | 10.15 | 13.41 | 6.83 | 7.05 | 7.56 | 4.99 | 6.98 | 3.75 | 6.66 | 4.98 |

TABLE 29

| | | Triglycerides | | | | | | | | | | | |
|---|---|---|---|---|---|---|---|---|---|---|---|---|---|
| Days | | −3 d | 7 d | 14 d | 21 d | 28 d | 35 d | 42 d | 49 d | 56 d | 70 d | 84 d | 112 d |
| Vehicle | Mean | 0.90 | 0.61 | 1.00 | 1.45 | 1.04 | 1.51 | 1.03 | 1.30 | 0.99 | 1.10 | 1.12 | 0.79 |
| | sem | 0.18 | 0.12 | 0.19 | 0.33 | 0.23 | 0.32 | 0.17 | 0.23 | 0.19 | 0.25 | 0.30 | 0.13 |
| 5H23 (0.1 mg/kg SD) | Mean | 0.69 | 0.54 | 0.57 | 0.67 | 0.59 | 0.70 | 0.78 | 0.85 | 1.09 | 0.89 | 1.18 | 0.98 |
| | sem | 0.13 | 0.10 | 0.11 | 0.17 | 0.15 | 0.14 | 0.22 | 0.20 | 0.40 | 0.25 | 0.39 | 0.27 |
| 5H23 (1 mg/kg SD) | Mean | 1.27 | 0.58 | 0.76 | 0.91 | 0.73 | 0.59 | 0.59 | 0.72 | 0.83 | 0.95 | 1.33 | 1.61 |
| | sem | 0.37 | 0.06 | 0.20 | 0.22 | 0.21 | 0.06 | 0.14 | 0.17 | 0.27 | 0.30 | 0.36 | 0.24 |
| 5H23 (10 mg/kg SD) | Mean | 1.12 | 0.61 | 0.64 | 0.68 | 0.54 | 0.97 | 0.55 | 0.64 | 0.65 | 0.59 | 0.65 | 0.71 |
| | sem | 0.18 | 0.09 | 0.12 | 0.15 | 0.09 | 0.38 | 0.09 | 0.13 | 0.12 | 0.12 | 0.11 | 0.12 |
| 5H23 (1 mg/kg q4w) | Mean | 1.24 | 0.65 | 0.68 | 0.77 | 0.65 | 0.57 | 0.56 | 0.55 | 0.57 | 0.49 | 0.53 | 0.53 |
| | sem | 0.36 | 0.18 | 0.19 | 0.28 | 0.11 | 0.11 | 0.09 | 0.13 | 0.14 | 0.10 | 0.08 | 0.07 |

The results from these animal studies demonstrate improved metabolic parameters with treatment with anti-beta klotho antibodies provided herein, for example, such as decreases in body weight, body mass index, abdominal circumference, skinfold thickness, glucose (e.g., serum glucose), insulin (e.g., serum insulin) and/or triglycerides (e.g., serum triglycerides).

Example 9: Epitope and Domain Mapping

Studies were performed in order to localize the binding site on human KLB of anti-beta klotho antibodies in the 5H23 epitope bin, including 5H23 as described in Example 3, with sequences shown in Tables 1-10 and FIGS. 1-3, and human anti-beta klotho antibodies in the 5H23 epitope bin, such as humanized 5H23 antibodies (e.g., VH SEQ ID NO: 271 and VL SEQ ID NO: 276). For example, FACS-based binding assays for domain mapping were performed on Expi293 cells (Life Technologies, A14635) that were transiently transfected with plasmids encoding variants of KLB: human, mouse, cynomolgus, a chimeric version in which the KL1 domain sequence of mouse KLB (M1-F506) replaces the KL1 domain of human KLB (M1-F508) to create mouse-human KLB (SEQ ID NO: 376), and a second chimera in which the human KL1 sequence (M1-F508) replaces the KL1 domain of mouse KLB (M1-F506) to create human-mouse KLB (SEQ ID NO: 374). Additionally, the expression vector pYD7 harboring no KLB sequence was transfected as a negative control.

In some studies, binding of a purified sample of a humanized 5H23 antibody (e.g., VH SEQ ID NO: 271 and VL SEQ ID NO: 276) to KLB variants was determined by FACS analysis. Two day post-transfection cells were co-incubated with purified antibodies: humanized 5H23 antibody (e.g., VH SEQ ID NO: 271 and VL SEQ ID NO: 276), a control antibody (e.g., VH SEQ ID NO: 358 and VL SEQ ID NO: 360), and a negative control antibody (e.g., anti-keyhole limpet hemocyanin (KLH) antibody expressed from a construct comprising SEQ ID NO: 424 and 425) diluted to 1 µg/ml in PBS/1% BSA/0.1% azide for 30 minutes at 4° C. After washing with PBS/1% BSA/0.1% azide, transfected cells were then co-incubated with labeled anti-human Fc (Jackson Immunoresearch) for 30 minutes at 4° C. After washing with PBS/1% BSA/0.1% azide, cells were acquired on flow cytometer (FACS Calibur) and analyzed by cytometric software (FlowJo). To display the resulting data, graphs plotting the number of cells as a function of fluorescence intensity were generated, and the median fluorescence intensity (MFI) was determined for each sample as shown in Table 30.

TABLE 30

| Antibody | Mouse KLB | Mouse-Human chimeric KLB | Human-Mouse chimeric KLB | Human KLB | Cynomolgus KLB | Empty Vector (-control) |
|---|---|---|---|---|---|---|
| h5H23 | 14.2 | 26.1 | 9.29 | 865 | 1909 | 8.29 |
| Control | 10.6 | 5.6 | 71.9 | 620 | 1757 | 6.82 |
| Neg. Control | 9.59 | 5.44 | 6.01 | 6.2 | 9.26 | 5.41 |

* Mean Fluorescence intensity calculated from FACS data using FlowJo analysis software; Neg. Control is anti-KLH antibody.

An exemplary humanized 5H23 antibody (e.g., VH SEQ ID NO: 271 and VL SEQ ID NO: 276) bound to human KLB and cynomolgus KLB, as indicated by a large proportion of cells having high-fluorescence intensity compared to cells treated with the anti-KLH negative control antibody, but the exemplary humanized 5H23 antibody did not bind to mouse KLB. The exemplary humanized 5H23 antibody also bound to the mouse-human KLB chimeric protein, but not the human-mouse KLB chimeric protein indicating that anti-beta klotho antibodies in the 5H23 epitope bin, including 5H23 as described in Example 3, with sequences shown in Tables 1-10 and FIGS. 1-3, and human anti-beta klotho antibodies in the 5H23 epitope bin, such as humanized 5H23 antibodies (e.g., VH SEQ ID NO: 271 and VL SEQ ID NO: 276) bind to the KL2 domain of human KLB. In contrast, the control antibody bound to the KL1 domain of human KLB as demonstrated by its binding to cells transfected with the human-mouse KLB chimeric protein, but not the mouse-human KLB chimeric protein.

In order to further identify specific binding residues within human beta klotho KL2 domain, shotgun mutagenesis was used to separately mutate individual residues of the KL2 domain of human beta klotho to an alanine (e.g., residues F508A-L1008A). The resulting beta klotho mutant proteins were expressed within HEK-293T cells and assayed by fluorescence-activated cell sorting (FACS) for binding to anti-beta klotho antibodies in the 5H23 epitope bin, including 5H23 as described in Example 3, with sequences shown in Tables 1-10 and FIGS. 1-3, and human anti-beta klotho antibodies in the 5H23 epitope bin, such as a humanized 5H23 antibody (e.g., VH SEQ ID NO: 271 and VL SEQ ID NO: 276), or a monovalent Fab fragment of the humanized 5H23 antibody. For example, screening of the beta klotho mutant proteins was conducted at a concentration of 0.5 µg/ml for the humanized 5H23 antibody, 1.0 µg/ml for the Fab fragment, and 2.0 µg/ml for a positive control polyclonal anti-beta klotho antibodies.

The resulting mapping identified three specific binding residues, H657, Y701 and R703, which were negative for binding by the humanized 5H23 antibody, but were positive for the control polyclonal anti-beta klotho antibodies. These residues represented amino acids whose side changes made the highest energetic contributions to the antibody-epitope integration as shown in Table 31. The locations of the three identified residues were modeled by showing them (dark spheres) at the equivalent positions on human cytosolic beta-glucosidase (PDB ID #2JFE; Tribolo et al., J. Mol. Biol. 370, 964-975 (2007)), identified by BLAST alignment of the two proteins as shown in FIG. 6. The structure shows the equivalent of beta klotho residues 521-963. Lower reactivity of the Y701A and R703A mutations with the humanized 5H23 antibody indicates that Y701 and R703 are major energetic contributors to binding.

TABLE 31

| | Binding Reactivity (% WT) | |
|---|---|---|
| Protein Mutation | Humanized 5H23 Antibody | Control Polyclonal Antibody |
| H657A | 16.88 (±11.93) | 120.35 (±55.21) |
| Y701A | 0.64 (±0.09) | 43.37 (±5.78) |
| R703A | 1.64 (±1.69) | 131.59 (±19.98) |

Thus, the anti-beta klotho antibodies provided herein, including 5H23 and antibodies in the 5H23 epitope bin recognize an epitope in the KLB2 domain that comprises residues H657, Y701 and/or R703. Such antibodies, as described in Example 3 and repressed by and comprising CDR sequences in Tables 1-10 and FIGS. 1-3, are useful as agonist antibodies to induce FGF19-mediate and/or FGF21- mediated signaling, including, for example, to reduce body weight, food intake, BMI, insulin, glucose and/or triglycerides.

Additionally, the anti-beta klotho antibodies provided herein share the common feature of competing with each other for the binding of beta klotho (see, e.g., Example 3 describing antibodies in the 5H23 epitope bin). This competitive inhibition indicates that each antibody binds to the same region of beta klotho (e.g., the same epitope), thereby asserting similar effects. As further exemplified herein, the anti-beta klotho antibodies include humanized anti-beta klotho antibodies, including humanized anti-beta klotho antibodies derived from or based on 5H23, 1C17, 1D19, 2L12, 3L3, 3N20, 4P5, 5C23, 5F7 and/or 1G19 having CDR sequence as described in Tables 1-10 or FIGS. 1-3, such as anti-beta klotho antibodies, including humanized anti-beta klotho antibodies, bind to a specific domain of human beta klotho (e.g., KL2 (residues S509-S1044) as described above). Moreover, such binding can be largely attributed to particular amino acid residues within the KL2 region (e.g., H657, Y701 and R703 as described above), which comprise the epitope recognized by the anti-beta klotho antibodies described herein. Taken together, these results demonstrate that the effects observed for an anti-beta klotho antibody that is derived from or based on 5H23 or an antibody in the 5H23 eptitope bin, including an antibody having one or more CDRs described in Tables 1-10 or FIGS. 1-3, can be extrapolated to other anti-beta klotho antibodies described herein having the same or similar eptitope specificity (e.g., the same or similar CDRs). For example, the in vitro activities of antibodies as shown in Examples 4-7 and above, as well as the in vivo effects demonstrated in Example 8 for an exemplary humanized anti-beta klotho antibody, are representative of the activities and effects of the the anti-beta klotho antibodies described herein.

The embodiments of the present disclosure described above are intended to be merely exemplary, and those skilled in the art will recognize, or be able to ascertain using no more than routine experimentation, numerous equivalents to the specific procedures described herein. All such equivalents are considered to be within the scope of the present disclosure and are covered by the following claims. Furthermore, as used in this specification and claims, the singular forms "a," "an" and "the" include plural forms unless the content clearly dictates otherwise. Thus, for example, reference to "an antibody" may include a mixture of two or more such antibodies, and the like. Additionally, ordinarily skilled artisans will recognize that operational sequences must be set forth in some specific order for the purpose of explanation and claiming, but the present disclosure contemplates various changes beyond such specific order.

The contents of all references described herein are hereby incorporated by reference.

Other embodiments are within the following claims.

What is claimed:

1. An isolated polynucleotide or polynucleotides encoding an antibody or binding fragment thereof that binds human beta klotho, wherein the antibody or binding fragment thereof comprises
   a heavy chain variable region (VH) comprising a VH complementarity determining region (CDR)1, a VH CDR2, and a VH CDR3 from the amino acid sequence of SEQ ID NO:271; and
   a light chain variable region (VL) comprising a VL CDR1, a VL CDR2, and a VL CDR3 from the amino acid sequence of SEQ ID NO:276.

2. The isolated polynucleotide or polynucleotides of claim 1, wherein:
   (a) the VH CDR1 comprises the amino acid sequence of SEQ ID NO:1, the VH CDR2 comprises the amino acid sequence of SEQ ID NO:2, the VH CDR3 comprises the amino acid sequence of SEQ ID NO:3, the VL CDR1 comprises the amino acid sequence of SEQ ID NO:4, the VL CDR2 comprises the amino acid sequence of SEQ ID NO:5, and the VL CDR3 comprises the amino acid sequence of SEQ ID NO:6;
   (b) the VH CDR1 comprises the amino acid sequence of SEQ ID NO:7, the VH CDR2 comprises the amino acid sequence of SEQ ID NO:8, the VH CDR3 comprises the amino acid sequence of SEQ ID NO:9, the VL CDR1 comprises the amino acid sequence of SEQ ID NO:10, the VL CDR2 comprises the amino acid sequence of SEQ ID NO:11, and the VL CDR3 comprises the amino acid sequence of SEQ ID NO:6;
   (c) the VH CDR1 comprises the amino acid sequence of SEQ ID NO:12, the VH CDR2 comprises the amino acid sequence of SEQ ID NO:2, the VH CDR3 comprises the amino acid sequence of SEQ ID NO:3, the VL CDR1 comprises the amino acid sequence of SEQ ID NO:4, the VL CDR2 comprises the amino acid sequence of SEQ ID NO:5, and the VL CDR3 comprises the amino acid sequence of SEQ ID NO:6;
   (d) the VH CDR1 comprises the amino acid sequence of SEQ ID NO:13, the VH CDR2 comprises the amino acid sequence of SEQ ID NO:14, the VH CDR3 comprises the amino acid sequence of SEQ ID NO:15, the VL CDR1 comprises the amino acid sequence of SEQ ID NO:16, the VL CDR2 comprises the amino acid sequence of SEQ ID NO: 11, and the VL CDR3 comprises the amino acid sequence of SEQ ID NO:17;
   (e) the VH CDR1 comprises the amino acid sequence of SEQ ID NO:18, the VH CDR2 comprises the amino acid sequence of SEQ ID NO:19, the VH CDR3 comprises the amino acid sequence of SEQ ID NO:20, the VL CDR1 comprises the amino acid sequence of SEQ ID NO:21, the VL CDR2 comprises the amino acid sequence of SEQ ID NO:22, and the VL CDR3 comprises the amino acid sequence of SEQ ID NO:23; or
   (f) the VH CDR1 comprises the amino acid sequence of SEQ ID NO:1, the VH CDR2 comprises the amino acid sequence of SEQ ID NO:24, the VH CDR3 comprises the amino acid sequence of SEQ ID NO:3, the VL CDR1 comprises the amino acid sequence of SEQ ID NO:4, the VL CDR2 comprises the amino acid sequence of SEQ ID NO:5, and the VL CDR3 comprises the amino acid sequence of SEQ ID NO:6.

3. The isolated polynucleotide or polynucleotides of claim 1, wherein:
   the VH CDR1 comprises the amino acid sequence of SEQ ID NO:12, the VH CDR2 comprises the amino acid sequence of SEQ ID NO:2, the VH CDR3 comprises the amino acid sequence of SEQ ID NO:3, the VL CDR1 comprises the amino acid sequence of SEQ ID NO:4, the VL CDR2 comprises the amino acid sequence of SEQ ID NO:5, and the VL CDR3 comprises the amino acid sequence of SEQ ID NO:6.

4. The isolated polynucleotide or polynucleotides of claim 1, wherein
   the VH comprises an amino acid sequence that is at least 90% identical to the amino acid sequence of SEQ ID NO:271 and the VL comprises an amino acid sequence that is at least 90% identical to the amino acid sequence of SEQ ID NO:276.

5. The isolated polynucleotide or polynucleotides of claim 1, wherein
   the VH comprises the amino acid sequence of SEQ ID NO:271 and the VL comprises the amino acid sequence of SEQ ID NO:276.

6. A vector or vectors comprising the isolated polynucleotide or polynucleotides of claim 5.

7. A cell comprising the vector or vectors of claim 6.

8. A method of producing an antibody or binding fragment thereof, the method comprising: (i) culturing the cell of claim 7; and (ii) isolating the antibody or binding fragment thereof.

9. The method of claim 8, wherein the method further comprises formulating the antibody or binding fragment thereof as a sterile pharmaceutical formulation.

10. A cell comprising the isolated polynucleotide or polynucleotides of claim 5.

11. The isolated polynucleotide or polynucleotides of claim 1, wherein the antibody or binding fragment thereof is a humanized antibody.

12. The isolated polynucleotide or polynucleotides of claim 1, wherein the antibody is a human IgG1 antibody, a human IgG2 antibody, or a human IgG4 antibody.

13. A vector or vectors comprising the isolated polynucleotide or polynucleotides of claim 1.

14. A cell comprising the vector or vectors of claim 13.

15. A method of producing an antibody or binding fragment thereof, the method comprising: (i) culturing the cell of claim 14; and (ii) isolating the antibody or binding fragment thereof.

16. The method of claim 15, wherein the method further comprises formulating the antibody or binding fragment thereof as a sterile pharmaceutical formulation.

17. A cell comprising the isolated polynucleotide or polynucleotides of claim 1.

18. An isolated polynucleotide or polynucleotides encoding an antibody that binds human beta klotho, wherein
the antibody comprises a heavy chain comprising amino acids 23-472 of SEQ ID NO:317 and a light chain comprising amino acids 23-240 of SEQ ID NO:319.

19. A vector or vectors comprising the isolated polynucleotide or polynucleotides of claim 18.

20. A cell comprising the vector or vectors of claim 19.

21. A method of producing an antibody, the method comprising: (i) culturing the cell of claim 20; and (ii) isolating the antibody.

22. The method of claim 21, wherein the method further comprises formulating the antibody as a sterile pharmaceutical formulation.

23. A cell comprising the isolated polynucleotide or polynucleotides of claim 18.

* * * * *

```
                              SEQUENCE LISTING

Sequence total quantity: 431
SEQ ID NO: 1              moltype = AA  length = 10
FEATURE                   Location/Qualifiers
REGION                    1..10
                          note = 5H23 VH CDR1 - Exemplary
source                    1..10
                          mol_type = protein
                          organism = synthetic construct
SEQUENCE: 1
GYTFTSYDIN                                                                10

SEQ ID NO: 2              moltype = AA  length = 17
FEATURE                   Location/Qualifiers
REGION                    1..17
                          note = 5H23 VH CDR2- Exemplary
source                    1..17
                          mol_type = protein
                          organism = synthetic construct
SEQUENCE: 2
WIYPGDGSTK YNEKFKG                                                        17

SEQ ID NO: 3              moltype = AA  length = 11
FEATURE                   Location/Qualifiers
REGION                    1..11
                          note = 5H23 VH CDR3- Exemplary
source                    1..11
                          mol_type = protein
                          organism = synthetic construct
SEQUENCE: 3
SDYYGSRSFA Y                                                              11

SEQ ID NO: 4              moltype = AA  length = 15
FEATURE                   Location/Qualifiers
REGION                    1..15
                          note = 5H23 VL CDR1- Exemplary
source                    1..15
                          mol_type = protein
                          organism = synthetic construct
SEQUENCE: 4
RASKSVSTSG YVYMH                                                          15

SEQ ID NO: 5              moltype = AA  length = 7
```

```
FEATURE                 Location/Qualifiers
REGION                  1..7
                        note = 5H23 VL CDR2- Exemplary
source                  1..7
                        mol_type = protein
                        organism = synthetic construct
SEQUENCE: 5
LASYLES                                                                 7

SEQ ID NO: 6            moltype = AA  length = 9
FEATURE                 Location/Qualifiers
REGION                  1..9
                        note = 5H23 VL CDR3- Exemplary
source                  1..9
                        mol_type = protein
                        organism = synthetic construct
SEQUENCE: 6
QHSRDLTFP                                                               9

SEQ ID NO: 7            moltype = AA  length = 8
FEATURE                 Location/Qualifiers
REGION                  1..8
                        note = 5H23 VH CDR1 - IMGT
source                  1..8
                        mol_type = protein
                        organism = synthetic construct
SEQUENCE: 7
GYTFTSYD                                                                8

SEQ ID NO: 8            moltype = AA  length = 8
FEATURE                 Location/Qualifiers
REGION                  1..8
                        note = 5H23 VH CDR2 - IMGT
source                  1..8
                        mol_type = protein
                        organism = synthetic construct
SEQUENCE: 8
IYPGDGST                                                                8

SEQ ID NO: 9            moltype = AA  length = 13
FEATURE                 Location/Qualifiers
REGION                  1..13
                        note = 5H23 VH CDR3 - IMGT
source                  1..13
                        mol_type = protein
                        organism = synthetic construct
SEQUENCE: 9
ARSDYYGSRS FAY                                                          13

SEQ ID NO: 10           moltype = AA  length = 10
FEATURE                 Location/Qualifiers
REGION                  1..10
                        note = 5H23 VL CDR1- IMGT
source                  1..10
                        mol_type = protein
                        organism = synthetic construct
SEQUENCE: 10
KSVSTSGYVY                                                              10

SEQ ID NO: 11           moltype =     length =
SEQUENCE: 11
000

SEQ ID NO: 12           moltype = AA  length = 5
FEATURE                 Location/Qualifiers
REGION                  1..5
                        note = 5H23 VH CDR1 - Kabat
source                  1..5
                        mol_type = protein
                        organism = synthetic construct
SEQUENCE: 12
SYDIN                                                                   5

SEQ ID NO: 13           moltype = AA  length = 7
FEATURE                 Location/Qualifiers
REGION                  1..7
                        note = 5H23 VH CDR1 - Chothia
source                  1..7
                        mol_type = protein
```

```
                                    -continued
                        organism = synthetic construct
SEQUENCE: 13
GYTFTSY                                                                 7

SEQ ID NO: 14           moltype = AA   length = 4
FEATURE                 Location/Qualifiers
REGION                  1..4
                        note = 5H23 VH CDR2 - Chothia
source                  1..4
                        mol_type = protein
                        organism = synthetic construct
SEQUENCE: 14
PGDG                                                                    4

SEQ ID NO: 15           moltype = AA   length = 9
FEATURE                 Location/Qualifiers
REGION                  1..9
                        note = 5H23 VH CDR3 - Chothia
source                  1..9
                        mol_type = protein
                        organism = synthetic construct
SEQUENCE: 15
DYYGSRSFA                                                               9

SEQ ID NO: 16           moltype = AA   length = 11
FEATURE                 Location/Qualifiers
REGION                  1..11
                        note = 5H23 VL CDR1- Chothia
source                  1..11
                        mol_type = protein
                        organism = synthetic construct
SEQUENCE: 16
SKSVSTSGYV Y                                                           11

SEQ ID NO: 17           moltype = AA   length = 6
FEATURE                 Location/Qualifiers
REGION                  1..6
                        note = 5H23 VL CDR3- Chothia
source                  1..6
                        mol_type = protein
                        organism = synthetic construct
SEQUENCE: 17
SRDLTF                                                                  6

SEQ ID NO: 18           moltype = AA   length = 6
FEATURE                 Location/Qualifiers
REGION                  1..6
                        note = 5H23 VH CDR1 - Contact
source                  1..6
                        mol_type = protein
                        organism = synthetic construct
SEQUENCE: 18
TSYDIN                                                                  6

SEQ ID NO: 19           moltype = AA   length = 13
FEATURE                 Location/Qualifiers
REGION                  1..13
                        note = 5H23 VH CDR2 - Contact
source                  1..13
                        mol_type = protein
                        organism = synthetic construct
SEQUENCE: 19
WIGWIYPGDG STK                                                         13

SEQ ID NO: 20           moltype = AA   length = 12
FEATURE                 Location/Qualifiers
REGION                  1..12
                        note = 5H23 VH CDR3 - Contact
source                  1..12
                        mol_type = protein
                        organism = synthetic construct
SEQUENCE: 20
ARSDYYGSRS FA                                                          12

SEQ ID NO: 21           moltype = AA   length = 11
FEATURE                 Location/Qualifiers
REGION                  1..11
                        note = 5H23 VL CDR1 - Contact
source                  1..11
```

```
                        mol_type = protein
                        organism = synthetic construct
SEQUENCE: 21
STSGYVYMHW N                                                           11

SEQ ID NO: 22           moltype = AA  length = 10
FEATURE                 Location/Qualifiers
REGION                  1..10
                        note = 5H23 VL CDR2 - Contact
source                  1..10
                        mol_type = protein
                        organism = synthetic construct
SEQUENCE: 22
LLIYLASYLE                                                             10

SEQ ID NO: 23           moltype = AA  length = 8
FEATURE                 Location/Qualifiers
REGION                  1..8
                        note = 5H23 VL CDR3 - Contact
source                  1..8
                        mol_type = protein
                        organism = synthetic construct
SEQUENCE: 23
QHSRDLTF                                                                8

SEQ ID NO: 24           moltype = AA  length = 10
FEATURE                 Location/Qualifiers
REGION                  1..10
                        note = 5H23 VH CDR2 - AbM
source                  1..10
                        mol_type = protein
                        organism = synthetic construct
SEQUENCE: 24
WIYPGDGSTK                                                             10

SEQ ID NO: 25           moltype = AA  length = 120
FEATURE                 Location/Qualifiers
REGION                  1..120
                        note = 5H23 VH Sequence
source                  1..120
                        mol_type = protein
                        organism = synthetic construct
SEQUENCE: 25
QVQLQQSGPE LVKPGALVKI SCKASGYTFT SYDINWVKQR PGQGLEWIGW IYPGDGSTKY       60
NEKFKGKATL TADKSSRTAY MQLSSLTSEN SAVYFCARSD YYGSRSFAYW GQGTLVTVSA      120

SEQ ID NO: 26           moltype = AA  length = 111
FEATURE                 Location/Qualifiers
REGION                  1..111
                        note = 5H23 VL Sequence
source                  1..111
                        mol_type = protein
                        organism = synthetic construct
SEQUENCE: 26
DIVLTQSPAS LAVSLGQRAT ISCRASKSVS TSGYVYMHWN QQKPGQPPKL LIYLASYLES       60
GVPARFSGSG SGTDFTLNIH PVEEEDAAIY YCQHSRDLTF PFGGGTKLEI K               111

SEQ ID NO: 27           moltype = AA  length = 11
FEATURE                 Location/Qualifiers
REGION                  1..11
                        note = 1C17 VH CDR1 - Exemplary
source                  1..11
                        mol_type = protein
                        organism = synthetic construct
SEQUENCE: 27
GYSITSGYYW N                                                           11

SEQ ID NO: 28           moltype = AA  length = 16
FEATURE                 Location/Qualifiers
REGION                  1..16
                        note = 1C17 VH CDR2 - Exemplary
source                  1..16
                        mol_type = protein
                        organism = synthetic construct
SEQUENCE: 28
YINYDGNSNY TPSLKN                                                      16

SEQ ID NO: 29           moltype = AA  length = 13
FEATURE                 Location/Qualifiers
```

```
REGION                  1..13
                        note = 1C17 VH CDR3 - Exemplary
source                  1..13
                        mol_type = protein
                        organism = synthetic construct
SEQUENCE: 29
KGAYYSNYDS FDV                                                             13

SEQ ID NO: 30           moltype = AA  length = 11
FEATURE                 Location/Qualifiers
REGION                  1..11
                        note = 1C17 VL CDR1 - Exemplary
source                  1..11
                        mol_type = protein
                        organism = synthetic construct
SEQUENCE: 30
KASQDINSYL S                                                               11

SEQ ID NO: 31           moltype = AA  length = 7
FEATURE                 Location/Qualifiers
REGION                  1..7
                        note = 1C17 VL CDR2 - Exemplary
source                  1..7
                        mol_type = protein
                        organism = synthetic construct
SEQUENCE: 31
RANRLVD                                                                     7

SEQ ID NO: 32           moltype = AA  length = 9
FEATURE                 Location/Qualifiers
REGION                  1..9
                        note = 1C17 VL CDR3 - Exemplary
source                  1..9
                        mol_type = protein
                        organism = synthetic construct
SEQUENCE: 32
LQYDEFPFT                                                                   9

SEQ ID NO: 33           moltype = AA  length = 9
FEATURE                 Location/Qualifiers
REGION                  1..9
                        note = 1C17 VH CDR1 - IMGT
source                  1..9
                        mol_type = protein
                        organism = synthetic construct
SEQUENCE: 33
GYSITSGYY                                                                   9

SEQ ID NO: 34           moltype = AA  length = 7
FEATURE                 Location/Qualifiers
REGION                  1..7
                        note = 1C17 VH CDR2 - IMGT
source                  1..7
                        mol_type = protein
                        organism = synthetic construct
SEQUENCE: 34
INYDGNS                                                                     7

SEQ ID NO: 35           moltype = AA  length = 15
FEATURE                 Location/Qualifiers
REGION                  1..15
                        note = 1C17 VH CDR3 - IMGT
source                  1..15
                        mol_type = protein
                        organism = synthetic construct
SEQUENCE: 35
ARKGAYYSNY DSFDV                                                           15

SEQ ID NO: 36           moltype = AA  length = 6
FEATURE                 Location/Qualifiers
REGION                  1..6
                        note = 1C17 VL CDR1 - IMGT
source                  1..6
                        mol_type = protein
                        organism = synthetic construct
SEQUENCE: 36
QDINSY                                                                      6

SEQ ID NO: 37           moltype =     length =
```

| | | |
|---|---|---|
| SEQUENCE: 37 000 | | |
| SEQ ID NO: 38 FEATURE REGION source | moltype = AA  length = 6 Location/Qualifiers 1..6 note = 1C17 VH CDR1 - Kabat 1..6 mol_type = protein organism = synthetic construct | |
| SEQUENCE: 38 SGYYWN | | 6 |
| SEQ ID NO: 39 FEATURE REGION source | moltype = AA  length = 8 Location/Qualifiers 1..8 note = 1C17 VH CDR1 - Chothia 1..8 mol_type = protein organism = synthetic construct | |
| SEQUENCE: 39 GYSITSGY | | 8 |
| SEQ ID NO: 40 SEQUENCE: 40 000 | moltype =   length = | |
| SEQ ID NO: 41 FEATURE REGION source | moltype = AA  length = 11 Location/Qualifiers 1..11 note = 1C17 VH CDR3 - Chothia 1..11 mol_type = protein organism = synthetic construct | |
| SEQUENCE: 41 GAYYSNYDSF D | | 11 |
| SEQ ID NO: 42 FEATURE REGION source | moltype = AA  length = 7 Location/Qualifiers 1..7 note = 1C17 VL CDR1 - Chothia 1..7 mol_type = protein organism = synthetic construct | |
| SEQUENCE: 42 SQDINSY | | 7 |
| SEQ ID NO: 43 FEATURE REGION source | moltype = AA  length = 6 Location/Qualifiers 1..6 note = 1C17 VL CDR3 - Chothia 1..6 mol_type = protein organism = synthetic construct | |
| SEQUENCE: 43 YDEFPF | | 6 |
| SEQ ID NO: 44 FEATURE REGION source | moltype = AA  length = 7 Location/Qualifiers 1..7 note = 1C17 VH CDR1 - Contact 1..7 mol_type = protein organism = synthetic construct | |
| SEQUENCE: 44 TSGYYWN | | 7 |
| SEQ ID NO: 45 FEATURE REGION source | moltype = AA  length = 12 Location/Qualifiers 1..12 note = 1C17 VH CDR2 - Contact 1..12 mol_type = protein organism = synthetic construct | |
| SEQUENCE: 45 WMGYINYDGN SN | | 12 |
| SEQ ID NO: 46 FEATURE | moltype = AA  length = 14 Location/Qualifiers | |

```
REGION                  1..14
                        note = 1C17 VH CDR3 - Contact
source                  1..14
                        mol_type = protein
                        organism = synthetic construct
SEQUENCE: 46
ARKGAYYSNY DSFD                                                         14

SEQ ID NO: 47           moltype = AA   length = 7
FEATURE                 Location/Qualifiers
REGION                  1..7
                        note = 1C17 VL CDR1 - Contact
source                  1..7
                        mol_type = protein
                        organism = synthetic construct
SEQUENCE: 47
NSYLSWV                                                                  7

SEQ ID NO: 48           moltype = AA   length = 10
FEATURE                 Location/Qualifiers
REGION                  1..10
                        note = 1C17 VL CDR2 - Contact
source                  1..10
                        mol_type = protein
                        organism = synthetic construct
SEQUENCE: 48
TLIYRANRLV                                                              10

SEQ ID NO: 49           moltype = AA   length = 8
FEATURE                 Location/Qualifiers
REGION                  1..8
                        note = 1C17 VL CDR3 - Contact
source                  1..8
                        mol_type = protein
                        organism = synthetic construct
SEQUENCE: 49
LQYDEFPF                                                                 8

SEQ ID NO: 50           moltype = AA   length = 9
FEATURE                 Location/Qualifiers
REGION                  1..9
                        note = 1C17 VH CDR2 - AbM
source                  1..9
                        mol_type = protein
                        organism = synthetic construct
SEQUENCE: 50
YINYDGNSN                                                                9

SEQ ID NO: 51           moltype = AA   length = 122
FEATURE                 Location/Qualifiers
REGION                  1..122
                        note = 1C17 VH Sequence
source                  1..122
                        mol_type = protein
                        organism = synthetic construct
SEQUENCE: 51
QVQLQESGPG LVKPSQSLSL TCSVTGYSIT SGYYWNWIRQ FPGNKLEWMG YINYDGNSNY        60
TPSLKNRISI TRDTSKNQFF LKLNSVTPED TATYYCARKG AYYSNYDSFD VWGTGTTVTV       120
SS                                                                     122

SEQ ID NO: 52           moltype = AA   length = 107
FEATURE                 Location/Qualifiers
REGION                  1..107
                        note = 1C17 VL Sequence
source                  1..107
                        mol_type = protein
                        organism = synthetic construct
SEQUENCE: 52
DIKMTQSPSS MYASLGERVT ITCKASQDIN SYLSWVQQKP GKSPKTLIYR ANRLVDGVPS        60
RFSGSGSGQD YSLTISSLEY EDMGIYYCLQ YDEFPFTFGS GTKLEIK                     107

SEQ ID NO: 53           moltype = AA   length = 10
FEATURE                 Location/Qualifiers
REGION                  1..10
                        note = 1D19 VH CDR1- Exemplary
source                  1..10
                        mol_type = protein
                        organism = synthetic construct
SEQUENCE: 53
```

```
GYTFTRYDIN                                                              10

SEQ ID NO: 54           moltype = AA  length = 17
FEATURE                 Location/Qualifiers
REGION                  1..17
                        note = 1D19 VH CDR2- Exemplary
source                  1..17
                        mol_type = protein
                        organism = synthetic construct
SEQUENCE: 54
WIYPGDSSTK FNENFKD                                                      17

SEQ ID NO: 55           moltype = AA  length = 11
FEATURE                 Location/Qualifiers
REGION                  1..11
                        note = 1D19 VH CDR3- Exemplary
source                  1..11
                        mol_type = protein
                        organism = synthetic construct
SEQUENCE: 55
SDYYGSRSFT Y                                                            11

SEQ ID NO: 56           moltype = AA  length = 15
FEATURE                 Location/Qualifiers
REGION                  1..15
                        note = 1D19 VL CDR1- Exemplary
source                  1..15
                        mol_type = protein
                        organism = synthetic construct
SEQUENCE: 56
RASKSVSTSG YSYMH                                                        15

SEQ ID NO: 57           moltype = AA  length = 7
FEATURE                 Location/Qualifiers
REGION                  1..7
                        note = 1D19 VL CDR2- Exemplary
source                  1..7
                        mol_type = protein
                        organism = synthetic construct
SEQUENCE: 57
LASNLES                                                                 7

SEQ ID NO: 58           moltype = AA  length = 9
FEATURE                 Location/Qualifiers
REGION                  1..9
                        note = 1D19 VL CDR3- Exemplary
source                  1..9
                        mol_type = protein
                        organism = synthetic construct
SEQUENCE: 58
QHSRELPYT                                                               9

SEQ ID NO: 59           moltype = AA  length = 8
FEATURE                 Location/Qualifiers
REGION                  1..8
                        note = 1D19 VH CDR1 - IMGT
source                  1..8
                        mol_type = protein
                        organism = synthetic construct
SEQUENCE: 59
GYTFTRYD                                                                8

SEQ ID NO: 60           moltype = AA  length = 8
FEATURE                 Location/Qualifiers
REGION                  1..8
                        note = 1D19 VH CDR2 - IMGT
source                  1..8
                        mol_type = protein
                        organism = synthetic construct
SEQUENCE: 60
IYPGDSST                                                                8

SEQ ID NO: 61           moltype = AA  length = 13
FEATURE                 Location/Qualifiers
REGION                  1..13
                        note = 1D19 VH CDR3 - IMGT
source                  1..13
                        mol_type = protein
                        organism = synthetic construct
```

```
SEQUENCE: 61
ARSDYYGSRS FTY                                                          13

SEQ ID NO: 62           moltype = AA  length = 10
FEATURE                 Location/Qualifiers
REGION                  1..10
                        note = 1D19 VL CDR1 - IMGT
source                  1..10
                        mol_type = protein
                        organism = synthetic construct
SEQUENCE: 62
KSVSTSGYSY                                                              10

SEQ ID NO: 63           moltype =   length =
SEQUENCE: 63
000

SEQ ID NO: 64           moltype = AA  length = 5
FEATURE                 Location/Qualifiers
REGION                  1..5
                        note = 1D19 VH CDR1 - Kabat
source                  1..5
                        mol_type = protein
                        organism = synthetic construct
SEQUENCE: 64
RYDIN                                                                   5

SEQ ID NO: 65           moltype = AA  length = 7
FEATURE                 Location/Qualifiers
REGION                  1..7
                        note = 1D19 VH CDR1 - Chothia
source                  1..7
                        mol_type = protein
                        organism = synthetic construct
SEQUENCE: 65
GYTFTRY                                                                 7

SEQ ID NO: 66           moltype = AA  length = 4
FEATURE                 Location/Qualifiers
REGION                  1..4
                        note = 1D19 VH CDR2 - Chothia
source                  1..4
                        mol_type = protein
                        organism = synthetic construct
SEQUENCE: 66
PGDS                                                                    4

SEQ ID NO: 67           moltype = AA  length = 9
FEATURE                 Location/Qualifiers
REGION                  1..9
                        note = 1D19 VH CDR3 - Chothia
source                  1..9
                        mol_type = protein
                        organism = synthetic construct
SEQUENCE: 67
DYYGSRSFT                                                               9

SEQ ID NO: 68           moltype = AA  length = 11
FEATURE                 Location/Qualifiers
REGION                  1..11
                        note = 1D19 VL CDR1 - Chothia
source                  1..11
                        mol_type = protein
                        organism = synthetic construct
SEQUENCE: 68
SKSVSTSGYS Y                                                            11

SEQ ID NO: 69           moltype = AA  length = 6
FEATURE                 Location/Qualifiers
REGION                  1..6
                        note = 1D19 VL CDR3 - Chothia
source                  1..6
                        mol_type = protein
                        organism = synthetic construct
SEQUENCE: 69
SRELPY                                                                  6

SEQ ID NO: 70           moltype = AA  length = 6
FEATURE                 Location/Qualifiers
```

```
REGION                     1..6
                           note = 1D19 VH CDR1 - Contact
source                     1..6
                           mol_type = protein
                           organism = synthetic construct
SEQUENCE: 70
TRYDIN                                                                      6

SEQ ID NO: 71              moltype = AA  length = 13
FEATURE                    Location/Qualifiers
REGION                     1..13
                           note = 1D19 VH CDR2 - Contact
source                     1..13
                           mol_type = protein
                           organism = synthetic construct
SEQUENCE: 71
WIGWIYPGDS STK                                                             13

SEQ ID NO: 72              moltype = AA  length = 12
FEATURE                    Location/Qualifiers
REGION                     1..12
                           note = 1D19 VH CDR3 - Contact
source                     1..12
                           mol_type = protein
                           organism = synthetic construct
SEQUENCE: 72
ARSDYYGSRS FT                                                              12

SEQ ID NO: 73              moltype = AA  length = 11
FEATURE                    Location/Qualifiers
REGION                     1..11
                           note = 1D19 VL CDR1 - Contact
source                     1..11
                           mol_type = protein
                           organism = synthetic construct
SEQUENCE: 73
STSGYSYMHW Y                                                               11

SEQ ID NO: 74              moltype = AA  length = 10
FEATURE                    Location/Qualifiers
REGION                     1..10
                           note = 1D19 VL CDR2 - Contact
source                     1..10
                           mol_type = protein
                           organism = synthetic construct
SEQUENCE: 74
LLIYLASNLE                                                                 10

SEQ ID NO: 75              moltype = AA  length = 8
FEATURE                    Location/Qualifiers
REGION                     1..8
                           note = 1D19 VL CDR3 - Contact
source                     1..8
                           mol_type = protein
                           organism = synthetic construct
SEQUENCE: 75
QHSRELPY                                                                    8

SEQ ID NO: 76              moltype = AA  length = 10
FEATURE                    Location/Qualifiers
REGION                     1..10
                           note = 1D19 VH CDR2 - AbM
source                     1..10
                           mol_type = protein
                           organism = synthetic construct
SEQUENCE: 76
WIYPGDSSTK                                                                 10

SEQ ID NO: 77              moltype = AA  length = 120
FEATURE                    Location/Qualifiers
REGION                     1..120
                           note = 1D19 VH Sequence
source                     1..120
                           mol_type = protein
                           organism = synthetic construct
SEQUENCE: 77
QVQPQESGPE LVKPGALVKI SCKASGYTFT RYDINWMKQR PGQGLEWIGW IYPGDSSTKF           60
NENFKDKATL TADKSSSTAY MQLSSLTSEN STVYFCARSD YYGSRSFTYW GQGTLVTVSA          120
```

```
SEQ ID NO: 78          moltype = AA  length = 111
FEATURE                Location/Qualifiers
REGION                 1..111
                       note = 1D19 VL Sequence
source                 1..111
                       mol_type = protein
                       organism = synthetic construct
SEQUENCE: 78
DIVLTQSPAS LAVSLGQRAT ISCRASKSVS TSGYSYMHWY QQKPGQPPKL LIYLASNLES      60
GVPARFSGSG SGTDFTLNIH PVEEEDAATY YCQHSRELPY TFGGGTKLEI K               111

SEQ ID NO: 79          moltype = AA  length = 10
FEATURE                Location/Qualifiers
REGION                 1..10
                       note = 2L12 VH CDR1- Exemplary
source                 1..10
                       mol_type = protein
                       organism = synthetic construct
SEQUENCE: 79
GYTFTRYDIN                                                             10

SEQ ID NO: 80          moltype = AA  length = 17
FEATURE                Location/Qualifiers
REGION                 1..17
                       note = 2L12 VH CDR2- Exemplary
source                 1..17
                       mol_type = protein
                       organism = synthetic construct
SEQUENCE: 80
WIYPGDDSTK YNEKFKG                                                     17

SEQ ID NO: 81          moltype = AA  length = 11
FEATURE                Location/Qualifiers
REGION                 1..11
                       note = 2L12 VH CDR3- Exemplary
source                 1..11
                       mol_type = protein
                       organism = synthetic construct
SEQUENCE: 81
SDYYGSRSFV Y                                                           11

SEQ ID NO: 82          moltype = AA  length = 15
FEATURE                Location/Qualifiers
REGION                 1..15
                       note = 2L12 VL CDR1- Exemplary
source                 1..15
                       mol_type = protein
                       organism = synthetic construct
SEQUENCE: 82
RASKSVSTSG YSYLH                                                       15

SEQ ID NO: 83          moltype = AA  length = 7
FEATURE                Location/Qualifiers
REGION                 1..7
                       note = 2L12 VL CDR2- Exemplary
source                 1..7
                       mol_type = protein
                       organism = synthetic construct
SEQUENCE: 83
LASNLES                                                                7

SEQ ID NO: 84          moltype = AA  length = 9
FEATURE                Location/Qualifiers
REGION                 1..9
                       note = 2L12 VL CDR3- Exemplary
source                 1..9
                       mol_type = protein
                       organism = synthetic construct
SEQUENCE: 84
QHSGELPYT                                                              9

SEQ ID NO: 85          moltype = AA  length = 8
FEATURE                Location/Qualifiers
REGION                 1..8
                       note = 2L12 VH CDR1 - IMGT
source                 1..8
                       mol_type = protein
                       organism = synthetic construct
SEQUENCE: 85
```

```
GYTFTRYD                                                                         8

SEQ ID NO: 86            moltype = AA   length = 8
FEATURE                  Location/Qualifiers
REGION                   1..8
                         note = 2L12 VH CDR2 - IMGT
source                   1..8
                         mol_type = protein
                         organism = synthetic construct
SEQUENCE: 86
IYPGDDST                                                                         8

SEQ ID NO: 87            moltype = AA   length = 13
FEATURE                  Location/Qualifiers
REGION                   1..13
                         note = 2L12 VH CDR3 - IMGT
source                   1..13
                         mol_type = protein
                         organism = synthetic construct
SEQUENCE: 87
ARSDYYGSRS FVY                                                                  13

SEQ ID NO: 88            moltype = AA   length = 10
FEATURE                  Location/Qualifiers
REGION                   1..10
                         note = 2L12 VL CDR1 - IMGT
source                   1..10
                         mol_type = protein
                         organism = synthetic construct
SEQUENCE: 88
KSVSTSGYSY                                                                      10

SEQ ID NO: 89            moltype =     length =
SEQUENCE: 89
000

SEQ ID NO: 90            moltype = AA   length = 5
FEATURE                  Location/Qualifiers
REGION                   1..5
                         note = 2L12 VH CDR1 - Kabat
source                   1..5
                         mol_type = protein
                         organism = synthetic construct
SEQUENCE: 90
RYDIN                                                                            5

SEQ ID NO: 91            moltype = AA   length = 7
FEATURE                  Location/Qualifiers
REGION                   1..7
                         note = 2L12 VH CDR1 - Chothia
source                   1..7
                         mol_type = protein
                         organism = synthetic construct
SEQUENCE: 91
GYTFTRY                                                                          7

SEQ ID NO: 92            moltype = AA   length = 4
FEATURE                  Location/Qualifiers
REGION                   1..4
                         note = 2L12 VH CDR2 - Chothia
source                   1..4
                         mol_type = protein
                         organism = synthetic construct
SEQUENCE: 92
PGDD                                                                             4

SEQ ID NO: 93            moltype = AA   length = 9
FEATURE                  Location/Qualifiers
REGION                   1..9
                         note = 2L12 VH CDR3 - Chothia
source                   1..9
                         mol_type = protein
                         organism = synthetic construct
SEQUENCE: 93
DYYGSRSFV                                                                        9

SEQ ID NO: 94            moltype = AA   length = 11
FEATURE                  Location/Qualifiers
REGION                   1..11
```

```
                    note = 2L12 VL CDR1- Chothia
source              1..11
                    mol_type = protein
                    organism = synthetic construct
SEQUENCE: 94
SKSVSTSGYS Y                                                                11

SEQ ID NO: 95       moltype = AA   length = 6
FEATURE             Location/Qualifiers
REGION              1..6
                    note = 2L12 VL CDR3- Chothia
source              1..6
                    mol_type = protein
                    organism = synthetic construct
SEQUENCE: 95
SGELPY                                                                      6

SEQ ID NO: 96       moltype = AA   length = 6
FEATURE             Location/Qualifiers
REGION              1..6
                    note = 2L12 VH CDR1 - Contact
source              1..6
                    mol_type = protein
                    organism = synthetic construct
SEQUENCE: 96
TRYDIN                                                                      6

SEQ ID NO: 97       moltype = AA   length = 13
FEATURE             Location/Qualifiers
REGION              1..13
                    note = 2L12 VH CDR2 - Contact
source              1..13
                    mol_type = protein
                    organism = synthetic construct
SEQUENCE: 97
WIGWIYPGDD STK                                                              13

SEQ ID NO: 98       moltype = AA   length = 12
FEATURE             Location/Qualifiers
REGION              1..12
                    note = 2L12 VH CDR3 - Contact
source              1..12
                    mol_type = protein
                    organism = synthetic construct
SEQUENCE: 98
ARSDYYGSRS FV                                                               12

SEQ ID NO: 99       moltype = AA   length = 11
FEATURE             Location/Qualifiers
REGION              1..11
                    note = 2L12 VL CDR1 - Contact
source              1..11
                    mol_type = protein
                    organism = synthetic construct
SEQUENCE: 99
STSGYSYLHW Y                                                                11

SEQ ID NO: 100      moltype = AA   length = 10
FEATURE             Location/Qualifiers
REGION              1..10
                    note = 2L12 VL CDR2 - Contact
source              1..10
                    mol_type = protein
                    organism = synthetic construct
SEQUENCE: 100
LLIYLASNLE                                                                  10

SEQ ID NO: 101      moltype = AA   length = 8
FEATURE             Location/Qualifiers
REGION              1..8
                    note = 2L12 VL CDR3 - Contact
source              1..8
                    mol_type = protein
                    organism = synthetic construct
SEQUENCE: 101
QHSGELPY                                                                    8

SEQ ID NO: 102      moltype = AA   length = 10
FEATURE             Location/Qualifiers
```

```
REGION                  1..10
                        note = 2L12 VH CDR2 - AbM
source                  1..10
                        mol_type = protein
                        organism = synthetic construct
SEQUENCE: 102
WIYPGDDSTK                                                                  10

SEQ ID NO: 103          moltype = AA  length = 120
FEATURE                 Location/Qualifiers
REGION                  1..120
                        note = 2L12 VH Sequence
source                  1..120
                        mol_type = protein
                        organism = synthetic construct
SEQUENCE: 103
QVQLQQSGPE LVKPGALVKI SCKASGYTFT RYDINWVKKR PGQGLEWIGW IYPGDDSTKY       60
NEKFKGKATL TADKSSSTAY MQLSSLTSEN SAVYFCARSD YYGSRSFVYW GQGTLVTVSA      120

SEQ ID NO: 104          moltype = AA  length = 111
FEATURE                 Location/Qualifiers
REGION                  1..111
                        note = 2L12 VL Sequence
source                  1..111
                        mol_type = protein
                        organism = synthetic construct
SEQUENCE: 104
DIVLTQSPAS LPVSLGQRAT ISCRASKSVS TSGYSYLHWY QQKPGQPPKL LIYLASNLES       60
GVPARFSGSG SGTDFTLNIH PVEEEDAATY YCQHSGELPY TFGGGTKLEI K              111

SEQ ID NO: 105          moltype = AA  length = 10
FEATURE                 Location/Qualifiers
REGION                  1..10
                        note = 3L3 VH CDR1 - Exemplary
source                  1..10
                        mol_type = protein
                        organism = synthetic construct
SEQUENCE: 105
GYTFTSYDIN                                                                  10

SEQ ID NO: 106          moltype = AA  length = 17
FEATURE                 Location/Qualifiers
REGION                  1..17
                        note = 3L3 VH CDR2 - Exemplary
source                  1..17
                        mol_type = protein
                        organism = synthetic construct
SEQUENCE: 106
WIYPGDGSPK YDEKFKG                                                          17

SEQ ID NO: 107          moltype = AA  length = 11
FEATURE                 Location/Qualifiers
REGION                  1..11
                        note = 3L3 VH CDR3 - Exemplary
source                  1..11
                        mol_type = protein
                        organism = synthetic construct
SEQUENCE: 107
SDYYGSRSFV Y                                                                11

SEQ ID NO: 108          moltype = AA  length = 15
FEATURE                 Location/Qualifiers
REGION                  1..15
                        note = 3L3 VL CDR1- Exemplary
source                  1..15
                        mol_type = protein
                        organism = synthetic construct
SEQUENCE: 108
RASKSVSTSG YSYVH                                                            15

SEQ ID NO: 109          moltype = AA  length = 7
FEATURE                 Location/Qualifiers
REGION                  1..7
                        note = 3L3 VL CDR2- Exemplary
source                  1..7
                        mol_type = protein
                        organism = synthetic construct
SEQUENCE: 109
LASNLES                                                                      7
```

```
SEQ ID NO: 110          moltype = AA   length = 9
FEATURE                 Location/Qualifiers
REGION                  1..9
                        note = 3L3 VL CDR3- Exemplary
source                  1..9
                        mol_type = protein
                        organism = synthetic construct
SEQUENCE: 110
QHSGELPYT                                                                   9

SEQ ID NO: 111          moltype = AA   length = 8
FEATURE                 Location/Qualifiers
REGION                  1..8
                        note = 3L3 VH CDR1 - IMGT
source                  1..8
                        mol_type = protein
                        organism = synthetic construct
SEQUENCE: 111
GYTFTSYD                                                                    8

SEQ ID NO: 112          moltype = AA   length = 8
FEATURE                 Location/Qualifiers
REGION                  1..8
                        note = 3L3 VH CDR2 - IMGT
source                  1..8
                        mol_type = protein
                        organism = synthetic construct
SEQUENCE: 112
IYPGDGSP                                                                    8

SEQ ID NO: 113          moltype = AA   length = 13
FEATURE                 Location/Qualifiers
REGION                  1..13
                        note = 3L3 VH CDR3 - IMGT
source                  1..13
                        mol_type = protein
                        organism = synthetic construct
SEQUENCE: 113
ARSDYYGSRS FVY                                                             13

SEQ ID NO: 114          moltype = AA   length = 10
FEATURE                 Location/Qualifiers
REGION                  1..10
                        note = 3L3 VL CDR1- IMGT
source                  1..10
                        mol_type = protein
                        organism = synthetic construct
SEQUENCE: 114
KSVSTSGYSY                                                                 10

SEQ ID NO: 115          moltype =     length =
SEQUENCE: 115
000

SEQ ID NO: 116          moltype = AA   length = 5
FEATURE                 Location/Qualifiers
REGION                  1..5
                        note = 3L3 VH CDR1 - Kabat
source                  1..5
                        mol_type = protein
                        organism = synthetic construct
SEQUENCE: 116
SYDIN                                                                       5

SEQ ID NO: 117          moltype = AA   length = 7
FEATURE                 Location/Qualifiers
REGION                  1..7
                        note = 3L3 VH CDR1 - Chothia
source                  1..7
                        mol_type = protein
                        organism = synthetic construct
SEQUENCE: 117
GYTFTSY                                                                     7

SEQ ID NO: 118          moltype = AA   length = 4
FEATURE                 Location/Qualifiers
REGION                  1..4
                        note = 3L3 VH CDR2 - Chothia
```

```
source                      1..4
                            mol_type = protein
                            organism = synthetic construct
SEQUENCE: 118
PGDG                                                                    4

SEQ ID NO: 119              moltype = AA  length = 9
FEATURE                     Location/Qualifiers
REGION                      1..9
                            note = 3L3 VH CDR3 - Chothia
source                      1..9
                            mol_type = protein
                            organism = synthetic construct
SEQUENCE: 119
DYYGSRSFV                                                               9

SEQ ID NO: 120              moltype = AA  length = 11
FEATURE                     Location/Qualifiers
REGION                      1..11
                            note = 3L3 VL CDR1- Chothia
source                      1..11
                            mol_type = protein
                            organism = synthetic construct
SEQUENCE: 120
SKSVSTSGYS Y                                                           11

SEQ ID NO: 121              moltype = AA  length = 6
FEATURE                     Location/Qualifiers
REGION                      1..6
                            note = 3L3 VL CDR3- Chothia
source                      1..6
                            mol_type = protein
                            organism = synthetic construct
SEQUENCE: 121
SGELPY                                                                  6

SEQ ID NO: 122              moltype = AA  length = 6
FEATURE                     Location/Qualifiers
REGION                      1..6
                            note = 3L3 VH CDR1 - Contact
source                      1..6
                            mol_type = protein
                            organism = synthetic construct
SEQUENCE: 122
TSYDIN                                                                  6

SEQ ID NO: 123              moltype = AA  length = 13
FEATURE                     Location/Qualifiers
REGION                      1..13
                            note = 3L3 VH CDR2 - Contact
source                      1..13
                            mol_type = protein
                            organism = synthetic construct
SEQUENCE: 123
WIGWIYPGDG SPK                                                         13

SEQ ID NO: 124              moltype = AA  length = 12
FEATURE                     Location/Qualifiers
REGION                      1..12
                            note = 3L3 VH CDR3 - Contact
source                      1..12
                            mol_type = protein
                            organism = synthetic construct
SEQUENCE: 124
ARSDYYGSRS FV                                                          12

SEQ ID NO: 125              moltype = AA  length = 11
FEATURE                     Location/Qualifiers
REGION                      1..11
                            note = 3L3 VL CDR1- Contact
source                      1..11
                            mol_type = protein
                            organism = synthetic construct
SEQUENCE: 125
STSGYSYVHW Y                                                           11

SEQ ID NO: 126              moltype = AA  length = 10
FEATURE                     Location/Qualifiers
REGION                      1..10
```

```
                     note = 3L3 VL CDR2- Contact
source               1..10
                     mol_type = protein
                     organism = synthetic construct
SEQUENCE: 126
LLIYLASNLE                                                                    10

SEQ ID NO: 127       moltype = AA  length = 8
FEATURE              Location/Qualifiers
REGION               1..8
                     note = 3L3 VL CDR3- Contact
source               1..8
                     mol_type = protein
                     organism = synthetic construct
SEQUENCE: 127
QHSGELPY                                                                       8

SEQ ID NO: 128       moltype = AA  length = 10
FEATURE              Location/Qualifiers
REGION               1..10
                     note = 3L3 VH CDR2 - AbM
source               1..10
                     mol_type = protein
                     organism = synthetic construct
SEQUENCE: 128
WIYPGDGSPK                                                                    10

SEQ ID NO: 129       moltype = AA  length = 120
FEATURE              Location/Qualifiers
REGION               1..120
                     note = 3L3 VH Sequence
source               1..120
                     mol_type = protein
                     organism = synthetic construct
SEQUENCE: 129
QVQPQESGPE LVKPGTLVKI SCKASGYTFT SYDINWVKQR PGQGLEWIGW IYPGDGSPKY              60
DEKFKGKATL TADKSSSTAY MQLSSLTSEN SAVYFCARSD YYGSRSFVYW GQGTLVTVSA            120

SEQ ID NO: 130       moltype = AA  length = 111
FEATURE              Location/Qualifiers
REGION               1..111
                     note = 3L3 VL Sequence
source               1..111
                     mol_type = protein
                     organism = synthetic construct
SEQUENCE: 130
DIVLTQSPAS LAVSLGQRAT ISCRASKSVS TSGYSYVHWY QQKPGQPPKL LIYLASNLES              60
GVPARFSGRG SGTDFTLNIH PVEEEDAATY YCQHSGELPY TFGGGTKLEI K                     111

SEQ ID NO: 131       moltype = AA  length = 10
FEATURE              Location/Qualifiers
REGION               1..10
                     note = 3N20 VH CDR1- Exemplary
source               1..10
                     mol_type = protein
                     organism = synthetic construct
SEQUENCE: 131
GYIFTNYGIS                                                                    10

SEQ ID NO: 132       moltype = AA  length = 17
FEATURE              Location/Qualifiers
REGION               1..17
                     note = 3N20 VH CDR2- Exemplary
source               1..17
                     mol_type = protein
                     organism = synthetic construct
SEQUENCE: 132
EIYPRSGNTY YNEKFKG                                                            17

SEQ ID NO: 133       moltype = AA  length = 11
FEATURE              Location/Qualifiers
REGION               1..11
                     note = 3N20 VH CDR3- Exemplary
source               1..11
                     mol_type = protein
                     organism = synthetic construct
SEQUENCE: 133
HWDGVLDYFD Y                                                                  11
```

```
SEQ ID NO: 134         moltype = AA  length = 17
FEATURE                Location/Qualifiers
REGION                 1..17
                       note = 3N20 VL CDR1- Exemplary
source                 1..17
                       mol_type = protein
                       organism = synthetic construct
SEQUENCE: 134
KSSQSLLNSG NQKNYLA                                                           17

SEQ ID NO: 135         moltype = AA  length = 7
FEATURE                Location/Qualifiers
REGION                 1..7
                       note = 3N20 VL CDR2- Exemplary
source                 1..7
                       mol_type = protein
                       organism = synthetic construct
SEQUENCE: 135
GASTRES                                                                       7

SEQ ID NO: 136         moltype = AA  length = 9
FEATURE                Location/Qualifiers
REGION                 1..9
                       note = 3N20 VL CDR3- Exemplary
source                 1..9
                       mol_type = protein
                       organism = synthetic construct
SEQUENCE: 136
LNDHSYPFT                                                                     9

SEQ ID NO: 137         moltype = AA  length = 8
FEATURE                Location/Qualifiers
REGION                 1..8
                       note = 3N20 VH CDR1 - IMGT
source                 1..8
                       mol_type = protein
                       organism = synthetic construct
SEQUENCE: 137
GYIFTNYG                                                                      8

SEQ ID NO: 138         moltype = AA  length = 8
FEATURE                Location/Qualifiers
REGION                 1..8
                       note = 3N20 VH CDR2 - IMGT
source                 1..8
                       mol_type = protein
                       organism = synthetic construct
SEQUENCE: 138
IYPRSGNT                                                                      8

SEQ ID NO: 139         moltype = AA  length = 13
FEATURE                Location/Qualifiers
REGION                 1..13
                       note = 3N20 VH CDR3 - IMGT
source                 1..13
                       mol_type = protein
                       organism = synthetic construct
SEQUENCE: 139
ARHWDGVLDY FDY                                                               13

SEQ ID NO: 140         moltype = AA  length = 12
FEATURE                Location/Qualifiers
REGION                 1..12
                       note = 3N20 VL CDR1 - IMGT
source                 1..12
                       mol_type = protein
                       organism = synthetic construct
SEQUENCE: 140
QSLLNSGNQK NY                                                                12

SEQ ID NO: 141         moltype =     length =
SEQUENCE: 141
000

SEQ ID NO: 142         moltype = AA  length = 5
FEATURE                Location/Qualifiers
REGION                 1..5
                       note = 3N20 VH CDR1 - Kabat
source                 1..5
```

```
                                  mol_type = protein
                                  organism = synthetic construct
SEQUENCE: 142
NYGIS                                                                             5

SEQ ID NO: 143        moltype = AA  length = 7
FEATURE               Location/Qualifiers
REGION                1..7
                      note = 3N20 VH CDR1 - Chothia
source                1..7
                      mol_type = protein
                      organism = synthetic construct
SEQUENCE: 143
GYIFTNY                                                                           7

SEQ ID NO: 144        moltype = AA  length = 4
FEATURE               Location/Qualifiers
REGION                1..4
                      note = 3N20 VH CDR2 - Chothia
source                1..4
                      mol_type = protein
                      organism = synthetic construct
SEQUENCE: 144
PRSG                                                                              4

SEQ ID NO: 145        moltype = AA  length = 9
FEATURE               Location/Qualifiers
REGION                1..9
                      note = 3N20 VH CDR3 - Chothia
source                1..9
                      mol_type = protein
                      organism = synthetic construct
SEQUENCE: 145
WDGVLDYFD                                                                         9

SEQ ID NO: 146        moltype = AA  length = 13
FEATURE               Location/Qualifiers
REGION                1..13
                      note = 3N20 VL CDR1- Chothia
source                1..13
                      mol_type = protein
                      organism = synthetic construct
SEQUENCE: 146
SQSLLNSGNQ KNY                                                                   13

SEQ ID NO: 147        moltype = AA  length = 6
FEATURE               Location/Qualifiers
REGION                1..6
                      note = 3N20 VL CDR3- Chothia
source                1..6
                      mol_type = protein
                      organism = synthetic construct
SEQUENCE: 147
DHSYPF                                                                            6

SEQ ID NO: 148        moltype = AA  length = 6
FEATURE               Location/Qualifiers
REGION                1..6
                      note = 3N20 VH CDR1 - Contact
source                1..6
                      mol_type = protein
                      organism = synthetic construct
SEQUENCE: 148
TNYGIS                                                                            6

SEQ ID NO: 149        moltype = AA  length = 13
FEATURE               Location/Qualifiers
REGION                1..13
                      note = 3N20 VH CDR2 - Contact
source                1..13
                      mol_type = protein
                      organism = synthetic construct
SEQUENCE: 149
WIGEIYPRSG NTY                                                                   13

SEQ ID NO: 150        moltype = AA  length = 12
FEATURE               Location/Qualifiers
REGION                1..12
                      note = 3N20 VH CDR3 - Contact
```

```
source                   1..12
                         mol_type = protein
                         organism = synthetic construct
SEQUENCE: 150
ARHWDGVLDY FD                                                         12

SEQ ID NO: 151           moltype = AA   length = 13
FEATURE                  Location/Qualifiers
REGION                   1..13
                         note = 3N20 VL CDR1 - Contact
source                   1..13
                         mol_type = protein
                         organism = synthetic construct
SEQUENCE: 151
LNSGNQKNYL AWY                                                        13

SEQ ID NO: 152           moltype = AA   length = 10
FEATURE                  Location/Qualifiers
REGION                   1..10
                         note = 3N20 VL CDR2 - Contact
source                   1..10
                         mol_type = protein
                         organism = synthetic construct
SEQUENCE: 152
LLIYGASTRE                                                            10

SEQ ID NO: 153           moltype = AA   length = 8
FEATURE                  Location/Qualifiers
REGION                   1..8
                         note = 3N20 VL CDR3 - Contact
source                   1..8
                         mol_type = protein
                         organism = synthetic construct
SEQUENCE: 153
LNDHSYPF                                                              8

SEQ ID NO: 154           moltype = AA   length = 10
FEATURE                  Location/Qualifiers
REGION                   1..10
                         note = 3N20 VH CDR2 - AbM
source                   1..10
                         mol_type = protein
                         organism = synthetic construct
SEQUENCE: 154
EIYPRSGNTY                                                            10

SEQ ID NO: 155           moltype = AA   length = 120
FEATURE                  Location/Qualifiers
REGION                   1..120
                         note = 3N20 VH Sequence
source                   1..120
                         mol_type = protein
                         organism = synthetic construct
SEQUENCE: 155
QVQLQESGAE LARPGASVKL SCKVSGYIFT NYGISWVKQR TGQGLEWIGE IYPRSGNTYY      60
NEKFKGKATL TADMSSSTAY MDLRSLTSED SAVYFCARHW DGVLDYFDYW GQGTSLTVSS     120

SEQ ID NO: 156           moltype = AA   length = 113
FEATURE                  Location/Qualifiers
REGION                   1..113
                         note = 3N20 VL Sequence
source                   1..113
                         mol_type = protein
                         organism = synthetic construct
SEQUENCE: 156
DIVMTQSPSS LSVSAGEKVT MSCKSSQSLL NSGNQKNYLA WYQQKPGQPP KLLIYGASTR      60
ESGVPDRFTG SGSGTDFTLT ISSVQAEDLA VYYCLNDHSY PFTFGAGTKL ELK            113

SEQ ID NO: 157           moltype = AA   length = 10
FEATURE                  Location/Qualifiers
REGION                   1..10
                         note = 4P5 VH CDR1 - Exemplary
source                   1..10
                         mol_type = protein
                         organism = synthetic construct
SEQUENCE: 157
GYTFTRYDIN                                                            10

SEQ ID NO: 158           moltype = AA   length = 17
```

```
FEATURE                 Location/Qualifiers
REGION                  1..17
                        note = 4P5 VH CDR2 - Exemplary
source                  1..17
                        mol_type = protein
                        organism = synthetic construct
SEQUENCE: 158
WIYPGDDSTK YNEKFKG                                                     17

SEQ ID NO: 159          moltype = AA  length = 11
FEATURE                 Location/Qualifiers
REGION                  1..11
                        note = 4P5 VH CDR3 - Exemplary
source                  1..11
                        mol_type = protein
                        organism = synthetic construct
SEQUENCE: 159
SDYYGSRSFV Y                                                           11

SEQ ID NO: 160          moltype = AA  length = 15
FEATURE                 Location/Qualifiers
REGION                  1..15
                        note = 4P5 VL CDR1 - Exemplary
source                  1..15
                        mol_type = protein
                        organism = synthetic construct
SEQUENCE: 160
RASKSVSTSG YSYMH                                                       15

SEQ ID NO: 161          moltype = AA  length = 7
FEATURE                 Location/Qualifiers
REGION                  1..7
                        note = 4P5 VL CDR2 - Exemplary
source                  1..7
                        mol_type = protein
                        organism = synthetic construct
SEQUENCE: 161
LASNLES                                                                7

SEQ ID NO: 162          moltype = AA  length = 9
FEATURE                 Location/Qualifiers
REGION                  1..9
                        note = 4P5 VL CDR3 - Exemplary
source                  1..9
                        mol_type = protein
                        organism = synthetic construct
SEQUENCE: 162
HHSGELPYT                                                              9

SEQ ID NO: 163          moltype = AA  length = 8
FEATURE                 Location/Qualifiers
REGION                  1..8
                        note = 4P5 VH CDR1 - IMGT
source                  1..8
                        mol_type = protein
                        organism = synthetic construct
SEQUENCE: 163
GYTFTRYD                                                               8

SEQ ID NO: 164          moltype = AA  length = 8
FEATURE                 Location/Qualifiers
REGION                  1..8
                        note = 4P5 VH CDR2 - IMGT
source                  1..8
                        mol_type = protein
                        organism = synthetic construct
SEQUENCE: 164
IYPGDDST                                                               8

SEQ ID NO: 165          moltype = AA  length = 13
FEATURE                 Location/Qualifiers
REGION                  1..13
                        note = 4P5 VH CDR3 - IMGT
source                  1..13
                        mol_type = protein
                        organism = synthetic construct
SEQUENCE: 165
ARSDYYGSRS FVY                                                         13
```

| | | |
|---|---|---|
| SEQ ID NO: 166 | moltype = AA length = 10 | |
| FEATURE | Location/Qualifiers | |
| REGION | 1..10 | |
| | note = 4P5 VL CDR1- IMGT | |
| source | 1..10 | |
| | mol_type = protein | |
| | organism = synthetic construct | |
| SEQUENCE: 166 | | |
| KSVSTSGYSY | | 10 |
| | | |
| SEQ ID NO: 167 | moltype =    length = | |
| SEQUENCE: 167 | | |
| 000 | | |
| | | |
| SEQ ID NO: 168 | moltype = AA length = 5 | |
| FEATURE | Location/Qualifiers | |
| REGION | 1..5 | |
| | note = 4P5 VH CDR1 - Kabat | |
| source | 1..5 | |
| | mol_type = protein | |
| | organism = synthetic construct | |
| SEQUENCE: 168 | | |
| RYDIN | | 5 |
| | | |
| SEQ ID NO: 169 | moltype = AA length = 7 | |
| FEATURE | Location/Qualifiers | |
| REGION | 1..7 | |
| | note = 4P5 VH CDR1 - Chothia | |
| source | 1..7 | |
| | mol_type = protein | |
| | organism = synthetic construct | |
| SEQUENCE: 169 | | |
| GYTFTRY | | 7 |
| | | |
| SEQ ID NO: 170 | moltype = AA length = 4 | |
| FEATURE | Location/Qualifiers | |
| REGION | 1..4 | |
| | note = 4P5 VH CDR2 - Chothia | |
| source | 1..4 | |
| | mol_type = protein | |
| | organism = synthetic construct | |
| SEQUENCE: 170 | | |
| PGDD | | 4 |
| | | |
| SEQ ID NO: 171 | moltype = AA length = 9 | |
| FEATURE | Location/Qualifiers | |
| REGION | 1..9 | |
| | note = 4P5 VH CDR3 - Chothia | |
| source | 1..9 | |
| | mol_type = protein | |
| | organism = synthetic construct | |
| SEQUENCE: 171 | | |
| DYYGSRSFV | | 9 |
| | | |
| SEQ ID NO: 172 | moltype = AA length = 11 | |
| FEATURE | Location/Qualifiers | |
| REGION | 1..11 | |
| | note = 4P5 VL CDR1- Chothia | |
| source | 1..11 | |
| | mol_type = protein | |
| | organism = synthetic construct | |
| SEQUENCE: 172 | | |
| SKSVSTSGYS Y | | 11 |
| | | |
| SEQ ID NO: 173 | moltype = AA length = 6 | |
| FEATURE | Location/Qualifiers | |
| REGION | 1..6 | |
| | note = 4P5 VL CDR3- Chothia | |
| source | 1..6 | |
| | mol_type = protein | |
| | organism = synthetic construct | |
| SEQUENCE: 173 | | |
| SGELPY | | 6 |
| | | |
| SEQ ID NO: 174 | moltype = AA length = 6 | |
| FEATURE | Location/Qualifiers | |
| REGION | 1..6 | |
| | note = 4P5 VH CDR1 - Contact | |
| source | 1..6 | |

-continued

```
                           mol_type = protein
                           organism = synthetic construct
SEQUENCE: 174
TRYDIN                                                                 6

SEQ ID NO: 175             moltype = AA    length = 13
FEATURE                    Location/Qualifiers
REGION                     1..13
                           note = 4P5 VH CDR2 - Contact
source                     1..13
                           mol_type = protein
                           organism = synthetic construct
SEQUENCE: 175
WIGWIYPGDD STK                                                        13

SEQ ID NO: 176             moltype = AA    length = 12
FEATURE                    Location/Qualifiers
REGION                     1..12
                           note = 4P5 VH CDR3 - Contact
source                     1..12
                           mol_type = protein
                           organism = synthetic construct
SEQUENCE: 176
ARSDYYGSRS FV                                                         12

SEQ ID NO: 177             moltype = AA    length = 11
FEATURE                    Location/Qualifiers
REGION                     1..11
                           note = 4P5 VL CDR1- Contact
source                     1..11
                           mol_type = protein
                           organism = synthetic construct
SEQUENCE: 177
STSGYSYMHW Y                                                          11

SEQ ID NO: 178             moltype = AA    length = 10
FEATURE                    Location/Qualifiers
REGION                     1..10
                           note = 4P5 VL CDR2- Contact
source                     1..10
                           mol_type = protein
                           organism = synthetic construct
SEQUENCE: 178
LLIYLASNLE                                                            10

SEQ ID NO: 179             moltype = AA    length = 8
FEATURE                    Location/Qualifiers
REGION                     1..8
                           note = 4P5 VL CDR3- Contact
source                     1..8
                           mol_type = protein
                           organism = synthetic construct
SEQUENCE: 179
HHSGELPY                                                               8

SEQ ID NO: 180             moltype = AA    length = 10
FEATURE                    Location/Qualifiers
REGION                     1..10
                           note = 4P5 VH CDR2 - AbM
source                     1..10
                           mol_type = protein
                           organism = synthetic construct
SEQUENCE: 180
WIYPGDDSTK                                                            10

SEQ ID NO: 181             moltype = AA    length = 120
FEATURE                    Location/Qualifiers
REGION                     1..120
                           note = 4P5 VH Sequence
source                     1..120
                           mol_type = protein
                           organism = synthetic construct
SEQUENCE: 181
QVQLQQSGPE LVKPGALVKI SCKASGYTFT RYDINWVKKR PGQGLEWIGW IYPGDDSTKY      60
NEKFKGKATL TADKSSSTAY MQLSSLTSEN SAVYFCARSD YYGSRSFVYW GQGTLVTVSA     120

SEQ ID NO: 182             moltype = AA    length = 111
FEATURE                    Location/Qualifiers
REGION                     1..111
```

```
                    note = 4P5 VL Sequence
source              1..111
                    mol_type = protein
                    organism = synthetic construct
SEQUENCE: 182
DILLTQSPAS LAVSLGQRAT ISCRASKSVS TSGYSYMHWY QQKPGQPPKL LIYLASNLES    60
GVPARFSGRG SGTDFTLNIH PVEEEDAATY YCHHSGELPY TFGGGTKLEI K            111

SEQ ID NO: 183      moltype = AA  length = 10
FEATURE             Location/Qualifiers
REGION              1..10
                    note = 5C23 VH CDR1- Exemplary
source              1..10
                    mol_type = protein
                    organism = synthetic construct
SEQUENCE: 183
GYTFTRYDIN                                                           10

SEQ ID NO: 184      moltype = AA  length = 17
FEATURE             Location/Qualifiers
REGION              1..17
                    note = 5C23 VH CDR2- Exemplary
source              1..17
                    mol_type = protein
                    organism = synthetic construct
SEQUENCE: 184
WIYPGDGSTK YNEKFEG                                                   17

SEQ ID NO: 185      moltype = AA  length = 11
FEATURE             Location/Qualifiers
REGION              1..11
                    note = 5C23 VH CDR3- Exemplary
source              1..11
                    mol_type = protein
                    organism = synthetic construct
SEQUENCE: 185
SDYYGSRSFV Y                                                         11

SEQ ID NO: 186      moltype = AA  length = 15
FEATURE             Location/Qualifiers
REGION              1..15
                    note = 5C23 VL CDR1- Exemplary
source              1..15
                    mol_type = protein
                    organism = synthetic construct
SEQUENCE: 186
RASKSVSTSG YSYMH                                                     15

SEQ ID NO: 187      moltype = AA  length = 7
FEATURE             Location/Qualifiers
REGION              1..7
                    note = 5C23 VL CDR2- Exemplary
source              1..7
                    mol_type = protein
                    organism = synthetic construct
SEQUENCE: 187
LASNLES                                                               7

SEQ ID NO: 188      moltype = AA  length = 9
FEATURE             Location/Qualifiers
REGION              1..9
                    note = 5C23 VL CDR3- Exemplary
source              1..9
                    mol_type = protein
                    organism = synthetic construct
SEQUENCE: 188
QHSRELPYT                                                             9

SEQ ID NO: 189      moltype = AA  length = 8
FEATURE             Location/Qualifiers
REGION              1..8
                    note = 5C23 VH CDR1 - IMGT
source              1..8
                    mol_type = protein
                    organism = synthetic construct
SEQUENCE: 189
GYTFTRYD                                                              8

SEQ ID NO: 190      moltype = AA  length = 8
```

```
FEATURE                 Location/Qualifiers
REGION                  1..8
                        note = 5C23 VH CDR2 - IMGT
source                  1..8
                        mol_type = protein
                        organism = synthetic construct
SEQUENCE: 190
IYPGDGST                                                                    8

SEQ ID NO: 191          moltype = AA  length = 13
FEATURE                 Location/Qualifiers
REGION                  1..13
                        note = 5C23 VH CDR3 - IMGT
source                  1..13
                        mol_type = protein
                        organism = synthetic construct
SEQUENCE: 191
ARSDYYGSRS FVY                                                             13

SEQ ID NO: 192          moltype = AA  length = 10
FEATURE                 Location/Qualifiers
REGION                  1..10
                        note = 5C23 VL CDR1- IMGT
source                  1..10
                        mol_type = protein
                        organism = synthetic construct
SEQUENCE: 192
KSVSTSGYSY                                                                 10

SEQ ID NO: 193          moltype =    length =
SEQUENCE: 193
000

SEQ ID NO: 194          moltype = AA  length = 5
FEATURE                 Location/Qualifiers
REGION                  1..5
                        note = 5C23 VH CDR1 - Kabat
source                  1..5
                        mol_type = protein
                        organism = synthetic construct
SEQUENCE: 194
RYDIN                                                                       5

SEQ ID NO: 195          moltype = AA  length = 7
FEATURE                 Location/Qualifiers
REGION                  1..7
                        note = 5C23 VH CDR1 - Chothia
source                  1..7
                        mol_type = protein
                        organism = synthetic construct
SEQUENCE: 195
GYTFTRY                                                                     7

SEQ ID NO: 196          moltype = AA  length = 4
FEATURE                 Location/Qualifiers
REGION                  1..4
                        note = 5C23 VH CDR2 - Chothia
source                  1..4
                        mol_type = protein
                        organism = synthetic construct
SEQUENCE: 196
PGDG                                                                        4

SEQ ID NO: 197          moltype = AA  length = 9
FEATURE                 Location/Qualifiers
REGION                  1..9
                        note = 5C23 VH CDR3 - Chothia
source                  1..9
                        mol_type = protein
                        organism = synthetic construct
SEQUENCE: 197
DYYGSRSFV                                                                   9

SEQ ID NO: 198          moltype = AA  length = 11
FEATURE                 Location/Qualifiers
REGION                  1..11
                        note = 5C23 VL CDR1- Chothia
source                  1..11
                        mol_type = protein
```

-continued

```
                        organism = synthetic construct
SEQUENCE: 198
SKSVSTSGYS Y                                                               11

SEQ ID NO: 199          moltype = AA   length = 6
FEATURE                 Location/Qualifiers
REGION                  1..6
                        note = 5C23 VL CDR3- Chothia
source                  1..6
                        mol_type = protein
                        organism = synthetic construct
SEQUENCE: 199
SRELPY                                                                     6

SEQ ID NO: 200          moltype = AA   length = 6
FEATURE                 Location/Qualifiers
REGION                  1..6
                        note = 5C23 VH CDR1 - Contact
source                  1..6
                        mol_type = protein
                        organism = synthetic construct
SEQUENCE: 200
TRYDIN                                                                     6

SEQ ID NO: 201          moltype = AA   length = 13
FEATURE                 Location/Qualifiers
REGION                  1..13
                        note = 5C23 VH CDR2 - Contact
source                  1..13
                        mol_type = protein
                        organism = synthetic construct
SEQUENCE: 201
WIGWIYPGDG STK                                                             13

SEQ ID NO: 202          moltype = AA   length = 12
FEATURE                 Location/Qualifiers
REGION                  1..12
                        note = 5C23 VH CDR3 - Contact
source                  1..12
                        mol_type = protein
                        organism = synthetic construct
SEQUENCE: 202
ARSDYYGSRS FV                                                              12

SEQ ID NO: 203          moltype = AA   length = 11
FEATURE                 Location/Qualifiers
REGION                  1..11
                        note = 5C23 VL CDR1 - Contact
source                  1..11
                        mol_type = protein
                        organism = synthetic construct
SEQUENCE: 203
STSGYSYMHW Y                                                               11

SEQ ID NO: 204          moltype = AA   length = 10
FEATURE                 Location/Qualifiers
REGION                  1..10
                        note = 5C23 VL CDR2 - Contact
source                  1..10
                        mol_type = protein
                        organism = synthetic construct
SEQUENCE: 204
LLIYLASNLE                                                                 10

SEQ ID NO: 205          moltype = AA   length = 8
FEATURE                 Location/Qualifiers
REGION                  1..8
                        note = 5C23 VL CDR3 - Contact
source                  1..8
                        mol_type = protein
                        organism = synthetic construct
SEQUENCE: 205
QHSRELPY                                                                   8

SEQ ID NO: 206          moltype = AA   length = 10
FEATURE                 Location/Qualifiers
REGION                  1..10
                        note = 5C23 VH CDR2 - AbM
source                  1..10
```

```
                          mol_type = protein
                          organism = synthetic construct
SEQUENCE: 206
WIYPGDGSTK                                                              10

SEQ ID NO: 207            moltype = AA   length = 120
FEATURE                   Location/Qualifiers
REGION                    1..120
                          note = 5C23 VH Sequence
source                    1..120
                          mol_type = protein
                          organism = synthetic construct
SEQUENCE: 207
QVQPQESGPE LVKPGALVKI SCKASGYTFT RYDINWVKKR PGQGLEWIGW IYPGDGSTKY         60
NEKFEGKATL TADKSSSTAY MQLSSLTSEN SAVYFCARSD YYGSRSFVYW GQGTLVTVSA        120

SEQ ID NO: 208            moltype = AA   length = 111
FEATURE                   Location/Qualifiers
REGION                    1..111
                          note = 5C23 VL Sequence
source                    1..111
                          mol_type = protein
                          organism = synthetic construct
SEQUENCE: 208
DIVLTQSPDS LTVSLGQRAT ISCRASKSVS TSGYSYMHWY QQKPGQPPKL LIYLASNLES         60
GVPARFSGSG SGTDFTLNIH PVEEEDAATY YCQHSRELPY TFGGGTKLEI K                 111

SEQ ID NO: 209            moltype = AA   length = 10
FEATURE                   Location/Qualifiers
REGION                    1..10
                          note = 5F7 VH CDR1 - Exemplary
source                    1..10
                          mol_type = protein
                          organism = synthetic construct
SEQUENCE: 209
GYTFTRYDIN                                                              10

SEQ ID NO: 210            moltype = AA   length = 17
FEATURE                   Location/Qualifiers
REGION                    1..17
                          note = 5F7 VH CDR2 - Exemplary
source                    1..17
                          mol_type = protein
                          organism = synthetic construct
SEQUENCE: 210
WIYPGDISTK YNEKFKG                                                      17

SEQ ID NO: 211            moltype = AA   length = 11
FEATURE                   Location/Qualifiers
REGION                    1..11
                          note = 5F7 VH CDR3 - Exemplary
source                    1..11
                          mol_type = protein
                          organism = synthetic construct
SEQUENCE: 211
SDYYGSRSFV Y                                                            11

SEQ ID NO: 212            moltype = AA   length = 15
FEATURE                   Location/Qualifiers
REGION                    1..15
                          note = 5F7 VL CDR1- Exemplary
source                    1..15
                          mol_type = protein
                          organism = synthetic construct
SEQUENCE: 212
RASKSVSTSG YSYMH                                                        15

SEQ ID NO: 213            moltype = AA   length = 7
FEATURE                   Location/Qualifiers
REGION                    1..7
                          note = 5F7 VL CDR2- Exemplary
source                    1..7
                          mol_type = protein
                          organism = synthetic construct
SEQUENCE: 213
LASNLES                                                                 7

SEQ ID NO: 214            moltype = AA   length = 9
FEATURE                   Location/Qualifiers
```

```
REGION                      1..9
                            note = 5F7 VL CDR3- Exemplary
source                      1..9
                            mol_type = protein
                            organism = synthetic construct
SEQUENCE: 214
QHSRELPYT                                                                 9

SEQ ID NO: 215              moltype = AA  length = 8
FEATURE                     Location/Qualifiers
REGION                      1..8
                            note = 5F7 VH CDR1 - IMGT
source                      1..8
                            mol_type = protein
                            organism = synthetic construct
SEQUENCE: 215
GYTFTRYD                                                                  8

SEQ ID NO: 216              moltype = AA  length = 8
FEATURE                     Location/Qualifiers
REGION                      1..8
                            note = 5F7 VH CDR2 - IMGT
source                      1..8
                            mol_type = protein
                            organism = synthetic construct
SEQUENCE: 216
IYPGDIST                                                                  8

SEQ ID NO: 217              moltype = AA  length = 13
FEATURE                     Location/Qualifiers
REGION                      1..13
                            note = 5F7 VH CDR3 - IMGT
source                      1..13
                            mol_type = protein
                            organism = synthetic construct
SEQUENCE: 217
ARSDYYGSRS FVY                                                           13

SEQ ID NO: 218              moltype = AA  length = 10
FEATURE                     Location/Qualifiers
REGION                      1..10
                            note = 5F7 VL CDR1- IMGT
source                      1..10
                            mol_type = protein
                            organism = synthetic construct
SEQUENCE: 218
KSVSTSGYSY                                                               10

SEQ ID NO: 219              moltype =     length =
SEQUENCE: 219
000

SEQ ID NO: 220              moltype = AA  length = 5
FEATURE                     Location/Qualifiers
REGION                      1..5
                            note = 5F7 VH CDR1 - Kabat
source                      1..5
                            mol_type = protein
                            organism = synthetic construct
SEQUENCE: 220
RYDIN                                                                     5

SEQ ID NO: 221              moltype = AA  length = 7
FEATURE                     Location/Qualifiers
REGION                      1..7
                            note = 5F7 VH CDR1 - Chothia
source                      1..7
                            mol_type = protein
                            organism = synthetic construct
SEQUENCE: 221
GYTFTRY                                                                   7

SEQ ID NO: 222              moltype = AA  length = 4
FEATURE                     Location/Qualifiers
REGION                      1..4
                            note = 5F7 VH CDR2 - Chothia
source                      1..4
                            mol_type = protein
                            organism = synthetic construct
```

```
SEQUENCE: 222
PGDI                                                                              4

SEQ ID NO: 223           moltype = AA   length = 9
FEATURE                  Location/Qualifiers
REGION                   1..9
                         note = 5F7 VH CDR3 - Chothia
source                   1..9
                         mol_type = protein
                         organism = synthetic construct
SEQUENCE: 223
DYYGSRSFV                                                                         9

SEQ ID NO: 224           moltype = AA   length = 11
FEATURE                  Location/Qualifiers
REGION                   1..11
                         note = 5F7 VL CDR1 - Chothia
source                   1..11
                         mol_type = protein
                         organism = synthetic construct
SEQUENCE: 224
SKSVSTSGYS Y                                                                     11

SEQ ID NO: 225           moltype = AA   length = 6
FEATURE                  Location/Qualifiers
REGION                   1..6
                         note = 5F7 VL CDR3 - Chothia
source                   1..6
                         mol_type = protein
                         organism = synthetic construct
SEQUENCE: 225
SRELPY                                                                            6

SEQ ID NO: 226           moltype = AA   length = 6
FEATURE                  Location/Qualifiers
REGION                   1..6
                         note = 5F7 VH CDR1 - Contact
source                   1..6
                         mol_type = protein
                         organism = synthetic construct
SEQUENCE: 226
TRYDIN                                                                            6

SEQ ID NO: 227           moltype = AA   length = 13
FEATURE                  Location/Qualifiers
REGION                   1..13
                         note = 5F7 VH CDR2 - Contact
source                   1..13
                         mol_type = protein
                         organism = synthetic construct
SEQUENCE: 227
WIGWIYPGDI STK                                                                   13

SEQ ID NO: 228           moltype = AA   length = 12
FEATURE                  Location/Qualifiers
REGION                   1..12
                         note = 5F7 VH CDR3 - Contact
source                   1..12
                         mol_type = protein
                         organism = synthetic construct
SEQUENCE: 228
ARSDYYGSRS FV                                                                    12

SEQ ID NO: 229           moltype = AA   length = 11
FEATURE                  Location/Qualifiers
REGION                   1..11
                         note = 5F7 VL CDR1- Contact
source                   1..11
                         mol_type = protein
                         organism = synthetic construct
SEQUENCE: 229
STSGYSYMHW Y                                                                     11

SEQ ID NO: 230           moltype = AA   length = 10
FEATURE                  Location/Qualifiers
REGION                   1..10
                         note = 5F7 VL CDR2- Contact
source                   1..10
                         mol_type = protein
```

```
                        organism = synthetic construct
SEQUENCE: 230
LLIYLASNLE                                                                  10

SEQ ID NO: 231          moltype = AA  length = 8
FEATURE                 Location/Qualifiers
REGION                  1..8
                        note = 5F7 VL CDR3- Contact
source                  1..8
                        mol_type = protein
                        organism = synthetic construct
SEQUENCE: 231
QHSRELPY                                                                    8

SEQ ID NO: 232          moltype = AA  length = 10
FEATURE                 Location/Qualifiers
REGION                  1..10
                        note = 5F7 VH CDR2 - AbM
source                  1..10
                        mol_type = protein
                        organism = synthetic construct
SEQUENCE: 232
WIYPGDISTK                                                                  10

SEQ ID NO: 233          moltype = AA  length = 120
FEATURE                 Location/Qualifiers
REGION                  1..120
                        note = 5F7 VH Sequence
source                  1..120
                        mol_type = protein
                        organism = synthetic construct
SEQUENCE: 233
QVQPQESGPE LVKPGALVKI SCKASGYTFT RYDINWVKQR PGQGLEWIGW IYPGDISTKY           60
NEKFKGKATL TADKSSSTAY MQLNSLTSEN SAVYFCARSD YYGSRSFVYW GQGTLVTVSA          120

SEQ ID NO: 234          moltype = AA  length = 111
FEATURE                 Location/Qualifiers
REGION                  1..111
                        note = 5F7 VL Sequence
source                  1..111
                        mol_type = protein
                        organism = synthetic construct
SEQUENCE: 234
DIVLTQSPAS LAVSLGQRAT ISCRASKSVS TSGYSYMHWY QQKPGQPPKL LIYLASNLES           60
GVPARFSGSG SGTDFTLNIH PVEEEDAATY YCQHSRELPY TFGGGTKVEI K                  111

SEQ ID NO: 235          moltype = AA  length = 11
FEATURE                 Location/Qualifiers
REGION                  1..11
                        note = 1G19 VH CDR1- Exemplary
source                  1..11
                        mol_type = protein
                        organism = synthetic construct
SEQUENCE: 235
GYSITSGYYW N                                                                11

SEQ ID NO: 236          moltype = AA  length = 16
FEATURE                 Location/Qualifiers
REGION                  1..16
                        note = 1G19 VH CDR2- Exemplary
source                  1..16
                        mol_type = protein
                        organism = synthetic construct
SEQUENCE: 236
YINYGGSNNY NPSLKN                                                           16

SEQ ID NO: 237          moltype = AA  length = 13
FEATURE                 Location/Qualifiers
REGION                  1..13
                        note = 1G19 VH CDR3- Exemplary
source                  1..13
                        mol_type = protein
                        organism = synthetic construct
SEQUENCE: 237
RGAYYSNYDS FDV                                                              13

SEQ ID NO: 238          moltype = AA  length = 11
FEATURE                 Location/Qualifiers
REGION                  1..11
```

```
                              note = 1G19 VL CDR1- Exemplary
source                        1..11
                              mol_type = protein
                              organism = synthetic construct
SEQUENCE: 238
KASQDINSYL S                                                          11

SEQ ID NO: 239                moltype = AA  length = 7
FEATURE                       Location/Qualifiers
REGION                        1..7
                              note = 1G19 VL CDR2- Exemplary
source                        1..7
                              mol_type = protein
                              organism = synthetic construct
SEQUENCE: 239
RANRLVD                                                                7

SEQ ID NO: 240                moltype = AA  length = 9
FEATURE                       Location/Qualifiers
REGION                        1..9
                              note = 1G19 VL CDR3- Exemplary
source                        1..9
                              mol_type = protein
                              organism = synthetic construct
SEQUENCE: 240
LQYDEFPYT                                                              9

SEQ ID NO: 241                moltype = AA  length = 9
FEATURE                       Location/Qualifiers
REGION                        1..9
                              note = 1G19 VH CDR1 - IMGT
source                        1..9
                              mol_type = protein
                              organism = synthetic construct
SEQUENCE: 241
GYSITSGYY                                                              9

SEQ ID NO: 242                moltype = AA  length = 7
FEATURE                       Location/Qualifiers
REGION                        1..7
                              note = 1G19 VH CDR2 - IMGT
source                        1..7
                              mol_type = protein
                              organism = synthetic construct
SEQUENCE: 242
INYGGSN                                                                7

SEQ ID NO: 243                moltype = AA  length = 15
FEATURE                       Location/Qualifiers
REGION                        1..15
                              note = 1G19 VH CDR3 - IMGT
source                        1..15
                              mol_type = protein
                              organism = synthetic construct
SEQUENCE: 243
ARRGAYYSNY DSFDV                                                      15

SEQ ID NO: 244                moltype = AA  length = 6
FEATURE                       Location/Qualifiers
REGION                        1..6
                              note = 1G19 VL CDR1 - IMGT
source                        1..6
                              mol_type = protein
                              organism = synthetic construct
SEQUENCE: 244
QDINSY                                                                 6

SEQ ID NO: 245                moltype =    length =
SEQUENCE: 245
000

SEQ ID NO: 246                moltype = AA  length = 6
FEATURE                       Location/Qualifiers
REGION                        1..6
                              note = 1G19 VH CDR1 - Kabat
source                        1..6
                              mol_type = protein
                              organism = synthetic construct
SEQUENCE: 246
```

```
SGYYWN                                                                                6

SEQ ID NO: 247       moltype = AA   length = 8
FEATURE              Location/Qualifiers
REGION               1..8
                     note = 1G19 VH CDR1 - Chothia
source               1..8
                     mol_type = protein
                     organism = synthetic construct
SEQUENCE: 247
GYSITSGY                                                                              8

SEQ ID NO: 248       moltype =    length =
SEQUENCE: 248
000

SEQ ID NO: 249       moltype = AA   length = 11
FEATURE              Location/Qualifiers
REGION               1..11
                     note = 1G19 VH CDR3 - Chothia
source               1..11
                     mol_type = protein
                     organism = synthetic construct
SEQUENCE: 249
GAYYSNYDSF D                                                                         11

SEQ ID NO: 250       moltype = AA   length = 7
FEATURE              Location/Qualifiers
REGION               1..7
                     note = 1G19 VL CDR1- Chothia
source               1..7
                     mol_type = protein
                     organism = synthetic construct
SEQUENCE: 250
SQDINSY                                                                               7

SEQ ID NO: 251       moltype = AA   length = 6
FEATURE              Location/Qualifiers
REGION               1..6
                     note = 1G19 VL CDR3- Chothia
source               1..6
                     mol_type = protein
                     organism = synthetic construct
SEQUENCE: 251
YDEFPY                                                                                6

SEQ ID NO: 252       moltype = AA   length = 7
FEATURE              Location/Qualifiers
REGION               1..7
                     note = 1G19 VH CDR1 - Contact
source               1..7
                     mol_type = protein
                     organism = synthetic construct
SEQUENCE: 252
TSGYYWN                                                                               7

SEQ ID NO: 253       moltype = AA   length = 12
FEATURE              Location/Qualifiers
REGION               1..12
                     note = 1G19 VH CDR2 - Contact
source               1..12
                     mol_type = protein
                     organism = synthetic construct
SEQUENCE: 253
WMGYINYGGS NN                                                                        12

SEQ ID NO: 254       moltype = AA   length = 14
FEATURE              Location/Qualifiers
REGION               1..14
                     note = 1G19 VH CDR3 - Contact
source               1..14
                     mol_type = protein
                     organism = synthetic construct
SEQUENCE: 254
ARRGAYYSNY DSFD                                                                      14

SEQ ID NO: 255       moltype = AA   length = 7
FEATURE              Location/Qualifiers
REGION               1..7
```

```
                        note = 1G19 VL CDR1 - Contact
source                  1..7
                        mol_type = protein
                        organism = synthetic construct
SEQUENCE: 255
NSYLSWF                                                                   7

SEQ ID NO: 256          moltype = AA  length = 10
FEATURE                 Location/Qualifiers
REGION                  1..10
                        note = 1G19 VL CDR2 - Contact
source                  1..10
                        mol_type = protein
                        organism = synthetic construct
SEQUENCE: 256
TLIYRANRLV                                                               10

SEQ ID NO: 257          moltype = AA  length = 8
FEATURE                 Location/Qualifiers
REGION                  1..8
                        note = 1G19 VL CDR3 - Contact
source                  1..8
                        mol_type = protein
                        organism = synthetic construct
SEQUENCE: 257
LQYDEFPY                                                                  8

SEQ ID NO: 258          moltype = AA  length = 9
FEATURE                 Location/Qualifiers
REGION                  1..9
                        note = 1G19 VH CDR2 - AbM
source                  1..9
                        mol_type = protein
                        organism = synthetic construct
SEQUENCE: 258
YINYGGSNN                                                                 9

SEQ ID NO: 259          moltype = AA  length = 122
FEATURE                 Location/Qualifiers
REGION                  1..122
                        note = 1G19 VH Sequence
source                  1..122
                        mol_type = protein
                        organism = synthetic construct
SEQUENCE: 259
QVQLQESGPG LVKPSQSLSL TCSVTGYSIT SGYYWNWIRQ FPGNKLEWMG YINYGGSNNY        60
NPSLKNRISI TRDTSKNQFF LKLTSVTTED TATYYCARRG AYYSNYDSFD VWGTGTTVTV       120
SS                                                                     122

SEQ ID NO: 260          moltype = AA  length = 107
FEATURE                 Location/Qualifiers
REGION                  1..107
                        note = 1G19 VL Sequence
source                  1..107
                        mol_type = protein
                        organism = synthetic construct
SEQUENCE: 260
DIKMTQSPSS MYASLGERVT ITCKASQDIN SYLSWFQQKP GKSPKTLIYR ANRLVDGVPS        60
RFSGSGSGQD YSLTISSLEY EEMGIYYCLQ YDEFPYTFGG GTKLEIK                     107

SEQ ID NO: 261          moltype = AA  length = 10
FEATURE                 Location/Qualifiers
REGION                  1..10
                        note = consensus CDR1 sequence of anti-beta klotho
                         antibodies VH domain
VARIANT                 6
                        note = Xaa = Arg or Ser
source                  1..10
                        mol_type = protein
                        organism = synthetic construct
SEQUENCE: 261
GYTFTXYDIN                                                               10

SEQ ID NO: 262          moltype = AA  length = 17
FEATURE                 Location/Qualifiers
REGION                  1..17
                        note = consensus CDR2 sequence of anti-beta klotho
                         antibodies VH domain
VARIANT                 7
```

```
                          note = Xaa = Gly, Asp, Ser or Ile
source                    1..17
                          mol_type = protein
                          organism = synthetic construct
SEQUENCE: 262
WIYPGDXSTK YNEKFKG                                                      17

SEQ ID NO: 263            moltype = AA  length = 11
FEATURE                   Location/Qualifiers
REGION                    1..11
                          note = consensus CDR2 sequence of anti-beta klotho
                           antibodies VH domain
VARIANT                   10
                          note = Xaa = Val, Thr or Ala
source                    1..11
                          mol_type = protein
                          organism = synthetic construct
SEQUENCE: 263
SDYYGSRSFX Y                                                            11

SEQ ID NO: 264            moltype = AA  length = 16
FEATURE                   Location/Qualifiers
REGION                    1..16
                          note = consensus CDR3 sequence of anti-beta klotho
                           antibodies VH domain
VARIANT                   5
                          note = Xaa = Asp or Gly
VARIANT                   7
                          note = Xaa = Asn or Ser
VARIANT                   8
                          note = Xaa = Ser or Asn
VARIANT                   11
                          note = Xaa = Thr or Asn
source                    1..16
                          mol_type = protein
                          organism = synthetic construct
SEQUENCE: 264
YINYXGXXNY XPSLKN                                                       16

SEQ ID NO: 265            moltype = AA  length = 13
FEATURE                   Location/Qualifiers
REGION                    1..13
                          note = consensus CDR3 sequence of anti-beta klotho
                           antibodies VH domain
VARIANT                   1
                          note = Xaa = Lys or Arg
source                    1..13
                          mol_type = protein
                          organism = synthetic construct
SEQUENCE: 265
XGAYYSNYDS FDV                                                          13

SEQ ID NO: 266            moltype = AA  length = 15
FEATURE                   Location/Qualifiers
REGION                    1..15
                          note = consensus CDR1 sequence of anti-beta klotho
                           antibodies VL domain
VARIANT                   14
                          note = Xaa = Met, Leu or Val
source                    1..15
                          mol_type = protein
                          organism = synthetic construct
SEQUENCE: 266
RASKSVSTSG YSYXH                                                        15

SEQ ID NO: 267            moltype = AA  length = 9
FEATURE                   Location/Qualifiers
REGION                    1..9
                          note = consensus CDR3 sequence of anti-beta klotho
                           antibodies VL domain
VARIANT                   1
                          note = Xaa = Gln or His
VARIANT                   4
                          note = Xaa = Arg or Gly
source                    1..9
                          mol_type = protein
                          organism = synthetic construct
SEQUENCE: 267
XHSXELPYT                                                                9
```

```
SEQ ID NO: 268            moltype = AA   length = 9
FEATURE                   Location/Qualifiers
REGION                    1..9
                          note = consensus CDR3 sequence of anti-beta klotho
                           antibodies VL domain
VARIANT                   8
                          note = Xaa = Phe or Tyr
source                    1..9
                          mol_type = protein
                          organism = synthetic construct
SEQUENCE: 268
LQYDEFPXT                                                                  9

SEQ ID NO: 269            moltype = AA   length = 120
FEATURE                   Location/Qualifiers
REGION                    1..120
                          note = vH1
source                    1..120
                          mol_type = protein
                          organism = synthetic construct
SEQUENCE: 269
QVQLVQSGAE VKKPGASVKV SCKASGYTFT SYDINWVRQA PGQGLEWMGW IYPGDGSTKY    60
NEKFKGRVTI TRDTSASTAY MELSSLRSED TAVYYCARSD YYGSRSFAYW GQGTLVTVSS   120

SEQ ID NO: 270            moltype = AA   length = 120
FEATURE                   Location/Qualifiers
REGION                    1..120
                          note = vH2
source                    1..120
                          mol_type = protein
                          organism = synthetic construct
SEQUENCE: 270
QVQLVQSGPE VKKPGASVKV SCKASGYTFT SYDINWVRQR PGQGLEWMGW IYPGDGSTKY    60
NEKFKGRVTI TADKSARTAY MELSSLTSED TAVYYCARSD YYGSRSFAYW GQGTLVTVSS   120

SEQ ID NO: 271            moltype = AA   length = 120
FEATURE                   Location/Qualifiers
REGION                    1..120
                          note = vH3
source                    1..120
                          mol_type = protein
                          organism = synthetic construct
SEQUENCE: 271
QVQLQQSGAE VKKPGASVKV SCKASGYTFT SYDINWVRQA PGQGLEWIGW IYPGDGSTKY    60
NEKFKGKATI TRDTSASTAY MELSSLRSED TAVYFCARSD YYGSRSFAYW GQGTLVTVSS   120

SEQ ID NO: 272            moltype = AA   length = 120
FEATURE                   Location/Qualifiers
REGION                    1..120
                          note = vH4
source                    1..120
                          mol_type = protein
                          organism = synthetic construct
SEQUENCE: 272
QVQLVQSGPE VKKPGASVKV SCKASGYTFT SYDINWVRQR PGQGLEWIGW IYPGDGSTKY    60
NEKFKGRVTI TADKSARTAY MELSSLTSED TAVYYCARSD YYGSRSFAYW GQGTLVTVSS   120

SEQ ID NO: 273            moltype = AA   length = 120
FEATURE                   Location/Qualifiers
REGION                    1..120
                          note = vH5
source                    1..120
                          mol_type = protein
                          organism = synthetic construct
SEQUENCE: 273
QVQLVQSGAE VKKPGASVKV SCKASGYTFT SYDINWVRQA PGQGLEWIGW IYPGDGSTKY    60
NEKFKGKATL TADTSASTAY MELSSLRSEN TAVYFCARSD YYGSRSFAYW GQGTLVTVSS   120

SEQ ID NO: 274            moltype = AA   length = 120
FEATURE                   Location/Qualifiers
REGION                    1..120
                          note = vH6
source                    1..120
                          mol_type = protein
                          organism = synthetic construct
SEQUENCE: 274
QVQLVQSGAE VKKPGASVKV SCKASGYTFT SYDINWVKQA PGQGLEWIGW IYPGDGSTKY    60
NEKFKGKATL TADKSARTAY MELSSLRSEN TAVYFCARSD YYGSRSFAYW GQGTLVTVSS   120
```

```
SEQ ID NO: 275          moltype = AA  length = 111
FEATURE                 Location/Qualifiers
REGION                  1..111
                        note = vL1
source                  1..111
                        mol_type = protein
                        organism = synthetic construct
SEQUENCE: 275
DIVLTQSPDS LAVSLGERAT INCRASKSVS TSGYVYMHWN QQKPGQPPKL LIYLASYLES    60
GVPDRFSGSG SGTDFTLTIS SVQAEDAAIY YCQHSRDLTF PFGGGTKLEI K           111

SEQ ID NO: 276          moltype = AA  length = 111
FEATURE                 Location/Qualifiers
REGION                  1..111
                        note = vL2
source                  1..111
                        mol_type = protein
                        organism = synthetic construct
SEQUENCE: 276
DIVMTQSPDS LAVSLGERAT INCRASKSVS TSGYVYMHWY QQKPGQPPKL LIYLASYLES    60
GVPDRFSGSG SGTDFTLTIS SVQAEDVAVY YCQHSRDLTF PFGGGTKLEI K           111

SEQ ID NO: 277          moltype = AA  length = 111
FEATURE                 Location/Qualifiers
REGION                  1..111
                        note = vL3
source                  1..111
                        mol_type = protein
                        organism = synthetic construct
SEQUENCE: 277
DIVMTQSPDS LAVSLGERAT INCRASKSVS TSGYVYMHWN QQKPGQPPKL LIYLASYLES    60
GVPDRFSGSG SGTDFTLTIS SVQAEDVAIY YCQHSRDLTF PFGGGTKLEI K           111

SEQ ID NO: 278          moltype = AA  length = 25
FEATURE                 Location/Qualifiers
REGION                  1..25
                        note = Humanized Anti-Beta Klotho VH FR1
source                  1..25
                        mol_type = protein
                        organism = synthetic construct
SEQUENCE: 278
QVQLVQSGAE VKKPGASVKV SCKAS                                         25

SEQ ID NO: 279          moltype = AA  length = 25
FEATURE                 Location/Qualifiers
REGION                  1..25
                        note = Humanized Anti-Beta Klotho VH FR1
source                  1..25
                        mol_type = protein
                        organism = synthetic construct
SEQUENCE: 279
QVQLQQSGAE VKKPGASVKV SCKAS                                         25

SEQ ID NO: 280          moltype = AA  length = 25
FEATURE                 Location/Qualifiers
REGION                  1..25
                        note = Humanized Anti-Beta Klotho VH FR1
source                  1..25
                        mol_type = protein
                        organism = synthetic construct
SEQUENCE: 280
QVQLVQSGPE VKKPGASVKV SCKAS                                         25

SEQ ID NO: 281          moltype = AA  length = 14
FEATURE                 Location/Qualifiers
REGION                  1..14
                        note = Humanized Anti-Beta Klotho VH FR2
source                  1..14
                        mol_type = protein
                        organism = synthetic construct
SEQUENCE: 281
WVRQAPGQGL EWMG                                                     14

SEQ ID NO: 282          moltype = AA  length = 14
FEATURE                 Location/Qualifiers
REGION                  1..14
                        note = Humanized Anti-Beta Klotho VH FR2
source                  1..14
```

```
                        mol_type = protein
                        organism = synthetic construct
SEQUENCE: 282
WVRQAPGQGL EWIG                                                        14

SEQ ID NO: 283          moltype = AA   length = 14
FEATURE                 Location/Qualifiers
REGION                  1..14
                        note = Humanized Anti-Beta Klotho VH FR2
source                  1..14
                        mol_type = protein
                        organism = synthetic construct
SEQUENCE: 283
WVKQAPGQGL EWIG                                                        14

SEQ ID NO: 284          moltype = AA   length = 32
FEATURE                 Location/Qualifiers
REGION                  1..32
                        note = Humanized Anti-Beta Klotho VH FR3
source                  1..32
                        mol_type = protein
                        organism = synthetic construct
SEQUENCE: 284
RVTITRDTSA STAYMELSSL RSEDTAVYYC AR                                    32

SEQ ID NO: 285          moltype = AA   length = 32
FEATURE                 Location/Qualifiers
REGION                  1..32
                        note = Humanized Anti-Beta Klotho VH FR3
source                  1..32
                        mol_type = protein
                        organism = synthetic construct
SEQUENCE: 285
KATITRDTSA STAYMELSSL RSEDTAVYFC AR                                    32

SEQ ID NO: 286          moltype = AA   length = 32
FEATURE                 Location/Qualifiers
REGION                  1..32
                        note = Humanized Anti-Beta Klotho VH FR3
source                  1..32
                        mol_type = protein
                        organism = synthetic construct
SEQUENCE: 286
KATLTADTSA STAYMELSSL RSENTAVYFC AR                                    32

SEQ ID NO: 287          moltype = AA   length = 32
FEATURE                 Location/Qualifiers
REGION                  1..32
                        note = Humanized Anti-Beta Klotho VH FR3
source                  1..32
                        mol_type = protein
                        organism = synthetic construct
SEQUENCE: 287
KATLTADKSA RTAYMELSSL RSENTAVYFC AR                                    32

SEQ ID NO: 288          moltype = AA   length = 11
FEATURE                 Location/Qualifiers
REGION                  1..11
                        note = Humanized Anti-Beta Klotho VH FR4
source                  1..11
                        mol_type = protein
                        organism = synthetic construct
SEQUENCE: 288
WGQGTLVTVS S                                                           11

SEQ ID NO: 289          moltype = AA   length = 23
FEATURE                 Location/Qualifiers
REGION                  1..23
                        note = Humanized Anti-Beta Klotho VL FR1
source                  1..23
                        mol_type = protein
                        organism = synthetic construct
SEQUENCE: 289
DIVLTQSPDS LAVSLGERAT INC                                              23

SEQ ID NO: 290          moltype = AA   length = 23
FEATURE                 Location/Qualifiers
REGION                  1..23
                        note = Humanized Anti-Beta Klotho VL FR1
```

```
source                  1..23
                        mol_type = protein
                        organism = synthetic construct
SEQUENCE: 290
DIVMTQSPDS LAVSLGERAT INC                                            23

SEQ ID NO: 291          moltype = AA   length = 15
FEATURE                 Location/Qualifiers
REGION                  1..15
                        note = Humanized Anti-Beta Klotho VL FR2
source                  1..15
                        mol_type = protein
                        organism = synthetic construct
SEQUENCE: 291
WNQQKPGQPP KLLIY                                                     15

SEQ ID NO: 292          moltype = AA   length = 15
FEATURE                 Location/Qualifiers
REGION                  1..15
                        note = Humanized Anti-Beta Klotho VL FR2
source                  1..15
                        mol_type = protein
                        organism = synthetic construct
SEQUENCE: 292
WYQQKPGQPP KLLIY                                                     15

SEQ ID NO: 293          moltype = AA   length = 32
FEATURE                 Location/Qualifiers
REGION                  1..32
                        note = Humanized Anti-Beta Klotho VL FR3
source                  1..32
                        mol_type = protein
                        organism = synthetic construct
SEQUENCE: 293
GVPDRFSGSG SGTDFTLTIS SVQAEDAAIY YC                                   32

SEQ ID NO: 294          moltype = AA   length = 32
FEATURE                 Location/Qualifiers
REGION                  1..32
                        note = Humanized Anti-Beta Klotho VL FR3
source                  1..32
                        mol_type = protein
                        organism = synthetic construct
SEQUENCE: 294
GVPDRFSGSG SGTDFTLTIS SVQAEDVAVY YC                                   32

SEQ ID NO: 295          moltype = AA   length = 32
FEATURE                 Location/Qualifiers
REGION                  1..32
                        note = Humanized Anti-Beta Klotho VL FR3
source                  1..32
                        mol_type = protein
                        organism = synthetic construct
SEQUENCE: 295
GVPDRFSGSG SGTDFTLTIS SVQAEDVAIY YC                                   32

SEQ ID NO: 296          moltype = AA   length = 10
FEATURE                 Location/Qualifiers
REGION                  1..10
                        note = Humanized Anti-Beta Klotho VL FR4
source                  1..10
                        mol_type = protein
                        organism = synthetic construct
SEQUENCE: 296
FGGGTKLEIK                                                           10

SEQ ID NO: 297          moltype = AA   length = 1044
FEATURE                 Location/Qualifiers
REGION                  1..1044
                        note = human beta klotho
source                  1..1044
                        mol_type = protein
                        organism = Homo sapiens
SEQUENCE: 297
MKPGCAAGSP GNEWIFFSTD EITTRYRNTM SNGGLQRSVI LSALILLRAV TGFSGDGRAI     60
WSKNPNFTPV NESQLFLYDT FPKNFFWGIG TGALQVEGSW KKDGKGPSIW DHFIHTHLKN    120
VSSTNGSSDS YIFLEKDLSA LDFIGVSFYQ FSISWPRLFP DGIVTVANAK GLQYYSTLLD    180
ALVLRNIEPI VTLYHWDLPL ALQEKYGGWK NDTIIDIFND YATYCFQMFG DRVKYWITIH    240
NPYLVAWHGY GTGMHAPGEK GNLAAVYTVG HNLIKAHSKV WHNYNTHFRP HQKGWLSITL    300
```

```
GSHWIEPNRS ENTMDIFKCQ QSMVSVLGWF ANPIHGDGDY PEGMRKKLFS VLPIFSEAEK    360
HEMRGTADFF AFSFGPNNFK PLNTMAKMGQ NVSLNLREAL NWIKLEYNNP RILIAENGWF    420
TDSRVKTEDT TAIYMMKNFL SQVLQAIRLD EIRVFGYTAW SLLDGFEWQD AYTIRRGLFY    480
VDFNSKQKER KPKSSAHYYK QIIRENGFSL KESTPDVQGQ FPCDFSWGVT ESVLKPESVA    540
SSPQFSDPHL YVWNATGNRL LHRVEGVRLK TRPAQCTDFV NIKKQLEMLA RMKVTHYRFA    600
LDWASVLPTG NLSAVNRQAL RYYRCVVSEG LKLGISAMVT LYYPTHAHLG LPEPLLHADG    660
WLNPSTAEAF QAYAGLCFQE LGDLVKLWIT INEPNRLSDI YNRSGNDTYG AAHNLLVAHA    720
LAWRLYDRQF RPSQRGAVSL SLHADWAEPA NPYADSHWRA AERFLQFEIA WFAEPLFKTG    780
DYPAAMREYI ASKHRRGLSS SALPRLTEAE RRLLKGTVDF CALNHFTTRF VMHEQLAGSR    840
YDSDRDIQFL QDITRLSSPT RLAVIPWGVR KLLRWVRRNY GDMDIYITAS GIDDQALEDD    900
RLRKYYLGKY LQEVLKAYLI DKVRIKGYYA FKLAEEKSKP RFGFFTSDFK AKSSIQFYNK    960
VISSRGFPFE NSSSRCSQTQ ENTECTVCLF LVQKKPLIFL GCCFFSTLVL LLSIAIFQRQ   1020
KRRKFWKAKN LQHIPLKKGK RVVS                                         1044

SEQ ID NO: 298           moltype = DNA   length = 3132
FEATURE                  Location/Qualifiers
misc_feature             1..3132
                         note = human beta klotho coding sequence
source                   1..3132
                         mol_type = genomic DNA
                         organism = Homo sapiens
SEQUENCE: 298
atgaagccag gctgtgcggc aggatctcca gggaatgaat ggattttctt cagcactgat      60
gaaataacca cacgctatag aatacaatg tccaacgggg gattgcaaag atctgtcatc     120
ctgtcagcac ttattctgct acgagctgtt actggattct tggagatgg aagagctata     180
tggtctaaaa atcctaattt tactccggta aatgaaagtc agctgttct ctatgacact     240
ttccctaaaa acttttttctg gggtattggg actggagcat tgcaagtgga agggagttga    300
aagaaggatg aaaaggacc ttctatatgg gatcatttca tccacacaca ccttaaaaat     360
gtcagcagca cgaatggttc cagtgacagt tatattttc tggaaaaaga cttatcagcc     420
ctggattta taggagtttc ttttttatcaa ttttcaattt cctggccaat gctttttccc     480
gatgaatag taacgttgc caacgcaaaa ggtctgcagt actacagtac tcttctggac     540
gctctagtgc ttagaaacat tgaacctata gttactttat accactggga tttgccttttg   600
gcactacaag aaaaatatgg ggggtggaaa atgatacca taatagatat cttcaatgac     660
tatgccacat actgtttcca gatgttttgg gaccgtgtca aatattgat tacaattcac     720
aacccatatc tagtggcttg gcatgggtat gggacaggta tgcatgcccc tggagaagaa     780
ggaaatttag cagctgtcta cactgtggga cacaacttga tcaaggctca ctcgaaagtt     840
tggcataact acaacacaca tttccgccca catcagaagg gttggttatc gatcacgttg     900
ggatctcatt ggatcgagcc aaaccggtcg gaaaacacga tggatatatt caaatgtcaa     960
caatccatg ttttctgtgct tggatggttt gccaaccta tccatgggga tggcgactat    1020
ccagagggga tgagaaagaa gttgttctcc gttctaccca ttttctctga agcagagaag    1080
catgagatga gaggcacagc tgatttcttt gcctttctt ttggacccaa caacttcaag     1140
ccctaaaca ccatggctaa aatgggacaa aatgtttcac ttaatttaag agaagcgctg    1200
aactggatta aactggaata caacaaccct cgaatcttga ttgctgagaa tggctggttc    1260
acagacagtc gtgtgaaaac agaagacacc acgccatct acatgatgaa gaatttcctc    1320
agccaggtgc ttcaagcaat aaggttagat gaaatacgag tgtttggtta tactgcctgg    1380
tctctcctgg atggctttga atggcaggat gcttacacca tccgccgagg attatttat    1440
gtggattta acagtaaaca gaaagagcgg aaacctaagt cttcagcaca ctactacaaa    1500
cagatcatac gagaaaatgg ttttttctta aaagagtcca cgccagatgt gcagggccag    1560
tttcctgtg acttctcctg ggtgtcact gaatctgttc ttaagcccga gtctgtggct    1620
tcgtccccac agttcagcga tcctcatctg tacgtgtgga acgccactgg caacagactg    1680
ttgcaccgag tggaagggtg gaggctgaaa acacgacccg ctcaatgcac agattttgta    1740
aacatcaaaa aacaacttga gatgttggca agaatgaaag tcaccacta ccggtttgct    1800
ctggattggg cctcggtcct tcccactgg aacctgtccg cggtgaaccg acaggccctg    1860
aggtactaca ggtgcgtggt cagtgagggg ctgaagcttg gcatctccgc gatggtcacc    1920
ctgtattatc cgacccacgc ccacctaggc ctccccgagc tctgttgca tgccgacggg    1980
tggctgaacc catcgacggc cgaggccttc caggcctacg ctgggctgtg cttccaggag    2040
ctggggggacc tggtgaagct ctggatcacc atcaacgagc ctaaccggct aagtgacatc    2100
tacaaccgct ctggcaacga cacctacggg gcggcgcaca acctgctggt ggcccacgcc    2160
ctggcctggc gcctctacga ccggcagttc aggccctcac agcgcgggc cgtgtcgctg    2220
tcgctgcaca cggactgggc ggaacccgcc aaccccatg ctgactcgca ctggagggcg    2280
gccgagcgct tcctgcagtt cgagatcgcc tggttcgccg agccgctctt caagaccggg    2340
gactaccccg cggccatgag ggaatacatt gcctccaagc accgacgggg gctttccagc    2400
tcggccctgc cgcgcctcac cgaggccgaa aggaggctgc tcaagggcac ggtcgacttc    2460
tgcgcgctca accacttcac cactaggttc gtgatgcacg agcagctgg cggcagccgc    2520
tacgactcgg acagggacat ccagtttctg caggacatca cccgcctgag ctcccccacg    2580
cgcctggctg tgattcctg gggggtgcgc aagctgctgc ggtgggtccg gaggaactac    2640
ggcgacatgg acatttacat caccgccagt ggcatcgacg accaggctct ggaggatgac    2700
cggctccgga gtactaccct agggaagtac cttcaggagg tgctgaaagc atacctgatt    2760
gataaagtca gaatcaaagg ctattatgca ttcaaactgg ctgaagagaa atctaaaccc    2820
agatttggat tcttcacatc tgattttaaa gctaaatcct caatacaatt ttacaacaaa    2880
gtgatcagca gcaggggctt ccctttttgag aacagtagtt ctagatgcag tcagacccaa    2940
gaaaatacag agtgcactgt ctgccttatt cttgtgcaga gaaaccact gatattcctg    3000
ggttgttgct tcttctccac cctggttcta ctcttatcaa ttgccatttt tcaaaggcag    3060
aagagaagaa agtttggaa agcaaaaac ttacaacaca taccattaaa gaaggcaag    3120
agagttgtta gc                                                      3132

SEQ ID NO: 299           moltype = AA    length = 1044
FEATURE                  Location/Qualifiers
REGION                   1..1044
```

|  | note = cynomolgus monkey (cyno) beta klotho |
| --- | --- |
| source | 1..1044 |
|  | mol_type = protein |
|  | organism = Macaca fascicularis |

SEQUENCE: 299

```
MKPGCAAGSP GNEWIFFSTD EITIRYRNTM SNGGLQRSVI LSALTLLRAV TGFSGDGRAV   60
WSKNPNFTPV NESQLFLYDT FPKNFFWGVG TGALQVEGSW KKDGKGPSIW DHFVHTHLKN  120
VSSTNGSSDS YIFLEKDLSA LDFIGVSFYQ FSISWPRLFP DGIVTVANAK GLQYYNTLLD  180
SLVLRNIEPI VTLYHWDLPL ALQEKYGGWK NDTIIDIFND YATYCFQTFG DRVKYWITIH  240
NPYLVAWHGY GTGMHAPGEK GNLAAVYTVG HNLIKAHSKV WHNYNTHFRP HQKGWLSITL  300
GSHWIEPNRS ENTMDILKCQ QSMVSVLGWF ANPIHGDGDY PEGMKKKLLS ILPLFSEAEK  360
NEVRGTADFF AFSFGPNNFK PLNTMAKMGQ NVSLNLREAL NWIKLEYNNP RILIAENGWF  420
TDSHVKTEDT TAIYMMKNFL SQVLQAIRLD EIRVFGYTAW SLLDGFEWQD AYTIRRGLFY  480
VDFNSKQKER KPKSSAHYYK QIIRENGFSL KEATPDVQGQ FPCDFSWGVT ESVLKPESVA  540
SSPQFSDPYL YVWNATGNRL LHRVEGVRLK TRPAQCTDFV NIKKQLEMLA RMKVTHYRFA  600
LDWASVLPTG NLSAVNRQAL RYYRCVVSEG LKLGISAMVT LYYPTHAHLG LPEPLLHAGG  660
WLNPSTVEAF QAYAGLCFQE LGDLVKLWIT INEPNRLSDI YNRSGNDTYG AAHNLLVAHA  720
LAWRLYDRQF RPSQRGAVSL SLHADWAEPA NPYADSHWRA AERFLQFEIA WFAEPLFKTG  780
DYPAAMREYI ASKHRRGLSS SALPRLTEAE RRLLKGTVDF CALNHFTTRF VMHEQLAGSR  840
YDSDRDIQFL QDITRLSSPT RLAVIPWGVR KLLRWVRRNY GDMDIYITAS GIDDQALEDD  900
RLRKYYLEKY LQEVLKAYLI DKVRIKGYYA FKLAEEKSKP RFGFFTSDFK AKSSIQFYNK  960
MISSSGFPSE NSSSRCSQTQ KNTECTVCLF LVQKKPLIFL GCCFFSTLVL LLSITIFHRQ 1020
KRRKFWKAKN LQHIPLKKGK RVLS                                       1044
```

|  |  |
| --- | --- |
| SEQ ID NO: 300 | moltype = DNA length = 3135 |
| FEATURE | Location/Qualifiers |
| misc_feature | 1..3135 |
|  | note = cynomolgus monkey (cyno) beta klotho |
| source | 1..3135 |
|  | mol_type = other DNA |
|  | organism = Macaca fascicularis |

SEQUENCE: 300

```
atgaagcctg gatgtgccgc cggaagcccc ggcaacgagt ggatcttctt cagcaccgac   60
gagatcacca tccggtacag aaacaccatg agcaacggcg gcctgcagcg gagcgtgatc  120
ctgtctgctc tgaccctgct gagagccgtg accggcttca gcggagatgg cagagccgtg  180
tggtccaaga cccccaactt cacccccgtg aacgagagcc agctgttcct gtacgatacc  240
ttccccaaga acttcttctg gggcgtgggc acaggcgccc tgcaggtgga aggatcctgg  300
aagaaggacg gcaagggccc cagcatctgg gaccactttg tgcacaccca cctgaagaac  360
gtgtccagca ccaacggcag cagcgacagc tacatctttc tggaaaagga cctgagcgcc  420
ctggacttca tcggcgtgtc cttctaccag ttcagcatca gctggccaag actgttcccc  480
gacggcatcg tgacagtggc caatgccaag ggcctgcagt actacaacac cctgctggac  540
agcctggtgc tgcggaacat cgagcccatc gtgaccctgt accactggga cctgccactg  600
gctctgcagg agaaatacgg cggctggaag aacgacacca tcatcgacat cttcaacgac  660
tacgccacct actgcttcca gaccttcggc gacagagtga gtactggat cacaatccac  720
aaccccacc tggtggcctg gcacggctat ggcaccggaa tgcatgcccc tggcgagaag  780
ggaaatctgg ccgccgtgta caccgtgggc cacaacctga tcaaggccca cagcaaagtg  840
tggcacaact acaataccca cttccggccc caccagaagg gctggctgtc tatcacactg  900
ggcagccact ggatcgagcc taaccgcagc gagaacacca tggacatcct gaagtgccag  960
cagagcatgg tgtccgtgct gggatggttc gccaacccca ttcacggcga cggcgattac 1020
cccgagggca tgaagaagaa gctgctgagc atcctgcccc tgttcagcga ggccgagaag 1080
aacgagctgc ggggcaccgc cgatttcttc gcctttagct tcggccccaa caacttcaag 1140
cccctgaata ccatggccaa gatgggccag aatgtgtccc tgaacctgag agaggccctg 1200
aactggatca agctggagta caacaacccc cggatcctga tcgccgagaa cggctggttc 1260
accgacagcc acgtgaaaac cgaggacacc accgccatct atatgatgaa gaacttcctg 1320
agccagctgc tgcaggctat ccggctggat gagatcgtga gttccggcta caccgcctgg 1380
tcactgctgg acggcttcga atggcaggac gcctacacca tcagacgggg cctgttctac 1440
gtggacttca cagcaagca gaaagagcgg aagcccaaga gcagcgccca ctactacaag 1500
cagatcatca gagagaatgg cttcagcctg aagaggcca ccccgacgt gcagggccag 1560
ttcccttgtg attttctcttg gggcgtgacc gagagcgtgc tgaagcctga aagcgtggcc 1620
agcagccccc agttcagcga cccttacctg tacgtggaa acgccaccgg caacggcctg 1680
ctgcatagag tggaaggcgt gcggctgaaa accagacccg ccagtgcac cgacttcgtg 1740
aacatcaaga acagctgga atgctggcc ggatgaaag tgacccacta cagattcgcc 1800
ctggactggg ccagcgtgct gcctaccgga atctgagcg ccgtgaacag acaggccctg 1860
cggtactaca gatgcggtgt gtccgagggc tgaagctgg gcatcagcgc catggtcaca 1920
ctgtactacc ctacccacgc ccacctggga ctgcctgaac tctgctgca tgctggcggc 1980
tggctgaacc ctagcaccgt ggaagccttt caggcctacg ccgggctgtg cttccaggaa 2040
ctgggcgacc tcgtgaagct gtggatcacc atcaacgagc caacagact gagcgacatc 2100
tacaacagaa gcggcaacga cacctacggc gctgcccaca tcctggtt ggctcatgcg 2160
ctggcttggc ggctgtacga cagacagttc cggccttctc agcggggagc cgtgtctctg 2220
tctctgcatg ccgattggc cgagcccgcc aaccctacg ccgactctca ttggagagcc 2280
gccgagcggt tcctgcagtt cgagatcgct tggtttgccg agcccctgtt caagaccggc 2340
gattaccctg ccgccatgag agtatatc gccagcaagc acagacgggg cctgagcagc 2400
tctgccctgc ctagactgac cgaggccgag cggagactga gaagggaac cgtggatttc 2460
tgcgcctga accacttcac caccagattc gtgatgcacg agcagctagc cggcagcaga 2520
tacgacagca accgggacat ccagtttctg caggacatca cccggctgag cagcccctaca 2580
agactggccg tgatcccttg gggagtgcgc aagctgctga gatgggtgcg cagaaactac 2640
ggcgacatgg atatctacat caccgccagc ggcatcgacg accaggccct ggaagatgac 2700
cggctgcgga agtactacct ggaaaagtac ctgcaggaag tgctgaaggc ctacctgatc 2760
gacaaagtgc ggatcaaggg ctactacgcc ttcaagctgc cgaggaaaa gagcaagccc 2820
```

```
agattcggct tcttcaccag cgacttcaag gccaagagca gcatccagtt ctacaacaag    2880
atgatcagca gcagcggctt ccccagcgag aacagcagct ccagatgcag ccagacccga    2940
aaaaacaccg agtgtaccgt gtgcctgttc ctggtgcaga agaagcccct gatcttcctg    3000
ggctgctgct tctttagcac cctggtgctg ctgctgtcca tcaccatctt ccaccggcag    3060
aagcggagaa agttctggaa ggccaaaaac ctgcagcaca tcccccctga gaaaggcaag    3120
cgggtgctga gctga                                                    3135

SEQ ID NO: 301          moltype = AA  length = 1043
FEATURE                 Location/Qualifiers
REGION                  1..1043
                        note = Mouse beta klotho
source                  1..1043
                        mol_type = protein
                        organism = Mus musculus
SEQUENCE: 301
MKTGCAAGSP GNEWIFFSSD ERNTRSRKTM SNRALQRSAV LSAFVLLRAV TGFSGDGKAI      60
WDKKQYVSPV NPSQLFLYDT FPKNFSWGVG TGAFQVEGSW KTDGRGPSIW DRYVYSHLRG     120
VNGTDRSTDS YIFLEKDLLA LDFLGVSFYQ FSISWPRLFP NGTVAAVNAQ GLRYYRALLD     180
SLVLRNIEPI VTLYHWDLPL TLQEEYGGWK NATMIDLFND YATYCFQTFG DRVKYWITIH     240
NPYLVAWHGF GTGMHAPGEK GNLTAVYTVG HNLIKAHSKV WHNYDKNFRP HQKGWLSITL     300
GSHWIEPNRT DNMEDVINCQ HSMSSVLGWF ANPIHGDGDY PEFMKTGAMI PEFSEAEKEE     360
VRGTADFFAF SFGPNNFRPS NTVVKMGQNV SLNLRQVLNW IKLEYDDPQI LISENGWFTD     420
SYIKTEDTTA IYMMKNFLNQ VLQAIKFDEI RVFGYTAWTL LDGFEWQDAY TTRRGLFYVD     480
FNSEQKERKP KSSAHYYKQI IQDNGFPLKE STPDMKGRFP CDFSWGVTES VLKPEFTVSS     540
PQFTDPHLYV WNVTGNRLLY RVEGVRLKTR PSQCTDYVSI KKRVEMLAKM KVTHYQFALD     600
WTSILPTGNL SKVNRQVLRY YRCVVSEGLK LGVFPMVTLY HPTHSHLGLP LPLLSSGGWL     660
NMNTAKAFQD YAELCFRELG DLVKLWITIN EPNRLSDMYN RTSNDTYRAA HNLMIAHAQV     720
WHLYDRQYRP VQHGAVSLSL HCDWAEPANP FVDSHWKAAE RFLQFEIAWF ADPLFKTGDY     780
PSVMKEYIAS KNQRGLSSSV LPRFTAKESR LVKGTVDFYA LNHFTTRFVI HKQLNTNRSV     840
ADRDVQFLQD ITRLSSPSRL AVTPWGVRKL LAWIRRNYRD RDIYITANGI DDLALEDDQI     900
RKYYLEKYVQ EALKAYLIDK VKIKGYYAFK LTEEKSKPRF GFFTSDFRAK SSVQFYSKLI     960
SSSSGLPAENR SPACGQPAED TDCTICSFLV EKKPLIFFGC CFISTLAVLL SITVFHHQKR    1020
RKFQKARNLQ NIPLKKGHSR VFS                                            1043

SEQ ID NO: 302          moltype = DNA  length = 3129
FEATURE                 Location/Qualifiers
misc_feature            1..3129
                        note = Mouse beta klotho
source                  1..3129
                        mol_type = genomic DNA
                        organism = Mus musculus
SEQUENCE: 302
atgaagacag gctgtgcagc agggtctccg gggaatgaat ggattttctt cagctctgat     60
gaaagaaaca cacgctctag gaaaacaatg tccaacaggg cactgcaaag atctgccgtg    120
ctgtctgcgt ttgttctgct gcgagctgtt accggcttct ccggagcggg aaagcaata    180
tgggataaaa acagtacgt gagtccggta aaccaagtc agctgttcct ctatgacact    240
ttccctcaaa acttttcctg gggcgttggg accggagcat ttcaagtgga agggagttgg    300
aagacagatg gaagaggacc ctcgatctgg gatcggtacg tctactcaca cctgagaggt    360
gtcaacggca cagacagatc cactgacagt tacatctttc tggaaaaaga cttgttggct    420
ctggattttt taggagtttc ttttttatcag ttctcaatct cctggccacg gttgtttccc    480
aatggaacag tagcagcagt gaatgcgcaa ggtctccggt actaccgtgc acttcgtgga    540
tcgctggtac ttaggaatat cgagcccatt gttaccttgt accattggga tttgcctctg    600
acgctccagg aagaatatgg gggctggaaa aatgcaacta tgatagatct cttcaacgac    660
tatgccacat actgcttcca gacctttgga gaccgtgtca aatattggat tacaattcac    720
aaccccttacc ttgttgcttg gcatgggttt ggcacaggta tgcatgccag aggagagaag    780
ggaaatttaa cagctgtcta cactgtggga cacaacctga tcaaggcaca ttcgaaagtg    840
tggcataact acgacaaaaa cttccgcccc atcagaagg gttggctctc catcaccttg    900
gggtcccatt ggatagagcc aaacagaaca gacaacatgg aggacgtgat caactgccag    960
cactccatgt cctctgtgct tggatggttc gccaaccaca tccacgggga cggcgactac   1020
cctgagttca tgaagacggg cgccatgatc cccgagttct ctgaggcaga gaaggaggag   1080
gtgagggca cggctgattt ctttgccttt tccttcgggc caacaacttc aggccctca   1140
aacaccgtg tgaaaatggg acaaaatgta tcactcaact taaggcaggt gctgaactgg   1200
attaaactgg aatacgatga ccctcaaatc ttgatttcgg agaacggctg gttcacagat   1260
agctatataa agacagagga caccacggcc atctacatga tggaaaattt cctaaaccag   1320
gttcttcaag caataaaatt tgatgaaatc cgcgtgtttg gttatacggc ctggactctc   1380
ctggatggct ttgagtggca ggatgccat acgacccgac gagggctgtt ttatgtggac   1440
tttaacagtg agcagaaga gaggaaaccc aagtcctcgg ctcattacta caagcagatc   1500
atacaagaca acggcttccc tttgaaagag tccacgccaa acatgaaggg tcggttcccc   1560
tgtgattttct cttgggagt cactgagtct gttcttaagc ccgagtttac ggtctctcc   1620
ccgcagtttta ccgatcctca cctgtatgtg tggaatgtca ctggcaacag attgctctac   1680
cgagtggaag gggtaaggct gaaaacaaga ccatcccagt gcacagatta tgtgagcatc   1740
aaaaaacaga ttgaaatgtt ggcaaaatg aaagtcaccc actaccagtt tgctctggac   1800
tggacctcta tccttcccac tggcaatctg tccaaagtta cagacaagt gttaaggtac   1860
tataggttgg tggtgagcga aggactgaag ctgggcgtt tcccatgac gcgttgtac   1920
cacccaaccc actcccatct cggcctcccc ctgccacttc tgagcagtgg ggggtggcta   1980
aacatgaaca cagccaaggc cttccaggac tacgctgagc tgtgcttccg ggagttgggg   2040
gacttggtga agctctggat caccatcaat gagcctaaca ggctgagtga catgtacaac   2100
cgcacgagta atgacaccta ccgtgcagcc cacaacctga tgatcgccca tgcccaggtc   2160
tggcacctct atgataggca gtataggccg gtccagcatg gggctgtgtc gctgtcctta   2220
```

```
cattgcgact gggcagaacc tgccaacccc tttgtggatt cacactgaa ggcagccgag    2280
cgcttcctcc agtttgagat cgcctggttt gcagatccgc tcttcaagac tggcgactat    2340
ccatcggtta tgaaggaata catcgcctcc aagaaccagc gagggctgtc tagctcagtc    2400
ctgccgcgct tcaccgcgaa ggagagcagg ctggtgaagg gtaccgtcga cttctacgca    2460
ctgaaccact tcactacgag gttcgtgata cacaagcagc tgaacaccaa ccgctcagtt    2520
gcagacaggg acgtccagtt cctgcaggac atcacccgcc taagctcgcc cagccgcctg    2580
gctgtaacac cctggggagt gcgcaagctc cttgcgtgga tccggaggaa ctacagagac    2640
agggatatct acatcacagc caatggcatc gatgacctgg ctctagagga tgatcagatc    2700
cgaaagtact acttggagaa gtatgtccag gaggctctga aagcatatct cattgacaag    2760
gtcaaaatca aaggctacta tgcattcaaa ctgactgaag agaaatctaa gcctagattt    2820
ggattttttca cctctgactt cagagctaag tcctctgtcc agttttacag caagctgatc    2880
agcagcagtg gcctccccgc tgagaacaga agtcctgcgt gtggtcagcc tgcggaagac    2940
acagactgca ccatttgctc atttctcgtg gagaagaaac cactcatctt cttcggttgc    3000
tgcttcatct ccactctggc tgtactgcta tccatcaccg tttttcatca tcaaaagaga    3060
agaaaattcc agaaagcaag gaacttacaa aatataccat tgaagaaagg ccacagcaga    3120
gttttcagc                                                            3129

SEQ ID NO: 303         moltype = DNA  length = 651
FEATURE                Location/Qualifiers
misc_feature           1..651
                       note = full length FGF19 (NM_005117.2)
source                 1..651
                       mol_type = other DNA
                       organism = synthetic construct
SEQUENCE: 303
atgcggagcg ggtgtgtggt ggtccacgta tggatcctgg ccggcctctg gctggccgtg    60
gccgggcgcc ccctcgcctt ctcggacgcg gggccccacg tgcactacgg ctggggcgac    120
cccatccgcc tgcggcacct gtacacctcc ggccccacg ggctctccag ctgcttcctg    180
cgcatccgtg ccgacggcgt cgtggactgc gcgggggcc agagcgcgca cagttttgctg    240
gagatcaagg cagtcgctct gcggaccgtg gccatcaagg gcgtgcacag cgtgcggtac    300
ctctgcatgg gcgccgacgg caagatgcag gggctgcttc agtactcgga ggaagactgt    360
gctttcgagg aggagatccg cccagatggc tacaatgtgt accgatccga gaagcaccgc    420
ctcccggtct ccctgagcag tgccaaacag cggcagctgt acaagaacag aggctttctt    480
ccactctctc atttcctgcc catgctgccc atggtcccag aggagcctga ggacctcagg    540
ggccacttgg aatctgacat gttctcttcg ccctctggaga ccgacagcat ggacccattt    600
gggcttgtca ccggactgga ggccgtgagg agtcccagct ttgagaagta a              651

SEQ ID NO: 304         moltype = AA  length = 216
FEATURE                Location/Qualifiers
REGION                 1..216
                       note = full length FGF19 (NP_005108.1)
source                 1..216
                       mol_type = protein
                       organism = synthetic construct
SEQUENCE: 304
MRSGCVVVHV WILAGLWLAV AGRPLAFSDA GPHVHYGWGD PIRLRHLYTS GPHGLSSCFL    60
RIRADGVVDC ARGQSAHSLL EIKAVALRTV AIKGVHSVRY LCMGADGKMQ GLLQYSEEDC    120
AFEEEIRPDG YNVYRSEKHR LPVSLSSAKQ RQLYKNRGFL PLSHFLPMLP MVPEEPEDLR    180
GHLESDMFSS PLETDSMDPF GLVTGLEAVR SPSFEK                              216

SEQ ID NO: 305         moltype = DNA  length = 630
FEATURE                Location/Qualifiers
misc_feature           1..630
                       note = A full length FGF21
source                 1..630
                       mol_type = other DNA
                       organism = synthetic construct
SEQUENCE: 305
atggactcgg acgagaccgg gttcgagcac tcaggactgt gggtttctgt gctggctggt    60
cttctgctgg gagcctgcca ggcacacccc atccctgact ccagtcctct cctgcaattc    120
gggggccaag tccggcagcg gtacctctac acagatgatg cccagcagac agaagcccac    180
ctggagatca ggaggatgg acggtgggg ggcgctgctg accagagccc gaaagtctc    240
ctgcagctga aagccttgaa gccggagtt attcaaatct gggagtcaa gacatccagg    300
ttcctgtgcc agcggccaga tggggccctg tatggatcgc tccactttga ccctgaggcc    360
tgcagcttcc gggagctgct tcttgaggac ggatacaatg tttaccagtc gaagcccac    420
ggcctcccgc tgcacctgcc agggaacaag tccccacacc gggaccctgc accccgagga    480
ccagctcgct tcctgccact accaggcctg cccccgcac cccggagcc acccggaatc    540
ctggccccccc agcccccga tgtgggctcc tcggaccctc tgagcatggt gggaccttcc    600
cagggccgaa gccccagcta cgcttcctga                                     630

SEQ ID NO: 306         moltype = AA  length = 209
FEATURE                Location/Qualifiers
REGION                 1..209
                       note = A full length FGF21
source                 1..209
                       mol_type = protein
                       organism = synthetic construct
SEQUENCE: 306
MDSDETGFEH SGLWVSVLAG LLLGACQAHP IPDSSPLLQF GGQVRQRYLY TDDAQQTEAH    60
```

```
LEIREDGTVG GAADQSPESL LQLKALKPGV IQILGVKTSR FLCQRPDGAL YGSLHFDPEA   120
CSFRELLLED GYNVYQSEAH GLPLHLPGNK SPHRDPAPRG PARFLPLPGL PPAPPEPPGI   180
LAPQPPDVGS SDPLSMVGPS QGRSPSYAS                                    209

SEQ ID NO: 307           moltype = DNA  length = 2469
FEATURE                  Location/Qualifiers
misc_feature             1..2469
                         note = human FGFR1c NM_023110.2 (also designated FGFR
                         alpha-IIIc)
source                   1..2469
                         mol_type = genomic DNA
                         organism = Homo sapiens
SEQUENCE: 307
atgtggagct ggaagtgcct cctcttctgg gctgtgctgg tcacagccac actctgcacc   60
gctaggccgt ccccgacctt gcctgaacaa gcccagccct ggggagcccc tgtggaagtg   120
gagtccttcc tggtccaccc cggtgacctg ctgcagcttc gctgtcggct gcgggacgat   180
gtgcagagca tcaactggct gcgggacggg gtgcagctgg cggaaagcaa ccgcacccgc   240
atcacagggg aggaggtgga ggtgcaggac tccgtgccag cagactccgg cctctatgct   300
tgcgtaacca gcagcccctc gggcagtgac accacctact tctccgtcaa tgtttcagat   360
gctctcccct cctcggagga tgatgatgat gatgatgact cctcttcaga ggagaaagaa   420
acagataaca ccaaaccaaa ccgtatgccc gtagctccat attggacatc accagaaaag   480
atggaaaaga aattgcatgc agtgccggct gccaagacag tgaagttcaa atgccccttc   540
agtgggacac caaacccaac actgcgctgg ttgaaaaatg gcaagaattc aaacctgac   600
cacagaattg gaggctacaa ggtccgttat gccacctgga gcatcataat ggactctgtg   660
gtgccctctg acaagggcaa ctacacctgc attgtggaga tgagtacggc agcatcaac    720
cacacatacc agctggatgt cgtggagcgg tcccctcacc ggcccatcct gcaagcaggg   780
ttgcccgcca acaaaacagt ggccctgggt agcaacgtgg agttcatgtg taaggtgtac   840
agtgacccgc agccgcacat ccagtggcta aagcacatcg aggtgaatgg gagcaagatt   900
ggcccagaca acctgcctta tgtccagatc ttgaagactg ctggagttaa taccaccgac   960
aaagagatgg aggtgcttca cttaagaaat gtctccttg aggacgcagg ggagtatacg   1020
tgcttggcgg gtaactctat cggactctcc catcactctg catggttgac cgttctggaa   1080
gccctggaag agaggccggc agtgatgacc tcgcccctgt acctggagat catcatctat   1140
tgcacagggg ccttcctcat ctcctgcatg gtggggtcgg tcatcgtcta caagatgaag   1200
agtggtacca agaagagtga cttccacagc caggatggct tgcacaagct ggccaagagc   1260
atccctctgc gcagacaggt aacagtgtct gctgactcca gtgcatccat gaactctgga   1320
gttcttctgg ttcggccatc acggctctcc tccagtggga ctcccatgct agcagggtc    1380
tctgagtatg agcttcccga agaccctcgc tgggagctgc ctcgggacag actggtctta   1440
ggcaaacccc tgggagaggg ctgctttggg caggtggtgt tggcagaggc tatcgggctg   1500
gacaaggaca acccaaccgt gtgaccaaa gtggctgtga agatgttgaa gtcggacgca   1560
acagagaaag acttgtcaga cctgatctca gaaatggaga tgatgaagat gatcgggaag   1620
cataagaata tcatcaacct gctgggggcc tgcacgcagg atggtcccct gtatgtcatc   1680
gtggagtatg cctccaaggg caacctgcgg gagtacctgc aggcccggag gccccaggg    1740
ctggaatact gctacaaccc cagccacaac ccagaggacc cgcgcaggct ggccaggcag    1800
gtgtcctgcg cctaccaggt ggcccgagcg atggagtatc tggcctccaa gaagtgcata   1860
caccgagacc tggcagccag gaatgtcctg gtgacagagg acaatgtgat gaagatagca   1920
gactttggcc tcgcacggga cattcaccac atcgactact ataaaagac aaccaacggc    1980
cgactccctg tgaagtggat ggcacccgag gcattatttg accggatcta cacccaccag   2040
agtgatgtgt ggtctttcgg ggtgctcctg tgggagatct tcactctggg cggctcccca   2100
taccccggtg tgcctgtgga ggaactttc aagctgctga aggagggtca ccgcatggac    2160
aagcccagta actgcaccaa cgagctgtac atgatgatgc gggactgctg gcatgcagtg   2220
ccctcacaga gacccaccttcaagcagctg gtggaagacc tggaccgcat cgtggccttg   2280
acctccaacc aggagtacct ggacctgtcc atgcccctgg accagtactc ccccagcttt   2340
cccgacaccc ggagctctac gtgcctcca ggggaggatt ccgtcttctc tcatgagccg    2400
ctgcccgagg agccctgcct gccccgacac ccagcccagc ttgccaatgg cggactcaaa   2460
cgccgctga                                                           2469

SEQ ID NO: 308           moltype = AA  length = 822
FEATURE                  Location/Qualifiers
REGION                   1..822
                         note = human FGFR1c NP_075598.2 (also designated FGFR
                         alpha-IIIc)
source                   1..822
                         mol_type = protein
                         organism = Homo sapiens
SEQUENCE: 308
MWSWKCLLFW AVLVTATLCT ARPSPTLPEQ AQPWGAPVEV ESFLVHPGDL LQLRCRLRDD   60
VQSINWLRDG VQLAESNRTR ITGEEVEVQD SVPADSGLYA CVTSSPSGSD TTYFSVNVSD   120
ALPSSEDDDD DDDSSSEEKE TDNTKPNRMP VAPYWTSPEK MEKKLHAVPA AKTVKFKCPS   180
SGTPNPTLRW LKNGKEFKPD HRIGGYKVRY ATWSIIMDSV VPSDKGNYTC IVENEYGSIN   240
HTYQLDVVER SPHRPILQAG LPANKTVALG SNVEFMCKVY SDPQPHIQWL KHIEVNGSKI   300
GPDNLPYVQI LKTAGVNTTD KEMEVLHLRN VSFEDAGEYT CLAGNSIGLS HHSAWLTVLE   360
ALEERPAVMT SPLYLEIIIY CTGAFLISCM VGSVIVYKMK SGTKKSDFHS QMAVHKLAKS   420
IPLRRQVTVS ADSSASMNSG VLLVRPSRLS SSGTPMLAGV SEYELPEDPR WELPRDRLVL   480
GKPLGEGCFG QVVLAEAIGL DKDKPNRVTK VAVKMLKSDA TEKDLSDLIS EMEMMKMIGK   540
HKNIINLLGA CTQDGPLYVI VEYASKGNLR EYLQARRPPG LEYCYNPSHN PEEQLSSKDL   600
VSCAYQVARG MEYLASKKCI HRDLAARNVL VTEDNVMKIA DFGLARDIHH IDYYKKTTNG   660
RLPVKWMAPE ALFDRIYTHQ SDVWSFGVLL WEIFTLGGSP YPGVPVEELF KLLKEGHRMD   720
KPSNCTNELY MMMRDCWHAV PSQRPTFKQL VEDLDRIVAL TSNQEYLDLS MPLDQYSPSF   780
PDTRSSTCSS GEDSVFSHEP LPEEPCLPRH PAQLANGGLK RR                      822
```

```
SEQ ID NO: 309            moltype = AA   length = 374
FEATURE                   Location/Qualifiers
REGION                    1..374
                          note = example of extracellular region of FGFR1c
source                    1..374
                          mol_type = protein
                          organism = synthetic construct
SEQUENCE: 309
MWSWKCLLFW AVLVTATLCT ARPSPTLPEQ AQPWGAPVEV ESFLVHPGDL LQLRCRLRDD   60
VQSINWLRDG VQLAESNRTR ITGEEVEVQD SVPADSGLYA CVTSSPSGSD TTYFSVNVSD  120
ALPSSEDDDD DDDSSSEEKE TDNTKPNRMP VAPYWTSPEK MEKKLHAVPA AKTVKFKCPS  180
SGTPNPTLRW LKNGKEFKPD HRIGGYKVRY ATWSIIMDSV VPSDKGNYTC IVENEYGSIN  240
HTYQLDVVER SPHRPILQAG LPANKTVALG SNVEFMCKVY SDPQPHIQWL KHIEVNGSKI  300
GPDNLPYVQI LKTAGVNTTD KEMEVLHLRN VSFEDAGEYT CLAGNSIGLS HHSAWLTVLE  360
ALEERPAVMT SPLY                                                    374

SEQ ID NO: 310            moltype = DNA   length = 2466
FEATURE                   Location/Qualifiers
misc_feature              1..2466
                          note = Coding sequence of human FGFR2c (NM_000141.4)
source                    1..2466
                          mol_type = genomic DNA
                          organism = Homo sapiens
SEQUENCE: 310
atggtcagct ggggtcgttt catctgcctg gtcgtggtca ccatggcaac cttgtccctg    60
gcccggccct ccttcagttt agttgaggat accacattag agccagaaga gccaccaacc   120
aaataccaaa tctctcaacc agaagtgtac gtggctgcgc cagggagtc gctagaggtg    180
cgctgcctgt tgaaagatgc cgccgtgatc agttggacta aggatggggt gcacttgggg   240
cccaacaata ggacagtgct tattggggag tacttgcaga taaagggcac acgcctaga    300
gactccggcc tctatgcttt tactgccagt aggactggag acagtgaaac ttggtacttc   360
atggtgaatg tcacagatgc catctcatcc ggagatgatg aggatgacac cgatggtgcg   420
gaagattttg tcagtgagaa cagtaacaac aagagagcac catactggac aaacacagaa   480
aagatggaaa agcggctcca tgctgtgcct gcggccaaca ctgtcaagtt tcgctgccca   540
gccggggcga acccaatgcc aaccatgcgg tggctgaaaa acgggaagga gtttaagcag   600
gagcatcgca ttgaggcta caggtacga accagcact ggagcctcat tatggaaagt    660
gtggtcccat ctgacaaggg aaattatacc tgtgtagtgg agaatgaata cgggtccatc   720
aatcacacgt accacctgga tgttgtggag cgatcgcctc accggcccat cctccaagcc   780
ggactgccgg caaatgcctc cacgttggtc ggaggagacg tagagttttgt ctgcaaggtt  840
tacagtgatg cccagcccca catccagtgg atcaagcacg tggaaaagaa cggcagtaaa   900
tacgggcccg acgggctgcc ctacctcaag gttctcaagg ccgccggtgt taacaccacg   960
gacaaagaga ttgaggttct ctatattcgg aatgtaactt tgaggacgc tggggaatat   1020
acgttcgttgg cgggtaattc tattgggata tcctttcact ctgcatggtt acagttctga  1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagtt ccagctcctc catgaactcc   1320
aacacccgc tggtgaggat aacaacacgc ctctcttcaa cggcagacac ccccatgctg   1380
gcaggggtct ccgagtatga acttccagag gacccaaaat gggagtttcc aagagataag   1440
ctgacactgg gcaagccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctc tttggagcct gcacacagga tgggcctctc   1680
tatgtcatag ttgagtatgc ctctaaaggc aacctccgag aatacctccg agcccggagg   1740
ccaccgggga tggagtactc ctatgacatt aaccgtgttc ctgaggagca gatgacttc    1800
aaggacttgg tgtcatgcac ctaccagctg gccagaggca tggagtactt ggcttcccaa   1860
aaatgtattc atcgagattt agcagccaga aatgttttgg taacagaaaa caatgtcgatg  1920
aaaatagcag actttggact cgccagagat atcaacaata tagactatta caaaaagacc   1980
accaatgggc ggcttccagt caagtggatg ctccagaag cccgtttga tagagtatac    2040
actcatcaga gtgatgtctg gtccttcggg gtgttaatgt gggagatctt cactttaggg   2100
ggctcgccct acccagggat tcccgtggag gaacttttta gctgctgaa ggaaggacac   2160
agaatggata gccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga ggaatacttg gacctcagcc aacctctcga acatattca    2340
cctagttacc ctgacacaag aagttcttgt tcttcaggag atgattctgt tttttctcca   2400
gaccccatgc cttacgaacc atgccttcct cagtatccac acataaacgg cagtgttaaa   2460
acatga                                                              2466

SEQ ID NO: 311            moltype = AA   length = 821
FEATURE                   Location/Qualifiers
REGION                    1..821
                          note = human FGFR2c (NP_000132.3)
source                    1..821
                          mol_type = protein
                          organism = Homo sapiens
SEQUENCE: 311
MVSWGRFICL VVVTMATLSL ARPSFSLVED TTLEPEEPPT KYQISQPEVY VAAPGESLEV    60
RCLLKDAAVI SWTKDGVHLG PNNRTVLIGE YLQIKGATPR DSGLYACTAS RTVDSETWYF   120
MVNVTDAISS GDDEDDTGA EDFVSENSNN KRAPYWTNTE KMEKRLHAVP AANTVKFRCP    180
```

```
AGGNPMPTMR WLKNGKEFKQ EHRIGGYKVR NQHWSLIMES VVPSDKGNYT CVVENEYGSI 240
NHTYHLDVVE RSPHRPILQA GLPANASTVV GGDVEFVCKV YSDAQPHIQW IKHVEKNGSK 300
YGPDGLPYLK VLKAAGVNTT DKEIEVLYIR NVTFEDAGEY TCLAGNSIGI SFHSAWLTVL 360
PAPGREKEIT ASPDYLEIAI YCIGVFLIAC MVVTVILCRM KNTTKKPDFS SQPAVHKLTK 420
RIPLRRQVTV SAESSSSMNS NTPLVRITTR LSSTADTPML AGVSEYELPE DPKWEFPRDK 480
LTLGKPLGEG CFGQVVMAEA VGIDKDKPKE AVTVAVKMLK DDATEKDLSD LVSEMEMMKM 540
IGKHKNIINL LGACTQDGPL YVIVEYASKG NLREYLRARR PPGMEYSYDI NRVPEEQMTF 600
KDLVSCTYQL ARGMEYLASQ KCIHRDLAAR NVLVTENNVM KIADFGLARD INNIDYYKKT 660
TNGRLPVKWM APEALFDRVY THQSDVWSFG VLMWEIFTLG GSPYPGIPVE ELFKLLKEGH 720
RMDKPANCTN ELYMMMRDCW HAVPSQRPTF KQLVEDLDRI LTLTTNEEYL DLSQPLEQYS 780
PSYPDTRSSC SSGDDSVFSP DPMPYEPCLP QYPHINGSVK T                    821

SEQ ID NO: 312          moltype = DNA  length = 2421
FEATURE                 Location/Qualifiers
misc_feature            1..2421
                        note = human FGFR3c (NM_000142.4)
source                  1..2421
                        mol_type = genomic DNA
                        organism = Homo sapiens
SEQUENCE: 312
atgggcgccc ctgcctgcgc cctcgcgctc tgcgtggccg tggccatcgt ggccggcgcc 60
tcctcggagt ccttggggac ggagcagcgc gtcgtgggcc gagcggcaga agtcccggcc 120
ccagagcccg gccagcagga gcagttggtc ttcggcagcg gggatgctgt ggagctgagc 180
tgtcccccgc cgggggtgg tcccatgggg cccactgtct gggtcaagga tggcacaggg 240
ctggtgccct cggagcgtgt cctggtgggg cccagcggc tgcaggtgct gaatgcctcc 300
cacgaggact ccggggccta cagctgccgc cagcggctca cgcagcgcgt actgtgccac 360
ttcagtgtgc gggtgacaga cgctccatcc tcgggagatg acgaagacgg ggaggacgag 420
gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctcccgc accggcccca cctgcaggc ggggctgccg 780
gccaaccgga cggcggtgct gggcagcgac gtggagttcc actgcaaggt gtacagtgac 840
gcacagcccc acatccagtg gctcaagcac gtggaggtga atggcagcaa ggtgggcccg 900
gacggcacac cctacgttac cgtgctcaag acggcgggcg ctaacaccac cgacaaggag 960
ctagaggttc tctccttgca caacgtcacc tttgaggacg ccggggagta cacctgcctg 1020
gcgggcaatt ctattgggtt ttctcatcac tctgcgtggc tggtggtgct gccagccgag 1080
gaggagctgg tggaggctga cgaggcgggc agtgtatatg caggcatcct cagctacggg 1140
gtgggcttct tcctgttcat cctggtggtg gcggctgtga cgctctgccg cctgcgcagc 1200
cccccaaga aaggcctggg ctcccccacc gtgcacaaga tctcccgctt cccgctcaag 1260
cgacaggtgt ccctggagtc caacgcgtcc atgagctcca cacaccact ggtgcgcatc 1320
gcaaggctgt cctcaggga gggccccacg ctggccaatg tctccgagct cgagctgcct 1380
gccgacccca atgggagct gtctcgggcc cggctgaccc tgggcaagcc ccttggggag 1440
ggctgcttcg gccaggtggt catggcgag ccatcggca ttgacaagga ccgggccgcc 1500
aagcctgtca ccgtagccgt gaagatgctg aaagacgatg ccactgacaa ggacctgtcg 1560
gacctggtgt ctgagatgga gatgatgaag atgatcggaa aacacaaaaa catcatcaac 1620
ctgctgggcg cctgcacgca gggcgggccc ctgtacgtgc tggtggagta cgcggccaag 1680
ggtaacctgc gggagtttct gcgggcgcgg cggccccgg gctggactac tcccttcgac 1740
acctgcaagc cgcccgagga gcagctcacc ttcaaggacc tggtgtcctg tgcctaccag 1800
gtggccgtgg gcatggagta cttggcctcc cagaagtgca tccacagggc cctggctgcg 1860
cgcaatgtgc tggtgaccga ggacaacgtg atgaagatcg cagacttcgg gctggccgcg 1920
gacgtgcaca acctcgacta ctacaagaag acaaccaacg gccggctgcc cgtgaagtgg 1980
atggcgcctg aggccttgtt tgaccgagtc tacactcacc agagtgacgt ctggtccttt 2040
ggggtcctgc tctgggagat cttcacgctg ggggctctcc cgtacccggg catccctgtg 2100
gaggagctct tcaagctgct gaaggagggc caccgcatgg acaagcccgc caactgcaca 2160
cacgacctgt acatgatcat gcgggagtgc tggcatgccg cgcccctcca gaggcccacc 2220
ttcaagcagc tggtggagga cctggaccgt gtccttaccg tgacgtccac cgacgagtac 2280
ctggacctgt cggcgccttt cgagcagtac tcccgggtg gccaggacac cccagctcc 2340
agctcctcag gggacgactc cgtgtttgcc cacgacctgc tgccccggc ccacccagc 2400
agtgggggct cgcggacgtg a                                         2421

SEQ ID NO: 313          moltype = AA  length = 806
FEATURE                 Location/Qualifiers
REGION                  1..806
                        note = human FGFR3c (NP_000133.1)
source                  1..806
                        mol_type = protein
                        organism = Homo sapiens
SEQUENCE: 313
MGAPACALAL CVAVAIVAGA SSESLGTEQR VVGRAAEVPG PEPGQQEQLV FGSGDAVELS 60
CPPPGGGPMG PTVWVKDGTG LVPSERVLVG PQRLQVLNAS HEDSGAYSCR QRLTQRVLCH 120
FSVRVTDAPS SGDDEDGEDE AEDTGVDTGA PYWTRPERMD KKLLAVPAAN TVRFRCPAAG 180
NPTPSISWLK NGREFRGEHR IGGIKLRHQQ WSLVMESVVP SDRGNYTCVV ENKFGSIRQT 240
YTLDVLERSP HRPILQAGLP ANQTAVLGSD VEFHCKVYSD AQPHIQWLKH VEVNGSKVGP 300
DGTPYVTVLK TAGANTTDKE LEVLSLHNVT FEDAGEYTCL AGNSIGFSHH SAWLVVLPAE 360
EELVEADEAG SVYAGILSYG VGFFLFILVV AAVTLCRLRS PPKKGLGSPT VHKISRFPLK 420
RQVSLESNAS MSSNTPLVRI ARLSSGEGPT LANVSELELP ADPKWELSRA RLTLGKPLGE 480
GCFGQVVMAE AIGIDKDRAA KPVTVAVKML KDDATDKDLS DLVSEMEMMK MIGKHKNIIN 540
```

```
LLGACTQGGP LYVLVEYAAK GNLREFLRAR RPPGLDYSFD TCKPPEEQLT FKDLVSCAYQ  600
VARGMEYLAS QKCIHRDLAA RNVLVTEDNV MKIADFGLAR DVHNLDYYKK TTNGRLPVKW  660
MAPEALFDRV YTHQSDVWSF GVLLWEIFTL GGSPYPGIPV EELFKLLKEG HRMDKPANCT  720
HDLYMIMREC WHAAPSQRPT FKQLVEDLDR VLTVTSTDEY LDLSAPFEQY SPGGQDTPSS  780
SSSGDDSVFA HDLLPPAPPS SGGSRT                                     806

SEQ ID NO: 314          moltype = DNA   length = 2409
FEATURE                 Location/Qualifiers
misc_feature            1..2409
                        note = human FGFR4 (NM_002011.4)
source                  1..2409
                        mol_type = genomic DNA
                        organism = Homo sapiens
SEQUENCE: 314
atgcggctgc tgctggccct gttgggggtc ctgctgagtg tgcctgggcc tccagtcttg   60
tccctggagg cctctgagga agtggagctt gagcccgtgc tggctcccag cctggagcag  120
caagagcagg agctgacagt agcccttggg cagcctgtgc gtctgtgctg tgggcgggct  180
gagcgtggtg gccactggta caaggagggc agtcgcctag cacctgctgc ccgtgtacgg  240
ggctggaggg gccgcctaga gattgccagc ttcctacctg aggatgctgg ccgctacctc  300
tgcctggcac gaggctccat gatcgtcctg cagaatctca ccttgattac aggtgactcc  360
ttgacctcca gcaacgatga tgaggacccc aagtcccata gggacccctc gaataggcac  420
agttacccc agcaagcacc ctactggaca cacccccagc gcatggagaa gaaactgcat  480
gcagtacctg cggggaacac cgtcaagttc cgctgtccag ctgcaggcaa ccccacgccc  540
accatccgct ggcttaagga tggacaggcc tttcatgggg agaaccgcat tggaggcatt  600
cggctgcgcc atcagcactg gagtctcgtg atggagagcg tggtgccctc ggaccgcggc  660
acatacacct gcctggtaga aacgctgtg ggcagcatcc gctataacta cctgctagat  720
gtgctggagc ggtccccgca ccggcccatc ctgcaggccg gctcccggc caacaccaca  780
gccgtggtgg cagcgacgt ggagctgctg tgcaaggtgt acagcgatgc ccagccccac  840
atccagtggc tgaagcacat cgtcatcaac ggcagcagct cggagccga cggtttcccc  900
tatgtgcaag tcctaaagac tgcagacatc aatagctcag aggtggaggt cctgtacctg  960
cggaacgtgt cagccgagga cgcaggcgag tacacctgcc tcgcaggcaa ttccatcggc 1020
ctctcctacc agtctgcctg gctcacggtg ctgccagagg aggacccac atggaccgca 1080
gcagcgcccg aggccaggta tacggacatc atcctgtacg cgtcgggctc cctggccttg 1140
gctgtgctcc tgctgctggc cgggctctgt cgagggcagg cgctccacgg ccggcaccc 1200
cgcccgcccg ccactgtgca gaagctctcc cgcttccctg tggcccgaca gttctcctg 1260
gagtcaggct cttccggcaa gtcaagctca tccctggtac gaggcgtgcg tctctcctcc 1320
agcggcccg ccttgctcgc cggcctcgtg agtctagatc tacctctcga cccactatgg 1380
gagttccccc gggacaggct ggtgcttggg aagcccctag gcgagggctg cttttggcag 1440
gtagtacgtg cagaggcctt tggcatggac cctgcccggc ctgaccaagc cagcactgtg 1500
gccgtcaaga tgctcaaaga caacgcctct gacaaggacc tggccgacct ggtctcggaa 1560
atggaggtga tgaagctgat cggccgcaca aagaacatca tcaacctgct ggtgtctgc 1620
acccaggaag ggcccctgta cgtgatcgtg gagtgcgccg ccaagggaaa cctgcgggag 1680
ttcctgcggg cccggccgcc cccaggcccc gacctcagcc ccgacggtcc tcggagcgag 1740
gaggggccgc tctccttccc agtcctggtc tcctgcgcct accaggtggc ccgaggcatg 1800
cagtatctgg agtcccggaa gtgtatccac cgggactgg ctgcccgcaa tgtgctggtg 1860
actgaggaca atgtgatgaa gattgctgac tttgggctgg cccgcggcgt ccaccacatt 1920
gactactata aaaaaccag caacggccgc ctgcctgtga gtggatggc gcccgaggcc 1980
ttgtttgacc gggtgtacac acaccagagt gacgtgtggt cttttgggat cctgctatgg 2040
gagatcttca ccctcggggg ctccccgtat cctggcatcc cggtggagga gctgttctcg 2100
ctgctgcggg agggacatcg gatggaccga ccccacact gcccccagaa gctgtacggg 2160
ctgatgcgtg agtgctggca cgcagcgccc tcccagagac ctaccttcaa gcagctggtg 2220
gaggcgctgg acaaggtcct gctggccgtc tctgaggagt acctcgacct ccgcctgacc 2280
ttcggaccct attccccctc tggtgggac gccagcagca cctgctcctc cagcgattct 2340
gtcttcagcc acgacccct gccattggga tccagctcct cccccttcgg gtctggggtg 2400
cagacatga                                                        2409

SEQ ID NO: 315          moltype = AA   length = 802
FEATURE                 Location/Qualifiers
REGION                  1..802
                        note = human FGFR4 (NP_002002.3)
source                  1..802
                        mol_type = protein
                        organism = Homo sapiens
SEQUENCE: 315
MRLLLALLGV LLSVPGPPVL SLEASEEVEL EPCLAPSLEQ QEQELTVALG QPVRLCCGRA   60
ERGGHWYKEG SRLAPAGRVR GWRGRLEIAS FLPEDAGRYL CLARGSMIVL QNLTLITGDS  120
LTSSNDDEDP KSHRDPSNRH SYPQQAPYWT HPQRMEKKLH AVPAGNTVKF RCPAAGNPTP  180
TIRWLKDGQA FHGENRIGGI RLRHQHWSLV MESVVPSDRG TYTCLVENAV GSIRYNYLLD  240
VLERSPHRPI LQAGLPANTT AVVGSDVELL CKVYSDAQPH IQWLKHIVIN GSSFGADGFP  300
YVQVLKTADI NSSEVEVLYL RNVSAEDAGE YTCLAGNSIG LSYQSAWLTV LPEEDPTWTA  360
AAPEARYTDI ILYASGSLAL AVLLLLAGLY RGQALHGRHP RPPATVQKLS RFPLARQFSL  420
ESGSSGKSSS SLVRGVRLSS SGPALLAGLV SLDLPLDPLW EFPRDRLVLG KPLGEGCFGQ  480
VVRAEAFGMD PARPDQASTV AVKMLKDNAS DKDLADLVSE MEVMKLIGRH KNIINLLGVC  540
TQEGPLYVIV ECAAKGNLRE FLRARRPPGP DLSPDGPRSS EGPLSFPVLV SCAYQVARGM  600
QYLESRKCIH RDLAARNVLV TEDNVMKIAD FGLARGVHHI DYYKKTSNGR LPVKWMAPEA  660
LFDRVYTHQS DVWSFGILLW EIFTLGGSPY PGIPVEELFS LLREGHRMDR PPHCPPELYG  720
LMRECWHAAP SQRPTFKQLV EALDKVLLAV SEEYLDLRLT FGPYSPSGGD ASSTCSSSDS  780
VFSHDPLPLG SSSFPFGSGV QT                                          802
```

```
SEQ ID NO: 316            moltype = AA   length = 330
FEATURE                   Location/Qualifiers
REGION                    1..330
                          note = human IgG1 Fc with two amino acid changes to alanine
source                    1..330
                          mol_type = protein
                          organism = synthetic construct
SEQUENCE: 316
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPALAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 317            moltype = AA   length = 472
FEATURE                   Location/Qualifiers
REGION                    1..472
                          note = Humanized 5H23-vH3-human IgG1 (E233A)(L235A)
source                    1..472
                          mol_type = protein
                          organism = synthetic construct
SEQUENCE: 317
MDMRVPAQLL GLLLLWLRGA RCQVQLQQSG AEVKKPGASV KVSCKASGYT FTSYDINWVR   60
QAPGQGLEWI GWIYPGDGST KYNEKFKGKA TITRDTSAST AYMELSSLRS EDTAVYFCAR  120
SDYYGSRSFA YWGQGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCDKTHT CPPCPAPALA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR EEMTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 318            moltype = AA   length = 107
FEATURE                   Location/Qualifiers
REGION                    1..107
                          note = Human kappa constant region of light chain
source                    1..107
                          mol_type = protein
                          organism = Homo sapiens
SEQUENCE: 318
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 319            moltype = AA   length = 240
FEATURE                   Location/Qualifiers
REGION                    1..240
                          note = humanized 5H23-vL2-human kappa constant region of
                            light chain
source                    1..240
                          mol_type = protein
                          organism = synthetic construct
SEQUENCE: 319
MDMRVPAQLL GLLLLWLRGA RCDIVMTQSP DSLAVSLGER ATINCRASKS VSTSGYVYMH   60
WYQQKPGQPP KLLIYLASYL ESGVPDRFSG SGSGTDFTLT ISSVQAEDVA VYYCQHSRDL  120
TPFGGGTKL EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC  240

SEQ ID NO: 320            moltype = AA   length = 120
FEATURE                   Location/Qualifiers
REGION                    1..120
                          note = vH7
source                    1..120
                          mol_type = protein
                          organism = synthetic construct
SEQUENCE: 320
QVQLVQSGAE VKKPGSSVKV SCKASGYTFT SYDINWVRQA PGQGLEWIGW IYPGDGSTKY   60
NEKFKGRATL TADKSTSTAY MELSSLRSED TAVYYCARSD YYGSRSFAYW GQGTLVTVSS  120

SEQ ID NO: 321            moltype = AA   length = 120
FEATURE                   Location/Qualifiers
REGION                    1..120
                          note = vH8
source                    1..120
                          mol_type = protein
                          organism = synthetic construct
SEQUENCE: 321
QVQLVQSGAE VKKPGSSVKV SCKASGYTFT SYDINWVRQA PGQGLEWIGW IYPGDGSTKY   60
NEKFKGRATL TADKSTRTAY MELSSLRSED TAVYYCARSD YYGSRSFAYW GQGTLVTVSS  120
```

```
SEQ ID NO: 322              moltype = AA  length = 120
FEATURE                     Location/Qualifiers
REGION                      1..120
                            note = vH9
source                      1..120
                            mol_type = protein
                            organism = synthetic construct
SEQUENCE: 322
QVQLVQSGAE VKKPGSSVKV SCKASGYTFT SYDINWVRQA PGQGLEWIGW IYPGDGSTKY    60
NEKFKGRATI TADKSTSTAY MELSSLRSED TAVYYCARSD YYGSRSFAYW GQGTLVTVSS   120

SEQ ID NO: 323              moltype = AA  length = 120
FEATURE                     Location/Qualifiers
REGION                      1..120
                            note = 5H23v1-3
source                      1..120
                            mol_type = protein
                            organism = synthetic construct
SEQUENCE: 323
QVQLVQSGAE VKKPGASVKV SCKASGYTFT SYDINWVRQA PGQRLEWMGW IYPGDGSTKY    60
NEKFKGRVTI TRDTSASTAY MELSSLRSED TAVYYCARSD YYGSRSFAYW GQGTLVTVSS   120

SEQ ID NO: 324              moltype = AA  length = 120
FEATURE                     Location/Qualifiers
REGION                      1..120
                            note = 5H23v1-46
source                      1..120
                            mol_type = protein
                            organism = synthetic construct
SEQUENCE: 324
QVQLVQSGAE VKKPGASVKV SCKASGYTFT SYDINWVRQA PGQGLEWMGW IYPGDGSTKY    60
NEKFKGRVTM TRDTSTSTVY MELSSLRSED TAVYYCARSD YYGSRSFAYW GQGTLVTVSS   120

SEQ ID NO: 325              moltype = AA  length = 111
FEATURE                     Location/Qualifiers
REGION                      1..111
                            note = vL4
source                      1..111
                            mol_type = protein
                            organism = synthetic construct
SEQUENCE: 325
DIVLTQSPDS LAVSLGERAT INCRASKSVS TSGYVYMHWN QQKPGQPPKL LIYLASYLES    60
GVPDRFSGSG SGTDFTLTIS SLQAEDVAVY YCQHSRDLTF PFGGGTKVEI K            111

SEQ ID NO: 326              moltype = AA  length = 111
FEATURE                     Location/Qualifiers
REGION                      1..111
                            note = vL5
source                      1..111
                            mol_type = protein
                            organism = synthetic construct
SEQUENCE: 326
DIVMTQSPDS LAVSLGERAT INCRASKSVS TSGYVYMHWN QQKPGQPPKL LIYLASYLES    60
GVPDRFSGSG SGTDFTLTIS SLQAEDVAVY YCQHSRDLTF PFGGGTKVEI K            111

SEQ ID NO: 327              moltype = AA  length = 111
FEATURE                     Location/Qualifiers
REGION                      1..111
                            note = v1-39a
source                      1..111
                            mol_type = protein
                            organism = synthetic construct
SEQUENCE: 327
DIQMTQSPSS LSASVGDRVT ITCRASKSVS TSGYVYMHWY QQKPGKAPKL LIYLASYLES    60
GVPSRFSGSG SGTDFTLTIS SLQPEDFATY YCQHSRDLTF PFGQGTKLEI K            111

SEQ ID NO: 328              moltype = AA  length = 111
FEATURE                     Location/Qualifiers
REGION                      1..111
                            note = v1-39b
source                      1..111
                            mol_type = protein
                            organism = synthetic construct
SEQUENCE: 328
DIQMTQSPSS LSASVGDRVT ITCRASKSVS TSGYVYMHWY QQKPGKAPKL LIYLASYLES    60
GVPSRFSGSG SGTDFTLTIS SVQPEDFATY YCQHSRDLTF PFGGGTKLEI K            111

SEQ ID NO: 329              moltype = AA  length = 111
FEATURE                     Location/Qualifiers
```

```
REGION                  1..111
                        note = v1-39c
source                  1..111
                        mol_type = protein
                        organism = synthetic construct
SEQUENCE: 329
DIQMTQSPSS LSASVGDRVT ITCRASKSVS TSGYVYMHWN QQKPGKAPKL LIYLASYLES    60
GVPSRFSGSG SGTDFTLTIS SLQPEDFATY YCQHSRDLTF PFGGGTKLEI K            111

SEQ ID NO: 330          moltype = AA  length = 111
FEATURE                 Location/Qualifiers
REGION                  1..111
                        note = v1-39d
source                  1..111
                        mol_type = protein
                        organism = synthetic construct
SEQUENCE: 330
DIQMTQSPSS LSASVGDRVT ITCRASKSVS TSGYVYMHWY QQKPGKPPKL LIYLASYLES    60
GVPSRFSGSG SGTDFTLTIS SLQPEDFATY YCQHSRDLTF PFGGGTKLEI K            111

SEQ ID NO: 331          moltype = AA  length = 111
FEATURE                 Location/Qualifiers
REGION                  1..111
                        note = v1-39e
source                  1..111
                        mol_type = protein
                        organism = synthetic construct
SEQUENCE: 331
DIQLTQSPSS LSASVGDRVT ITCRASKSVS TSGYVYMHWY QQKPGKAPKL LIYLASYLES    60
GVPSRFSGSG SGTDFTLTIS SLQPEDFATY YCQHSRDLTF PFGGGTKLEI K            111

SEQ ID NO: 332          moltype = AA  length = 111
FEATURE                 Location/Qualifiers
REGION                  1..111
                        note = v1-39f
source                  1..111
                        mol_type = protein
                        organism = synthetic construct
SEQUENCE: 332
DIQMTQSPSS LSASVGDRVT ITCRASKSVS TSGYVYMHWY QQKPGKPPKL LIYLASYLES    60
GVPSRFSGSG SGTDFTLTIS SVQPEDFATY YCQHSRDLTF PFGGGTKLEI K            111

SEQ ID NO: 333          moltype = AA  length = 111
FEATURE                 Location/Qualifiers
REGION                  1..111
                        note = v1-39g
source                  1..111
                        mol_type = protein
                        organism = synthetic construct
SEQUENCE: 333
DIQLTQSPSS LSASVGDRVT ITCRASKSVS TSGYVYMHWY QQKPGKPPKL LIYLASYLES    60
GVPSRFSGSG SGTDFTLTIS SVQPEDFATY YCQHSRDLTF PFGGGTKLEI K            111

SEQ ID NO: 334          moltype = AA  length = 111
FEATURE                 Location/Qualifiers
REGION                  1..111
                        note = v1-39h
source                  1..111
                        mol_type = protein
                        organism = synthetic construct
SEQUENCE: 334
DIQLTQSPSS LSASVGDRVT ITCRASKSVS TSGYVYMHWN QQKPGKPPKL LIYLASYLES    60
GVPSRFSGSG SGTDFTLTIS SVQPEDFATY YCQHSRDLTF PFGGGTKLEI K            111

SEQ ID NO: 335          moltype = AA  length = 111
FEATURE                 Location/Qualifiers
REGION                  1..111
                        note = v1-39i
source                  1..111
                        mol_type = protein
                        organism = synthetic construct
SEQUENCE: 335
DIQMTQSPSS LSASVGDRVT ITCRASKSVS TSGYVYMHWY QQKPGKAPKL LIYLASYLES    60
GVPSRFSGSG SGTDFTLTIS SLQEEDFATY YCQHSRDLTF PFGGGTKLEI K            111

SEQ ID NO: 336          moltype = AA  length = 111
FEATURE                 Location/Qualifiers
REGION                  1..111
                        note = v1-39j
```

```
                        -continued source                  1..111
                        mol_type = protein
                        organism = synthetic construct
SEQUENCE: 336
DIQMTQSPSS LSASVGDRVT ITCRASKSVS TSGYVYMHWY QQKPGKAPKL LIYLASYLES    60
GVPSRFSGSG SGTDFTLTIS SVQEEDFATY YCQHSRDLTF PFGGGTKLEI K            111

SEQ ID NO: 337          moltype = AA  length = 111
FEATURE                 Location/Qualifiers
REGION                  1..111
                        note = v1-39k
source                  1..111
                        mol_type = protein
                        organism = synthetic construct
SEQUENCE: 337
DIQMTQSPSS LSASVGDRVT ITCRASKSVS TSGYVYMHWN QQKPGKPPKL LIYLASYLES    60
GVPSRFSGSG SGTDFTLTIS SVQEEDFATY YCQHSRDLTF PFGGGTKLEI K            111

SEQ ID NO: 338          moltype = AA  length = 111
FEATURE                 Location/Qualifiers
REGION                  1..111
                        note = v1-39l
source                  1..111
                        mol_type = protein
                        organism = synthetic construct
SEQUENCE: 338
DIQLTQSPSS LSASVGDRVT ITCRASKSVS TSGYVYMHWN QQKPGKPPKL LIYLASYLES    60
GVPSRFSGSG SGTDFTLTIS SVQEEDAATY YCQHSRDLTF PFGGGTKLEI K            111

SEQ ID NO: 339          moltype = AA  length = 111
FEATURE                 Location/Qualifiers
REGION                  1..111
                        note = v1-39m
source                  1..111
                        mol_type = protein
                        organism = synthetic construct
SEQUENCE: 339
DIQMTQSPSS LSASVGDRVT ITCRASKSVS TSGYVYMHWY QQKPGKPPKL LIYLASYLES    60
GVPSRFSGSG SGTDFTLTIS SVQEEDFATY YCQHSRDLTF PFGGGTKLEI K            111

SEQ ID NO: 340          moltype = AA  length = 111
FEATURE                 Location/Qualifiers
REGION                  1..111
                        note = v1-39n
source                  1..111
                        mol_type = protein
                        organism = synthetic construct
SEQUENCE: 340
DIQMTQSPSS LSASVGDRVT ITCRASKSVS TSGYVYMHWY QQKPGKPPKL LIYLASYLES    60
GVPSRFSGSG SGTDFTLTIS SVQEEDAATY YCQHSRDLTF PFGGGTKLEI K            111

SEQ ID NO: 341          moltype = AA  length = 111
FEATURE                 Location/Qualifiers
REGION                  1..111
                        note = v1-39o
source                  1..111
                        mol_type = protein
                        organism = synthetic construct
SEQUENCE: 341
DIQMTQSPSS LSASVGDRVT ITCRASKSVS TSGYVYMHWY QQKPGKPPKL LIYLASYLES    60
GVPSRFSGSG SGTDFTLTIS SVQPEDFATY YCQHSRDLTF PFGGQTKLEI K            111

SEQ ID NO: 342          moltype = AA  length = 111
FEATURE                 Location/Qualifiers
REGION                  1..111
                        note = v1-39p
source                  1..111
                        mol_type = protein
                        organism = synthetic construct
SEQUENCE: 342
DIQMTQSPSS LSASVGDRVT ITCRASKSVS TSGYVYMHWY QQKPGKPPKL LIYLASYLES    60
GVPSRFSGSG SGTDFTLTIS SVQEEDFATY YCQHSRDLTF PFGGQTKLEI K            111

SEQ ID NO: 343          moltype = AA  length = 111
FEATURE                 Location/Qualifiers
REGION                  1..111
                        note = v3-20a
source                  1..111
                        mol_type = protein
```

-continued

```
                          organism = synthetic construct
SEQUENCE: 343
EIVLTQSPAT LSLSPGERAT LSCRASKSVS TSGYVYMHWY QQKPGQAPRL LIYLASYLES    60
GIPARFSGSG SGTDFTLTIS RLEPEDFAVY YCQHSRDLTF PFGQGTKLEI K            111

SEQ ID NO: 344            moltype = AA  length = 111
FEATURE                   Location/Qualifiers
REGION                    1..111
                          note = v3-20b
source                    1..111
                          mol_type = protein
                          organism = synthetic construct
SEQUENCE: 344
EIVLTQSPAT LSLSPGERAT LSCRASKSVS TSGYVYMHWY QQKPGQAPRL LIYLASYLES    60
GIPARFSGSG SGTDFTLTIS RVEPEDFAVY YCQHSRDLTF PFGGGTKLEI K            111

SEQ ID NO: 345            moltype = AA  length = 111
FEATURE                   Location/Qualifiers
REGION                    1..111
                          note = v3-20c
source                    1..111
                          mol_type = protein
                          organism = synthetic construct
SEQUENCE: 345
EIVLTQSPAT LSLSPGERAT LSCRASKSVS TSGYVYMHWN QQKPGQAPRL LIYLASYLES    60
GIPARFSGSG SGTDFTLTIS RLEPEDFAVY YCQHSRDLTF PFGGGTKLEI K            111

SEQ ID NO: 346            moltype = AA  length = 111
FEATURE                   Location/Qualifiers
REGION                    1..111
                          note = v3-20d
source                    1..111
                          mol_type = protein
                          organism = synthetic construct
SEQUENCE: 346
EIVLTQSPAT LSLSPGERAT LSCRASKSVS TSGYVYMHWY QQKPGQPPRL LIYLASYLES    60
GIPARFSGSG SGTDFTLTIS RLEPEDFAVY YCQHSRDLTF PFGGGTKLEI K            111

SEQ ID NO: 347            moltype = AA  length = 111
FEATURE                   Location/Qualifiers
REGION                    1..111
                          note = v3-20e
source                    1..111
                          mol_type = protein
                          organism = synthetic construct
SEQUENCE: 347
EIVLTQSPAT LSLSPGERAT LSCRASKSVS TSGYVYMHWY QQKPGQAPRL LIYLASYLES    60
GIPARFSGSG SGTDFTLTIS RLEPEDAAVY YCQHSRDLTF PFGGGTKLEI K            111

SEQ ID NO: 348            moltype = AA  length = 111
FEATURE                   Location/Qualifiers
REGION                    1..111
                          note = v3-20f
source                    1..111
                          mol_type = protein
                          organism = synthetic construct
SEQUENCE: 348
EIVLTQSPAT LSLSPGERAT LSCRASKSVS TSGYVYMHWN QQKPGQAPRL LIYLASYLES    60
GIPARFSGSG SGTDFTLTIS RVEPEDFAVY YCQHSRDLTF PFGGGTKLEI K            111

SEQ ID NO: 349            moltype = AA  length = 111
FEATURE                   Location/Qualifiers
REGION                    1..111
                          note = v3-20g
source                    1..111
                          mol_type = protein
                          organism = synthetic construct
SEQUENCE: 349
EIVLTQSPAT LSLSPGERAT LSCRASKSVS TSGYVYMHWY QQKPGQPPRL LIYLASYLES    60
GIPARFSGSG SGTDFTLTIS RVEPEDFAVY YCQHSRDLTF PFGGGTKLEI K            111

SEQ ID NO: 350            moltype = AA  length = 111
FEATURE                   Location/Qualifiers
REGION                    1..111
                          note = v3-20h
source                    1..111
                          mol_type = protein
                          organism = synthetic construct
SEQUENCE: 350
```

```
EIVLTQSPAT LSLSPGERAT LSCRASKSVS TSGYVYMHWY QQKPGQAPRL LIYLASYLES    60
GIPARFSGSG SGTDFTLTIS RLEEEDFAVY YCQHSRDLTF PFGGGTKLEI K            111

SEQ ID NO: 351            moltype = AA   length = 111
FEATURE                   Location/Qualifiers
REGION                    1..111
                          note = v3-20i
source                    1..111
                          mol_type = protein
                          organism = synthetic construct
SEQUENCE: 351
EIVLTQSPAT LSLSPGERAT LSCRASKSVS TSGYVYMHWN QQKPGQAPRL LIYLASYLES    60
GIPARFSGSG SGTDFTLTIS RVEEEDFAVY YCQHSRDLTF PFGGGTKLEI K            111

SEQ ID NO: 352            moltype = AA   length = 111
FEATURE                   Location/Qualifiers
REGION                    1..111
                          note = v3-20j
source                    1..111
                          mol_type = protein
                          organism = synthetic construct
SEQUENCE: 352
EIVLTQSPAT LSLSPGERAT LSCRASKSVS TSGYVYMHWN QQKPGQPPRL LIYLASYLES    60
GIPARFSGSG SGTDFTLTIS RVEEEDAAVY YCQHSRDLTF PFGGGTKLEI K            111

SEQ ID NO: 353            moltype = AA   length = 111
FEATURE                   Location/Qualifiers
REGION                    1..111
                          note = hz5H23v1-39
source                    1..111
                          mol_type = protein
                          organism = synthetic construct
SEQUENCE: 353
DIQMTQSPSS LSASVGDRVT ITCRASKSVS TSGYVYMHWY QQKPGKAPKL LIYLASYLES    60
GVPSRFSGSG SGTDFTLTIS SLQPEDFATY YCQHSRDLTF PFGGGTKLEI K            111

SEQ ID NO: 354            moltype = AA   length = 111
FEATURE                   Location/Qualifiers
REGION                    1..111
                          note = hz5H23v3-20
source                    1..111
                          mol_type = protein
                          organism = synthetic construct
SEQUENCE: 354
EIVLTQSPAT LSLSPGERAT LSCRASKSVS TSGYVYMHWY QQKPGQAPRL LIYLASYLES    60
GIPARFSGSG SGTDFTLTIS RLEPEDFAVY YCQHSRDLTF PFGGGTKLEI K            111

SEQ ID NO: 355            moltype = AA   length = 111
FEATURE                   Location/Qualifiers
REGION                    1..111
                          note = hz5H23v4-1
source                    1..111
                          mol_type = protein
                          organism = synthetic construct
SEQUENCE: 355
DIVMTQSPDS LAVSLGERAT INCRASKSVS TSGYVYMHWY QQKPGQPPKL LIYLASYLES    60
GVPDRFSGSG SGTDFTLTIS SLQAEDVAVY YCQHSRDLTF PFGGGTKLEI K            111

SEQ ID NO: 356            moltype = AA   length = 1043
FEATURE                   Location/Qualifiers
REGION                    1..1043
                          note = Rat beta klotho
source                    1..1043
                          mol_type = protein
                          organism = Rattus norvegicus
SEQUENCE: 356
MKTGCAAGSP GNEWVFFSSD ERSTRSRKTM SNGALQRSAV LSALVLLRAV TGFSGDGKAI    60
WDKKQYVSPV NPGQLFLYDT FPKNFSWGVG TGAFQVEGSW KADGRGPSIW DRYVDSHLRG   120
VNSTDRSTDS YVFLEKDLLA LDFLGVSFYQ FSISWPRLFP NGTVAAVNAK GLQYYRALLD   180
SLVLRNIEPI VTLYHWDLPL TLQEEYGGWK NATMIDLFND YATYCFQTFG DRVKYWITIH   240
NPYLVAWHGF GTGMHAPGEK GNLTAVYTVG HNLIKAHSKV WHNYDKNFRP HQKGWLSITL   300
GSHWIEPNRT ENMEDVINCQ HSMSSVLGWF ANPIHGDGDY PEFMKTSSVI PEFSEAEKEE   360
VRGTADFFAF SFGPNNFRPS NTVVKMGQNV SLNLRQVLNW IKLEYDNPRI LISENGWFTD   420
SYIKTEDTTA IYMMKNFLNQ VLQAIKFDEI QVFGYTAWTL LDGFEWQDAY TTRRGLFYVD   480
FNSEQKERKP KSSAHYYKQI IQDNGFPLQE STPDMKGQFP CDFSWGVTES VLKPEFTVSS   540
PQFTDPHLYV WNVTGNRLLY RVEGVRLKTR PSQCTDYVSI KKVEMLAKM KVTHYQFALD   600
WTSILPTGNL SKINRQVLRY YRCVVSEGLK LGISPMVTLY HPTHSHLGLP MPLLSSGGWL   660
NTNTAKAFQD YAGLCFKELG DLVKLWITIN EPNRLSDMYN RTSNDTYRAA HNLMIAHAQV   720
WHLYDRQYRP VQHGAVSLSL HSDWAEPANP YVESHWKAAE RFLQFEIAWF ADPLFKTGDY   780
```

```
PLAMKEYIAS KKQRGLSSSV LPRFTLKESR LVKGTIDFYA LNHFTTRFVI HKQLNTNCSV    840
ADRDVQFLQD ITRLSSPSRL AVTPWGMRKL LGWIRRNYRD MDIYVTANGI DDLALEDDQI    900
RKYYLEKYVQ EALKAYLIDK VKIKGYYAFK LTEEKSKPRF GFFTSDFKAK SSVQFYSKLI    960
SSSGFSSENR SPACGQPPED TECAICSFLT QKKPLIFFGC CFISTLAALL SITIFHHRKR   1020
RKFQKARNLQ NIPLKKGHSR VFS                                          1043

SEQ ID NO: 357            moltype = DNA  length = 3132
FEATURE                   Location/Qualifiers
misc_feature              1..3132
                          note = Rat beta klotho
source                    1..3132
                          mol_type = genomic DNA
                          organism = Rattus norvegicus
SEQUENCE: 357
atgaagacag gctgtgcagc agggtctcca gggaatgaat gggttttctt cagctctgat     60
gaaagaagca cacgctctag gaaaacaatg tccaacggag cactgcaaag atctgccgtg    120
ctgtctgcat tggttctgct gcgagctgtt accggcttct ctggagacgg aaaagcaata    180
tgggataaaa aacaatacgt gagtccggta aacccaggtc agctgttcct ctatgacact    240
ttccctaaaa acttttcctg gggcgttggg accggagcat tcaagtgga agggagttgg    300
aaggcagatg gaagaggacc ctcgatctgg gaccgttatg tcgactcaca cctgagaggt    360
gtcaacagca cagacagatc cactgacagt tatgtctttc tggaaaagga cttgctggct    420
ctggattttt taggagtttc ttttatcag ttctcaatct cctggccgtc tgtgttcccc    480
aacggaacag tagcagctgt gaatgcaaaa ggtctccagt actacagagc acttctggac    540
tcgctggtac ttaggaatat cgaacccatt gttaccttat accattggga tttgcctttg    600
acgctacagg aagaatatgg gggctggaaa atgcaacta tgatagatct cttcaatgac    660
tatgccacat actgcttcca gacctttgga gaccgtgtca aatattggat tacaattgac    720
aaccccttacc tcgttgcttg gcatgggttt ggcacaggta tgcatgcgcc aggagagaag    780
ggaaatttaa cagctgtcta cactgtggga cacaacctga tcaaggcgca ttcgaaagtg    840
tggcataact acgacaaaaa cttccgcccc catcagaagg gttggctctc catcaccttg    900
gggtcccatt ggatagaacc aaacagaaca gaaaacatgg aggacgtgat caactgcccag    960
cactccatgt cttctgtgct cggatggttt gccaacccca tccacggaga cggcgactac   1020
cccgagttca tgaagacgag ctccgtaatc ctgagttct ctgaggcaga aggaggag    1080
gtgcggggca ctgctgactt ctttgccttt tccttcgggc caacaatttt caggccctcg    1140
aacaccgtgg taaaaatggg acaaaatgta tcactcaagt taagacaggt gctgaactgg    1200
attaaactag aatatgacaa ccctcgaatc ttgatttcgg agaaggctg gttcacagat    1260
agttatataa agacggaaga taccacggcc atctacatga tgaagaattt cctcaaccag   1320
gttcttcaag caataaagtt tgatgaaata caagtgtttg ttatacggc ttggactctc    1380
ctggatggct ttgagtggca ggatgcctac acgacccgac gagggctgtt ttatgtggac    1440
tttaatagtg agcagaaaga gaggaaaccc aagtcctccg ctcattacta caaacagatt    1500
atacaagaca acggttcccc tttgcaagaa tccacaccag acatgaaggg tcagtttccc    1560
tgtgacttct cctggggagt cactgagtct gttcttaagc cggagtttac ggtgtcctcc    1620
ccacagttta ctgatcctca cctgtatgtg tggaatgtca ctggcaacag attgctatac    1680
cgagtggaag gagtcaggct aaaaaacaaga ccgtcccaat gcacagatta tgtgagcactc    1740
aaaaaacgag ttgaaatgtt ggccaaaatg aaagtcaccc actaccagtt tgctctggac    1800
tggacctcta tcctccctac cggaaatctg tctaaaatta atagacaagt gttgaggtac    1860
tataggtgtg tggtgagcga aggactgaag ctgggcatct ccctatggt gacgttgtac    1920
cacccgaccc actcccatct aggcctcccc atgccacttc tgaacagtgg gggatggcta    1980
aacaccaaca cagccaaggc cttccaggac tacgcaggcc tgtgcttcaa ggagctgggg    2040
gacttggtaa agctctggat caccatcaat gaacccaata ggctgagtga catgtacaac    2100
cgcacgagta acgacaccta ccgtgcggcc acaacctga tgatcgccca tgcccaggtc    2160
tggcacctct atgataggca gtataggccg tccagcacg aggctgtgtc gctgtcctta    2220
cattccgact gggcagaacc tgccaacccc tatgtggagt ctcactggaa ggcagccgag    2280
cgcttcctcc agtttgagat cgcctggttt gcggatccac tcttcaagac tggtgactac    2340
ccgctggcca tgaaggaata catcgcctcc aagaagcagc gagggctgtc tagctcagtc    2400
ctgccgcgct ttacccttgaa ggagagcagg ctggtgaagg gaccatcga ctttttacgca    2460
ctgaaccact tcactactag attcgtgata cacaagcagt tgaatacaca ctgctcagtg    2520
gcagacaggg acgtccagtt cctgcaggac atcacccgcc tgagctcgcc cagtcgccta    2580
gccgtaacgc cctggggaat gcgcaagctc cttgggtgga tccggaggaa ctacagagac    2640
atggatatct acgtcacage caatgggatt gatgatcttg ctctagagga cgatcagatt    2700
agaaagtact acttggagaa gtacgtccag gaggctctga agcatatct gattgacaag    2760
gtcaaaatca aaggctacta tgcattcaaa ctgactgaag agaaatcaa gcctagattt    2820
ggattttca catctgactt caaagctaaa tcttctgtac agtttttatag caagctgatc    2880
agcagcagcg gcttctcctc tgagaacaga agtcctgcct gtggtcagcc tccagaaaga    2940
acagaatgcg ccatttgctc cttccttaca cagaagacact cactcatctt ctttggttgt    3000
tgcttcatct ccactctggc tgcactgcta tcaatcacta ttttcatca tcggaagaga    3060
agaaaattcc agaaagcaag gaacttacaa aatataccat tgaagaaggg gcacagaga    3120
gttttttagct aa                                                      3132

SEQ ID NO: 358            moltype = AA  length = 472
FEATURE                   Location/Qualifiers
REGION                    1..472
                          note = Heavy Chain SEQ ID NO: 32 in U.S. Publication
                          US20110135657
source                    1..472
                          mol_type = protein
                          organism = synthetic construct
SEQUENCE: 358
MDMRVPAQLL GLLLLWLRGA RCQVTLKESG PVLVKPTETL TLTCTVSGFS LNNARMGVSW     60
IRQPPGKALE WLAHIFSNDE KSYSTSLKSR LTISKDTSKS QVVLIMTNMD PVDTATYYCA    120
```

```
RSVVTGGYYY DGMDVWGQGT TVTVSSASTK GPSVFPLAPC SRSTSESTAA LGCLVKDYFP    180
EPVTVSWNSG ALTSGVHTFP AVLQSSGLYS LSSVVTVPSS NFGTQTYTCN VDHKPSNTKV    240
DKTVERKCCV ECPPCPAPPV AGPSVFLFPP KPKDTLMISR TPEVTCVVVD VSHEDPEVQF    300
NWYVDGVEVH NAKTKPREEQ FNSTFRVVSV LTVVHQDWLN GKEYKCKVSN KGLPAPIEKT    360
ISKTKGQPRE PQVYTLPPSR EEMTKNQVSL TCLVKGFYPS DIAVEWESNG QPENNYKTTP    420
PMLDSDGSFF LYSKLTVDKS RWQQGNVFSC SVMHEALHNH YTQKSLSLSP GK            472

SEQ ID NO: 359          moltype = DNA   length = 1419
FEATURE                 Location/Qualifiers
misc_feature            1..1419
                        note = Coding sequence of Heavy Chain SEQ ID NO: 32 in U.S.
                          Publication US20110135657
source                  1..1419
                        mol_type = other DNA
                        organism = synthetic construct
SEQUENCE: 359
atggacatga gggtccccgc tcagctcctg gggctcctgc tactctggct ccgaggtgcc    60
agatgtcagg tgacgctgaa agagtccgga ccggtcctgg tgaaaccaac tgaaacccta    120
actctcacgt gcactgtcag cggcttctct ctcaacaacg caagaatggg tgtgtcttgg    180
atcagacagc caccaggtaa agcgcttgag tggctggcac acatcttctc caacgatgag    240
aagagctact ctaccagcct caagtctcgt ctgaccatca gtaaagatac gtccaagtcc    300
caagtctgtc tcatcatgac taacatgcaa cccgtgactg ccgcgaccta ctactgtgcg    360
aggagcgtcg tgaccggtgg ctactactac gacggcatgg atgtgtgggg tcagggtacg    420
acggtgaccg tcagcagcgc gagcaccaag ggtccgtccg tgtttccgct cgcccccgt     480
agccggagca cctcagagtc tactgccgca ctaggctgcc tggtgaagga ctacttccct    540
gaacccgtga cagtgagctg gaactccgga gcactgacgg cgggcgtgca cacctttccc    600
gctgtcttgc agtctagcgg cctgtattcg ctctccagcg tggtcactgt accgtccagc    660
aatttcggaa cccagaccta cacatgtaac gtcgatcata aaccgtccaa cactaaggta    720
gacaaaaccg tggaaaggaa atgctgcgtg gagtgtcccc cctgcccagc tccgccagtg    780
gcaggcccca gcgtgttcct gttcccccca aagccaaaag cacccctgat gatctcgaga    840
accccggagg tgacttgcgt cgtcgtcgat gtctcccatg aggatccaga agtacagttc    900
aactggtacg tggacggcgt ggaagtgcac aatgcaaaaa cgaagccccg agaagagcag    960
ttcaactcca cattccgggt ggtatcagtc ctgactgtgg tccaccagga ttggctgaac    1020
gggaaggaat acaaatgtaa agtgagcaat aagggtctgc ccgccaccgt cgagaaaact    1080
atctcaaaaa ctaagggtca gcctcgcgag cctcaagtgt atacgctgcc gccaagtagg    1140
gaggagatga ccaaaaacca ggtgtcactg acatgtctgg tgaaaggctt ctaccccagc    1200
gacatcgccg tggagtggga gtcaaatggc cagccggaga caactacaa gaccacaccg     1260
ccgatgctgg actcagacgg gtccttttc ctctattcca agctcaccgt cgacaaaagc     1320
cgttggcagc agggaaacgt attctcatgc tctgtgatgc acgaggccct tcacaaccat    1380
tacactcaga aatcgttgtc cctttctccc ggaaaatga                          1419

SEQ ID NO: 360          moltype = AA   length = 236
FEATURE                 Location/Qualifiers
REGION                  1..236
                        note = Light Chain SEQ ID No: 14 in U.S. Publication
                          US20110135657
source                  1..236
                        mol_type = protein
                        organism = synthetic construct
SEQUENCE: 360
MDMRVPAQLL GLLLLWLRGA RCSYVLTQPP SVSVAPGQTA RITCGGNNIG SESVHWYQQK    60
PGQAPVLVVY DDSDRPSGIP ERFSGSNSGN TATLTISRVE AGDEADYYCQ VWDGNSDHVV    120
FGGGTKLTVL GQPKANPTVT LFPPSSEELQ ANKATLVCLI SDFYPGAVTV AWKADGSPVK    180
AGVETTKPSK QSNNKYAASS YLSLTPEQWK SHRSYSCQVT HEGSTVEKTV APTECS        236

SEQ ID NO: 361          moltype = DNA   length = 711
FEATURE                 Location/Qualifiers
misc_feature            1..711
                        note = Coding sequence for Light Chain SEQ ID No: 14 in
                          U.S. Publication US20110135657
source                  1..711
                        mol_type = other DNA
                        organism = synthetic construct
SEQUENCE: 361
atggacatga gggtccccgc tcagctcctg gggctcctgc tactctggct ccgaggtgcc    60
agatgttcat acgtgctgac tcagccccca tccgtgtctg tggcaccgg acaaactgcc      120
aggatcactt gcggagggaa taacatcggt agcgagagcg tccactggta ccagcaaaaa    180
ccaggccagg caccggtcct cgtggtatac gacgattctg accgaccgtc cggcatccca    240
gaaagattct cggctagcaa ctctggcaac acggctaccc tgaccatcag ccgtgtcgag    300
gccggtgacg aggcggatta ctactgccag gtgtgggacg ggaactcga tcatgtggtg     360
ttcggcggag gcactaagct gaccgtattg ggtcagccca agcaaatcc caccgtgacg     420
ctctttcccc ctagctccga ggagctgcag gcgaacaagg caactcttgt ctgtctcatc    480
tcggacttct atcccggagc ggtgaccgtc gcatggaaag cagatggttc tccggtcaaa    540
gcaggcgtgg aaacgaccaa gcccttcaaa cagatgaaca acaagtactg tgccgctctc    600
tacctaagcc tgacaccgga gcagtggaag agccaccggt catacagctg ccaggtaact    660
catgaaggct caacagtgga gaaaaccgtg gcgccaaccg agtgttcctg a             711

SEQ ID NO: 362          moltype = AA   length = 98
FEATURE                 Location/Qualifiers
```

```
REGION                  1..98
                        note = IGHV1-3
source                  1..98
                        mol_type = protein
                        organism = synthetic construct
SEQUENCE: 362
QVQLVQSGAE VKKPGASVKV SCKASGYTFT SYAMHWVRQA PGQRLEWMGW INAGNGNTKY    60
SQKFQGRVTI TRDTSASTAY MELSSLRSED TAVYYCAR                           98

SEQ ID NO: 363          moltype = AA   length = 98
FEATURE                 Location/Qualifiers
REGION                  1..98
                        note = IGHV1-18
source                  1..98
                        mol_type = protein
                        organism = synthetic construct
SEQUENCE: 363
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCAR                           98

SEQ ID NO: 364          moltype = AA   length = 98
FEATURE                 Location/Qualifiers
REGION                  1..98
                        note = IGHV1-46
source                  1..98
                        mol_type = protein
                        organism = synthetic construct
SEQUENCE: 364
QVQLVQSGAE VKKPGASVKV SCKASGYTFT SYYMHWVRQA PGQGLEWMGI INPSGGSTSY    60
AQKFQGRVTM TRDTSTSTVY MELSSLRSED TAVYYCAR                           98

SEQ ID NO: 365          moltype = AA   length = 98
FEATURE                 Location/Qualifiers
REGION                  1..98
                        note = IGHV1-69
source                  1..98
                        mol_type = protein
                        organism = synthetic construct
SEQUENCE: 365
QVQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCAR                           98

SEQ ID NO: 366          moltype = AA   length = 121
FEATURE                 Location/Qualifiers
REGION                  1..121
                        note = U00583
source                  1..121
                        mol_type = protein
                        organism = synthetic construct
SEQUENCE: 366
QVQLVQSGAE VKKPGSSVKV SCKASGGTFS SYAISWVRQA PGQGLEWMGG IIPIFGTANY    60
AQKFQGRVTI TADKSTSTAY MELSSLRSED TAVYYCARGD ILTGLNWFDP WGQGTLVTVS   120
S                                                                  121

SEQ ID NO: 367          moltype = AA   length = 101
FEATURE                 Location/Qualifiers
REGION                  1..101
                        note = IGKV4-1
source                  1..101
                        mol_type = protein
                        organism = synthetic construct
SEQUENCE: 367
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQYYST P                      101

SEQ ID NO: 368          moltype = AA   length = 95
FEATURE                 Location/Qualifiers
REGION                  1..95
                        note = IGKV1-39
source                  1..95
                        mol_type = protein
                        organism = synthetic construct
SEQUENCE: 368
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTP                              95

SEQ ID NO: 369          moltype = AA   length = 90
FEATURE                 Location/Qualifiers
REGION                  1..90
```

|   |   |
|---|---|
|  | note = IGKV3-20 |
| source | 1..90 |
|  | mol_type = protein |
|  | organism = synthetic construct |

SEQUENCE: 369
```
EIVLTQSPAT LSLSPGERAT LSCRASQSVS SSYLAWYQQK PGQAPRLLIY GASSRATGIP    60
ARFSGSGSGT DFTLTISRLE PEDFAVYYCQ                                    90
```

|   |   |
|---|---|
| SEQ ID NO: 370 | moltype = AA  length = 450 |
| FEATURE | Location/Qualifiers |
| REGION | 1..450 |
|  | note = hIgK-5H23(VH)-hIgG1(E233A)(L235A) (5H23 chimera) |
| source | 1..450 |
|  | mol_type = protein |
|  | organism = synthetic construct |

SEQUENCE: 370
```
QVQLQQSGPE LVKPGALVKI SCKASGYTFT SYDINWVKQR PGQGLEWIGW IYPGDGSTKY    60
NEKFKGKATL TADKSSRTAY MQLSSLTSEN SAVYFCARSD YYGSRSFAYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPALAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450
```

|   |   |
|---|---|
| SEQ ID NO: 371 | moltype = DNA  length = 1419 |
| FEATURE | Location/Qualifiers |
| misc_feature | 1..1419 |
|  | note = Coding sequence of hIgK-5H23(VH)-hIgG1(E233A)(L235A) (5H23 chimera) |
| source | 1..1419 |
|  | mol_type = other DNA |
|  | organism = synthetic construct |

SEQUENCE: 371
```
atggacatga gggtccccgc tcagctcctg gggctcctgc tactctggct ccgaggtgcc    60
agatgtcaag tgcaacttca acagtcaggc ccagaactcg tcaaaccngg agcactcgtg   120
aagatctcgt gcaaggcgtc gggttacact ttcacgtcct acgacatcaa ttgggtgaag   180
cagaggcctg gacagggcct ggagtggatt ggatggatct accggggga tgggtctacc   240
aagtacaacg aaaagttcaa aggcaaagcc actctgaccg cagacaagcc cagcagaacc   300
gcgtacatgc agttgtcatc cctgaccagc gagaactcgg ccgtctactt tgtgctcgc   360
tccgattact atggatcccg gagcttcgcc tactggggac agggaactct ggtgactgtg   420
tcatcggcta gcaccaaggg cccatcggtc ttccccctgg caccctcctc caagagcacc   480
tctgggggca cagcggccct gggctgcctg gtcaaggact acttccccga accggtgacg   540
gtgtcgtgga actcaggcgc cctgaccagc ggcgtgcaca ccttcccggc tgtcctacag   600
tcctcaggac tctactccct cagcagcgtg gtgaccgtgc cctccagcag cttgggcacc   660
cagacctaca tctgcaacgt gaatcacaag cccagcaaca ccaaggtgga caagaaagtt   720
gagcccaaat cttgtgacaa aactcacaca tgcccaccgt gcccagcacc tgcactcgcg   780
ggggggaccgt cagtcttcct cttccccca aaacccaagg acaccctcat gatctcccgg   840
acccctgagg tcacatgcgt ggtggtggac gtgagccacg aagaccctga ggtcaagttc   900
aactggtacg tggacggcgt ggaggtgcat aatgccaaga caaagccgcg ggaggagcag   960
tacaacagca cgtaccgtgt ggtcagcgtc ctcaccgtcc tgcaccagga ctggctgaat  1020
ggcaaggagt acaagtgcaa ggtctccaac aaagccctcc cagcccccat cgagaaaacc  1080
atctccaaag ccaaagggca gccccgagaa ccacaggtgt acaccctgcc cccatcccgg  1140
gaggagatga ccaagaacca ggtcagcctg acctgcctgg tcaaaggctt ctatcccagc  1200
gacatcgccg tggagtggga gcaatgggg cagccggaga acaactacaa gaccacgcct  1260
cccgtgctgg actccgacgg ctccttcttc ctctacagca agctcaccgt ggacaagagc  1320
aggtggcagc aggggaacgt cttctcatgc tccgtgatgc atgaggctct gcacaaccac  1380
tacacgcaga gagcctctc cctgtctccg ggtaaatga                          1419
```

|   |   |
|---|---|
| SEQ ID NO: 372 | moltype = AA  length = 218 |
| FEATURE | Location/Qualifiers |
| REGION | 1..218 |
|  | note = hIgK-5H23(VL)-hIgK (5H23 chimera) |
| source | 1..218 |
|  | mol_type = protein |
|  | organism = synthetic construct |

SEQUENCE: 372
```
DIVLTQSPAS LAVSLGQRAT ISCRASKSVS TSGYVYMHWN QQKPGQPPKL LIYLASYLES    60
GVPARFSGSG SGTDFTLNIH PVEEEDAAIY YCQHSRDLTF PFGGGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218
```

|   |   |
|---|---|
| SEQ ID NO: 373 | moltype = DNA  length = 723 |
| FEATURE | Location/Qualifiers |
| misc_feature | 1..723 |
|  | note = Coding sequence of hIgK-5H23(VL)-hIgK (5H23 chimera) |
| source | 1..723 |
|  | mol_type = other DNA |
|  | organism = synthetic construct |

-continued

```
SEQUENCE: 373
atggacatga gggtcccgc  tcagctcctg gggctcctgc tactctggct ccgaggtgcc   60
agatgtgaca tcgtcctgac tcagagcccc gcatccctcg ccgtgtcact tggtcaaaga  120
gctaccattt cctgccgcgc atcgaagtct gtgagcactt ccggctacgt ctacatgcac  180
tggaaccagc agaagccagg acaaccgccg aagctgctaa tctatctcgc gtcatacctg  240
gaatcgggag tgccggcgag gttttcggga tcgggctccg gaaccgactt cacccctgaat  300
atccatccag tggaagagga ggatgccgcc atctactact gtcagcacag ccgggatctc  360
actttccctt cggcggagg  gacgaaattg gaaatcaaac gtacggtggc tgcaccatct  420
gtcttcatct tcccgccatc tgatgagcag ttgaaatctg gaactgcctc tgttgtgtgc  480
ctgctgaata acttctatcc cagagaggcc aaagtacagt ggaaggtgga taacgccctc  540
caatcgggta actcccagga gagtgtcaca gagcaggaca gcaaggacag cacctacagc  600
ctcagcagca ccctgacgct gagcaaagca gactacgaga acacaaagt  ctacgcctgc  660
gaagtcaccc atcagggcct gagctcgccc gtcacaaaga gcttcaacag ggagagtgt   720
tag                                                                 723

SEQ ID NO: 374      moltype = AA  length = 1045
FEATURE             Location/Qualifiers
REGION              1..1045
                    note = human KLB (M1-F508)- mouse KLB (P507-S1043)
source              1..1045
                    mol_type = protein
                    organism = synthetic construct
SEQUENCE: 374
MKPGCAAGSP GNEWIFFSTD EITTRYRNTM SNGGLQRSVI LSALILLRAV TGFSGDGRAI   60
WSKNPNFTPV NESQLFLYDT FPKNFFWGIG TGALQVEGSW KKDGKGPSIW DHFIHTHLKN  120
VSSTNGSSDS YIFLEKDLSA LDFIGVSFYQ FSISWPRLFP DGIVTVANAK GLQYYSTLLD  180
ALVLRNIEPI VTLYHWDLPL ALQEKYGGWK NDTIIDIFND YATYCFQMFG DRVKYWITIH  240
NPYLVAWHGY GTGMHAPGEK GNLAAVYTVG HNLIKAHSKV WHNYNTHFRP HQKGWLSITL  300
GSHWIEPNRS ENTMDIFKCQ QSMVSVLGWF ANPIHGDGDY PEGMRKKLFS VLPIFSEAEK  360
HEMRGTADFF AFSFGPNNFK PLNTMAKMGQ NVSLNLREAL NWIKLEYNNP RILIAENGWF  420
TDSRVKTEDT TAIYMMKNFL SQVLQAIRLD EIRVFGYTAW SLLDGFEWQD AYTIRRGLFY  480
VDFNSKQKER KPKSSAHYYK QIIRENGFPL KESTPDMKGR FPCDFSWGVT ESVLKPEFTV  540
SSPQFTDPHL YVWNVTGNRL LYRVEGVRLK TRPSQCTDYV SIKKRVEMLA KMKVTHYQFA  600
LDWTSILPTG NLSKVNRQVL RYYRCVVSEG LKLGVFPMVT LYHPTHSHLG LPLPLLSSGG  660
WLNMNTAKAF QDYAELCFRE LGDLVKLWIT INEPNRLSDM YNRTSNDTYR AAHNLMIAHA  720
QVWHLYDRQY RPVQHGAVSL SLHCDWAEPA NPFVDSHWKA AERFLQFEIA WFADPLFKTG  780
DYPSVMKEYI ASKNQRGLSS SVLPRFTAKE SRLVKGTVDF YALNHFTTRF VIHKQLNTNR  840
SVADRDVQFL QDITRLSSPS RLAVTPWGVR KLLAWIRRNY RDRDIYITAN GIDDLALEDD  900
QIRKYYLEKY VQEALKAYLI DKVKIKGYYA FKLTEEKSKP RFGFFTSDFR AKSSVQFYSK  960
LISSSGLPAE NRSPACGQPA EDTDCTICSF LVEKKPLIFF GCCFISTLAV LLSITVFHHQ 1020
KRRKFQKARN LQNIPLKKGH SRVFS                                       1045

SEQ ID NO: 375      moltype = DNA  length = 3138
FEATURE             Location/Qualifiers
misc_feature        1..3138
                    note = Coding sequence of human KLB (M1-F508)- mouse KLB
                    (P507-S1043)
source              1..3138
                    mol_type = other DNA
                    organism = synthetic construct
SEQUENCE: 375
atgaagccag gctgtgcggc aggatctcca gggaatgaat ggattttctt cagcactgat   60
gaaataacca cacgctatag gaatacaatg tccaacgggg gattgcaaag atctgtcatc  120
ctgtcagcac ttattctgct acgagctgtt actggattct ctggagatgg aagagctata  180
tggtctaaaa atcctaattt tactccggta aatgaaagtc agctgtttct ctatgacact  240
ttccctaaaa actttttctg gggtattggg actggagcat gcaagtgga  agggagttgg  300
aagaaggatg gaaaaggacc ttctatatgg gatcatttca tccacacaca ccttaaaaat  360
gtcagcagca cgaatggttc cagtgacagt tatattttc  tggaaaaaga cttatcagcc  420
ctggatttta taggagtttc ttttatcaa  ttttcaattt cctggccaag gctttttccc  480
gatggaatag taacagttgc caacgcaaaa ggtctgcagt actacagtac tcttctggac  540
gctctagtgc ttagaaacat tgaacctata gttactttat accactggga tttgcctttg  600
gcactacaag aaaaatatgg ggggtggaaa aatgatacca atagatat  cttcaatgac  660
tatgccacat actgtttcca gatgtttggg accgtgtca  aatattggat tacaattcac  720
aacccatatc tagtggcttg gcatgggtat ggacaggtta tgcatgccc  tggagagaag  780
ggaaatttag cagctgtcta cactgtggga cacaacttga tcaaggctca ctcgaaagtt  840
tggcataact acaacacaca tttccgccca atcagaagg  gttggttatc gatcacgttg  900
ggatctcatt ggatcgagcc aaaccggtcg aaaacacga  tggatatatt caatgtcaa  960
caatccatgg tttctgtgct tggatggttt gccaaccct  tccatgggga tggcgactat 1020
ccagagggga tgagaaagaa gttgttctcc gttctaccca tttctctga  agcagagaag 1080
catgagatga gaggcacagc tgatttcttt gccttttctt ttggacccaa caacttcaag 1140
cccctaaaca ccatggctaa aatgggacaa aatgtttcac ttaatttaag agaagcgctg 1200
aactggatta aactggaata caacaaccct cgaatcttga ttgctgagaa tggctggttc 1260
acagacagtc gtgtgaaaac agaagacacc acggccatct acatgatgaa gaatttcctc 1320
agcagtcc   ttcaagcaat aaggttagat gaaatacgag tgtttggtta tactgcctgg 1380
tctctcctgg atggctttga atggcaggat gcttacacca tccgccgagg attatttat  1440
gtggatttta acagtaaaca gaaagagcgg aaacctaagt cttcagcaca ctactacaaa 1500
cagatcatac gagaaaatgg ttttcctttg aaagagtcca cgccagacat gaagggtcgg 1560
ttcccctgtg atttctcttg gggagtcact gagtctgttc ttaagccga  gtttacggtc 1620
tcctccccgc agtttaccga tcctcacctg tatgtgtgga atgtcactgg caacagattg 1680
```

```
ctctaccgag tggaagggggt aaggctgaaa acaagaccat cccagtgcac agattatgtg    1740
agcatcaaaa aacgagttga aatgttggca aaaatgaaag tcacccacta ccagtttgct    1800
ctggactgga cctctatcct tcccactggc aatctgtcca agttaacag acaagtgtta     1860
aggtactata ggtgtgtggt gagcgaagga ctgaagctgg gcgtcttccc catggtgacg    1920
ttgtaccacc caacccactc ccatctcggc ctcccccctgc cacttctgag cagtgggggg   1980
tggctaaaca tgaacacagc caaggccttc caggactacg ctgagctgtg cttccgggga   2040
ttgggggact tggtgaagct ctggatcacc atcaatgagc taacaggct gagtgacatg    2100
tacaaccgca cgagtaatga cacctaccgt gcagcccaca acctgatgat cgcccatgcc   2160
caggtctggc acctctatga taggcagtat aggccggtcc agcatggggc tgtgtcgctg    2220
tccttacatt gcgactgggc agaacctgcc aaccccttttg tggattcaca ctggaaggca   2280
gccgagcgct tcctccagtt tgagatcgcc tggtttgcag atccgctctt caagactggc   2340
gactatccat cggttatgaa ggaatacatc gcctccaaga accagcgagg gctgtctagc    2400
tcagtcctgc cgcgcttcac cgcgaaggag agcaggctgt gaagggtac cgtcgacttc    2460
tacgcactga accacttcac tacgaggttc gtgataccaa agcagctgaa caccaaccgc   2520
tcagttgcag acaggggacgt ccagttcctg caggacatca cccgcctaag ctcgcccagc    2580
cgcctggctg taacaccctg gggagtgcgc aagctccttg cgtggatccg gagaactac    2640
agagacaggg atatctacat cacagccaat ggcatcgatg acctggctct agaggatgat    2700
cagatccgaa agtactactt ggagaagtat gtccaggagg ctctgaaagc atatctcatt   2760
gacaaggtca aaatcaaagg ctactatgca ttcaaactgg ctgaagagaa atctaagcct    2820
agatttggat tttcacctc tgacttcaga gctaagtcct ctgtccagtt ttacagcaag    2880
ctgatcagca gcagtggcct ccccgctgag aacgaagtc ctgcgtgtgg tcagcctgcg    2940
gaagacacag actgcaccat ttgctcattt ccgtgtgaga agaaaaccact catcttcttg   3000
ggttgctgct tcatctccac tctggctgta ctgctatcca tcaccgtttt tcatcatcaa    3060
aagagaagaa aattccagaa agcaaggaac ttacaaaata taccattgaa gaaaggccac   3120
agcagagttt tcagctga                                                 3138
```

| SEQ ID NO: 376 | moltype = AA length = 1042 |
|---|---|
| FEATURE | Location/Qualifiers |
| REGION | 1..1042 |
| | note = Mouse KLB (M1-F506) - human KLB(S509-S1044) |
| source | 1..1042 |
| | mol_type = protein |
| | organism = synthetic construct |

```
SEQUENCE: 376
MKTGCAAGSP GNEWIFFSSD ERNTRSRKTM SNRALQRSAV LSAFVLLRAV TGFSGDGKAI     60
WDKKQYVSPV NPSQLFLYDT FPKNFSWGVG TGAFQVEGSW KTDGRGPSIW DRYVYSHLRG    120
VNGTDRSTDS YIFLEKDLLA LDFLGVSFYQ FSISWPRLFP NGTVAAVNAQ GLRYYRALLD    180
SLVLRNIEPI VTLYHWDLPL TLQEEYGGWK NATMIDLFND YATYCFQTFG DRVKYWITIH    240
NPYLVAWHGF GTGMHAPGEK GNLTAVYTVG HNLIKAHSKV WHNYDKNFRP HQKGWLSITL    300
GSHWIEPNRT DNMEDVINCQ HSMSSVLGWF ANPIHGDGDY PEFMKTGAMI PEFSEAEKEE    360
VRGTADFFAF SFGPNNFRPS NTVVKMGQNV SLNLRQVLNW IKLEYDDPQI LISENGWFTD    420
SYIKTEDTTA IYMMKNFLNQ VLQAIKFDEI RVFGYTAWTL LDGFEWQDAY TTRRGLFYVD    480
FNSEQKERKP KSSAHYYKQI IQDNGFSLKE STPDVQGQFP CDFSWGVTES VLKPESVASS    540
PQFSDPHLYV WNATGNRLLH RVEGVRLKTR PAQCTDFVNI KKQLEMLARM KVTHYRFALD    600
WASVLPTGNL SAVNRQALRY YRCVVSEGLK LGISAMVTLY YPTHAHLGLP EPLLHADGWL    660
NPSTAEAFQA YAGLCFQELG DLVKLWITIN EPNRLSDIYN RSGNDTYGAA HNLLVAHALA    720
WRLYDRQFRP SQRGAVSLSL HADWAEPANP YADSHWRAAE RFLQFEIAWF AEPLFKTGDY    780
PAAMREYIAS KHRRGLSSSA LPRLTEAERR LLKGTVDFCA LNHFTTRFVM HEQLAGSRYD    840
SDRDIQFLQD ITRLSSPTRL AVIPWGVRKL LRWVRRNYGD MDIYITASGI DDQALEDDRL    900
RKYYLGKYLQ EVLKAYLIDK VRIKGYYAFK LAEEKSKPRF GFFTSDFKAK SSIQFYNKVI    960
SSRGFPPENS SSRCSQTQEN TECTVCLFLV QKKPLIFLGC CFFSTLVLLL SIAIFQRQKR   1020
RKFWKAKNLQ HIPLKKGKRV VS                                            1042
```

| SEQ ID NO: 377 | moltype = DNA length = 3129 |
|---|---|
| FEATURE | Location/Qualifiers |
| misc_feature | 1..3129 |
| | note = Coding sequence of Mouse KLB (M1-F506) - human KLB(S509-S1044) |
| source | 1..3129 |
| | mol_type = other DNA |
| | organism = synthetic construct |

```
SEQUENCE: 377
atgaagacag gctgtgcagc agggtctccg gggaatgaat ggattttctt cagctctgat     60
gaaagaaaca cacgctctag gaaaacaatg tccaacaggg cactgcaaag atctgccgtg    120
ctgtctgcgt tgttctgct gcgagctgtt accggcttct ccggagacgg aaaagcaata    180
tgggataaaa aacagtacgt gagtccggta aacccaagtc agctgttcct ctatgacact    240
ttccctaaaa acttttcctg gggcgttggg accggagcat tcaagtgga agggagttgg    300
aagacagatg gaagaggacc ctcgatctgg gatcggtacg tctactcaca cctgagaggt    360
gtcaacggca cagacagatc cactgacagt tacatctttt tggaaaagga cttgttggct    420
ctggattttt taggagtttc ttttatcag ttctcaatct cctggccacg gttgtttccc    480
aatgaaacag tagcagcagt gaatgcgcaa ggtctccggt actaccgtgc acttctggac    540
tcgctggtac ttaggaatat cgagcccatt gttaccttgt accattggga tttgcctctg    600
acgctccagg aagaatatgg gggctggaaa aatgcaacta tgatagatct cttcaacgac    660
tatgccacat actgcttcca gacctttgga gaccgtgtca aatattgata ttacaattcac   720
aaccccttac ttgttgcttg catgggtttt ggcacaggta tgcatgcacc aggagagaag    780
ggaaatttaa cagctgtcta cactgtggga cacaacctga tcaaggcaca ttcgaaagtg    840
tggcataact acgacaaaaa cttccgcccc atcagaagg gttggctctc catcaccttg    900
gggtcccatt ggatagagcc aaacagaaca gacaacatgg aggacgtgat caactgccag    960
cactccagtg cctctgtgct tggatggtc gccaacccca tccacgggga cggcgactac   1020
```

```
cctgagttca tgaagacggg cgccatgatc cccgagttct ctgaggcaga gaaggaggag   1080
gtgaggggca cggctgattt ctttgccttt tccttcgggc caacaactt caggccctca   1140
aacaccgtgg tgaaatggg acaaaatgta tcactcaact taaggcaggt gctgaactgg   1200
attaaactgg aatacgatga ccctcaaatc ttgatttcgg agaacggctg gttcacagat   1260
agctatataa agacaggaga caccacggcc atctacatca tgaagaattt cctaaaccag   1320
gttcttcaag caataaaatt tgatgaaatc cgcgtgtttg gttatacggc ctggactctc   1380
ctggatggct ttgagtggca ggatgcctat acgacccgac gagggctgtt ttatgtggac   1440
tttaacagtg agcagaaaga gaggaaaccc aagtcctcgg ctcattacta caagcagatc   1500
atacaagaca acggcttctc tttaaaagag tccacgccag atgtgcaggg ccagtttccc   1560
tgtgacttct cctgggggtgt cactgaatct gttcttaagc ccgagtctgt ggcttcgtcc   1620
ccacagttca gcgatcctca tctgtacgtg tggaacgcca ctggcaacag actgttgcac   1680
cgagtggaag gggtgaggct gaaaacacga cccgctcaat gcacagattt tgtaaacatc   1740
aaaaaacaac ttgagatgtt ggcaagaatg aaagtcaccc actaccggtt tgctctggat   1800
tgggctcgg tccttcccac tggcaacctg tccgcggtga accgacaggc cctgaggtac   1860
tacaggtgcg tggtcagtga ggggctgaag cttggcatct ccgcgatggt caccctgtat   1920
tatccgaccc acgccacctt aggcctcccc gagcctctgt tgcatgccga cgggtggctg   1980
aacccatcga cggccgaggc cttccaggcc tacgctgggc tgtgcttcca ggagctgggg   2040
gacctggtga agctctggat caccatcaac gagcctaacc tggtaagtga catctacaac   2100
cgctctggca acgacaccta cgggcggcgc cacaacctgc tggtggccca cgccctggcc   2160
tggcgcctct acgaccggca gttcaggccc tcacagcgcg gggccgtgtc gctgtcgctg   2220
cacgcggact gggcggaacc cgccaacccc tatgctgact cgcactggag ggcggccgag   2280
cgcttcctgc agttcgagat cgcctggttc gccgagccgc tcttcaagac cggggactac   2340
cccgcggcca tgagggaata cattgcctcc aagcaccgac gggggctttc cagctcggcc   2400
ctgccgcgcc tcaccgaggc cgaaaggagg ctgctcaagg gcacggtcga cttctgcgcg   2460
ctcaaccact tcaccactag gttcgtgatg cacgagcagc tggccggcag ccgctacgac   2520
tcggacaggg acatccagtt tctgcaggac atcacccgcc tgagctcccc cacgcgcctg   2580
gctgtgattc cctgggggt gcgcaagctg ctgcggtggg tccggaggaa ctacggcgac   2640
atggacattt acatcaccgc cagtggcatc gacgaccagg ctctggagga tgaccggctc   2700
cggaagtact acctagggaa gtaccttcag gaggtgctga agcatacct gattgataaa   2760
gtcagaataa aaggctatta tgcattcaaa ctggctgaag agaaatctaa acccagattt   2820
ggattcttca catctgattt taaagctaaa tcctcaatac aatttttacaa caaagtgatc   2880
agcagcaggg gcttcccttt tgagaacagt agttctagat gcagtcagac ccaagaaaat   2940
acagagtgca ctgtctgctt attccttgtg cagaagaaac cactgatatt cctgggttgt   3000
tgcttcttct ccaccctggt tctactctta tcaattgcca ttttttcaaag gcagaagaga   3060
agaaagtttt ggaaagcaaa aaacttacaa cacataccat taaagaaagg caagagagtt   3120
gttagctag                                                          3129

SEQ ID NO: 378        moltype = AA  length = 25
FEATURE               Location/Qualifiers
REGION                1..25
                      note = Humanized Anti-Beta Klotho VH FR1
source                1..25
                      mol_type = protein
                      organism = synthetic construct
SEQUENCE: 378
QVQLVQSGAE VKKPGSSVKV SCKAS                                        25

SEQ ID NO: 379        moltype = AA  length = 32
FEATURE               Location/Qualifiers
REGION                1..32
                      note = Humanized Anti-Beta Klotho VH FR3
source                1..32
                      mol_type = protein
                      organism = synthetic construct
SEQUENCE: 379
RATLTADKST STAYMELSSL RSEDTAVYYC AR                                32

SEQ ID NO: 380        moltype = AA  length = 32
FEATURE               Location/Qualifiers
REGION                1..32
                      note = Humanized Anti-Beta Klotho VH FR3
source                1..32
                      mol_type = protein
                      organism = synthetic construct
SEQUENCE: 380
RATLTADKST RTAYMELSSL RSEDTAVYYC AR                                32

SEQ ID NO: 381        moltype = AA  length = 32
FEATURE               Location/Qualifiers
REGION                1..32
                      note = Humanized Anti-Beta Klotho VH FR3
source                1..32
                      mol_type = protein
                      organism = synthetic construct
SEQUENCE: 381
RATITADKST STAYMELSSL RSEDTAVYYC AR                                32

SEQ ID NO: 382        moltype = AA  length = 23
FEATURE               Location/Qualifiers
```

```
REGION                      1..23
                            note = Humanized Anti-Beta Klotho VL FR1
source                      1..23
                            mol_type = protein
                            organism = synthetic construct
SEQUENCE: 382
DIQMTQSPSS LSASVGDRVT ITC                                              23

SEQ ID NO: 383              moltype = AA  length = 23
FEATURE                     Location/Qualifiers
REGION                      1..23
                            note = Humanized Anti-Beta Klotho VL FR1
source                      1..23
                            mol_type = protein
                            organism = synthetic construct
SEQUENCE: 383
DIQLTQSPSS LSASVGDRVT ITC                                              23

SEQ ID NO: 384              moltype = AA  length = 23
FEATURE                     Location/Qualifiers
REGION                      1..23
                            note = Humanized Anti-Beta Klotho VL FR1
source                      1..23
                            mol_type = protein
                            organism = synthetic construct
SEQUENCE: 384
EIVLTQSPAT LSLSPGERAT LSC                                              23

SEQ ID NO: 385              moltype = AA  length = 15
FEATURE                     Location/Qualifiers
REGION                      1..15
                            note = Humanized Anti-Beta Klotho VL FR2
source                      1..15
                            mol_type = protein
                            organism = synthetic construct
SEQUENCE: 385
WYQQKPGKAP KLLIY                                                       15

SEQ ID NO: 386              moltype = AA  length = 15
FEATURE                     Location/Qualifiers
REGION                      1..15
                            note = Humanized Anti-Beta Klotho VL FR2
source                      1..15
                            mol_type = protein
                            organism = synthetic construct
SEQUENCE: 386
WNQQKPGKAP KLLIY                                                       15

SEQ ID NO: 387              moltype = AA  length = 15
FEATURE                     Location/Qualifiers
REGION                      1..15
                            note = Humanized Anti-Beta Klotho VL FR2
source                      1..15
                            mol_type = protein
                            organism = synthetic construct
SEQUENCE: 387
WYQQKPGKPP KLLIY                                                       15

SEQ ID NO: 388              moltype = AA  length = 15
FEATURE                     Location/Qualifiers
REGION                      1..15
                            note = Humanized Anti-Beta Klotho VL FR2
source                      1..15
                            mol_type = protein
                            organism = synthetic construct
SEQUENCE: 388
WNQQKPGKPP KLLIY                                                       15

SEQ ID NO: 389              moltype = AA  length = 15
FEATURE                     Location/Qualifiers
REGION                      1..15
                            note = Humanized Anti-Beta Klotho VL FR2
source                      1..15
                            mol_type = protein
                            organism = synthetic construct
SEQUENCE: 389
WYQQKPGQAP RLLIY                                                       15

SEQ ID NO: 390              moltype = AA  length = 15
```

```
FEATURE                 Location/Qualifiers
REGION                  1..15
                        note = Humanized Anti-Beta Klotho VL FR2
source                  1..15
                        mol_type = protein
                        organism = synthetic construct
SEQUENCE: 390
WNQQKPGQAP RLLIY                                                     15

SEQ ID NO: 391          moltype = AA  length = 15
FEATURE                 Location/Qualifiers
REGION                  1..15
                        note = Humanized Anti-Beta Klotho VL FR2
source                  1..15
                        mol_type = protein
                        organism = synthetic construct
SEQUENCE: 391
WYQQKPGQPP RLLIY                                                     15

SEQ ID NO: 392          moltype = AA  length = 15
FEATURE                 Location/Qualifiers
REGION                  1..15
                        note = Humanized Anti-Beta Klotho VL FR2
source                  1..15
                        mol_type = protein
                        organism = synthetic construct
SEQUENCE: 392
WNQQKPGQPP RLLIY                                                     15

SEQ ID NO: 393          moltype = AA  length = 32
FEATURE                 Location/Qualifiers
REGION                  1..32
                        note = Humanized Anti-Beta Klotho VL FR3
source                  1..32
                        mol_type = protein
                        organism = synthetic construct
SEQUENCE: 393
GVPDRFSGSG SGTDFTLTIS SLQAEDVAVY YC                                  32

SEQ ID NO: 394          moltype = AA  length = 32
FEATURE                 Location/Qualifiers
REGION                  1..32
                        note = Humanized Anti-Beta Klotho VL FR3
source                  1..32
                        mol_type = protein
                        organism = synthetic construct
SEQUENCE: 394
GVPSRFSGSG SGTDFTLTIS SLQPEDFATY YC                                  32

SEQ ID NO: 395          moltype = AA  length = 32
FEATURE                 Location/Qualifiers
REGION                  1..32
                        note = Humanized Anti-Beta Klotho VL FR3
source                  1..32
                        mol_type = protein
                        organism = synthetic construct
SEQUENCE: 395
GVPSRFSGSG SGTDFTLTIS SVQPEDFATY YC                                  32

SEQ ID NO: 396          moltype = AA  length = 32
FEATURE                 Location/Qualifiers
REGION                  1..32
                        note = Humanized Anti-Beta Klotho VL FR3
source                  1..32
                        mol_type = protein
                        organism = synthetic construct
SEQUENCE: 396
GVPSRFSGSG SGTDFTLTIS SLQEEDFATY YC                                  32

SEQ ID NO: 397          moltype = AA  length = 32
FEATURE                 Location/Qualifiers
REGION                  1..32
                        note = Humanized Anti-Beta Klotho VL FR3
source                  1..32
                        mol_type = protein
                        organism = synthetic construct
SEQUENCE: 397
GVPSRFSGSG SGTDFTLTIS SVQEEDFATY YC                                  32
```

```
SEQ ID NO: 398            moltype = AA  length = 32
FEATURE                   Location/Qualifiers
REGION                    1..32
                          note = Humanized Anti-Beta Klotho VL FR3
source                    1..32
                          mol_type = protein
                          organism = synthetic construct
SEQUENCE: 398
GVPSRFSGSG SGTDFTLTIS SVQEEDAATY YC                                  32

SEQ ID NO: 399            moltype = AA  length = 32
FEATURE                   Location/Qualifiers
REGION                    1..32
                          note = Humanized Anti-Beta Klotho VL FR3
source                    1..32
                          mol_type = protein
                          organism = synthetic construct
SEQUENCE: 399
GIPARFSGSG SGTDFTLTIS RLEPEDFAVY YC                                  32

SEQ ID NO: 400            moltype = AA  length = 32
FEATURE                   Location/Qualifiers
REGION                    1..32
                          note = Humanized Anti-Beta Klotho VL FR3
source                    1..32
                          mol_type = protein
                          organism = synthetic construct
SEQUENCE: 400
GIPARFSGSG SGTDFTLTIS RVEPEDFAVY YC                                  32

SEQ ID NO: 401            moltype = AA  length = 32
FEATURE                   Location/Qualifiers
REGION                    1..32
                          note = Humanized Anti-Beta Klotho VL FR3
source                    1..32
                          mol_type = protein
                          organism = synthetic construct
SEQUENCE: 401
GIPARFSGSG SGTDFTLTIS RLEPEDAAVY YC                                  32

SEQ ID NO: 402            moltype = AA  length = 32
FEATURE                   Location/Qualifiers
REGION                    1..32
                          note = Humanized Anti-Beta Klotho VL FR3
source                    1..32
                          mol_type = protein
                          organism = synthetic construct
SEQUENCE: 402
GIPARFSGSG SGTDFTLTIS RLEEEDFAVY YC                                  32

SEQ ID NO: 403            moltype = AA  length = 32
FEATURE                   Location/Qualifiers
REGION                    1..32
                          note = Humanized Anti-Beta Klotho VL FR3
source                    1..32
                          mol_type = protein
                          organism = synthetic construct
SEQUENCE: 403
GIPARFSGSG SGTDFTLTIS RVEEEDFAVY YC                                  32

SEQ ID NO: 404            moltype = AA  length = 32
FEATURE                   Location/Qualifiers
REGION                    1..32
                          note = Humanized Anti-Beta Klotho VL FR3
source                    1..32
                          mol_type = protein
                          organism = synthetic construct
SEQUENCE: 404
GIPARFSGSG SGTDFTLTIS RVEEEDAAVY YC                                  32

SEQ ID NO: 405            moltype = AA  length = 10
FEATURE                   Location/Qualifiers
REGION                    1..10
                          note = Humanized Anti-Beta Klotho VL FR4
source                    1..10
                          mol_type = protein
                          organism = synthetic construct
SEQUENCE: 405
FGGGTKVEIK                                                           10
```

```
SEQ ID NO: 406          moltype = AA  length = 10
FEATURE                 Location/Qualifiers
REGION                  1..10
                        note = Humanized Anti-Beta Klotho VL FR4
source                  1..10
                        mol_type = protein
                        organism = synthetic construct
SEQUENCE: 406
FGQGTKLEIK                                                                  10

SEQ ID NO: 407          moltype = AA  length = 10
FEATURE                 Location/Qualifiers
REGION                  1..10
                        note = Humanized Anti-Beta Klotho VL FR4
source                  1..10
                        mol_type = protein
                        organism = synthetic construct
SEQUENCE: 407
FGGQTKLEIK                                                                  10

SEQ ID NO: 408          moltype = AA  length = 1042
FEATURE                 Location/Qualifiers
REGION                  1..1042
                        note = hamster beta klotho
source                  1..1042
                        mol_type = protein
                        organism = Cricetulus griseus
SEQUENCE: 408
MKAGCAAGSP GNEWIFLSSY ERNTRSKKTM SNRALQRSVV LSAFVLLRAV TGLSGDGKAI    60
WDKKQYVSPV NASQLFLYDT FPKNFFWGVG TGAFQVEGNW QADGRGPSIW DRFIYTHLRD   120
VSITEKSADS YIFLEKDLLA LDFLGVSFYQ FSISWPRLFP NGTVASVNAK GLQYYNKLLD   180
SLILRNIEPV VTLYHWDLPL ALQEDYGGWK NATMIDLFND YATYCFQTFG DRVKYWITIH   240
NPYLVAWHGF ATGMHAPGET GNLTAVYIVG HNLIKAHSKV WHNYDKNFRP HQKGLLSITL   300
GSHWIEPNKT ENMADTISCQ HSMAFVLGWF ANPIHADGDY PEFMKTLSTM PVFSEAEKEE   360
VRGTADFFAF SFGPNNFRPS NTVVKMGQNV SLNLRQVLNW IKLEYDNPRI LISENGWFTD   420
SDIKTEDTTA IYMMKHFLNQ VLQAIQFDEI RVFGYTAWSL LDGFEWQYAY TSRRGLFYVD   480
FNSEQKERKP KTSAHYYKQI IQENGFPLKE STPDMQGQFP CDFSWGVTES VLKPEFMVSS   540
PQFTDPHLYV WNATGNRLLQ RVEGVRLKTK PSHCTDYVSI KKRVEMLAKM KVTHYQFALD   600
WATILPTGNL SEVNRQVLRY YRCVVSEGLK LGVSPMVTLY HPTHSHLGLP EPLLNSGGWL   660
NTYTAKAFQD YAGLCFQELG DLVKLWITIN EPNRLSDMYN RTSNDTYRAA HNLMIAHAQV   720
WRLYDRQYRP VQHGAVSLSL HSDWVEPANP YVDSHWKAAE RFLLFEIAWF ADPLFKTGDY   780
PLAMKEYIAS KNQQGLSRSV LPRFTPEESR LVKGTIDFYA LNHFTTRFVI HKQLNSSRSM   840
ADRDVQFLQD ITRLSSPSRL AVMPWGARKL LGWIQRNYGD MDIYITANGI DDLALENDGI   900
RKYYLEKYIQ EALKAYLIDK VKIKGYYAFK LTEEKSKPRF GFFTSDFKAK SSVEFYSKLI   960
SRSGFPSETS NPACGQPPED TDCTICSFFT QKKSLIFFGC CFISTLAVLL SITIFHHRKR  1020
RFHKSKNLEN IPLKEGHSRV LS                                           1042

SEQ ID NO: 409          moltype = DNA  length = 3042
FEATURE                 Location/Qualifiers
misc_feature            1..3042
                        note = Coding sequence of hamster beta klotho
source                  1..3042
                        mol_type = genomic DNA
                        organism = Cricetulus griseus
SEQUENCE: 409
atgtccaaca gggcactgca aagatctgtc gtgctgtcag cgtttgttct gctgcgagct    60
gttaccggat tgtctggaga cgggaaagcg atatgggata aaaaacagta cgtgagtccg   120
gtgaatgcaa gtcagctgtt tctctatgac actttcccta aaaacttttt ctggggtgtt   180
ggaactggag catttcaagt ggaagggaat tggcaggcag acggaagagg accctcgatt   240
tgggatcgtt tcatctacac acacctgaga gatgtcagca tcacagagaa atccgccgac   300
agttacattt tcctggaaaa agatttgttg gctctggatt ttttaggagt ttcttttttat   360
cagttctcaa tctcctggcc acggttgttc cccaatggaa cagtagcatc cgtgaatgca   420
aaaggtctcc aatactacaa caaacttctg gactcgctga acttaggaa tattgagccc   480
gttgttacct tataccattg ggatttgcct ttggcgctac aggaagacta tggggttgg   540
aaaaatgcaa ctatgataga tctcttcaat gactatgcca catactgctt ccagaccttt   600
ggagaccgtg tcaagtattg gattacaatt cacaacccttt acctggttgc ttggcatggg   660
tttgccacag gtatgcatgc gccaggagag acgggaaatt taacagctgt ctacattgtg   720
ggacacaacc tgatcaaggc tcattcgaaa gtgtggcata actacgacaa aaacttccgc   780
ccccatcaga agggttttgct gtccattacc ttggggtccc actgatagaa ccaaacaaa   840
acagaaaaca tggccgatac aatcagctgc cagcactcta tggcttttgt gcttgggtgg   900
tttgccaacc ccatccatgc agacggcgac tacctgagt tcatgaaaac attgtccacc   960
atgccagtgt tctctgaggc agagaaggag gaggtgaggg gcacagctga cttcttttgcc  1020
ttttccttttg ggcccaacaa tttcaggccc tcgaacttcg ttgtgaaaat ggacaaaat  1080
gtatcactca acttaagaca ggtgctgaac tggattaaat taagaatatga caacccctga  1140
atcttgattt cggagaatgg ctggttcaca gatagtgaca taagacaga ggacaccaca  1200
gccatctaca tgatgaagca ttttctcaac caggttcttc aagcaataca gtttgatgaa  1260
atacgagtgt ttggttacac ggcctggtct ctcctggatg gctttgaatg gcagtatgcc  1320
tacacgtctc gccgaggact gttttatgtg gactttaata gtgaacagaa agaaaggaaa  1380
```

```
cccaagacct cggcacatta ctacaaacag atcatacaag aaaatggttt ccctttgaaa   1440
gagtccacgc cagacatgca gggtcagttt ccctgtgact tctcctgggg ggtcaccgag   1500
tctgttctta agccggagtt tatggtttcc tccccacagt ttaccgaccc tcacctgtat   1560
gtgtggaatg ccactggcaa cagattgcta cagcgagtag aaggagtaag gctaaaaaca   1620
aaaccatccc actgcacaga ctatgttagc atcaaaaaac gagttgagat gttggccaaa   1680
atgaaagtca cccactacca gtttgctctg gactgggcca ccatccttcc cactggcaat   1740
ctgtctgaag ttaatagaca agtactaagg tactataggt gtgtggtgag cgaaggactg   1800
aagctgggcg tctctcccat ggtgacgttg taccacccca cccactccca tctaggcctc   1860
cctgagccgc ttcttaacag tggggatgg ctaaacactt acaccgccaa ggccttccag   1920
gactacgcag gactgtgctt ccaggaacta ggggacttgg tgaagctctg gatcaccatc   1980
aatgagccta ataggctgag tgacatgtac aaccgcacga gtaatgacac ctaccgtgca   2040
gcccataacc tgatgattgc ccatgcccag gtctggcgtc tctacgacag gcagtatagg   2100
ccagtccagc atggagctgt gtcgctgtcc ctacattctg actgggtgga acctgccaac   2160
ccctatgtgg actcacactg gaaggcagcg gagcgcttcc tcctgtttga gatcgcctgg   2220
ttcgctgatc cgctcttcaa gactggcgac tatccactgg ccatgaagga gtacatcgcc   2280
tccaagaacc agcaagggct gtcccgctca gtcctgccgc gcttcacccc agaggagagc   2340
aggctggtga agggcaccat cgacttctac gcactgaacc acttcactac taggttcgtg   2400
atacacaaac agctcaaacg cagccgctct atggcagaca gggacgtcca gttcctgcaa   2460
gacatcaccc gcctgagctc gcccagccgc ctggctgtta tgccctgggg agcacgcaag   2520
ctgcttgggt ggatccagag gaactatggg gacatggaca tctacatcac agccaatggc   2580
atcgatgatc tggctctgga aatgatggg atccgaaagt actacttgga gaagtacatc   2640
caggagcgtc tgaaagcata cctcattgac aaagtcaaaa tcaaaggcta ttatgcattc   2700
aaactgactg aagagaaatc taagcctaga tttggatttt tcacatctga cttcaaagct   2760
aagtcatctg tagagtttta tagcaagttg atcagcagaa gtggcttccc ctctgagact   2820
agcaatcccg catgtggtca gcctccagaa gacacagact gcaccatctg ctcattttc   2880
actcagaaga aatctctgat cttctttggt tgttgctcta tctccactct ggctgtactg   2940
ctgtcaatca ccatttttca tcatcgaaag agaagatttc ataaatcaaa gaacttagaa   3000
aatataccat tgaaggaagg ccacagtaga gttcttagct aa                      3042

SEQ ID NO: 410         moltype = AA   length = 1044
FEATURE                Location/Qualifiers
REGION                 1..1044
                       note = Rabbit beta klotho
source                 1..1044
                       mol_type = protein
                       organism = Oryctolagus cuniculus
SEQUENCE: 410
MKPGCAAGSP GNEWVSFCTD ERNRRCRETM SSGRLRRSVM LSAFILLRAV TGFPGDGRAV    60
WSQNPNLSPV NESQLFLYDT FPKNFFWGVG TGAFQVEGSW KKDGKGLSVW DHFIATHLNV   120
SSRDGSSDSY IFLEKDLSAL DFLGVSFYQF SISWPRLFPD GTVAVANAKG LQYYNRLLDS   180
LLLRNIEPVV TLYHWDLPWA LQEKYGGWKN ETLIDLFNDY ATYCFQTFGD RVKYWITIHN   240
PYLVAWHGYG TGLHAPKEKG NVAAVYTVGH NLLKAHSKVW HNYNRNFRPH QKGWLSITLG   300
SHWIEPNRAE SIVDILKCQQ SMVSVLGWFA NPIHGDGDYP EVMTKKLLSV LPAFSEAEKN   360
EVRGTADFFA FSFGPNNFKP LNTMAKMGQN VSLNLRQVLN WIKLEYGNPR ILIAENGWFT   420
DSYVQTEDTT AIYMMKNFLN QVLQAIRLDG VRVFGYTAWS LLDGFEWQDA YNTRRGLFYV   480
DFNSEQRERR PKSSAHYYKQ VIGENGFTLR EATPDLQGQF PCDFSWGVTE SVLKPESVAS   540
SPQFSDPHLY VWNATGNRML HRVEGVRLKT RPAQCTDFIT IKKQLEMLAR MKVTHFRFAL   600
DWASVLPTGN LSEVNRQALR YYRCVVTEGL KLNISPMVTL YYPTHAHLGL PAPLLHSGGW   660
LDPSTAKAFR DYAGLCFREL GDLVKLWITI NEPNRLSDVY NRTSNDTYQA AHNLLIAHAL   720
VWHLYDRQYR PSQRGALSLS LHSDWAEPAN PYVASHWQAA ERFLQFEIAW FAEPLFKTGD   780
YPVAMREYIA SKTRRGLSSS VLPRFSDAER RLVKGAADFY ALNHFTTRFV MHEQQNGSRY   840
DSDRDVQFLQ DITRLASPSR LAVMPWGEGK LLRWMRNNYG DLDVYITANG IDDQALQNDQ   900
LRQYYLEKYV QEALKAYLID KIKIKGYYAF KLTEEKSKPR FGFFTSDFKA KSSIQFYNKL   960
ITSNGFPSEN GGPRCNQTQG NPECTVCLLL LQKKPLIFFS CCFFCTLVLL SSITIFHRRK  1020
RRKFWKAKDL QHIPLKKGHK RVLS                                         1044

SEQ ID NO: 411         moltype = DNA   length = 5737
FEATURE                Location/Qualifiers
misc_feature           1..5737
                       note = Coding sequence of Rabbit beta klotho
source                 1..5737
                       mol_type = genomic DNA
                       organism = Oryctolagus cuniculus
SEQUENCE: 411
tgaagccgtg ataagacggt cccgcagttc gtggcaaatg aagccaggct gtgcggcagg     60
atctccaggg aatgaatggg tttccttctg caccgatgaa agaaacagac gctgtaggga    120
aacgatgtcc agcggacgcc tgcggagatc tgtcatgctg tcagccttca tcctgctgcg    180
agccgtgact gggttccccg gagacggaag agctgtatgg tcgcaaaatc ctaatttgag    240
tccggtaaac gaaagtcagc tgttctcta tgacacttc ccaaaaaact ttttctgggg    300
tgtggggact ggagccttcc aagtggaagg gagttggaag aaggatggga aaggactctc    360
tgtatgggat catttcatcg ctacacacct gaacgtcagc agccgcgatg gctccagtga    420
cagctacatt tttttggaga aagacttatc ggcgctggat tttttaggag tctcttttta    480
tcagttttca atttcctggc caagactgtt cccggatggc acagtagcag tcgccaatgc    540
aaaaggtctc cagtactata atcggctcct ggactcttca cttctagaa acattgaaac    600
tgtagtcact ttataccatt gggatctgcc ttgggcgcta caagaaaaat acggggggtg    660
gaaaaacgag acgttgattg atttattcaa tgactatgcc acctactgtt tccagacgtt    720
tggggaccgt gtcaaatact ggatcaccat tcacaatccc tatctggtgg cttggcatgg    780
ctacgggaca ggtctgcatg ctccgggaga aaggggaat gtggcagctg tctacactgt    840
gggacacaac ctgcttaagg ctcattcaaa agtctggcac aactacaaca ggaatttccg    900
```

```
cccgcatcag aaaggctggc tgtcgatcac gctgggatcc cactggattg agccaaacag    960
agcggaaagc atcgtggaca tactcaagtc ccagcagtcc atggtctcgg tgctgggctg   1020
gtttgccaac ccgatccacg gggacgggga ctacccagag gtgatgacaa agaagctgct   1080
ctccgtcctg cccgctttct cagaagcaga gaagaacgag gtacgaggca ccgcagactt   1140
ctttgccttt tcgtttggac ccaacaactt caagccctta aacaccatgg ctaaaatggg   1200
gcagaatgtg tcactcaatc taagacaggt gctgaactgg attaaactgg aatatggcaa   1260
ccctcgaatc ctgatcgctg agaacggctg gttcacagac agttacgtgc aaacagaaga   1320
caccacagcc atctacatga tgaagaattt cctcaaccag gttcttcaag caataaggtt   1380
ggatggagtc cgagtgtttg gctacactgc ctggtctctc ctggatggct tcgaatggca   1440
ggacgcttac aacacccgcc gtggactgtt ttatgtggac ttcaacagcg aacagagaga   1500
aagaaggccc aagtcctcgg cgcattacta taaacaggtc ataggagaaa acggcttcac   1560
gctcagagag gccaccccgg atctgcaggg gcagtttccc tgtgacttct cctggggcgt   1620
caccgagtct gttcttaagc ccgagtcggt ggcttcctcg ccacagttca gcgaccctca   1680
cctctacgtg tggaacgcca ctggcaaccg aatgcttcac cgggtggaag gggtgaggct   1740
gaaaacacgg cccgctcagt gcacagattt catcaccatc aagaaacaac tcgagattgtt   1800
ggcaagaatg aaagtcaccc acttccggtt tgctctggac tgggcctcgg tccttcccac   1860
gggcaacctg tccgaggtga accgacaagc cctgaggtac tacaggtgtg tggtcaccga   1920
ggggctgaag ctcaacatct cgcccatggt caccttgcta taccgaccc atgcccacct   1980
gggcctgccc gcgccgctgc tgcacagcgg ggggtggctg gacccatcca cggccaaggc   2040
cttccgcgac tacgcagggc tgtgcttccg ggagctgggg gacctggtga agctctggat   2100
caccatcaac gagcccaacc ggctgagcga cgtctacaac cgcaccagca acgacaccta   2160
ccaggccgcc cacaacctgc tgatcgccga cgcgctcgtg tggcacctgt acgaccgcca   2220
gtaccggccg tcgcagcgcg gggcgctgtc gctgtccctg cactcggact gggccgagcc   2280
cgccaacccc tacgtggcct cgcactggca ggcggccgag cgcttcctgc agttcgagat   2340
tgcgtggttc gccgagcccc tgttcaagac cggggactac ccggtggcca tgagggagta   2400
catcgcctcc aagaccggcc gcgggctctc cagctccgct ctgccccgct tcagcgacgc   2460
cgagcggcgg ctggtcaagg gcgccgcgca cttctacgcc ctcaaccact tcaccaccga   2520
gttcgtgatg cacgagcagc agaacggcag ccgctacgac tcggacaggg acgtgcagtt   2580
cctgcaggac atcacccgcc tggcctcacc cagccgcctg gccgtgatgc cctggggcga   2640
gggcagtctg ctgcggtgga tgcggaacaa ctacggacac ctggacgtct acatcacggc   2700
caatggcatc gacgaccagg ccctgcagaa cgaccagctt cgccagtact acctggaga   2760
gtacgtccag gaggctctga aagcatatct gatagataaa ataaaatca aaggctatta   2820
tgcattcaaa ctgactgaag aaaaatctaa acccaggttt ggattcttca cctctgattt   2880
caaaggccaag tcttcaatac agttttacaa caaactaatt accagcaacg gcttcccgtc   2940
tgagaacggc ggtcctagat gcaatcagac tcaaggaaat cccgagtgca ccgtctgctt   3000
actcctcctg cagaagaagc cgctgatatt cttttagctgc tgcttcttct gcaccctggt   3060
tctactctca tcaattacca tctttcacag acggaagaga agaaaattt ggaaagcaaa   3120
ggacttacaa cacataccat taaagaaagg ccacaagaga gtccttagct aaagtgaact   3180
tatttctctc tgaagagttt agaaattcac tccagttcca tatgctggta acacaaaaga   3240
catacccgta ttgtacacag agtatttgag atactgtgct aaccaaggcg atgacaatca   3300
aaacctctgc catgtggttg aatgcatttt cccttaagcg gtgacaatca gcgaactcag   3360
ttcttggttc taaaggaggc ttcgcactgc cactaggcta tgagtattac ctgacgcatt   3420
gctttgtcaa gtttgatgag ctgtttcgca tcattctcta gcttttctta gataccaata   3480
gctactatgg taaagttgt ttttaaaagt caaactctgt aaggcttcac agcagattta   3540
aaactattct ttacactgga tctgtgattt tgtcactcgt agcaaggtgc tttcccctttt   3600
tggtcctagt ggctctcaaa tagaaagcaa acacatctta gggtaatcta cttatctata   3660
gccaatcaca gcactgaccc acaactacac aaatccgtta gctcttctcc ataaaacacc   3720
taattttgtg atcttttaag taatctgaaa tgtaaaagta tgacttccgt aacccatctc   3780
atggaaagat cgactaagga gagccatacc cagctgtgag gacaatttag tcactaatct   3840
caccgtactg caacttcctc ctttagagca ggcattcctt accattttg taagatgaca   3900
tgatttagca tctagaaccc ctatctgcag tttcttttcta tggcttacct acatttcaag   3960
aatattgaac ggaaaatttc agaaagattt ccaagtttta aattgtgtac tagcattagt   4020
gcatgatgaa atctcatttt cttgctcca tcctgcacag gatgtgaaac atccctctgt   4080
ccagcaagtc caagctacct atattactca cttgatagtc accatggtta tccagctgtt   4140
attacttgct catacccagg taaccctttt ttattttaat atagctccaa agtataagac   4200
tagtgatgaa aaggaggtaa gtcatcaaat atggaaggac agattaactc tggcactaag   4260
tgggaatgct gcaggtttta caggaaaaca aaattcagtc agtggtttaa agcatcctct   4320
gaggtacctg gggcacaatc tccacagata aggggaaaga gcactgacaa agactaaaca   4380
tcctaaaaag acgcaatgtt ctacttactg gccatcagaa taatggccaa aggaccctat   4440
acttgcttgc tctctagcca agttcgctg cacataggtg tagaatgcag cgactgaccc   4500
tggatgcgat tcagaatgct gatctgagtg aactagtttt ttatacagca cttttttaaag   4560
cctagaattc ttccatctga acttgggagt tttgactttt tgaaattaa ttgtgcttaa   4620
gatttattca gtgattctaa acactggagg tagaaaactg tatacccatt atgcctatta   4680
attttcttg attagccaac attttaaataa ccacaaagtg gccagtcgtt gtctttccct   4740
ttcaggaatt taagtcaaag gatgctgctg cctgcgatgc tggcacttca tagggggtgac   4800
agtttgtgtc cctgcggttc cacttcctat ccagctccct gctaatggct tgggagagcc   4860
ctgcacccac atgggagacc caaaagcaga tcctgctgct ttcagcctgc tgcggccact   4920
tggagtatga accagtggat ggaagatcaa tgtctctccc aacaattctt tgaataaatt   4980
ttttcaaaag tcaaaataaa attctccagc tcaaaaagct ttagtagaaa acgatcctac   5040
attaaggcgg ttgtgattgt atcccaagtg catctacgtt acaaaccaaa ttgagtatgc   5100
aattcagtat gctactagac tataaggaga aaacagccaa ttcaaacaaa ataccaaagt   5160
cacgtgcagt taatttgctt tctggttggc caaatgtttt tttttctcttc ttgccaccac   5220
tgttttacat gtactttaga agaaatttg acttttgct tcctttgaga aatcactatt   5280
atcaaaggca attcataatt acaagtggtc cattgtctta agagctcaag attatagcc   5340
ttcaaacttg ccaaactcct caaatagtga agctcctaac gaagggttta caacatcctg   5400
ttccttaggg gttatatttt taagtgactg taatttaccct aacaaattta atctggctat   5460
ctattggtaa tacatgtaat attcaggttt atcataaacc cacttaaaaa ctaaaggtta   5520
agtggaagtt gctgcttttc aaagtaacag gcttctcagg ggaaaatatc accttagcgt   5580
ccacctggta ctacatctcg tgtattcact gtaacccatc tttccgaaca tgtctgatat   5640
```

```
atatggaaac aacactagtg cttagcctct ggaaatgagg ccaggatttt gtgattaaat    5700
gtctaattta ttccaaataa actgatttac gccaata                              5737

SEQ ID NO: 412          moltype = AA  length = 1045
FEATURE                 Location/Qualifiers
REGION                  1..1045
                        note = Dog beta klotho
source                  1..1045
                        mol_type = protein
                        organism = Canis lupus
SEQUENCE: 412
MKPGCAAGSP GNEWIFLSTD ESNTHYRKTM CNHGLQRSVI LSAFILLGAV PGFSGDGRAI    60
WSKNPHFSPV NESQLFLYDT FPKNFFWGVG TGAFQVEGNW KTDGKGPSIW DHFIHTHLKN   120
VNSMNSSSDS YIFLEKDLSA LDFIGVSFYQ FSISWPRLFP DGIAAVANAK GLQYYNSLLD   180
ALVLRNIEPI VTLYHWDLPL ALQEKYGGWK NETITDIFND YATYCFQTFG DRVKYWITIH   240
NPYLVAWHGY GTGMHAPGEK GNLAAVYTVG HNLIKAHSKV WHNYNTNFRP YQKGLLSITL   300
GSHWIEPNRS ENMMDILKCQ QSMVSVLGWF ANPIHGNGDY PEVMKKKLLS TLPLFSEAEK   360
NEVRGTADFF AFSFGPNNFK PQNTMAKMGQ NVSLNLREVL NWIKLEYGNP RILIAENGWF   420
TDSHVKTEDT TAIYMMKNFL NQVLQAIRFD EIQVFGYTAW SLLDGFEWQD AYSTRRGLFY   480
VDFNSKQKER KPKSSAYYYK QIIQENGFTF KESTPDVQGQ FPCDFSWGVT ESVLKPKVVA   540
SSPQFSDPHL YVWNVTGNRL LHRVEGVRLK TRPAQCTDFV SIKRQLEMLA RMNVTHYRFA   600
LDWPSILPTG NLSTVNRQAL RYYRCVVSES LKLSISPMVT LYYPTHAHLG LPSPLLHSGG   660
WLNASTARAF QDYAGLCFQE LGDLVKLWIT INEPNRLSDV YSHTSSDTYR AAHNLLIAHA   720
LVWHLYDRRY RPAQRGAVSL SLHSDWAEPA NPYADSHWKA AERFLQFEIA WFAEPLFKTG   780
DYPPAMREYI ASKNRQGLSR STLPRFTDEE RRLVKGAADF YALNHFTTRF VMHARQNGSR   840
YDADRDVQFL QDITCLSSPS RLAVLPWGER KVLRWIQKNY GDVDVYITAS GIDDQSLEND   900
ELRKYYLEKY IQEALKAHLI DKVKVKGYYA FKLTEEKSKP RFGFFTSEFK AKSSVQLYNK   960
LISNSGFPSE NRSPRCSETQ RNTECMVCLF LVQKKPLIFF SCCFFSTLVL LSSITILHKR  1020
KRRKIWKAKN LQHIPLKKSK NSLQS                                        1045

SEQ ID NO: 413          moltype = DNA  length = 4350
FEATURE                 Location/Qualifiers
misc_feature            1..4350
                        note = Coding sequence of dog beta klotho
source                  1..4350
                        mol_type = genomic DNA
                        organism = Canis lupus
SEQUENCE: 413
acaatcacaa gcttttactg aagcgttgat aagacaggcg agcagttagt ggcaaatgaa    60
gccaggctgt gcggctggat ctccagggaa tgaatggatt ttcctcagca ccgatgaaag   120
caacacacac tataggaaaa caatgtgcaa ccacgggcta cagagatctg tcatcctgtc   180
agcatttatt ctcctaggag ctgttcctgg attctctgga gacggaagag ctatatggtc   240
taaaatcct cattttagtc cggtaaatga aagtcagctg tttctctatg acacttttcg   300
taaaaacttt ttttgggcg ttgggactgg agcatttcaa gtggaaggga attggaaagc   360
agatggaaaa ggaccctcta tatgggatca tttcatccac acacacctta aaaatgtcaa   420
cagcatgaat agttccagtg acagttacat ttttctggaa aaagacctat cagccctgga   480
ttttatcgga gtttcttttt atcaattttc aatttcctgg caaggcttt tccccgatgg   540
aatagcagca gttgccaacg caaaaggtct ccagtactac aattctcttc tcgatgctct   600
agtacttagg aacattgaac ctatagttac tttataccat tgggattgc ctttggcact   660
acaagaaaaa tatggggggt ggaaaaatga accataacg gatatcttca atgactatgc   720
cacctactgt ttccagacgt tcggggatcg tgtcaaatac tggattacaa ttcacaatcc   780
atatctagtt gcttggcatg ggtatggac aggtatgcac gcgcctggag agaagggaaa   840
cttagcagct gtctacactg tgggacacaa cctaatcaag gctcattcga agtttggca   900
taactacaac acaaatttcc gcccatatca gaagggtttg ttatcaatca cgttgggatc   960
ccattggatt gaaccaaaca gatcagaaaa catgatgat atactcaaat gtcaacaatc  1020
catggtttca gtgctcgggt ggtttgccaa cccccatcca gggaatggag actatcaga  1080
agtgatgaaa aagaagttgc tctccactct accccttttc tctgaagcag agaagaatga  1140
agtgaggggc acagctgact tctttgcctt tccctttgga cccaacaatt tcaagcccca  1200
gaaccaccatg gctaaaatgg gacaaaatgt gtcactcaat ttaagagaag tgctgaattg  1260
gattaaactg gaatatggca acccccgaat cttgattgct gagaatggct ggttcacaga  1320
cagtcatgtg aaaacagaag ataccacagc catttacatg atgaagaatt tcctcaacca  1380
ggttcttcaa gcaataaggt ttgacgaaat acaagtgttt ggctacactg cttggtctct  1440
cctggatggc tttgaatggc aggatgctta ctccactcgc cgaggattat tttatgtgga  1500
ttttaatagt aaacaaaaag aaagaaagcc caagtcttgc gcatattact ataacagat  1560
catacaagaa aatggtttta ctttcaaaga gtccacccca gatgtgcagg gtcagtttcc  1620
ctgtgacttc tcatggggtg tcaccgaatc tgtccttaag cccaaagtcg tggcttcctc  1680
cccacagttc agcgaccctc acctgtacgt gtggaatgtg acaggcaaca gactgttgca  1740
ccgagtggaa ggggtgaggc tgaagacacg gccgctcaa tgcacagatt ttgtcagcat  1800
caaaagacaa cttgagatgt tggcgaggat gaacgtcact cactacaggt ttgctctgga  1860
ctggccctcc atccttccca ccggcaacct gtccacggtt aaccgacaag cctgaggta  1920
ctacaggtgt gtggtcagcg agtcgctgaa gctcagcatc tccccgatgg tcacgctgta  1980
ctacccgacc cacgcccacc tgggcctccc ctcgccgctg ctgcacagcg ggggctggct  2040
gaacgcgtcc accgcccgcg ccttccagga ctatgccggc tgtgcttcc aggagctggg  2100
ggacctggtg aagctctgga tcaccatcaa tgagcctaac agcctcagcg acgtctacag  2160
ccacaccagc agcgacacct accgggcagc gcacaacctg ctgatcgccc acgccctggt  2220
gtggcacctg tacgaccggc ggtaccggcc ggcgcagcgc ggggccgtgt cgctgtcctc  2280
gcactcggac tgggcggagc ccgccaaccc ctacgccgac tcgcactgga aggcggccga  2340
gcgcttcctg cagttcgaaa tcgcctggtt cgccgagccg ctcttcaaga ccggggacta  2400
cccgccggcc atgagggagt acatcgcctc caagaacagg caggggctct cgcgctccac  2460
```

```
cctgccccgc ttcaccgacg aggagaggag gctggtcaag ggcgccgccg acttctacgc    2520
gctgaaccac ttcaccacca ggttcgtgat gcacgcgcgc cagaacggca gccgctacga    2580
cgcggaccgc gacgtccagt tcctgcagga catcacctgc ctgagctccc ccagccgcct    2640
ggccgtcctg ccctgggggg agcgcaaggt gctcaggtgg atccagaaga actacggaga    2700
cgtggacgtg tacatcacgg ccagtggcat cgatgaccag tctctggaaa atgatgagct    2760
cagaaaatac tacttggaga aatacatcca ggaggctctg aaagcacacc taattgataa    2820
agtcaaagtc aaaggctatt atgcattcaa actgactgaa gaaaaatcta aacccagatt    2880
tggattcttc acgtctgaat tcaaagctaa atcctcagtt cagctttaca caaactgat    2940
cagcaacagt ggcttccctt ctgagaacag gagtcctaga tgcagtgaga ctcaaagaaa    3000
cacagagtgc atggtctgct tatttcttgt gcaaaagaaa ccactgatat tctttagttg    3060
ttgcttcttc tctaccctgg ttctactttc atcgattacc attcttcata gcgaaagag    3120
aagaaaaatt tggaaagcaa agaacttaca acatatacca ttaaagtgag gccacagaaa    3180
gttcttagtg aaactgatcc tatttctgtc tgcatgatag aaagtctaaa aattcactcc    3240
agtcccaaat actggtaaca tagaagcaaa tttgaaacac tagtagtaac caaggtgatg    3300
acaatcaagg tctctgctgt gtggtccaaa tgaattttcc attaggtgtt gacatcactg    3360
aatacagttt ttagatctga agactaagat ctagagagta agctaggatt atctgataca    3420
atgcttcatt aagtttaata agctgttatc catcattctt ctctggcttc cttctagaaa    3480
taccaatagc taattatagc aacttagaaa aaagtgctaa ttttgctaga tccatagca    3540
gaaatctaaa actcttaaca ctggatattc agtgattatt ctatcacttc taacaaggtg    3600
cttttcccct ttagaagata tacaatatggg taaatagtgc tcctttatca tccattccag    3660
cactttttt tccagcata gactcttaaa cacattgatc ctagtttttc tcaatagaaa    3720
taaaaatca tttagaaaac atggaatttt gtgaggtctc tccttgcatt agatctgagt    3780
tttttttaaa aaaagactt aacttccata acccatctca tgggaagatc acaggactaa    3840
gattaaggag agttagaccc atcaactgcc tgaggagaca gcactcaacc tcacagtaca    3900
gcaaattcct tgggacaaac tgacagcaat cttccgcact tggattgttg aggcagcaca    3960
caagatctta acatacttag gaaagttaaa tattctaaaa agatgtaaag ttttatttt    4020
attatcaagt cttcaaagga ccatattatt ccataagact tgctctctcc tgagttccac    4080
tcttctgaca ctatgtgtat atggggacac tcaaactgca ccttgacatt gcaactttgg    4140
atacaattca gaatgtaaat gtttgaagga cttaaaactt tctccactgc acctttgaa    4200
gctgggatta agtaaaatcg aactgggagt ttgacttttt tgaactctgt gcttgattta    4260
ttcactgtat tctaaatttt aaggaaaacc tgaatgtaaa cccattcata cccttctctt    4320
gggttagtaa acatttaacc acccatttca                                    4350

SEQ ID NO: 414             moltype = AA  length = 120
FEATURE                    Location/Qualifiers
REGION                     1..120
                           note = 5H23v1-69
source                     1..120
                           mol_type = protein
                           organism = synthetic construct
SEQUENCE: 414
QVQLVQSGAE VKKPGSSVKV SCKASGYTFT SYDINWVRQA PGQGLEWMGW IYPGDGSTKY     60
NEKFKGRVTI TADESTSTAY MELSSLRSED TAVYYCARSD YYGSRSFAYW GQGTLVTVSS    120

SEQ ID NO: 415             moltype = AA  length = 710
FEATURE                    Location/Qualifiers
REGION                     1..710
                           note = Human FGFR1 beta-IIIc, NP_075594.1
source                     1..710
                           mol_type = protein
                           organism = synthetic construct
SEQUENCE: 415
RPSPTLPEQD ALPSSEDDDD DDDSSSEEKE TDNTKPNPVA PYWTSPEKME KKLHAVPAAK     60
TVKFKCPSSG TPNPTLRWLK NGKEFKPDHR IGGYKVRYAT WSIIMDSVVP SDKGNYTCIV    120
ENEYGSINHT YQLDVVERSP HRPILQAGLP ANKTVALGSN VEFMCKVYSD PQPHIQWLKH    180
IEVNGSKIGP DNLPYVQILK TAGVNTTDKE MEVLHLRNVS FEDAGEYTCL AGNSIGLSHH    240
SAWLTVLEAL EERPAVMTSP LYLEIIIYCT GAFLISCMVG SVIVYKMKSG TKKSDFHSQM    300
AVHKLAKSIP LRRQVTVSAD SSASMNSGVL LVRPSRLSSS GTPMLAGVSE YELPEDPRWE    360
LPRDRLVLGK PLGEGCFGQV VLAEAIGLDK DKPNRVTKVA VKMLKSDATE KDLSDLISEM    420
EMMKMIGKHK NIINLLGACT QDGPLYVIVE YASKGNLREY LQARRPPGLE YCYNPSHNPE    480
EQLSSKDLVS CAYQVARGME YLASKKCIHR DLAARNVLVT EDNVMKIADF GLARDIHHID    540
YYKKTTNGRL PVKWMAPEAL FDRIYTHQSD VWSFGVLLWE IFTLGGSPYP GVPVEELFKL    600
LKEGHRMDKP SNCTNELYMM MRDCWHAVPS QRPTFKQLVE DLDRIVALTS NQEYLDLSMP    660
LDQYSPSFPD TRSSTCSSGE DSVFSHEPLP EEPCLPRHPA QLANGGLKRR              710

SEQ ID NO: 416             moltype = AA  length = 710
FEATURE                    Location/Qualifiers
REGION                     1..710
                           note = mouse-FGFR1 (R22-E287) (Beta-IIIc, NP_001073378)
                             fused to human FGFR1 (I286-R731, NP_075594)
source                     1..710
                           mol_type = protein
                           organism = synthetic construct
SEQUENCE: 416
RPAPTLPEQD ALPSSEDDDD DDDSSSEEKE TDNTKPNPVA PYWTSPEKME KKLHAVPAAK     60
TVKFKCPSSG TPNPTLRWLK NGKEFKPDHR IGGYKVRYAT WSIIMDSVVP SDKGNYTCIV    120
ENEYGSINHT YQLDVVERSP HRPILQAGLP ANKTVALGSN VEFMCKVYSD PQPHIQWLKH    180
IEVNGSKIGP DNLPYVQILK TAGVNTTDKE MEVLHLRNVS FEDAGEYTCL AGNSIGLSHH    240
SAWLTVLEAL EERPAVMTSP LYLEIIIYCT GAFLISCMVG SVIVYKMKSG TKKSDFHSQM    300
```

```
AVHKLAKSIP LRRQVTVSAD SSASMNSGVL LVRPSRLSSS GTPMLAGVSE YELPEDPRWE    360
LPRDRLVLGK PLGEGCFGQV VLAEAIGLDK DKPNRVTKVA VKMLKSDATE KDLSDLISEM    420
EMMKMIGKHK NIINLLGACT QDGPLYVIVE YASKGNLREY LQARRPPGLE YCYNPSHNPE    480
EQLSSKDLVS CAYQVARGME YLASKKCIHR DLAARNVLVT EDNVMKIADF GLARDIHHID    540
YYKKTTNGRL PVKWMAPEAL FDRIYTHQSD VWSFGVLLWE IFTLGGSPYP GVPVEELFKL    600
LKEGHRMDKP SNCTNELYMM MRDCWHAVPS QRPTFKQLVE DLDRIVALTS NQEYLDLSMP    660
LDQYSPSFPD TRSSTCSSGE DSVFSHEPLP EEPCLPRHPA QLANGGLKRR               710

SEQ ID NO: 417          moltype = AA  length = 710
FEATURE                 Location/Qualifiers
REGION                  1..710
                        note = hamster-FGFR1 (R54-E319) (Beta-IIIc) XP_007610900.1
                         fused to human FGFR1 (I286-R731, NP_075594)
source                  1..710
                        mol_type = protein
                        organism = synthetic construct
SEQUENCE: 417
RPAPTLPEQD ALPSSEDDDD DDDSSSEEKE TDNTKPNPVA PYWTSPEKME KKLHAVPAAK     60
TVKFKCPSSG TPNPTLRWLK NGKEFKPDHR IGGYKVRYAT WSIIMDSVVP SDKGNYTCIV    120
ENEYGSINHT YQLDVVERSP HRPILQAGLP ANKTVALGSN VEFMCKVYSD PQPHIQWLKH    180
IEVNGSKIGP DNLPYVQILK TAGVNTTDKE MEVLHLRNVS FEDAGEYTCL AGNSIGLSHH    240
SAWLTVLEAL EERPAVMTSP LYLEIIIYCT GAFLISCMVG SVIVYKMKSG TKKSDFHSQM    300
AVHKLAKSIP LRRQVTVSAD SSASMNSGVL LVRPSRLSSS GTPMLAGVSE YELPEDPRWE    360
LPRDRLVLGK PLGEGCFGQV VLAEAIGLDK DKPNRVTKVA VKMLKSDATE KDLSDLISEM    420
EMMKMIGKHK NIINLLGACT QDGPLYVIVE YASKGNLREY LQARRPPGLE YCYNPSHNPE    480
EQLSSKDLVS CAYQVARGME YLASKKCIHR DLAARNVLVT EDNVMKIADF GLARDIHHID    540
YYKKTTNGRL PVKWMAPEAL FDRIYTHQSD VWSFGVLLWE IFTLGGSPYP GVPVEELFKL    600
LKEGHRMDKP SNCTNELYMM MRDCWHAVPS QRPTFKQLVE DLDRIVALTS NQEYLDLSMP    660
LDQYSPSFPD TRSSTCSSGE DSVFSHEPLP EEPCLPRHPA QLANGGLKRR               710

SEQ ID NO: 418          moltype = AA  length = 710
FEATURE                 Location/Qualifiers
REGION                  1..710
                        note = dog-FGFR1 (R22-E287) (Beta-IIIc), XP_005629909.1
                         fused to human FGFR1 (I286-R731, NP_075594)
source                  1..710
                        mol_type = protein
                        organism = synthetic construct
SEQUENCE: 418
RPAPTLPEQD ALPSSEDDDD DDDSSSEEKE TDNTKPNPVA PYWTSPEKME KKLHAVPAAK     60
TVKFKCPSSG TPNPTLRWLK NGKEFKPDHR IGGYKVRYAT WSIIMDSVVP SDKGNYTCIV    120
ENEYGSINHT YQLDVVERSP HRPILQAGLP ANKTVALGSN VEFMCKVYSD PQPHIQWLKH    180
IEVNGSKIGP DNLPYVQILK TAGVNTTDKE MEVLHLRNVS FEDAGEYTCL AGNSIGLSHH    240
SAWLTVLEAL EERPAAMTSP LYLEIIIYCT GAFLISCMVG SVIVYKMKSG TKKSDFHSQM    300
AVHKLAKSIP LRRQVTVSAD SSASMNSGVL LVRPSRLSSS GTPMLAGVSE YELPEDPRWE    360
LPRDRLVLGK PLGEGCFGQV VLAEAIGLDK DKPNRVTKVA VKMLKSDATE KDLSDLISEM    420
EMMKMIGKHK NIINLLGACT QDGPLYVIVE YASKGNLREY LQARRPPGLE YCYNPSHNPE    480
EQLSSKDLVS CAYQVARGME YLASKKCIHR DLAARNVLVT EDNVMKIADF GLARDIHHID    540
YYKKTTNGRL PVKWMAPEAL FDRIYTHQSD VWSFGVLLWE IFTLGGSPYP GVPVEELFKL    600
LKEGHRMDKP SNCTNELYMM MRDCWHAVPS QRPTFKQLVE DLDRIVALTS NQEYLDLSMP    660
LDQYSPSFPD TRSSTCSSGE DSVFSHEPLP EEPCLPRHPA QLANGGLKRR               710

SEQ ID NO: 419          moltype = AA  length = 710
FEATURE                 Location/Qualifiers
REGION                  1..710
                        note = rat-FGFR1 (R22-E287) (Beta-IIIc), XP_006253387.1
                         fused to human FGFR1 (I286-R731, NP_075594)
source                  1..710
                        mol_type = protein
                        organism = synthetic construct
SEQUENCE: 419
RPAPTLPEQD ALPSSEDDDD DDDSSSEEKE TDNTKPNPVA PYWTSPEKME KKLHAVPAAK     60
TVKFKCPSSG TPSPTLRWLK NGKEFKPDHR IGGYKVRYAT WSIIMDSVVP SDKGNYTCIV    120
ENEYGSINHT YQLDVVERSP HRPILQAGLP ANKTVALGSN VEFMCKVYSD PQPHIQWLKH    180
IEVNGSKIGP DNLPYVQILK TAGVNTTDKE MEVLHLRNVS FEDAGEYTCL AGNSIGLSHH    240
SAWLTVLEAL EERPAVMTSP LYLEIIIYCT GAFLISCMVG SVIVYKMKSG TKKSDFHSQM    300
AVHKLAKSIP LRRQVTVSAD SSASMNSGVL LVRPSRLSSS GTPMLAGVSE YELPEDPRWE    360
LPRDRLVLGK PLGEGCFGQV VLAEAIGLDK DKPNRVTKVA VKMLKSDATE KDLSDLISEM    420
EMMKMIGKHK NIINLLGACT QDGPLYVIVE YASKGNLREY LQARRPPGLE YCYNPSHNPE    480
EQLSSKDLVS CAYQVARGME YLASKKCIHR DLAARNVLVT EDNVMKIADF GLARDIHHID    540
YYKKTTNGRL PVKWMAPEAL FDRIYTHQSD VWSFGVLLWE IFTLGGSPYP GVPVEELFKL    600
LKEGHRMDKP SNCTNELYMM MRDCWHAVPS QRPTFKQLVE DLDRIVALTS NQEYLDLSMP    660
LDQYSPSFPD TRSSTCSSGE DSVFSHEPLP EEPCLPRHPA QLANGGLKRR               710

SEQ ID NO: 420          moltype = AA  length = 713
FEATURE                 Location/Qualifiers
REGION                  1..713
                        note = rabbit-FGFR1 (R22-E288) (Beta-IIIc), XP_008272198.1
                         fused to human FGFR1 (I286-R731, NP_075594)
```

```
source                  1..713
                        mol_type = protein
                        organism = synthetic construct
SEQUENCE: 420
RPAAPTLPEQ DALPSSEDDD DDDDSSSEEK ETDNTKPNRM PVAPYWTSPE KMEKKLHAVP    60
AAKTVKFKCP SSGTPNPTLR WLKNGKEFKP DHRIGGYKVR YATWSIIMDS VVPSDKGNYT   120
CIVENEYGSI NHTYQLDVVE RSPHRPILQA GLPANKTVAL GSNVEFMCKV YSDPQPHIQW   180
LKHIEVNGSK IGPDNLPYVQ ILKTAGVNTT DKEMEVLHLR NVSFEDAGEY TCLAGNSIGL   240
SHHSAWLTVL EALEERPAVM TSPLYLEIII YCTGAFLISC MVGSVIVYKM KSGTKKSDFH   300
SQMAVHKLAK SIPLRRQVTV SADSSASMNS GVLLVRPSRL SSSGTPMLAG VSEYELPEDP   360
RWELPRDRLV LGKPLGEGCF GQVVLAEAIG LDKDKPNRVT KVAVKMLKSD ATEKDLSDLI   420
SEMEMMKMIG KHKNIINLLG ACTQDGPLYV IVEYASKGNL REYLQARRPP GLEYCYNPSH   480
NPEEQLSSKD LVSCAYQVAR GMEYLASKKC IHRDLAARNV LVTEDNVMKI ADFGLARDIH   540
HIDYYKKTTN GRLPVKWMAP EALFDRIYTH QSDVWSFGVL LWEIFTLGGS PYPGVPVEEL   600
FKLLKEGHRM DKPSNCTNEL YMMMRDCWHA VPSQRPTFKQ LVEDLDRIVA LTSNQEYLDL   660
SMPLDQYSPS FPDTRSSTCS SGEDSVFSHE PLPEEPCLPR HPAQLANGGL KRR          713

SEQ ID NO: 421          moltype = AA length = 465
FEATURE                 Location/Qualifiers
REGION                  1..465
                        note = hIgK alpha-KLH VH mIgG1
source                  1..465
                        mol_type = protein
                        organism = synthetic construct
SEQUENCE: 421
MDMRVPAQLL GLLLLWLRGA RCQVQLVQSG AEVKKPGASV KVSCKASGYT FTGYHMHWVR    60
QAPGQGLEWM GWINPNSGGT NYAQKFQGRV TMTRDTSIST AYMELSRLRS DDTAVYYCAR   120
DRGSYYWFDP WGQGTLVTVS SAKTTPPSVY PLAPGSAAQT NSMVTLGCLV KGYFPEPVTV   180
TWNSGSLSSG VHTFPAVLQS DLYTLSSSVT VPSSTWPSET VTCNVAHPAS STKVDKKIVP   240
RDCGCKPCIC TVPEVSSVFI FPPKPKDVLT ITLTPKVTCV VVDISKDDPE VQFSWFVDDV   300
EVHTAQTQPR EEQFNSTFRS VSELPIMHQD WLNGKEFKCR VNSAAFPAPI EKTISKTKGR   360
PKAPQVYTIP PPKEQMAKDK VSLTCMITDF FPEDITVEWQ WNGQPAENYK NTQPIMDTDG   420
SYFVYSKLNV QKSNWEAGNT FTCSVLHEGL HNHHTEKSLS HSPGK                   465

SEQ ID NO: 422          moltype = AA length = 471
FEATURE                 Location/Qualifiers
REGION                  1..471
                        note = hIgK alpha-KLH VH mIgG2-alpha
source                  1..471
                        mol_type = protein
                        organism = synthetic construct
SEQUENCE: 422
MDMRVPAQLL GLLLLWLRGA RCQVQLVQSG AEVKKPGASV KVSCKASGYT FTGYHMHWVR    60
QAPGQGLEWM GWINPNSGGT NYAQKFQGRV TMTRDTSIST AYMELSRLRS DDTAVYYCAR   120
DRGSYYWFDP WGQGTLVTVS SAKTTAPSVY PLAPVCGDTT GSSVTLGCLV KGYFPEPVTL   180
TWNSGSLSSG VHTFPAVLQS DLYTLSSSVT VTSSTWPSQS ITCNVAHPAS STKVDKKIEP   240
RGPTIKPCPP CKCPAPNLLG GPSVFIFPPK IKDVLMISLS PIVTCVVVDV SEDDPDVQIS   300
WFVNNVEVHT AQTQTHREDY NSTLRVVSAL PIQHQDWMSG KEFKCKVNNK DLPAPIERTI   360
SKPKGSVRAP QVYVLPPPEE EMTKKQVTLT CMVTDFMPED IYVEWTNNGK TELNYKNTEP   420
VLDSDGSYFM YSKLRVEKKN WVERNSYSCS VVHEGLHNHH TTKSFSRTPG K            471

SEQ ID NO: 423          moltype = AA length = 236
FEATURE                 Location/Qualifiers
REGION                  1..236
                        note = hIgK alpha-KLH VL mKappa
source                  1..236
                        mol_type = protein
                        organism = synthetic construct
SEQUENCE: 423
MDMRVPAQLL GLLLLWLRGA RCDIQMTQSP SSLSASVGDR VTITCRASQG IRNDLGWYQQ    60
KPGKAPKRLI YAASSLQSGV PSRFSGSGSG TEFTLTISSL QPEDFATYYC LQHNSYPLTF   120
GGGTKVEIKR ADAAPTVSIF PPSSEQLTSG GASVVCFLNN FYPKDINVKW KIDGSERQNG   180
VLNSWTDQDS KDSTYSMSST LTLTKDEYER HNSYTCEATH KTSTSPIVKS FNRNEC       236

SEQ ID NO: 424          moltype = AA length = 471
FEATURE                 Location/Qualifiers
REGION                  1..471
                        note = hIgK-KLH-(VH)-hIgG1(E233A)(L235A)
source                  1..471
                        mol_type = protein
                        organism = synthetic construct
SEQUENCE: 424
MDMRVPAQLL GLLLLWLRGA RCQVQLVQSG AEVKKPGASV KVSCKASGYT FTGYHMHWVR    60
QAPGQGLEWM GWINPNSGGT NYAQKFQGRV TMTRDTSIST AYMELSRLRS DDTAVYYCAR   120
DRGSYYWFDP WGQGTLVTVS SASTKGPSVF PLAPSSKSTS GGTAALGCLV KDYFPEPVTV   180
SWNSGALTSG VHTFPAVLQS SGLYSLSSVV TVPSSSLGTQ TYICNVNHKP SNTKVDKKVE   240
PKSCDKTHTC PPCPAPALAG GPSVFLFPPK PKDTLMISRT PEVTCVVVDV SHEDPEVKFN   300
WYVDGVEVHN AKTKPREEQY NSTYRVVSVL TVLHQDWLNG KEYKCKVSNK ALPAPIEKTI   360
SKAKGQPREP QVYTLPPSRE EMTKNQVSLT CLVKGFYPSD IAVEWESNGQ PENNYKTTPP   420
```

```
VLDSDGSFFL YSKLTVDKSR WQQGNVFSCS VMHEALHNHY TQKSLSLSPG K             471

SEQ ID NO: 425          moltype = AA   length = 236
FEATURE                 Location/Qualifiers
REGION                  1..236
                        note = hIgK-KLH-(VL)-hIgK
source                  1..236
                        mol_type = protein
                        organism = synthetic construct
SEQUENCE: 425
MDMRVPAQLL GLLLLWLRGA RCDIQMTQSP SSLSASVGDR VTITCRASQG IRNDLGWYQQ      60
KPGKAPKRLI YAASSLQSGV PSRFSGSGSG TEFTLTISSL QPEDFATYYC LQHNSYPLTF     120
GGGTKVEIKR TVAAPSVFIF PPSDEQLKSG TASVVCLLNN FYPREAKVQW KVDNALQSGN     180
SQESVTEQDS KDSTYSLSST LTLSKADYEK HKVYACEVTH QGLSSPVTKS FNRGEC         236

SEQ ID NO: 426          moltype = AA   length = 264
FEATURE                 Location/Qualifiers
REGION                  1..264
                        note = Example of extracellular region of FGFR1c
                        (beta-IIIc, NP_075594)
source                  1..264
                        mol_type = protein
                        organism = synthetic construct
SEQUENCE: 426
RPSPTLPEQD ALPSSEDDDD DDDSSSEEKE TDNTKPNPVA PYWTSPEKME KKLHAVPAAK      60
TVKFKCPSSG TPNPTLRWLK NGKEFKPDHR IGGYKVRYAT WSIIMDSVVP SDKGNYTCIV     120
ENEYGSINHT YQLDVVERSP HRPILQAGLP ANKTVALGSN VEFMCKVYSD PQPHIQWLKH     180
IEVNGSKIGP DNLPYVQILK TAGVNTTDKE MEVLHLRNVS FEDAGEYTCL AGNSIGLSHH     240
SAWLTVLEAL EERPAVMTSP LYLE                                            264

SEQ ID NO: 427          moltype = AA   length = 354
FEATURE                 Location/Qualifiers
REGION                  1..354
                        note = Example of extracellular region of FGFR1c
                        (Alpha-IIIc, NP_056934)
source                  1..354
                        mol_type = protein
                        organism = synthetic construct
SEQUENCE: 427
RPSPTLPEQA QPWGAPVEVE SFLVHPGDLL QLRCRLRDDV QSINWLRDGV QLAESNRTRI      60
TGEEVEVQDS VPADSGLYAC VTSSPSGSDT TYFSVNVSDA LPSSEDDDDD DDSSSEEKET     120
DNTKPNPMPV APYWTSPEKM EKKLHAVPAA KTVKFKCPSS GTPNPTLRWL KNGKEFKPDH     180
RIGGYKVRYA TWSIIMDSVV PSDKGNYTCI VENEYGSINH TYQLDVVERS PHRPILQAGL     240
PANKTVALGS NVEFMCKVYS DPQPHIQWLK HIEVNGSKIG PDNLPYVQIL KTAGVNTTDK     300
EMEVLHLRNV SFEDAGEYTC LAGNSIGLSH HSAWLTVLEA LEERPAVMTS PLYE           354

SEQ ID NO: 428          moltype = DNA   length = 630
FEATURE                 Location/Qualifiers
misc_feature            1..630
                        note = A full length FGF21, NM_019113.2
source                  1..630
                        mol_type = other DNA
                        organism = synthetic construct
SEQUENCE: 428
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggcgctgctg accagagccc gaaagtctcc     240
ctgcagctga aagccttgaa gccgggagtt attcaaatct tgggagtcaa gacatccagg     300
ttcctgtgcc agcggccaga tgggcccctg tatggatcgc tccactttga ccctgaggcc     360
tgcagcttcc gggagctgct tcttgaggac ggatacaatg tttaccagtc gaagcccac      420
ggcctcccgc tgcacctgcc agggaacaag tccccacacc gggaccctgc accccgagga     480
ccagctcgct tcctgccact accaggcctg ccccccgcac tccggagcc acccggaatc     540
ctggccccc agcccccga tgtgggctcc tcggaccctc tgagcatggt gggaccttcc      600
cagggccgaa gccccagcta cgcttcctga                                      630

SEQ ID NO: 429          moltype = AA   length = 209
FEATURE                 Location/Qualifiers
REGION                  1..209
                        note = A full length FGF21, NP_061986.1
source                  1..209
                        mol_type = protein
                        organism = synthetic construct
SEQUENCE: 429
MDSDETGFEH SGLWVSVLAG LLLGACQAHP IPDSSPLLQF GGQVRQRYLY TDDAQQTEAH      60
LEIREDGTVG GAADQSPESL LQLKALKPGV IQILGVKTSR FLCQRPDGAL YGSLHFDPEA     120
CSFRELLLED GYNVYQSEAH GLPLHLPGNK SPHRDAPRG PARFLPLPGL PPALPEPPGI     180
LAPQPPDVGS SDPLSMVGPS QGRSPSYAS                                       209
```

```
SEQ ID NO: 430         moltype = AA  length = 124
FEATURE                Location/Qualifiers
REGION                 1..124
                       note = VH SEQ ID NO: 68 in U.S. Patent Publication
                         20110135657
source                 1..124
                       mol_type = protein
                       organism = synthetic construct
SEQUENCE: 430
QVTLKESGPV LVKPTETLTL TCTVSGFSLN NARMGVSWIR QPPGKALEWL AHIFSNDEKS   60
YSTSLKSRLT ISKDTSKSQV VLIMTNMDPV DTATYYCARS VVTGGYYYDG MDVWGQGTTV  120
TVSS                                                               124

SEQ ID NO: 431         moltype = AA  length = 108
FEATURE                Location/Qualifiers
REGION                 1..108
                       note = VH SEQ ID NO: 50 in U.S. Patent Publication
                         20110135657
source                 1..108
                       mol_type = protein
                       organism = synthetic construct
SEQUENCE: 431
SYVLTQPPSV SVAPGQTARI TCGGNNIGSE SVHWYQQKPG QAPVLVVYDD SDRPSGIPER   60
FSGSNSGNTA TLTISRVEAG DEADYYCQVW DGNSDHVVFG GGTKLTVL               108
```